United States Patent
Edmund et al.

(10) Patent No.: US 12,247,004 B2
(45) Date of Patent: Mar. 11, 2025

(54) 2-AMINO-N-(AMINO-OXO-ARYL-LAMBDA⁶-SULFANYLIDENE)ACETAMIDE COMPOUNDS AND THEIR THERAPEUTIC USE

(71) Applicant: Oxford Drug Design Limited, London (GB)

(72) Inventors: Grace Edmund, London (GB); Michael H. Charlton, Oxford (GB); Paul William Finn, Faringdon (GB); Aigars Jirgensons, Riga (LV); Marija Skvorcova, Riga (LV); Janis Veliks, Riga (LV); Liene Grigorjeva, Riga (LV)

(73) Assignee: Oxford Drug Design Limited, London (GB)

(*) Notice: Subject to any disclaimer, the term of this patent is extended or adjusted under 35 U.S.C. 154(b) by 393 days.

(21) Appl. No.: 17/786,089

(22) PCT Filed: Dec. 18, 2020

(86) PCT No.: PCT/EP2020/087126
§ 371 (c)(1),
(2) Date: Jun. 16, 2022

(87) PCT Pub. No.: WO2021/123237
PCT Pub. Date: Jun. 24, 2021

(65) Prior Publication Data
US 2023/0114875 A1    Apr. 13, 2023

Related U.S. Application Data

(60) Provisional application No. 62/950,311, filed on Dec. 19, 2019.

(51) Int. Cl.
| | | |
|---|---|---|
| *C07C 381/10* | (2006.01) |
| *C07C 313/06* | (2006.01) |
| *C07D 213/71* | (2006.01) |
| *C07D 215/36* | (2006.01) |
| *C07D 231/18* | (2006.01) |
| *C07D 277/16* | (2006.01) |
| *C07D 307/79* | (2006.01) |
| *C07D 317/50* | (2006.01) |
| *C07D 333/34* | (2006.01) |
| *C07D 333/52* | (2006.01) |
| *C07D 495/04* | (2006.01) |

(52) U.S. Cl.
CPC .......... *C07C 381/10* (2013.01); *C07C 313/06* (2013.01); *C07D 213/71* (2013.01); *C07D 215/36* (2013.01); *C07D 231/18* (2013.01); *C07D 277/16* (2013.01); *C07D 307/79* (2013.01); *C07D 317/50* (2013.01); *C07D 333/34* (2013.01); *C07D 333/52* (2013.01); *C07D 495/04* (2013.01)

(58) Field of Classification Search
CPC ... C07C 313/06; C07C 381/10; C07D 213/71; C07D 215/36; C07D 231/18; C07D 277/16; C07D 307/79; C07D 317/50; C07D 333/34; C07D 333/52; C07D 495/04
See application file for complete search history.

(56) References Cited

U.S. PATENT DOCUMENTS
2018/0022696 A1    1/2018   Jirgensons et al.

FOREIGN PATENT DOCUMENTS
| | | |
|---|---|---|
| CN | 109674797 A | 4/2019 |
| WO | WO-2016/129983 A1 | 8/2016 |
| WO | WO-2017/221002 A1 | 12/2017 |
| WO | WO-2018/065611 A1 | 4/2018 |

OTHER PUBLICATIONS

Chemical Abstracts, Chemical Compounds from CAS Registry with Registry Nos. 1786215-48-2; 1786212-05-2; 1786200-20-1; and 1786086-91-6, dated Jun. 22, 2015 (2 pages).
Gadakh et al., "Aminoacyl-tRNA synthetase inhibitors as antimicrobial agents: a patent review from 2006 till present," Expert Opin Ther Pat. 22(12): 1453-65 (2012).
Hurdle et al., "Prospects for aminoacyl-tRNA synthetase inhibitors as new antimicrobial agents," Antimicrobial Agents and Chemotherapy. 49(12): 4821-33 (2005).
International Preliminary Report on Patentability for International Application No. PCT/EP2020/087126, issued May 17, 2022 (6 pages).
International Search Report and Written Opinion for International Application No. PCT/EP2020/087126, mailed Mar. 25, 2021 (8 pages).

(Continued)

*Primary Examiner* — Alicia L Otton
(74) *Attorney, Agent, or Firm* — Clark & Elbing LLP

(57) ABSTRACT

The present invention pertains generally to the field of therapeutic compounds. More specifically the present invention pertains to certain 2-amino-N-(amino-oxo-aryl-λ⁶-sulfanylidene)acetamide compounds (referred to herein as ANASIA compounds) that, inter alia, inhibit (e.g., selectively inhibit) bacterial aminoacyl-tRNA synthetase (aaRS) (e.g., bacterial leucyl-tRNA synthetase, LeuRS). The present invention also pertains to pharmaceutical compositions comprising such compounds, and the use of such compounds and compositions, both in vitro and in vivo, to inhibit (e.g., selectively inhibit) bacterial aminoacyl-tRNA synthetase; to treat disorders that are ameliorated by the inhibition (e.g., selective inhibition) of bacterial aminoacyl-tRNA synthetase; to treat bacterial infections; etc.

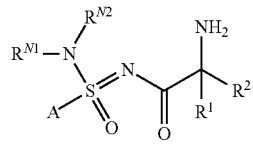

24 Claims, No Drawings

(56) References Cited

OTHER PUBLICATIONS

Laupland et al., "Treatment of *Staphylococcus aureus* colonization and prophylaxis for infection with topical intranasal mupirocin: An evidence-based review," Clin Infect Dis. 37(7): 933-8 (2003).
Ochsner et al., "Aminoacyl-tRNA synthetases: essential and still promising targets for new anti-infective agents," Expert Opin Investig Drugs. 16(5): 573-93 (2007).
Pham et al., "Aminoacyl-tRNA synthetases as drug targets in eukaryotic parasites," Int J Parasitol Drugs Drug Resist. 4(1):1-13 (2014).
Vondenhoff et al., "Aminoacyl-tRNA synthetase inhibitors as potential antibiotics," Eur J Med Chem. 46(11): 5227-36 (2011).

2-AMINO-N-(AMINO-OXO-ARYL-LAMBDA⁶-SULFANYLIDENE)ACETAMIDE COMPOUNDS AND THEIR THERAPEUTIC USE

RELATED APPLICATION

This application is related to U.S. provisional patent application No. 62/950,311 filed 19 Dec. 2019, the contents of which are incorporated herein by reference in their entirety.

TECHNICAL FIELD

The present invention pertains generally to the field of therapeutic compounds.

More specifically the present invention pertains to certain 2-amino-N-(amino-oxo-aryl-$\lambda^6$-sulfanylidene)acetamide compounds (referred to herein as ANASIA compounds) that, inter alia, inhibit (e.g., selectively inhibit) bacterial aminoacyl-tRNA synthetase (aaRS) (e.g., bacterial leucyl-tRNA synthetase, LeuRS). The present invention also pertains to pharmaceutical compositions comprising such compounds, and the use of such compounds and compositions, both in vitro and in vivo, to inhibit (e.g., selectively inhibit) bacterial aminoacyl-tRNA synthetase; to treat disorders that are ameliorated by the inhibition (e.g., selective inhibition) of bacterial aminoacyl-tRNA synthetase; to treat bacterial infections; etc.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Bacterial Aminoacyl-tRNA Synthetase

Widespread resistance to currently used antibacterial drugs has encouraged the search for novel chemotherapeutics with slow or completely blocked resistance development. This could be achieved by targeting functional bacterial proteins, the mutation of which leads to reduction of bacterial fitness.

Bacterial enzymes called aminoacyl-tRNA synthetases (aaRS) have been recognized as such molecular targets for drug development. See, e.g., Gadakh et al., 2012; Vondenhoff et al., 2011; and Pham et al., 2014.

The aminoacyl-tRNA synthetase (aaRS) family of enzymes catalyse the addition of proteinogenic amino acids to their cognate tRNA. The product aminoacyl-tRNA participates in the translation of messenger RNA into protein at the ribosome. The aaRS mechanism proceeds as follows: it binds ATP and the corresponding amino acid and forms an aminoacyl-adenylate intermediate, releasing inorganic pyrophosphate (PPi). The adenylate-aaRS complex binds the appropriate tRNA molecule, and the amino acid is transferred from the aminoacyl-AMP to either the 2'- or the 3'-OH of the last tRNA nucleotide at the 3'-end.

The mechanism can be summarized in the following reaction series:

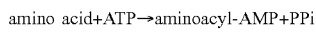

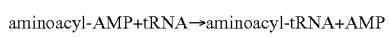

Two classes of aminoacyl-tRNA synthetases (aaRS) are known: "Class I" (with two highly conserved sequence motifs, and which aminoacylates at the 2'-OH of a terminal adenosine nucleotide on tRNA) and "Class II" (with three highly conserved sequence motifs, and which aminoacylates at the 3'-OH of a terminal adenosine on tRNA). Included among the known aminoacyl-tRNA synthetases are: Alanyl-tRNA synthetase; Arginyl-tRNA synthetase; Aspartyl-tRNA synthetase; Glutamyl-tRNA synthetase; Glycyl-tRNA synthetase; Histidyl-RNA synthetase; Isoleucyl-tRNA synthetase; Leucyl-tRNA synthetase; Lysyl-tRNA synthetase; Methionyl-tRNA synthetase; Phenylalanyl-tRNA synthetase; Seryl-tRNA synthetase; Threonyl-tRNA synthetase; Tryptophanyl-tRNA synthetase; Tyrosyl-tRNA synthetase; and Valyl-tRNA synthetase.

Bacterial aminoacyl-tRNA synthetases (aaRS) possess several features that render them promising broad-spectrum antibacterial drug targets; they are essential for viability, found in all bacterial pathogens, and are in many cases sufficiently structurally distinct from their eukaryotic counterparts to allow selective targeting (see, e.g., Hurdle et al., 2005; Ochsner et al., 2007). Furthermore, there exists both chemical and clinical validation for these enzymes as useful targets for antibacterial chemotherapy.

However, despite the potential promise of this family of targets, only one aaRS inhibitor with a relatively limited indication has to date been approved for the management of bacterial infection. Specifically, mupirocin (also known as Bactroban and Centany; shown below) is an inhibitor of isoleucyl-tRNA synthetase that has been approved for use as a topical agent for nasal decolonization of *Staphylococcus aureus* and for the treatment of superficial skin infection (see, e.g., Laupland et al., 2003).

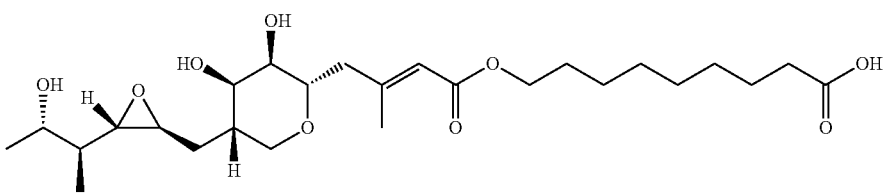 [SMILES: C/C(=C\C(=O)OCCCCCCCCC(=O)O)C[C@@H]1OC[C@H](C[C@@H]2O[C@H]2[C@@H](C)[C@H](C)O)[C@@H](O)[C@H]1O]

Several inhibitors for other bacterial tRNA synthetases have been developed; however, so far none have been approved for use in medicine.

The inventors have identified a novel class of small molecule inhibitors of bacterial aminoacyl-tRNA synthetase (specifically, bacterial leucyl-tRNA synthetase) which are useful in the treatment of a range of conditions, including bacterial infections.

Known Compounds

Jirgensons et al., 2016, describe certain N-acyl-arylsulfonamide derivatives of the following formula as aminoacyl-tRNA synthetase inhibitors which are useful, inter alia, in the treatment of bacterial infections.

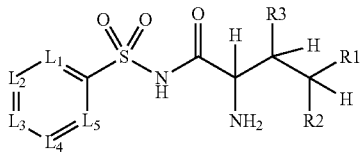

Finn et al., 2018, describe certain 2-amino-N-(arylsulfinyl)-acetamide compounds of the following formula as inhibitors of bacterial aminoacyl-tRNA synthetase inhibitors which are useful, inter alia, in the treatment of bacterial infections.

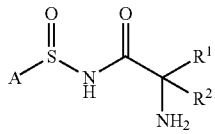

In contrast to these known compounds, the aminoacyl-tRNA synthetase inhibitors described herein have the following formula:

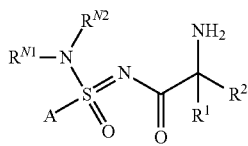

SUMMARY OF THE INVENTION

One aspect of the invention pertains to certain 2-amino-N-(amino-oxo-aryl-$\lambda^6$-sulfanylidene)acetamide compounds (referred to herein as ANASIA compounds), as described herein.

Another aspect of the invention pertains to a composition (e.g., a pharmaceutical composition) comprising an ANASIA compound, as described herein, and a pharmaceutically acceptable carrier or diluent.

Another aspect of the invention pertains to a method of preparing a composition (e.g., a pharmaceutical composition) comprising the step of mixing an ANASIA compound, as described herein, and a pharmaceutically acceptable carrier or diluent.

Another aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.), in vitro or in vivo, comprising contacting the synthetase with an effective amount of an ANASIA compound, as described herein.

Another aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.) function in a cell (e.g., a bacterial cell), in vitro or in vivo, comprising contacting the cell with an effective amount of an ANASIA compound, as described herein.

Another aspect of the present invention pertains to an ANASIA compound as described herein for use in a method of treatment of the human or animal body by therapy, for example, for use in a method of treatment of a disorder (e.g., a disease) as described herein.

Another aspect of the present invention pertains to use of an ANASIA compound, as described herein, in the manufacture of a medicament, for example, for use in a method of treatment, for example, for use in a method of treatment of a disorder (e.g., a disease) as described herein.

Another aspect of the present invention pertains to a method of treatment, for example, a method of treatment of a disorder (e.g., a disease) as described herein, comprising administering to a subject in need of treatment a therapeutically-effective amount of an ANASIA compound, as described herein, preferably in the form of a pharmaceutical composition.

In one embodiment, the treatment is treatment of a disorder of the human or animal body that is ameliorated by the inhibition (e.g., selective inhibition) of bacterial aminoacyl-tRNA synthetase (aaRS) (e.g., bacterial leucyl-tRNA synthetase, LeuRS).

In one embodiment, the treatment is treatment of a bacterial infection.

Another aspect of the present invention pertains to a kit comprising (a) an ANASIA compound, as described herein, preferably provided as a pharmaceutical composition and in a suitable container and/or with suitable packaging; and (b) instructions for use, for example, written instructions on how to administer the compound.

Another aspect of the present invention pertains to an ANASIA compound obtainable by a method of synthesis as described herein, or a method comprising a method of synthesis as described herein.

Another aspect of the present invention pertains to an ANASIA compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

One aspect of the present invention relates to certain compounds that may conveniently be described as 2-amino-N-(amino-oxo-aryl-$\lambda^6$-sulfanylidene)acetamide compounds. One simple example of such compounds is 2-amino-N-(amino-oxo-phenyl-$\lambda^6$-sulfanylidene)acetamide, shown below.

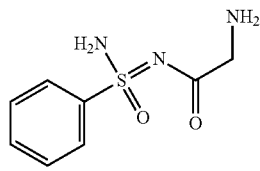

The compounds are characterized by a —S(=O)(NH$_2$)=NH—C(=O)—C(NH$_2$)< linkage, with an aryl group (referred to herein as -A) attached to the sulfur atom (at the far left), and two groups (referred to herein as —R$^1$ and —R$^2$) attached to the alpha carbon atom (at the far right).

The —NH$_2$ group that is attached to the sulfur atom may optionally be substituted with one or two substituents (for example, —NR$^{N1}$R$^{N2}$). Accordingly, more generally, the compounds are characterized by a —S(=O)(NR$^{N1}$R$^{N2}$)=NH—C(=O)—C(NH$_2$)< linkage.

Thus, one aspect of the present invention pertains to compounds of the following formula, and pharmaceutically acceptable salts, hydrates, and solvates thereof, wherein -A, —R$^{N1}$, —R$^{N2}$, —R$^1$, and —R$^2$ are as defined herein (for convenience, collectively referred to herein as "2-amino-N-(amino-oxo-aryl-$\lambda^6$-sulfanylidene)acetamide compounds" or "ANASIA compounds"):

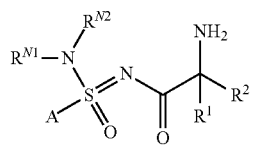

The left-hand group, A-S(=O)(NR$^{N1}$R$^{N2}$)=NH—, may be conveniently considered to be an arylsulfonimidamide moiety. The right-hand group, —C(=O)—CR$^1$R$^2$—NH$_2$, may be conveniently considered to be an alpha-amino acid residue.

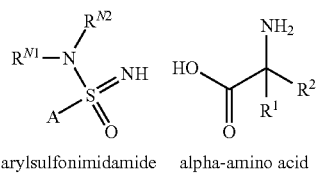

arylsulfonimidamide    alpha-amino acid

Some embodiments of the invention include the following:

(1) A compound selected from compounds of the following formula, and pharmaceutically acceptable salts, hydrates, and solvates thereof:

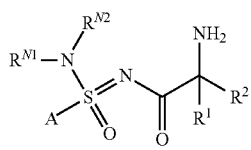

wherein:
-A is independently -A$^C$ or -A$^H$;
-A$^C$ is independently phenyl or naphthyl, and is optionally substituted with one or more substituents —R$^X$;
-A$^H$ is independently C$_{5-12}$heteroaryl, and is optionally substituted with one or more substituents —R$^X$;
and wherein:
each —R$^X$ is independently selected from:
—R$^{XX}$, —R$^{XXU}$, —R$^{XXV}$,
—F, —Cl, —Br, —I,
—OH, —OR$^{XX}$,
-L$^{XX}$-OH, -L$^{XX}$-OR$^{XX}$,
—CF$_3$, —CHF$_2$, —OCF$_3$, —OCHF$_2$,
—NH$_2$, —NHR$^{XX}$, —NR$^{XX}$$_2$, —R$^{XM}$,
-L$^{XX}$-NH$_2$, -L$^{XX}$-NHR$^{XX}$, -L$^{XX}$-NR$^{XX}$$_2$, -L$^{XX}$-R$^{XM}$,
—C(=O)OH, —C(=O)OR$^{XX}$, —OC(=O)R$^X$,
—C(=O)NH$_2$, —C(=O)NHR$^{XX}$, —C(=O)NR$^{XX}$$_2$,
—C(=O)R$^{XM}$,
—NHC(=O)R$^{XX}$, —NR$^{XN}$C(=O)R$^{XX}$
—NHC(=O)NH$_2$, —NHC(=O)NHR$^{XX}$, —NHC(=O)NR$^{XX}$$_2$, —NHC(=O)R$^{XM}$,
—NR$^{XN}$C(=O)NH$_2$, —NR$^{XN}$C(=O)NHR$^{XX}$,
—NR$^{XN}$C(=O)NR$^{XX}$$_2$, —NR$^{XN}$C(=O)R$^{XM}$,
—NHC(=O)OR$^{XX}$, —NR$^{XN}$C(=O)OR$^{XX}$
—OC(=O)NH$_2$, —OC(=O)NHR$^{XX}$, —OC(=O)NR$^{XX}$$_2$, —OC(=O)R$^{XM}$,
—NHC(=NH)NH$_2$,
—C(=O)R$^{XX}$,
—S(=O)NH$_2$, —S(=O)NHR$^{XX}$, —S(=O)NR$^{XX}$$_2$,
—S(=O)R$^{XM}$
S(=O)$_2$NH$_2$, —S(=O)$_2$NHR$^{XX}$, —S(=O)$_2$NR$^{XX}$$_2$,
—S(=O)$_2$R$^{XM}$,
—NHS(=O)R$^{XX}$, —NR$^{XN}$S(=O)R$^X$,
—NHS(=O)$_2$R$^{XX}$, —NR$^{XN}$S(=O)$_2$R$^{XX}$,
—S(=O)R$^{XX}$, —S(=O)$_2$R$^{XX}$,
—SH, —SR$^{XX}$, —CN, and —NO$_2$;
and additionally, two adjacent groups —R$^X$, if present, may together form:
—O—CH$_2$—O—, —O—CH$_2$CH$_2$—O—, —CH$_2$—CH$_2$—O—, —CH$_2$—CH$_2$CH$_2$—O—,
—CH$_2$—O—CH$_2$—, or —CH$_2$—CH$_2$—O—CH$_2$—;

wherein:
each -L$^{XX}$- is linear or branched saturated C$_{1-4}$alkylene;
each —R$^{XX}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
each —R$^{XXU}$ is independently linear or branched C$_{2-4}$alkenyl;
each —R$^{XXV}$ is independently linear or branched C$_{2-4}$alkynyl;
each —R$^{XN}$ is linear or branched saturated C$_{1-4}$alkyl;
each —R$^{XM}$ is independently azetidino, pyrrolidino, piperidino, piperazino, morpholino, azepano, or diazepano, and is:
optionally substituted with one or more groups selected from:
—R$^{XMM}$, —C(=O)R$^{XMM}$, —C(=O)OR$^{XMM}$, and —S(=O)$_2$R$^{XMM}$;
wherein each —R$^{XMM}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
—R$^1$ is independently —H or —R$^{11}$;
—R$^{11}$ is independently —R$^{11A}$ or —R$^{11B}$;
—R$^{11A}$ is independently:
—R$^{A1}$, —R$^{A2}$, —R$^{A3}$, —R$^{A4}$, —R$^{A5}$, -L$^A$-R$^{A2}$, -L$^A$-R$^{A3}$, -L$^A$-R$^{A4}$, or -L$^A$-R$^{A5}$;
each —R$^{A1}$ is linear or branched saturated C$_{1-6}$alkyl, and is optionally substituted with one or more groups —R$^{AA2}$;
each —R$^{A2}$ is saturated C$_{3-6}$cycloalkyl, and is optionally substituted with one or more groups —R$^{AA1}$ and one or more groups —R$^{AA2}$;
each —R$^{A3}$ is non-aromatic C$_{3-7}$heterocyclyl, and is optionally substituted with one or more groups —R$^{AA1}$ and one or more groups —R$^{AA2}$;
each —R$^{A4}$ is independently phenyl or naphthyl, and is optionally substituted with one or more groups —R$^{AA1}$ and one or more groups —R$^{AA2}$;
each —R$^{A5}$ is C$_{5-10}$heteroaryl, and is optionally substituted with one or more groups —R$^{AA1}$ and one or more groups —R$^{AA2}$;
each -L$^A$- is linear or branched saturated C$_{1-4}$alkylene;
each —R$^{AA1}$ is independently selected from:
—R$^{AA}$,
L$^{AA}$-OH, -L$^{AA}$-OR$^{AA}$,
L$^{AA}$-NH$_2$, -L$^{AA}$-NHR$^{AA}$, -L$^{AA}$-N(R$^{AA}$)$_2$, and -L$^{AA}$-R$^{AM}$;
each —R$^{AA2}$ is independently from:
—F, —Cl, —Br, —I,
—OH, —OR$^{AA}$,
—CF$_3$, —CHF$_2$, —OCF$_3$, —OCHF$_2$,
—NH$_2$, —NHR$^{AA}$, —N(R$^{AA}$)$_2$, —R$^{AM}$,
—C(=O)OH, —C(=O)OR$^{AA}$, —OC(=O)R$^{AA}$,
—C(=O)NH$_2$, —C(=O)NHR$^{AA}$, —C(=O)N(R$^{AA}$)$_2$, —C(=O)R$^{AM}$,
—NHC(=O)R$^{AA}$, —NR$^{AN}$C(=O)R$^{AA}$,
—NHC(=O)NH$_2$, —NHC(=O)NHR$^{AA}$, —NHC(=O)N(R$^{AA}$)$_2$, —NHC(=O)R$^{AM}$,
—NR$^{AN}$C(=O)NH$_2$, —NR$^{AN}$C(=O)NHR$^{AA}$, —NR$^{AN}$C(=O)N(R$^{AA}$)$_2$, —NR$^{AN}$C(=O)R$^{AM}$,
—NHC(=O)OR$^{AA}$, —NR$^{AN}$C(=O)OR$^{AA}$,
—OC(=O)NH$_2$, —OC(=O)NHR$^{AA}$, —OC(=O)N(R$^{AA}$)$_2$, —OC(=O)R$^{AM}$,
—NHC(=NH)NH$_2$,
—C(=O)R$^{AA}$,
S(=O)NH$_2$, —S(=O)NHR$^{AA}$, —S(=O)N(R$^{AA}$)$_2$, —S(=O)R$^{AM}$,
—S(=O)$_2$NH$_2$, —S(=O)$_2$NHR$^{AA}$, —S(=O)$_2$N(R$^{AA}$)$_2$, —S(=O)$_2$R$^{AM}$,
—NHS(=O)R$^{AA}$, —NR$^{AN}$S(=O)R$^{AA}$,
—NHS(=O)$_2$R$^{AA}$, —NR$^{AN}$S(=O)$_2$R$^{AA}$,
—S(=O)R$^{AA}$, —S(=O)$_2$R$^{AA}$,
—SH, —SR$^{AA}$, —CN, and —NO$_2$;
wherein:
each -L$^{AA}$- is linear or branched saturated C$_{1-4}$alkylene;
each —R$^{AA}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
each —R$^{AN}$ is linear or branched saturated C$_{1-4}$alkyl;
each —R$^{AM}$ is independently azetidino, pyrrolidino, piperidino, piperazino, morpholino, azepano, or diazepano, and is:
optionally substituted with one or more groups selected from:
—R$^{AMM}$, —C(=O)R$^{AMM}$, —C(=O)OR$^{AMM}$, and —S(=O)$_2$R$^{AMM}$;
wherein each —R$^{AMM}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
—R$^{11B}$ is independently selected from:
—F, —Cl, —Br, —I,
—OH, —OR$^{BB}$,
—CF$_3$, —CHF$_2$, —OCF$_3$, —OCHF$_2$,
—NH$_2$, —NHR$^{BB}$, —NR$^{BB}$$_2$, —R$^{BM}$,
—C(=O)OH, —C(=O)OR$^{BB}$, —OC(=O)R$^{BB}$,
—C(=O)NH$_2$, —C(=O)NHR$^{BB}$, —C(=O)NR$^{BB}$$_2$, —C(=O)R$^{BM}$,
—NHC(=O)R$^{BB}$, —NR$^{BN}$C(=O)R$^{BB}$,
—NHC(=O)NH$_2$, —NHC(=O)NHR$^{BB}$, —NHC(=O)NR$^{BB}$$_2$, —NHC(=O)R$^{BM}$,
—NR$^{BN}$C(=O)NH$_2$, —NR$^{BN}$C(=O)NHR$^{BB}$, —NR$^{BN}$C(=O)NR$^{BB}$$_2$, —NR$^{BN}$O(=O)R$^{BM}$,
—NHC(=O)OR$^{BB}$, —NR$^{BN}$C(=O)OR$^{BB}$,
—OC(=O)NH$_2$, —OC(=O)NHR$^{BB}$, —OC(=O)NR$^{BB}$$_2$, —OC(=O)R$^{BM}$,
—NHC(=NH)NH$_2$,
—C(=O)R$^{BB}$,
—S(=O)NH$_2$, —S(=O)NHR$^{BB}$, —S(=O)NR$^{BB}$$_2$, —S(=O)R$^{BM}$,
—S(=O)$_2$NH$_2$, —S(=O)$_2$NHR$^{BB}$, —S(=O)$_2$NR$^{BB}$$_2$, —S(=O)$_2$R$^{BM}$,
—NHS(=O)R$^{BB}$, —NR$^{BN}$S(=O)R$^{BB}$,
—NHS(=O)$_2$R$^{BB}$, —NR$^{BN}$S(=O)$_2$R$^{BB}$,
—S(=O)R$^{BB}$, —S(=O)$_2$R$^{BB}$,
—SH, —SR$^{BB}$, —CN, and —NO$_2$;
wherein:
each —R$^{BB}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
each —R$^{BN}$ is linear or branched saturated C$_{1-4}$alkyl;
each —R$^{BM}$ is independently azetidino, pyrrolidino, piperidino, piperazino, morpholino, azepano, or diazepano, and is:
optionally substituted with one or more groups selected from:
—R$^{BMM}$, —C(=O)R$^{BMM}$, —C(=O)OR$^{BMM}$, and —S(=O)$_2$R$^{BMM}$;

wherein each —$R^{BMM}$ is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$;

—$R^2$ is independently —H or —$R^{22}$;

—$R^{22}$ is independently —$R^{22C}$ or —$R^{22D}$;

—$R^{22C}$ is independently:
—$R^{C1}$, —$R^{C2}$, —$R^{C3}$, —$R^{C4}$, —$R^{C5}$, -$L^C$-$R^{C2}$, -$L^C$-$R^{C3}$, -$L^C$-$R^{C4}$, or -$L^C$-$R^{C5}$;

each —$R^{C1}$ is linear or branched saturated $C_{1-6}$alkyl, and is optionally substituted with one or more groups —$R^{CC2}$;

each —$R^{C2}$ is saturated $C_{3-6}$cycloalkyl, and is optionally substituted with one or more groups —$R^{CC1}$ and one or more groups —$R^{CC2}$;

each —$R^{C3}$ is non-aromatic $C_{3-7}$heterocyclyl, and is optionally substituted with one or more groups —$R^{CC1}$ and one or more groups —$R^{CC2}$;

each —$R^{C4}$ is independently phenyl or naphthyl, and is optionally substituted with one or more groups —$R^{CC1}$ and one or more groups —$R^{CC2}$;

each —$R^{C5}$ is $C_{5-10}$heteroaryl, and is optionally substituted with one or more groups —$R^{CC1}$ and one or more groups —$R^{CC2}$;

each -$L^C$- is linear or branched saturated $C_{1-4}$alkylene;

each —$R^{CC1}$ is independently selected from:
—$R^{CC}$
-$L^{CC}$-OH, -$L^{CC}$-$OR^{CC}$,
-$L^{CC}$-$NH_2$, -$L^{CC}$-$NHR^{CC}$, -$L^{CC}$-$N(R^{CC})_2$, and -$L^{CC}$-$R^{CM}$;

each —$R^{CC2}$ is independently selected from:
—F, —Cl, —Br, —I,
—OH, —$OR^{CC}$
—$CF_3$, —$CHF_2$, —$OCF_3$, —$OCHF_2$,
—$NH_2$, —$NHR^{CC}$, —$N(R^{CC})_2$, —$R^{CM}$,
—C(=O)OH, —C(=O)$OR^{CC}$, —OC(=O)$R^{CC}$
—C(=O)$NH_2$, —C(=O)$NHR^{CC}$, —C(=O)N$(R^{CC})_2$,
—C(=O)$R^{CM}$
—NHC(=O)$R^{CC}$, —$NR^{CN}$C(=O)$R^{CC}$
—NHC(=O)$NH_2$, —NHC(=O)$NHR^{CC}$, —NHC(=O)N$(R^{CC})_2$, —NHC(=O)$R^{CM}$
—$NR^{CN}$C(=O)$NH_2$, —$NR^{CN}$C(=O)$NHR^{CC}$, —$NR^{CN}$C(=O)N$(R^{CC})_2$,
—$NR^{CN}$C(=O)$R^{CM}$,
—NHC(=O)$OR^{CC}$, —$NR^{CN}$C(=O)$OR^{CC}$
—OC(=O)$NH_2$, —OC(=O)$NHR^{CC}$, —OC(=O)N$(R^{CC})_2$, —OC(=O)$R^{CM}$
—NHC(=NH)$NH_2$,
—C(=O)$R^{CC}$
—S(=O)$NH_2$, —S(=O)$NHR^{CC}$, —S(=O)N$(R^{CC})_2$, —S(=O)$R^{CM}$
—S(=O)$_2NH_2$, —S(=O)$_2NHR^{CC}$, —S(=O)$_2$N$(R^{CC})_2$, —S(=O)$_2R^{CM}$,
—NHS(=O)$R^{CC}$, —$NR^{CN}$S(=O)$R^{CC}$
—NHS(=O)$_2R^{CC}$, —$NR^{CN}$S(=O)$_2R^{CC}$,
—S(=O)$R^{CC}$, —S(=O)$_2R^{CC}$,
—SH, —$SR^{CC}$, —CN, and —$NO_2$;

wherein:
each -$L^{CC}$- is linear or branched saturated $C_{1-4}$alkylene;

each —$R^{CC}$ is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$;

each —$R^{CN}$ is linear or branched saturated $C_{1-4}$alkyl;

each —$R^{CM}$ is independently azetidino, pyrrolidino, piperidino, piperazino, morpholino, azepano, or diazepano, and is:

optionally substituted with one or more groups selected from:
—$R^{CMM}$, —C(=O)$R^{CMM}$, —C(=O)$OR^{CMM}$, and —S(=O)$_2R^{CMM}$;

wherein each —$R^{CMM}$ is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$;

—$R^{22D}$ is independently selected from:
—F, —Cl, —Br, —I,
—OH, —$OR^{DD}$,
—$CF_3$, —$CHF_2$, —$OCF_3$, —$OCHF_2$,
—$NH_2$, —$NHR^{DD}$, —$NR^{DD}_2$, —$R^{DM}$,
—C(=O)OH, —C(=O)$OR^{DD}$, —OC(=O)$R^{DD}$,
—C(=O)$NH_2$, —C(=O)$NHR^{DD}$, —C(=O)$NR^{DD}_2$,
—C(=O)$R^{DM}$
—NHC(=O)$R^{DD}$, —$NR^{DN}$C(=O)$R^{DD}$,
—NHC(=O)$NH_2$, —NHC(=O)$NHR^{DD}$, —NHC(=O)$NR^{DD}_2$, —NHC(=O)$R^{DM}$
—$NR^{DN}$C(=O)$NH_2$, —$NR^{DN}$C(=O)$NHR^{DD}$, —$NR^{DN}$C(=O)$NR^{DD}_2$, —$NR^{DN}$C(=O)$R^{DM}$,
—NHC(=O)$OR^{DD}$, —$NR^{DN}$C(=O)$OR^{DD}$
—OC(=O)$NH_2$, —OC(=O)$NHR^{DD}$, —OC(=O)$NR^{DD}_2$, —OC(=O)$R^{DM}$
—NHC(=NH)$NH_2$,
—C(=O)$R^{DD}$,
—S(=O)$NH_2$, —S(=O)$NHR^{DD}$, —S(=O)$NR^{DD}_2$, —S(=O)$R^{DM}$,
—S(=O)$_2NH_2$, —S(=O)$_2NHR^{DD}$, —S(=O)$_2NR^{DD}_2$, —S(=O)$_2R^{DM}$,
—NHS(=O)$R^{DD}$, —$NR^{DN}$S(=O)$R^{DD}$
—NHS(=O)$_2R^{DD}$, —$NR^{DN}$S(=O)$_2R^{DD}$,
—S(=O)$R^{DD}$, —S(=O)$_2R^{DD}$,
—SH, —$SR^{DD}$, —CN, and —$NO_2$;

wherein:
each —$R^{DD}$ is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$;

each —$R^{DN}$ is linear or branched saturated $C_{1-4}$alkyl;

each —$R^{DM}$ is independently azetidino, pyrrolidino, piperidino, piperazino, morpholino, azepano, or diazepano, and is:

optionally substituted with one or more groups selected from:
—$R^{DMM}$, —C(=O)$R^{DMM}$, —C(=O)$OR^{DMM}$, and —S(=O)$_2R^{DMM}$;

wherein each —$R^{DMM}$ is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$;

or —$R^1$ and —$R^2$, together with the carbon atom to which they are attached, form a saturated $C_{3-6}$cycloalkyl or a non-aromatic $C_{3-7}$heterocyclyl, and is optionally substituted with one or more groups —$R^{CC2}$;

and wherein:
—$R^{N1}$ is independently —H or —$R^N$;
—$R^{N2}$ is independently —H or —$R^N$;
each —$R^N$ is independently linear or branched saturated $C_{1-6}$alkyl, phenyl, or —$CH_2$-phenyl, wherein each phenyl is optionally substituted with one or more groups selected from —F, —Cl, —Br, -Me, —OH, —OMe, —CF$_3$, and —OCF$_3$; or —R$^{N1}$ and R$^{N2}$, taken together, form C$_{2-6}$alkylene.

For convenience, the following table sets out the various groups mentioned above.

Substituents Table 1
List of Groups

| | | | | | | |
|---|---|---|---|---|---|---|
| A | A$^C$ | R$^X$ | L$^{XX}$ | | | |
| | A$^H$ | | R$^{XX}$ | | | |
| | | | R$^{XXU}$ | | | |
| | | | R$^{XXV}$ | | | |
| | | | R$^{XN}$ | | | |
| | | | R$^{XM}$ | R$^{XMM}$ | | |
| R$^1$ | R$^{11}$ | R$^{11A}$ | R$^{A1}$ | R$^{AA1}$ | L$^{AA}$ | |
| | | | R$^{A2}$ | R$^{AA2}$ | R$^{AA}$ | |
| | | | R$^{A3}$ | | R$^{AN}$ | |
| | | | R$^{A4}$ | | R$^{AM}$ | R$^{AMM}$ |
| | | | R$^{A5}$ | | | |
| | | | L$^A$ | | | |
| | | R$^{11B}$ | R$^{BB}$ | | | |
| | | | R$^{BN}$ | | | |
| | | | R$^{BM}$ | R$^{BMM}$ | | |
| R$^2$ | R$^{22}$ | R$^{22C}$ | R$^{C1}$ | R$^{CC1}$ | L$^{CC}$ | |
| | | | R$^{C2}$ | R$^{CC2}$ | R$^{CC}$ | |
| | | | R$^{C3}$ | | R$^{CN}$ | |
| | | | R$^{C4}$ | | R$^{CM}$ | R$^{CMM}$ |
| | | | R$^{C5}$ | | | |
| | | | L$^C$ | | | |
| | | R$^{22D}$ | R$^{DD}$ | | | |
| | | | R$^{DN}$ | | | |
| | | | R$^{DM}$ | R$^{DMM}$ | | |
| R$^{N1}$ | R$^N$ | | | | | |
| R$^{N2}$ | R$^N$ | | | | | |

For the avoidance of doubt, it is intended that the —NH$_2$ group which is attached to a carbon atom in the —S(=O)(NR$^{N1}$R$^{N2}$)=NH—C(=O)—C(NH$_2$)< linkage) is unmodified (e.g., is unsubstituted; is unprotected; etc.). However, it may be protonated, i.e., to form —NH$_3^+$.

Furthermore, for the avoidance of doubt, it is not intended that any part of the —S(=O)(NR$^{N1}$R$^{N2}$)=NH—C(=O)—C(NH$_2$)< linkage forms part of ring. However, in certain embodiments, as described herein, —R$^{N1}$ and —R$^{N2}$, together with the nitrogen atom to which they are attached, may form a ring.

Furthermore, for the avoidance of doubt, it is not intended that -A and —R$^1$, taken together, or -A and —R$^2$, taken together, form part of a ring. For example, it is not intended that -A and —R$^1$ are additionally linked, other than via the —S(=O)(NR$^{N1}$R$^{N2}$)=NH—C(=O)—C(NH$_2$)(R$^2$)— linkage. Similarly, it is not intended that -A and —R$^2$ are additionally linked, other than via the —S(=O)(NR$^{N1}$R$^{N2}$)=NH—C(=O)—C(NH$_2$)(R$^1$)— linkage. However, in certain embodiments, as described herein, —R$^1$ and —R$^2$, together with the carbon atom to which they are attached, may form a ring.

Similarly, for the avoidance of doubt, it is not intended that -A and —R$^{N1}$, taken together, or -A and —R$^{N2}$, taken together, form part of a ring. Similarly, for the avoidance of doubt, it is not intended that —R$^1$ and —R$^{N1}$, taken together, or —R$^1$ and —R$^{N2}$, taken together, form part of a ring. Similarly, for the avoidance of doubt, it is not intended that —R$^2$ and —R$^{N1}$ taken together, or —R$^2$ and —R$^{N2}$, taken together, form part of a ring.

Note that the compounds have at least one chiral centre, specifically, the sulfur atom which forms part of the sulfonimidamido group, marked with an asterisk (*) in the following formula. Unless otherwise stated, the sulfur atom at this position may be in either (R) or (S) configuration.

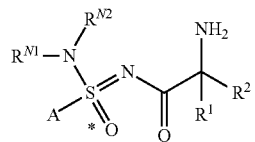

Also note that, depending upon the identity of the groups —R$^1$ and —R$^2$, the compounds may have a second chiral centre, specifically, the carbon atom to which —R$^1$ and —R$^2$ are attached, marked with a hash (#) in the following formula. Unless otherwise stated, the carbon atom at this position may be in either (R) or (S) configuration.

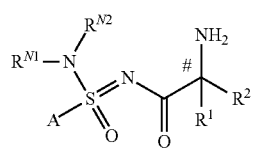

For the avoidance of doubt, and unless otherwise stated, a reference to a compound or compounds without specifying the configuration of one or both chiral centres is intended to encompass all possible configurations. For example, the following formula (which is silent with respect to stereochemistry):

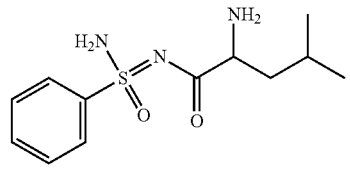 [SMILES: CC(C)CC(N)C(=O)N=S(N)(=O)c1ccccc1]

is intended to encompass all four diastereomers:

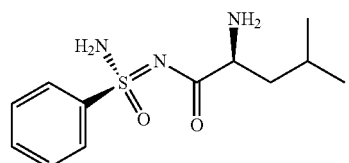

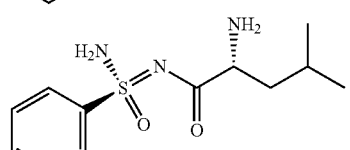

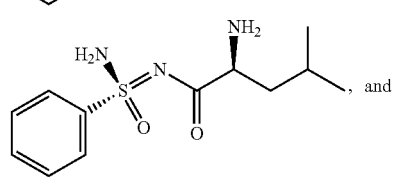

-continued

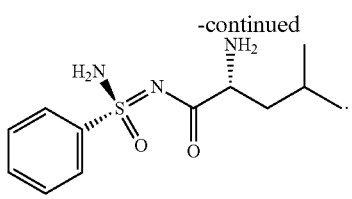

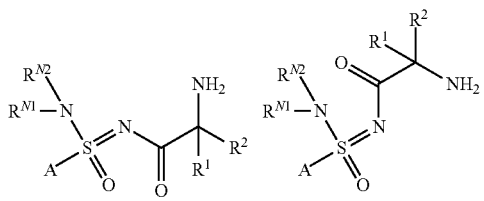

Similarly, the following formula (which is silent with respect to the stereochemistry at the sulfur atom):

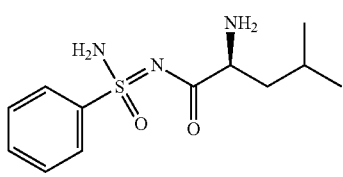 [SMILES: CC(C)C[C@H](N)C(=O)N=S(N)(=O)c1ccccc1]

is intended to encompass both diastereomers:

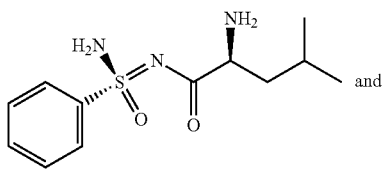

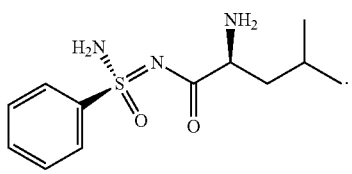

Note that, depending upon the identity of —$R^{N1}$ and —$R^{N2}$, tautomerism of the sulfonimidamide linkage is possible, as shown below. Primarily, the compounds are depicted herein in one tautomeric form. However, unless otherwise stated, a reference to a compound or compounds with one tautomeric form is intended to be encompass both tautomeric forms.

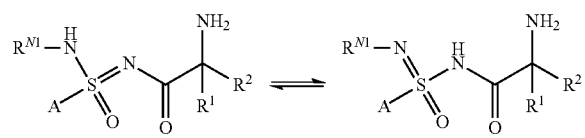

Note that, in principle, stereoisomerism (e.g., cis, trans, E, Z) about the S=N double bond is possible, for example, as shown below. Primarily, the compounds are depicted herein in one configuration. However, unless otherwise stated, a reference to a compound or compounds with one configuration is intended to encompass both configurations.

The Group -A (2) A compound according to (1), wherein -A is -$A^C$.

(3) A compound according to (1), wherein -A is -$A^H$.

The Group -$A^C$ (4) A compound according to any one of (1) to (3), wherein -$A^C$, if present, is phenyl or naphthyl, and is optionally substituted with 1, 2, or 3 substituents —$R^X$.

(5) A compound according to any one of (1) to (3), wherein -$A^C$, if present, is phenyl, and is optionally substituted with one or more substituents —$R^X$.

(6) A compound according to any one of (1) to (3), wherein -$A^C$, if present, is phenyl, and is optionally substituted with 1, 2, or 3 substituents —$R^X$.

(7) A compound according to any one of (1) to (3), wherein -$A^C$, if present, is independently selected from:

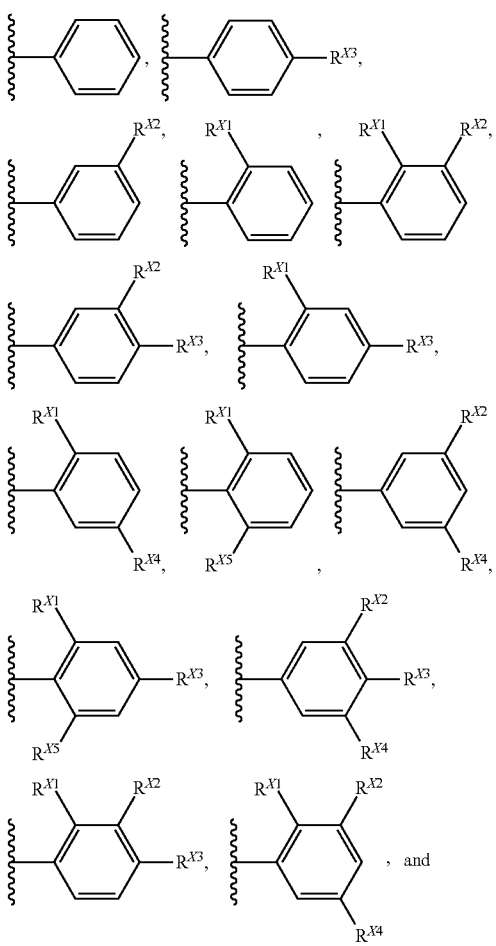

-continued

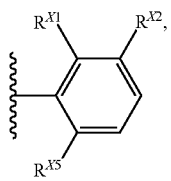

wherein each —R$^{X1}$, —R$^{X2}$, —R$^{X3}$, —R$^{X4}$, and —R$^{X5}$, is independently as defined for —R$^X$.

(8) A compound according to any one of (1) to (3), wherein -A$^C$, if present, is independently selected from:

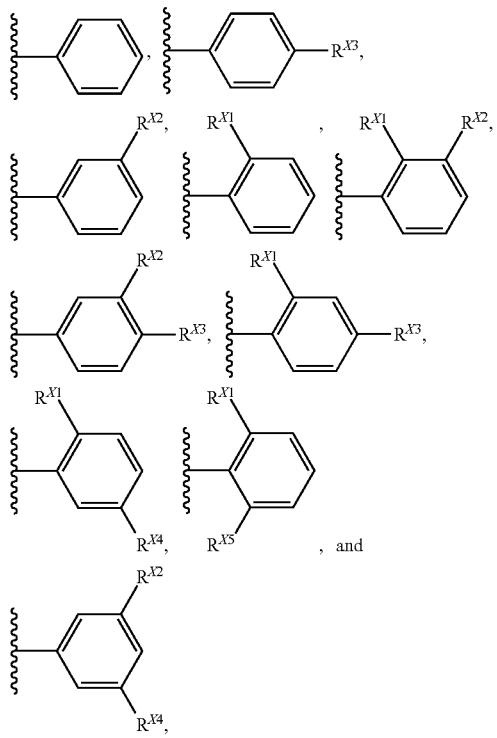

wherein each —R$^{X1}$, —R$^{X2}$, —R$^{X3}$, —R$^{X4}$, and —R$^{X5}$ is independently as defined for —R$^X$.

(9) A compound according to any one of (1) to (3), wherein -A$^C$, if present, is independently selected from:

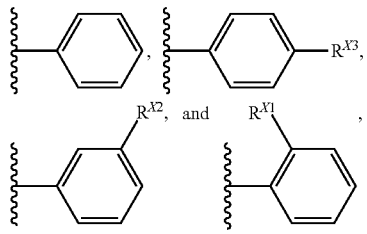

wherein each —R$^{X1}$, —R$^{X2}$, and —R$^{X3}$ is independently as defined for —R$^X$.

(10) A compound according to any one of (1) to (3), wherein -A$^C$, if present, is independently selected from:

wherein each —R$^{X1}$, —R$^{X2}$, and —R$^{X3}$ is independently as defined for —R$^X$.

(11) A compound according to any one of (1) to (3), wherein -A$^C$, if present, is:

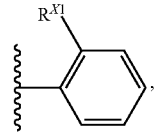

wherein —R$^{X1}$ is independently as defined for —R$^X$.

(12) A compound according to any one of (1) to (3), wherein -A$^C$, if present, is:

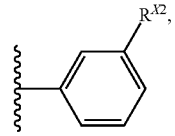

wherein —R$^{X2}$ is independently as defined for —R$^X$.

(13) A compound according to any one of (1) to (3), wherein -A$^C$, if present, is:

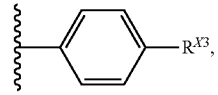

wherein —R$^{X3}$ is independently as defined for —R$^X$.

(14) A compound according to any one of (1) to (3), wherein -A$^C$, if present, is phenyl.

(15) A compound according to any one of (1) to (3), wherein -A$^C$, if present, is naphthyl, and is optionally substituted with one or more substituents —R$^X$.

(16) A compound according to any one of (1) to (3), wherein -A$^C$, if present, is naphthyl, and is optionally substituted with 1, 2, or 3 substituents —R$^X$.

(17) A compound according to any one of (1) to (3), wherein -A$^C$, if present, is naphthyl.

(18) A compound according to any one of (1) to (3), wherein -A$^C$, if present, is naphth-1-yl, and is optionally substituted with one or more substituents —R$^X$.

(19) A compound according to any one of (1) to (3), wherein -A$^C$, if present, is naphth-2-yl, and is optionally substituted with one or more substituents —R$^X$.

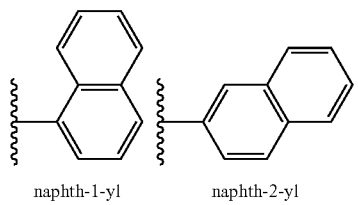

naphth-1-yl    naphth-2-yl

(20) A compound according to any one of (1) to (3), wherein -$A^C$, if present, is naphth-1-yl.

(21) A compound according to any one of (1) to (3), wherein -$A^C$, if present, is naphth-2-yl.

The Group -$A^H$

(22) A compound according to any one of (1) to (21), wherein -$A^H$, if present, is $C_{5-10}$heteroaryl, and is optionally substituted with one or more substituents —$R^X$.

(23) A compound according to any one of (1) to (21), wherein -$A^H$, if present, is $C_{5-10}$heteroaryl, and is optionally substituted with 1, 2, or 3 substituents —$R^X$.

(24) A compound according to any one of (1) to (21), wherein -$A^H$, if present, is $C_{5-6}$heteroaryl or $C_{5-10}$heteroaryl, and is optionally substituted with one or more substituents —$R^X$.

(25) A compound according to any one of (1) to (21), wherein -$A^H$, if present, is furanyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, indolyl, benzimidazolyl, indazolyl, benzofuranyl, benzothienyl, benzooxazolyl, benzoisoxazolyl, benzothiazolyl, benzoisothiazolyl, thienylpyridinyl, thienylthiophenyl, quinolinyl, isoquinolinyl, cinnolinyl, quinazolinyl, quinoxalinyl, phthalazinyl, or benzopyranyl, and is optionally substituted with one or more substituents —$R^X$.

(26) A compound according to any one of (1) to (21), wherein -$A^H$, if present, is furanyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, indolyl, benzimidazolyl, indazolyl, benzofuranyl, benzothienyl, benzooxazolyl, benzoisoxazolyl, benzothiazolyl, benzoisothiazolyl, quinolinyl, isoquinolinyl, cinnolinyl, quinazolinyl, quinoxalinyl, phthalazinyl, or benzopyranyl, and is optionally substituted with one or more substituents —$R^X$.

Monocyclic Groups:

(27) A compound according to any one of (1) to (21), wherein -$A^H$, if present, is furanyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, and is optionally substituted with one or more substituents —$R^X$.

(28) A compound according to any one of (1) to (21), wherein -$A^H$, if present, is pyridyl, pyridazinyl, pyrimidinyl, or pyrazinyl, and is optionally substituted with one or more substituents —$R^X$.

(29) A compound according to any one of (1) to (21), wherein -$A^H$, if present, is pyridyl, thienyl, or thiazolyl, and is optionally substituted with one or more substituents —$R^X$.

(30) A compound according to any one of (1) to (21), wherein -$A^H$, if present, is thienyl, and is optionally substituted with one or more substituents —$R^X$.

(31) A compound according to any one of (1) to (21), wherein -$A^H$, if present, is independently selected from:

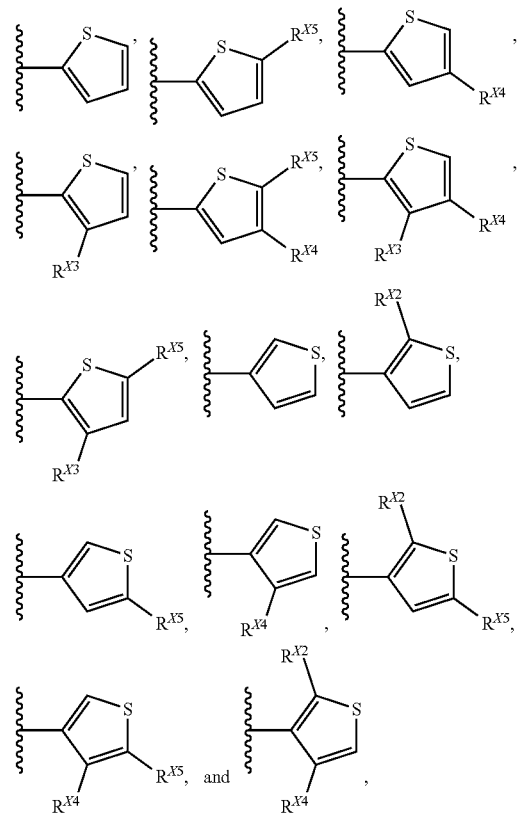

wherein each —$R^{X2}$, —$R^{X3}$, —$R^{X4}$, and —$R^{X5}$ is independently as defined for —$R^X$.

(32) A compound according to any one of (1) to (21), wherein -$A^H$, if present, is independently selected from:

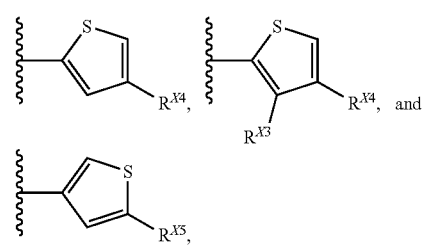

wherein each —$R^{X3}$, —$R^{X4}$, and —$R^{X5}$ is independently as defined for —$R^X$.

(33) A compound according to any one of (1) to (21), wherein -$A^H$, if present, is independently selected from:

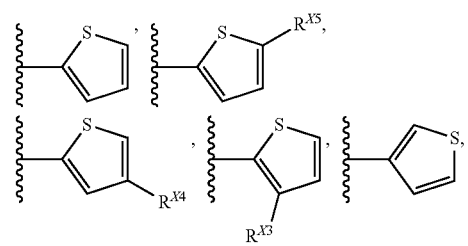

-continued

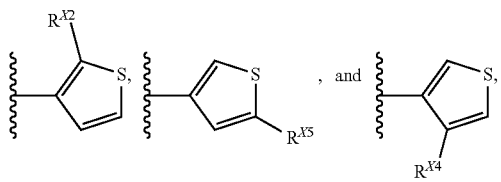

wherein each —$R^{X2}$, —$R^{X3}$, —$R^{X4}$, and —$R^{X5}$ is independently as defined for —$R^X$.

(34) A compound according to any one of (1) to (21), wherein -$A^H$, if present, is thien-2-yl, and is optionally substituted with one or more substituents —$R^X$.

(35) A compound according to any one of (1) to (21), wherein -$A^H$, if present, is independently selected from:

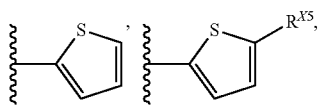

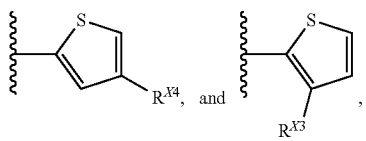

wherein each —$R^{X3}$, —$R^{X4}$, and —$R^{X5}$ is independently as defined for —$R^X$.

(36) A compound according to any one of (1) to (21), wherein -$A^H$, if present, is independently selected from:

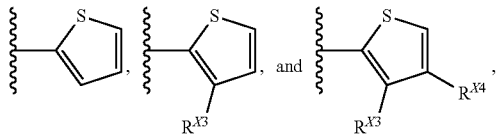

wherein each —$R^{X3}$ and —$R^{X4}$ is independently as defined for —$R^X$.

(37) A compound according to any one of (1) to (21), wherein -$A^H$, if present, is independently selected from:

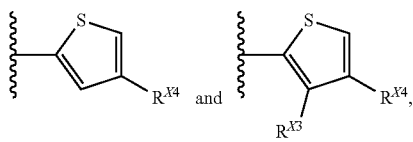

wherein each —$R^{X3}$ and —$R^{X4}$ is independently as defined for —$R^X$.

(38) A compound according to any one of (1) to (21), wherein -$A^H$, if present, is thien-3-yl, and is optionally substituted with one or more substituents —$R^X$.

(39) A compound according to any one of (1) to (21), wherein -$A^H$, if present, is independently selected from:

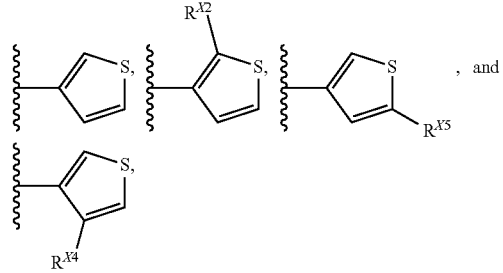

wherein each —$R^{X2}$, —$R^{X4}$, and —$R^{X5}$ is independently as defined for —$R^X$.

(40) A compound according to any one of (1) to (21), wherein -$A^H$, if present, is:

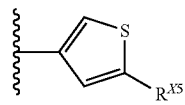

wherein —$R^{X5}$ is as defined for —$R^X$.

(41) A compound according to any one of (1) to (21), wherein -$A^H$, if present, is thiazolyl, and is optionally substituted with one or more substituents —$R^X$.

(42) A compound according to any one of (1) to (21), wherein -$A^H$, if present, is independently selected from:

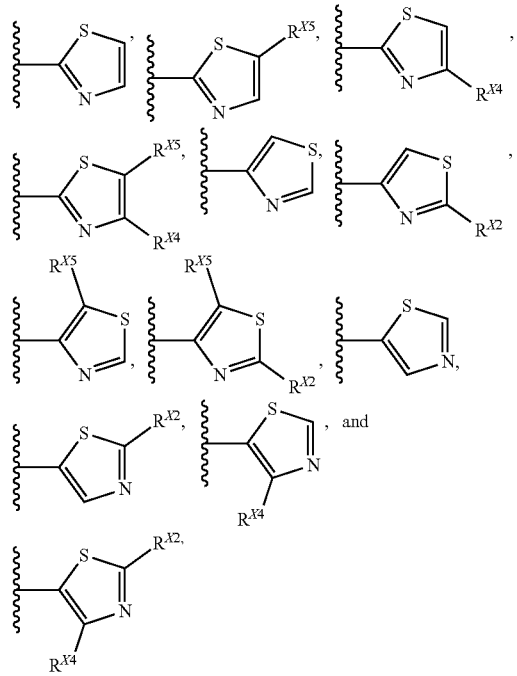

wherein each —$R^{X2}$, —$R^{X4}$, and —$R^{X5}$ is independently as defined for —$R^X$.

(43) A compound according to any one of (1) to (21), wherein -$A^H$, if present, is thiazol-2-yl, and is optionally substituted with one or more substituents —$R^X$.

(44) A compound according to any one of (1) to (21), wherein -$A^H$, if present, is independently selected from:

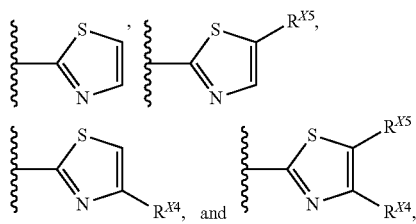

wherein each —R$^{X4}$ and —R$^{X5}$ are independently as defined for —R$^X$.

(45) A compound according to any one of (1) to (21), wherein -A$^H$, if present, is thiazol-4-yl, and is optionally substituted with one or more substituents —R$^X$.

(46) A compound according to any one of (1) to (21), wherein -A$^H$, if present, is independently selected from:

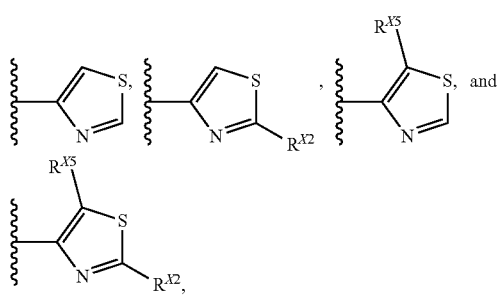

wherein each —R$^{X2}$ and —R$^{X5}$ are independently as defined for —R$^X$.

(47) A compound according to any one of (1) to (21), wherein -A$^H$, if present, is thiazol-5-yl, and is optionally substituted with one or more substituents —R$^X$.

(48) A compound according to any one of (1) to (21), wherein -A$^H$, if present, is independently selected from:

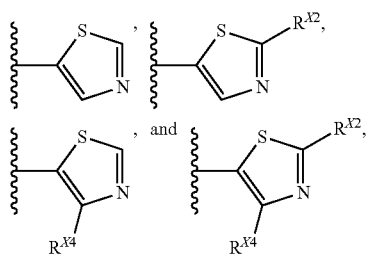

wherein each —R$^{X2}$ and —R$^{X4}$ are independently as defined for —R$^X$.

(49) A compound according to any one of (1) to (21), wherein -A$^H$, if present, is independently pyrazolyl or imidazolyl, and is optionally substituted with one or more substituents —R$^X$.

(50) A compound according to any one of (1) to (21), wherein -A$^H$, if present, is pyrazolyl, and is optionally substituted with one or more substituents —R$^X$.

(51) A compound according to any one of (1) to (21), wherein -A$^H$, if present, is independently 1H-pyrazol-3-yl, 1H-pyrazol-4-yl, 1H-pyrazol-5-yl, or pyrazol-1-yl, and is optionally substituted with one or more substituents —R$^X$.

(52) A compound according to any one of (1) to (21), wherein -A$^H$, if present, is 1H-pyrazol-3-yl, and is optionally substituted with one or more substituents —R$^X$.

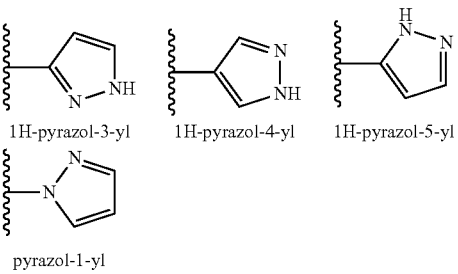

(53) A compound according to any one of (1) to (21), wherein -A$^H$, if present, is imidazolyl, and is optionally substituted with one or more substituents —R$^X$.

(54) A compound according to any one of (1) to (21), wherein -A$^H$, if present, is independently 1H-imidazol-2-yl, 1H-imidazol-5-yl, 1H-imidazol-4-yl, or imidazol-1-yl, and is optionally substituted with one or more substituents —R$^X$.

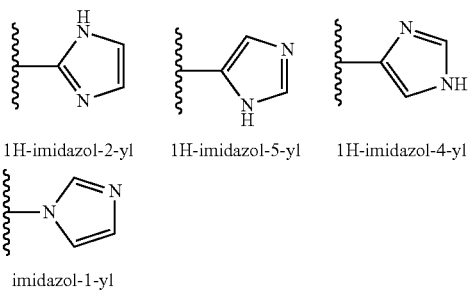

(55) A compound according to any one of (1) to (21), wherein -A$^H$, if present, is pyridyl, and is optionally substituted with one or more substituents —R$^X$.

(56) A compound according to any one of (1) to (21), wherein -A$^H$, if present, is pyrid-2-yl, and is optionally substituted with one or more substituents —R$^X$.

(57) A compound according to any one of (1) to (21), wherein -A$^H$, if present, is pyrid-3-yl, and is optionally substituted with one or more substituents —R$^X$.

(58) A compound according to any one of (1) to (21), wherein -A$^H$, if present, is pyrid-4-yl, and is optionally substituted with one or more substituents —R$^X$.

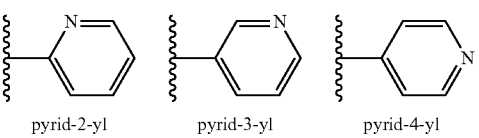

Fused Bicyclic Groups:

(59) A compound according to any one of (1) to (21), wherein -A$^H$, if present, is indolyl, benzimidazolyl, indazolyl, benzofuranyl, benzothienyl, benzooxazolyl, benzoisoxazolyl, benzothiazolyl, benzoisothiazolyl, thienylpyridinyl, thienylthiophenyl, quinolinyl, isoquinolinyl, cinnolinyl, quinazolinyl, quinoxalinyl, phthalazinyl, or benzopyranyl, and is optionally substituted with one or more substituents —R$^X$.

(60) A compound according to any one of (1) to (21), wherein -A$^H$, if present, is indolyl, benzimidazolyl, indazolyl, benzofuranyl, benzothienyl, benzooxazolyl, benzoisoxazolyl, benzothiazolyl, benzoisothiazolyl, quinolinyl, isoquinolinyl, cinnolinyl, quinazolinyl, quinoxalinyl, phthalazinyl, or benzopyranyl, and is optionally substituted with one or more substituents —$R^X$.

(61) A compound according to any one of (1) to (21), wherein -$A^H$, if present, is indolyl, benzimidazolyl, indazolyl, benzofuranyl, benzothienyl, quinolinyl, isoquinolinyl, quinazolinyl, or quinoxalinyl, and is optionally substituted with one or more substituents —$R^X$.

(62) A compound according to any one of (1) to (21), wherein -$A^H$, if present, is benzofuranyl, benzothienyl, quinolinyl, or isoquinolinyl, and is optionally substituted with one or more substituents —$R^X$.

(63) A compound according to any one of (1) to (21), wherein -$A^H$, if present, is benzofuranyl or benzothienyl, and is optionally substituted with one or more substituents —$R^X$.

(64) A compound according to any one of (1) to (21), wherein -$A^H$, if present, is benzothienyl, and is optionally substituted with one or more substituents —$R^X$.

(65) A compound according to any one of (1) to (21), wherein -$A^H$, if present, is benzothien-2-yl, and is optionally substituted with one or more substituents —$R^X$.

(66) A compound according to any one of (1) to (21), wherein -$A^H$, if present, is benzothien-3-yl, and is optionally substituted with one or more substituents —$R^X$.

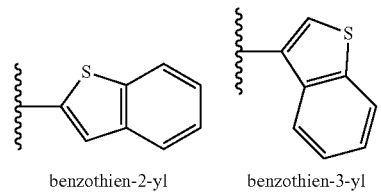

benzothien-2-yl     benzothien-3-yl

(67) A compound according to any one of (1) to (21), wherein -$A^H$, if present, is benzothiazolyl, and is optionally substituted with one or more substituents —$R^X$.

(68) A compound according to any one of (1) to (21), wherein -$A^H$, if present, is 1,2-benzothiazol-3-yl, and is optionally substituted with one or more substituents —$R^X$.

(69) A compound according to any one of (1) to (21), wherein -$A^H$, if present, is 1,3-benzothiazol-2-yl, and is optionally substituted with one or more substituents —$R^X$.

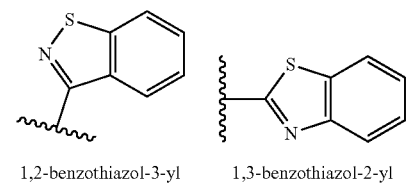

1,2-benzothiazol-3-yl     1,3-benzothiazol-2-yl

(70) A compound according to any one of (1) to (21), wherein -$A^H$, if present, is thienopyridinyl, and is optionally substituted with one or more substituents —$R^X$.

(71) A compound according to any one of (1) to (21), wherein -$A^H$, if present, is thieno[3,2-b]pyridinyl, and is optionally substituted with one or more substituents —$R^X$.

(72) A compound according to any one of (1) to (21), wherein -$A^H$, if present, is thieno[3,2-b]pyridin-2-yl, and is optionally substituted with one or more substituents —$R^X$.

(73) A compound according to any one of (1) to (21), wherein -$A^H$, if present, is thieno[3,2-b]pyridin-3-yl, and is optionally substituted with one or more substituents —$R^X$.

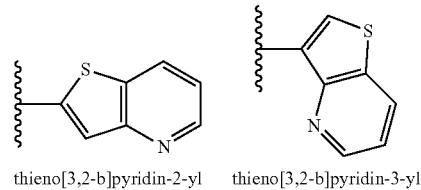 [SMILES: *c1cc2ncccc2s1 ; *c1csc2cccnc12]

thieno[3,2-b]pyridin-2-yl     thieno[3,2-b]pyridin-3-yl

(74) A compound according to any one of (1) to (21), wherein -$A^H$, if present, is thienothiophenyl, and is optionally substituted with one or more substituents —$R^X$.

(75) A compound according to any one of (1) to (21), wherein -$A^H$, if present, is thieno[3,2-b]thiophenyl, and is optionally substituted with one or more substituents —$R^X$.

(76) A compound according to any one of (1) to (21), wherein -$A^H$, if present, is thieno[3,2-b]thiophen-5-yl, and is optionally substituted with one or more substituents —$R^X$.

(77) A compound according to any one of (1) to (21), wherein -$A^H$, if present, is thieno[3,2-b]thiophen-6-yl, and is optionally substituted with one or more substituents —$R^X$.

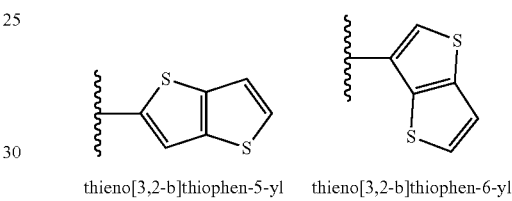

thieno[3,2-b]thiophen-5-yl     thieno[3,2-b]thiophen-6-yl

(78) A compound according to any one of (1) to (21), wherein -$A^H$, if present, is quinolinyl or isoquinolinyl, and is optionally substituted with one or more substituents —$R^X$.

(79) A compound according to any one of (1) to (21), wherein -$A^H$, if present, is quinolinyl, and is optionally substituted with one or more substituents —$R^X$.

(80) A compound according to any one of (1) to (21), wherein -$A^H$, if present, is quinolin-7-yl, and is optionally substituted with one or more substituents —$R^X$.

The Group(s) —$R^X$.

(81) A compound according to any one of (1) to (80), wherein each —$R^X$, if present, is independently selected from:

—$R^{XX}$
—F, —Cl, —Br, —I,
—OH, —$OR^{XX}$,
-$L^{XX}$-OH, -$L^{XX}$-$OR^{XX}$,
—$CF_3$, —$CHF_2$, —$OCF_3$, —$OCHF_2$,
—$NH_2$, —$NHR^{XX}$, —$NR^{XX}_2$, —$R^{XM}$
-$L^{XX}$-$NH_2$, -$L^{XX}$-$NHR^{XX}$, -$L^{XX}$-$NR^{XX}_2$, -$L^{XX}$-$R^{XM}$,
—C(=O)OH, —C(=O)$OR^{XX}$, —OC(=O)$R^X$,
—C(=O)$NH_2$, —C(=O)$NHR^{XX}$, —C(=O)$NR^{XX}_2$,
—C(=O)$R^{XM}$
—NHC(=O)$R^{XX}$, —$NR^{XN}$C(=O)$R^{XX}$
—NHC(=O)$NH_2$, —NHC(=O)$NHR^{XX}$, —NHC(=O)$NR^{XX}_2$, —NHC(=O)$R^{XM}$
—$NR^{XN}$C(=O)$NH_2$, —$NR^{XN}$C(=O)$NHR^{XX}$, —$NR^{XN}$C(=O)$NR^{XX}_2$, —$NR^{XN}$C(=O)$R^{XM}$,
—NHC(=O)$OR^{XX}$, —$NR^{XN}$C(=O)$OR^{XX}$
—OC(=O)$NH_2$, —OC(=O)$NHR^{XX}$, —OC(=O)$NR^{XX}_2$, —OC(=O)$R^{XM}$
—NHC(=NH)$NH_2$,
—C(=O)$R^{XX}$,

—S(=O)NH$_2$, —S(=O)NHR$^{XX}$, —S(=O)NR$^{XX}$$_2$,
—S(=O)R$^{XM}$
—S(=O)$_2$NH$_2$, —S(=O)$_2$NHR$^{XX}$, —S(=O)$_2$NR$^{XX}$$_2$,
—S(=O)$_2$R$^{XM}$
—NHS(=O)R$^{XX}$, —NR$^{XN}$S(=O)R$^{XX}$,
—NHS(=O)$_2$R$^{XX}$, —NR$^{XN}$S(=O)$_2$R$^{XX}$
—S(=O)R$^{XX}$, —S(=O)$_2$R$^{XX}$,
—SH, —SR$^{XX}$, —CN, and —NO$_2$;
and additionally, two adjacent groups —R$^X$, if present, may together form:
—O—CH$_2$—O—, —O—CH$_2$CH$_2$—O—, —CH$_2$—CH$_2$—O—, —CH$_2$—CH$_2$CH$_2$—O—, —CH$_2$—O—CH$_2$—, or —CH$_2$—CH$_2$—O—CH$_2$—.

(82) A compound according to any one of (1) to (80), wherein each —R$^X$, if present, is independently selected from:
—R$^{XX}$, —R$^{XXU}$, —R$^{XXV}$
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}$$_2$, —R$^{XM}$,
—C(=O)OH, —C(=O)OR$^{XX}$, —OC(=O)R$^X$,
—C(=O)NH$_2$, —C(=O)NHR$^{XX}$, —C(=O)NR$^{XX}$$_2$,
—C(=O)R$^{XM}$
—NHC(=O)R$^{XX}$, —NR$^{XN}$C(=O)R$^{XX}$
—C(=O)R$^{XX}$,
—S(=O)NH$_2$, —S(=O)NHR$^{XX}$, —S(=O)NR$^{XX}$$_2$,
—S(=O)R$^{XM}$
—S(=O)$_2$NH$_2$, —S(=O)$_2$NHR$^{XX}$, —S(=O)$_2$NR$^{XX}$$_2$,
—S(=O)$_2$R$^{XM}$
—NHS(=O)R$^{XX}$, —NR$^{XN}$S(=O)R$^{XX}$
—NHS(=O)$_2$R$^{XX}$, —NR$^{XN}$S(=O)$_2$R$^{XX}$,
—S(=O)R$^{XX}$, —S(=O)$_2$R$^{XX}$,
—SR$^{XX}$, —CN, and —NO$_2$.

(83) A compound according to any one of (1) to (80), wherein each —R$^X$, if present, is independently selected from:
—R$^{XX}$
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}$$_2$, —R$^{XM}$,
—C(=O)OH, —C(=O)OR$^{XX}$, —OC(=O)R$^X$,
—C(=O)NH$_2$, —C(=O)NHR$^{XX}$, —C(=O)NR$^{XX}$$_2$,
—C(=O)R$^{XM}$
—NHC(=O)R$^{XX}$, —NR$^{XN}$C(=O)R$^{XX}$
—C(=O)R$^{XX}$,
—S(=O)NH$_2$, —S(=O)NHR$^{XX}$, —S(=O)NR$^{XX}$$_2$,
—S(=O)R$^{XM}$
—S(=O)$_2$NH$_2$, —S(=O)$_2$NHR$^{XX}$, —S(=O)$_2$NR$^{XX}$$_2$,
—S(=O)$_2$R$^{XM}$
—NHS(=O)R$^{XX}$, —NR$^{XN}$S(=O)R$^{XX}$
—NHS(=O)$_2$R$^{XX}$, —NR$^{XN}$S(=O)$_2$R$^{XX}$
—S(=O)R$^{XX}$, —S(=O)$_2$R$^{XX}$,
—SR$^{XX}$, —CN, and —NO$_2$.

(84) A compound according to any one of (1) to (80), wherein each —R$^X$, if present, is independently selected from:
—R$^{XX}$, —R$^{XXU}$, —R$^{XX}$
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}$$_2$, —R$^{XM}$,
—C(=O)OH, —C(=O)OR$^{XX}$, —OC(=O)R$^X$,
—SR$^{XX}$, —CN, and —NO$_2$.

(85) A compound according to any one of (1) to (80), wherein each —R$^X$, if present, is independently selected from:
—R$^{XX}$, —R$^{XXU}$
—F, —Cl, —Br,
—OH, —OR$^{XX}$,
—CF$_3$, —CHF$_2$, —OCF$_3$, —OCHF$_2$,
—C(=O)NH$_2$, —C(=O)NHR$^{XX}$, —C(=O)NR$^{XX}$$_2$,
—C(=O)R$^{XM}$
—C(=O)R$^{XX}$, and
—CN;
and additionally, two adjacent groups —R$^X$, if present, may together form:
—O—CH$_2$—O— or —CH$_2$—CH$_2$—O—.

(86) A compound according to any one of (1) to (80), wherein each —R$^X$, if present, is independently selected from:
—R$^{XX}$
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}$$_2$, —R$^{XM}$, and
—CN.

(87) A compound according to any one of (1) to (80), wherein each —R$^X$, if present, is independently selected from:
—R$^{XX}$
—F, —Cl, —Br, —I,
—OH, —OR$^{XX}$,
—CF$_3$, —CHF$_2$, —OCF$_3$, and —OCHF$_2$.

(88) A compound according to any one of (1) to (80), wherein each —R$^X$, if present, is independently selected from:
—R$^{XX}$
—F, —Cl, —Br, and —I.

(89) A compound according to any one of (1) to (80), wherein each —R$^X$, if present, is independently selected from:
—R$^{XX}$, —F, and —Cl.

The Group -L$^{XX}$-

(90) A compound according to any one of (1) to (89), wherein each -L$^{XX}$-, if present, is independently —CH$_2$CH$_2$CH$_2$—, —CH$_2$CH$_2$—, —CH(CH$_3$)CH$_2$—, —CH(CH$_3$)—, or —CH$_2$—.

(91) A compound according to any one of (1) to (89), wherein each -L$^{XX}$-, if present, is independently —CH$_2$CH$_2$— or —CH$_2$—.

(92) A compound according to any one of (1) to (89), wherein each -L$^{XX}$-, if present, is —CH$_2$—.

The Group —R$^{XX}$

(93) A compound according to any one of (1) to (92), wherein each —R$^{XX}$, if present, is independently linear or branched saturated C$_{1-4}$alkyl, phenyl, or —CH$_2$-phenyl.

(94) A compound according to any one of (1) to (92), wherein each —R$^{XX}$, if present, is linear or branched saturated C$_{1-4}$alkyl.

(95) A compound according to any one of (1) to (92), wherein each —R$^{XX}$, if present, is -Me.

The Group —R$^{XXU}$

(96) A compound according to any one of (1) to (95), wherein each —R$^{XXU}$, if present, is independently —CH=CH$_2$ or —CH$_2$—CH=CH$_2$.

(97) A compound according to any one of (1) to (95), wherein each —R$^{XXU}$, if present, is —CH=CH$_2$.

The Group —$R^{XXV}$

(98) A compound according to any one of (1) to (97), wherein each —$R^{XXV}$, if present, is independently —CH≡CH or —CH$_2$—C≡CH.

(99) A compound according to any one of (1) to (97), wherein each —$R^{XXV}$, if present, is —CH≡CH.

The Group —$R^{XN}$ (100) A compound according to any one of (1) to (99), wherein each —$R^{XN}$, if present, is independently -Me, -Et, -nPr, or -iPr.

(101) A compound according to any one of (1) to (99), wherein each —$R^{XN}$, if present, is -Me.

The Group —$R^{XM}$ (102) A compound according to any one of (1) to (101), wherein each —$R^{XM}$, if present, is independently pyrrolidino, piperidino, piperazino, or morpholino, and is:
  optionally substituted with one or more groups selected from:
  —$R^{XMM}$, —C(=O)$R^{XMM}$, —C(=O)O$R^{XMM}$ and —S(=O)$_2 R^{XMM}$.

(103) A compound according to any one of (1) to (101), wherein each —$R^{XM}$, if present, is independently pyrrolidino, piperidino, piperazino, or morpholino.

The Group —$R^{XMM}$ (104) A compound according to any one of (1) to (103), wherein each —$R^{XMM}$ if present, is independently linear or branched saturated $C_{1-4}$alkyl, phenyl, or —CH$_2$-phenyl.

(105) A compound according to any one of (1) to (103), wherein each —$R^{XMM}$ if present, is linear or branched saturated $C_{1-4}$alkyl.

(106) A compound according to any one of (1) to (103), wherein each —$R^{XMM}$ if present, is -Me.

The Group —$R^1$ (107) A compound according to any one of (1) to (106), wherein —$R^1$ is —$R^{11}$.

(108) A compound according to any one of (1) to (106), wherein —$R^1$ is —H.

The Group —$R^{11}$ (109) A compound according to any one of (1) to (108), wherein —$R^{11}$, if present, is —$R^{11A}$.

(110) A compound according to any one of (1) to (108), wherein —$R^{11}$, if present, is —$R^{11B}$.

The Group —$R^{11A}$ (111) A compound according to any one of (1) to (110), wherein —$R^{11A}$, if present, is independently —$R^{41}$, —$R^{44}$, -$L^A$, —$R^{42}$, -$L^A$, —$R^{44}$, or -$L^A$, —$R^{45}$.

(112) A compound according to any one of (1) to (110), wherein —$R^{11A}$, if present, is independently —$R^{41}$, -$L^A$, —$R^{42}$, -$L^A$, —$R^{44}$, or -$L^A$, —$R^{45}$.

(113) A compound according to any one of (1) to (110), wherein —$R^{11A}$, if present, is independently —$R^{41}$ or -$L^A$, —$R^{42}$.

(114) A compound according to any one of (1) to (110), wherein —$R^{11A}$, if present, is $R^{41}$.

(115) A compound according to any one of (1) to (110), wherein —$R^{11A}$, if present, is -$L^A$-$R^{42}$.

(116) A compound according to any one of (1) to (110), wherein —$R^{11A}$, if present, is -$L^A$-$R^{44}$.

(117) A compound according to any one of (1) to (110), wherein —$R^{11A}$, if present, is -$L^A$-$R^{45}$.

The Group —$R^{41}$ (118) A compound according to any one of (1) to (117), wherein each —$R^{41}$, if present, is independently -Me, -Et, -nPr, -iPr, -nBu, -iBu, -sBu, or -tBu; and is optionally substituted with one or more groups —$R^{AA2}$.

(119) A compound according to any one of (1) to (117), wherein each —$R^{41}$, if present, is -iBu; and is optionally substituted with one or more groups —$R^{AA2}$.

(120) A compound according to any one of (1) to (117), wherein each —$R^{41}$, if present, is -sBu; and is optionally substituted with one or more groups —$R^{AA2}$.

(121) A compound according to any one of (1) to (117), wherein each —$R^{41}$, if present, is -iPr; and is optionally substituted with one or more groups —$R^{AA2}$.

(122) A compound according to any one of (1) to (117), wherein each —$R^{41}$, if present, is -Me; and is optionally substituted with one or more groups —$R^{AA2}$.

(123) A compound according to any one of (1) to (117), wherein each —$R^{41}$, if present, is independently -Me, -Et, -nPr, -iPr, -nBu, -iBu, -sBu, or -tBu.

(124) A compound according to any one of (1) to (117), wherein each —$R^{41}$, if present, is independently -iPr, -iBu, or -sBu.

(125) A compound according to any one of (1) to (117), wherein each —$R^{41}$, if present, is -iBu.

(126) A compound according to any one of (1) to (117), wherein each —$R^{41}$, if present, is -sBu.

(127) A compound according to any one of (1) to (117), wherein each —$R^{41}$, if present, is -iPr.

(128) A compound according to any one of (1) to (117), wherein each —$R^{41}$, if present, is -Me.

The Group —$R^{42}$ (129) A compound according to any one of (1) to (128), wherein each —$R^{42}$, if present, is independently cyclopropyl, cyclobutyl, cyclopentyl, or cyclohexyl, and is optionally substituted with one or more groups —$R^{AA1}$ and one or more groups —$R^{AA2}$.

(1304) A compound according to any one of (1) to (128), wherein each —$R^{42}$, if present, is independently cyclopropyl, cyclobutyl, cyclopentyl, or cyclohexyl.

(131) A compound according to any one of (1) to (128), wherein each —$R^{42}$, if present, is independently cyclopropyl.

The Group —$R^{43}$ (132) A compound according to any one of (1) to (131), wherein each —$R^{43}$, if present, is independently oxetanyl, tetrahydrofuranyl, tetrahydropyranyl, dioxanyl, azetidinyl, pyrrolidinyl, piperidinyl, piperazinyl, morpholinyl, azepanyl, or diazepanyl, and is optionally substituted with one or more groups —$R^{AA1}$ and one or more groups —$R^{AA2}$.

(133) A compound according to any one of (1) to (131), wherein each —$R^{43}$, if present, is independently tetrahydrofuranyl, tetrahydropyranyl, dioxanyl, pyrrolidinyl, piperidinyl, piperazinyl, or morpholinyl, and is optionally substituted with one or more groups —$R^{AA1}$ and one or more groups —$R^{AA2}$.

(134) A compound according to any one of (1) to (131), wherein each —$R^{43}$, if present, is independently tetrahydrofuranyl, tetrahydropyranyl, or dioxanyl, and is optionally substituted with one or more groups —$R^{AA1}$ and one or more groups —$R^{AA2}$.

(135) A compound according to any one of (1) to (131), wherein each —$R^{43}$, if present, is independently pyrrolidinyl, piperidinyl, piperazinyl, or morpholinyl, and is optionally substituted with one or more groups —$R^{AA1}$ and one or more groups —$R^{AA2}$.

(136) A compound according to any one of (1) to (131), wherein each —$R^{43}$, if present, is independently tetrahydrofuranyl, tetrahydropyranyl, dioxanyl, pyrrolidinyl, piperidinyl, piperazinyl, or morpholinyl.

(137) A compound according to any one of (1) to (131), wherein each —$R^{43}$, if present, is independently tetrahydrofuranyl, tetrahydropyranyl, or dioxanyl.

(138) A compound according to any one of (1) to (131), wherein each —$R^{A3}$, if present, is independently pyrrolidinyl, piperidinyl, piperazinyl, or morpholinyl.

The Group —$R^{A4}$ (139) A compound according to any one of (1) to (138), wherein each —$R^{A4}$, if present, is phenyl, and is optionally substituted with one or more groups —$R^{AA1}$ and one or more groups —$R^{AA2}$.

(140) A compound according to any one of (1) to (138), wherein each —$R^{A4}$, if present, is phenyl.

The Group —$R^{A5}$ (141) A compound according to any one of (1) to (140), wherein each —$R^{A5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, pyrazinyl, indolyl, benzoimidazolyl, indazolyl, benzofuranyl, benzothienyl, benzooxazolyl, benzothiazolyl, benzoisoxazolyl, benzoisothiazolyl, quinolinyl, isoquinolinyl, cinnolinyl, quinoxalinyl, quinazolinyl, or phthalazinyl, and is optionally substituted with one or more groups —$R^{AA1}$ and one or more groups —$R^{AA2}$.

(142) A compound according to any one of (1) to (140), wherein each —$R^{A5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl, and is optionally substituted with one or more groups —$R^{AA1}$ and one or more groups —$R^{AA2}$.

(143) A compound according to any one of (1) to (140), wherein each —$R^{A5}$, if present, is independently furanyl, thienyl, pyrrolyl, imidazolyl, oxazolyl, thiazolyl, pyrazolyl, isoxazolyl, or isothiazolyl, and is optionally substituted with one or more groups —$R^{AA1}$ and one or more groups —$R^{AA2}$.

(144) A compound according to any one of (1) to (140), wherein each —$R^{A5}$, if present, is independently pyridyl, pyridazinyl, pyrimidinyl, or pyrazinyl, and is optionally substituted with one or more groups —$R^{AA1}$ and one or more groups —$R^{AA2}$.

(145) A compound according to any one of (1) to (140), wherein each —$R^{A5}$, if present, is independently imidazolyl or indolyl, and is optionally substituted with one or more groups —$R^{AA1}$ and one or more groups —$R^{AA2}$.

(146) A compound according to any one of (1) to (140), wherein each —$R^{A5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl.

(147) A compound according to any one of (1) to (140), wherein each —$R^{A5}$, if present, is independently furanyl, thienyl, pyrrolyl, imidazolyl, oxazolyl, thiazolyl, pyrazolyl, isoxazolyl, or isothiazolyl.

(148) A compound according to any one of (1) to (140), wherein each —$R^{A5}$, if present, is independently pyridyl, pyridazinyl, pyrimidinyl, or pyrazinyl.

(149) A compound according to any one of (1) to (140), wherein each —$R^{A5}$, if present, is independently imidazolyl or indolyl.

The Group -$L^A$-

(150) A compound according to any one of (1) to (149), wherein each -$L^A$-, if present, is independently —$CH_2CH_2CH_2$—, —$CH_2CH_2$—, —$CH(CH_3)CH_2$—, —$CH(CH_3)$—, or —$CH_2$—.

(151) A compound according to any one of (1) to (149), wherein each -$L^A$-, if present, is independently —$CH_2CH_2$— or —$CH_2$—.

(152) A compound according to any one of (1) to (149), wherein each -$L^A$-, if present, is —$CH_2$—.

The Group —$R^{AA1}$ (153) A compound according to any one of (1) to (152), wherein each —$R^{AA1}$, if present, is —$R^{AA}$.

The Group —$R^{AA2}$ (154) A compound according to any one of (1) to (153), wherein each —$R^{AA2}$, if present, is independently selected from:
 —F, —Cl, —Br, —I,
 —OH, —$OR^{AA}$,
 —$OCF_3$,
 —$NH_2$, —$NHR^{AA}$, —$N(R^{AA})_2$, —$R^{AM}$,
 —C(=O)OH, —C(=O)$OR^{AA}$, —OC(=O)$R^{AA}$,
 —C(=O)$NH_2$, —C(=O)$NHR^{AA}$, —C(=O)$N(R^{AA})_2$,
 —C(=O)$R^{AM}$,
 —NHC(=O)$R^{AA}$, —$NR^{AN}$C(=O)$R^{AA}$,
 —C(=O)$R^{AA}$,
 —S(=O)$NH_2$, —S(=O)$NHR^{AA}$, —S(=O)$N(R^{AA})_2$,
 —S(=O)$R^{AM}$,
 —S(=O)$_2NH_2$, —S(=O)$_2NHR^{AA}$, —S(=O)$_2N(R^{AA})_2$,
 —S(=O)$_2R^{AM}$,
 —NHS(=O)$R^{AA}$, —$NR^{AN}$S(=O)$R^{AA}$,
 —NHS(=O)$_2R^{AA}$, —$NR^{AN}$S(=O)$_2R^{AA}$,
 —S(=O)$R^{AA}$, S(=O)$_2R^{AA}$,
 —SH, —$SR^{AA}$, —CN, and —$NO_2$.

(155) A compound according to any one of (1) to (153), wherein each —$R^{AA2}$, if present, is independently selected from:
 —F, —Cl, —Br, —I,
 —OH, —$OR^{AA}$,
 —$OCF_3$,
 —$NH_2$, —$NHR^{AA}$, —$N(R^{AA})_2$, —$R^{AM}$, and
 —CN.

(156) A compound according to any one of (1) to (153), wherein each —$R^{AA2}$, if present, is independently selected from:
 —F, —Cl, —Br, —I,
 —OH, —$OR^{AA}$, and
 —$OCF_3$.

(157) A compound according to any one of (1) to (153), wherein each —$R^{AA2}$, if present, is independently selected from:
 —OH, —$OR^{AA}$,
 —$NH_2$, —$NHR^{AA}$, —$N(R^{AA})_2$, —$R^{AM}$,
 —C(=O)OH, —C(=O)$OR^{AA}$,
 —C(=O)$NH_2$, —C(=O)$NHR^{AA}$, —C(=O)$N(R^{AA})_2$,
 —C(=O)$R^{AM}$,
 —NHC(=NH)$NH_2$,
 —SH, and —$SR^{AA}$.

(158) A compound according to any one of (1) to (153), wherein each —$R^{AA2}$, if present, is independently selected from:
 —OH,
 —$NH_2$,
 —C(=O)OH,
 —C(=O)$NH_2$,
 —NHC(=NH)$NH_2$,
 —SH, and —SMe.

The Group -$L^{AA}$-

(159) A compound according to any one of (1) to (158), wherein each -$L^{AA}$-, if present, is independently —$CH_2CH_2CH_2$—, —$CH_2CH_2$—, —$CH(CH_3)CH_2$—, —$CH(CH_3)$—, or —$CH_2$—.

(160) A compound according to any one of (1) to (158), wherein each -$L^{AA}$-, if present, is independently —$CH_2CH_2$ or —$CH_2$—.

The Group —$R^{AA}$ (161) A compound according to any one of (1) to (160), wherein each —$R^{AA}$, if present, is independently linear or branched saturated $C_{1-4}$alkyl, phenyl, or —$CH_2$-phenyl.

(162) A compound according to any one of (1) to (160), wherein each —$R^{AA}$, if present, is linear or branched saturated $C_{1-4}$alkyl.

(163) A compound according to any one of (1) to (160), wherein each —$R^{AA}$, if present, is -Me.

The Group —$R^{AN}$ (164) A compound according to any one of (1) to (163), wherein each —$R^{AN}$, if present, is independently -Me, -Et, -nPr, or -iPr.

(165) A compound according to any one of (1) to (163), wherein each —$R^{AN}$, if present, is -Me.

The Group —$R^{AM}$ (166) A compound according to any one of (1) to (165), wherein each —$R^{AM}$, if present, is independently pyrrolidino, piperidino, piperazino, or morpholino, and is:
  optionally substituted with one or more groups selected from:
    —$R^{AMM}$, —C(=O)$R^{AMM}$, —C(=O)O$R^{AMM}$, and —S(=O)$_2R^{AMM}$.

(167) A compound according to any one of (1) to (165), wherein each —$R^{AM}$, if present, is independently pyrrolidino, piperidino, piperazino, or morpholino.

The Group —$R^{AMM}$ (168) A compound according to any one of (1) to (167), wherein each —$R^{AMM}$, if present, is independently linear or branched saturated $C_{1-4}$alkyl, phenyl, or —$CH_2$-phenyl.

(169) A compound according to any one of (1) to (167), wherein each —$R^{AMM}$, if present, is linear or branched saturated $C_{1-4}$alkyl.

(170) A compound according to any one of (1) to (167), wherein each —$R^{AMM}$, if present, is -Me.

The Group —$R^{11A}$: Some Specific Groups (171) A compound according to any one of (1) to (110), wherein —$R^{11A}$, if present, is independently selected from:
  —$CH_3$ (e.g., as in alanine),
  —$CH_2CH(CH_3)_2$ (e.g., as in leucine),
  —$CH(CH_3)CH_2CH_3$ (e.g., as in isoleucine),
  —$CH_2CH_2$—S—$CH_3$ (e.g., as in methionine),
  —$CH_2$-(phenyl) (e.g., as in phenylalanine),
  —$CH_2$-(1H-indol-3-yl) (e.g., as in tryptophan),
  —$CH(CH_3)_2$ (e.g., as in valine),
  —$CH_2$—C(=O)$NH_2$ (e.g., as in asparagine),
  —$CH_2$—SH (e.g., as in cysteine),
  —$CH_2CH_2$—C(=O)$NH_2$ (e.g., as in glutamine),
  —$CH_2$—OH (e.g., as in serine),
  —CH(OH)$CH_3$ (e.g., as in threonine),
  —$CH_2$-(4-hydroxy-phenyl) (e.g., as in tyrosine),
  —$CH_2CH_2CH_2$—NH—C(=NH)—$NH_2$ (e.g., as in arginine),
  —$CH_2$-(1H-imidazol-4-yl) (e.g., as in histidine),
  —$CH_2CH_2CH_2CH_2$—$NH_2$ (e.g., as in lysine),
  —$CH_2$—C(=O)OH (e.g., as in aspartic acid), and
  —$CH_2CH_2$—C(=O)OH (e.g., as in glutamic acid).

(172) A compound according to any one of (1) to (110), wherein —$R^{11A}$, if present, is independently selected from:
  —$CH_2CH(CH_3)_2$ (e.g., as in leucine),
  —$CH(CH_3)CH_2CH_3$ (e.g., as in isoleucine),
  —$CH(CH_3)_2$ (e.g., as in valine).

(173) A compound according to any one of (1) to (110), wherein —$R^{11A}$, if present, is —$CH_2CH(CH_3)_2$ (e.g., as in leucine).

(174) A compound according to any one of (1) to (110), wherein —$R^{11A}$, if present, is —$CH(CH_3)CH_2CH_3$ (e.g., as in isoleucine).

(175) A compound according to any one of (1) to (110), wherein —$R^{11A}$, if present, is —$CH(CH_3)_2$ (e.g., as in valine).

The Group —$R^{11B}$ (176) A compound according to any one of (1) to (175), wherein —$R^{11B}$, if present, is independently selected from:
  —F, —Cl, —Br, —I,
  —OH, —O$R^{BB}$,
  —$OCF_3$,
  —$NH_2$, —NH$R^{BB}$, —N$R^{BB}_2$, —$R^{BM}$,
  —C(=O)OH, —C(=O)O$R^{BB}$, —OC(=O)$R^{BB}$,
  —C(=O)$NH_2$, —C(=O)NH$R^{BB}$, —C(=O)N$R^{BB}_2$,
  —C(=O)$R^{BM}$,
  —NHC(=O)$R^{BB}$, —N$R^{BN}$C(=O)$R^{BB}$,
  —C(=O)$R^{BB}$,
  —S(=O)$NH_2$, —S(=O)NH$R^{BB}$, —S(=O)N$R^{BB}_2$,
  —S(=O)$R^{BM}$,
  —S(=O)$_2NH_2$, —S(=O)$_2$NH$R^{BB}$, —S(=O)$_2$N$R^{BB}_2$,
  —S(=O)$_2R^{BM}$,
  —NHS(=O)$R^{BB}$, —N$R^{BN}$S(=O)$R^{BB}$,
  —NHS(=O)$_2R^{BB}$, —N$R^{BN}$S(=O)$_2R^{BB}$,
  —S(=O)$R^{BB}$, —S(=O)$_2R^{BB}$,
  —S$R^{BB}$, —CN, and —$NO_2$.

(177) A compound according to any one of (1) to (175), wherein each —$R^{11B}$, if present, is independently selected from:
  —F, —Cl, —Br, —I,
  —OH, —O$R^{BB}$,
  —$OCF_3$,
  —$NH_2$, —NH$R^{BB}$, —N$R^{BB}_2$, —$R^{BM}$,
  —S$R^{BB}$, and —CN.

(178) A compound according to any one of (1) to (175), wherein each —$R^{11B}$, if present, is independently selected from:
  —F, —Cl, —Br, —I,
  —OH, —O$R^{BB}$,
  —$OCF_3$, and
  —S$R^{BB}$.

(179) A compound according to any one of (1) to (175), wherein each —$R^{11B}$, if present, is independently selected from:
  —F, —Cl, —Br, —I,
  —OH, —O$R^{BB}$, and
  —$OCF_3$.

The Group —$R^{BB}$ (180) A compound according to any one of (1) to (179), wherein each —$R^{BB}$, if present, is independently linear or branched saturated $C_{1-4}$alkyl, phenyl, or —$CH_2$-phenyl.

(181) A compound according to any one of (1) to (179), wherein each —$R^{BB}$, if present, is linear or branched saturated $C_{1-4}$alkyl.

(182) A compound according to any one of (1) to (179), wherein each —$R^{BB}$, if present, is -Me.

The Group —$R^{BN}$ (183) A compound according to any one of (1) to (182), wherein each —$R^{BN}$, if present, is independently -Me, -Et, -nPr, or -iPr.

(184) A compound according to any one of (1) to (182), wherein each —$R^BN$, if present, is -Me.

The Group —$R^{BM}$ (185) A compound according to any one of (1) to (184), wherein each —$R^{BM}$, if present, is independently pyrrolidino, piperidino, piperazino, or morpholino, and is:
  optionally substituted with one or more groups selected from:
    —$R^{BMM}$, —C(=O)$R^{BMM}$, —C(=O)O$R^{BMM}$, and —S(=O)$_2R^{BMM}$.

(186) A compound according to any one of (1) to (184), wherein each —$R^{BM}$, if present, is independently pyrrolidino, piperidino, piperazino, or morpholino.

The Group —$R^{BMM}$ (187) A compound according to any one of (1) to (186), wherein each —$R^{BMM}$, if present, is independently linear or branched saturated $C_{1-4}$alkyl, phenyl, or —$CH_2$-phenyl.

(188) A compound according to any one of (1) to (186), wherein each —$R^{BMM}$, if present, is linear or branched saturated $C_{1-4}$alkyl.

(189) A compound according to any one of (1) to (186), wherein each —$R^{BMM}$, if present, is -Me.

The Group —$R^2$ (190) A compound according to any one of (1) to (189), wherein —$R^2$ is —H.

(191) A compound according to any one of (1) to (189), wherein —$R^2$ is —$R^{22}$.

The Group —$R^{22}$ (192) A compound according to any one of (1) to (191), wherein —$R^{22}$, if present, is —$R^{22C}$.

(193) A compound according to any one of (1) to (191), wherein —$R^{22}$, if present, is —$R^{22D}$.

The Group —$R^{22C}$ (194) A compound according to any one of (1) to (193), wherein —$R^{22C}$, if present, is independently —$R^{C1}$, —$R^{C4}$, -$L^C$-$R^{C4}$, or -$L^C$-$R^{C5}$.

(195) A compound according to any one of (1) to (193), wherein —$R^{22C}$, if present, is independently —$R^{C1}$, -$L^C$-$R^{C4}$, or -$L^C$-$R^{C5}$.

(196) A compound according to any one of (1) to (193), wherein —$R^{22C}$, if present, is independently —$R^{C1}$ or -$L^C$-$R^{C4}$.

(197) A compound according to any one of (1) to (193), wherein —$R^{22C}$, if present, is —$R^{C1}$.

(198) A compound according to any one of (1) to (193), wherein —$R^{22C}$, if present, is -$L^C$-$R^{C4}$.

(199) A compound according to any one of (1) to (193), wherein —$R^{22C}$, if present, is -$L^C$-$R^{C5}$.

The Group —$R^{C1}$.

(200) A compound according to any one of (1) to (199), wherein each —$R^{C1}$, if present, is independently -Me, -Et, -nPr, -iPr, -nBu, -iBu, -sBu, or -tBu; and is optionally substituted with one or more groups —$R^{CC2}$.

(201) A compound according to any one of (1) to (199), wherein each —$R^{C1}$, if present, is independently -Me; and is optionally substituted with one or more groups —$R^{CC2}$.

(202) A compound according to any one of (1) to (199), wherein each —$R^{C1}$, if present, is independently -iPr; and is optionally substituted with one or more groups —$R^{CC2}$.

(203) A compound according to any one of (1) to (199), wherein each —$R^{C1}$, if present, is independently -iBu; and is optionally substituted with one or more groups —$R^{CC2}$.

(204) A compound according to any one of (1) to (199), wherein each —$R^{C1}$, if present, is independently -Me, -Et, -nPr, -iPr, -nBu, -iBu, -sBu, or -tBu.

(205) A compound according to any one of (1) to (199), wherein each —$R^{C1}$, if present, is independently -Me.

(206) A compound according to any one of (1) to (199), wherein each —$R^{C1}$, if present, is independently -iPr.

(207) A compound according to any one of (1) to (199), wherein each —$R^{C1}$, if present, is independently -iBu.

The Group —$R^{C2}$.

(208) A compound according to any one of (1) to (207), wherein each —$R^{C2}$, if present, is independently cyclopropyl, cyclobutyl, cyclopentyl, or cyclohexyl, and is optionally substituted with one or more groups —$R^{CC1}$ and one or more groups —$R^{CC2}$.

(209) A compound according to any one of (1) to (207), wherein each —$R^{C2}$, if present, is independently cyclopropyl, cyclobutyl, cyclopentyl, or cyclohexyl.

The Group —$R^{C3}$.

(210) A compound according to any one of (1) to (209), wherein each —$R^{C3}$, if present, is independently oxetanyl, tetrahydrofuranyl, tetrahydropyranyl, dioxanyl, azetidinyl, pyrrolidinyl, piperidinyl, piperazinyl, morpholinyl, azepanyl, or diazepanyl, and is optionally substituted with one or more groups —$R^{CC1}$ and one or more groups —$R^{CC2}$.

(211) A compound according to any one of (1) to (209), wherein each —$R^{C3}$, if present, is independently tetrahydrofuranyl, tetrahydropyranyl, dioxanyl, pyrrolidinyl, piperidinyl, piperazinyl, or morpholinyl, and is optionally substituted with one or more groups —$R^{CC1}$ and one or more groups —$R^{CC2}$.

(212) A compound according to any one of (1) to (209), wherein each —$R^{C3}$, if present, is independently tetrahydrofuranyl, tetrahydropyranyl, or dioxanyl, and is optionally substituted with one or more groups —$R^{CC1}$ and one or more groups —$R^{CC2}$.

(213) A compound according to any one of (1) to (209), wherein each —$R^{C3}$, if present, is independently pyrrolidinyl, piperidinyl, piperazinyl, or morpholinyl, and is optionally substituted with one or more groups —$R^{CC1}$ and one or more groups —$R^{CC2}$.

(214) A compound according to any one of (1) to (209), wherein each —$R^{C3}$, if present, is independently tetrahydrofuranyl, tetrahydropyranyl, dioxanyl, pyrrolidinyl, piperidinyl, piperazinyl, or morpholinyl.

(215) A compound according to any one of (1) to (209), wherein each —$R^{C3}$, if present, is independently tetrahydrofuranyl, tetrahydropyranyl, or dioxanyl.

(216) A compound according to any one of (1) to (209), wherein each —$R^{C3}$, if present, is independently pyrrolidinyl, piperidinyl, piperazinyl, or morpholinyl.

The Group —$R^{C4}$ (217) A compound according to any one of (1) to (216), wherein each —$R^{C4}$, if present, is phenyl, and is optionally substituted with one or more groups —$R^{CC1}$ and one or more groups —$R^{CC2}$.

(218) A compound according to any one of (1) to (216), wherein each —$R^{C4}$, if present, is phenyl.

The Group —$R^{C5}$ (219) A compound according to any one of (1) to (218), wherein each —$R^{C5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, pyrazinyl, indolyl, benzoimidazolyl, indazolyl, benzofuranyl, benzothienyl, benzooxazolyl, benzothiazolyl, benzoisoxazolyl, benzoisothiazolyl, quinolinyl, isoquinolinyl, cinnolinyl, quinoxalinyl, quinazolinyl, or phthalazinyl, and is optionally substituted with one or more groups —$R^{CC1}$ and one or more groups —$R^{CC2}$.

(220) A compound according to any one of (1) to (218), wherein each —$R^{C5}$, if present, is independently furanyl, thienyl, pyrrolyl, imidazolyl, oxazolyl, thiazolyl, pyrazolyl, isoxazolyl, isothiazolyl, pyridyl, pyridazinyl, pyrimidinyl, or pyrazinyl, and is optionally substituted with one or more groups —$R^{CC1}$ and one or more groups —$R^{CC2}$.

(221) A compound according to any one of (1) to (218), wherein each —$R^{C5}$, if present, is independently furanyl, thienyl, pyrrolyl, imidazolyl, oxazolyl, thiazolyl, pyrazolyl, isoxazolyl, or isothiazolyl, and is optionally substituted with one or more groups —$R^{CC1}$ and one or more groups —$R^{CC2}$.

(222) A compound according to any one of (1) to (218), wherein each —$R^{C5}$, if present, is independently pyridyl, pyridazinyl, pyrimidinyl, or pyrazinyl, and is optionally substituted with one or more groups —$R^{CC1}$ and one or more groups —$R^{CC2}$.

(223) A compound according to any one of (1) to (218), wherein each —$R^{C5}$, if present, is independently imidazolyl or indolyl, and is optionally substituted with one or more groups —$R^{CC1}$ and one or more groups —$R^{CC2}$.

(224) A compound according to any one of (1) to (218), wherein each —$R^{C5}$, if present, is independently furanyl, thienyl, pyrrolyl, imidazolyl, oxazolyl, thiazolyl, pyrazolyl, isoxazolyl, pyridyl, pyridazinyl, pyrimidinyl, or pyrazinyl.

(225) A compound according to any one of (1) to (218), wherein each —$R^{C5}$, if present, is independently furanyl, thienyl, pyrrolyl, imidazolyl, oxazolyl, thiazolyl, pyrazolyl, isoxazolyl, or isothiazolyl.

(226) A compound according to any one of (1) to (218), wherein each —$R^{C5}$, if present, is independently pyridyl, pyridazinyl, pyrimidinyl, or pyrazinyl.

(227) A compound according to any one of (1) to (218), wherein each —$R^{C5}$, if present, is independently imidazolyl or indolyl.

The Group -$L^C$-

(228) A compound according to any one of (1) to (227), wherein each -$L^C$-, if present, is independently —CH$_2$CH$_2$CH$_2$—, —CH$_2$CH$_2$—, —CH(CH$_3$)CH$_2$—, —CH(CH$_3$)—, or —CH$_2$—.

(229) A compound according to any one of (1) to (227), wherein each -$L^C$-, if present, is independently —CH$_2$CH$_2$— or —CH$_2$—.

(230) A compound according to any one of (1) to (227), wherein each -$L^C$-, if present, is —CH$_2$—.

The Group —$R^{CC1}$ (231) A compound according to any one of (1) to (230), wherein each —$R^{CC1}$, if present, is —$R^{CC}$.

The Group —$R^{CC2}$ (232) A compound according to any one of (1) to (231), wherein each —$R^{CC2}$, if present, is independently selected from:
 —F, —Cl, —Br, —I,
 —OH, —OR$^{CC}$,
 —OCF$_3$,
 —NH$_2$, —NHR$^{CC}$, —N(R$^{CC}$)$_2$, —R$^{CM}$,
 —C(=O)OH, —C(=O)OR$^{CC}$, —OC(=O)R$^{CC}$,
 —C(=O)NH$_2$, —C(=O)NHR$^{CC}$, —C(=O)N(R$^{CC}$)$_2$,
  —C(=O)R$^{CM}$,
 —NHC(=O)R$^{CC}$, —NR$^{CN}$C(=O)R$^{CC}$,
 —C(=O)R$^{CC}$,
 —S(=O)NH$_2$, —S(=O)NHR$^{CC}$, —S(=O)N(R$^{CC}$)$_2$,
  —S(=O)R$^{CM}$,
 —S(=O)$_2$NH$_2$, —S(=O)$_2$NHR$^{CC}$, —S(=O)$_2$N(R$^{CC}$)$_2$,
  —S(=O)$_2$R$^{CM}$,
 —NHS(=O)R$^{CC}$, —NR$^{CN}$S(=O)R$^{CC}$,
 —NHS(=O)$_2$R$^{CC}$, —NR$^{CN}$S(=O)$_2$R$^{CC}$,
 —S(=O)R$^{CC}$, —S(=O)$_2$R$^{CC}$,
 —SH, —SR$^{CC}$, —CN, and —NO$_2$.

(233) A compound according to any one of (1) to (231), wherein each —$R^{CC2}$, if present, is independently selected from:
 —F, —Cl, —Br, —I,
 —OH, —OR$^{CC}$,
 —OCF$_3$,
 —NH$_2$, —NHR$^{CC}$, —N(R$^{CC}$)$_2$, —R$^{CM}$, and
 —CN.

(234) A compound according to any one of (1) to (231), wherein each —$R^{CC2}$, if present, is independently selected from:
 —F, —Cl, —Br, —I,
 —OH, —OR$^{CC}$, and
 —OCF$_3$.

(235) A compound according to any one of (1) to (231), wherein each —$R^{CC2}$, if present, is independently selected from:
 —OH, —OR$^{CC}$
 —NH$_2$, —NHR$^{CC}$, —N(R$^{CC}$)$_2$, —R$^{CM}$,
 —C(=O)OH, —C(=O)OR$^{CC}$,
 —C(=O)NH$_2$, —C(=O)NHR$^{CC}$, —C(=O)N(R$^{CC}$)$_2$,
  —C(=O)R$^{CM}$,
 —NHC(=NH)NH$_2$,
 —SH, and —SR$^{CC}$.

(236) A compound according to any one of (1) to (231), wherein each —$R^{CC2}$, if present, is independently selected from:
 —OH,
 —NH$_2$,
 —C(=O)OH,
 —C(=O)NH$_2$,
 —NHC(=NH)NH$_2$,
 —SH, and —SMe.

The Group -$L^{CC}$-

(237) A compound according to any one of (1) to (236), wherein each -$L^{CC}$-, if present, is independently —CH$_2$CH$_2$CH$_2$—, —CH$_2$CH$_2$—, —CH(CH$_3$)CH$_2$—, —CH(CH$_3$)—, or —CH$_2$—.

(238) A compound according to any one of (1) to (236), wherein each -$L^{CC}$-, if present, is independently —CH$_2$CH$_2$— or —CH$_2$—.

(239) A compound according to any one of (1) to (236), wherein each -$L^{CC}$-, if present, is —CH$_2$—.

The Group —$R^{CC}$ (240) A compound according to any one of (1) to (239), wherein each —$R^{CC}$, if present, is independently linear or branched saturated $C_{1-4}$alkyl, phenyl, or —CH$_2$-phenyl.

(241) A compound according to any one of (1) to (239), wherein each —$R^{CC}$, if present, is linear or branched saturated $C_{1-4}$alkyl.

(242) A compound according to any one of (1) to (239), wherein each —$R^{CC}$, if present, is -Me.

The Group —$R^{CN}$ (243) A compound according to any one of (1) to (242), wherein each —$R^{CN}$, if present, is independently -Me, -Et, -nPr, or -iPr.

(244) A compound according to any one of (1) to (242), wherein each —$R^{CN}$, if present, is -Me.

The Group —$R^{CM}$ (245) A compound according to any one of (1) to (244), wherein each —$R^{CM}$, if present, is independently pyrrolidino, piperidino, piperazino, or morpholino, and is:
 optionally substituted with one or more groups selected from:
  —R$^{CMM}$, —C(=O)R$^{CMM}$, —C(=O)OR$^{CMM}$, and
  —S(=O)$_2$R$^{CMM}$.

(246) A compound according to any one of (1) to (244), wherein each —$R^{CM}$, if present, is independently pyrrolidino, piperidino, piperazino, or morpholino.

The Group —$R^{CMM}$ (247) A compound according to any one of (1) to (246), wherein each —$R^{CMM}$ if present, is independently linear or branched saturated $C_{1-4}$alkyl, phenyl, or —CH$_2$-phenyl.

(248) A compound according to any one of (1) to (246), wherein each —$R^{CMM}$ if present, is linear or branched saturated $C_{1-4}$alkyl.

(249) A compound according to any one of (1) to (246), wherein each —$R^{CMM}$ if present, is -Me.

The Group —$R^{22C}$: Some Specific Groups (250) A compound according to any one of (1) to (193), wherein —$R^{22C}$, if present, is independently selected from:
- —$CH_3$ (e.g., as in alanine),
- —$CH_2CH(CH_3)_2$ (e.g., as in leucine),
- —$CH(CH_3)CH_2CH_3$ (e.g., as in isoleucine),
- —$CH_2CH_2$—S—$CH_3$ (e.g., as in methionine),
- —$CH_2$-(phenyl) (e.g., as in phenylalanine),
- —$CH_2$-(1H-indol-3-yl) (e.g., as in tryptophan),
- —$CH(CH_3)_2$ (e.g., as in valine),
- —$CH_2$—C(=O)$NH_2$ (e.g., as in asparagine),
- —$CH_2$—SH (e.g., as in cysteine),
- —$CH_2CH_2$—C(=O)$NH_2$ (e.g., as in glutamine),
- —$CH_2$—OH (e.g., as in serine),
- —CH(OH)$CH_3$ (e.g., as in threonine),
- —$CH_2$-(4-hydroxy-phenyl) (e.g., as in tyrosine),
- —$CH_2CH_2CH_2$—NH—C(=NH)—$NH_2$ (e.g., as in arginine),
- —$CH_2$-(1H-imidazol-4-yl) (e.g., as in histidine),
- —$CH_2CH_2CH_2CH_2$—$NH_2$ (e.g., as in lysine),
- —$CH_2$—C(=O)OH (e.g., as in aspartic acid), and
- —$CH_2CH_2$—C(=O)OH (e.g., as in glutamic acid).

The Group —$R^{22D}$ (251) A compound according to any one of (1) to (250), wherein —$R^{22D}$, if present, is independently selected from:
- —F, —Cl, —Br, —I,
- —OH, —$OR^{DD}$,
- —$OCF_3$,
- —$NH_2$, —$NHR^{DD}$, —$NR^{DD}{}_2$, —$R^{DM}$,
- —C(=O)OH, —C(=O)$OR^{DD}$, —OC(=O)$R^{DD}$,
- —C(=O)$NH_2$, —C(=O)$NHR^{DD}$, —C(=O)$NR^{DD}{}_2$, —C(=O)$R^{DM}$,
- —NHC(=O)$R^{DD}$, —$NR^{DN}$C(=O)$R^{DD}$,
- —C(=O)$R^{DD}$,
- —S(=O)$NH_2$, —S(=O)$NHR^{DD}$, —S(=O)$NR^{DD}{}_2$, —S(=O)$R^{DM}$,
- —S(=O)$_2NH_2$, —S(=O)$_2NHR^{DD}$, —S(=O)$_2NR^{DD}{}_2$, —S(=O)$_2R^{DM}$,
- —NHS(=O)$R^{DD}$, —$NR^{DN}$S(=O)$R^{DD}$,
- —NHS(=O)$_2R^{DD}$, —$NR^{DN}$S(=O)$_2R^{DD}$
- —S(=O)$R^{DD}$, —S(=O)$_2R^{DD}$,
- —$SR^{DD}$, —CN, and —$NO_2$.

(252) A compound according to any one of (1) to (250), wherein each —$R^{22D}$, if present, is independently selected from:
- —F, —Cl, —Br, —I,
- —OH, —$OR^{DD}$,
- —$OCF_3$,
- —$NH_2$, —$NHR^{DD}$, —$NR^{DD}{}_2$, —$R^{DM}$,
- —$SR^{DD}$, and —CN.

(253) A compound according to any one of (1) to (250), wherein each —$R^{22D}$, if present, is independently selected from:
- —F, —Cl, —Br, —I,
- —OH, —$OR^{DD}$,
- —$OCF_3$, and
- —$SR^{DD}$.

(254) A compound according to any one of (1) to (250), wherein each —$R^{22D}$, if present, is independently selected from:
- —F, —Cl, —Br, —I,
- —OH, —$OR^{DD}$, and
- —$OCF_3$.

The Group —$R^{DD}$ (255) A compound according to any one of (1) to (254), wherein each —$R^{DD}$, if present, is independently linear or branched saturated $C_{1-4}$alkyl, phenyl, or —$CH_2$-phenyl.

(256) A compound according to any one of (1) to (254), wherein each —$R^{DD}$, if present, is linear or branched saturated $C_{1-4}$alkyl.

(257) A compound according to any one of (1) to (254), wherein each —$R^{DD}$, if present, is -Me.

The Group —$R^{DN}$ (258) A compound according to any one of (1) to (257), wherein each —$R^{DN}$, if present, is independently -Me, -Et, -nPr, or -iPr.

(259) A compound according to any one of (1) to (257), wherein each —$R^{DN}$, if present, is -Me.

The Group —$R^{DM}$ (260) A compound according to any one of (1) to (259), wherein each —$R^{DM}$, if present, is independently pyrrolidino, piperidino, piperazino, or morpholino, and is:
optionally substituted with one or more groups selected from:
—$R^{DMM}$, —C(=O)$R^{DMM}$, —C(=O)$OR^{DMM}$, and —S(=O)$_2R^{DMM}$ (261) A compound according to any one of (1) to (259), wherein each —$R^{DM}$, if present, is independently pyrrolidino, piperidino, piperazino, or morpholino.

The Group —$R^{DMM}$ (262) A compound according to any one of (1) to (261), wherein each —$R^{DMM}$, if present, is independently linear or branched saturated $C_{1-4}$alkyl, phenyl, or —$CH_2$-phenyl.

(263) A compound according to any one of (1) to (261), wherein each —$R^{DMM}$, if present, is linear or branched saturated $C_{1-4}$alkyl.

(264) A compound according to any one of (1) to (261), wherein each —$R^{DMM}$, if present, is -Me.

The Groups $R^1$ and $R^2$ Taken Together (265) A compound according to any one of (1) to (106), wherein —$R^1$ and —$R^2$, together with the carbon atom to which they are attached, form a saturated $C_{3-6}$cycloalkyl or a non-aromatic $C_{3-7}$heterocyclyl, and is optionally substituted with one or more groups —$R^{CC2}$.

(266) A compound according to any one of (1) to (106), wherein —$R^1$ and —$R^2$, together with the carbon atom to which they are attached, form a saturated $C_{3-6}$cycloalkyl, and is optionally substituted with one or more groups —$R^{CC2}$.

(267) A compound according to any one of (1) to (106), wherein —$R^1$ and —$R^2$, together with the carbon atom to which they are attached, form a saturated $C_5$cycloalkyl, and is optionally substituted with one or more groups —$R^{CC2}$.

The optional substituents —$R^{C22}$ may be, for example, as defined above.

Some Preferred Combinations of $R^1$ and $R^2$ (268) A compound according to any one of (1) to (106), wherein:
- —$R^1$ is independently —CH($CH_3$)$CH_2CH_3$, —$CH_2$CH($CH_3$)$_2$, or —CH($CH_3$)$_2$; and
- —$R^2$ is —H.

(269) A compound according to any one of (1) to (106), wherein:
- —$R^1$ is independently —CH($CH_3$)$CH_2CH_3$ or —$CH_2$CH($CH_3$)$_2$; and
- —$R^2$ is —H.

(270) A compound according to any one of (1) to (106), wherein:
- —$R^1$ is —$CH_2$CH($CH_3$)$_2$; and
- —$R^2$ is —H.

The Group —$R^{N1}$ (271) A compound according to any one of (1) to (270), wherein —$R^{N1}$ is —H.

(272) A compound according to any one of (1) to (270), wherein —$R^{N1}$ is —$R^N$.

The Group —$R^{N2}$ (273) A compound according to any one of (1) to (272), wherein —$R^{N2}$ is —H.

(274) A compound according to any one of (1) to (272), wherein —$R^{N2}$ is —$R^N$.

The Group —$R^N$ (275) A compound according to any one of (1) to (274), wherein each —$R^N$, if present, is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$.

(276) A compound according to any one of (1) to (274), wherein each —$R^N$, if present, is independently linear or branched saturated $C_{1-4}$alkyl, phenyl, or —$CH_2$-phenyl.

(277) A compound according to any one of (1) to (274), wherein each —$R^N$, if present, is independently linear or branched saturated $C_{1-4}$alkyl.

(278) A compound according to any one of (1) to (274), wherein each —$R^N$, if present, is -Me.

The Groups —$R^{N1}$ and —$R^{N2}$.

(279) A compound according to any one of (1) to (278), wherein —$R^{N1}$ and —$R^{N2}$, taken together, form $C_{2-6}$alkylene.

(280) A compound according to any one of (1) to (278), wherein —$R^{N1}$ and —$R^{N2}$, taken together, form —$(CH_2)_2$—, —$(CH_2)_3$—, —$(CH_2)_4$—, or —$(CH_2)_5$—.

Chiral Centres (281) A compound according to any one of (1) to (280), wherein the sulfur atom which forms part of the sulfonimidamido group (i.e., marked with an asterisk (*) in the following formula), is in the (R) configuration.

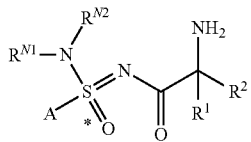

(282) A compound according to any one of (1) to (280), wherein the sulfur atom which forms part of the sulfonimidamido group (i.e., marked with an asterisk (*) in the previous formula) is in the (S) configuration.

(283) A compound according to any one of (1) to (282), wherein the carbon atom to which —$R^1$ and —$R^2$ are attached (i.e., marked with a hash (#) in the following formula) is in the (R) configuration.

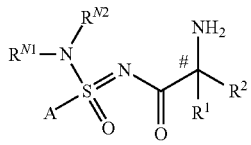

(284) A compound according to any one of (1) to (282), wherein the carbon atom to which —$R^1$ and —$R^2$ are attached (i.e., marked with a hash (#) in the previous formula) is in the (S) configuration.

(285) A compound according to any one of (1) to (282), wherein $R^2$ is —H, and which is a compound selected from compounds of the following formula, and pharmaceutically acceptable salts, hydrates, and solvates thereof:

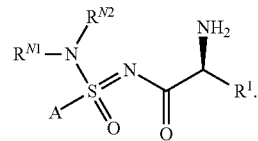

(286) A compound according to any one of (1) to (280), wherein:
the sulfur atom which forms part of the sulfonimidamido group (i.e., marked with an asterisk (*) in the following formula) is in the (R) configuration; and
the carbon atom to which —$R^1$ and —$R^2$ are attached (i.e., marked with a hash (#) in the following formula) is in the (R) configuration.

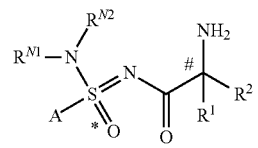

(287) A compound according to any one of (1) to (280), wherein:
the sulfur atom which forms part of the sulfonimidamido group (i.e., marked with an asterisk (*) in the above formula) is in the (R) configuration; and
the carbon atom to which —$R^1$ and —$R^2$ are attached (i.e., marked with a hash (#) in the above formula) is in the (S) configuration.

(288) A compound according to any one of (1) to (280), wherein:
the sulfur atom which forms part of the sulfonimidamido group (i.e., marked with an asterisk (*) in the above formula) is in the (S) configuration; and
the carbon atom to which —$R^1$ and —$R^2$ are attached (i.e., marked with a hash (#) in the above formula) is in the (R) configuration.

(289) A compound according to any one of (1) to (280), wherein:
the sulfur atom which forms part of the sulfonimidamido group (i.e., marked with an asterisk (*) in the above formula) is in the (S) configuration; and
the carbon atom to which —$R^1$ and —$R^2$ are attached (i.e., marked with a hash (#) in the above formula) is in the (S) configuration.

Some Preferred Combinations (290) A compound according to any one of (1) to (280), wherein:
—$R^1$ is independently —$CH(CH_3)CH_2CH_3$, —$CH_2CH(CH_3)_2$, or —$CH(CH_3)_2$;
—$R^2$ is —H; and
the carbon atom to which —$R^1$ and —$R^2$ are attached is in the (S) configuration.

(291) A compound according to any one of (1) to (280), wherein:
—$R^1$ is independently —$CH(CH_3)CH_2CH_3$ or —$CH_2CH(CH_3)_2$;
—$R^2$ is —H; and
the carbon atom to which —$R^1$ and —$R^2$ are attached is in the (S) configuration.

(292) A compound according to any one of (1) to (280), wherein:
- —R¹ is —CH₂CH(CH₃)₂;
- —R² is —H; and
- the carbon atom to which —R¹ and —R² are attached is in the (S) configuration.

Some Specific Compounds (293) A compound according to (1), which is selected from compounds of the following formulae, and pharmaceutically acceptable salts, hydrates, and solvates thereof:

| Code | Structure |
|---|---|
| ANASIA-001 | 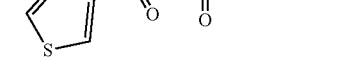 |
| ANASIA-002 | |
| ANASIA-003 | |
| ANASIA-004 | |
| ANASIA-005 | |
| ANASIA-006 | |
| ANASIA-007 | |
| ANASIA-008 | 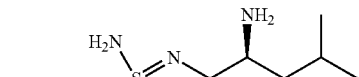 |
| ANASIA-009 | 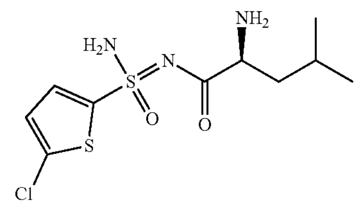 [SMILES: CC(C)C[C@H](N)C(=O)N=S(N)(=O)c1ccc(Cl)s1] |
| ANASIA-010 | 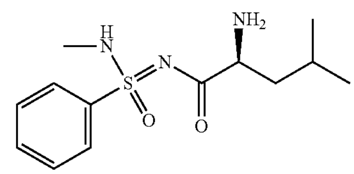 [SMILES: CNS(=O)(=NC(=O)[C@@H](N)CC(C)C)c1ccccc1] |
| ANASIA-011 | 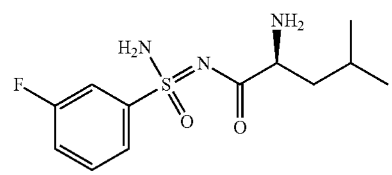 [SMILES: CC(C)C[C@H](N)C(=O)N=S(N)(=O)c1cccc(F)c1] |
| ANASIA-012 | 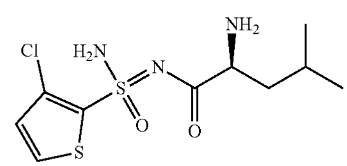 [SMILES: CC(C)C[C@H](N)C(=O)N=S(N)(=O)c1sccc1Cl] |
| ANASIA-013 | 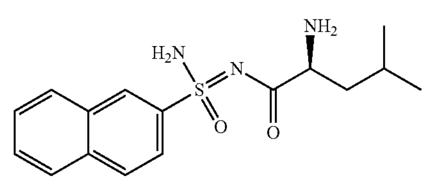 [SMILES: CC(C)C[C@H](N)C(=O)N=S(N)(=O)c1ccc2ccccc2c1] |
| ANASIA-014 | 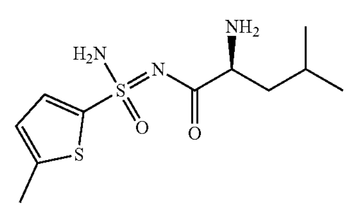 [SMILES: Cc1ccc(S(N)(=O)=NC(=O)[C@@H](N)CC(C)C)s1] |
| ANASIA-015 | 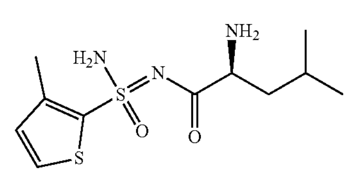 [SMILES: Cc1ccsc1S(N)(=O)=NC(=O)[C@@H](N)CC(C)C] |

| Code | Structure |
|---|---|
| ANASIA-016 | 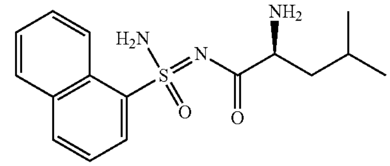 [SMILES: CC(C)C[C@H](N)C(=O)N=S(N)(=O)c1cccc2ccccc12] |
| ANASIA-017 | 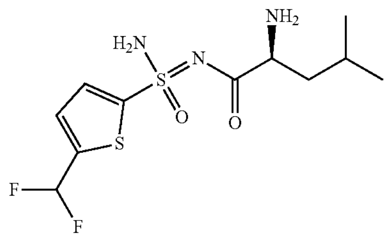 [SMILES: CC(C)C[C@H](N)C(=O)N=S(N)(=O)c1ccc(C(F)F)s1] |
| ANASIA-018 | 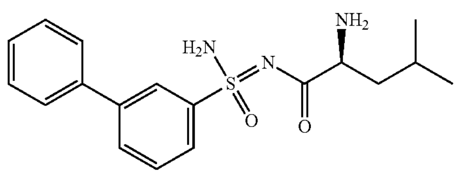 [SMILES: CC(C)C[C@H](N)C(=O)N=S(N)(=O)c1cccc(-c2ccccc2)c1] |
| ANASIA-019 | 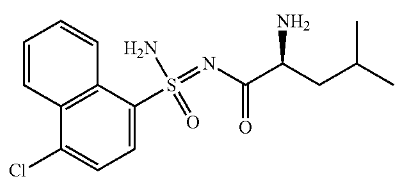 [SMILES: CC(C)C[C@H](N)C(=O)N=S(N)(=O)c1ccc(Cl)c2ccccc12] |
| ANASIA-020 | 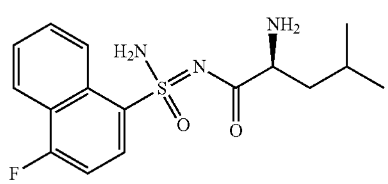 [SMILES: CC(C)C[C@H](N)C(=O)N=S(N)(=O)c1ccc(F)c2ccccc12] |
| ANASIA-021 | 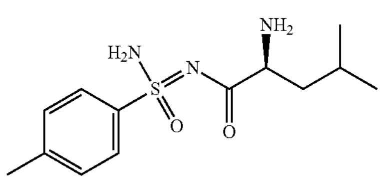 [SMILES: Cc1ccc(S(N)(=O)=NC(=O)[C@@H](N)CC(C)C)cc1] |
| ANASIA-022 | 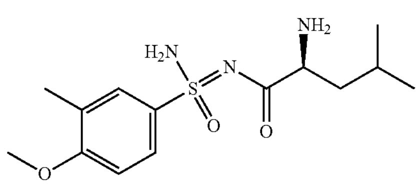 [SMILES: COc1ccc(S(N)(=O)=NC(=O)[C@@H](N)CC(C)C)cc1C] |
| ANASIA-023 | 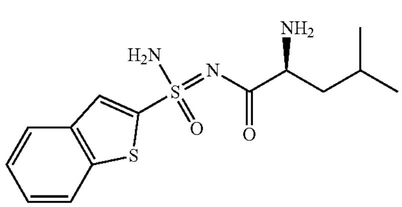 [SMILES: CC(C)C[C@H](N)C(=O)N=S(N)(=O)c1cc2ccccc2s1] |

| Code | Structure |
|---|---|
| ANASIA-024 | 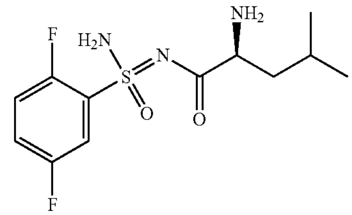 [SMILES: CC(C)C[C@H](N)C(=O)N=S(N)(=O)c1cc(F)ccc1F] |
| ANASIA-025 | 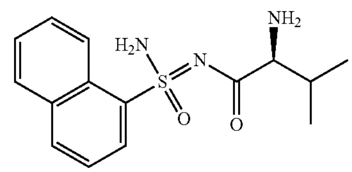 [SMILES: CC(C)[C@H](N)C(=O)N=S(N)(=O)c1cccc2ccccc12] |
| ANASIA-026 | 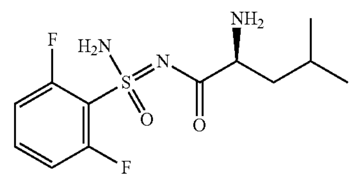 [SMILES: CC(C)C[C@H](N)C(=O)N=S(N)(=O)c1c(F)cccc1F] |
| ANASIA-027 | 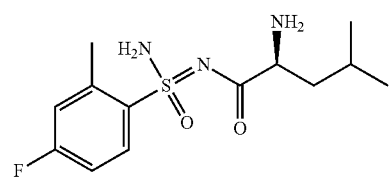 [SMILES: Cc1cc(F)ccc1S(N)(=O)=NC(=O)[C@@H](N)CC(C)C] |
| ANASIA-028 | 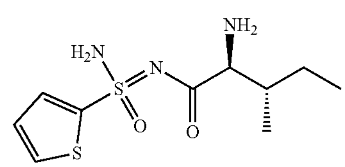 [SMILES: CC[C@H](C)[C@H](N)C(=O)N=S(N)(=O)c1cccs1] |
| ANASIA-029 | 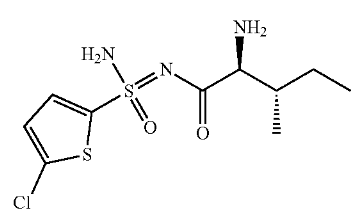 [SMILES: CC[C@H](C)[C@H](N)C(=O)N=S(N)(=O)c1ccc(Cl)s1] |
| ANASIA-030 | 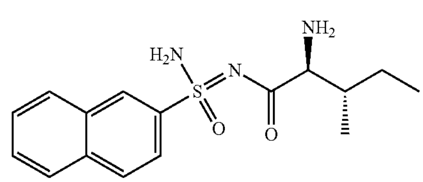 [SMILES: CC[C@H](C)[C@H](N)C(=O)N=S(N)(=O)c1ccc2ccccc2c1] |
| ANASIA-031 | 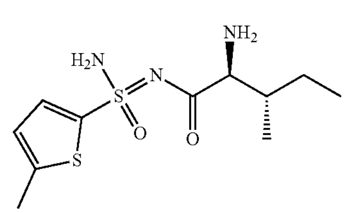 [SMILES: CC[C@H](C)[C@H](N)C(=O)N=S(N)(=O)c1ccc(C)s1] |

| Code | Structure |
|------|-----------|
| ANASIA-032 | 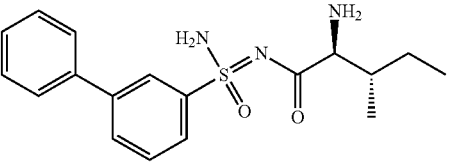 [SMILES: CC[C@H](C)[C@H](N)C(=O)N=S(N)(=O)c1cccc(-c2ccccc2)c1] |
| ANASIA-033 | 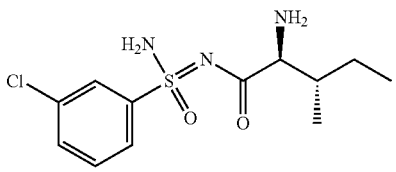 [SMILES: CC[C@H](C)[C@H](N)C(=O)N=S(N)(=O)c1cccc(Cl)c1] |
| ANASIA-034 | 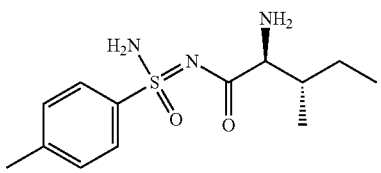 [SMILES: CC[C@H](C)[C@H](N)C(=O)N=S(N)(=O)c1ccc(C)cc1] |
| ANASIA-035 | 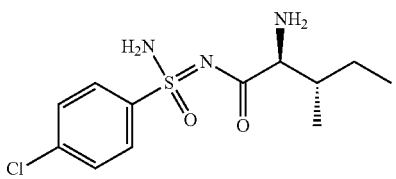 [SMILES: CC[C@H](C)[C@H](N)C(=O)N=S(N)(=O)c1ccc(Cl)cc1] |
| ANASIA-036 | 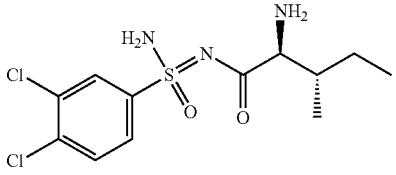 [SMILES: CC[C@H](C)[C@H](N)C(=O)N=S(N)(=O)c1ccc(Cl)c(Cl)c1] |
| ANASIA-037 | 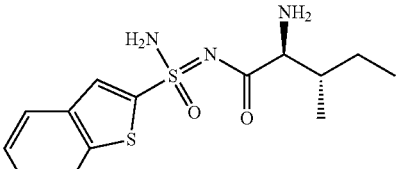 |
| ANASIA-038 | 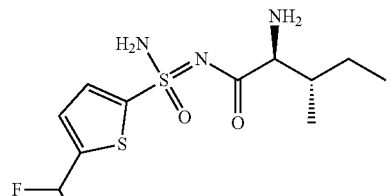 |
| ANASIA-039 | 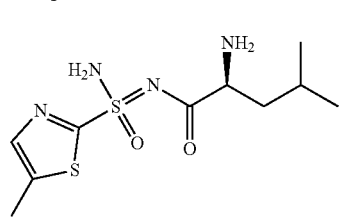 |
| Code | Structure |
|------|-----------|
| ANASIA-040 | 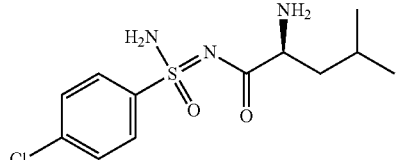 |
| ANASIA-041 | 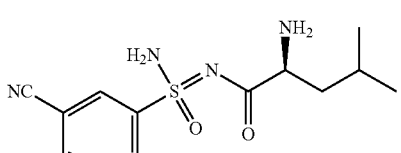 |
| ANASIA-042 | 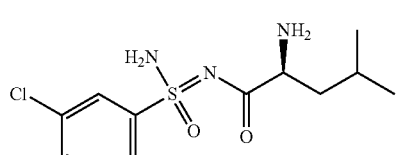 |
| ANASIA-043 | 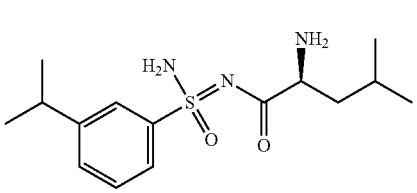 [SMILES: CC(C)C[C@H](N)C(=O)N=S(N)(=O)c1cccc(C(C)C)c1] |
| ANASIA-044 | 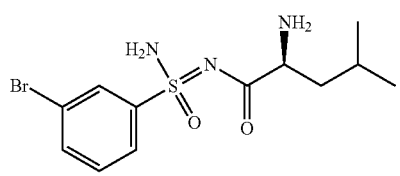 [SMILES: CC(C)C[C@H](N)C(=O)N=S(N)(=O)c1cccc(Br)c1] |
| ANASIA-045 | 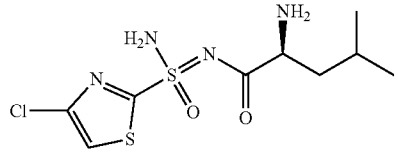 [SMILES: CC(C)C[C@H](N)C(=O)N=S(N)(=O)c1nc(Cl)cs1] |
| ANASIA-046 | 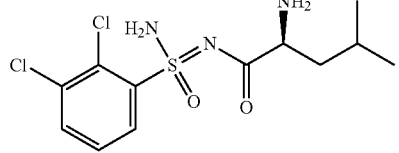 |
| ANASIA-047 | 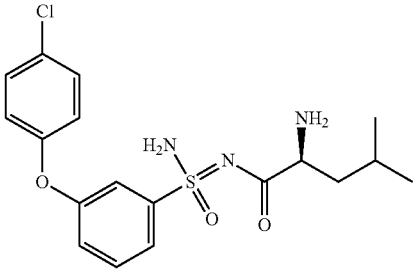 [SMILES: CC(C)C[C@H](N)C(=O)N=S(N)(=O)c1cccc(Oc2ccc(Cl)cc2)c1] |

-continued

| Code | Structure |
|---|---|
| ANASIA-048 | 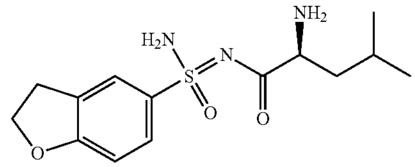 [SMILES: CC(C)C[C@H](N)C(=O)N=S(N)(=O)c1ccc2c(c1)CCO2] |
| ANASIA-049 | 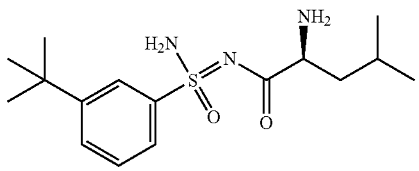 [SMILES: CC(C)C[C@H](N)C(=O)N=S(N)(=O)c1cccc(C(C)(C)C)c1] |
| ANASIA-050 | 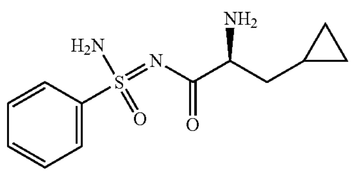 [SMILES: N[C@@H](CC1CC1)C(=O)N=S(N)(=O)c1ccccc1] |
| ANASIA-051 | 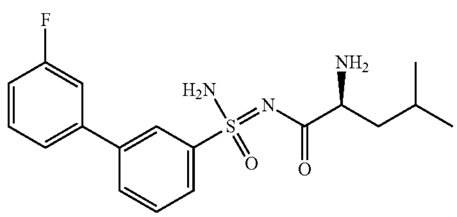 [SMILES: CC(C)C[C@H](N)C(=O)N=S(N)(=O)c1cccc(-c2cccc(F)c2)c1] |
| ANASIA-052 | 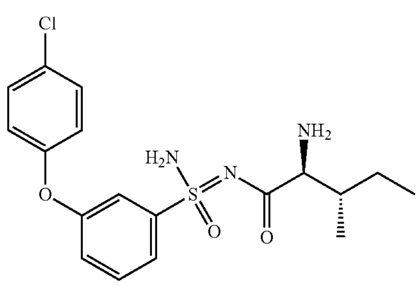 [SMILES: CC[C@H](C)[C@H](N)C(=O)N=S(N)(=O)c1cccc(Oc2ccc(Cl)cc2)c1] |
| ANASIA-053 | 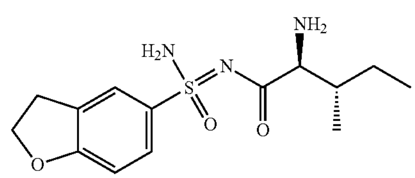 [SMILES: CC[C@H](C)[C@H](N)C(=O)N=S(N)(=O)c1ccc2c(c1)CCO2] |
| ANASIA-054 | 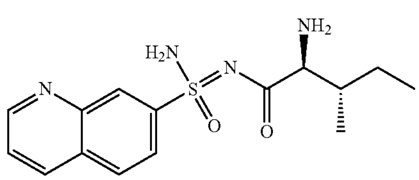 [SMILES: CC[C@H](C)[C@H](N)C(=O)N=S(N)(=O)c1ccc2cccnc2c1] |
| ANASIA-055 | 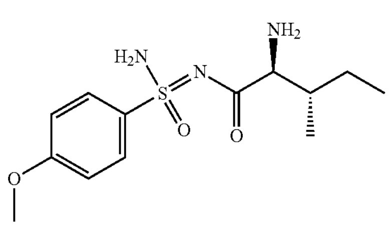 [SMILES: CC[C@H](C)[C@H](N)C(=O)N=S(N)(=O)c1ccc(OC)cc1] |

-continued

| Code | Structure |
|---|---|
| ANASIA-056 | 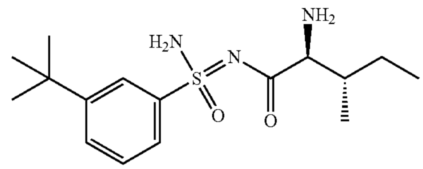 [SMILES: CC[C@H](C)[C@H](N)C(=O)N=S(N)(=O)c1cccc(C(C)(C)C)c1] |
| ANASIA-057 | 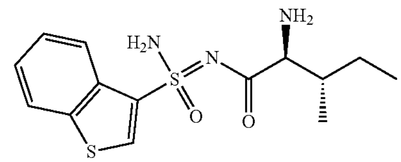 [SMILES: CC[C@H](C)[C@H](N)C(=O)N=S(N)(=O)c1csc2ccccc12] |
| ANASIA-058 | 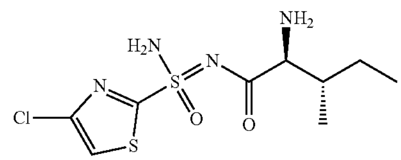 [SMILES: CC[C@H](C)[C@H](N)C(=O)N=S(N)(=O)c1nc(Cl)cs1] |
| ANASIA-059 | 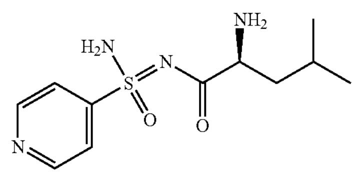 [SMILES: CC(C)C[C@H](N)C(=O)N=S(N)(=O)c1ccncc1] |
| ANASIA-060 | 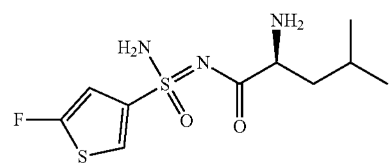 [SMILES: CC(C)C[C@H](N)C(=O)N=S(N)(=O)c1csc(F)c1] |
| ANASIA-061 | 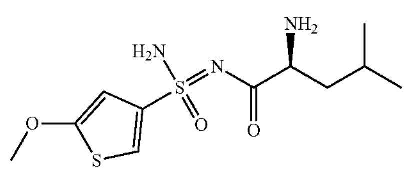 [SMILES: COc1cc(S(N)(=O)=NC(=O)[C@@H](N)CC(C)C)cs1] |
| ANASIA-062 | 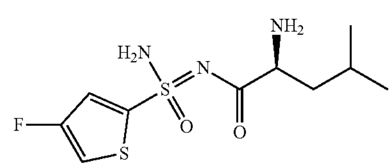 [SMILES: CC(C)C[C@H](N)C(=O)N=S(N)(=O)c1cc(F)cs1] |
| ANASIA-063 | 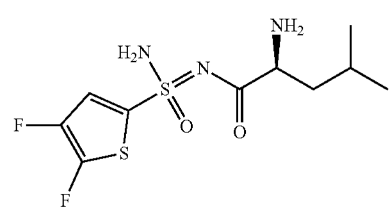 [SMILES: CC(C)C[C@H](N)C(=O)N=S(N)(=O)c1cc(F)c(F)s1] |

| Code | Structure |
|---|---|
| ANASIA-064 | 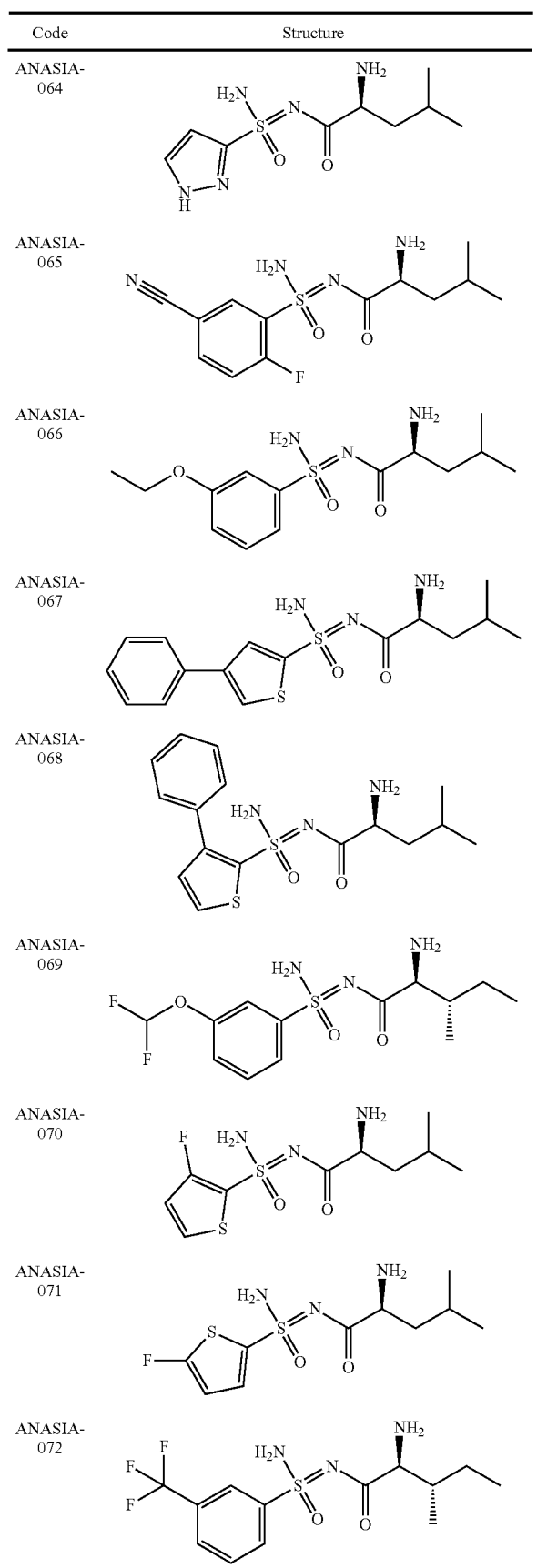 |
| ANASIA-065 | |
| ANASIA-066 | |
| ANASIA-067 | |
| ANASIA-068 | |
| ANASIA-069 | |
| ANASIA-070 | |
| ANASIA-071 | |
| ANASIA-072 | |
| Code | Structure |
|---|---|
| ANASIA-073 | 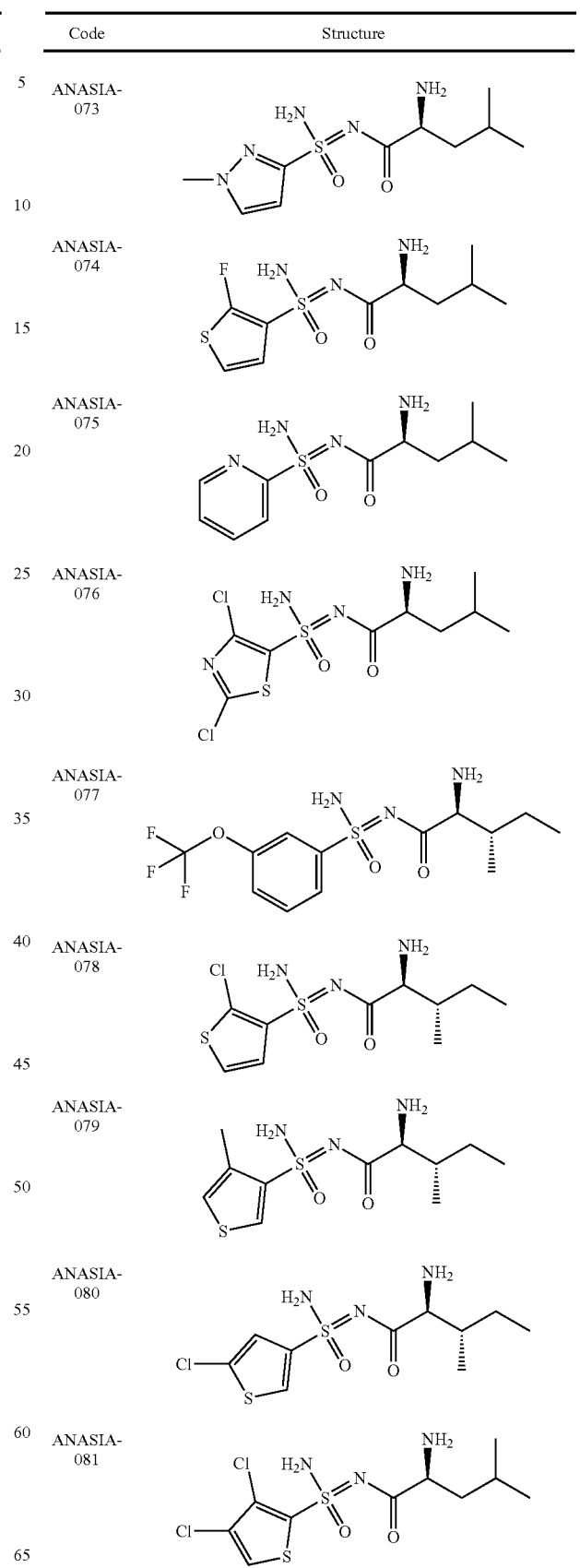 |
| ANASIA-074 | |
| ANASIA-075 | |
| ANASIA-076 | |
| ANASIA-077 | |
| ANASIA-078 | |
| ANASIA-079 | |
| ANASIA-080 | |
| ANASIA-081 | |

-continued
| Code | Structure |
|---|---|
| ANASIA-082 | 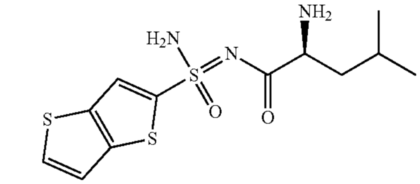 [SMILES: CC(C)C[C@H](N)C(=O)N=S(N)(=O)c1cc2sccc2s1] |
| ANASIA-083 | 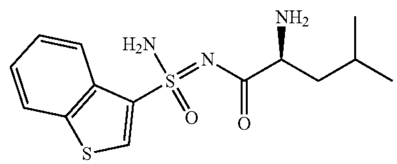 [SMILES: CC(C)C[C@H](N)C(=O)N=S(N)(=O)c1csc2ccccc12] |
| ANASIA-084 | 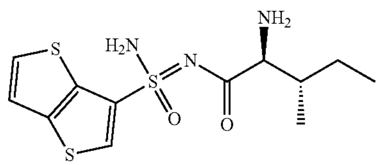 [SMILES: CC[C@H](C)[C@H](N)C(=O)N=S(N)(=O)c1csc2ccsc12] |
| ANASIA-085 | 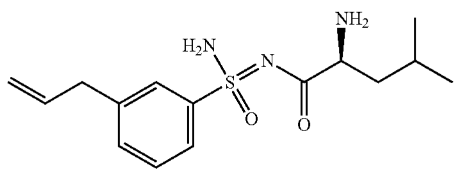 [SMILES: C=CCc1cccc(S(N)(=O)=NC(=O)[C@@H](N)CC(C)C)c1] |
| ANASIA-086 | 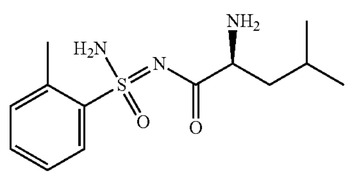 [SMILES: Cc1ccccc1S(N)(=O)=NC(=O)[C@@H](N)CC(C)C] |
| ANASIA-087 | 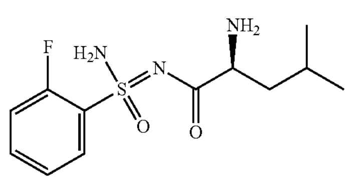 [SMILES: CC(C)C[C@H](N)C(=O)N=S(N)(=O)c1ccccc1F] |
| ANASIA-088 | 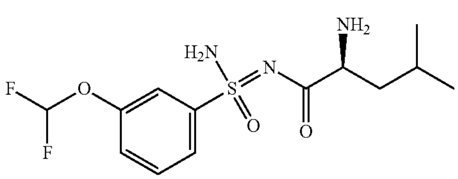 [SMILES: CC(C)C[C@H](N)C(=O)N=S(N)(=O)c1cccc(OC(F)F)c1] |
| ANASIA-089 | 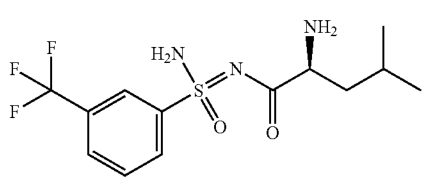 |
| ANASIA-090 | 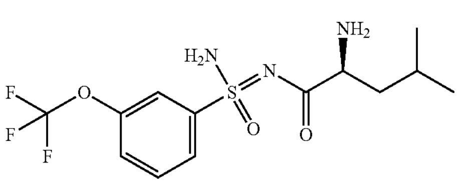 [SMILES: CC(C)C[C@H](N)C(=O)N=S(N)(=O)c1cccc(OC(F)(F)F)c1] |
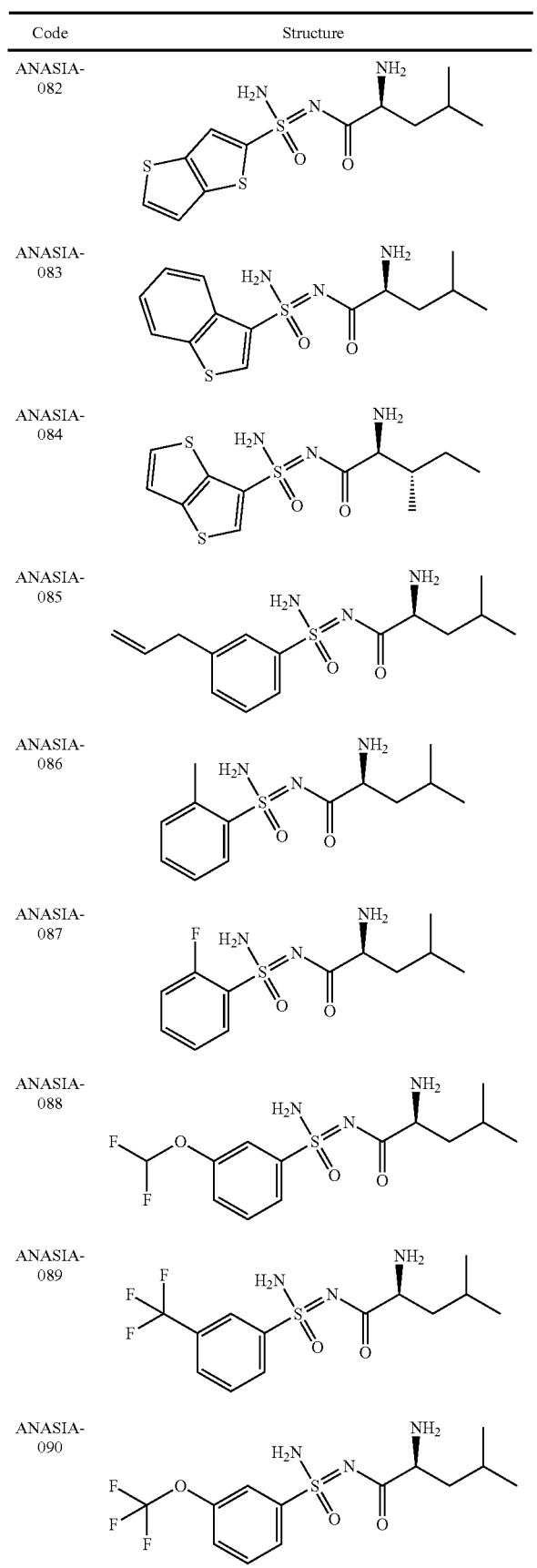
-continued
| Code | Structure |
|---|---|
| ANASIA-091 | 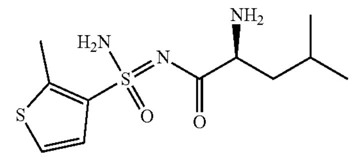 [SMILES: Cc1sccc1S(N)(=O)=NC(=O)[C@@H](N)CC(C)C] |
| ANASIA-092 | 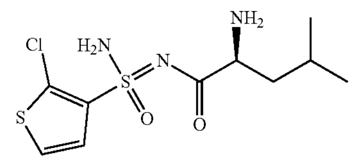 [SMILES: CC(C)C[C@H](N)C(=O)N=S(N)(=O)c1ccsc1Cl] |
| ANASIA-093 | 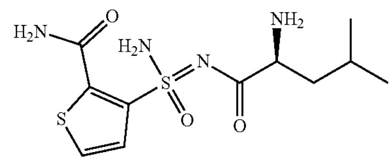 [SMILES: CC(C)C[C@H](N)C(=O)N=S(N)(=O)c1ccsc1C(N)=O] |
| ANASIA-094 | 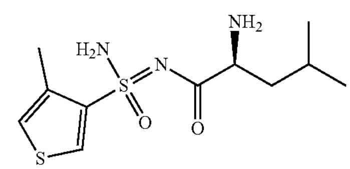 [SMILES: Cc1cscc1S(N)(=O)=NC(=O)[C@@H](N)CC(C)C] |
| ANASIA-095 | 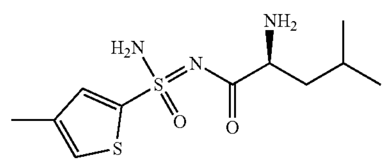 [SMILES: Cc1csc(S(N)(=O)=NC(=O)[C@@H](N)CC(C)C)c1] |
| ANASIA-096 | 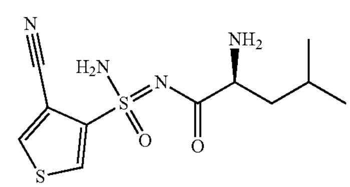 [SMILES: CC(C)C[C@H](N)C(=O)N=S(N)(=O)c1cscc1C#N] |
| ANASIA-097 | 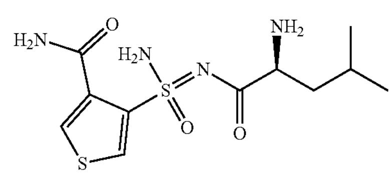 [SMILES: CC(C)C[C@H](N)C(=O)N=S(N)(=O)c1cscc1C(N)=O] |
| ANASIA-098 | 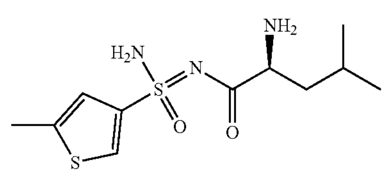 [SMILES: Cc1cc(S(N)(=O)=NC(=O)[C@@H](N)CC(C)C)cs1] |
| ANASIA-099 | 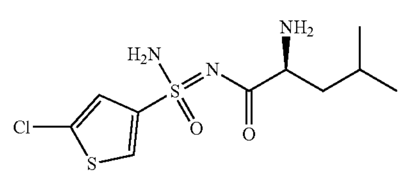 [SMILES: CC(C)C[C@H](N)C(=O)N=S(N)(=O)c1csc(Cl)c1] |
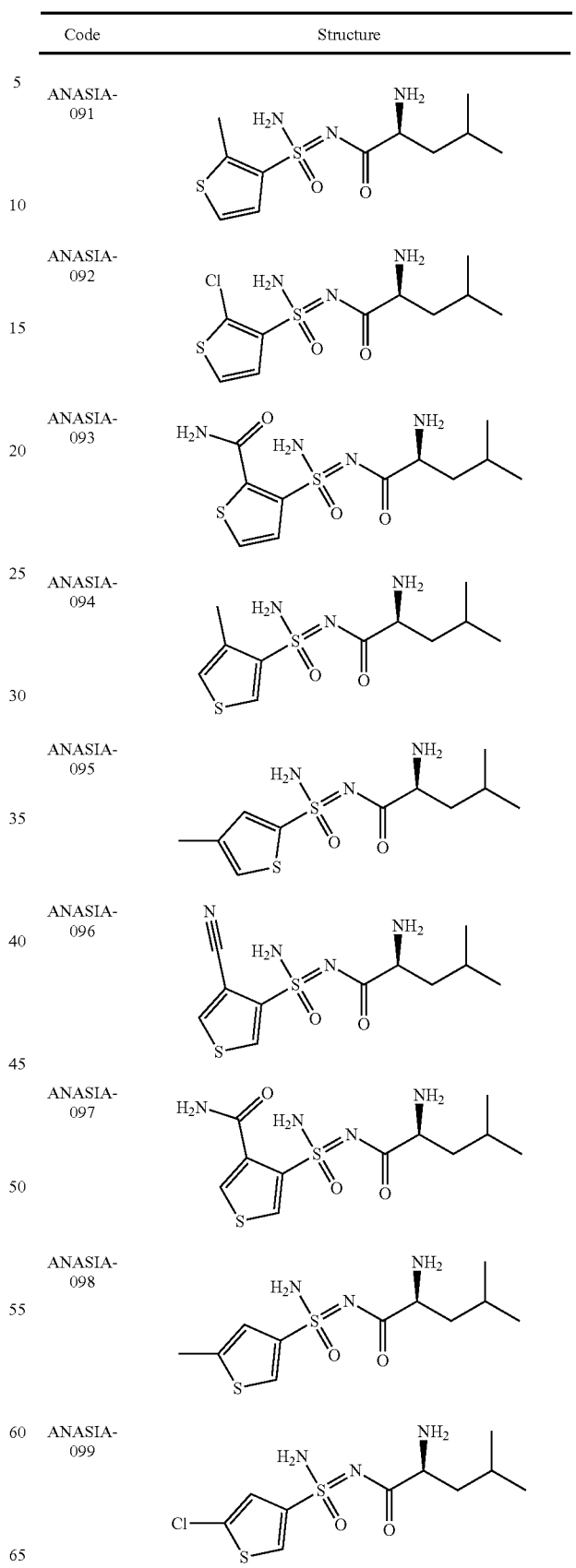

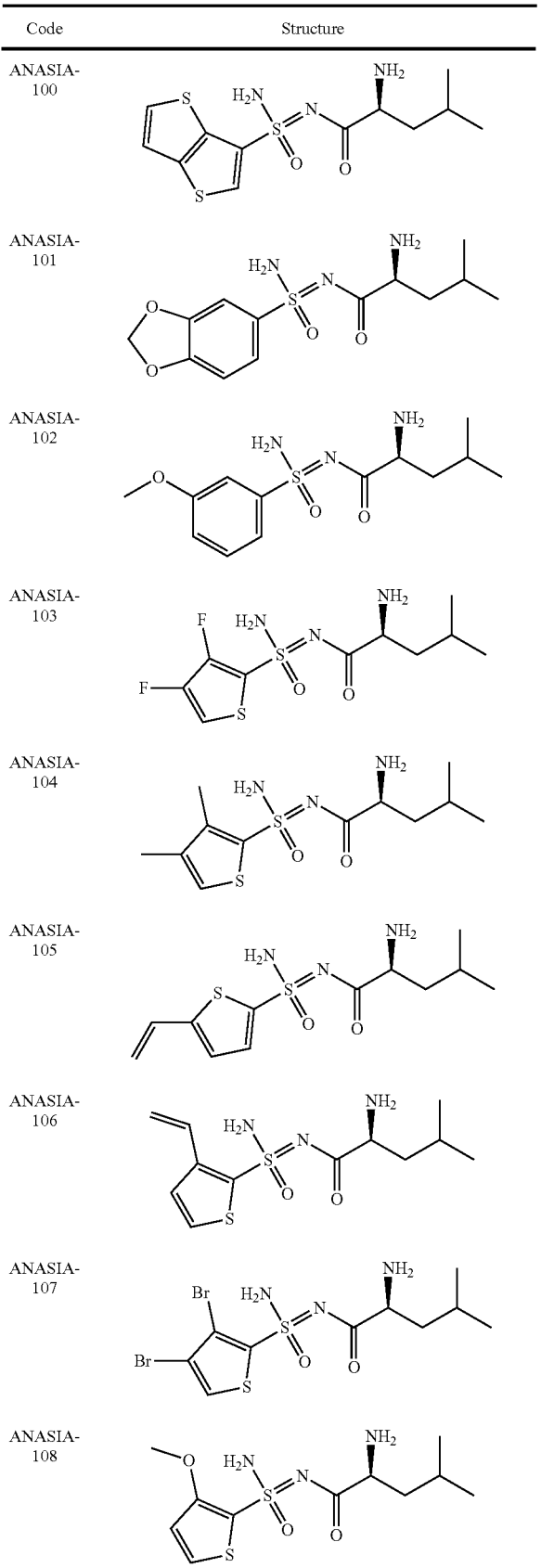
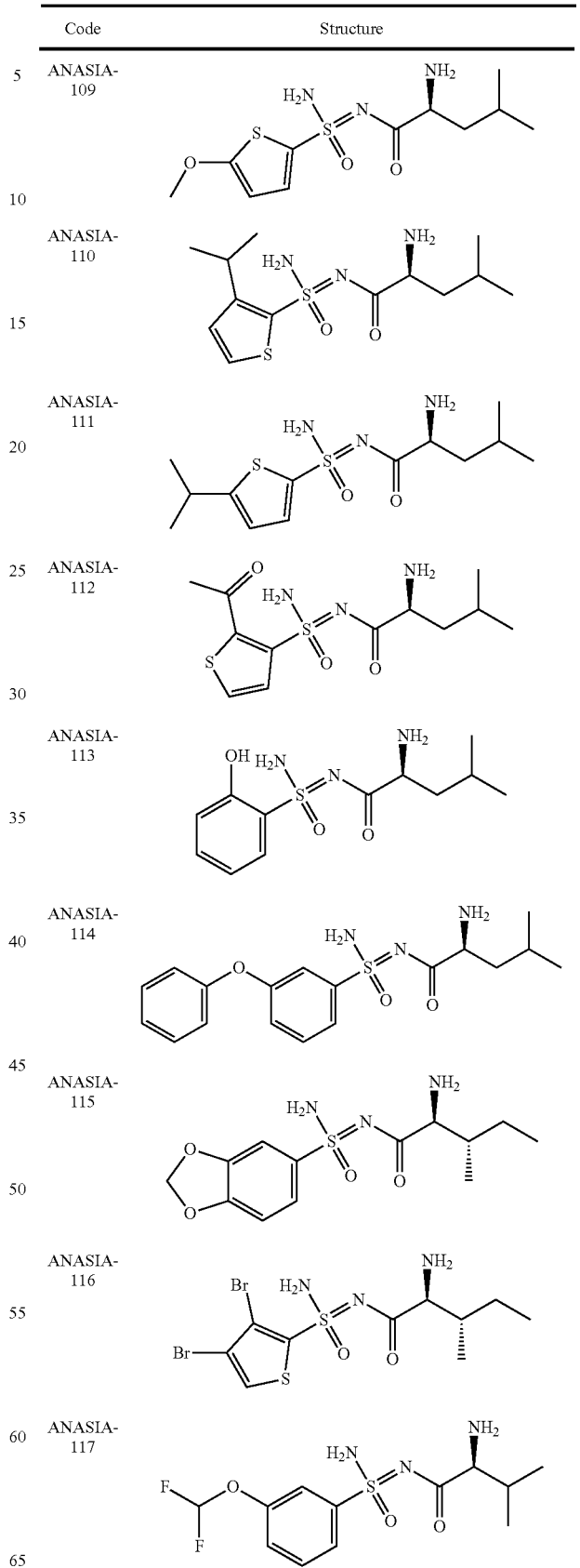

-continued

| Code | Structure |
|---|---|
| ANASIA-118 | (thieno[3,2-b]thiophene sulfonimidamide with leucine-like group, valine side chain) |
| ANASIA-119 | (3-ethylthiophene-2-sulfonimidamide coupled with leucine) |
| ANASIA-120 | (3,5-dichlorothiophene-2-sulfonimidamide coupled with leucine) |
| ANASIA-121 | (4,5-dichlorothiophene-2-sulfonimidamide coupled with leucine) |
| ANASIA-122 | (5-chloro-4-methylthiophene-3-sulfonimidamide coupled with leucine) |
| ANASIA-123 | (phenyl sulfonimidamide coupled with 1-amino-3-methylcyclopentane carbonyl) |
| ANASIA-124 | (4-chlorothiophene-2-sulfonimidamide coupled with leucine) |
| ANASIA-125 | (4,5-dichlorothiophene-3-sulfonimidamide coupled with leucine) |
| ANASIA-126 | (2-(difluoromethyl)thiophene-3-sulfonimidamide coupled with leucine) |
| ANASIA-127 | (4-isopropylthiazole-2-sulfonimidamide coupled with leucine) |
| ANASIA-128 | (4,5-dimethylthiazole-2-sulfonimidamide coupled with leucine) |
| ANASIA-129 | (2-methylthiazole-4-sulfonimidamide coupled with leucine) |
| ANASIA-130 | (4-phenylthiophene-3-sulfonimidamide coupled with leucine) |
| ANASIA-131 | (thieno[3,2-b]pyridine-3-sulfonimidamide coupled with leucine) |
| ANASIA-132 | (benzo[d]isothiazole-3-sulfonimidamide coupled with leucine) |
| ANASIA-133 | (4-ethylthiophene-2-sulfonimidamide coupled with leucine) |

| Code | Structure |
|---|---|
| ANASIA-134 | [structure: 2,5-dichlorothiophene-3-sulfonimidamide linked via S(=O)(=N-) to C(=O)-CH(NH2)-CH2-CH(CH3)2] |
| ANASIA-135 | [structure: 5-cyanothiophene-3-sulfonimidamide linked to leucinamide] |
| ANASIA-136 | [structure: 4-cyanothiophene-2-sulfonimidamide linked to leucinamide] |
| ANASIA-137 | [structure: 2-methylthiazole-5-sulfonimidamide linked to leucinamide] |
| ANASIA-138 | [structure: thieno[3,2-b]thiophene-2-sulfonimidamide linked to isoleucinamide] |

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -A, —$R^{N1}$, —$R^{N2}$, —$R^1$, —$R^2$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Substantially Purified Forms

One aspect of the present invention pertains to ANASIA compounds, in purified form.

In one embodiment, the compound is in substantially purified form and/or in a form substantially free from contaminants.

In one embodiment, the compound is in a substantially purified form with a purity of least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the compound is in a form substantially free from contaminants wherein the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the compound is in a substantially purified form with an optical purity of at least 60% (i.e., 60% of the compound, on a molar basis, is the desired stereoisomer or enantiomer, and 40% is undesired stereoisomer(s) or enantiomer), e.g., at least 70%, e.g., at least 80%, e.g., at least 90%, e.g., at least 95%, e.g., at least 97%, e.g., at least 98%, e.g., at least 99%.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-3}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

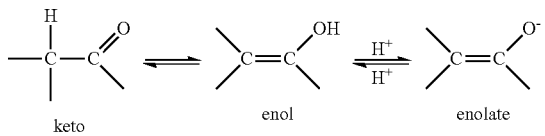

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; S may be in any isotopic form, including $^{32}S$, $^{33}S$, $^{34}$, $^{35}S$, and $^{36}S$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO⁻), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —NH₂ may be —NH₃⁺), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, formic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Hydrates and Solvates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a hemi-hydrate, a mono-hydrate, a sesqui-hydrate, a di-hydrate, a tri-hydrate, etc.

Unless otherwise specified, a reference to a particular compound also includes solvate and hydrate forms thereof.

Chemically Protected Forms

It may be convenient or desirable to prepare, purify, and/or handle the compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Greene and P. Wuts; 4th Edition; John Wiley and Sons, 2006).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH₃, —OAc).

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulfonyl)ethyloxy amide (—NH—Psec); or, in suitable cases (e.g., cyclic amines), as a nitroxide radical (>N—O·).

Prodrugs

It may be convenient or desirable to prepare, purify, and/or handle the compound in the form of a prodrug. The term "prodrug," as used herein, pertains to a compound which, when metabolised (e.g., in vivo), yields the desired active compound. Typically, the prodrug is inactive, or less active than the desired active compound, but may provide advantageous handling, administration, or metabolic properties.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

Methods for the chemical synthesis of the ANASIA compounds are described herein. These and/or other well-known methods may be modified and/or adapted in known ways in order to provide alternative or improved methods of synthesis of the ANASIA compounds.

Compositions

One aspect of the present invention pertains to a composition (e.g., a pharmaceutical composition) comprising an ANASIA compound, as described herein, and a pharmaceutically acceptable carrier, diluent, or excipient.

Another aspect of the present invention pertains to a method of preparing a composition (e.g., a pharmaceutical composition) comprising mixing an ANASIA compound, as described herein, and a pharmaceutically acceptable carrier, diluent, or excipient.

Uses

The ANASIA compounds, as described herein, are useful, for example, in the treatment of disorders (e.g., diseases) that are ameliorated by the inhibition (e.g., selective inhibition) of bacterial aminoacyl-tRNA synthetase (aaRS) (e.g., bacterial leucyl-tRNA synthetase, LeuRS; etc.), as described herein.

Selectivity

In one embodiment, the inhibition of bacterial aminoacyl-tRNA synthetase (aaRS) is selective inhibition, e.g., with respect to mammalian aminoacyl-tRNA synthetase (aaRS), e.g., the corresponding mammalian aminoacyl-tRNA synthetase.

In one embodiment, the inhibition of bacterial aminoacyl-tRNA synthetase (aaRS) is selective inhibition, e.g., with respect to human aminoacyl-tRNA synthetase (aaRS), e.g., the corresponding human aminoacyl-tRNA synthetase.

For example, in one embodiment, the ANASIA compound selectively inhibits bacterial leucyl-tRNA synthetase (LeuRS), as compared to human leucyl-tRNA synthetase (LeuRS).

Use in Methods of Inhibiting Bacterial Aminoacyl-tRNA Synthetase

One aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.), in vitro or in vivo, comprising contacting the synthetase with an effective amount of an ANASIA compound, as described herein.

One aspect of the present invention pertains to a method of inhibiting (e.g., selectively inhibiting) bacterial aminoacyl-tRNA synthetase (aaRS) (e.g., bacterial leucyl-tRNA synthetase, LeuRS, etc.) function in a cell (e.g., a bacterial cell), in vitro or in vivo, comprising contacting the cell with an effective amount of an ANASIA compound, as described herein.

One of ordinary skill in the art is readily able to determine whether or not a candidate compound inhibits bacterial aminoacyl-tRNA synthetase (e.g., bacterial leucyl-tRNA synthetase, etc.). For example, suitable assays are described herein or are known in the art.

In one embodiment, the method is performed in vitro.

In one embodiment, the method is performed in vivo.

In one embodiment, the ANASIA compound is provided in the form of a pharmaceutically acceptable composition.

One aspect of the present invention pertains to a method of inhibiting bacterial aminoacyl-tRNA synthetase (e.g., bacterial leucyl-tRNA synthetase, etc.), in a cell (e.g., a bacterial cell), in vitro or in vivo, comprising contacting the cell with an effective amount of an ANASIA compound, as described herein.

For example, a sample of cells may be grown in vitro and a compound brought into contact with said cells, and the effect of the compound on those cells observed. As an example of "effect," the morphological status of the cells (e.g., alive or dead, etc.) may be determined. Where the compound is found to exert an influence on the cells, this may be used as a prognostic or diagnostic marker of the efficacy of the compound in methods of treating a patient carrying cells of the same cellular type.

Use in Methods of Therapy

Another aspect of the present invention pertains to an ANASIA compound, as described herein, for use in a method of treatment of the human or animal body by therapy, for example, for use in a method of treatment of a disorder (e.g., a disease) as described herein.

Use in the Manufacture of Medicaments

Another aspect of the present invention pertains to use of an ANASIA compound, as described herein, in the manufacture of a medicament, for example, for use in a method of treatment, for example, for use a method of treatment of a disorder (e.g., a disease) as described herein.

In one embodiment, the medicament comprises the ANASIA compound.

Methods of Treatment

Another aspect of the present invention pertains to a method of treatment, for example, a method of treatment of a disorder (e.g., a disease) as described herein, comprising administering to a subject in need of treatment a therapeutically-effective amount of an ANASIA compound, as described herein, preferably in the form of a pharmaceutical composition.

Disorders Treated—Disorders Ameliorated by the Inhibition of Bacterial Aminoacyl-tRNA Synthetase In one embodiment (e.g., of use in methods of therapy, of use in the manufacture of medicaments, of methods of treatment), the treatment is treatment of a disorder (e.g., a disease) that is ameliorated by the inhibition (e.g., selective inhibition) of bacterial aminoacyl-tRNA synthetase (e.g., bacterial leucyl-tRNA synthetase, etc.).

Disorders Treated—Bacterial Infections

In one embodiment (e.g., of use in methods of therapy, of use in the manufacture of medicaments, of methods of treatment), the treatment is treatment of: a bacterial infection.

In one embodiment, the bacteria are Gram-positive bacteria (i.e., the bacterial infection is an infection with Gram-positive bacteria; the bacterial infection is a Gram-positive bacterial infection; etc.).

In one embodiment, the bacteria are Gram-negative bacteria.

In one embodiment, the bacteria are aerobic bacteria.
In one embodiment, the bacteria are anaerobic bacteria.
In one embodiment, the bacteria are intracellular bacteria.
In one embodiment, the bacteria are:
Staphylococci, for example *S. aureus*;
Enterococci, for example *E. faecalis*;
Streptococci, for example *S. pneumoniae*;
*Haemophilus*, for example *H. influenza*;
*Moraxella*, for example *M. catarrhalis*;
*Klebsiella*, for example *K. pneumoniae*;
*Acinetobacter*, for example *A. baumanii*;
*Pseudomonas*, for example *P. aeruginosa*;
*Proteus*, for example *P. mirabilis*;
*Neisseria*, for example *Neisseria gonorrhoeae*;
Clostridioides, for example Clostridioides *difficile*;
*Campylobacter*, for example *C. jejuni*;
*Salmonella*, for example *S. typhi*;
*Shigella*, for example *S. flexneri*;
*Enterobacter*, for example *E. cloacae*;
*Citrobacter*, for example *C. freundii*;
*Serratia*, for example *Serratia marcescens*; or
*Escherichia*, for example *E. coli*.
In one embodiment, the bacteria are:
Mycobacteria, for example *M. tuberculosis*.
In one embodiment, the bacteria are:
*Chlamydia*, for example, *C. trachomatis*;
*Rickettsiae*, for example, *R. prowazekii*; or
*Mycoplasma*, for example, *M. pneumoniae*.

Type/Location of Infection

The infection may be associated with a particular location, organ, etc.
In one embodiment, the infection is:
a central nervous system infection;
an external ear infection;
an infection of the middle ear, including acute otitis media;
an infection of the cranial sinuses;
an eye infection;
an infection of the oral cavity, including an infection of the teeth, gums, or mucosa;
an upper respiratory tract infection;
a lower respiratory tract infection;
a genitourinary infection;
a urinary tract infection;
an intra-abdominal infection;
a gastrointestinal infection;
a gynecological infection;
septicaemia;
a bone or joint infection;
a skin or skin structure infection;
bacterial endocarditis;
a wound infection; or
a burn infection.

Prophylaxis

The treatment may be treatment as prophylaxis, for example: antibacterial prophylaxis in surgery; and antibacterial prophylaxis in immunosuppressed patients, including patients receiving cancer chemotherapy, or organ transplant patients.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

For example, treatment of bacterial infection includes the prophylaxis of bacterial infection, reducing the incidence of bacterial infection, alleviating the symptoms of bacterial infection, etc.

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

One aspect of the present invention pertains to a compound as described herein, in combination with one or more (e.g., 1, 2, 3, 4, etc.) additional therapeutic agents, for example, other anti-bacterial agents.

The particular combination would be at the discretion of the physician who would select dosages using their common general knowledge and dosing regimens known to a skilled practitioner.

The agents (i.e., the ANASIA compound described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

The agents (i.e., the compound described here, plus one or more other agents) may be formulated together in a single dosage form, or alternatively, the individual agents may be formulated separately and presented together in the form of a kit, optionally with instructions for their use.

Other Uses

The ANASIA compounds described herein may also be used as cell culture additives to inhibit bacterial aminoacyl-tRNA synthetase (e.g., bacterial leucyl-tRNA synthetase, etc.).

The ANASIA compounds described herein may also be used as part of an in vitro assay, for example, in order to determine whether a candidate host is likely to benefit from treatment with the compound in question.

The ANASIA compounds described herein may also be used as a standard, for example, in an assay, in order to identify other active compounds, other bacterial aminoacyl-tRNA synthetase inhibitors, etc.

Kits

One aspect of the invention pertains to a kit comprising (a) an ANASIA compound as described herein, or a composition comprising an ANASIA compound as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The ANASIA compound or pharmaceutical composition comprising the ANASIA compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human.

Formulations

While it is possible for an ANASIA compound to be administered alone, it is preferable to present it as a pharmaceutical formulation (e.g., composition, preparation, medicament) comprising at least one ANASIA compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising mixing at least one ANASIA compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or mixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprise a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichloro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 10 μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the ANASIA compounds, and compositions comprising the ANASIA compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular ANASIA compound, the route of administration, the time of administration, the rate of excretion of the ANASIA compound, the duration of the treatment, other drugs, compounds, and/or materials used in combination, the severity of the disorder, and the species, sex, age, weight, condition, general health, and prior medical history of the patient. The amount of ANASIA compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the ANASIA compound is in the range of about 0.1 mg to about 5000 mg (more typically about 10 mg to about 3000 mg) per kilogram body weight of the subject per day. Where the compound is a salt, an ester, an amide, a prodrug, or the like, the amount administered is calculated on the basis of the parent compound and so the actual weight to be used is increased proportionately.

General Chemical Synthesis

Methods for the chemical synthesis of ANASIA compounds are described herein may be prepared by techniques known in the art. These and/or other well-known methods may be modified and/or adapted in order to facilitate the synthesis of additional compounds described herein.

In the following general schemes, where specific reaction conditions like, temperature, duration of reaction, acids, bases, reagents, solvents, coupling agents, etc. are mentioned, it is understood that other reaction conditions like, temperature, duration of reaction, acids, bases, reagents, solvents, coupling agents, etc. may also be used and are therefore included within the scope of this disclosure.

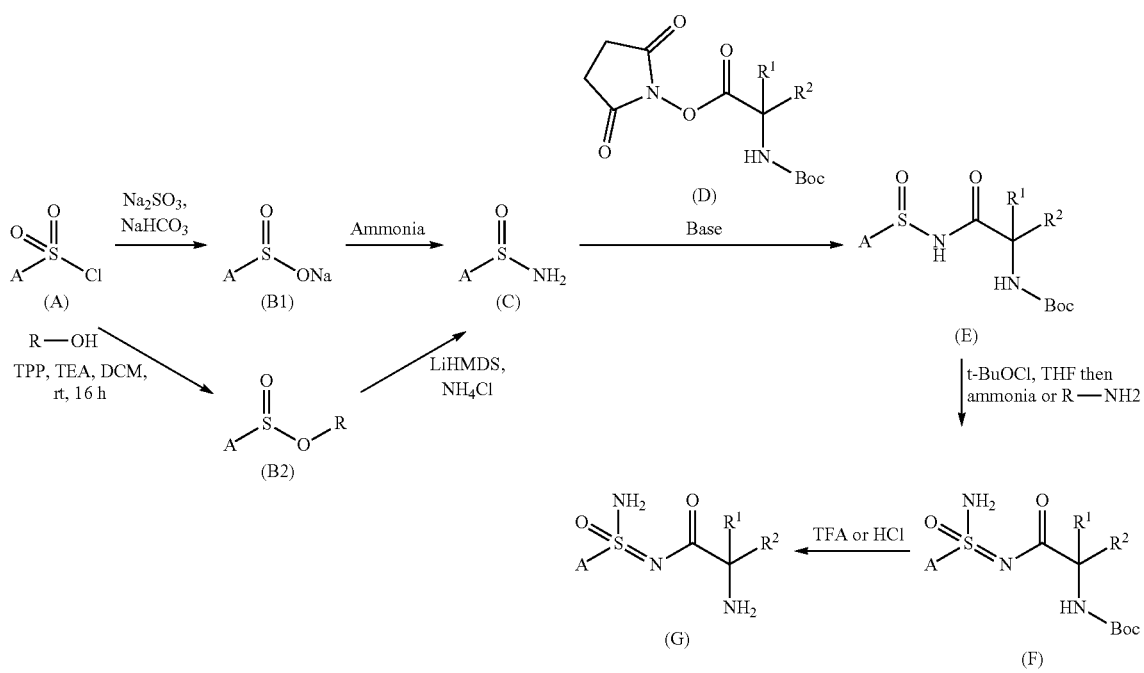

General Scheme 1

One of several possible approaches for the synthesis of sulfonimidamide derivatives of formula (G) is illustrated in the scheme shown above. By using this approach, an appropriate aryl sulfonyl chloride of formula (A) reacts with sodium sulphite and sodium carbonate in water to give the sodium sulfinate of formula (B1). This may then be converted to the aryl sulfinamide of formula (C) by reaction with oxalyl chloride or thionyl chloride followed by ammonia. Alternatively, the sulfonyl chloride of formula (A) reacts with an alcohol in the presence of a base like TEA and triphenylphosphine to give the active ester of formula (B2) which upon reaction with LiHMDS/ammonium chloride gives the compound of formula (C).

The product of formula (C) can be acylated with activated amino acid of formula (D) in the presence of suitable base to give the corresponding acylsulfinamide of formula (E). The product of formula (E) can be converted to the sulfonimidamides intermediate of formula (F) via reaction with t-butyl hypochlorite followed by reaction with appropriate amine or ammonia. The product (F) can be deprotected to give the target sulfonimidamide derivative of formula (G). Individual stereoisomers (enantiomers, diastereomers) of (G) or its precursor (F) may then be isolated by applying appropriate separation methods, if desired.

Another possible approach for the synthesis of sulfonimidamide derivatives of formula (G) is illustrated in the scheme shown above. By using this approach, the respective sulfonyl chlorides of Formula (A) are available in commercial source or can be prepared from the method known in the art. For example, the respective mercapto compound can be converted into sulphonyl chloride when reacted with sodium hypochloride and concentrated hydrochloric acid to give the sulfonyl chloride of formula (A). The sulfonyl chloride of formula (A) can be converted into sulfonamide of formula (H) when reacted with ammonia. The sulphonamide of formula (H) on treatment with TBDMS chloride and a base like sodium hydride or TEA results into formation of TBDMS protected sulfonamide of formula (1). The TBDMS protected sulfonamide of formula (1) upon reaction with freshly prepared PPh$_3$Cl$_2$ and DIPEA; followed by ammonia gives TBDMS protected sulfonimidamide intermediate of formula (J). The sulfonimidamide intermediate of formula (J) can be converted into key intermediate of formula (K) on treatment with HCl in dioxane or TFA. The intermediate of formula (K) can be acylated with activated amino acid ester of formula (D) in the presence of suitable base like DBU or sodium hydride to give the compound of formula (L) as a mixture of diastereomers. The isomers can also be separated by analytical techniques such as chiral chromatography or reverse phase HPLC. Finally, the Boc group of the intermediate of Formula (L) can be cleaved with HCl or TFA to give the final compound of Formula (G).

General Scheme 2

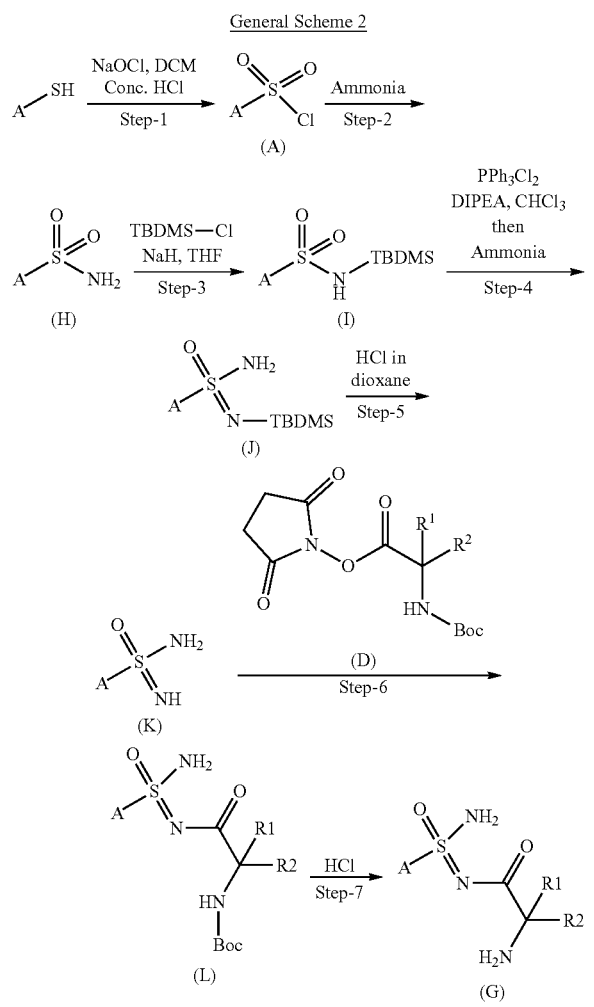

General Scheme 3

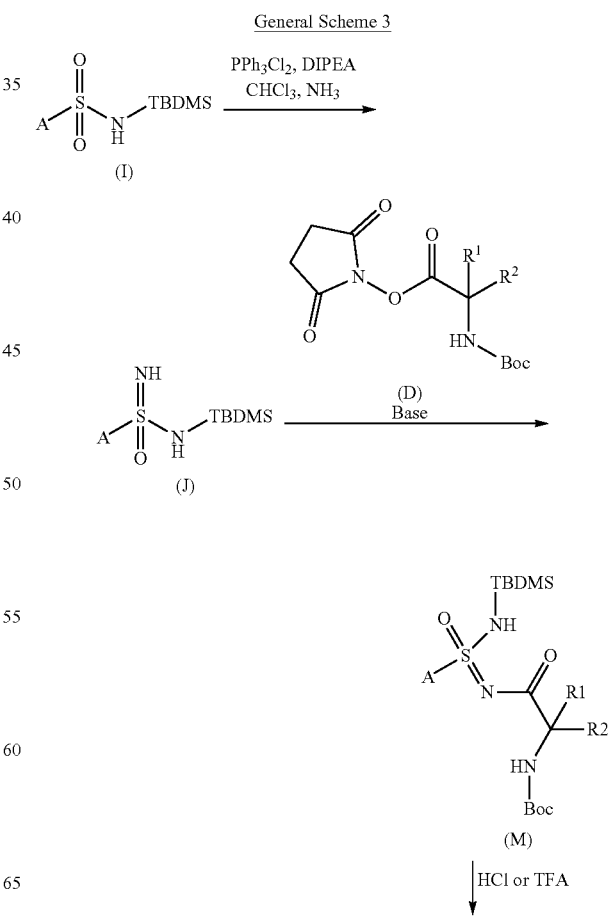

-continued

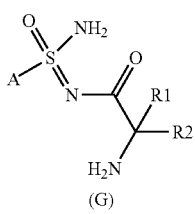

(G)

Another possible approach for the synthesis of sulfonimidamide derivatives of formula (G) is illustrated in the scheme shown above. By using this approach, the intermediate of formula (J) can be acylated with activated amino acid of formula (D) in the presence of suitable base to give the compound of formula (M) which upon de-protection using HCl or TFA gives the final compound of Formula (G).

Synthesis of 2,5-dioxopyrrolidin-1-yl (tert-butoxycarbonyl)-L-leucinate (Int-X1

To a stirred solution of N-Boc-L-leucine (2 g, 8.64 mmol) in DMF (20 mL) was added EDC.HCl (2.48 g, 12.9 mmol) followed by N-hydroxysuccinimide (1.19 g, 1.03 mmol) and stirred at room temperature for 16 h. After completion of the reaction as indicated by TLC, the reaction mixture was poured into water and extracted with ethyl acetate. The combined organic layer was washed with brine, dried over $Na_2SO_4$ and evaporated under vacuum to give the title compound, Int-X1, as an off-white solid (1.7 g, 29.82%). MS-ESI: 229.1 (M+H-Boc).

The following intermediates were made according to the procedure described for Int-X1.

Synthesis Table 1

| Structure | Compound ID | Precursor | Analytical data |
|---|---|---|---|
| 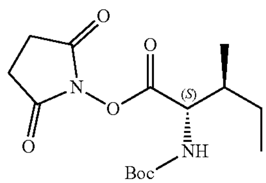 | Int-X2 | | $^1$H-NMR (400 MHz, DMSO-$d_6$) δ: 7.59 (d, 1H), 4.23 (t, 1H), 2.78 (s, 4H), 1.75 (brs, 1H); 11.45-1.60 (m, 1H), 1.40-1.20 (m, 1H), 1.38 (s, 9H), 0.95 (d, 3H), 0.84 (t, 3H) |
| 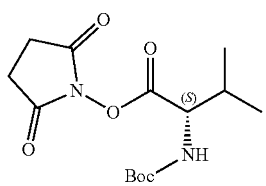 | Int-X3 | | $^1$H-NMR (400 MHz, DMSO-$d_6$) δ: 7.59 (d, 1H), 4.21 (t, 1H), 2.75 (s, 4H), 2.20-2.10 (m, 1H); 1.39 (s, 9H), 0.83 (d, 6H) |
| 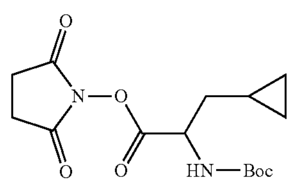 [SMILES: CC(C)(C)OC(=O)NC(CC1CC1)C(=O)ON1C(=O)CCC1=O] | Int-X4 | | MS-ESI: 227.2 (M + H − Boc) |

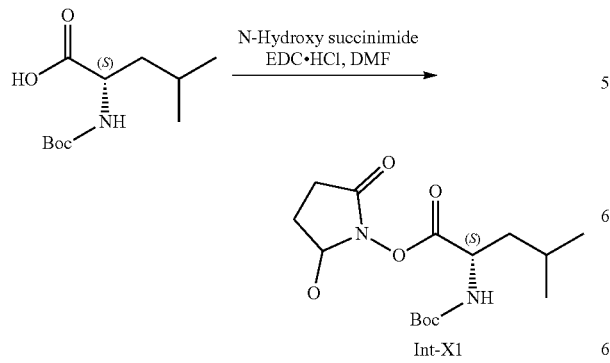

Synthesis of 2,5-dioxopyrrolidin-1-v 1-((tert-butoxycarbonyl)amino)-3-methylcyclopentane-1-carboxylate (Int-X5

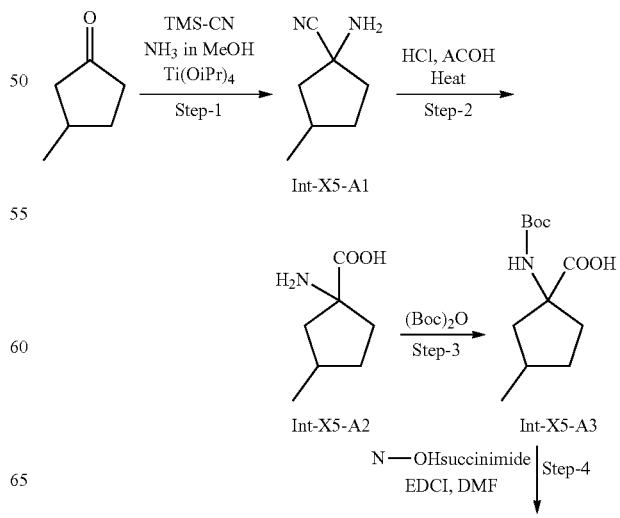

-continued

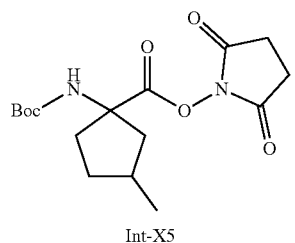

Int-X5

Step-1: To a stirred solution of titanium tetraisopropoxide (6.96 g, 24.48 mmol) and 7M methanolic ammonia (3.36 g, 197.95 mmol) was added 3-methylcyclopentan-1-one (2 g, 20.40 mmol) at 0° C. and the reaction mixture was stirred at room temperature for 4 h. Then, the reaction was cooled to −10° C. and TMS-CN (2.09 g, 21.02 mmol) was added slowly and the reaction mixture was allowed to stir at room temperature for 12 h. After completion of the reaction as indicated by TLC, the reaction mixture was filtered through a celite bed and then poured into water and extracted with dichloromethane. The combined organic layer was washed with brine, dried over $Na_2SO_4$ and evaporated under vacuum to give 1-amino-3-methylcyclopentane-1-carbonitrile as yellow oil (2.6 g, Quantitative). LCMS ESI (m/z): 125.21 (M+1)

Step-2: To a stirred solution of 1-amino-3-methylcyclopentane-1-carbonitrile (0.7 g, 5.64 mmol) in dioxane (3.5 mL) was added conc. HCl (7 mL) and stirred at 75° C. for 16 h. After completion of the reaction as indicated by TLC, the reaction mixture was evaporated under vacuum to give 1-amino-3-methylcyclopentane-1-carboxylic acid as brown solid (0.75 g, 92.9%). LCMS ESI (m/z): 144.22 (M+1)

Step-3: To a stirred solution of 1-amino-3-methylcyclopentane-1-carboxylic acid (3 g, 20.97 mmol) in dioxane (60 mL) was added 2M aqueous NaOH solution (3.36 g, 83.91 mmol) and Boc anhydride (5.49 g, 25.17 mmol) at 0° C. under nitrogen atmosphere and stirred at room temperature for 3 h. After completion of the reaction as indicated by TLC, the reaction mixture was poured into cold water and extracted with DCM to remove impurities. The pH of the aqueous layer was adjusted to slightly acidic (~6 pH) using dil. HCl and extracted with ethyl acetate. The combined organic layer was washed with brine, dried over $Na_2SO_4$ and evaporated under vacuum to give 1-((tert-butoxycarbonyl)amino)-3-methylcyclopentane-1-carboxylic acid as a yellow oil (1.73 g, 33.93%).

Step-4: To a stirred solution of 1-((tert-butoxycarbonyl)amino)-3 methyl cyclopentane-1-carboxylic acid (1.73 g, 7.1193 mmol) in DMF (17.3 mL) was added EDC.HCl (1.63 g, 8.5432 mmol) followed by N-hydroxysuccinimide (1.29 g, 8.5432 mmol) and stirred at room temperature for 3 h. After completion of the reaction as indicated by TLC, the reaction mixture was poured into water and extracted with ethyl acetate. The combined organic layer was washed with brine, dried over $Na_2SO_4$ and evaporated under vacuum to give the crude, which was further purified by column chromatography (40% ethyl acetate in hexane) to afford 2,5-dioxopyrrolidin-1-yl 1-((tert-butoxycarbonyl)amino)-3-methylcyclopentane-1-carboxylate (Int-X5) as a white solid (0.9 g, 37.19%). LCMS ESI (m/z): 341.3 (M+1).

Synthesis of 5-(difluoromethyl)thiophene-2-sulfonyl chloride (Int-Y1

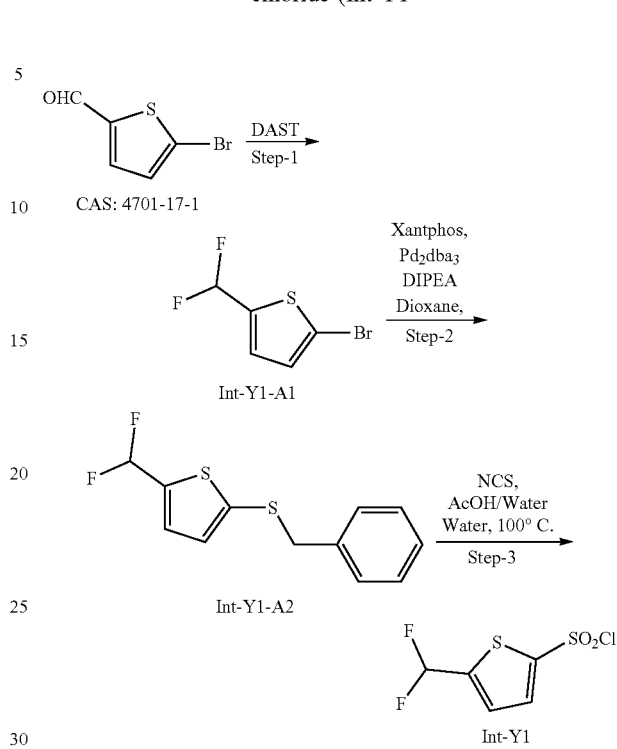

Step-1: To a cooled solution of 5-bromothiophene-2-carbaldehyde (10 g, 52.9 mmol) in DCM (20 mL), DAST (12.7 g, 78 mmol) was added and the mixture allowed to stir at room temperature overnight. The reaction mixture was quenched with ice water and extracted with ethyl acetate (3×50 mL). The combined organic layer was dried over $Na_2SO_4$ and concentrated under vacuum. The crude was purified by silica gel column chromatography to obtain Int-Y1-A1 (5.1 g, 46.36%).

Step-2: To a degassed solution of 2-bromo-5-(difluoromethyl)thiophene (1.5 g, 7 mmol) and DIPEA (1.8 g, 14 mmol) in dioxane (15 mL), Xantphos (0.40 g, 0.7 mmol), $Pd_2dba_3$ (0.32 g, 0.35 mmol) and benzyl mercaptan (0.87 g, 7 mmol) was added and the reaction mixture heated at 100° C. for 4 h. After completion of the reaction as indicated by TLC, the reaction mixture was filtered through celite and the filtrate poured into water and extracted with ethyl acetate. The combined organic layer was washed with brine, dried over $Na_2SO_4$ and evaporated under vacuum. This reaction was repeated twice and the crude product of all the three batches mixed and subjected to silica gel column chromatography to give Int-Y1-A2 (5 g, 92%).

Step-3: To a stirred solution of 2-(benzylthio)-5-(difluoromethyl)thiophene (4 g, 15.4 mmol) in acetic acid (65 mL) and water (8 mL), N-chlorosuccinimide (8.3 g, 6.2 mmol) was added in portions at room temperature and stirred for 2 h. After completion of the reaction as indicated by TLC, the reaction mixture was poured into water and extracted with ethyl acetate (3×25 mL). The combined organic layer was washed with brine, dried over $Na_2SO_4$ and evaporated under vacuum. The crude mixture was purified by silica gel column chromatography (ethyl acetate/hexane: 1:10) to give the title compound, Int-Y1, (3.1 g, 85%). It was used immediately for the next step without analysis.

Synthesis of thieno[3,2-b]thiophene-2-sulfonyl chloride (Int-Y2

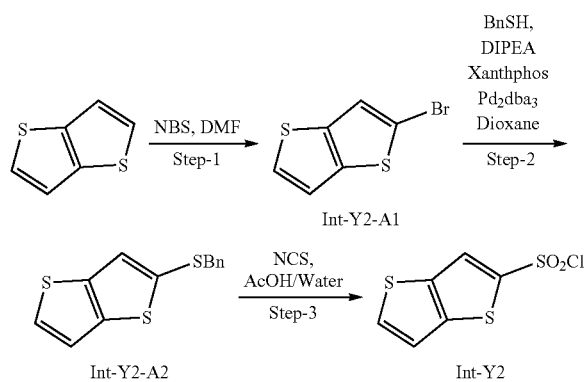

Step-1: To the solution of thieno[3,2-b]thiophene (1 g, 7.13 mmol) in DMF (8 mL) was added N-bromosuccinimide (1.27 g, 7.13 mmol) portionwise at 0° C. and the reaction mixture was allowed to stir at 0° C. for 4 h. After completion of the reaction, the reaction mixture was poured into ice cold water and extracted with ethyl acetate (2×50 mL). The combined organic layer was washed with ice cold water (4×100 mL), dried over $Na_2SO_4$ and evaporated under vacuum to give Int-Y2-A1 (1.2 g, 76%). $^1$H NMR (400 MHz, DMSO-$d_6$) δ 7.74 (d, J=5.2 Hz, 1H), 7.66 (s, 1H), 7.41 (d, J=5.2 Hz, 1H).

Step-2-3: Made according to the procedure described for Int-Y1 (Step-2-3).

Synthesis of 5-chlorothiophene-3-sulfonyl chloride (Int-Y3

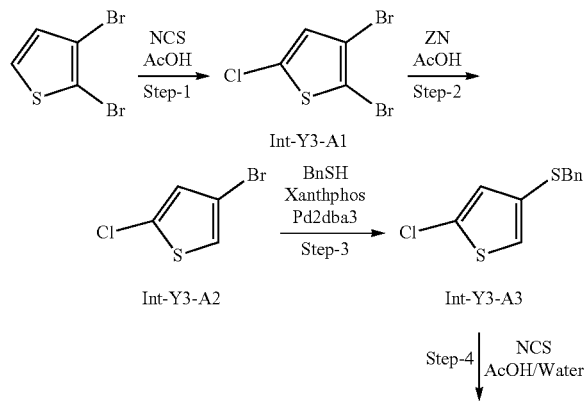

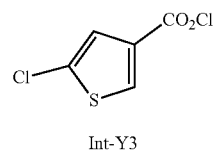

Step-1: To the solution of 2,3-dibromothiophene (10 g, 41.33 mmol) in acetic acid (100 mL) was added N-Chlorosuccinimide (5.84 g, 43.81 mmol) portion wise and the reaction mixture refluxed for 3 h. After completion of the reaction as indicated by TLC, the reaction mixture was poured into water (500 mL) and extracted with ethyl acetate (500 mL). The organic layer was washed with dilute NaOH solution (3×500 mL), brine (500 mL) and dried over $Na_2SO_4$ and evaporated under vacuum to give Int-Y3-A1 (10.1 g, 88%). $^1$H NMR (400 MHz, CDCl$_3$) δ 6.80 (s, 1H).

Step-2: To the suspension of 2,3-dibromo-5-chlorothiophene (7.2 g, 26.05 mmol) in acetic acid (80 mL) was added Zn dust (17 g, 260.51 mmol) and reaction mixture was heated at 100° C. for 16 h. After 16 h heating, the reaction mixture was filtered through celite and the filtrate partitioned between water (300 mL) and ethyl acetate (300 mL). The organic layer was washed with saturated solution of sodium bicarbonate (5×300 mL), dried over $Na_2SO_4$ and evaporated under vacuum to give Int-Y3-A2 (4.5 g, 82%). $^1$H NMR (400 MHz, CDCl$_3$) δ 7.05 (d, J=1.6 Hz, 1H) 6.88 (d, J=1.6 Hz, 1H).

Step-3: To a degassed solution of 4-bromo-2-chlorothiophene (2 g, 10.12 mmol) and DIPEA (2.61 g, 20.25 mmol) in dioxane (20 mL) was added Xantphos (0.586 g, 1.01 mmol), Pd$_2$dba$_3$ (0.463 g, 0.5 mmol) and benzyl mercaptan (1.25 g, 10.12 mmol) and the reaction mixture heated at 100° C. overnight. After completion of the reaction as indicated by TLC, the reaction mixture was filtered through celite and the filtrate poured into water and extracted with ethyl acetate (2×70 mL). The combined organic layer was washed with brine (2×150 mL), dried over $Na_2SO_4$ and evaporated under vacuum to give Int-Y3-A3. (1.5 g, 62%). LCMS ESI (m/z): 240.6 (M+H) (yield over 3 steps (32.44%).

Step-4: To a stirred solution of 4-(benzylthio)-2-chlorothiophene (1.13 g, 4.70 mmol) in acetic acid (22.6 mL) and water (2.26 mL) was added N-chlorosuccinimide (1.88 g, 14.12 mmol) in portions at room temperature and stirred for 3 h. After completion of the reaction as indicated by TLC, the reaction mixture was evaporated under vacuum to remove acetic acid then partitioned between water (50 mL) and ethyl acetate (50 mL). The organic layer was washed with water (50 mL), dried over $Na_2SO_4$ and evaporated under vacuum. The crude product was subjected to silica gel column chromatography to give the title compound, Int-Y3 (0.79 g, 77.8%).

Synthesis of thieno[3,2-b]thiophene-3-sulfonyl chloride (Int-Y4

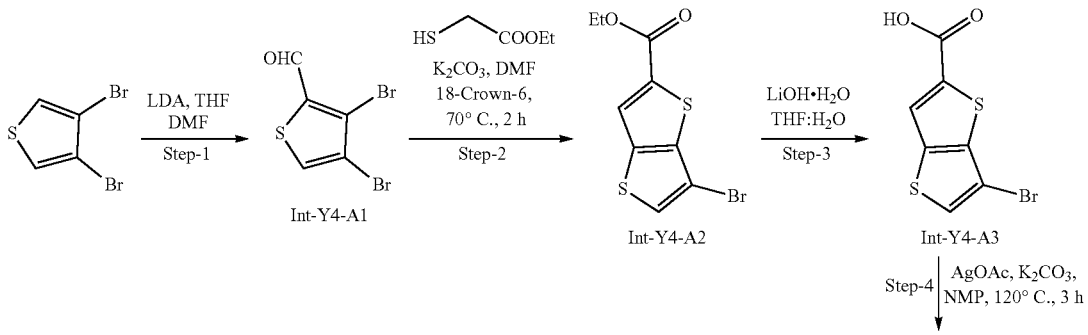

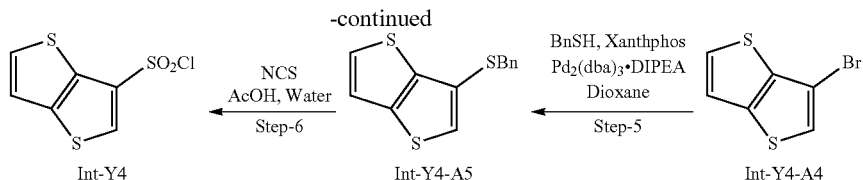

Step-1: To the solution of 3,4-dibromothiophene (15 g, 62.00 mmol) in THF (150 mL) was added lithium diisopropylamide (2M in THF) (62 mL, 123.96 mmol) at −78° C. and the reaction mixture allowed to stir at −78° C. for 2 h. DMF (5.77 mL, 74.38 mmol) was added dropwise to the reaction mixture and then allowed to stir at room temperature for an additional 1 h. After completion of the reaction as indicated by TLC, the reaction mixture was poured into NH$_4$Cl solution (500 mL) and extracted with ethyl acetate (500 mL). The organic layer was dried over Na$_2$SO$_4$ and evaporated under vacuum. The crude product was subjected to silica gel column chromatography to give 3,4-dibromothiophene-2-carbaldehyde (11 g, 65%). $^1$H NMR (400 MHz, DMSO-d$_6$) δ 9.85 (s, 1H), 8.46 (s, 1H).

Step-2: To the solution of 3,4-dibromothiophene-2-carbaldehyde (11 g, 40.74 mmol) in DMF (110 mL) was added ethyl thioglycolate (6 g, 48.88 mmol), potassium carbonate (17 g, 123.9 mmol) and 18-Crown-6 (1 g, 4.03 mmol). The reaction mixture was allowed to stir at 70° C. for 2 h. After completion of the reaction as indicated by LCMS, the reaction mixture was poured into ice cold water (200 mL). The solid was filtered and washed with water. The residue was dried under vacuum to give 6-bromothieno [3, 2-b] thiophene-2-carboxylate (12.5 g, Quantitative). $^1$H NMR (400 MHz, DMSO-d$_6$) δ 8.31 (s, 1H), 8.12 (s, 1H), 4.33 (q, J=7.1 Hz, 1H), 1.32 (t, J=6.8 Hz, 3H).

Step-3: To the solution of ethyl 6-bromothieno [3,2-b] thiophene-2-carboxylate (12.5 g, 42.94 mmol) in THF: Water (1:1) (120 mL) was added lithium hydroxide monohydrate (5.4 g, 129.26 mmol) and the reaction mixture heated at 70° C. for 3 h. After completion of the reaction as indicated by TLC, the reaction mixture was poured into water (200 mL) and acidified with 1N HCl (pH ~4), white precipitates were obtained which were filtered and dried under vacuum to give 6-bromothieno[3,2-b]thiophene-2-carboxylic acid (8.6, 76%). $^1$H NMR (400 MHz, DMSO-d$_6$) δ 13.54 (s, 1H), 8.21 (s, 1H), 8.08 (s, 1H).

Step-4: To a degassed solution of 6-bromothieno[3,2-b]thiophene-2-carboxylic acid (4.3 g, 16.34 mmol) in N-Methyl-2-pyrrolidone (45 mL) was added potassium carbonate (0.33 g, 2.45 mmol) and silver acetate (0.27 g, 1.63 mmol). The reaction mixture was heated at 120° C. for 3 h. After completion of the reaction as indicated by TLC, the reaction mixture was poured into water (200 mL) and extracted with ethyl acetate (2×200 mL). The combined organic layer was washed with brine (4×200 mL), dried over Na$_2$SO$_4$ and evaporated under vacuum. The crude product was subjected to silica gel column chromatography to give 3-bromothieno[3,2-b]thiophene (3 g, 41.89%). $^1$H NMR (400 MHz, DMSO-d$_6$) δ 7.82 (s, 1H), 7.79 (d, J=5.1 Hz, 1H), 7.56 (d, J=5.1 Hz, 1H).

Step-5: To a degassed solution of 3-bromothieno[3,2-b]thiophene (3.6 g, 16.43 mmol) and DIPEA (4.25 g, 32.86 mmol) in dioxane (36 mL) was added Xantphos (0.95 g, 1.64 mmol), Pd$_2$dba$_3$ (0.75 g, 0.82 mmol) and benzyl mercaptan (2.04 g, 16.43 mmol). The reaction mixture was heated at 100° C. for 3 h. After completion of the reaction as indicated by TLC, the reaction mixture was filtered through celite and the filtrate poured into water (100 mL) and extracted with ethyl acetate (2×100 mL). The combined organic layer was washed with brine (2×200 mL), dried over Na$_2$SO$_4$ and evaporated under vacuum. The crude product was subjected to silica gel column chromatography to give Int-Y4-A5 (3.4 g, 78.86%). $^1$H NMR (400 MHz, DMSO-d$_6$) δ 7.71 (d, J=5.2, 1H), 7.53 (s, 1H), 7.46 (d, J=5.2 Hz, 1H), 7.29-7.21 (m, 5H), 4.23 (s, 2H).

Step-6: To a stirred solution of 3-(benzylthio)thieno[3,2-b]thiophene (3.4 g, 12.95 mmol) in acetic acid (68 mL) and water (6.8 mL) was added N-chlorosuccinimide (5.18 g, 38.87 mmol) in portions at room temperature. The reaction mixture was stirred for 2 h. After completion of the reaction as indicated by TLC, the reaction mixture was evaporated under vacuum and then partitioned between water (150 mL) and ethyl acetate (150 mL). The organic layer was washed with water (150 mL), dried over Na$_2$SO$_4$ and evaporated under vacuum. The crude product was subjected to silica gel column chromatography to give the title compound, Int-Y4 (2.9 g, 93.75%).

Synthesis of benzo[d][1,3]dioxole-5-sulfonyl chloride (Int-Y5

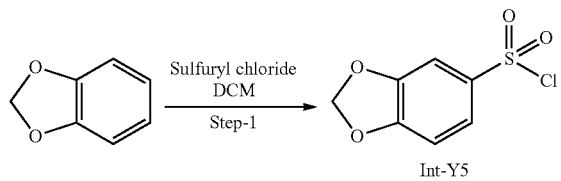 [SMILES: c1ccc2c(c1)OCO2 ; O=S(=O)(Cl)c1ccc2c(c1)OCO2]

Step-1: To a solution of benzo[d][1,3]dioxole (5 g) in DCM (50 mL) was added sulfuryl chloride (3 mL) at 0° C. and stirred for 5 min. After completion of the reaction as indicated by TLC, the reaction mixture was poured into ice water and extracted with ethyl acetate. The combined organic layer was washed with brine, dried over Na$_2$SO$_4$ and evaporated under vacuum to give the title compound, Int-Y5, as a liquid (3 g, 33.2%).

Synthesis of 4,5-dichlorothiophene-3-sulfonyl chloride (Int-Y6

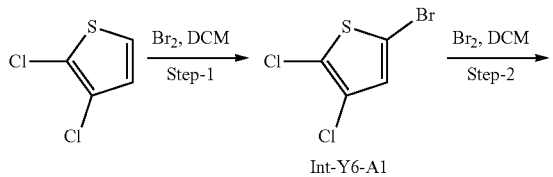

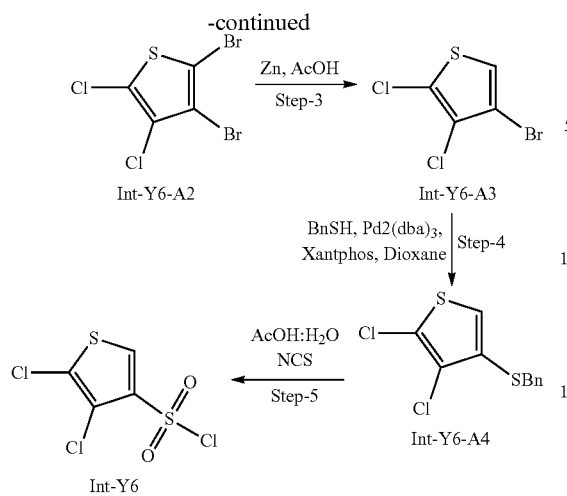

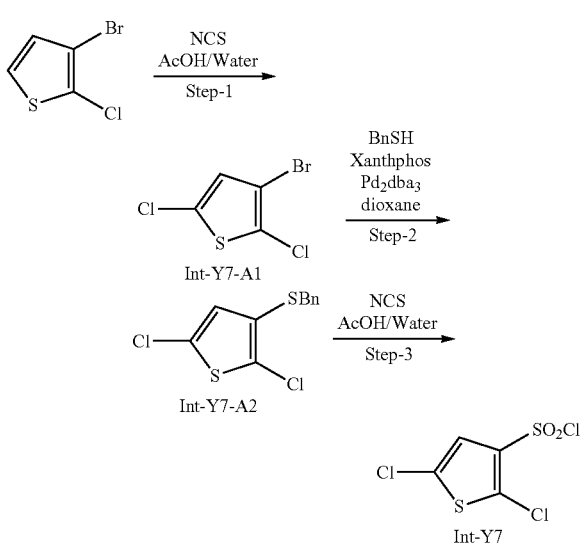

Synthesis of 2,5-dichlorothiophene-3-sulfonyl chloride (Int-Y7

Step-1: To a solution of 2,3-dichlorothiophene (10 g, 65.34 mmol) in CH$_2$Cl$_2$ (100 mL) was added bromine (10.10 mL, 196.0 mmol) at 0° C. and the reaction mixture allowed to stir at room temperature for overnight. After completion of the reaction as indicated by TLC, the reaction mixture was poured into saturated sodiumthiosulfate solution (200 mL) and extracted with DCM (2×200 mL). The combined organic layer was washed with sodium thiosulfate solution (200 mL), brine (200 mL) and dried over Na$_2$SO$_4$ and evaporated under vacuum to give Int-Y6-A1 (15 g, 98.98%).

Step-2: To the solution of 5-bromo-2,3-dichlorothiophene (15 g, 64.67 mmol) in CH$_2$Cl$_2$ (150 mL) was added bromine (10.0 mL, 194.0 mmol) at 0° C. and the reaction mixture allowed to stir at room temperature for 72 h. After completion of the reaction as indicated by TLC, the reaction mixture was poured into saturated sodiumthiosulphate solution (250 mL) and extracted with DCM (2×300 mL). The combined organic layer was dried over Na$_2$SO$_4$ and evaporated under vacuum. The crude was purified by silica gel column chromatography to give Int-Y6-A2 (15.5 g, 75.20%).

Step-3: To the suspension of 4,5-dibromo-2,3-dichlorothiophene (10 g, 26.23 mmol) in acetic acid (50 mL), Zn dust (8.56 g, 131.11 mmol) was added and the reaction mixture heated at 100° C. overnight. The reaction mixture was filtered through celite and the filtrate partitioned between water (300 mL) and ethyl acetate (500 mL). The organic layer was washed with saturated solution of sodium bicarbonate (5×300 mL), dried over Na$_2$SO$_4$ and evaporated under vacuum to give crude product. The crude product was purified by silica gel column chromatography to give Int-Y6-A3 (5.76 g, 77.19%).

Step-4: To a degassed solution of 4-bromo-2,3-dichlorothiophene (3 g, 12.93 mmol) and DIPEA (5.53 g, 32.33 mmol) in dioxane (30 mL), Xantphos (1.49 g, 2.58 mmol), Pd$_2$dba$_3$ (1.18 g, 12.93 mmol) and benzyl mercaptan (2.4 g, 19.40 mmol) was added and the reaction mixture heated at 100° C. overnight. After completion of the reaction as indicated by TLC, the reaction mixture was filtered through celite and the filtrate was poured into water and extracted with ethyl acetate. The combined organic layer was washed with brine, dried over Na$_2$SO$_4$ and evaporated under vacuum. The crude mixture was purified by silica gel column chromatography to give Int-Y6-A4 (2.5 g, 70.23%).

Step-5: To a stirred solution of 4-(benzylthio)-2,3-dichlorothiophene (3 g, 10.90 mmol) in acetic acid (27 mL) and water (3 mL), N-chlorosuccinimide (4.36 g, 32.70 mmol) was added in portions at room temperature and stirred for 1 h. After completion of the reaction as indicated by TLC, the reaction mixture was poured into water and extracted with ethyl acetate (3×25 mL). The combined organic layer was washed with brine, dried over Na$_2$SO$_4$ and evaporated under vacuum give the title compound, Int-Y6, (3.81 g, Quantitate). It was used immediately for the next step without analysis.

Step-1: To a solution of 3-bromo-2-chlorothiophene (5.0 g, 25.3 mmol) in AcOH (5 mL) was added N-chlorosuccinimide (3.58 g, 26.8 mmol) and the mixture was heated at 100° C. for 4 h. After completion of the reaction as indicated by TLC, the reaction mixture was quenched with ice water and extracted with ethyl acetate (3×50 mL). The combined organic layer was dried over Na$_2$SO$_4$ and concentrated under vacuum. The crude was purified by silica gel column chromatography to obtain Int-Y7-A1 (5.2 g, 97.96%). $^1$H NMR (400 MHz, DMSO) δ 7.36 (s, 1H).

Step-2: To a degassed solution of 3-bromo-2,5-dichlorothiophene (5.0 g, 21.5 mmol) and DIPEA (2.55 mL, 32.3 mmol) in dioxane (20 mL) was added Xantphos (2.49 g, 4.31 mmol), Pd$_2$(dba$_3$) (1.97 g, 2.15 mmol) and benzyl mercaptan (2.55 mL, 32.3 mmol). The reaction mixture was heated at 100° C. for 16 h. After completion of the reaction as indicated by TLC, the reaction mixture was filtered through celite and the filtrate poured into water (100 mL) and extracted with ethyl acetate (3×100 mL). The combined organic layer was washed with brine, dried over Na$_2$SO$_4$ and evaporated under vacuum to give Int-Y7-A2 (5 g, 84.75%). $^1$H NMR (400 MHz, DMSO): δ 7.32-7.23 (m, 6H), 4.21 (s, 2H).

Step-3: To a stirred solution of 3-(benzylthio)-2,5-dichlorothiophene (3.86 g, 14.0 mmol) in acetic acid (25 mL) and water (5 mL) was added N-chlorosuccinimide (5.61 g, 42.0 mmol) in portions at room temperature and stirred for 1 h. After completion of the reaction as indicated by TLC, the reaction mixture was poured into water (25 mL) and extracted with ethyl acetate (3×25 mL). The combined organic layer was washed with brine, dried over Na$_2$SO$_4$ and evaporated under vacuum to give Int-Y7. The crude mixture was used immediately for the next step without analysis.

The following intermediates were made according to the procedure described for Int-Y1.

Synthesis Table 2

| Structure | Compound ID | Precursor | Analytical data |
|---|---|---|---|
| benzo[b]thiophene-3-sulfonyl chloride structure | benzo[b]thiophene-3-sulfonyl chloride | 3-bromobenzo[b]thiophene structure | Used without analysis |
| [1,1'-biphenyl]-3-sulfonyl chloride structure | [1,1'-biphenyl]-3-sulfonyl chloride | 3-bromo-1,1'-biphenyl structure | Used without analysis |

Synthesis of benzenesulfinamide (Int-A-2.1

Synthesis of sodium thiophene-2-sulfinate (Int-A-2.20

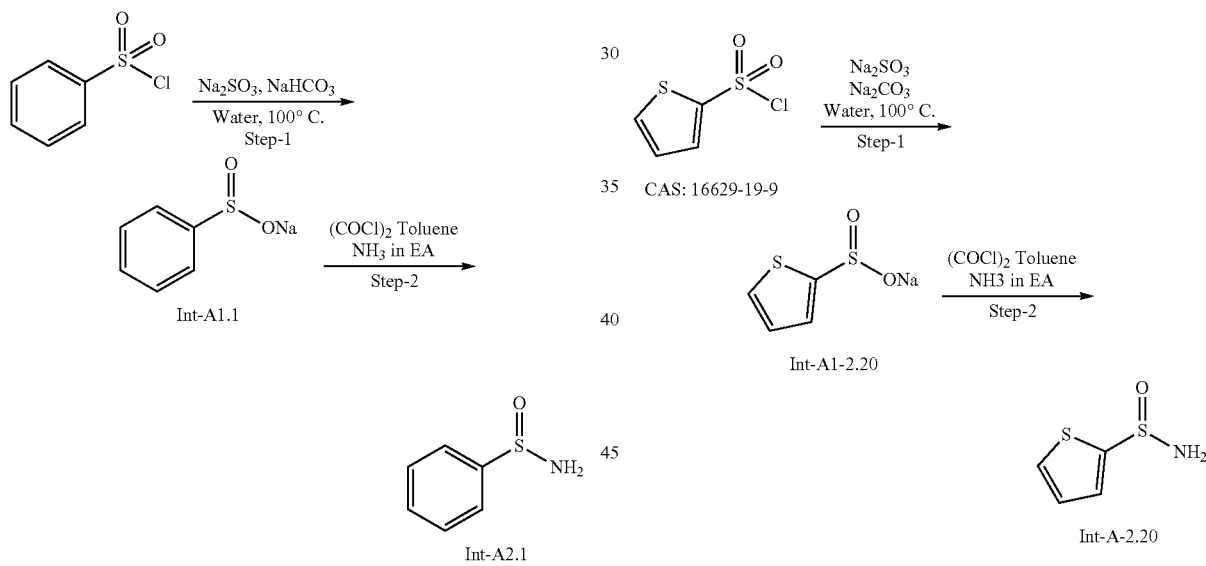

Step-1: A mixture of benzenesulfonyl chloride (15 g, 84 mmol), sodium sulphite (21.4 g, 160 mmol) and sodium bicarbonate (14.1 g, 16 mmol) in water (60 mL) was heated at 100° C. for 1 h. After completion of the reaction, water was removed under vacuum. The solid was refluxed in ethanol (150 mL) for 30 min and filtered. The filtrate was concentrated under vacuum to obtain Int-A-1.1 as a white solid (13 g, 94%). MS-ESI (−ve): 140.9 (M−Na).

Step-2: Oxalyl chloride (6 mL, 66 mmol) was added drop-wise to a stirring suspension of sodium benzenesulfinate (10 g, 60 mmol) in toluene (100 mL) at 0° C. and allowed to stir at room temperature for 2 h. A mixture of 30% aqueous ammonia (60 mL) and ethyl acetate (60 mL) was added to the reaction mixture and stirred for additional 1 h. After completion of the reaction as indicated by TLC the reaction mixture was poured into water and extracted with ethyl acetate. The combined organic layer was washed with brine, dried over Na₂SO₄ and evaporated under vacuum to give the title compound, Int-A-2.1, as an off-white solid (5.5 g, 65%). MS-ESI: 142.04 (M+H).

A mixture of thiophene-2-sulfonyl chloride (5 g, 27 mmol), sodium sulphite (6.9 g, 54 mmol) and sodium bicarbonate (5.8 g, 54 mmol) in water (30 mL) were heated at 100° C. for 1 h. After completion of the reaction, water was removed under vacuum. The solid was refluxed in ethanol (50 mL) for 30 min and filtered. The filtrate was concentrated under vacuum to obtain Int-A1-2.20 as a white solid (5 g, 100%). It was used further in the next step.

Oxalyl chloride (4.48 mL, 35 mmol) was added drop-wise to a stirring suspension of sodium thiophene-2-sulfinate (5 g, 29 mmol) in toluene (20 mL) at 0° C. and the mixture was allowed to stir at room temperature for 1 h. A mixture of 30% aqueous ammonia (20 mL) and ethyl acetate (20 mL) was added to the reaction mixture and stirred for additional 1 h. After completion of the reaction as indicated by TLC, the reaction mixture was poured into water and extracted with ethyl acetate. The combined organic layer was washed with brine, dried over Na₂SO₄ and evaporated under vacuum to give the title compound, Int-A-2.20, as an off-white solid (3 g, 69%). LCMS ESI (m/z): 148.1 (M+H).

The following intermediates were made according to the procedure described for Int-A-2.1.

Synthesis Table 3

| Structure | Compound ID | Precursor | Analytical data |
|---|---|---|---|
| 4-chlorophenyl sulfinamide | Int-A-2.4 | 4-chlorobenzenesulfonyl chloride | LCMS ESI (m/z): 175.8 (M + H) |
| 3-fluorophenyl sulfinamide | Int-A-2.5 | 3-fluorobenzenesulfonyl chloride | LCMS ESI (m/z): 159.9 (M + H) |
| 3,4-dichlorophenyl sulfinamide | Int-A-2.6 | 3,4-dichlorobenzenesulfonyl chloride | $^1$H NMR (400 MHz, DMSO-$d_6$) δ 7.80 (d, J = 8.4 Hz 1H), 7.79 (s, 1H), 7.59 (d, J = 8.4 Hz, 1H), 6.49 (s, 2H) |
| 2,3-dichlorophenyl sulfinamide | Int-A-2.7 | 2,3-dichlorobenzenesulfonyl chloride | LCMS ESI (m/z): 209.9 & 211.9 (M + H) |
| 2,5-difluorophenyl sulfinamide | Int-A-2.8 | 2,5-difluorobenzenesulfonyl chloride | LCMS ESI (m/z): 178.0 (M + H) |
| 3-methylphenyl sulfinamide | Int-A-2.9 | 3-methylbenzenesulfonyl chloride | LCMS ESI (m/z): 156.1 (M + H) |
| 4-methylphenyl sulfinamide | Int-A-2.10 | 4-methylbenzenesulfonyl chloride | LCMS ESI (m/z): 156.1 (M + H) |
| 4-methoxy-3-methylphenyl sulfinamide | Int-A-2.11 | 4-methoxy-3-methylbenzenesulfonyl chloride | $^1$H NMR (400 MHz, DMSO-$d_6$) δ 7.45 (dd, J = 8.4 Hz, 1H), 7.43 (s, 1H), 7.05 (d, J = 8.4 Hz, 1H), 6.09 (s, 2H), 3.81 (s, 3H), 2.18 (s, 3H) |
| 4-fluoro-2-methylphenyl sulfinamide | Int-A-2.12 | 4-fluoro-2-methylbenzenesulfonyl chloride | $^1$H NMR (400 MHz, DMSO-$d_6$) δ 7.84 (dd, 1H), 7.22 (ddd, 1H), 7.14 (dd, 1H), 6.06 (s, 2H), 2.36 (s, 3H) |

Synthesis Table 3

| Structure | Compound ID | Precursor | Analytical data |
|---|---|---|---|
| 4-methoxyphenyl sulfinamide | Int-A-2.13 | 4-methoxybenzenesulfonyl chloride | ¹H NMR (400 MHz, DMSO-d₆) δ 7.54 (d, J = 8.8 Hz, 2H), 7.06 (d, J = 8.8 Hz, 2H), 6.13 (s, 2H), 3.75 (s, 3H) |
| 3-isopropylphenyl sulfinamide | Int-A-2.14 | 3-isopropylbenzenesulfonyl chloride | LCMS ESI (m/z): 184.0 (M + H) |
| 3-tert-butylphenyl sulfinamide | Int-A-2.15 | 3-tert-butylbenzenesulfonyl chloride | LCMS ESI (m/z): 198.5 (M + H) |
| 3-cyanophenyl sulfinamide | Int-A-2.16 | 3-cyanobenzenesulfonyl chloride | LCMS ESI (m/z): 167.0 (M + H) |
| 2,3-dihydrobenzofuran-5-yl sulfinamide | Int-A-2.17 | 2,3-dihydrobenzofuran-5-sulfonyl chloride | ¹H NMR (400 MHz, DMSO-d₆) δ 7.47 (S, 1H), 7.36 (dd, J = 8.4 Hz, 1H), 6.86 (d, J = 8.4 Hz, 1H), 6.08 (s, 2H), 4.58 (t, J = 8.8 Hz, 2H), 3.21 (t, J = 8.8 Hz, 2H) |
| 3-bromophenyl sulfinamide | Int-A-2.18 | 3-bromobenzenesulfonyl chloride | LCMS ESI (m/z): 220.0 & 222.0 (M + H) |
| biphenyl-3-sulfinamide | Int-A-2.19 | biphenyl-3-sulfonyl chloride | LCMS ESI (m/z): 217.1 (M + H) |
| thiophene-3-sulfinamide | Int-A-2.21 | thiophene-3-sulfonyl chloride | LCMS ESI (m/z): 148.0 (M + H) |
| 5-chlorothiophene-2-sulfinamide | Int-A-2.22 | 5-chlorothiophene-2-sulfonyl chloride | LCMS ESI (m/z): 181.8 (M + H) |

Synthesis Table 3

| Structure | Compound ID | Precursor | Analytical data |
|---|---|---|---|
| 3-chlorothiophene-2-sulfinamide | Int-A-2.23 | 3-chlorothiophene-2-sulfonamide | LCMS ESI (m/z): 181.90 (M + H) |
| 5-methylthiophene-2-sulfinamide | Int-A-2.24 | 5-methylthiophene-2-sulfonyl chloride | ¹H NMR (400 MHz, DMSO-d₆) δ 7.09 (d, J = 3.6 Hz, 1H), 6.85 (d, 1H), 6.50 (s, 2H), 2.46 (s, 3H). |
| 3-methylthiophene-2-sulfinamide | Int-A-2.25 | 3-methylthiophene-2-sulfonyl chloride | LCMS ESI (m/z): 161.9 (M + H) |
| 5-(difluoromethyl)thiophene-2-sulfinamide | Int-A-2.26 | 5-(difluoromethyl)thiophene-2-sulfonyl chloride | ¹H NMR (400 MHz, DMSO-d₆) δ 7.44-7.42 (m, 1H), 7.32-7.30 (m, 1H), 6.85 (t, J = 55.6 Hz, 1H), 4.65 (s, 2H) |
| naphthalene-1-sulfinamide | Int-A-2.27 | naphthalene-1-sulfonyl chloride | LCMS ESI (m/z): 192.4 (M + H) |
| naphthalene-2-sulfinamide | Int-A-2.28 | naphthalene-2-sulfonyl chloride | LCMS ESI (m/z): 192.3 (M + H) |
| 4-chloronaphthalene-1-sulfinamide | Int-A-2.29 | 4-chloronaphthalene-1-sulfonyl chloride | ¹H NMR (400 MHz, DMSO-d₆) δ 8.30-8.26 (m, 2H), 8.05 (d, J = 7.6 Hz, 1H), 7.90 (d, J = 7.6 Hz, 1H), 7.80-7.73 (m, 2H), 6.37 (s, 2H) |
| 4-fluoronaphthalene-1-sulfinamide | Int-A-2.30 | 4-fluoronaphthalene-1-sulfonyl chloride | LCMS ESI (m/z): 207.8 (M + H) |
| 3-(4-chlorophenoxy)benzenesulfinamide | Int-A-2.31 | 3-phenoxybenzenesulfonyl chloride | LCMS ESI (m/z): 268.1 (M + H) |

Synthesis Table 3

| Structure | Compound ID | Precursor | Analytical data |
|---|---|---|---|
| (benzothiophene-3-sulfinamide) | Int-A-2.32 | (benzothiophene-3-sulfonyl chloride) | LCMS ESI (m/z): 198.16 (M + H) |
| (benzothiophene-2-sulfinamide) | Int-A-2.33 | (benzothiophene-2-sulfonyl chloride) | $^1$H NMR (400 MHz, DMSO-d$_6$) δ 8.10-8.00 (m, 1H), 7.94-7.92 (m, 1H), 7.68 (s, 1H), 7.45-7.40 (m, 2H), 6.75 (S, 2H) |
| (thieno[3,2-b]thiophene-2-sulfinamide) | Int-A-2.35 | (thieno[3,2-b]thiophene-2-SO$_2$Cl) | LCMS ESI (m/z): 204.2 (M + H) |
| (2-methylbenzenesulfinamide) | Int-A-2.36 | (2-methylbenzenesulfonyl chloride) | LCMS ESI (m/z): 156.2 (M + H) |
| (2-fluorobenzenesulfinamide) | Int-A-2.37 | (2-fluorobenzenesulfonyl chloride) | LCMS ESI (m/z): 160.1 (M + H) |
| (3-(difluoromethoxy)benzenesulfinamide) | Int-A-2.38 | (3-(difluoromethoxy)benzenesulfonyl chloride) | $^1$H NMR (400 MHz, DMSO) δ 7.59 (t, J = 8 Hz, 1H), 7.54-7.32 (m, 2H), 7.32 (t, J = 66 Hz, 1H), 6.40 (s, 2H) |
| (3-(trifluoromethyl)benzenesulfinamide) | Int-A-2.39 | (3-(trifluoromethyl)benzenesulfonyl chloride) | LCMS ESI (m/z): 210.1 (M + H) |
| (3-(trifluoromethoxy)benzenesulfinamide) | Int-A-2.40 | (3-(trifluoromethoxy)benzenesulfonyl chloride) | LCMS ESI (m/z): 226.1 (M + H) |
| (5-chlorothiophene-3-sulfinamide) | Int-A-2.41 | (5-chlorothiophene-3-SO$_2$Cl) | LCMS ESI (m/z): 182.1 (M + H) |

Synthesis Table 3

| Structure | Compound ID | Precursor | Analytical data |
|---|---|---|---|
| (thienothiophene sulfinamide) | Int-A-2.42 | (thienothiophene SO₂Cl) | LCMS ESI (m/z): 204.1 (M + H) |
| (benzodioxole sulfinamide) | Int-A-2.43 | (benzodioxole SO₂Cl) | LCMS ESI (m/z): 186.33 (M + H) |
| (dichlorothiophene sulfinamide) | Int-A-2.45 | (dichlorothiophene SO₂Cl) | LCMS ESI (m/z): 216.0 & 218.1 (M & M + 2) |
| (dichlorothiophene sulfinamide) | Int-A-2.46 | (dichlorothiophene SO₂Cl) | LCMS ESI (m/z): 217.9 (M + H) |

Synthesis of 3-chloro-2-fluorobenzenesulfinamide (Int-A-2.2

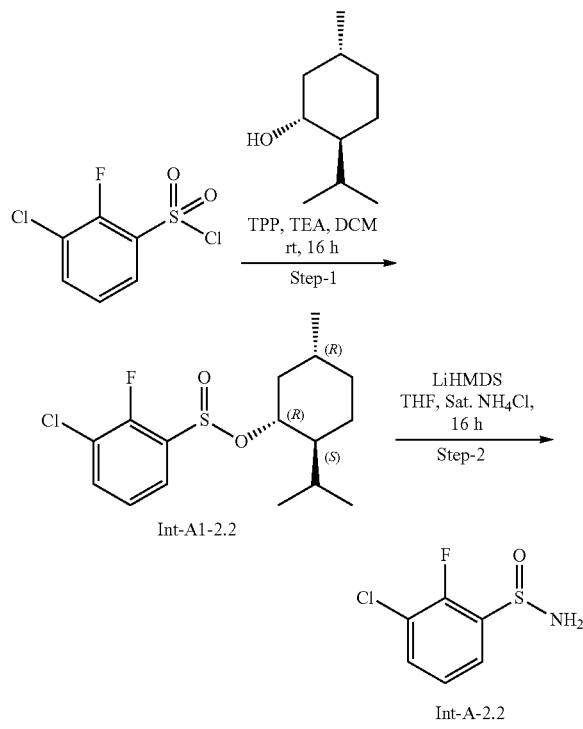

Step-1: To a stirred solution of 3-chloro-2-fluorobenzenesulfonyl chloride (5 g, 21.8 mmol) in DCM (50 mL), TEA (30.41 mL, 218.2 mmol), L-Menthol (3.4 g, 21.8 mmol) and triphenylphosphine (5.72 g, 21.8 mmol) were added at 0° C. and stirred for 16 h at room temperature. After completion of the reaction as indicated by TLC, the reaction mixture was poured into water and extracted with DCM. The combined organic layer was washed with brine, dried over $Na_2SO_4$ and evaporated under vacuum. The crude was purified by silica gel column chromatography (ethyl acetate/hexane: 1:9) to give Int-A1-2.2 as a solid (4 g, 55.09%). LCMS ESI (m/z): 349.8 (M+18).

Step-2: To a stirred solution of Int-A1-2.2 (4 g, 12.01 mmol) in THF (40 mL) was added 1 M LiHMDS in THF (3.50 mL, 18.02 mmol) at 0° C. and allowed to stir at 0° C. for 1.5 h. Saturated $NH_4Cl$ solution (32 mL) was added to the reaction mixture at 0° C. and stirred for additional 5 h at room temperature. After completion of the reaction as indicated by TLC, the reaction mixture was poured into water and extracted with ethyl acetate. The combined organic layer was washed with brine, dried over $Na_2SO_4$ and evaporated under vacuum to give the title compound, Int-A-2.2, as an off-white solid (1.5 g, 65.21%). LCMS ESI (m/z): 193.9 and 195.9 (M+H).

The following intermediates were made according to the procedure described for Int-A-2.2.

Synthesis Table 4

| Structure | Compound ID | Precursor | Analytical data |
|---|---|---|---|
| 3-chlorobenzenesulfinamide structure | Int-A-2.3 | 3-chlorobenzenesulfonyl chloride structure | LCMS ESI (m/z): 176.0 & 178.0 (M + H) |
| pyridine-3-sulfinamide structure | Int-A-2.34 | pyridine-3-sulfonyl chloride structure | LCMS ESI (m/z): 143.0 (M + H) |

Synthesis of 3-phenoxybenzenesulfinamide (Int-A-2.44)

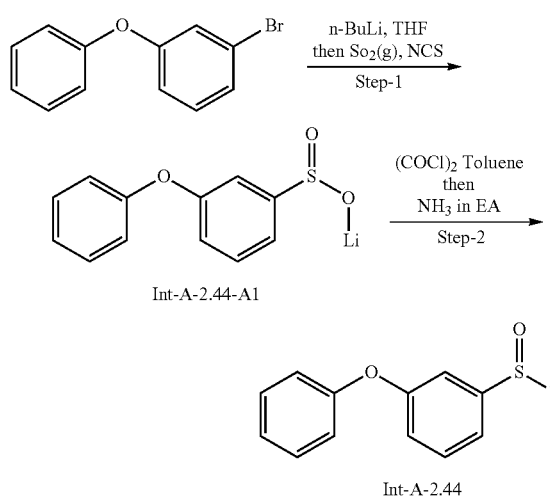

Step-1: To a stirred solution of 1-bromo-3-phenoxybenzene (3 g, 12.0 mmol) in THF (20 mL) was added n-BuLi (8 mL, 12.0 mmol, 1.6M in THF) at −78° C. and stirred for another 1 h at same temperature. SO₂ was purged into the reaction mixture for 1 h, at same temperature. After completion of the reaction, the reaction mixture was filtered and the residue triturated with ether/pentane and dried under vacuum to give 3-phenoxybenzenesulfinate (1.9 g, 84.92%). The isolated Li-salt was readily used in next step.

Step-2: To a suspension of lithium 3-phenoxybenzenesulfinate (1.97 g, 8.2 mmol) in toluene (20 mL), oxalyl chloride (1.4 mL, 16.4 mmol) was added at 0° C. and the reaction mixture allowed to stir at room temperature for 1 h. A mixture of 30% aqueous ammonia (30 mL) and ethyl acetate (30 mL) was added to the reaction mixture and stirred for an additional 1 h. After completion of the reaction as indicated by TLC, the reaction mixture was poured into water (100 mL) and extracted with ethyl acetate (3×100 mL). The combined organic layer was washed with brine, dried over Na₂SO₄ and evaporated under vacuum. The crude was purified by silica gel column chromatography (ethyl acetate/hexane: 1:1) to give 3-phenoxybenzenesulfinamide as an off-white solid (1.1 g, 57.50%). LCMS ESI (m/z): 234.3 (M+1).

Synthesis of 4-fluorothiophene-2-sulfinamide (Int-F-3.0)

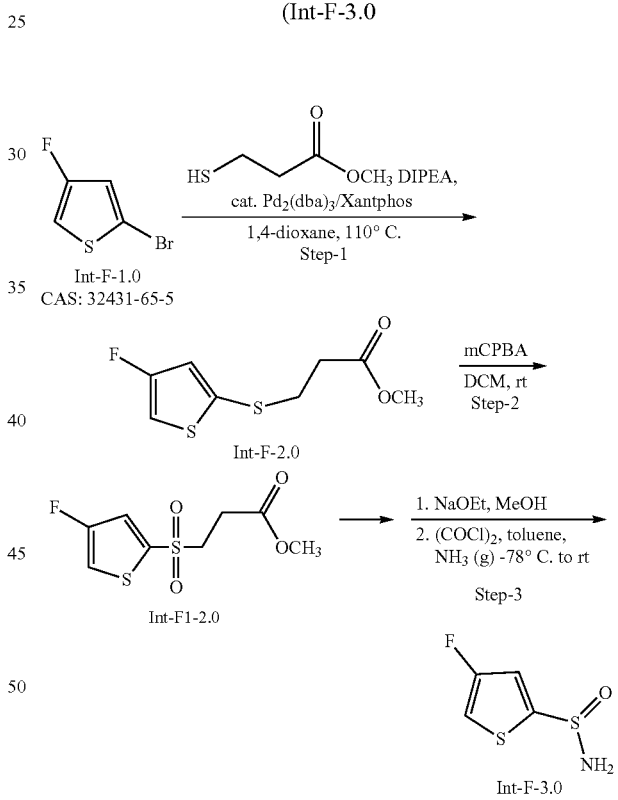

Step-1: A mixture of Int-F-1.0 (450 mg, 2.5 mmol), methyl 3-mercaptopropionate (0.269 mL, 2.5 mmol), Pd₂(dba)₃ (57 mg, 0.062 mmol), Xanthphos (72 mg, 0.12 mmol), and DIPEA (0.86 mL, 5.0 mmol) were heated in dioxane (6 mL) for 2 h. The mixture was cooled to room temperature and filtered through short celite column. The solvent was evaporated and the residue was purified by column chromatography on silica gel column eluting by a mixture of light petroleum ether and EtOAc (10:1) to give Int-F-2.0 (483 mg, 82%) which was subjected to Step-2.

Step-2: m-CPBA (1.12 g, 6.5 mmol) was added portion-wise to a stirred solution of Int-F-2.0 (1.12 g, 6.5 mmol) in DCM (17 mL) at 0° C. The mixture was warmed gradually to room temperature and stirred overnight before quenching the reaction with an aqueous solution of Na$_2$S$_2$O$_3$ (5 M) at 0° C. The organic phase was washed with water, dried over Na$_2$SO$_4$ and evaporated. The residue was purified by column chromatography on silica gel column eluting by a mixture of light petroleum ether and EtOAc (2:1-1:1) to give Int-F1-2.0 (518 mg, 95%) which was subjected to Step-3.

Step-3: Int-F1-2.0 (513 mg, 2.03 mmol) was dissolved in refluxing methanol (20 mL). A solution of 21% sodium ethoxide in ethanol (0.76 mL 2.03 mmol) was added and the resulting solution cooled to room temperature. The reaction mixture was concentrated and the remaining solid dried in vacuo. The residue was suspended in toluene (+2 drops of DMF) and to this was added oxalyl chloride at room temperature. The resulting mixture was stirred for 1 h then cooled to −78° C. and NH$_3$ was passed through. The mixture was evaporated and the residue purified by column chromatography to give Int-F-3.0 (272 mg, 81%). $^1$H NMR (300 MHz, Chloroform-d) δ 7.23 (dd, J=1.9, 1.2 Hz, 1H), 7.01 (dd, J=1.9, 0.6 Hz, 1H), 4.54 (s, 2H).

The following intermediates were made according to the procedure described for Int-F-3.0.

Synthesis Table 5

| Structure | Compound ID | Precursor | Analytical data |
|---|---|---|---|
| Ph-[thiophene]-S(O)NH$_2$ | Int-F-3.1 | Ph-[thiophene]-Br CAS: 10353-18-1 | $^1$H NMR (300 MHz, Chloroform-d) δ 7.58-7.47 (m, 3H), 7.47-7.31 (m, 3H), 7.19 (d, J = 5.1 Hz, 1H), 4.46 (s, 2H). |
| Ph-[thiophene]-S(O)NH$_2$ | Int-F-3.2 | Ph-[thiophene]-Br CAS: 10341-87-4 | $^1$H NMR (400 MHz, CDCl$_3$) 7.57 (d, J = 5.1 Hz, 1H), 7.55-7.51 (m, 2H), 7.46-7.36 (m, 3H), 7.20 (d, J = 5.1 Hz, 1H), 4.40 (bs, 2H). UPLCMS ESI (m/z): 224.2 (M + H)$^+$ |

Synthesis of tert-butyl ((2S)-4-methyl-1-oxo-1-((phenylsulfinyl)amino)pentan-2-yl)carbamate (Int-A-3.1

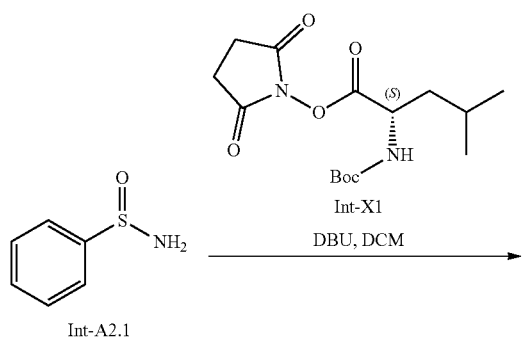

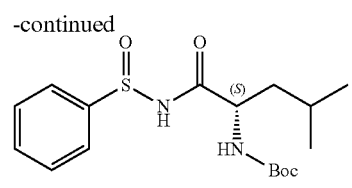

To a stirred solution of benzenesulfinamide (5.3 g, 37 mmol) in DCM (50 mL) was added DBU (11.2 g, 74 mmol) followed by Int-X1 (14.8 g, 45 mmol) at room temperature and stirred for 3 h. After completion of the reaction as indicated by TLC, the reaction mixture was poured into water and extracted with ethyl acetate. The combined organic layer was washed with brine, dried over Na$_2$SO$_4$ and evaporated under vacuum to give crude product. The crude product was purified by silica gel column chromatography (ethyl acetate/hexane: 1:1) to give the title compound, Int-A-3.1, as a solid (7.8 g, 59%). LCMS ESI (m/z): 377.2 (M+Na).

The following intermediates were made according to the procedure described for Int-A-3.1.

Synthesis Table 6

| Structure | Intermediate | Precursor-1 | Precursor-2 | LCMS ESI (m/z) |
|---|---|---|---|---|
| 3-Cl, 2-F phenyl sulfonamide Leu-Boc (S) | Int-A-3.2 | Int-A-2.2 | Int-X1 | LCMS ESI (m/z): 429.1 (M + Na) |
| 3-Cl phenyl sulfonamide Leu-Boc (S) | Int-A-3.3 | Int-A-2.3 | Int-X1 | LCMS ESI (m/z): 411.1 & 413.1 (M + Na) |
| 3-F phenyl sulfonamide Leu-Boc (S) | Int-A-3.5 | Int-A-2.5 | Int-X1 | LCMS ESI (m/z): 395.2 (M + Na) |
| 3-methylphenyl sulfonamide Leu-Boc (S) | Int-A-3.10 | Int-A-2.9 | Int-X1 | LCMS ESI (m/z): 391.2 (M + Na) |
| thiophene-2-sulfonamide Ile-Boc (S) | Int-A-3.26 | Int-A-2.20 | Int-X2 | LCMS ESI (m/z): 383.1 (M + Na) |
| thiophene-3-sulfonamide Leu-Boc (S) | Int-A-3.27 | Int-A-2.21 | Int-X1 | LCMS ESI (m/z): 383.1 (M + Na) |
| 5-Cl-thiophene-2-sulfonamide Leu-Boc (S) | Int-A-3.28 | Int-A-2.22 | Int-X1 | LCMS ESI (m/z): 417.1 & 419.1 (M + Na) |
| 5-Cl-thiophene-2-sulfonamide Ile-Boc (S) | Int-A-3.29 | Int-A-2.22 | Int-X2 | LCMS ESI (m/z): 417.2 (M + Na) |
| 3-Cl-thiophene-2-sulfonamide Leu-Boc (S) | Int-A-3.30 | Int-A-2.23 | Int-X1 | LCMS ESI (m/z): 417.15 (M + Na) |

-continued
Synthesis Table 6
| Structure | Intermediate | Precursor-1 | Precursor-2 | LCMS ESI (m/z) |
|---|---|---|---|---|
| 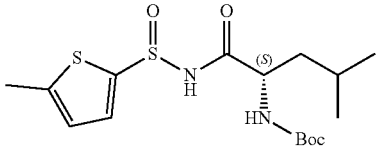 | Int-A-3.31 | Int-A-2.24 | Int-X1 | LCMS ESI (m/z): 397.2 (M + Na) |
| 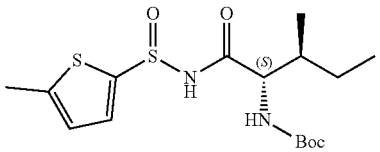 | Int-A-3.32 | Int-A-2.24 | Int-X2 | LCMS ESI (m/z): 397.2 (M + Na) |
| 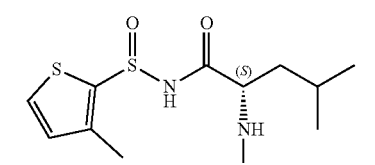 | Int-A-3.33 | Int-A-2.25 | Int-X1 | LCMS ESI (m/z): 397.2 (M + Na) |
| 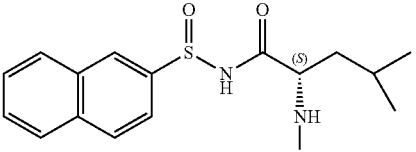 | Int-A-3.38 | Int-A-2.28 | Int-X1 | LCMS ESI (m/z): 427.1 (M + Na) |
| 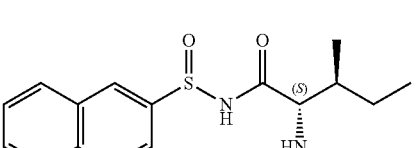 | Int-A-3.39 | Int-A-2.28 | Int-X2 | LCMS ESI (m/z): 427.2 (M + Na) |
| 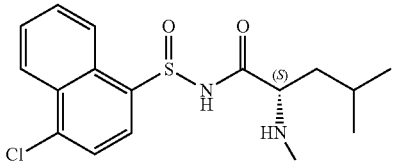 | Int-A-3.40 | Int-A-2.29 | Int-X1 | LCMS ESI (m/z): 437.2 (M − 1) |
| 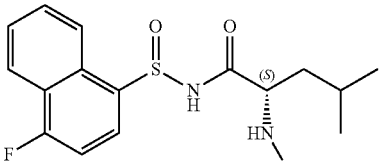 | Int-A-3.41 | Int-A-2.30 | Int-X1 | LCMS ESI (m/z): 445.2 (M + Na) |
| 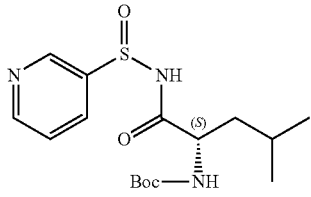 | Int-A-3.48 | Int-A-2.34 | Int-X1 | LCMS ESI (m/z): 356.2 (M + Na) |

Synthesis of tert-butyl ((2S)-4-methyl-1-oxo-1-((thiophen-2-ylsulfinyl)amino)pentan-2-yl)carbamate (Int-A-3.20

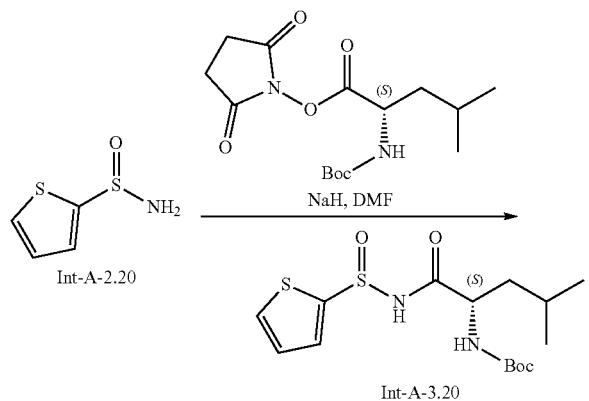

To a stirred solution of thiophene-2-sulfinamide (1.0 g, 6.8 mmol) in DMF (5 mL) was added 60% NaH (0.16 g, 6.8 mmol) at 0° C. and stirred for another 1 h at the same temperature. Int-X1 (2.23 g, 6.8 mmol) was added to the reaction mixture and stirred for another 4 h. After completion of the reaction as indicated by TLC, the reaction mixture was poured into water and extracted with ethyl acetate. The combined organic layer was washed with brine, dried over $Na_2SO_4$ and evaporated under vacuum to give crude product. The crude product was purified by silica gel column chromatography (ethyl acetate/hexane: 1:1) to give the title compound, Int-A-3.20, as a solid (2 g, 81.63%). LCMS ESI (m/z): 361.3 (M+1).

The following intermediates were made according to the procedure described for Int-A-3.20.

Synthesis Table 7

| Structure | Intermediate | Precursor-1 | Precursor-2 | LCMS ESI (m/z) |
|---|---|---|---|---|
| (4-Cl-phenyl sulfinyl Leu-Boc) | Int-A-3.4 | Int-A-2.4 | Int-X1 | LCMS ESI (m/z): 387.2 (M − 1) |
| (4-Cl-phenyl sulfinyl Ile-Boc) | Int-A-3.49 | Int-A-2.4 | Int-X2 | LCMS ESI (m/z): 387.2 & 389.4 (M + H) |
| (3-Cl-phenyl sulfinyl Ile-Boc) | Int-A-3.50 | Int-A-2.3 | Int-X2 | LCMS ESI (m/z): 289.1 (M + 1 − Boc) |
| (3,4-diCl-phenyl sulfinyl Leu-Boc) | Int-A-3.6 | Int-A-2.6 | Int-X1 | LCMS ESI (m/z): 445.1 (M + Na) |
| (3,4-diCl-phenyl sulfinyl Ile-Boc) | Int-A-3.7 | Int-A-2.6 | Int-X2 | LCMS ESI (m/z): 445.1 (M + Na) |

-continued

Synthesis Table 7

| Structure | Intermediate | Precursor-1 | Precursor-2 | LCMS ESI (m/z) |
|---|---|---|---|---|
| (2,3-dichlorophenyl sulfonamide of (S)-Leu-NHBoc) | Int-A-3.8 | Int-A-2.7 | Int-X1 | LCMS ESI (m/z): 445.1 & 447.0 (M + Na) |
| (2,5-difluorophenyl sulfonamide of (S)-Leu-NHBoc) | Int-A-3.9 | Int-A-2.8 | Int-X1 | LCMS ESI (m/z): 413.2 (M + Na) |
| (4-methylphenyl sulfonamide of (S)-Ile-NHBoc) | Int-A-3.11 | Int-A-2.10 | Int-X2 | LCMS ESI (m/z): 391.3 (M + Na) |
| (4-methylphenyl sulfonamide of (S)-Leu-NHBoc) | Int-A-3.12 | Int-A-2.10 | Int-X1 | LCMS ESI (m/z): 391.3 (M + Na) |
| (3-methyl-4-methoxyphenyl sulfonamide of (S)-Leu-NHBoc) | Int-A-3.13 | Int-A-2.11 | Int-X1 | LCMS ESI (m/z): 421.2 (M + Na) |
| (2-methyl-4-fluorophenyl sulfonamide of (S)-Leu-NHBoc) | Int-A-3.14 | Int-A-2.12 | Int-X1 | LCMS ESI (m/z): 409.2 (M + Na) |
| (4-methoxyphenyl sulfonamide of (S)-Ile-NHBoc) | Int-A-3.15 | Int-A-2.13 | Int-X2 | $^1$H NMR (400 MHz, DMSO-d$_6$) δ 7.59 (d, 2H), 7.16 (d, 2H), 4-3.90 (m, 1H), 3.81 (s, 3H), 1.70 (brs, 1H), 1.50-1.00 (m, 2H), 1.39 (s, 9H), 0.95-0.85 (m, 6H) |
| (3-isopropylphenyl sulfonamide of (S)-Leu-NHBoc) | Int-A-3.16 | Int-A-2.14 | Int-X1 | LCMS ESI (m/z): 419.3 (M + Na) |

Synthesis Table 7
| Structure | Intermediate | Precursor-1 | Precursor-2 | LCMS ESI (m/z) |
|---|---|---|---|---|
| 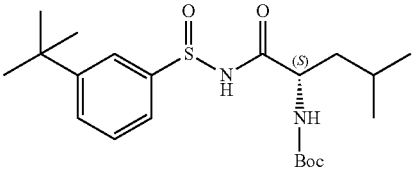 | Int-A-3.17 | Int-A-2.15 | Int-X1 | LCMS ESI (m/z): 411.3 (M + 1) |
| 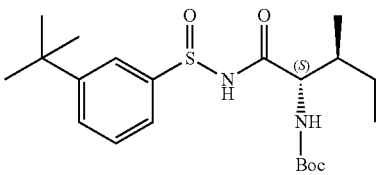 | Int-A-3.18 | Int-A-2.15 | Int-X2 | LCMS ESI (m/z): 411.3 (M + 1) |
| 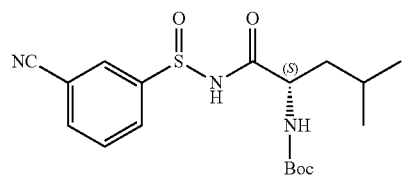 | Int-A-3.19 | Int-A-2.16 | Int-X1 | LCMS ESI (m/z): 378.4 (M − 1) |
| 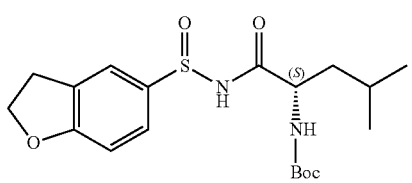 | Int-A-3.21 | Int-A-2.17 | Int-X1 | LCMS ESI (m/z): 419.2 (M + Na) |
| 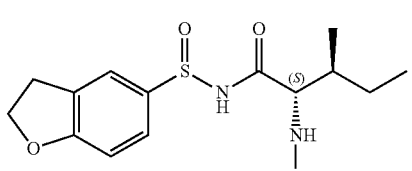 | Int-A-3.22 | Int-A-2.17 | Int-X2 | LCMS ESI (m/z): 419.3 (M + Na) |
| 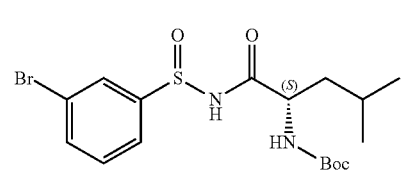 | Int-A-3.23 | Int-A-2.18 | Int-X1 | LCMS ESI (m/z): 433.3 & 435.3 (M + Na) |
| 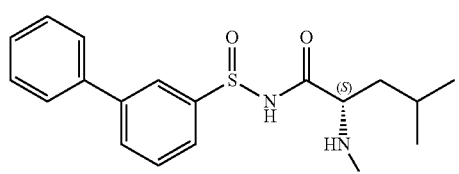 | Int-A-3.24 | Int-A-2.19 | Int-X1 | LCMS ESI (m/z): 453.1 (M + Na) |
| 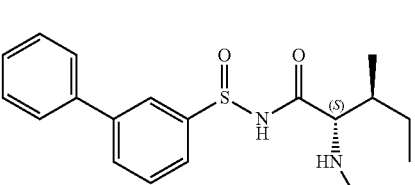 | Int-A-3.25 | Int-A-2.19 | Int-X2 | LCMS ESI (m/z): 453.2 (M + Na) |

-continued

Synthesis Table 7

| Structure | Intermediate | Precursor-1 | Precursor-2 | LCMS ESI (m/z) |
|---|---|---|---|---|
| (5-(difluoromethyl)thiophene-2-sulfonamide with Leu-Boc) | Int-A-3.34 | Int-A-2.26 | Int-X1 | LCMS ESI (m/z): 433.1 (M + Na) |
| (5-(difluoromethyl)thiophene-2-sulfonamide with Ile-Boc) | Int-A-3.35 | Int-A-2.26 | Int-X2 | LCMS ESI (m/z): 410.8 (M + H) |
| (naphthalene-1-sulfonamide with Leu-Boc) | Int-A-3.36 | Int-A-2.27 | Int-X1 | LCMS ESI (m/z): 427.20 (M + Na) |
| (naphthalene-1-sulfonamide with Val-Boc) | Int-A-3.37 | Int-A-2.27 | Int-X3 | LCMS ESI (m/z): 413.1 (M + Na) |
| (3-(4-chlorophenoxy)benzenesulfonamide with Leu-Boc) | Int-A-3.42 | Int-A-2.31 | Int-X1 | LCMS ESI (m/z): 479.3 (M − 1) |
| (3-(4-chlorophenoxy)benzenesulfonamide with Ile-Boc) | Int-A-3.43 | Int-A-2.31 | Int-X2 | LCMS ESI (m/z): 481.3 (M + 1) |
| (benzo[b]thiophene-3-sulfonamide with Ile-Boc) | Int-A-3.44 | Int-A-2.32 | Int-X2 | LCMS ESI (m/z): 411.2 (M + 1) |
| (benzo[b]thiophene-2-sulfonamide with Leu-Boc) | Int-A-3.45 | Int-A-2.33 | Int-X1 | LCMS ESI (m/z): 433.10 (M + Na) |

Synthesis Table 7

| Structure | Intermediate | Precursor-1 | Precursor-2 | LCMS ESI (m/z) |
|---|---|---|---|---|
| (benzothiophene-2-sulfonamide of (S)-isoleucine-NHBoc) | Int-A-3.46 | Int-A-2.33 | Int-X2 | LCMS ESI (m/z): 433.20 (M + Na) |
| (phenylsulfonamide of cyclopropylmethyl-Ala-NHBoc) | Int-A-3.47 | Int-A-2.1 | Int-X4 | LCMS ESI (m/z): 353.6 (M + 1) |
| (benzothiophene-3-sulfonamide of (S)-Leu-NHBoc) | Int-A-3.51 | Int-A-2.32 | Int-X1 | LCMS ESI (m/z): 411.2 (M + H) |
| (thienothiophene-2-sulfonamide of (S)-Leu-NHBoc) | Int-A-3.52 | Int-A-2.35 | Int-X1 | LCMS ESI (m/z): 417.2 (M + H) |
| (thienothiophene-2-sulfonamide of (S)-Ile-NHBoc) | Int-A-3.53 | Int-A-2.35 | Int-X2 | LCMS ESI (m/z): 439.3 (M + Na) |
| (phenylsulfonamide of methylcyclopentyl-NHBoc) | Int-A-3.54 | Int-A-2.1 | Int-X5 | LCMS ESI (−ve) (m/z): 365.38 (M − H) |
| (2-methylphenylsulfonamide of (S)-Leu-NHBoc) | Int-A-3.55 | Int-A-2.36 | Int-X1 | LCMS ESI (m/z): 369.4 (M + H) |
| (2-fluorophenylsulfonamide of (S)-Leu-NHBoc) | Int-A-3.56 | Int-A-2.37 | Int-X1 | LCMS ESI (m/z): 373.3 (M + H) |

Synthesis Table 7

| Structure | Intermediate | Precursor-1 | Precursor-2 | LCMS ESI (m/z) |
|---|---|---|---|---|
| 3-(difluoromethoxy)phenyl sulfonamide with (S)-Leu-Boc | Int-A-3.57 | Int-A-2.38 | Int-X1 | LCMS ESI (m/z): 421.4 (M + H) |
| 3-(difluoromethoxy)phenyl sulfonamide with (S)-Ile-Boc | Int-A-3.58 | Int-A-2.38 | Int-X2 | LCMS ESI (m/z): 421.4 (M + H) |
| 3-(difluoromethoxy)phenyl sulfonamide with (S)-Val-Boc | Int-A-3.59 | Int-A-2.38 | Int-X3 | LCMS ESI (m/z): 407.4 (M + 1) |
| 3-(trifluoromethyl)phenyl sulfonamide with (S)-Leu-Boc | Int-A-3.60 | Int-A-2.39 | Int-X1 | MS (m/z): 445.9 (M + Na) |
| 3-(trifluoromethyl)phenyl sulfonamide with (S)-Ile-Boc | Int-A-3.61 | Int-A-2.39 | Int-X2 | MS (m/z): 445.2 (M + Na) |
| 3-(trifluoromethoxy)phenyl sulfonamide with (S)-Leu-Boc | Int-A-3.62 | Int-A-2.40 | Int-X1 | LCMS ESI (m/z): 461.3 (M + Na) |
| 3-(trifluoromethoxy)phenyl sulfonamide with (S)-Ile-Boc | Int-A-3.63 | Int-A-2.40 | Int-X2 | LCMS ESI (m/z): 461.2 (M + Na) |
| 5-chlorothiophene sulfonamide with (S)-Leu-Boc | Int-A-3.64 | Int-A-2.41 | Int-X1 | LCMS ESI (m/z): 395.4 & 397.5 (M & M + 2) |
| 5-chlorothiophene sulfonamide with (S)-Ile-Boc | Int-A-3.65 | Int-A-2.41 | Int-X2 | LCMS ESI (m/z): 395.4 & 397.4 (M & M + 2) |

Synthesis Table 7

| Structure | Intermediate | Precursor-1 | Precursor-2 | LCMS ESI (m/z) |
|---|---|---|---|---|
| 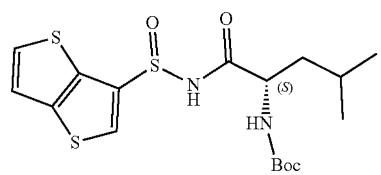 | Int-A-3.66 | Int-A-2.42 | Int-X1 | LCMS ESI (m/z): 417.4 (M + H) |
| 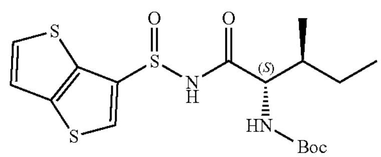 | Int-A-3.67 | Int-A-2.42 | Int-X2 | LCMS ESI (m/z): 417.4 (M + H) |
| 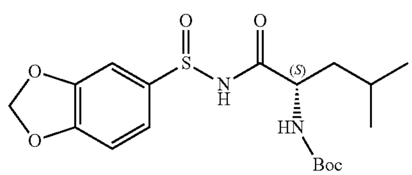 | Int-A-3.68 | Int-A-2.43 | Int-X1 | LCMS ESI (m/z): 399.4 (M + H) |
| 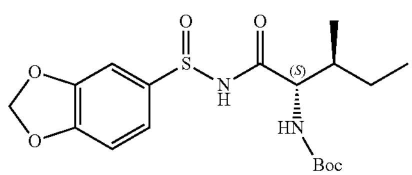 | Int-A-3.69 | Int-A-2.43 | Int-X2 | LCMS ESI (m/z): 399.4 (M + H) |
| 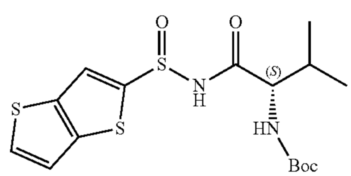 | Int-A-3.70 | Int-A-2.35 | Int-X3 | LCMS ESI (m/z): 425.2 (M + Na) |
| 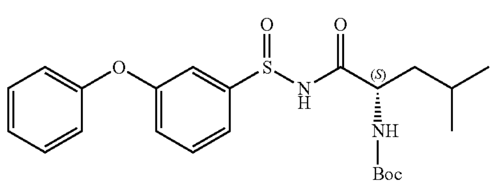 | Int-A-3.71 | Int-A-2.44 | Int-X1 | LCMS ESI (m/z): 447.5 (M + H) |
| 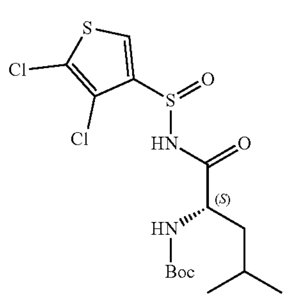 | Int-A-3.72 | Int-A-2.45 | Int-X1 | LCMS ESI (m/z): 372.9 & 374.9 (M-56) |

Synthesis Table 7

| Structure | Intermediate | Precursor-1 | Precursor-2 | LCMS ESI (m/z) |
|---|---|---|---|---|
| (5-chloro-2-chlorothiophene sulfonamide with leucine-NHBoc) | Int-A-3.73 | Int-A-2.46 | Int-X1 | LCMS ESI (m/z): 429.1 & 431.1 (M & M + 2) |
| (4-phenylthiophene-2-sulfonamide with leucine-NHBoc) | Int-A-3.74 | Int-F-3.1 | Int-X1 | UPLCMS ESI (m/z): 437.4 (M + H)+ |
| (3-phenylthiophene-2-sulfonamide with leucine-NHBoc) | Int-A-3.75 | Int-F-3.2 | Int-X1 | UPLCMS ESI (m/z): 437.4 (M + H)+ |

Synthesis of tert-butyl ((2S)-1-((amino(oxo)(phenyl)-λ6-sulfanylidene)amino)-4-methyl-1-oxopentan-2-yl)carbamate and tert-butyl ((S)-1-(((R)-amino(oxo)(phenyl)-λ6-sulfanylidene)amino)-4-methyl-1-oxopentan-2-yl)carbamate (Int-A-4.1, Int-A-4.1-Fr-1 and Int-A-4.1-Fr-2)

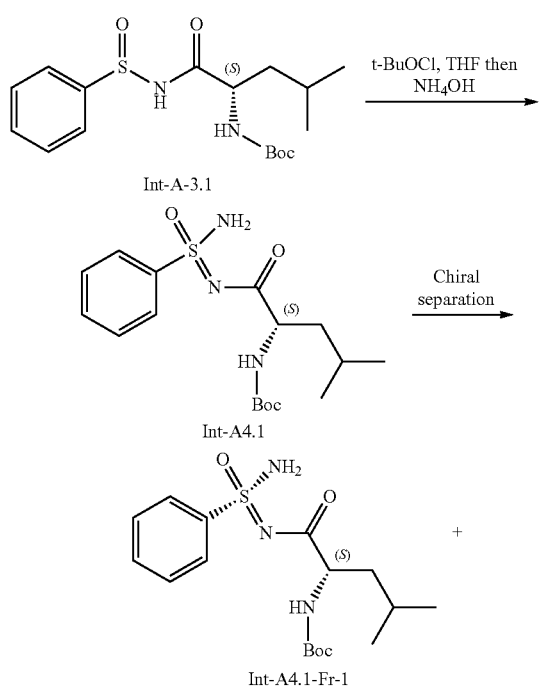

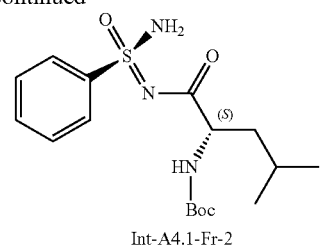

Int-A4.1-Fr-2

To a stirred solution of (Int-A-3.1) (1 g, 2.8 mmol) in THF (10 mL) was added tert-butyl hypochlorite (0.40 mL, 3.6 mmol) at 0° C. and stirred for another 1 h at the same temperature. 30% Ammonia solution (15 mL) was added to the reaction mixture and allowed to stir at room temperature for 1 h. After completion of the reaction as indicated by TLC, the reaction mixture was poured into water and extracted with ethyl acetate. The combined organic layer was washed with brine, dried over $Na_2SO_4$ and evaporated under vacuum. The crude was purified by silica gel column chromatography (ethyl acetate/hexane) to give the title compound, Int-A-4.1, as a mixture of diastereomers (0.40 g, 28%). LCMS ESI (m/z): 270.0 (M+H-Boc).

The diastereomers were separated by chiral prep HPLC (Column: YMC CHIRALART CELLULOSE_SC, Mobile phase: A=0.1% DEA in Heptane, B=IPA:ACN (70:30), A:B=75:25) to give Isomer-1 and Isomer-2. These isomers were eluted at retention time 8.73 min (Isomer-1) and 13.68 min (Isomer-2).

Synthesis of tert-butyl ((2S)-1-((amino(oxo)(thiophen-2-yl)-λ6-sulfanylidene)amino)-4-methyl-1-oxopentan-2-yl)carbamate (Int-A-4.20-Fr-1 and Int-A-4.20-Fr-2)

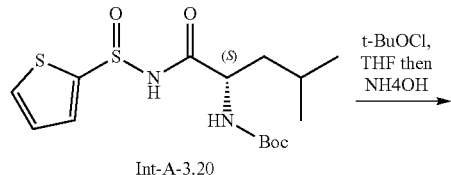

Int-A-3.20

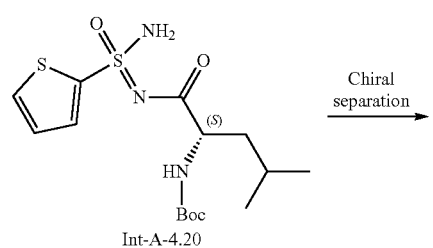

Int-A-4.20

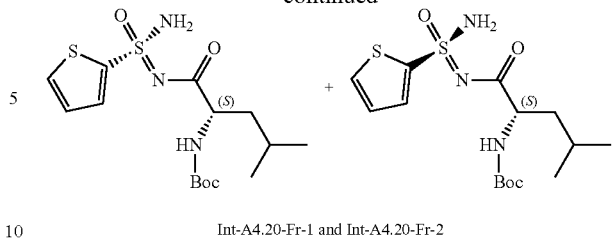

Int-A4.20-Fr-1 and Int-A4.20-Fr-2

To a stirred solution of (Int-A-3.20) (1 g, 2.7 mmol) in THF (5 mL) was added tert-butyl hypochlorite (0.39 mL, 3.6 mmol) at 0° C. and stirred for 1 h at the same temperature. 30% ammonia solution (15 mL) was added to the reaction mixture and ammonia gas purged at 0° C. The reaction mixture was allowed to stir at the same temperature for 2 h. After completion of the reaction as indicated by TLC, the reaction mixture was poured into water and extracted with ethyl acetate. The combined organic layer was washed with brine, dried over $Na_2SO_4$ and evaporated under vacuum to give the crude product. The crude was purified by silica gel column chromatography to give the title compound, Int-A-4.20, as a mixture of diastereomers (0.180 g, 17%). LCMS ESI (m/z): 376.3 (M+H).

The diastereomers were separated by chiral prep HPLC, DIACEL Chiral PAK_IG, Mobile phase: A=0.1% DEA in Heptane, B=IPA:ACN (75:30), A:B=85:15) to give Isomer-1 and Isomer-2. These isomers were eluted at retention time 10.25 min (Isomer-1) and 15.27 min (Isomer-2).

The following intermediates were made according to the procedure described for Int-A-4.1.

Synthesis Table 8

| Structure | Compound ID | Precursor | Analytical data/Chiral separation |
|---|---|---|---|
|  | Int-A-4.2<br>Int-A-4.2-Fr-1<br>Int-A-4.2-Fr-2 | Int-A-3.2 | LCMS ESI (m/z): 444.0 & 4464.1 (M + Na)<br>Chiral prep HPLC: DIACEL CHIRALPAK_IG<br>Mobile phase: Heptane_IPA-MeOH (70-30)_70:30<br>Isomer-1 (Fr-1): Retention time: 13.81 min<br>Isomer-2 (Fr-2): Retention time: 19.94 min |

Synthesis Table 8

| Structure | Compound ID | Precursor | Analytical data/Chiral separation |
|---|---|---|---|
| | Int-A-4.3<br>Int-A-4.3-Fr-1<br>Int-A-4.3-Fr-2 | Int-A-3.3 | LCMS ESI (m/z): 426.2 & 428.1 (M + Na)<br>Chiral prep HPLC: DIACEL CHIRALPAK_IG<br>Mobile phase: Heptane_IPA-ACN (70-30)_80:20<br>Isomer-1 (Fr-1): Retention time: 9.03 min<br>Isomer-2 (Fr-2): Retention time: 18.85 min |
| | Int-A-4.50<br>Int-A-4.50-Fr-1<br>Int-A-4.50-Fr-2 | Int-A-3.50 | LCMS ESI (m/z): 304.1 (M + 1 − Boc)<br>Chiral prep HPLC: YMC CHIRALART CELLULOSE_SC<br>Mobile phase: Hexane_IPA-MeOH (70-30)_90:10<br>Isomer-1 (Fr-1): Retention time: 10.66 min<br>Isomer-2 (Fr-2): Retention time: 15.78 min |

Synthesis Table 8

| Structure | Compound ID | Precursor | Analytical data/Chiral separation |
|---|---|---|---|
| | Int-A-4.4<br>Int-A-4.4-Fr-1<br>Int-A-4.4-Fr-2 | Int-A-3.4 | LCMS ESI (m/z): 304.1 (M + 1 − Boc)<br>Chiral prep HPLC: DIACEL Chiral PAK_IG<br>Mobile phase: Heptane_IPA-MeOH (70-30)_70:30<br>Isomer-1 (Fr-1): Retention time: 13.70 min<br>Isomer-2 (Fr-2): Retention time: 14.90 min |
| | Int-A-4.49<br>Int-A-4.49-Fr-1<br>Int-A-4.49-Fr-2 | Int-A-3.49 | LCMS ESI (m/z): 303.9 (M + 1 − Boc)<br>Chiral prep HPLC: DIACEL Chiral PAK_IG<br>Mobile phase: Heptane_IPA-MeOH (70-30)_70:30<br>Isomer-1 (Fr-1): Retention time: 15.66 min<br>Isomer-2 (Fr-2): Retention time: 23.79 min |

Synthesis Table 8

| Structure | Compound ID | Precursor | Analytical data/Chiral separation |
|---|---|---|---|
| | Int-A-4.5<br>Int-A-4.5-Fr-1<br>Int-A-4.5-Fr-2 | Int-A-3.5 | LCMS ESI (m/z): 410.1 (M + Na)<br>Chiral prep HPLC: DIACEL CHIRALPAK_IG;<br>Mobile phase: HEP_IPA-ACN (70-30)_80:20;<br>Isomer-1 (Fr-1): Retention time: 8.94 min<br>Isomer-2 (Fr-2): Retention time: 17.23 min |
| | Int-A-4.6<br>Int-A-4.6-Fr-1<br>Int-A-4.6-Fr-2 | Int-A-3.6 | LCMS ESI (m/z): 436.1, 438.3 & 439.1 (M + 1)<br>Chiral prep HPLC: DIACEL Chiral PAK_IG<br>Mobile phase: Heptane_IPA-MeOH (70-30)_70:30<br>Isomer-1 (Fr-1): Retention time: 10.51 min<br>Isomer-2 (Fr-2): Retention time: 19.66 min |
| | Int-A-4.7<br>Int-A-4.7-Fr-1<br>Int-A-4.7-Fr-2 | Int-A-3.7 | LCMS ESI (m/z): 338.1 & 340.0 [M + 1]+<br>Chiral prep HPLC: YMC CHIRALART CELLULOSE_SC<br>Mobile phase: Hexane_IPA-ACN (70-30)_92:8<br>Isomer-1 (Fr-1): Retention time: 8.16 min<br>Isomer-2 (Fr-2): Retention time: 9.91 min |

Synthesis Table 8

| Structure | Compound ID | Precursor | Analytical data/Chiral separation |
|---|---|---|---|
| (3,4-diCl-phenyl sulfonimidamide, (R) at S, coupled to (S)-Ile-NHBoc) | | | |
| (2,3-diCl-phenyl sulfonimidamide, coupled to (S)-Leu-NHBoc) | Int-A-4.8<br>Int-A-4.8-Fr-1<br>Int-A-4.8-Fr-2 | Int-A-3.8 | LCMS ESI (m/z): 445.1 & 447.0 (M + 1)<br>Chiral prep HPLC: YMC CHIRALART CELLULOSE_SC<br>Mobile phase: Heptane_IPA-ACN (70-30)_85:15<br>Isomer-1 (Fr-1): Retention time: 6.17 min<br>Isomer-2 (Fr-2): Retention time: 9.31 min |
| (2,3-diCl-phenyl sulfonimidamide, (S) at S, coupled to (S)-Leu-NHBoc) | | | |
| (2,3-diCl-phenyl sulfonimidamide, (R) at S, coupled to (S)-Leu-NHBoc) | | | |
| (2,5-diF-phenyl sulfonimidamide, coupled to (S)-Leu-NHBoc) | Int-A-4.9<br>Int-A-4.9-Fr-1<br>Int-A-4.9-Fr-2 | Int-A-3.9 | LCMS ESI (m/z): 306.1 (M + 1 − Boc)<br>Chiral prep HPLC: YMC CHIRALART CELLULOSE_SC<br>Mobile phase: Hexane_IPA-MeOH (70-30)_85:15<br>Isomer-1 (Fr-1): Retention time: 7.58 min<br>Isomer-2 (Fr-2): Retention time: 10.18 min |
| (2,5-diF-phenyl sulfonimidamide, (S) at S, coupled to (S)-Leu-NHBoc) | | | |
| (2,5-diF-phenyl sulfonimidamide, (R) at S, coupled to (S)-Leu-NHBoc) | | | |

| Structure | Compound ID | Precursor | Analytical data/Chiral separation |
|---|---|---|---|
| 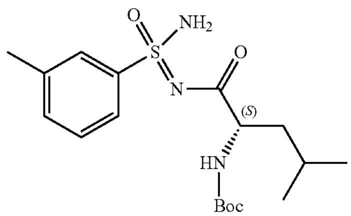 | Int-A-4.10<br>Int-A-4.10-Fr-1<br>Int-A-4.10-Fr-2 | Int-A-3.10 | LCMS ESI (m/z): 384.1 (M + 1)<br>Chiral prep HPLC: YMC CHIRALART CELLULOSE_SC<br>Mobile phase: 0.05% TFA in Heptane_IPA-ACN (70-30)_80:20<br>Isomer-1 (Fr-1): Retention time: 9.35 min<br>Isomer-2 (Fr-2): Retention time: 15.64 min |
| 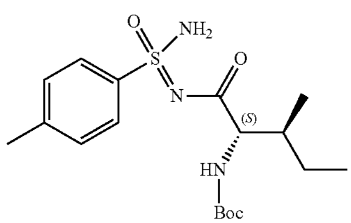 | Int-A-4.11 | Int-A-3.11 | LCMS ESI (m/z): 382.2 (M − 1)<br>Chiral prep HPLC: DIACEL Chiral PAK_IG<br>Mobile phase: Heptane_IPA-ACN (70-30)_70:30<br>Isomer-1 (Fr-1): Retention time: 9.26 min<br>Isomer-2 (Fr-2): Retention time: 14.62 min |

Synthesis Table 8

Synthesis Table 8

| Structure | Compound ID | Precursor | Analytical data/Chiral separation |
|---|---|---|---|
| 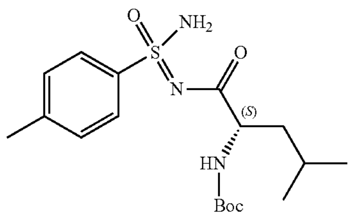 | Int-A-3.12<br>Int-A-4.12-Fr-1<br>Int-A-4.12-Fr-2 | Int-A-3.12 | LCMS ESI (m/z): 284.1 (M + 1 − Boc)<br>Chiral prep HPLC: YMC CHIRALART CELLULOSE_SC<br>Mobile phase: Heptane_IPA-MeOH (70-30)_85:15<br>Isomer-1 (Fr-1): Retention time: 11.35 min<br>Isomer-2 (Fr-2): Retention time: 14.30 min |
| 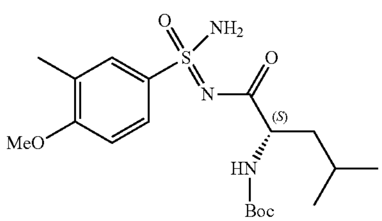 | Int-A-4.13<br>Int-A-4.13-Fr-1<br>Int-A-4.13-Fr-2 | Int-A-3.13 | LCMS ESI (m/z): 414.2 (M + 1)<br>Chiral prep HPLC: YMC CHIRALART CELLULOSE_SC<br>Mobile phase: Heptane_IPA-MeOH (70-30)_85:15<br>Isomer-1 (Fr-1): Retention time: 14.71 min<br>Isomer-2 (Fr-2): Retention time: 18.21 min |

Synthesis Table 8

| Structure | Compound ID | Precursor | Analytical data/Chiral separation |
|---|---|---|---|
| | Int-A-4.14<br>Int-A-4.14-Fr-1<br>Int-A-4.14-Fr-2 | Int-A-3.14 | LCMS ESI (m/z): 424.2 (M + 1)<br>Chiral prep HPLC: YMC CHIRALART CELLULOSE_SC<br>Mobile phase: Heptane_IPA-ACN (70-30)_92:8<br>Isomer-1 (Fr-1): Retention time: 10.23 min<br>Isomer-2 (Fr-2): Retention time: 18.22 min |
| | Int-A-4.15<br>Int-A-4.15-Fr-1<br>Int-A-4.15-Fr-2 | Int-A-3.15 | LCMS ESI (m/z): 400.3 (M + 1)<br>Chiral prep HPLC: YMC CHIRALART CELLULOSE_SC<br>Mobile phase: Heptane_IPA-ACN (70-30)_85:15<br>Isomer-1 (Fr-1): Retention time: 9.01 min<br>Isomer-2 (Fr-2): Retention time: 11.35 min |

Synthesis Table 8

| Structure | Compound ID | Precursor | Analytical data/Chiral separation |
|---|---|---|---|
| 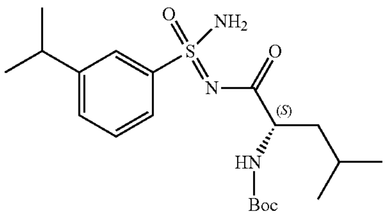 | Int-A-4.16<br>Int-A-4.16-Fr-1<br>Int-A-4.16-Fr-2 | Int-A-3.16 | LCMS ESI (m/z): 434.3 (M + Na)<br>Chiral prep HPLC: YMC CHIRALART CELLULOSE_SC<br>Mobile phase: Heptane_IPA-MeOH (70-30)_85:15<br>Isomer-1 (Fr-1): Retention time: 7.88 min<br>Isomer-2 (Fr-2): Retention time: 11.90 min |
| 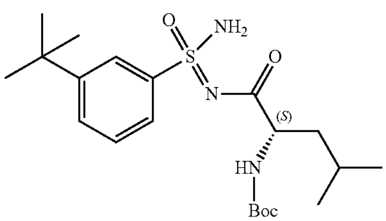 | Int-A-4.17<br>Int-A-4.17-Fr-1<br>Int-A-4.17-Fr-2 | Int-A-3.17 | LCMS ESI (m/z): 426.4 (M + 1)<br>Chiral prep HPLC: DIACEL Chiral PAK_IG<br>Mobile phase: Heptane_IPA-ACN (70-30)_75:25<br>Isomer-1 (Fr-1): Retention time: 5.95 min<br>Isomer-2 (Fr-2): Retention time: 7.91 min |

Synthesis Table 8

| Structure | Compound ID | Precursor | Analytical data/Chiral separation |
|---|---|---|---|
| | Int-A-4.18<br>Int-A-4.18-Fr-1<br>Int-A-4.18-Fr-2 | Int-A-3.18 | LCMS ESI (m/z): 426.5 (M + 1)<br>Chiral prep HPLC: YMC CHIRALART CELLULOSE_SC<br>Mobile phase: Heptane_IPA-ACN (70-30)_85:15<br>Isomer-1 (Fr-1): Retention time: 5.33 min<br>Isomer-2 (Fr-2): Retention time: 7.28 min |
| | Int-A-4.19<br>Int-A-4.19-Fr-1<br>Int-A-4.19-Fr-2 | Int-A-3.19 | LCMS ESI (m/z): 417.3 (M + Na)<br>Chiral prep HPLC: DIACEL Chiral PAK_IG<br>Mobile phase: Hexane_IPA-ACN (70-30)_75:25<br>Isomer-1 (Fr-1): Retention time: 7.37 min<br>Isomer-2 (Fr-2): Retention time: 13.84 min |
| 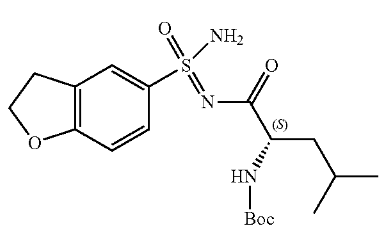 | Int-A-4.21<br>Int-A-4.21-Fr-1<br>Int-A-4.21-Fr-2 | Int-A-3.21 | LCMS ESI (m/z): 412.6 (M + 1) |

Synthesis Table 8

| Structure | Compound ID | Precursor | Analytical data/Chiral separation |
|---|---|---|---|
| (2,3-dihydrobenzofuran-5-yl sulfoximine, isoleucine-Boc structure; mixture) | Int-A-4.22<br>Int-A-4.22-Fr-1<br>Int-A-4.22-Fr-2 | Int-A-3.22 | LCMS ESI (m/z): 412.7 (M + 1)<br>Chiral prep HPLC: DIACEL Chiral PAK_IG<br>Mobile phase: Heptane_IPA-ACN (70-30)_70:30<br>Isomer-1 (Fr-1): Retention time: 13.25 min<br>Isomer-2 (Fr-2): Retention time: 18.51 min |
| (S-isomer at S) | | | |
| (R-isomer at S) | | | |
| (3-bromophenyl sulfoximine, leucine-Boc structure; mixture) | Int-A-4.23<br>Int-A-4.23-Fr-1<br>Int-A-4.23-Fr-2 | Int-A-3.23 | LCMS ESI (m/z): 448.3 & 450.3 (M + 1)<br>Chiral prep HPLC: DIACEL Chiral PAK_IG<br>Mobile phase: Heptane_IPA-ACN (70-30)_60:40<br>Isomer-1 (Fr-1): Retention time: 5.03 min<br>Isomer-2 (Fr-2): Retention time: 9.11 min |
| (S-isomer at S) | | | |
| (R-isomer at S) | | | |

Synthesis Table 8

| Structure | Compound ID | Precursor | Analytical data/Chiral separation |
|---|---|---|---|
| 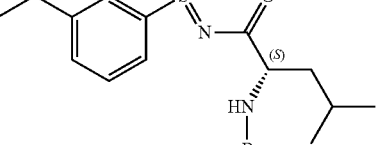 | Int-A-4.24<br>Int-A-4.24-Fr-1<br>Int-A-4.24-Fr-2 | Int-A-3.24 | LCMS ESI (m/z): 346.2 (M + 1 − Boc)<br>Chiral prep HPLC: DIACEL Chiral PAK_IG<br>Mobile phase: Heptane_IPA-ACN (70-30)_90:10<br>Isomer-1 (Fr-1): Retention time: 8.36 min<br>Isomer-2 (Fr-2): Retention time: 13.05 min |
| 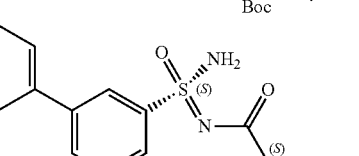 | | | |
| 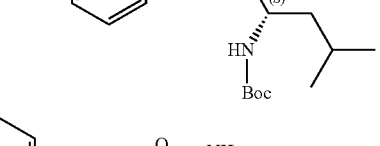 | | | |
| 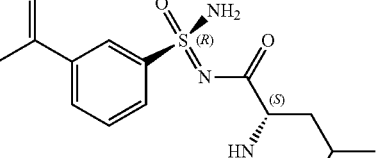 | Int-A-4.25<br>Int-A-4.25-Fr-1<br>Int-A-4.25-Fr-2 | Int-A-3.25 | LCMS ESI (m/z): 346.2 (M + 1 − Boc)<br>Chiral prep HPLC: YMC CHIRALART CELLULOSE_SC<br>Mobile phase: 0.1% DEA in Heptane_IPA-ACN (70-30)_85:15<br>Isomer-1 (Fr-1): Retention time: 8.27 min<br>Isomer-2 (Fr-2): Retention time: 10.36 min |
| 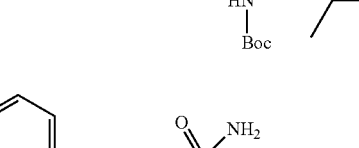 | | | |
| 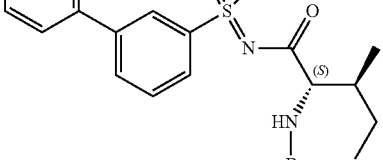 | | | |

Synthesis Table 8

| Structure | Compound ID | Precursor | Analytical data/Chiral separation |
|---|---|---|---|
| | Int-A-4.26<br>Int-A-4.26-Fr-1<br>Int-A-4.26-Fr-2 | Int-A-3.26 | LCMS ESI (m/z): 398.2 (M + Na)<br>Chiral prep HPLC: YMC CHIRALART CELLULOSE_SC<br>Mobile phase: 0.05% TFA in Heptane_IPA-MeOH (70-30)_85:15<br>Isomer-1 (Fr-1): Retention time: 8.64 min<br>Isomer-2 (Fr-2): Retention time: 12.76 min |
| | Int-A-4.27<br>Int-A-4.27-Fr-1<br>Int-A-4.27-Fr-2 | Int-A-3.27 | LCMS ESI (m/z): 398.1 (M + Na)<br>Chiral prep HPLC: DIACEL Chiral PAK_IG<br>Mobile phase: 0.1% DEA in Heptane_IPA-ACN (70-30)_85:15<br>Isomer-1 (Fr-1): Retention time: 20.36 min<br>Isomer-2 (Fr-2): Retention time: 31.01 min |

-continued

Synthesis Table 8

| Structure | Compound ID | Precursor | Analytical data/Chiral separation |
|---|---|---|---|
| (three structures: 5-chlorothiophene sulfoximine-Leu-Boc; (S)-sulfoximine isomer; (R)-sulfoximine isomer) | Int-A-4.28<br>Int-A-4.28-Fr-1<br>Int-A-4.28-Fr-2 | Int-A-3.28 | LCMS ESI (m/z): 309.96 (M + 1 − Boc)<br>Chiral prep HPLC: DIACEL Chiral PAK_IG<br>Mobile phase: 0.05% TFA in Heptane_IPA-ACN (70-30)_90:10<br>Isomer-1 (Fr-1): Retention time: 12.68 min<br>Isomer-2 (Fr-2): Retention time: 14.97 min |
| (three structures: 5-chlorothiophene sulfoximine-Ile-Boc; (S)-sulfoximine isomer; (R)-sulfoximine isomer) | Int-A-4.29<br>Int-A-4.29-Fr-1<br>Int-A-4.29-Fr-2 | Int-A-3.29 | LCMS ESI (m/z): 309.9 (M + H − Boc), 432.2 (M + Na)<br>Chiral prep HPLC: DIACEL Chiral PAK_IG<br>Mobile phase: Heptane_IPA-ACN (70-30)_90:10<br>Isomer-1 (Fr-1): Retention time: 22.81 min<br>Isomer-2 (Fr-2): Retention time: 33.01 min |

Synthesis Table 8

| Structure | Compound ID | Precursor | Analytical data/Chiral separation |
|---|---|---|---|
| 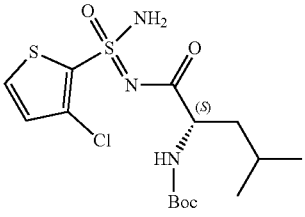 | Int-A-4.30<br>Int-A-4.30-Fr-1<br>Int-A-4.30-Fr-2 | Int-A-3.30 | LCMS ESI (m/z): 432.1 (M + Na)<br>Chiral prep HPLC: YMC CHIRALART CELLULOSE_SC<br>Mobile phase: Heptane_IPA-ACN (70-30)_85:15<br>Isomer-1 (Fr-1): Retention time: 6.80 min<br>Isomer-2 (Fr-2): Retention time: 9.33 min |
| 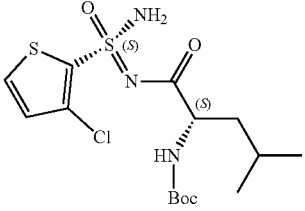 | | | |
| 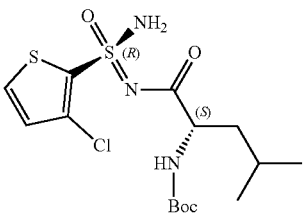 | | | |
| 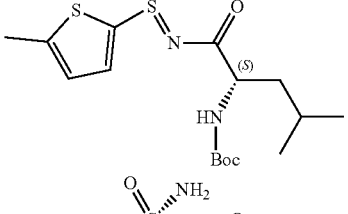 | Int-A-4.31<br>Int-A-4.31-Fr-1<br>Int-A-4.31-Fr-2 | Int-A-3.31 | LCMS ESI (m/z): 412.0 (M + Na)<br>Chiral prep HPLC: YMC CHIRALART CELLULOSE_SC<br>Mobile phase: Heptane_IPA-MeOH (70-30)_85:15<br>Isomer-1 (Fr-1): Retention time: 11.57 min<br>Isomer-2 (Fr-2): Retention time: 15.24 min |
| 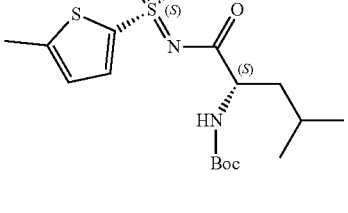 | | | |

Synthesis Table 8

| Structure | Compound ID | Precursor | Analytical data/Chiral separation |
|---|---|---|---|
| | Int-A-4.32<br>Int-A-4.32-Fr-1<br>Int-A-4.32-Fr-2 | Int-A-3.32 | LCMS ESI (m/z): 412.1 (M + Na)<br>Chiral prep HPLC: YMC CHIRALART CELLULOSE_SC<br>Mobile phase: Heptane_IPA-ACN (70-30)_92:8<br>Isomer-1 (Fr-1): Retention time: 13.80 min<br>Isomer-2 (Fr-2): Retention time: 25.79 min |
| | Int-A-4.33<br>Int-A-4.33-Fr-1<br>Int-A-4.33-Fr-2 | Int-A-3.33 | LCMS ESI (m/z): 412.4 (M + 1)<br>Chiral prep HPLC: YMC CHIRALART CELLULOSE_SC<br>Mobile phase: Heptane_IPA-ACN (70-30)_90:10<br>Isomer-1 (Fr-1): Retention time: 9.03 min<br>Isomer-2 (Fr-2): Retention time: 19.62 min |

Synthesis Table 8

| Structure | Compound ID | Precursor | Analytical data/Chiral separation |
|---|---|---|---|
| | Int-A-4.34<br>Int-A-4.34-Fr-1<br>Int-A-4.34-Fr-2 | Int-A-3.34 | LCMS ESI (m/z): 426.5 (M + 1)<br>Chiral prep HPLC: CHIRALPAK IG SFC<br>Mobile phase: Heptane_IPA-ACN (70-30)_92:8<br>Isomer-1 (Fr-1): Retention time: 18.37 min<br>Isomer-2 (Fr-2): Retention time: 21.06 min |
| 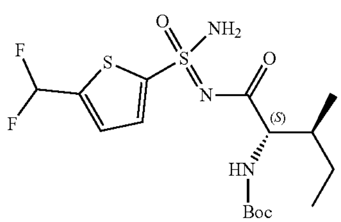 | Int-A-4.35 | Int-A-3.35 | LCMS ESI (m/z): 326.0 (M + H − Boc) |
| | Int-A-4.36<br>Int-A-4.36-Fr-1<br>Int-A-4.36-Fr-2 | Int-A-3.36 | LCMS ESI (m/z): 442.1 (M + 1)<br>Chiral prep HPLC: DIACEL Chiral PAK_IG<br>Mobile phase: Heptane_IPA-ACN (70-30)_90:10<br>Isomer-1 (Fr-1): Retention time: 9.30 min<br>Isomer-2 (Fr-2): Retention time: 21.62 min |

-continued

Synthesis Table 8

| Structure | Compound ID | Precursor | Analytical data/Chiral separation |
|---|---|---|---|
| (naphthalen-1-yl sulfonimidamide with (S)-Leu-Boc, (R) at S) | | | |
| (naphthalen-1-yl sulfonimidamide with (S)-Val-Boc) | Int-A-4.37 | Int-A-3.37 | LCMS ESI (m/z): 428.1 (M + Na) |
| (naphthalen-2-yl sulfonimidamide with (S)-Leu-Boc) | Int-A-4.38 | Int-A-3.38 | LCMS ESI (m/z): 442.2 (M + Na) |
| (naphthalen-2-yl sulfonimidamide with (S)-Ile-Boc) | Int-A-4.39 | Int-A-3.39 | LCMS ESI (m/z): 442.1 (M + 1) |
| (4-chloronaphthalen-1-yl sulfonimidamide with (S)-Leu-Boc) | Int-A-4.40 | Int-A-3.40 | LCMS ESI (m/z): 354.1 (M + H − Boc) |

Synthesis Table 8

| Structure | Compound ID | Precursor | Analytical data/Chiral separation |
|---|---|---|---|
| | Int-A-4.41<br>Int-A-4.41-Fr-1<br>Int-A-4.41-Fr-2 | Int-A-3.41 | LCMS ESI (m/z): 460.1 (M + 1)<br>Chiral prep HPLC: DIACEL Chiral PAK_IG<br>Mobile phase: Heptane_IPA-ACN (70-30)_80:20<br>Isomer-1 (Fr-1): Retention time: 16.57 min<br>Isomer-2 (Fr-2): Retention time: 20.56 min |
| | Int-A-4.42<br>Int-A-4.42-Fr-1<br>Int-A-4.42-Fr-2 | Int-A-3.42 | LCMS ESI (m/z): 496.7 (M + 1)<br>Chiral prep HPLC: DIACEL Chiral PAK_IG<br>Mobile phase: Heptane_IPA-MeOH (70-30)_90:10<br>Isomer-1 (Fr-1): Retention time: 14.23 min<br>Isomer-2 (Fr-2): Retention time: 18.05 min |

Synthesis Table 8

| Structure | Compound ID | Precursor | Analytical data/Chiral separation |
|---|---|---|---|
| | Int-A-4.43<br>Int-A-4.43-Fr-1<br>Int-A-4.43-Fr-2 | Int-A-3.43 | LCMS ESI (m/z): 496.2 (M + 1)<br>Chiral prep HPLC: YMC CHIRALART CELLULOSE_SC<br>Mobile phase: Heptane_IPA-MeOH (70-30)_90:10<br>Isomer-1 (Fr-1): Retention time: 7.00 min<br>Isomer-2 (Fr-2): Retention time: 11.41 min |
| | Int-A-4.44<br>Int-A-4.44-Fr-1<br>Int-A-4.44-Fr-2 | Int-A-3.44 | LCMS ESI (m/z): 426.30 (M + 1)<br>Chiral prep HPLC: YMC CHIRALART CELLULOSE_SC<br>Mobile phase: Heptane_IPA-ACN (70-30)_85:15<br>Isomer-1 (Fr-1): Retention time: 14.02 min<br>Isomer-2 (Fr-2): Retention time: 21.17 min |
| 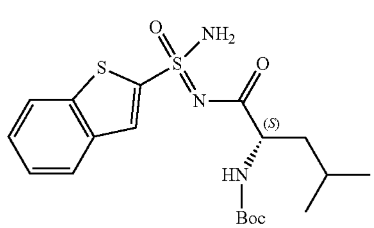 | Int-A-4.45 | Int-A-3.45 | LCMS ESI (m/z): 447.9 (M + Na) |

Synthesis Table 8

| Structure | Compound ID | Precursor | Analytical data/Chiral separation |
|---|---|---|---|
| (benzothiophene-2-sulfonimidoyl-NH2, S-configured isoleucine-Boc structure) | Int-A-4.46 | Int-A-3.46 | LCMS ESI (m/z): 424.3 (M + 1) |
| (phenyl sulfonimidoyl-NH2, S-cyclopropylalanine-Boc; plus (S,S) and (R,S) diastereomer structures) | Int-A-4.47<br>Int-A-4.47-Fr-1<br>Int-A-4.47-Fr-2 | Int-A-3.47 | LCMS ESI (m/z): 368.4 (M + 1)<br>Chiral prep HPLC: YMC CHIRALART CELLULOSE_SC<br>Mobile phase: Heptane_IPA-ACN (70-30)_70:30<br>Isomer-1 (Fr-1): Retention time: 7.73 min<br>Isomer-2 (Fr-2): Retention time: 11.12 min |
| (pyridyl sulfonimidoyl-NH2, S-leucine-Boc structure) | Int-A-4.48 | Int-A-3.48 | LCMS ESI (m/z): 271.0 (M + H − Boc) |
| (thienothiophene sulfonimidoyl-NH2, S-leucine-Boc structure) | Int-A-4.53 | Int-A-3.52 | LCMS ESI (m/z): 432.3 (M + H) |
| (thienothiophene sulfonimidoyl-NH2, S-isoleucine-Boc structure) | Int-A-4.54 | Int-A-3.53 | LCMS ESI (m/z): 432.3 (M + H) |

Synthesis Table 8

| Structure | Compound ID | Precursor | Analytical data/Chiral separation |
|---|---|---|---|
| (benzothiophene sulfonimidoyl leucine-Boc structures, 3 diastereomers) | Int-A-4.55<br>Int-A-4.55-Fr-1<br>Int-A-4.55-Fr-2 | Int-A-3.51 | LCMS ESI (m/z): 425.51 (M + 1)<br>Chiral prep HPLC: YMC CHIRALART CELLULOSE-SC<br>Mobile phase: Heptane_IPA-ACN (70-30)_93:7<br>Isomer-1 (Fr-1): Retention time: 15.18 min<br>Isomer-2 (Fr-2): Retention time: 28.21 min |
| (phenyl sulfonimidoyl 1-amino-3-methylcyclopentane-Boc structure) | Int-A-4.56 | Int-A-3.54 | LCMS ESI (m/z): 404.2 (M + Na) |
| (o-tolyl sulfonimidoyl leucine-Boc structures, 3 diastereomers) | Int-A-4.57<br>Int-A-4.57-Fr-1<br>Int-A-4.57-Fr-2 | Int-A-3.55 | LCMS ESI (m/z): 384.4 (M + H)<br>Chiral prep HPLC: YMC CHIRALART CELLULOSE_SC<br>Mobile phase: Heptane_IPA-MeOH (70-30)_93:7<br>Isomer-1 (Fr-1): Retention time: 21.79 min<br>Isomer-2 (Fr-2): Retention time: 41.46 min |

-continued

Synthesis Table 8

| Structure | Compound ID | Precursor | Analytical data/Chiral separation |
|---|---|---|---|
| (structures: 2-fluorophenyl sulfoximine-Leu-Boc, mixture and (R)-S and (S)-S isomers) | Int-A-4.58<br>Int-A-4.58-Fr-1<br>Int-A-4.58-Fr-2 | Int-A-3.56 | LCMS ESI (m/z): 388.4 (M + H)<br>Chiral prep HPLC: CHIRALPAK IG SFC<br>Mobile phase: Heptane_IPA-ACN (70-30)_88:12<br>Isomer-1 (Fr-1): Retention time: 34.83 min<br>Isomer-2 (Fr-2): Retention time: 47.37 min |
| (structures: 3-(difluoromethoxy)phenyl sulfoximine-Leu-Boc, mixture and (S)-S and (R)-S isomers) | Int-A-4.59<br>Int-A-4.59-Fr-1<br>Int-A-4.59-Fr-2 | Int-A-3.57 | LCMS ESI (m/z): 436.5 (M + 1)<br>Chiral prep HPLC: CHIRALPAK IG SFC<br>Mobile phase: n-HEPTANE_IPA (75:25)<br>Isomer-1 (Fr-1): Retention time: 29.25 min<br>Isomer-2 (Fr-2): Retention time: 53.26 min |

-continued

Synthesis Table 8

| Structure | Compound ID | Precursor | Analytical data/Chiral separation |
|---|---|---|---|
| (three structures shown: sulfoximine with difluoromethoxy phenyl group linked to Boc-protected isoleucine derivative, with different stereochemistry designations) | Int-A-4.60<br>Int-A-4.60-Fr-1<br>Int-A-4.60-Fr-2 | Int-A-3.58 | LCMS ESI (m/z): 436.60 (M + 1)<br>Chiral prep HPLC: CHIRALPAK IG SFC<br>Mobile phase: n-HEPTANE_IPA: ACN (70:30)_90:10<br>Isomer-1 (Fr-1): Retention time: 26.50 min<br>Isomer-2 (Fr-2): Retention time: 32.70 min |
| (three structures shown: sulfoximine with difluoromethoxy phenyl group linked to Boc-protected valine derivative, with different stereochemistry designations) | Int-A-4.61<br>Int-A-4.61-Fr-1<br>Int-A-4.61-Fr-2 | Int-A-3.59 | LCMS ESI (m/z): 422.5 (M + 1)<br>Chiral prep HPLC: YMC CHIRALART CELLULOSE_SC,<br>Mobile phase: HEPTANE_IPA:MEOH (70:30)_94:6<br>Isomer-1 (Fr-1): Retention time: 18.95 min<br>Isomer-2 (Fr-2): Retention time: 29.53 min |

-continued

Synthesis Table 8

| Structure | Compound ID | Precursor | Analytical data/Chiral separation |
|---|---|---|---|
| (three structures: 3-CF3-phenyl sulfonimidamide-N-acyl-Leu-NHBoc; mixture, (S) at S, and (R) at S isomers) | Int-A-4.62<br>Int-A-4.62-Fr-1<br>Int-A-4.62-Fr-2 | Int-A-3.60 | LCMS ESI (m/z): 438.6 (M + H)<br>Chiral prep HPLC: YMC-Actus Triart<br>Mobile phase: Heptane_IPA-ACN (70-30)_88:12<br>Isomer-1 (Fr-1): Retention time: 22.17 min<br>Isomer-2 (Fr-2): Retention time: 30.83 min |
| (three structures: 3-CF3-phenyl sulfonimidamide-N-acyl-Ile-NHBoc; mixture, (S) at S, and (R) at S isomers) | Int-A-4.63<br>Int-A-4.63-Fr-1<br>Int-A-4.63-Fr-2 | Int-A-3.61 | LCMS ESI (m/z): 438.3 (M + H)<br>Chiral prep HPLC: YMC CHIRALART CELLULOSE_SC<br>Mobile phase: Heptane_IPA-MeOH (70-30)_95:5<br>Isomer-1 (Fr-1): Retention time: 10.25 min<br>Isomer-2 (Fr-2): Retention time: 12.55 min |
| (3-OCF3-phenyl sulfonimidamide-N-acyl-Leu-NHBoc) | Int-A-4.64 | Int-A-3.62 | LCMS ESI (m/z): 454.4 (M + 1) |

Synthesis Table 8

| Structure | Compound ID | Precursor | Analytical data/Chiral separation |
|---|---|---|---|
| (three structures: 3-OCF3-phenyl sulfonimidamide coupled to Boc-Ile, shown as mixture, (S)-sulfur, and (R)-sulfur isomers) | Int-A-4.65<br>Int-A-4.65-Fr-1<br>Int-A-4.65-Fr-2 | Int-A-3.63 | Chiral prep HPLC:<br>YMC CHIRALART<br>CELLULOSE_SC<br>Mobile phase:<br>Heptane_IPA-<br>MeOH (70-30)_96:4<br>Isomer-1 (Fr-1):<br>Retention time: 26.60 min<br>Isomer-2 (Fr-2):<br>Retention time: 46.85 min |
| (three structures: 5-chlorothiophene sulfonimidamide coupled to Boc-Leu, mixture, (S)-sulfur, (R)-sulfur) | Int-A-4.66<br>Int-A-4.66-Fr-1<br>Int-A-4.66-Fr-2 | Int-A-3.64 | LCMS ESI (m/z): 410.4 & 414.4 (M & M + 2)<br>Chiral prep HPLC:<br>YMC CHIRALART<br>CELLULOSE_SC<br>Mobile phase:<br>Heptane_IPA-85:15<br>Isomer-1 (Fr-1):<br>Retention time: 16.70 min<br>Isomer-2 (Fr-2):<br>Retention time: 30.73 min |
| (two structures: 5-chlorothiophene sulfonimidamide coupled to Boc-Ile, mixture and (S)-sulfur isomer) | Int-A-4.67<br>Int-A-4.67-Fr-1<br>Int-A-4.67-Fr-2 | Int-A-3.65 | LCMS ESI (m/z): 410.4 & 412.4 (M + 2)<br>Chiral prep HPLC:<br>CHIRALPAK IG SFC<br>Mobile phase:<br>Heptane_IPA-ACN (70-30)_83:17<br>Isomer-1 (Fr-1):<br>Retention time: 17.88 min<br>Isomer-2 (Fr-2):<br>Retention time: 24.72 min |

Synthesis Table 8
| Structure | Compound ID | Precursor | Analytical data/Chiral separation |
|---|---|---|---|
| 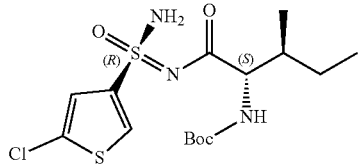 | Int-A-4.68 | Int-A-3.66 | LCMS ESI (m/z): 432.4 (M + H) |
| 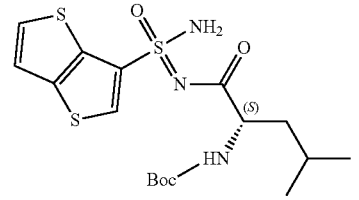 | Int-A-4.69 | Int-A-3.67 | LCMS ESI (m/z): 432.4 (M + H) |
| 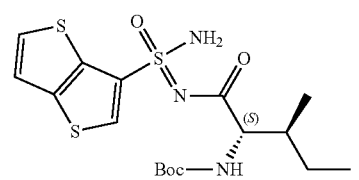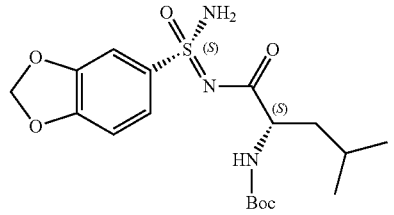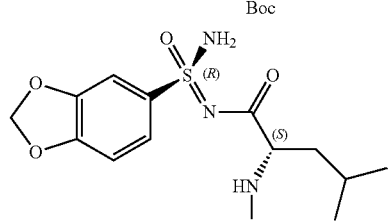 | Int-A-4.70<br>Int-A-4.70-Fr-1<br>Int-A-4.70-Fr-2 | Int-A-3.68 | LCMS ESI (m/z): 314.3 (M + H)<br>Chiral prep HPLC:<br>YMC CHIRALART<br>CELLULOSE_SC<br>Mobile phase:<br>Heptane-IPA:ACN (70:30)_93:7<br>Isomer-1 (Fr-1):<br>Retention time: 27.44 min<br>Isomer-2 (Fr-2):<br>Retention time: 39.56 min |

-continued

Synthesis Table 8

| Structure | Compound ID | Precursor | Analytical data/Chiral separation |
|---|---|---|---|
| 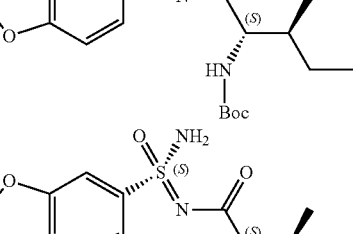 | Int-A-4.71<br>Int-A-4.71-Fr-1<br>Int-A-4.71-Fr-2 | Int-A-3.69 | LCMS ESI (m/z): 414.6 (M + 1)<br>Chiral prep HPLC: YMC CHIRALART CELLULOSE_SC,<br>Mobile phase: 0.1% TFA-Heptane_IPA:MeOH (70:30)_85:15<br>Isomer-1 (Fr-1): Retention time: 17.18 min<br>Isomer-2 (Fr-2): Retention time: 30.48 min |
| 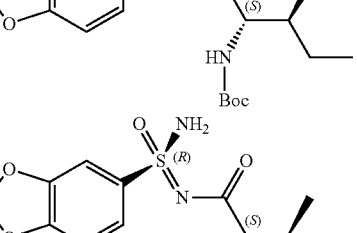 | | | |
|  | | | |
| 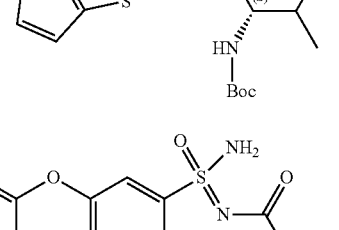 | Int-A-4.72 | Int-A-3.70 | LCMS ESI (m/z): 418.2 (M + H) |
| 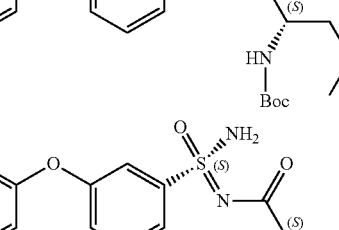 | Int-A-4.73<br>Int-A-4.73-Fr-1<br>Int-A-4.73-Fr-2 | Int-A-3.71 | LCMS ESI (m/z): 462.6 (M + H)<br>Chiral prep HPLC: CHIRALPAK IG SFC,<br>Mobile phase: n-Heptane_IPA:MeOH (70:30)_70:30<br>Isomer-1 (Fr-1): Retention time: 14.38 min<br>Isomer-2 (Fr-2): Retention time: 26.38 min |
| 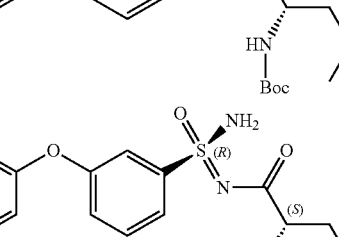 | | | |
|  | | | |

-continued

Synthesis Table 8

| Structure | Compound ID | Precursor | Analytical data/Chiral separation |
|---|---|---|---|
| | Int-A-4.76<br>Int-A-4.76-Fr-1<br>Int-A-4.76-Fr-2 | Int-A-3.72 | LCMS ESI (m/z):<br>444.1 & 446.0 (M & M + 2)<br>Chiral prep HPLC:<br>YMC CELLULOSE_SC<br>Mobile phase:<br>n-Heptane_IPA (87:13)<br>Isomer-1 (Fr-1):<br>Retention time: 13.19 min<br>Isomer-2 (Fr-2):<br>Retention time: 29.81 min |
| 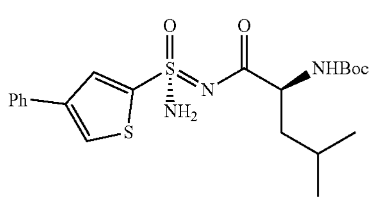 [SMILES: CC(C)C[C@H](NC(=O)OC(C)(C)C)C(=O)N=[S@](N)(=O)c1cc(-c2ccccc2)cs1] | Int-A-4.78 | Int-A-3.74 | LCMS ESI (m/z): 452.5 (M + H)$^+$<br>Chiral prep HPLC:<br>CHIRALPAK IC<br>Mobile phase:<br>Heptane-IPA-DCM (55-25-20)<br>Isomer-1 (Fr-1):<br>Retention time: 5.24 min<br>Isomer-2 (Fr-2):<br>Retention time: 12.73 min |
| 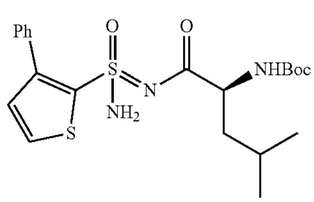 [SMILES: CC(C)C[C@H](NC(=O)OC(C)(C)C)C(=O)N=S(N)(=O)c1sccc1-c1ccccc1] | Int-A-4.79 | Int-A-3.75 | LCMS ESI (m/z): 452.5 (M + H)$^+$ |

Synthesis Table 8

| Structure | Compound ID | Precursor | Analytical data/Chiral separation |
|---|---|---|---|
| (2,5-dichlorothiophene sulfonimidamide-Leu-Boc structure) | Int-A-4.77<br>Int-A-4.77-Fr-1<br>Int-A-4.77-Fr-2 | Int-A-3.73 | LCMS ESI (m/z): 444.1, 446.1 (M & M + 1)<br>Chiral prep HPLC: YMC CHIRALART CELLULOSE_SC<br>Mobile phase: Heptane_IPA (85:15)<br>Isomer-1 (Fr-1): Retention time: 10.99 min<br>Isomer-2 (Fr-2): Retention time: 28.98 min |
| (S)-isomer structure | | | |
| (R)-isomer structure | | | |

Synthesis of (S)-2-amino-N—((S)-amino(oxo)(phenyl)-λ6-sulfanylidene)-4-methylpentanamide hydrochloride and (S)-2-amino-N—((R)-amino(oxo)(phenyl)-λ6-sulfanylidene)-4-methylpentanamide hydrochloride (ANASIA-003-1/2

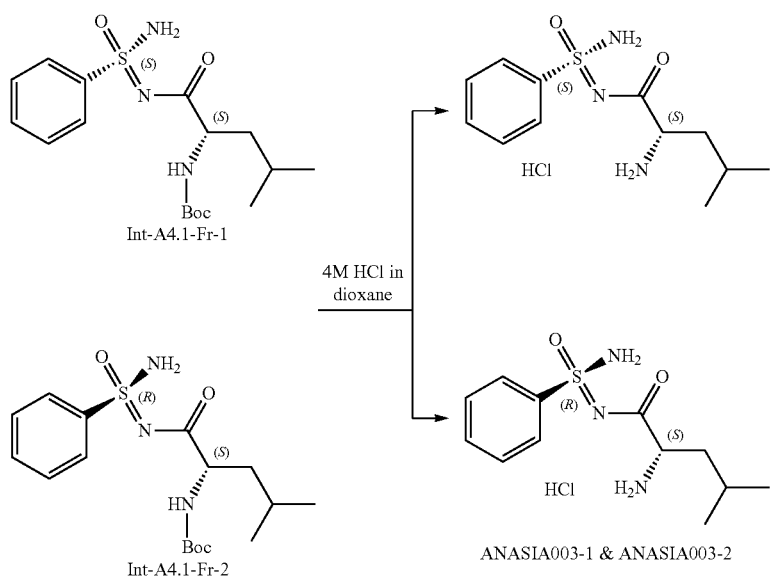

To a solution of Int-A-4.1-Fr-1 (Isomer-1) (90 mg, 0.24 mmol) in 1,4-Dioxane (2 mL) was added 4 M HCl in 1,4-dioxane (2 mL) at 0° C. The reaction mixture was allowed to stir at room temperature for 1 h. After completion of the reaction as indicated by TLC, the reaction mixture was concentrated under reduced pressure followed by trituration with n-pentane and diethyl ether to give the title compound, ANASIA-003-1, as a hydrochloride salt (59 mg, 91%). $^1$H-NMR (400 MHz, DMSO-$d_6$) δ: 7.95 (brs, 5H), 7.91-7.81 (m, 2H), 7.65-7.59 (m, 3H), 3.69-3-67 (m, 1H); 1.73-1.53 (m, 2H); 1.44-1.38 (m, 1H), 0.87-0.86 (d, J=4.4 Hz 3H), 0.86-0.85 (d, J=6.4 Hz, 3H, LCMS ESI (m/z): 269.9 (M+1), Purity 100% @ 210 nm.

To a solution of Int-A-4.1-Fr-2 (Isomer-2) (77 mg, 0.21 mmol) in 1,4-dioxane (2 mL) was added 4 M HCl in 1,4-dioxane (2 mL) at 0° C. The reaction mixture was allowed to stir at room temperature for 1 h. After completion of the reaction as indicated by TLC, the reaction mixture was concentrated under reduced pressure. The product was triturated with n-pentane:diethyl ether to give the title compound, ANASIA-003-2, as a hydrochloride salt (54 mg, 100%). $^1$H-NMR (400 MHz, DMSO-$d_6$) δ: 7.97-7.91 (m, 6H), 7.91-7.81 (m, 3H), 3.70-3-60 (m, 1H), 1.73-1.65 (m, 2H), 1.58-1.55 (m, 1H), 0.91-0.90 (d, J=6.4 Hz 3H), 0.89-0.87 (d, J=6.4 Hz, 3H). LCMS ESI (m/z): 270.0 (M+1), Purity 100% @ 210 nm.

Synthesis of (S)-2-amino-N—((S)-amino(oxo)(thiophen-2-yl)-λ6-sulfanylidene)-4-methylpentanamide hydrochloride and (S)-2-amino-N—((R)-amino(oxo)(thiophen-2-yl)-λ6-sulfanylidene)-4-methyl pentanamide hydrochloride (ANASIA-007-1/2

To a solution of Int-A-4.20-Fr-1 (Isomer-1) (48 mg, 0.12 mmol) in 1,4-dioxane was added 4 M HCl in 1,4-dioxane (0.65 mL) at 0° C. The reaction mixture was allowed to stir at room temperature for 1 h. After completion of the reaction as indicated by TLC, the reaction mixture was concentrated under reduced pressure followed by trituration with n-pentane.

Further the compound was purified by prep HPLC (Column: REPACK $C_{18}$) Mobile phase: A=0.05% HCl in water, B=ACN) to give the title compound, ANASIA-007-1, as a hydrochloride salt (16 mg, 45%). $^1$H-NMR (400 MHz, DMSO-$d_6$) δ: 8.23 (brs, 2H), 8.16 (brs, 3H), 7.99 (dd, J=1.2 Hz, 1H), 7.73 (dd, J=1.2 Hz, 1H), 7.19 (dd, J=4.8 Hz, 1H), 3.68 (dd, J=5.6, 1H), 1.78-1.75 (m, 1H), 1.65-1.60 (m, 1H), 1.52-1.48 (m, 1H), 0.89-0.87 (two d, 6H). LCMS ESI (m/z): 276.2 (M+1), Purity at 210 nm: 99+%.

To a solution of Int-A-4.20-Fr-2 (Isomer-2) (40 mg, 0.10 mmol) was added 4 M HCl in 1,4-dioxane (0.65 mL) at 0° C. The reaction mixture was allowed to stir at room temperature for 1 h. After completion of the reaction as indicated by TLC, the reaction mixture was concentrated under reduced pressure. The product was triturated with n-pentane:diethyl ether to give the title compound, ANASIA-007-2, as a hydrochloride salt (18 mg, 51%). $^1$H-NMR (400 MHz, DMSO-$d_6$) δ: 8.30 (brs, 2H), 8.04 (brs, 3H), 8.00 (dd, J=1.4 Hz, 1H), 7.75 (dd, J=1.4, Hz, 1H), 7.21 (dd, J=3.8, 1H), 3.66-3.65 (m, 1H), 1.08-1.78 (m, 1H), 1.69-1.67 (m, 1H), 1.60-1.57 (m, 1H), 0.91-0.89 (two d, 6H). LCMS ESI (m/z): 276.3 (M+1), Purity at 210 nm: 99+%.

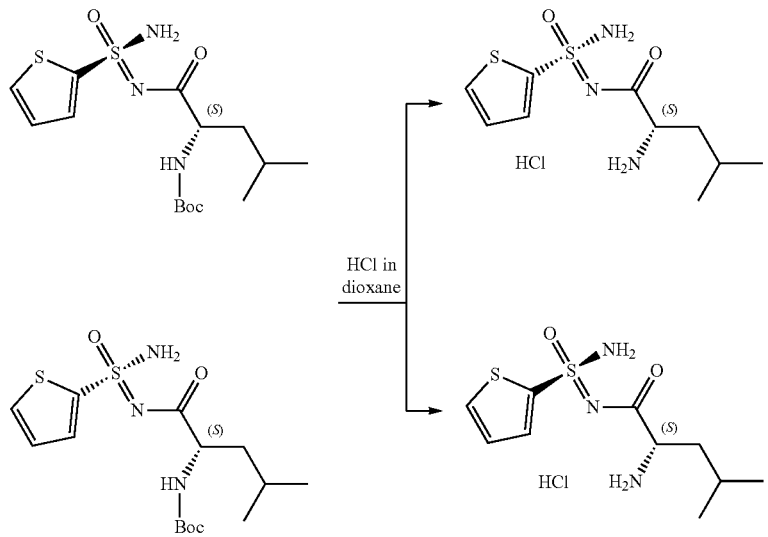

Int-A4.20-Fr-1 and Int-A4.20-Fr-2

ANASIA007-1 & ANASIA007-2

Synthesis of (2S)-2-amino-N-(amino(3-chloro-2-fluorophenyl)(oxo)-λ6-sulfanylidene)-4-methylpentanamide 2,2,2-trifluoroacetate (ANASIA-001

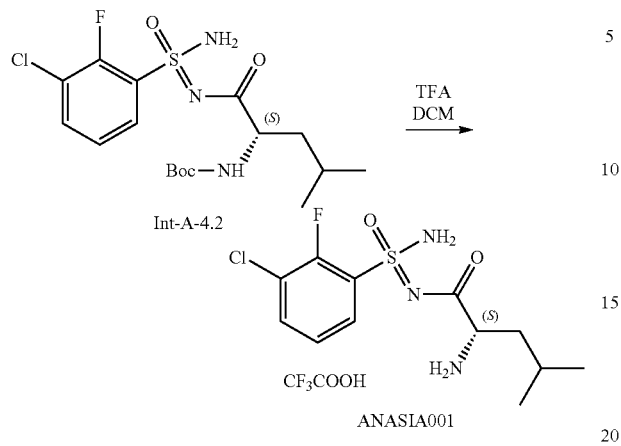

To a stirred solution of Int-A-4.2 (50 mg, 0.11 mmol) in DCM (0.5 mL) was added TFA (0.1 mL) and allowed to stir at room temperature for 1 h. After completion of the reaction as indicated by TLC, the reaction mixture was concentrated under reduced pressure followed by trituration with n-pentane and diethyl ether to give the title compound, ANASIA-001, as a TFA salt (25 mg, 65.78%). $^1$H-NMR (400 MHz, DMSO-$d_6$) δ: 8.04 (brs, 5H), 7.94-7.86 (m, 2H), 7.48-7.44 (m, 1H), 3.74-3.68 (m, 1H), 1.76-1.55 (m, 3H), 0.91-0.86 (m, 6H). LCMS ESI (m/z): 322.1 & 324.1 (M+H); Purity at 210 nm: 94.11%.

The following compounds were made according to the procedure described for ANASIA-003 and ANASIA-001 using HCl or TFA.

Synthesis Table 9

| Structure | Precursor | Analytical data |
|---|---|---|
| ANASIA-001-1 (HCl, S-isomer); ANASIA-001-2 (HCl, R-isomer) | Int-A-4.2-Fr-1<br>Int-A-4.2-Fr-2 | Isomer-1<br>$^1$H-NMR (400 MHz, DMSO-$d_6$) δ: 7.84-7.78 (m, 2H), 7.59 (brs, 5H), 7.40-7.37 (m, 1H), 3.53 (brs, 1H), 1.70-1.40 (m, 3H), 0.85 d, 6H).<br>LCMS ESI (m/z): 322.1 & 324.0 (M + H)<br>Purity at 210 nm: 93.73%<br>Isomer-2<br>$^1$H-NMR (400 MHz, DMSO-$d_6$) δ: 8.60-8.20 (m, 2H), 8.20-7.80 (m, 5H), 7.48-7.44 (m, 1H), 3.67 (brs, 1H), 1.76-1.55 (m, 3H), 0.91-0.86 (m, 6H).<br>LCMS ESI (m/z): 322.2 & 324.1 (M + H)<br>Purity at 210 nm: 95.31% |
| ANASIA-002 (CF$_3$COOH) | Int-A-4.3 | $^1$H-NMR (400 MHz, MeOD) δ: 8.0 (t, J = 2.4 Hz, 1H), 7.92 (t, J = 6.8 Hz, 1H), 7.69 (d, J = 8 Hz, 1H), 7.60 (t, J = 8 Hz, 1H), 3.79 (dd, 1H), 2.79 (brs, 1H), 1.30 (brs, 2H), 0.99 (two d, 6H).<br>LCMS ESI (m/z): 304.0 (M + H)<br>Purity at 210 nm: 99+% |

Synthesis Table 9

| Structure | Precursor | Analytical data |
|---|---|---|
| ANASIA-002-1 (3-Cl phenyl, (S) at S, H₂N-Leu, HCl)<br>ANASIA-002-2 (3-Cl phenyl, (R) at S, H₂N-Leu, HCl) | Int-A-4.3-Fr-1<br>Int-A-4.3-Fr-2 | Isomer-1<br>$^1$H-NMR (400 MHz, DMSO-$d_6$) δ: 8.14 (brs, 2H), 8.04 (brs, 3H), 7.92 (t, J = 3.6 Hz, 1H), 7.89-7.86 (m, 1H), 7.77-7.75 (m, 1H), 7.67 (t, J = 8 Hz, 1H), 3.77-3.65 (m, 1H), 1.74-1.72 (m, 1H), 1.62-1.58 (m, 1H), 1.46-1.44 (m, 1H), 0.87 (s, 6H).<br>LCMS ESI (m/z): 304.0 & 305.9 (M + H)<br>Purity at 210 nm: 99+%<br>Isomer-2<br>$^1$H-NMR (400 MHz, DMSO-$d_6$) δ: 8.16 (brs, 2H), 8.05 (brs, 3H), 7.94 (s, 1H), 7.89 (d, J = 8 Hz, 1H), 7.76 (d, J = 8 Hz, 1H), 7.66 (t, J = 8 Hz, 1H), 3.68 (brs, 1H), 1 79-1.76 (m, 1H), 1.72-1.65 (m, 1H), 1.61-1.57 (m, 1H), 0.9 (s, 6H).<br>LCMS ESI (m/z): 304.1 & 305.9 (M + H)<br>Purity at 210 nm: 95.46% |
| ANASIA-033-1 (3-Cl phenyl, (S) at S, (S,S)-Ile, HCl)<br>ANASIA-033-2 (3-Cl phenyl, (R) at S, (S,S)-Ile, HCl) | Int-A-4.50-Fr-1<br>Int-A-4.50-Fr-2 | Isomer-1<br>$^1$H-NMR (400 MHz, DMSO-$d_6$) δ: 8.0 (brs, 5H), 7.93 (s, 1H), 7.87 (d, J = 8 Hz, 1H), 7.74 (d, J = 8 Hz, 1H), 7.65 (t, J = 8 Hz, 1H), 3.63 (brs, 1H), 1.91 (brs, 1H), 1.49-1.43 (m, 1H), 1.30-1.22 (m, 1H), 0.88 (d, J = 6.4 Hz, 6H).<br>LCMS ESI (m/z): 302 (M − 1)<br>Purity @ 210 nm 97.86%<br>Isomer-2<br>$^1$H NMR (400 MHz, DMSO-$d_6$) δ 8.00 (brs, 5H), 7.93 (s, 1H), 7.88 (d, J = 7.8 Hz, 1H), 7.75 (d, J = 8.3 Hz, 1H), 7.65 (t, J = 7.9 Hz, 1H), 3.64 (brs, 1H), 1.92 (brs, 1H), 1.55-1.17 (m, 2H), 0.88 (two d, J = 7.0 Hz, 6H).<br>LCMS ESI (m/z): 301.8 (M − 1)<br>Purity @ 210 nm 95.05% |
| ANASIA-040-1 (4-Cl phenyl, (S) at S, H₂N-Leu, HCl)<br>ANASIA-040-2 (4-Cl phenyl, (R) at S, H₂N-Leu, HCl) | Int-A-4.4-Fr-1<br>Int-A-4.4-Fr-2 | Isomer-1<br>$^1$H NMR (400 MHz, DMSO-$d_6$) δ 8.08 (brs, 3H), 8.00 (brs, 2H), 7.90 (d, J = 8.6 Hz, 2H), 7.71 (d, J = 8.6 Hz, 2H), 3.66 (brs, 1H), 1.74-1.64 (m, 1H), 1.64-1.51 (m, 1H), 1.48-1.37 (m, 1H), 0.85 (two d, J = 5.9 Hz, 6H).<br>LCMS ESI (m/z): 304.0 & 306.1 (M + 1)<br>Purity at 210 nm: 96.99%<br>Isomer-2<br>$^1$H NMR (400 MHz, DMSO-$d_6$) δ 8.09 (brs, 2H), 7.99 (brs, 3H), 7.90 (d, J = 8.6 Hz, 2H), 7.70 (d, J = 8.6 Hz, 2H), 3.64 (brs, 1H), 1.82-1.50 (m, 3H), 0.97-0.80 (m, 6H).<br>LCMS ESI (m/z): 304.0 & 306.1 (M + 1)<br>Purity at 210 nm: 97.18% |

-continued

Synthesis Table 9

| Structure | Precursor | Analytical data |
|---|---|---|
| 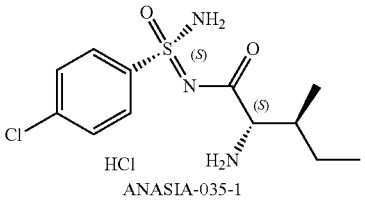<br>ANASIA-035-1<br>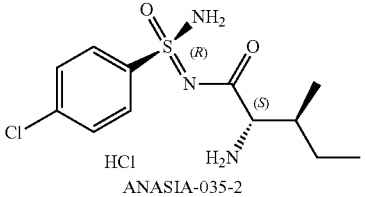<br>ANASIA-035-2 | Int-A-4.49-Fr-1<br>Int-A-4.49-Fr-2 | Isomer-1<br>$^1$H NMR (400 MHz, DMSO-d$_6$) δ 8.08 (brs, 2H), 7.97 (brs, 3H), 7.92 (d, J = 8.7 Hz, 2H), 7.70 (d, J = 8.7 Hz, 2H), 3.60 (brs, 1H), 1.91 (brs, 1H), 1.53-1.38 (m, 1H), 1.34-1.17 (m, 1H), 0.97-0.80 (m, 6H).<br>LCMS ESI (m/z): 304.1 & 305.9 (M + 1)<br>Purity at 210 nm: 97.32%<br>Isomer-2<br>$^1$H NMR (400 MHz, DMSO-d$_6$) δ 8.00 (brs, 5H), 7.92 (d, 2H), 7.71 (d, J = 8.7 Hz, 2H), 3.63 (brs, 1H), 1.90 (brs, 1H), 1.28-1.06 (m, 2H), 0.89-0.73 (m, 6H).<br>LCMS ESI (m/z): 304.1 & 306.1 (M + 1)<br>Purity at 210 nm: 92.43% |
| 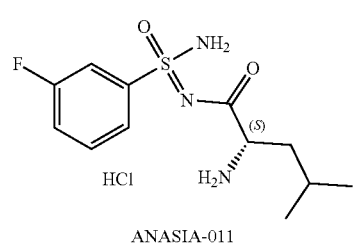<br>ANASIA-011 | Int-A-4.5 | $^1$H NMR (400 MHz, DMSO-d$_6$) δ 8.10 (brs, 2H), 8.0 (brs, 3H), 7.78-7.63 (m, 3H), 7.56-7.52 (m, 1H), 3.67 (brs, 1H), 1.77-1.44 (m, 3H), 0.91-0.84 (m, 6H).<br>LCMS ESI (m/z): 288.1 (M + H)<br>Purity at 220 nm: 93.04% |
| 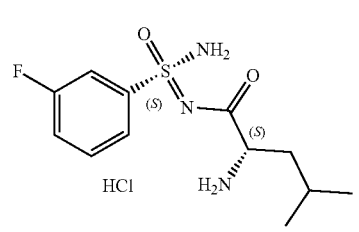<br>ANASIA-011-1<br>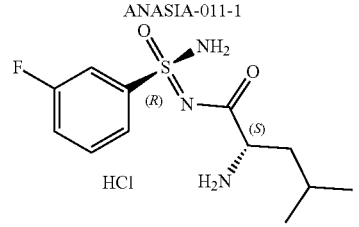<br>ANASIA-011-2 | Int-A-4.5-Fr-1<br>Int-A-4.5-Fr-2 | Isomer-1<br>$^1$H NMR (400 MHz, DMSO-d$_6$) δ 8.12 (brs, 2H), 8.02 (brs, 3H), 7.81-7.65 (m, 3H), 7.55 (t, J = 7.5 Hz, 1H), 3.69 (brs, 1H), 1.80-1.33 (m, 3H), 0.87 (two d, J = 5.8 Hz, 6H).<br>LCMS ESI (m/z): 288.1 (M + H)<br>Purity at 220 nm: 99.41%<br>Isomer-2<br>$^1$H NMR (400 MHz, DMSO-d$_6$) δ 8.13 (brs, 2H), 8.04 (brs, 3H), 7.84-7.63 (m, 3H), 7.55 (t, J = 8.3 Hz, 1H), 3.68 (brs, 1H), 1.85-1.51 (m, 3H), 0.90 (two d, J = 7.1 Hz, 6H).<br>LCMS ESI (m/z): 288.1 (M + H)<br>Purity at 210 nm: 99+% |
| 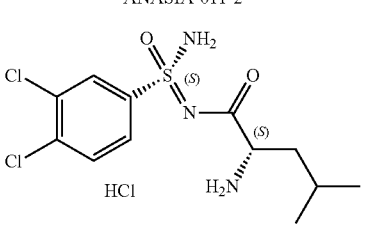<br>ANASIA-042-1<br>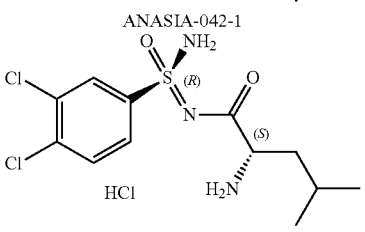<br>ANASIA-042-2 | Int-A-4.6-Fr-1<br>Int-A-4.6-Fr-2 | Isomer-1<br>$^1$H NMR (400 MHz, DMSO-d$_6$) δ 8.20 (brs, 2H), 8.09 (s, 1H), 7.99 (brs, 3H), 7.94 (d, J = 7.5 Hz, 1H), 7.85 (d, 1H), 3.70 (brs, 1H), 1.76-1.38 (m, 3H), 0.93-0.79 (m, 6H).<br>LCMS ESI (m/z): 338.1 & 340.0 (M + 1)<br>Purity at 210 nm: 93.20%<br>Isomer-2<br>$^1$H NMR (400 MHz, DMSO-d$_6$) δ 8.23 (brs, 2H), 8.11 (d, J = 1.8 Hz, 1H), 8.02 (brs, 3H), 7.93 (d, J = 8.5 Hz, 1H), 7.88 (d, J = 8.6 Hz, 1H), 3.67 (brs, 1H), 1.81-1.46 (m, 3H), 1.01-0.74 (m, 6H).<br>LCMS ESI (m/z): 338.2 & 340.0 (M + 1)<br>Purity at 210 nm: 91.84% |

-continued

Synthesis Table 9

| Structure | Precursor | Analytical data |
|---|---|---|
| 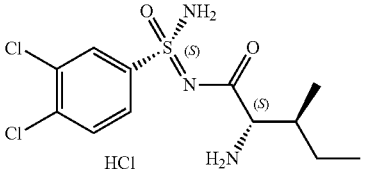 ANASIA-036-1 / ANASIA-036-2 | Int-A-4.7-Fr-1<br>Int-A-4.7-Fr-2 | Isomer-1<br>$^1$H NMR (400 MHz, DMSO-d$_6$) δ 8.18 (brs, 2H), 8.09 (d, J = 2.1 Hz, 1H), 7.95 (d, J = 8.5 Hz, 1H), 7.91-7.83 (m, 4H), 3.71 (brs, 1H), 1.92 (brs, 1H), 1.24-1.10 (m, 2H), 0.86-0.74 (m, 6H).<br>LCMS ESI (m/z): 338.0 & 340.0 (M + 1)<br>Purity at 210 nm: 99.52%<br>Isomer-2<br>$^1$H NMR (400 MHz, DMSO-d$_6$) δ 8.21 (brs, 2H), 8.10 (d, J = 2.1 Hz, 1H), 7.96-7.85 (m, 5H), 3.66 (brs, 1H), 1.90 (brs, 1H), 1.54-1.25 (m, 2H), 0.95-0.77 (m, 6H).<br>LCMS ESI (m/z): 338.0 & 340.0 (M + 1)<br>Purity at 210 nm: 99.50% |
| 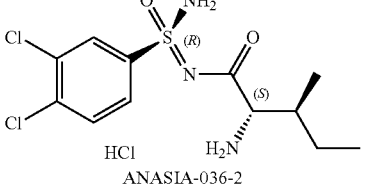 ANASIA-046-2 / ANASIA-046-1 | Int-A-4.8-Fr-1<br>Int-A-4.8-Fr-2 | Isomer-1<br>$^1$H NMR (400 MHz, DMSO-d$_6$) δ 8.99-7.99 (m, 6H), 7.94 (d, J = 7.9 Hz, 1H), 7.61 (t, J = 8.1 Hz, 1H), 3.73-3.60 (m, 1H), 1.83-1.48 (m, 3H), 0.93-0.82 (m, J = 6.3 Hz, 6H).<br>LCMS ESI (m/z): 338.3 & 340.3 (M + 1)<br>Purity at 210 nm: 96.97%<br>Isomer-2<br>$^1$H NMR (400 MHz, DMSO-d$_6$) δ 8.32 (brs, 2H), 8.09 (d, J = 8.0 Hz, 1H), 8.05-7.84 (m, 4H), 7.62 (t, J = 8.0 Hz, 1H), 3.79-3.65 (m, 1H), 1.89-1.63 (m, 2H), 1.55-1.37 (m, 1H), 0.87 (d, J = 6.2 Hz, 6H)<br>LCMS ESI (m/z): 338.3 & 340.3 (M + 1)<br>Purity at 210 nm: 97.17% |
| 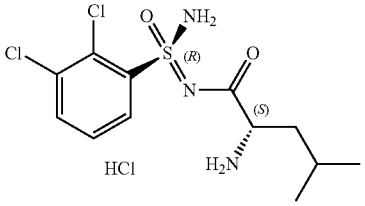 ANASIA-024-1 / ANASIA-024-2 | Int-A-4.9-Fr-1<br>Int-A-4.9-Fr-2 | Isomer-1<br>$^1$H NMR (400 MHz, DMSO-d$_6$) δ 8.38 (brs, 2H), 8.08 (brs, 3H), 7.77-7.51 (m, 3H), 3.69 (brs, 1H), 1.84-1.33 (m, 3H), 0.98-0.74 (m, 6H).<br>LCMS ESI (m/z): 306.0 (M + 1)<br>Purity at 210 nm: 99.01%<br>Isomer-2<br>$^1$H NMR (400 MHz, DMSO-d$_6$) δ 8.41 (brs, 2H), 8.07 (brs, 3H), 7.72-7.51 (m, 3H), 3.65 (brs, 1H), 1.79-1.55 (m, 3H), 0.95-0.74 (m, 6H).<br>LCMS ESI (m/z): 306.0 (M + 1)<br>Purity at 210 nm: 99.60% |
| 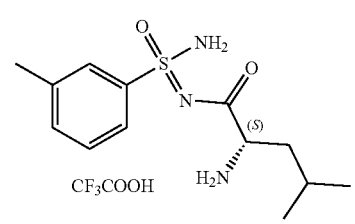 ANASIA-005 | Int-A-4.10 | $^1$H NMR (400 MHz, DMSO-d$_6$) δ 7.92 (brs, 5H), 7.71 (t, J = 8.7 Hz, 2H), 7.54-7.40 (m, 2H), 3.73-3.62 (m, 1H), 2.39 (s, 3H), 1.82-1.35 (m, 3H), 0.95-0.81 (m, 6H).<br>LCMS ESI (m/z): 284.0 (M + H)<br>Purity at 210 nm: 93.42% |

-continued

Synthesis Table 9

| Structure | Precursor | Analytical data |
|---|---|---|
| 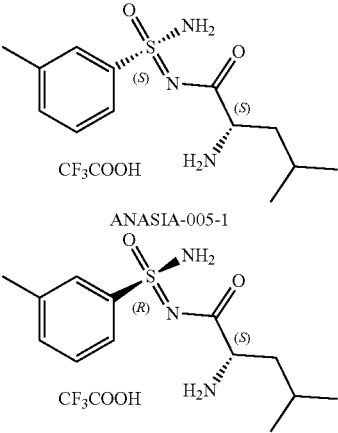<br>ANASIA-005-1<br><br>ANASIA-005-2 | Int-A-4.10-Fr-1<br>Int-A-4.10-Fr-2 | Isomer-1<br>$^1$H NMR (400 MHz, DMSO-d$_6$) δ 7.93 (brs, 5H), 7.78-7.67 (m, 2H), 7.56-7.43 (m, 2H), 3.74-3.61 (m, 1H), 2.40 (s, 3H), 1.84-1.49 (m, 3H), 1.01-0.78 (m, 6H).<br>LCMS ESI (m/z): 284.1 (M + H)<br>Purity at 210 nm: 96.72%<br>Isomer-2<br>$^1$H NMR (400 MHz, DMSO-d$_6$) δ 8.09-7.82 (m, 5H), 7.76-7.63 (m, 2H), 7.56-7.42 (m, 2H), 3.79-3.58 (m, 1H), 2.39 (S, 3H), 1.78-1.67 (m, 1H), 1.66-1.55 (m, 1H), 1.47-1.36 (m, 1H), 0.92 (d, 6H).<br>LCMS ESI (m/z): 284.1 (M + H)<br>Purity at 210 nm: 99+% |
| 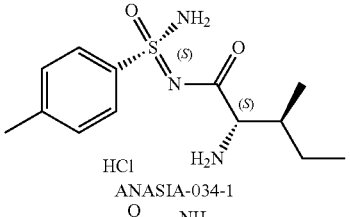<br>ANASIA-034-1<br>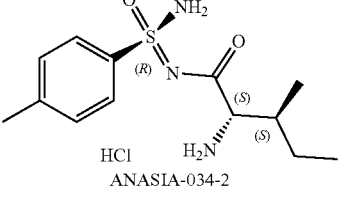<br>ANASIA-034-2 | Int-A-4.11-Fr-1<br>Int-A-4.11-Fr-2 | Isomer-1<br>$^1$H NMR (400 MHz, DMSO-d$_6$) δ 7.87 (s, 5H), 7.79 (d, J = 8.3 Hz, 2H), 7.40 (d, J = 8.1 Hz, 2H), 3.62 (brs, 1H), 2.38 (s, 3H), 1.90 (brs, 1H), 1.27-1.10 (m, 2H), 0.93-0.71 (m, 6H).<br>LCMS ESI (m/z): 284.0 (M + 1)<br>Purity at 210 nm: 97.97%<br>Isomer-2<br>$^1$H NMR (400 MHz, DMSO-d$_6$) δ 7.93 (brs, 3H), 7.89 (brs, 2H), 7.81 (d, J = 8.3 Hz, 2H), 7.40 (d, J = 8.1 Hz, 2H), 3.57 (s, 1H), 2.38 (s, 3H), 1.95-1.88 (m, 1H), 1.53-1.41 (m, J = 7.2 Hz, 1H), 1.32-1.20 (m, 1H), 0.96-0.80 (m, J = 7.1 Hz, 6H).<br>LCMS ESI (m/z): 284.0 (M + 1)<br>Purity at 210 nm: 99.81% |
| 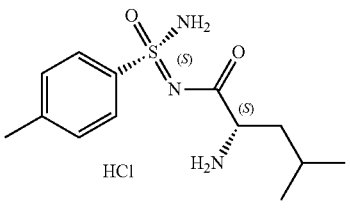<br>ANASIA-021-1<br>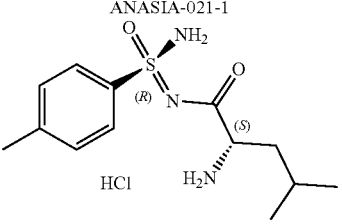<br>ANASIA-021-2 | Int-A-4.12-Fr-1<br>Int-A-4.12-Fr-2 | Isomer-1<br>$^1$H NMR (400 MHz, DMSO-d$_6$) δ 8.01 (brs, 3H), 7.89 (brs, 2H), 7.78 (d, J = 8.3 Hz, 2H), 7.40 (d, J = 8.1 Hz, 2H), 3.50-3.43 (m, 1H), 2.37 (s, 3H), 1.78-1.68 (m, 1H), 1.64-1.53 (m, 1H), 1.50-1.38 (m, 1H), 0.94-0.80 (m, 6H).<br>LCMS ESI (m/z): 284.0 (M + 1)<br>Purity at 210 nm: 99+%<br>Isomer-2<br>$^1$H NMR (400 MHz, DMSO-d$_6$) δ 8.02 (brs, 3H), 7.90 (s, 2H), 7.81 (d, J = 8.3 Hz, 2H), 7.40 (d, J = 8.2 Hz, 2H), 3.59 (brs, 1H), 2.38 (s, 3H), 1.82-1.48 (m, 3H), 0.89 (d, J = 6.6 Hz, 6H).<br>LCMS ESI (m/z): 284.1 (M + 1)<br>Purity at 210 nm: 99.64% |

Synthesis Table 9

| Structure | Precursor | Analytical data |
|---|---|---|
| 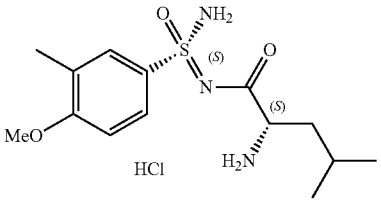<br>ANASIA-022-1<br>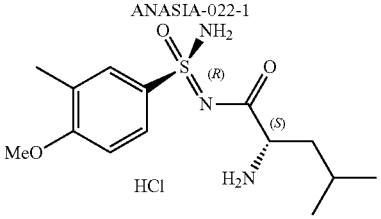<br>ANASIA-022-2 | Int-A-4.13-Fr-1<br>Int-A-4.13-Fr-2 | Isomer-1<br>$^1$H NMR (400 MHz, DMSO-$d_6$) δ 7.96 (brs, 3H), 7.78 (brs, 2H), 7.73 (dd, J = 8.7, 2.3 Hz, 1H), 7.67 (s, 1H), 7.13 (d, J = 8.8 Hz, 1H), 3.89 (s, 3H), 3.61 (brs, 1H), 2.18 (s, 3H), 1.80-1.68 (m, 1H), 1.66-1.54 (m, 1H), 1.49-1.38 (m, 1H), 0.86 (d, J = 6.5 Hz, 6H).<br>LCMS ESI (m/z): 314.1 (M + 1)<br>Purity at 210 nm: 97.54%<br>Isomer-2<br>$^1$H NMR (400 MHz, DMSO-$d_6$) δ 7.95 (brs, 3H), 7.79 (brs, 2H), 7.75 (dd, J = 8.7, 2.3 Hz, 1H), 7.69 (s, 1H), 7.12 (d, J = 8.8 Hz, 1H), 3.89 (s, 3H), 3.61 (brs, 1H), 2.21 (s, 3H), 1.83-1.46 (m, 3H), 0.89 (d, 6H).<br>LCMS ESI (m/z): 314.2 (M + H)<br>Purity at 210 nm: 96.60% |
| 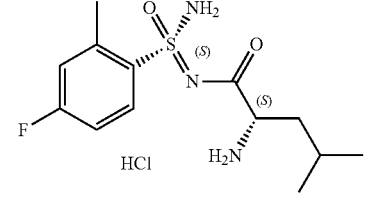<br>ANASIA-027-1<br>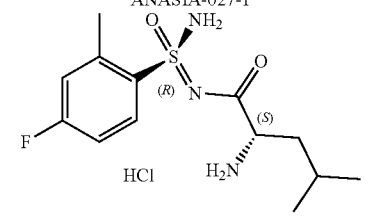<br>ANASIA-027-2 | Int-A-4.14-Fr-1<br>Int-A-4.14-Fr-2 | Isomer-1<br>$^1$H NMR (400 MHz, DMSO-$d_6$) δ 8.12 (s, 2H), 8.02 (brs, 4H), 7.43-7.21 (m, 2H), 3.66 (brs, 1H), 2.58 (s, 3H), 1.87-1.33 (m, 3H), 0.92-0.76 (m, 6H).<br>LCMS ESI (m/z): 302.6 (M + 1)<br>Purity at 210 nm: 99.74%<br>Isomer-2<br>$^1$H NMR (400 MHz, DMSO-$d_6$) δ 8.19-7.92 (m, 6H), 7.36-7.23 (m, 2H), 3.66 (brs, 1H), 2.59 (s, 3H), 1.84-1.51 (m, 3H), 0.89 (d, J = 6.9 Hz, 6H).<br>LCMS ESI (m/z): 302.6 (M + 1)<br>Purity at 210 nm: 90.02% |
| 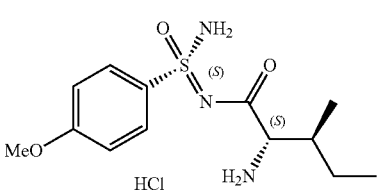<br>ANASIA-055-1<br>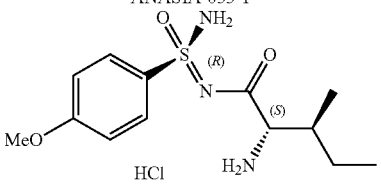<br>ANASIA-055-2 | Int-A-4.15-Fr-1<br>Int-A-4.15-Fr-2 | Isomer-1<br>$^1$H NMR (400 MHz, DMSO-$d_6$) δ 7.95-7.80 (m, 7H), 7.13 (d, J = 9.0 Hz, 2H), 3.83 (s, 3H), 3.66 (brs, 1H), 1.90 (brs, 1H), 1.33-1.05 (m, 2H), 0.96-0.70 (m, 6H).<br>LCMS ESI (m/z): 300.4 (M + 1)<br>Purity at 210 nm: 95.61%<br>Isomer-2<br>$^1$H NMR (400 MHz, DMSO-$d_6$) δ 8.16-7.75 (m, 7H), 7.12 (d, J = 12.9 Hz, 2H), 3.84 (s, 3H), 3.53-3.43 (m, 1H), 1.91 (brs, 1H), 1.55-1.40 (m, 1H), 1.35-1.19 (m, 1H), 0.99-0.81 (m, 6H).<br>LCMS ESI (m/z): 300.2 (M + 1)<br>Purity at 210 nm: 98.30% |

Synthesis Table 9

| Structure | Precursor | Analytical data |
|---|---|---|
| ANASIA-043-1<br>ANASIA-043-2 | Int-A-4.16-Fr-1<br>Int-A-4.16-Fr-2 | Isomer-1<br>$^1$H NMR (400 MHz, DMSO-$d_6$) δ 7.94 (brs, 3H), 7.89 (brs, 2H), 7.76 (s, 1H), 7.72 (d, J = 6.3 Hz, 1H), 7.58-7.49 (m, 2H), 3.69 (brs, 1H), 3.06-2.96 (m, 1H), 1.79-1.53 (m, 2H), 1.46-1.35 (m, 1H), 1.21 (d, J = 6.9 Hz, 6H), 0.92-0.81 (m, 6H).<br>LCMS ESI (m/z): 312.2 (M + 1)<br>Purity at 210 nm: 99.56%<br>Isomer-2<br>$^1$H NMR (400 MHz, DMSO-$d_6$) δ 8.03-7.90 (m, 5H), 7.79 (s, 1H), 7.68-7.78 (m, 1H), 7.58-7.50 (m, 2H), 3.66 (brs, 1H), 3.00 (hept, 1H), 1.83-1.49 (m, 3H), 1.22 (d, J = 6.9 Hz, 6H), 0.95-0.81 (m, 6H).<br>LCMS ESI (m/z): 312.2 (M + 1)<br>Purity at 210 nm: 97.93% |
| ANASIA-049-1<br>ANASIA-049-2 | Int-A-4.17-Fr-1<br>Int-A-4.17-Fr-2 | Isomer-1<br>$^1$H NMR (400 MHz, DMSO-$d_6$) δ 8.14-7.83 (m, 6H), 7-65-7.75 (m, 2H), 7.52 (t, J = 7.7 Hz, 1H), 3.68 (brs, 1H), 1.79-1.54 (m, 2H), 1.45-1.36 (m, 1H), 1.29 (s, 9H), 0.94-0.73 (m, 6H).<br>LCMS ESI (m/z): 326.5 (M + 1)<br>Purity at 210 nm: 99.58%<br>Isomer-2<br>$^1$H NMR (400 MHz, DMSO-$d_6$) δ 8.16-7.89 (m, 6H), 7.80-7.65 (m, 2H), 7.53 (t, J = 7.8 Hz, 1H), 3.61 (brs, 1H), 1.82-1.49 (m, 3H), 1.30 (s, 9H), 0.97-0.74 (m, 6H)<br>LCMS ESI (m/z): 326.4 (M + 1)<br>Purity at 210 nm: 99.41% |
| ANASIA-056-1<br>ANASIA-056-2 | Int-A-4.18-Fr-1<br>Int-A-4.18-Fr-2 | Isomer-1<br>$^1$H NMR (400 MHz, DMSO-$d_6$) δ 8.00-7.80 (m, 6H), 7.79-7.65 (m, 2H), 7.51 (t, J = 7.8 Hz, 1H), 3.63 (brs, 1H), 1.85 (brs, 1H), 1.28 (s, 9H), 1.24-1.01 (m, 2H), 0.88-0.67 (m, 6H)<br>LCMS ESI (m/z): 326.4 (M + 1)<br>Purity at 210 nm: 97.93%<br>Isomer-2<br>$^1$H NMR (400 MHz, DMSO-$d_6$) δ 8.16-7.87 (m, 6H), 7.74 (d, J = 7.6 Hz, 1H), 7.69 (d, J = 7.5 Hz, 1H), 7.52 (t, J = 7.8 Hz, 1H), 3.58 (brs, 1H), 2.01-1.85 (m, 1H), 1.52-1.39 (m, 1H), 1.30 (s, 9H), 1.23-1.05 (m, 1H), 0.86 (d, J = 6.9 Hz, 6H).<br>LCMS ESI (m/z): 326.4 (M + 1)<br>Purity at 210 nm: 99+% |

Synthesis Table 9

| Structure | Precursor | Analytical data |
|---|---|---|
| ANASIA-041-1 (NC-phenyl-S(=O)(=NH₂)(S)-N-C(=O)-CH(NH₂)-CH₂-CH(CH₃)₂, HCl) <br> ANASIA-041-2 ((R) isomer at S) | Int-A-4.19-Fr-1 <br> Int-A-4.19-Fr-2 | Isomer-1 <br> ¹H NMR (400 MHz, DMSO-d₆) δ 8.33 (s, 1H), 8.28-8.18 (m, 3H), 8.15 (d, J = 7.7 Hz, 1H), 8.04 (brs, 3H), 7.86 (t, J = 7.9 Hz, 1H), 3.69 (brs, 1H), 1.79-1.35 (m, 3H), 0.92-0.79 (m, 6H). <br> LCMS ESI (m/z): 295.1 (M + 1) <br> Purity at 210 nm: 92.28% <br> Isomer-2 <br> ¹H NMR (400 MHz, DMSO-d₆) δ 8.33 (s, 1H), 8.28-8.20 (m, 3H), 8.15 (d, J = 7.7 Hz, 1H), 8.02 (brs, 3H), 7.84 (t, J = 8.0 Hz, 1H), 3.70 (brs, 1H), 1.84-1.46 (m, 3H), 0.97-0.79 (m, 6H). <br> LCMS ESI (m/z): 295.1 (M + 1) <br> Purity at 210 nm: 93.51% |
| ANASIA-048 (2,3-dihydrobenzofuran-5-yl sulfoximine-leucinamide, HCl) | Int-A-4.21 | ¹H NMR (400 MHz, DMSO-d₆) δ 7.71 (s, 1H), 7.63 (dd, J = 8.4, 2.4 Hz, 1H), 6.90 (dd, J = 8.5, 2.7 Hz, 1H), 6.05 (brs, 4H), 4.64 (t, J = 8.8 Hz, 2H), 3.32-3.17 (m, 3H), 1.77-1.15 (m, 3H), 0.95-0.77 (m, 6H). <br> LCMS ESI (m/z): 312.5 (M + 1) <br> Purity at 210 nm: 96.10% |
| ANASIA-053-1 ((R) at S, with isoleucine side chain) <br> ANASIA-053-2 ((S) at S) | Int-A-4.22-Fr-1 <br> Int-A-4.22-Fr-2 | Isomer-1 <br> ¹H NMR (400 MHz, DMSO-d₆) δ 7.89 (brs, 3H), 7.78-7.70 (m, 3H), 7.67 (d, 1H), 6.93 (d, J = 8.8 Hz, 1H), 4.64 (t, 2H), 3.65 (brs, 1H), 3.19 (t, 2H), 1.87 (brs, 1H), 1.24-1.05 (m, 2H), 0.86 (m, 6H) <br> LCMS ESI (m/z): 312.3 (M + 1) <br> Purity at 210 nm: 99.74% <br> Isomer-2 <br> ¹H NMR (400 MHz, DMSO-d₆) δ 7.80-7.72 (m, 6H), 7.66 (d, 1H), 6.93 (d, J = 8.8 Hz, 1H), 4.63 (t, 2H), 3.61 (brs, 1H), 3.25-3.10 (m, 2H), 1.92 (brs, 1H), 1.24-1.05 (m, 2H), 0.91-0.73 (m, 6H) <br> LCMS ESI (m/z): 312.3 (M + 1) <br> Purity at 210 nm: 99+% |
| ANASIA-044-1 (Br-phenyl, (S) at S) <br> ANASIA-044-2 (Br-phenyl, (R) at S) | Int-A-4.23-Fr-1 <br> Int-A-4.23-Fr-2 | Isomer-1 <br> ¹H NMR (400 MHz, DMSO-d₆) δ 8.16-7.93 (m, 6H), 7.91-7.83 (m, J = 8.0 Hz, 2H), 7.58 (t, J = 7.9 Hz, 1H), 3.72-3.62 (m, 1H), 1.77-1.34 (m, 3H), 0.95-0.77 (m, 6H). <br> LCMS ESI (m/z): 348.2 & 350.3 (M + 1) <br> Purity at 210 nm: 93.21% <br> Isomer-2 <br> ¹H NMR (400 MHz, DMSO-d₆) δ 8.18-7.94 (m, 6H), 7.93-7.83 (m, 2H), 7.57 (t, J = 7.9 Hz, 1H), 3.68 (brs, 1H), 1.82-1.48 (m, 3H), 0.98-0.77 (m, 6H). <br> LCMS ESI (m/z): 348.2 & 350.3 (M + 1) <br> Purity at 210 nm: 90.41% |

Synthesis Table 9

| Structure | Precursor | Analytical data |
|---|---|---|
| ANASIA-018-1<br>ANASIA-018-2 | Int-A-4.24-Fr-1<br>Int-A-4.24-Fr-2 | Isomer-1<br>¹H NMR (400 MHz, DMSO-d$_6$) δ 8.15 (s, 1H), 8.04-7.93 (m, 6H), 7.90 (d, J = 7.9 Hz, 1H), 7.74-7.66 (m, 3H), 7.53 (t, J = 7.5 Hz, 2H), 7.45 (t, J = 7.3 Hz, 1H), 3.70 (brs, 1H), 1.81-1.58 (m, 2H), 1.51-1.36 (m, 1H), 0.84 (d, 6H).<br>LCMS ESI (m/z): 346.2 (M + 1)<br>Purity at 210 nm: 99.12%<br>Isomer-2<br>¹H NMR (400 MHz, DMSO-d$_6$) δ 8.19 (t, J = 1.6 Hz, 1H), 8.10-7.99 (m, 5H), 7.80-7.95 (m, 2H), 7.78-7.66 (m, 3H), 7.53 (t, J = 7.5 Hz, 2H), 7.44 (t, J = 7.3 Hz, 1H), 3.66 (brs, 1H), 1.86-1.50 (m, 3H), 0.88 (dd, 6H).<br>LCMS ESI (m/z): 346.2 (M + 1)<br>Purity at 210 nm: 98.15% |
| ANASIA-032-1<br>ANASIA-032-2 | Int-A-4.25-Fr-1<br>Int-A-4.25-Fr-2 | Isomer-1<br>¹H NMR (400 MHz, DMSO-d$_6$) δ 8.18 (t, J = 1.7 Hz, 1H), 8.04-7.85 (m, 7H), 7.75-7.66 (m, 3H), 7.53 (t, J = 7.5 Hz, 2H), 7.44 (dd, J = 8.3, 6.3 Hz, 1H), 3.67 (brs, 1H), 2.00-1.86 (m, 1H), 1.25-1.07 (m, 2H), 0.79-0.66 (m, 6H).<br>LCMS ESI (m/z): 346.2 (M + 1)<br>Purity at 210 nm: 99+%<br>Isomer-2<br>¹H NMR (400 MHz, DMSO-d$_6$) δ 8.19 (s, 1H), 8.04 (s, 2H), 8.00-7.87 (m, 5H), 7.77-7.66 (m, 3H), 7.59-7.50 (m, 2H), 7.44 (t, J = 7.3 Hz, 1H), 3.64 (brs, 1H), 1.92 (brs, 1H), 1.55-1.42 (m, 1H), 1.36-1.21 (m, 1H), 1.01-0.76 (m, 6H).<br>LCMS ESI (m/z): 346.0 (M + 1)<br>Purity at 210 nm: 99+% |
| ANASIA-028-1 | Int-A-4.26-Fr-1<br>Int-A-4.26-Fr-2 | Isomer-1<br>¹H NMR (400 MHz, DMSO-d$_6$) δ 8.19 (brs, 3H), 7.98 (d, J = 3.9 Hz, 1H), 7.94 (brs, 2H), 7.72 (d, J = 3.7 Hz, 1H), 7.21-7.15 (m, 1H), 3.64 (brs, 1H), 1.88 (brs, 1H), 1.42-1.14 (m, 2H), 0.88-0.73 (m, 6H).<br>LCMS ESI (m/z): 275.9 (M + 1)<br>Purity at 210 nm: 99+%<br>¹H NMR (400 MHz, DMSO-d$_6$) δ 8.29 (brs, 2H), 8.00 (dd, J = 5.0, 1.3 Hz, 1H), 7.95 (brs, 3H), 7.74 (d, J = 3.7 Hz, 1H), 7.20 (dd, J = 5.0, 3.8 Hz, 1H), 3.65 (brs, 1H), 1.93 (brs, 1H), 1.57-1.41 (m, 1H), 1.38-1.19 (m, 1H), 0.89 (two d, 7.2 Hz, 6H).<br>LCMS ESI (m/z): 276.0 (M + 1)<br>Purity at 240 nm: 99+% |
| ANASIA-008 | Int-A-4.27 | ¹H NMR (400 MHz, DMSO-d$_6$) δ 8.37-8.29 (m, 1H), 8.19-7.87 (m, 5H), 7.79-7.72 (m, 1H), 7.45-7.36 (m, 1H), 3.70-3.59 (m, 1H), 1.81-1.39 (m, 3H), 0.99-0.78 (m, 6H).<br>LCMS ESI (m/z): 276.0 (M + H)<br>Purity at 210 nm: 99+% |

-continued

Synthesis Table 9

| Structure | Precursor | Analytical data |
|---|---|---|
| 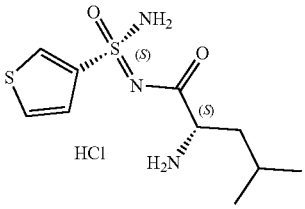<br>ANASIA-008-1<br>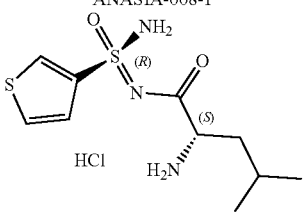<br>ANASIA-008-2 | Int-A-4.27-Fr-1<br>Int-A-4.27-Fr-2 | Isomer-1<br>$^1$H NMR (400 MHz, DMSO-d$_6$) δ 8.32 (s, 1H), 8.08 (brs, 3H), 8.00 (brs, 2H), 7.78-7.72 (m, 1H), 7.40 (d, J = 4.9 Hz, 1H), 3.64 (s, 1H), 1.81-1.68 (m, 1H), 1.67-1.56 (m, 1H), 1.54-1.41 (m, 1H), 0.87 (d, J = 4.3 Hz, 6H). LCMS ESI (m/z): 276.0 (M + H)<br>Purity at 210 nm: 99+%<br>Isomer-2<br>$^1$H NMR (400 MHz, DMSO-d$_6$) δ 8.33 (d, J = 1.7 Hz, 1H), 8.00 (s, 5H), 7.75 (dd, J = 4.9, 3.0 Hz, 1H), 7.43 (d, J = 5.0 Hz, 1H), 3.72-3.57 (m, 1H), 1.87-1.48 (m, 3H), 0.90 (two d, 6H).<br>LCMS ESI (m/z): 276.1 (M + H)<br>Purity at 210 nm: 99.43% |
| 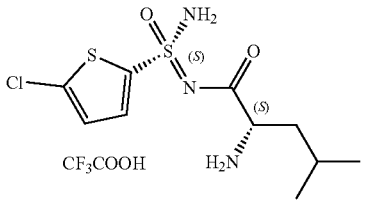<br>ANASIA-009-1<br>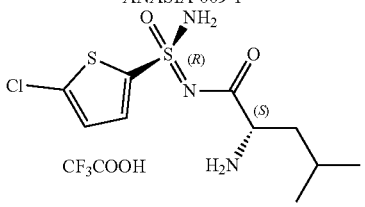<br>ANASIA-009-2 | Int-A-4.28-Fr-1<br>Int-A-4.28-Fr-2 | Isomer-1<br>$^1$H NMR (400 MHz, DMSO-d$_6$) δ 8.45 (brs, 2H), 8.21 (brs, 3H), 7.63 d, J = 4.1 Hz, 1H), 7.28 (d, J = 4.1 Hz, 1H), 3.64 (t, J = 7.7 Hz, 1H), 1.87-1.52 (m, 3H), 0.88 (two d, 6H).<br>LCMS ESI (m/z): 310.0 & 312.0 (M + H)<br>Purity at 210 nm: 98.29%<br>Isomer-2<br>$^1$H NMR (400 MHz, DMSO-d$_6$) δ 8.45 (brs, 2H), 8.22 (brs, 3H), 7.62 (d, J = 4.2 Hz, 1H), 7.28 (d, J = 4.1 Hz, 1H), 3.68-3.60 (m, 1H), 1.81-1.45 (m, 3H), 0.86 (two d, J = 6.4, 6H).<br>LCMS ESI (m/z): 310.0 & 312.0 (M + H)<br>Purity at 210 nm: 98.32% |
| 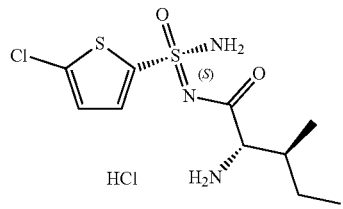<br>ANASIA-029-1<br>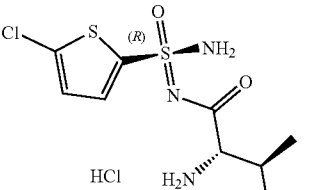<br>ANASIA-029-2 | Int-A-4.29-Fr-1<br>Int-A-4.29-Fr-2 | Isomer-1<br>$^1$H NMR (400 MHz, DMSO-d$_6$) δ 8.04 (brs, 5H), 7.61 (d, J = 4.0 Hz, 1H), 7.29 (d, J = 4.0 Hz, 1H), 3.72-3.61 (m, 1H), 1.98-1.86 (m, 1H), 1.55-1.19 (m, 2H), 1.01-0.82 (m, 6H).<br>LCMS ESI (m/z): 310.1 & 312.0 (M + H)<br>Purity at 220 nm: 97.34%<br>Isomer-2<br>$^1$H NMR (400 MHz, DMSO-d$_6$) δ 8.39 (brs, 2H), 8.00 (brs, 3H), 7.61 (d, J = 4 0 Hz, 1H), 7.30 (d, J = 4.0 Hz, 1H), 3.75-3.62 (m, 1H), 1.97-1.83 (m, 1H), 1.41-1.07 (m, 2H), 0.95-0.74 (m, 6H).<br>LCMS ESI (m/z): 310.1 & 312.1 (M + H)<br>Purity at 210 nm: 98.94% |

Synthesis Table 9

| Structure | Precursor | Analytical data |
|---|---|---|
| 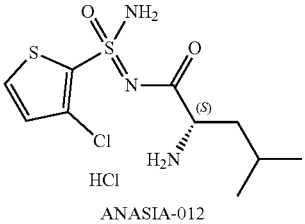<br>ANASIA-012 | Int-A-4.30 | $^1$H NMR (400 MHz, DMSO-d$_6$) δ 8.49 (brs, 2H), 8.06 (d, J = 5.3 Hz, 1H), 8.00 (brs, 3H), 7.26 (d, J = 5.3 Hz, 1H), 3.74 (brs, 1H), 1.85-1.37 (m, 3H), 0.91 (d, J = 6.4 Hz, 6H).<br>LCMS ESI (m/z): 310.0 & 312.0 (M + H)<br>Purity at 220 nm: 98.36% |
| 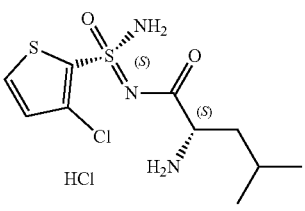<br>ANASIA-012-1<br>ANASIA-012-2 | Int-A-4.30-Fr-1<br>Int-A-4.30-Fr-2 | Isomer-1<br>$^1$H NMR (400 MHz, DMSO-d$_6$) δ 8.49 (brs, 3H), 8.06 (d, J = 5.3 Hz, 1H), 8.00 (brs, 2H), 7.26 (d, J = 5.3 Hz, 1H), 3.79-3.71 (m, 1H), 1.87-1.44 (m, 3H), 0.91 (d, J = 6.4 Hz, 6H).<br>LCMS ESI (m/z): 310.0 & 312.1 (M + H)<br>Purity at 220 nm: 99+%<br>Isomer-2<br>$^1$H NMR (400 MHz, DMSO-d$_6$) δ 8.49 (brs, 3H), 8.05 (d, J = 5.3 Hz, 1H), 8.03 (brs, 2H), 7.26 (d, J = 5.3 Hz, 1H), 3.75-3.67 (m, 1H), 1.89-1.67 (m, 2H), 1.67-1.54 (m, 1H), 0.93 (two d, 6H).<br>LCMS ESI (m/z): 310.0 & 312.1 (M + H)<br>Purity at 220 nm: 99+% |
| 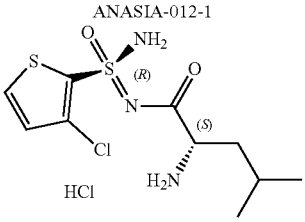<br>ANASIA-014-1<br>ANASIA-014-2 | Int-A-4.31-Fr-1<br>Int-A-4.31-Fr-2 | Isomer-1<br>$^1$H-NMR (400 MHz, DMSO-d$_6$) δ: 8.2 (brs, 2H), 8.06 (brs, 3H), 7.55 (d, J = 3.6 Hz, 1H), 6.92 (d, J = 4 Hz, 1H), 3.66 (brs, 1H), 2.5 (s, 3H), 1.78-1.77 (m, 1H), 1.64-1.62 (m, 1H), 1.53-1.50 (m, 1H), 0.89 (d, J = 6.4 Hz, 6H).<br>LCMS ESI (m/z): 290.0 (M + 1)<br>Purity at 210 nm: 99.74%<br>Isomer-2<br>$^1$H-NMR (400 MHz, DMSO-d$_6$) δ: 8.2 (bs, 2H), 8.05 (brs, 3H), 7.56 (d, J = 3.6 Hz, 1H), 6.91 (dd, J = 4 Hz, 1H), 3.65 (brs, 1H), 2.5 (s, 3H), 1.84-1.77 (m, 1H), 1.73-1.66 (m, 1H), 1.61-1.54 (m, 1H), 0.91 (two d, J = 6.4 Hz, 6H).<br>LCMS ESI (m/z): 290.0 (M + 1)<br>Purity at 210 nm: 99+% |
| 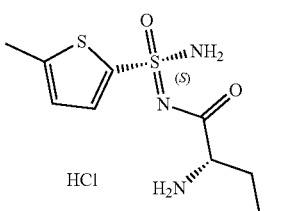<br>ANASIA-031 | Int-A-4.32 | $^1$H-NMR (400 MHz, DMSO-d$_6$) δ: 8.21 (m, 2H), 8.10-7.80 (m, 3H), 7.54 (dd, J = 3.6 Hz, 1H), 6.92 (d, J = 0.8 Hz, 1H), 3.66 (m, 1H), 1.91 (brs, 1H), 1.49-1.17 (m, 2H), 0.93-0.83 (m, 6H).<br>LCMS ESI (m/z): 290.01 (M + 1)<br>Purity at 210 nm: 95.64% |

-continued

Synthesis Table 9

| Structure | Precursor | Analytical data |
|---|---|---|
| ANASIA-031-1<br>ANASIA-031-2 | Int-A-4.32-Fr-1<br>Int-A-4.32-Fr-2 | Isomer-1<br>$^1$H NMR (400 MHz, DMSO-$d_6$) δ 8.08 (brs, 5H), 7.57 (d, J = 3.7 Hz, 1H), 6.92 (d, J = 3.7, 1H), 3.66 (brs, 1H), 2.5 (s, 3H), 2.03-1.89 (m, 1H), 1.60-1.17 (m, 2H), 1.03-0.80 (m, 6H).<br>LCMS ESI (m/z): 290.0 (M + 1)<br>Purity at 210 nm: 96.40%<br>Isomer-2<br>$^1$H-NMR (400 MHz, DMSO-$d_6$) δ: 8.2 (brs, 2H), 7.97 (brs, 3H), 7.55 (d, J = 3.6 Hz, 1H), 6.93 (dd, J = 3.6 Hz, 1H), 3.66-3.64 (m, 1H), 2.5 (s, 3H), 1.92-1.90 (m, 1H), 1.35-1.30 (m, 1H), 1.24-1.28 (m, 1H), 0.86 (t, J = 7.2 Hz, 6H).<br>LCMS ESI (m/z): 290.0 (M + 1)<br>Purity at 210 nm: 99+% |
| ANASIA-015-1<br>ANASIA-015-2 | Int-A-4.33-Fr-1<br>Int-A-4.33-Fr-2 | Isomer-1<br>$^1$H-NMR (400 MHz, DMSO-$d_6$) δ: 8.2 (brs, 2H), 8.02 (brs, 3H), 7.83 (d, J = 4.8 Hz, 1H), 7.03 (d, J = 5.2 Hz, 1H), 3.67 (brs, 1H), 2.44 (s, 3H), 1.80-1.75 (m, 1H), 1.67-1.60 (m, 1H), 1.50-1.43 (m, 1H), 0.88 (d, J = 6.8 Hz, 6H).<br>LCMS ESI (m/z): 290.0 (M + 1)<br>Purity at 210 nm: 96.56%<br>Isomer-2<br>$^1$H-NMR (400 MHz, DMSO-$d_6$) δ: 8.2 (s, 2H), 8.0 (brs, 3H), 7.84 (d, J = 5.2 Hz, 1H), 7.05 (d, J = 4.8 Hz, 1H), 3.67 (bs, 1H), 2.41 (s, 3H), 1.82-1.77 (m, 1H), 1.73-1.66 (m, 1H), 1.60-1.53 (m, 1H), 0.90 (two d, 6H).<br>LCMS ESI (m/z): 290.1 (M + 1)<br>Purity at 210 nm: 98.69% |

-continued

Synthesis Table 9

| Structure | Precursor | Analytical data |
|---|---|---|
| ANASIA-017; ANASIA-017-1; ANASIA-017-2 | Int-A-4.34<br>Int-A-4.34-Fr-1<br>Int-A-4.34-Fr-2 | $^1$H NMR (400 MHz, DMSO-d$_6$) δ 8.21 (s, 5H), 7.73 (m, 1H), 7.54 (s, 1H), 7.33 (d, 1H), 3.73-3.61 (m, 1H), 1.84-1.40 (m, 3H), 0.98-0.76 (m, 6H).<br>LCMS ESI (m/z): 326.1 (M + 1)<br>Purity at 210 nm: 99+%<br>Isomer-1<br>$^1$H NMR (400 MHz, DMSO) δ 8.51 (s, 2H), 8.08 (bs, 3H), 7.73-7.72 (m, 1H), 7.56-7.55 (m, 1H), 7.41 (t, J = 54.8 Hz, 1H), 3.72 (s, 1H), 1.78-1.74 (m, 1H), 1.67-1.60 (m, 1H), 1.52-1.47 (m, 1H), 0.89-0.86 (m, 6H).<br>LCMS ESI (m/z): 326.3 (M + H)<br>Purity at 210 nm: 99.0%<br>Isomer-2<br>$^1$H NMR (400 MHz, DMSO) δ 8.51 (bs, 2H), 8.04 (bs, 3H), 7.75-7.74 (m, 1H), 7.56-7.55 (m, 1H), 7.40 (t, J = 54.8 Hz, 1H), 3.73-3.71 (m, 1H), 1.79-1.78 (m, 1H), 1.70-1.68 (m, 1H), 1.61-1.57 (m, 1H), 0.93-0.89 (m, 6H).<br>LCMS ESI (m/z): 326.4 (M + H)<br>Purity at 210 nm: 100.0% |
| ANASIA-038 | Int-A-4.35-Fr-1<br>Int-A-4.35-Fr-2 | $^1$H NMR (400 MHz, DMSO-d$_6$) δ 8.48 (brs, 2H), 8.05 (brs, 3H), 7.73 (d, J = 3.8 Hz, 1H), 7.54 (d, J = 6.0 Hz, 1H), 7.33 (d, J = 54.7 Hz, 1H), 3.72-3.63 (m, 1H), 1.92 (brs, 1H), 1.54-1.20 (m, 2H), 0.96-0.67 (m, 6H).<br>LCMS ESI (m/z): 326.1 (M + 1)<br>Purity at 210 nm: 94.81% |
| ANASIA-016 | Int-A-4.36 | $^1$H NMR (400 MHz, DMSO-d$_6$) δ 8.70-8.59 (m, 1H), 8.40-8.20 (m, 3H), 8.10 (d, J = 9.1 Hz, 1H), 8.0-7.80 (m, 3H), 7.76-7.63 (m, 3H), 3.76-3.63 (m, 1H), 1.81-1.36 (m, 3H), 0.88-0.78 (m, 6H).<br>LCMS ESI (m/z): 320.1 (M + 1)<br>Purity at 210 nm: 96.14% |

Synthesis Table 9

| Structure | Precursor | Analytical data |
|---|---|---|
| ANASIA-016-1 (HCl) | Int-A-4.36-Fr-1<br>Int-A-4.36-Fr-2 | Isomer-1<br>$^1$H NMR (400 MHz, DMSO-d$_6$) δ 8.64 (d, J = 9.0 Hz, 1H), 8.38-8.23 (m, 4H), 8.13-8.06 (m, 1H), 7.90 bs, 3H), 7.76-7.64 (m, 3H), 3.73-3.62 (m, 1H), 1.76-1.56 (m, 2H), 1.31-1.18 (m, 1H), 0.84 (two d, J = 6.7 Hz, 6H).<br>LCMS ESI (m/z): 320.2 (M + 1)<br>Purity at 210 nm: 96.79% |
| ANASIA-016-2 (HCl) | | Isomer-2<br>$^1$H NMR (400 MHz, DMSO-d$_6$) δ 8.65 (d, J = 8.0 Hz, 1H), 8.34-8.21 (m, 3H), 8.10 (d, J = 7.8 Hz, 1H), 7.93 (bs, 3H), 7.76-7.63 (m, 3H), 3.70-3.57 (m, 1H), 1.80-1.61 (m, 2H), 1.57-1.46 (m, 1H), 0.84 (two d, 6H).<br>LCMS ESI (m/z): 320.1 (M + 1)<br>Purity at 210 nm: 96.60% |
| ANASIA-025 (HCl) | Int-A-4.37 | $^1$H NMR (400 MHz, DMSO-d$_6$) δ 8.70-8.60 (m, 1H), 8.39-8.23 (m, 4H), 8.10 (d, J = 7.9 Hz, 1H), 7.83 (brs, 3H), 7.76-7.61 (m, 3H), 3.65-3.55 (m, 1H), 2.35-2.25 (m, 1H), 0.91 (d, J = 7.1 Hz, 3H), 0.83 (d, J = 6.9 Hz, 3H).<br>LCMS ESI (m/z): 306.1 (M + 1)<br>Purity at 210 nm: 99+% |
| ANASIA-013 (HCl) | Int-A-4.38 | $^1$H NMR (400 MHz, DMSO-d$_6$) δ 8.61 (d, J = 2.5 Hz, 1H), 8.25-8.14 (m, 2H), 8.13-7.87 (m, 7H), 7.79-7.67 (m, 2H), 3.69 (s, 1H), 1.85-1.50 (m, 3H), 0.98-0.85 (m, 6H).<br>LCMS ESI (m/z): 320.1 (M + H)<br>Purity at 210 nm: 99+% |
| ANASIA-030 (HCl) | Int-A-4.39 | $^1$H NMR (400 MHz, DMSO-d$_6$) δ 8.60 (d, J = 8.9 Hz, 1H), 8.28-8.02 (m, 5H), 7.99-7.66 (m, 6H), 3.77-3.66 (m, 1H), 2.02-1.92 (m, 1H), 1.58-1.20 (m, 2H), 0.97-0.74 (m, 6H).<br>LCMS ESI (m/z): 320.2 (M + H)<br>Purity at 210 nm: 99.12% |
| ANASIA-019 (HCl) | Int-A-4.40 | $^1$H NMR (400 MHz, DMSO-d$_6$) δ 8.75 (t, J = 8.5 Hz, 1H), 8.35 (d, J = 6.3 Hz, 1H), 8.27 (dd, J = 8.0, 2.4 Hz, 1H), 8.16-7.72 (m, 8H), 3.70-3.52 (m, 1H), 1.77-1.35 (m, 3H), 0.91-0.72 (m, 6H).<br>LCMS ESI (m/z): 354.1 & 356.0 (M + 1)<br>Purity at 210 nm: 99+% |

Synthesis Table 9

| Structure | Precursor | Analytical data |
|---|---|---|
| 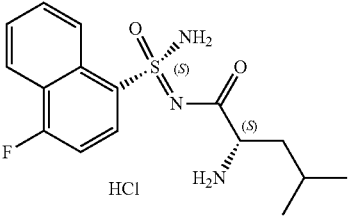<br>ANASIA-020-1<br>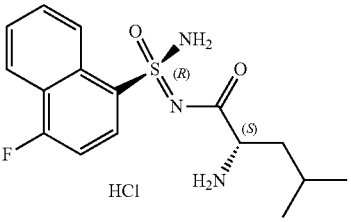<br>ANASIA-020-2 | Int-A-4.41-Fr-1<br>Int-A-4.41-Fr-2 | Isomer-1<br>$^1$H NMR (400 MHz, DMSO-$d_6$) δ 8.68 (d, J = 7.9 Hz, 1H), 8.38-8.27 (m, 3H), 8.25-8.17 (m, 1H), 7.87 (bs, 3H), 7.84-7.75 (m, 2H), 7.63-7.55 (m, 1H), 3.67 (brs, 1H), 1.80-1.52 (m, 2H), 1.32-1.17 (m, 1H), 0.95-0.75 (m, 6H).<br>LCMS ESI (m/z): 336.0 (M − 1)<br>Purity at 210 nm: 97.93%<br>Isomer-2<br>$^1$H NMR (400 MHz, DMSO-$d_6$) δ 8.70 (d, J = 8.8 Hz, 1H), 8.38-8.26 (m, 3H), 8.21 (d, J = 8.1 Hz, 1H), 7.95 (brs, 3H), 7.88-7.75 (m, 2H), 7.58 (t, J = 9.2 Hz, 1H), 3.60 (brs, 1H), 1.78-1.42 (m, 3H), 0.90-0.72 (m, 6H).<br>LCMS ESI (m/z): 336.0 (M − 1)<br>Purity at 210 nm: 98.68% |
| 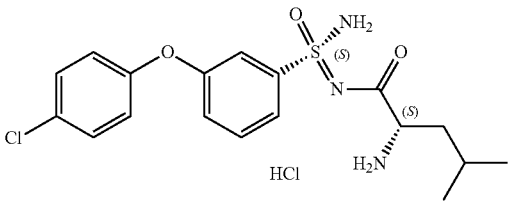<br>ANASIA-047-1<br>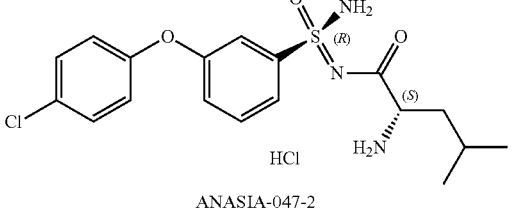<br>ANASIA-047-2 | Int-A-4.42-Fr-1<br>Int-A-4.42-Fr-2 | Isomer-1<br>$^1$H NMR (400 MHz, DMSO-$d_6$) δ 8.00 (brs, 5H), 7.72-7.59 (m, 2H), 7.49 (d, J = 8.7 Hz, 2H), 7.43 (s, 1H), 7.34 (d, J = 7.9 Hz, 1H), 7.07 (d, J = 8.7 Hz, 2H), 3.65 (brs, 1H), 1.79-1.31 (m, 3H), 0.86-0.74 (m, J = 6.3 Hz, 6H).<br>LCMS ESI (m/z): 396.4 & 398.3 (M + 1)<br>Purity at 210 nm: 97.21%<br>Isomer-2<br>$^1$H NMR (400 MHz, DMSO-$d_6$) δ 8.20-7.94 (m, 5H), 7.76-7.58 (m, 2H), 7.54-7.43 (m, 3H), 7.32 (d, J = 7.7 Hz, 1H), 7.10 (d, J = 8.8 Hz, 2H), 3.61 (brs, 1H), 1.79-1.49 (m, 3H), 0.98-0.78 (m, 6H).<br>LCMS ESI (m/z): 396.3 & 398.3 (M + 1)<br>Purity at 210 nm: 95.03% |
| 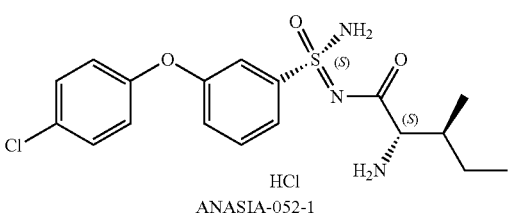<br>ANASIA-052-1<br>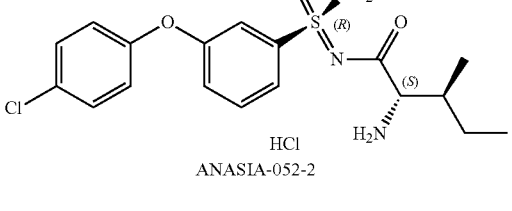<br>ANASIA-052-2 | Int-A-4.43-Fr-1<br>Int-A-4.43-Fr-2 | Isomer-1<br>$^1$H NMR (400 MHz, DMSO-$d_6$) δ 8.03 (brs, 2H), 7.90 (brs, 3H), 7.75-7.60 (m, 2H), 7.56-7.44 (m, 3H), 7.35 (d, J = 7.8 Hz, 1H), 7.07 (d, J = 8.9 Hz, 2H), 3.67 (brs, 1H), 1.89 (brs, 1H), 1.34-1.03 (m, 2H), 0.91-0.71 (m, 6H).<br>LCMS ESI (m/z): 396.3 & 398.3 (M + 1)<br>Purity at 210 nm: 95.03%<br>Isomer-2<br>$^1$H NMR (400 MHz, DMSO-$d_6$) δ 7.89 (brs, 5H), 7.71-7.62 (m, 2H), 7.56-7.46 (m, 3H), 7.35 (s, 1H), 7.11 (d, J = 8.9 Hz, 2H), 3.63 (brs, 1H), 1.95-1.82 (m, 1H), 1.53-1.16 (m, 2H), 0.96-0.79 (m, 6H)<br>LCMS ESI (m/z): 396.2 & 398.2 (M + 1)<br>Purity at 220 nm: 99.25% |

-continued

Synthesis Table 9

| Structure | Precursor | Analytical data |
|---|---|---|
| ANASIA-057-1 / ANASIA-057-2 | Int-A-4.44-Fr-1<br>Int-A-4.44-Fr-2 | Isomer-1<br>$^1$H NMR (400 MHz, DMSO-d$_6$) δ 8.70 (s, 1H), 8.30 (brs, 2H), 8.20-8.09 (m, 2H), 7.85 (brs, 3H), 7.60-7.45 (m, 2H), 3.68 (brs, 1H), 1.96 (brs, 1H), 1.04-0.92 (m, 2H), 0.81-0.63 (m, 6H).<br>LCMS ESI (m/z): 326.2 (M + 1)<br>Purity at 220 nm: 97.94%<br>Isomer-2<br>$^1$H NMR (400 MHz, DMSO-d$_6$) δ 8.68 (s, 1H), 8.15 (dd, J = 17.8, 7.9 Hz, 2H), 8.00 (brs, 5H), 7.62-7.43 (m, 2H), 3.64 (d, 1H), 1.94 (brs, 1H), 1.49-1.19 (m, 2H), 0.97-0.76 (m, 6H).<br>LCMS ESI (m/z): 326.2 (M + 1)<br>Purity at 220 nm: 99+% |
| ANASIA-023 | Int-A-4.45 | $^1$H NMR (400 MHz, DMSO-d$_6$) δ 8.52-8.40 (m, 2H), 8.21-7.99 (m, 6H), 7.59-7.45 (m, 2H), 3.69 (brs, 1H), 1.88-1.42 (m, 3H), 0.99-0.78 (m, 6H).<br>LCMS ESI (m/z): 326.1 (M + 1)<br>Purity at 210 nm: 94.59% |
| ANASIA-037 | Int-A-4.46 | $^1$H NMR (400 MHz, DMSO-d$_6$) δ 8.46 (brs, 2H), 8.19-7.89 (m, 6H), 7.61-7.46 (m, 2H), 3.68 (brs, 1H), 1.94 (brs, 1H), 1.56-1.23 (m, 2H), 0.98-0.79 (m, 6H).<br>LCMS ESI (m/z): 326.0 (M + 1)<br>Purity at 210 nm: 95.97% |
| ANASIA-050-1 / ANASIA-050-2 | Int-A-4.47-Fr-1<br>Int-A-4.47-Fr-2 | Isomer-1<br>$^1$H NMR (400 MHz, DMSO-d$_6$) δ 8.14-7.86 (m, 7H), 7.71-7.52 (m, 3H), 3.81-3.64 (m, 1H), 1.79-1.49 (m, 2H), 0.67-0.55 (m, 1H), 0.33 (m, 2H), 0.03 (s, 2H).<br>LCMS ESI (m/z): 268.30 (M + 1)<br>Purity at 220 nm: 97.30%<br>Isomer-2<br>$^1$H NMR (400 MHz, DMSO-d$_6$) δ 8.16-7.85 (m, 7H), 7.73-7.52 (m, 3H), 3.70 (brs, 1H), 1.81-1.57 (m, 2H), 0.83-0.70 (m, 1H), 0.49-0.34 (m, 2H), 0.22-0.01 (m, 2H).<br>LCMS ESI (m/z): 268.30 (M + 1)<br>Purity at 220 nm: 96.86% |
| ANASIA-006 | Int-A-4.48 | $^1$H NMR (400 MHz, DMSO-d$_6$) δ 9.05-9.03 (m, 1H), 8.82 (dd, 1H), 8.29-8.25 (m, 1H), 8.22 (brs, 2H), 7.94 (brs, 3H), 7.70-7.65 (m, 1H), 3.71 (brs, 1H), 1.80-1.40 (m, 3H), 0.95-0.75 (m, 6H).<br>LCMS ESI (m/z): 271.1 (M + H)<br>Purity at 210 nm: 97.89% |

Synthesis Table 9

| Structure | Precursor | Analytical data |
|---|---|---|
| 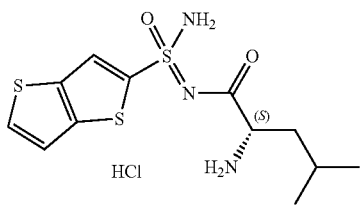<br>ANASIA-082 | Int-A-4.53 | $^1$H NMR (400 MHz, DMSO) δ 8.38-8.35 (m, 2H), 8.15 (d, J = 3.6 Hz, 1H), 7.96-7.95 (m, 3H), 7.54 (d, J = 5.2 Hz, 1H), 3.70 (m, 1H), 1.76-1.50 (m, 3H), 0.92-0.88 (m, 6H)<br>LCMS ESI (m/z): 332.2 (M + H)<br>Purity at 287 nm: 86.75% |
| 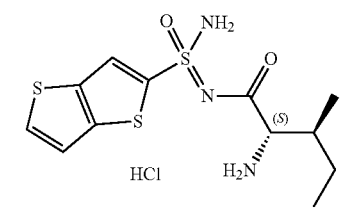<br>ANASIA-138 | Int-A-4.54 | $^1$H NMR (400 MHz, DMSO) δ 8.38 (s, 2H), 8.17 (d, J = 5.2 Hz, 1H), 7.97-7.95 (m, 4H), 7.54 (d, J = 5.6 Hz, 1H), 3.67 (brs, 1H), 1.51-1.49 (m, 1H), 1.33-1.30 (m, 1H), 1.24 (m, 1H), 0.94-0.84 (m, 6H).<br>LCMS ESI (m/z): 332.3 (M + H)<br>Purity at 210 nm: 95.87% |
| 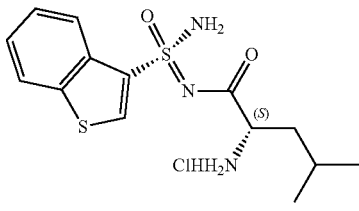<br>ANASIA-083-1<br>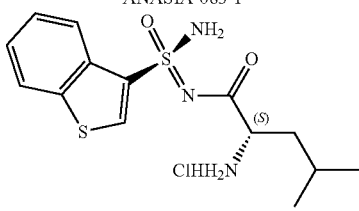<br>ANASIA-083-2 | Int-A-4.55-Fr-1<br>Int-A-4.55-Fr-2 | Isomer-1<br>$^1$H NMR (400 MHz, DMSO-d$_6$) δ 8.68 (s, 1H), 8.26 (bs, 2H), 8.18-8.11 (m, 2H), 7.92 (bs, 3H), 7.55-7.49 (m, 2H), 3.69-3.64 (m, 1H),<br>1.74-1.70 (m, 1H), 1.64-1.58 (m, 1H), 1.32-1.25 (m, 1H), 0.90-0.82 (m, 6H).<br>LCMS ESI (m/z): 326.3 (M + 1)<br>Purity at 220 nm: 96.24%<br>Isomer-2<br>$^1$H NMR (400 MHz, DMSO-d$_6$) δ 8.68 (s, 1H), 8.40-8.10 (m, 4H), 7.95 (bs, 3H), 7.60-7.46 (m, 2H), 3.66-3.64 (m, 1H), 1.73-1.69 (m, 1H), 1.56-1.54 (m, 1H), 1.27-1.23 (m, 1H), 0.90-0.85 (m, 6H).<br>LCMS ESI (m/z): 326.2 (M + 1)<br>Purity at 210 nm: 87.2% |
| 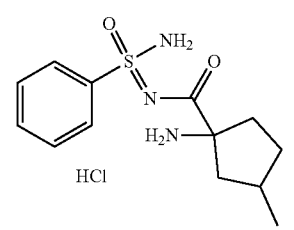 [SMILES: CC1CCC(N)(C(=O)N=S(N)(=O)c2ccccc2)C1 ; Cl]<br>ANASIA-123 | Int-A-4.56 | $^1$H NMR (400 MHz, DMSO-d$_6$) δ 7.95 (d, J = 8.8 Hz, 3H), 7.93-7.91 (m, 3H), 7.64-7.62 (m, 3H), 2.35-2.25 (m, 2H), 2.19-2.09 (m, 1H), 1.93-1.69 (m, 2H), 1.49-1.42 (m, 1H), 1.03-1.01 (m, 3H).<br>LCMS ESI (m/z): 282.4 (M + H)<br>Purity at 210 nm: 100% |

-continued

Synthesis Table 9

| Structure | Precursor | Analytical data |
|---|---|---|
| 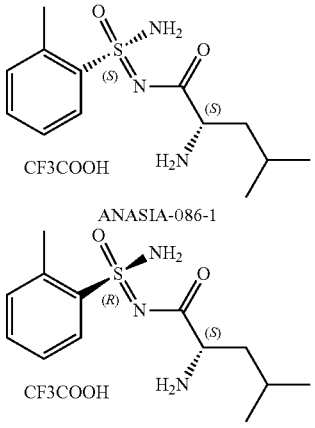<br>ANASIA-086-1<br>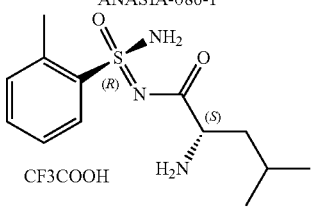<br>ANASIA-086-2 | Int-A-4.57-Fr-1<br>Int-A-4.57-Fr-2 | Isomer-1<br>$^1$H NMR (400 MHz, DMSO-d$_6$) δ 8.03-7.90 (m, 5H), 7.54 (t, J = 7.6 Hz), 7.45-7.39 (m, 2H), 3.70 (bs, 1H), 2.67 (s, 3H), 1.74-1.61 (m, 2H), 1.47-1.44 (m, 1H), 0.88 (d, J = 6 Hz, 6H).<br>LCMS ESI (m/z): 284.3 (M + 1)<br>Purity at 224 nm: 99.01%<br>Isomer-2<br>$^1$H NMR (400 MHz, DMSO-d$_6$) δ 8.00-7.97 (m, 3H), 7.89 (bs, 3H), 7.54 (t, J = 7.2 Hz), 7.45-7.40 (m, 2H), 3.69 (bs, 1H), 2.66 (s, 3H), 1.76-1.68 (m, 2H), 1.58-1.54 (m, 1H), 0.90 (two d, J = 6.8 Hz, 6H).<br>LCMS ESI (m/z): 284.3 (M + 1)<br>Purity at 210 nm: 100% |
| 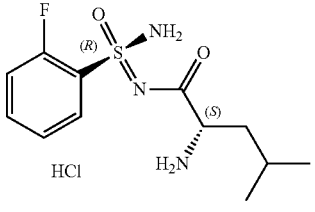<br>ANASIA-087-1<br>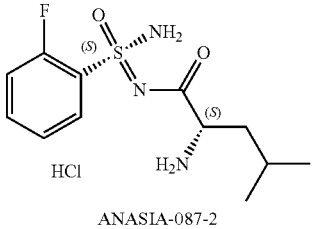<br>ANASIA-087-2 | Int-A-4.58-Fr-1<br>Int-A-4.58-Fr-2 | Isomer-1<br>$^1$H NMR (400 MHz, DMSO-d$_6$) δ 8.21 (bs, 2H), 7.99-7.90 (m, 4H), 7.72-7.71 (m, 1H), 7.48-7.41 (m, 2H), 3.70 (bs, 1H), 1.75-1.43 (m, 3H), 0.88-0.86 (m, 6H).<br>LCMS ESI (m/z): 288.2 (M + 1)<br>Purity at 210 nm: 100%<br>Isomer-2<br>$^1$H NMR (400 MHz, DMSO-d$_6$) δ 8.24 (s, 2H), 7.99-7.92 (m, 4H), 7.78-7.68 (m, 1H), 7.47-7.42 (m, 2H), 3.56 (bs, 1H), 1.85-1.50 (m, 3H), 0.89 (two d, J = 6.8 Hz, 6H)<br>LCMS ESI (m/z): 288.3 (M + 1)<br>Purity at 220 nm: 98.01% |
| 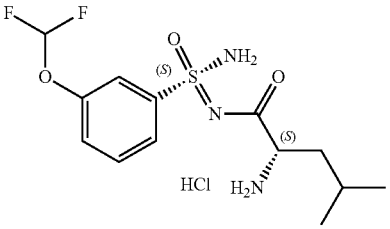<br>ANASIA-088-1<br>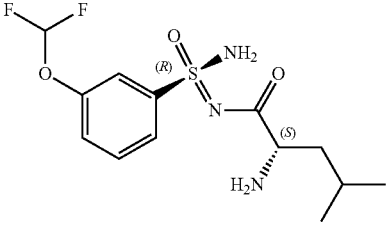<br>ANASIA-088-2 | Int-A-4.59-Fr-1<br>Int-A-4.59-Fr-2 | Isomer-1<br>$^1$H NMR (400 MHz, DMSO) δ 8.11 (bs, 2H), 8.02 (bs, 3H) 7.79 (d, J = 8.0 Hz, 1H), 7.72-7.68 (m, 2H), 7.51-7.49 (m, 1H), 7.37(t, J = 73.2 Hz, 1H), 3.68 (bs, 1H), 1.76-1.71 (m, 1H), 1.64-1.57 (m. 1H), 1.47-1.40 (m, 1H), 0.87 (two d, J = 6.0 Hz, 6H).<br>LCMS ESI (m/z): 336.5 (M + 1)<br>Purity at 230 nm: 97.0%<br>Isomer-2<br>$^1$H NMR (400 MHz, DMSO) δ 8.13 (s, 2H), 8.03 (s, 3H), 7.80 (d, J = 8.0 Hz, 1H), 7.71-7.67 (m, 2H), 7.51-7.49 (m, 1H), 7.41 (t, J = 73.2 Hz, 1H), 3.68 (bs, 1H), 1.80-1.55 (m, 3H), 0.91 (d, J = 7.2 Hz, 3H), 0.90 (t, J = 6.8 Hz, 3H).<br>LCMS ESI (m/z): 336.5 (M + 1)<br>Purity at 210 nm: 95.83% |

-continued

Synthesis Table 9

| Structure | Precursor | Analytical data |
|---|---|---|
| 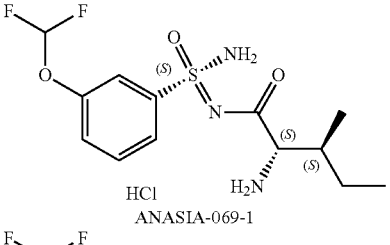<br>HCl ANASIA-069-1<br>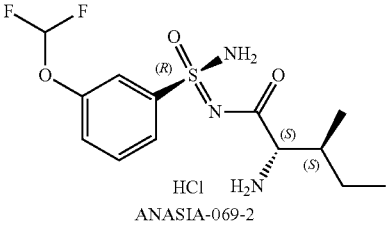<br>HCl ANASIA-069-2 | Int-A-4.60-Fr-1<br>Int-A-4.60-Fr-2 | Isomer-1<br>$^1$H NMR (400 MHz, DMSO) δ 8.13 (bs, 2H), 8.01 (bs, 3H), 7.81 (d, J = 7.6 Hz, 1H), 7.72-7.67 (m, 2H), 7.51 (m, 1H), 7.41 (t, J = 73.2 Hz, 1H), 3.64 (bs, 1H), 1.94 (bs, 1H), 1.55-1.25 (m, 2H), 0.92-0.87 (m, 6H).<br>LCMS ESI (m/z): 336.3 (M + 1)<br>Purity at 210 nm: 98.51%<br>Isomer-2<br>$^1$H NMR (400 MHz, DMSO) δ 8.13 (bs, 2H), 7.99 (bs, 3H), 7.80 (d, J = 7.6 Hz, 1H), 7.72-7.67 (m, 2H), 7.51 (d, J = 8 Hz, 1H), 7.38 (t, J = 73.2 Hz, 1H), 3.66 (bs, 1H), 1.94 (bs, 1H), 1.30-1.10 (m, 2H), 0.86-0.79 (m, 6H).<br>LCMS ESI (m/z): 336.3 (M + 1)<br>Purity at 210 nm: 99.89% |
| 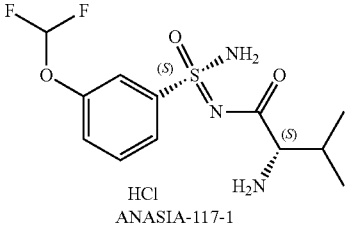<br>HCl ANASIA-117-1<br>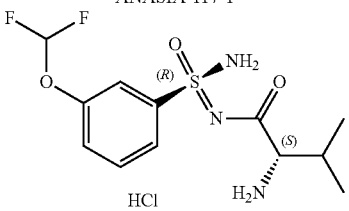<br>HCl ANASIA-117-2 | Int-A-4.61-Fr-1<br>Int-A-4.61-Fr-2 | Isomer-1<br>$^1$H NMR (400 MHz, DMSO) δ 8.14 (bs, 2H), 7.96 (bs, 3H), 7.81 (d, J = 8 Hz, 1H), 7.72-7.68 (m, 2H), 7.55-7.49 (m, 1H), 7.32 (t, J = 73.2 Hz, 1H), 3.68-3.59 (m, 1H), 2.08 (bs, 1H), 0.87-0.77 (m, 6H).<br>LCMS ESI (m/z): 322.3 (M + H)<br>Purity at 210 nm: 99.68%<br>Isomer-2<br>$^1$H NMR (400 MHz, DMSO) δ 8.25 (bs, 2H), 8.15 (bs, 3H), 7.82 (d, J = 7.6 Hz, 1H), 7.72-7.68 (m, 2H), 7.55-7.49 (m, 1H), 7.37 (t, J = 54.8 Hz, 1H), 3.68-3.59 (m, 1H), 2.27 (bs, 1H), 0.87-0.77 (m, 6H).<br>LCMS ESI (m/z): 322.3 (M + H)<br>Purity at 210 nm: 98.22% |
| 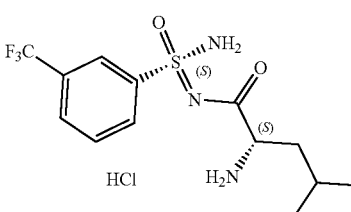<br>HCl ANASIA-089-1<br>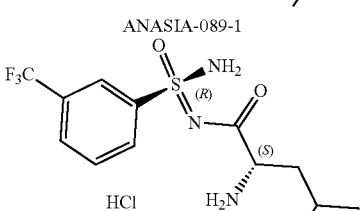<br>HCl ANASIA-089-2 | Int-A-4.62-Fr-1<br>Int-A-4.62-Fr-2 | Isomer-1<br>$^1$H NMR (400 MHz, DMSO-d$_6$) δ 8.22-8.20 (m, 4H), 8.08-8.02 (m, 4H), 7.89 (t, J = 8 Hz, 1H), 3.71 (bs, 1H), 1.70-1.69 (m, 1H), 1.60-1.57 (m, 1H), 1.42-1.41 (m, 1H), 0.91-0.83 (m, 6H).<br>LCMS ESI (m/z): 338.2 (M + H)<br>Purity at 210 nm: 97.44%<br>Isomer-2<br>$^1$H NMR (400 MHz, DMSO-d$_6$) δ 8.25-8.22 (m, 4H), 8.10-8.00 (m, 4H), 7.89 (t, J = 7.8 Hz, 1H), 3.67 (bs, 1H), 1.79-1.64 (m, 2H), 1.60-1.53 (m, 1H), 0.89 (two d, J = 7 Hz, 6H).<br>LCMS ESI (m/z): 338.2 (M + 1)<br>Purity at 210 nm: 95.49% |

Synthesis Table 9

| Structure | Precursor | Analytical data |
|---|---|---|
| ANASIA-072-1 (HCl) / ANASIA-072-2 (HCl) | Int-A-4.63-Fr-1<br>Int-A-4.63-Fr-2 | Isomer-1<br>$^1$H NMR (400 MHz, DMSO-$d_6$) δ 8.40-8.20 (m, 4H), 8.07 (d, J = 7.4 Hz, 1H), 7.91-7.87 (m, 4H), 3.69 (bs, 1H), 1.94-1.93 (m, 1H), 1.40-1.11 (m, 2H), 0.87-0.75 (m, 6H).<br>LCMS ESI (m/z): 338.3 (M + H)<br>Purity at 210 nm: 98.97%<br>Isomer-2<br>$^1$H NMR (400 MHz, DMSO-$d_6$) δ 8.25-8.20 (m, 4H), 8.08 (d, J = 7.6 Hz, 1H), 7.91-7.87 (m, 4H), 3.65 (bs, 1H), 1.94-1.90 (m, 1H), 1.55-1.20 (m, 2H), 0.95-0.86 (m, 6H).<br>LCMS ESI (m/z): 338.3 (M + H)<br>Purity at 222 nm: 96.41% |
| ANASIA-090 (CF$_3$COOH) | Int-A-4.64 | $^1$H NMR (400 MHz, DMSO d6) δ: 8.20-8.17 (m, 2H), 8.00-7.90 (m, 3H), 7.86-7.78 (m, 2H), 7.73 (d, J = 7.6 Hz, 1H), 3.72-3.71 (m, 1H), 1.74-1.69 (m, 2H), 1.59-1.56 (m, 1H), 0.92-0.85 (m, 6H)<br>LCMS ESI (m/z): 354.3 (M + 1)<br>Purity at 222 nm: 100% |
| ANASIA-077-1 (HCl) / ANASIA-077-2 (HCl) | Int-A-4.65-Fr-1<br>Int-A-4.65-Fr-2 | Isomer-1<br>$^1$H NMR (400 MHz, DMSO d6) δ: 8.18 (s, 2H), 7.97-7.70 (s, 7H), 3.70 (bs, 1H), 2.0-1.80 (m, 1H), 1.25-1.13 (m, 2H), 0.84-0.75 (m, 6H)<br>LCMS ESI (m/z): 354.3 (M + H)<br>Purity at 210 nm: 98.53%<br>Isomer-1<br>$^1$H NMR (400 MHz, DMSO d6) δ: 8.21 (s, 2H), 8.00-7.70 (s, 7H), 3.65 (bs, 1H), 2.0-1.85 (m, 1H), 1.55-1.20 (m, 2H), 0.95-0.85 (m, 6H)<br>LCMS ESI (m/z): 354.3 (M + H)<br>Purity at 210 nm: 97.37% |

Synthesis Table 9

| Structure | Precursor | Analytical data |
|---|---|---|
| ANASIA-099 | Int-A-4.66<br>Int-A-4.66-Fr-1<br>Int-A-4.66-Fr-2 | Racemic<br>¹H NMR (400 MHz, DMSO) δ 8.21-8.20 (m, 1H), 8.11-8.09 (m, 2H), 8.00 (bs, 3H), 7.43-7.39 (m, 1H), 3.70-3.60 (m, 1H), 1.77-1.48 (m, 3H), 0.92-0.87 (m, 6H).<br>LCMS ESI (m/z): 310.4 & 312.4 (M & M + 2)<br>Purity at 210 nm: 98.03%<br>Isomer-1<br>¹H NMR (400 MHz, DMSO d6) δ 8.19 (s, 1H), 8.00 (bs, 5H), 7.39 (s, 1H), 3.69 (s, 1H), 1.73-1.63 (m, 2H), 1.49-1.47 (m, 1H), 0.88 (bs, 6H).<br>LCMS ESI (m/z): 310.3, 312.3 (M & M + 2)<br>Purity at 210 nm: 100.00%<br>Isomer-2<br>¹H NMR (400 MHz, DMSO d6) δ 8.21 (s, 1H), 8.19 (bs, 2H), 8.02 (bs, 3H), 7.44 (s, 1H), 3.69-3.68 (m, 1H), 1.77-1.67 (m, 2H), 1.59-1.56 (m, 1H), 0.92-0.88 (m, 6H).<br>LCMS ESI (m/z): 310.3, 312.3 (M & M + 2)<br>Purity at 254 nm: 97.88% |
| ANASIA-099-1 | | |
| ANASIA-099-2 | | |
| ANASIA-080-1 | Int-A-4.67-Fr-1<br>Int-A-4.67-Fr-2 | Isomer-1<br>¹H NMR (400 MHz, DMSO-d₆) δ 8.22 (d, J = 2 Hz,1H), 8.02 (bs, 5H), 7.41 (d, J = 2 Hz, 1H), 3.66 (bs, 1H), 1.94 (bs, 1H), 1.23-1.16 (m, 2H), 0.85 (t, J = 6.8 Hz, 6H)<br>LCMS ESI (m/z): 310.3 & 312.3 (M & M + 2)<br>Purity at 210 nm: 100.0%<br>Isomer-2<br>¹H NMR (400 MHz, DMSO-d₆) δ 8.22 (d, J = 2 Hz, 1H), 8.04 (bs, 5H), 7.45 (d, J = 1.6 Hz, 1H), 3.63 (d, J = 3.6 Hz, 1H), 1.93 (m, 1H), 1.49-1.45 (m, 1H), 1.30-1.28 (m, 1H), 0.92-0.87 (m, 6H)<br>LCMS ESI (m/z): 310.3 & 312.3 (M & M + 2)<br>Purity at 210 nm: 100.0% |
| ANASIA-080-2 | | |
| ANASIA-100 | Int-A-4.68 | ¹H NMR (400 MHz, DMSO-d₆) δ 8.45-8.44 (dd, J = 5.4 Hz, J = 1.4 Hz, 1H), 8.29 (s, 2H), 8.03 (bs, 3H), 7.84-7.82 (m, 1H), 7.52-7.51 (dd, J = 5.3 Hz, J = 1.6 Hz, 1H), 3.69 (bs, 1H), 1.82-1.58 (m, 2H), 1.49-1.24 (m, 1H), 0.93-0.85 (m, 6H).<br>LCMS ESI (m/z): 332.3 (M + H)<br>Purity at 275 nm: 95.5% |
| ANASIA-084 | Int-A-4.69 | ¹H NMR (400 MHz, DMSO-d₆) δ 8.44 (dd, J = 6.4 Hz, J = 1.6 Hz, 1H), 8.32-8.27 (m, 2H), 7.92 (bs, 3H), 7.83-7.80 (m, 1H), 7.52-7.50 (m, 1H), 3.67 (bs, 1H), 1.99-1.93 (m, 1H), 1.50-1.46 (m, 1H), 1.33-1.19 (m, 1H), 0.94-0.86 (m, 3H), 0.79-0.74 (m, 3H)<br>LCMS ESI (m/z): 323.3 (M + H)<br>Purity at 210 nm: 97.08% |

Synthesis Table 9

| Structure | Precursor | Analytical data |
|---|---|---|
| ANASIA-101-1 (HCl) | Int-A-4.70 | Isomer-1<br>¹H NMR (400 MHz, DMSO d6) δ: 7.97 (bs, 3H), 7.88 (s, 2H), 7.49 (dd, J = 8 Hz, 1H), 7.36 (d, J = 2 Hz, 1H), 7.13 (d, J = 8 Hz, 1H), 6.19 (s, 2H), 3.67-3.65 (m, 1H), 1.74-1.73 (m, 1H), 1.65-1.59 (m, 1H), 1.47-1.44 (m, 1H), 0.89-0.87 (m, 6H).<br>LCMS ESI (m/z): 314.3 (M + H)<br>Purity at 210 nm: 98.09% |
| ANASIA-101-2 (HCl) | | Isomer-2<br>¹H NMR (400 MHz, DMSO d6) δ: 7.97 (bs, 3H), 7.88 (s, 2H), 7.49 (dd, J = 8 Hz, 1H), 7.36 (d, J = 2 Hz, 1H), 7.13 (d, J = 8 Hz, 1H), 6.19 (s, 2H), 3.67-3.65 (m, 1H), 1.74-1.73 (m, 1H), 1.65-1.59 (m, 1H), 1.47-1.44 (m, 1H), 0.89-0.87 (m, 6H).<br>LCMS ESI (m/z): 314.3 (M + H)<br>Purity at 256 nm: 94.12% |
| ANASIA-115-1 (HCl) | Int-A-4.71-Fr-1<br>Int-A-4.71-Fr-2 | Isomer-1<br>¹H-NMR (400 MHz, DMSO-d₆) δ: 7.88-7.86 (bs, 4H), 7.49-7.46 (dd, J = 8.2 Hz, J = 1.8 Hz, 1H), 7.37-7.36 (d, J = 4 Hz 1H), 7.13 (d, J = 8 Hz, 1H), 6.18 (s, 2H), 3.66 (bs, 1H), 1.93 (bs, 1H), 1.18-1.14 (m, 2H), 0.86-0.82 (m, 6H).<br>LCMS ESI (m/z): 314.4 (M + H)<br>Purity at 210 nm: 100.0% |
| ANASIA-115-2 (HCl) | | Isomer-2<br>¹H-NMR (400 MHz, DMSO-d₆) δ: 7.89 (bs, 4H), 7.49 (dd, J = 8.4 Hz, 1H), 7.39 (d, J = 2 Hz 1H), 7.13 (d, J = 8.4 Hz, 1H), 6.19 (s, 2H), 3.64 (bs, 1H), 1.92 (bs, 1H), 1.50-1.24 (m, 2H), 0.86-0.82 (m, 6H).<br>LCMS ESI (m/z): 314.3 (M + H)<br>Purity at 210 nm: 97.25% |
| ANASIA-118 (·HCl) | Int-A-4.72 | ¹H NMR (400 MHz, DMSO) δ 8.39 (bs, 2H), 8.16 (s, 1H), 7.96-7.94 (m, 4H), 7.55 (d, J = 5.2 Hz, 1H), 3.63-3.61 (m, 1H), 2.32 (m, 1H), 0.98-0.83 (m, 6H).<br>LCMS ESI (m/z): 318.2 (M + H)<br>Purity at 289 nm: 95.50% |
| ANASIA-114-1 (HCl) | Int-A-4.73-Fr-1<br>Int-A-4.73-Fr-2 | Isomer-1<br>¹H NMR (400 MHz, DMSO) 8.01-7.97 (bs, 5H), 7.65-7.62 (m, 2H), 7.48-7.44 (m, 3H), 7.33-7.30 (m, 1H), 7.24 (t, J = 7.4 Hz, 1H), 7.07 (d, J = 7.6 Hz, 2H), 3.68 (bs, 1H), 1.74-1.70 (m, 1H), 1.57-1.52 (m, 1H), 1.44-1.39 (m, 1H), 0.85 (d, J = 6.4 Hz, 6H).<br>LCMS ESI (m/z): 362.4 (M + H)<br>Purity at 210 nm: 98.46% |
| ANASIA-114-2 (HCl) | | Isomer-2<br>¹H NMR (400 MHz, DMSO)<br>δ 8.04 (bs, 2H), 7.98 (bs, 3H), 7.68-7.61 (m, 2H), 7.49-7.45 (m, 3H), 7.31-7.23 (m, 2H), 7.10-7.08 (m, 2H), 3.65 (bs, 1H), 1.60-1.66 (m, 2H), 1.60-1.50 (m, 1H), 0.91-0.87 (m, 6H).<br>LCMS ESI (m/z): 362.4 (M + H)<br>Purity at 210 nm: 96.61% |

-continued

Synthesis Table 9

| Structure | Precursor | Analytical data |
|---|---|---|
| 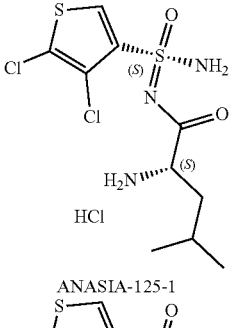<br>ANASIA-125-1<br><br>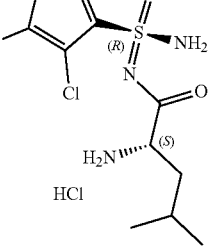<br>ANASIA-125-2 | Int-A-4.76-Fr-1<br>Int-A-4.76-Fr-2 | Isomer-1<br>$^1$H NMR (400 MHz, DMSO-d$_6$) δ 8.42 (s, 1H), 8.33 (s, 2H), 7.98 (s, 3H), 3.72 (bs, 1H), 1.80-1.68 (m, 2H), 1.50-1.43 (m, 1H), 0.89 (d, J = 6.4 Hz, 6H).<br>LCMS ESI (m/z): 344.5 & 346.5 (M & M + 2)<br>Purity at 210 nm: 94.07%<br>Isomer-2<br>$^1$H NMR (400 MHz, DMSO-d$_6$) δ 8.40 (s, 1H), 8.33 (bs, 2H), 7.97 (bs, 3H), 3.68 (bs, 1H), 1.79-1.69 (m, 2H), 1.51-1.43 (m, 1H), 0.92-0.89 (m, 6H).<br>LCMS ESI (m/z): 343.9 & 345.9 (M & M + 2)<br>Purity at 210 nm: 100.0% |
| 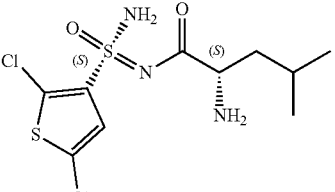<br>ANASIA-134-1<br><br>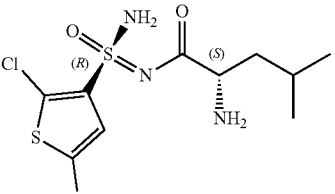<br>ANASIA-134-2 | Int-A-4.77-Fr-1<br>Int-A-4.77-Fr-2 | Isomer-1<br>$^1$H NMR (400 MHz, DMSO) δ 8.33 (bs, 2H), 7.99 (bs, 3H), 7.39 (s, 1H), 3.75 (bs, 1H), 1.77-1.65 (m, 2H), 1.50-1.47 (m, 1H),<br>0.89 (d, J = 6.0 Hz, 6H).<br>LCMS ESI (m/z): 444.1 & 446.1 (M & M + 2)<br>Purity at 210 nm: 100%<br>Isomer-2<br>$^1$H NMR (400 MHz, DMSO) δ 7.99 (bs, 5H), 7.99 (bs, 3H), 7.38 (s, 1H), 3.75 (bs, 1H), 1.77-1.40 (m, 3H),<br>0.89 (d, J = 6.0 Hz, 6H).<br>LCMS ESI (m/z): 344.1 & 346.1 (M & M + 2)<br>Purity at 210 nm: 100% |
| 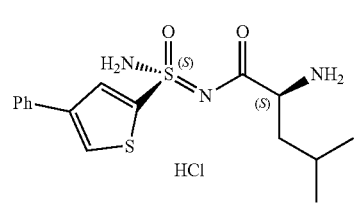<br>ANASIA-067-1 | Int-A-4.78 | $^1$H NMR (400 MHz, MeOD) δ 8.12 (d, J = 1.7 Hz, 1H), 8.06 (d, J = 1.7 Hz, 1H), 7.66 (d, J = 7.2 Hz, 2H), 7.43 (t, J = 7.5 Hz, 2H), 7.35 (t, J = 6.9 Hz, 1H), 3.86-3.79 (m, 1H), 1.90-1.75 (m, 2H), 1.68-1.56 (m, 1H), 1.00 (d, J = 6.4 Hz, 3H), 0.98 (d, J = 6.3 Hz, 3H).<br>$^{13}$C NMR (101 MHz, MeOD) δ 176.92, 143.70, 143.67, 135.48, 133.01, 130.16, 129.14, 128.84, 127.27, 55.59, 41.42, 25.63, 22.96, 22.21.<br>UPLCMS ESI (m/z): 352 (M + H)$^+$<br>Putity at 210 nm: 97.75%; at 254 nm: 97.24% |

Synthesis Table 9

| Structure | Precursor | Analytical data |
|---|---|---|
| 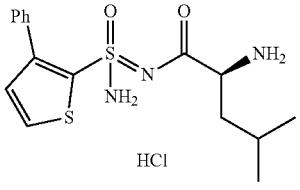 [SMILES: CC(C)C[C@H](N)C(=O)N=S(N)(=O)c1sccc1-c1ccccc1 ; Cl]  ANASIA-068 | Int-A-4.79 | $^1$H NMR (300 MHz, MeOD) δ 7.86 (d, J = 5.2 Hz, 1H), 7.65-7.54 (m, 2H), 7.43 (dt, J = 4.9, 2.2 Hz, 3H), 7.20-7.12 (m, 1H), 3.54-3.46 (m, 1H-1$^{st}$ diastereomer), 3.29-3.25 (m, 1H-2$^{nd}$ diastereomer), 1.77-1.49 (m, 2H), 1.49-1.35 (m, 1H), 0.93 (d, J = 6.5 Hz, 3H), 0.88 (d, J = 6.5 Hz, 3H). $^{13}$C NMR (101 MHz, MeOD) δ 176.58, 176.52, 147.23, 147.18, 137.25, 137.13, 135.74, 133.14, 132.99, 132.43, 132.39, 130.60, 129.70, 129.64, 129.31, 55.45, 55.28, 41.04, 40.86, 25.61, 23.41, 23.25, 21.72, 21.53. (peaks of 2 diastereomers). UPLCMS ESI (m/z): 352 (M + H)$^+$ Putity at 210 nm: 91.9%; at 254 nm: 93.14% |

Synthesis of (S)-2-amino-N—((S)-amino(3'-fluoro-[1,1'-biphenyl]-3-yl)(oxo)-λ6-sulfanylidene)-4-methylpentanamide hydrochloride and (S)-2-amino-N—((R)-amino(3'-fluoro-[1,1'-biphenyl]-3-yl)(oxo)-λ6-sulfanylidene)-4-methylpentanamide hydrochloride (ANASIA-051-1/2

Step-1: Synthesis of Int-A-4.51, Int-A-51-Fr-1 and Int-A-51-Fr-2

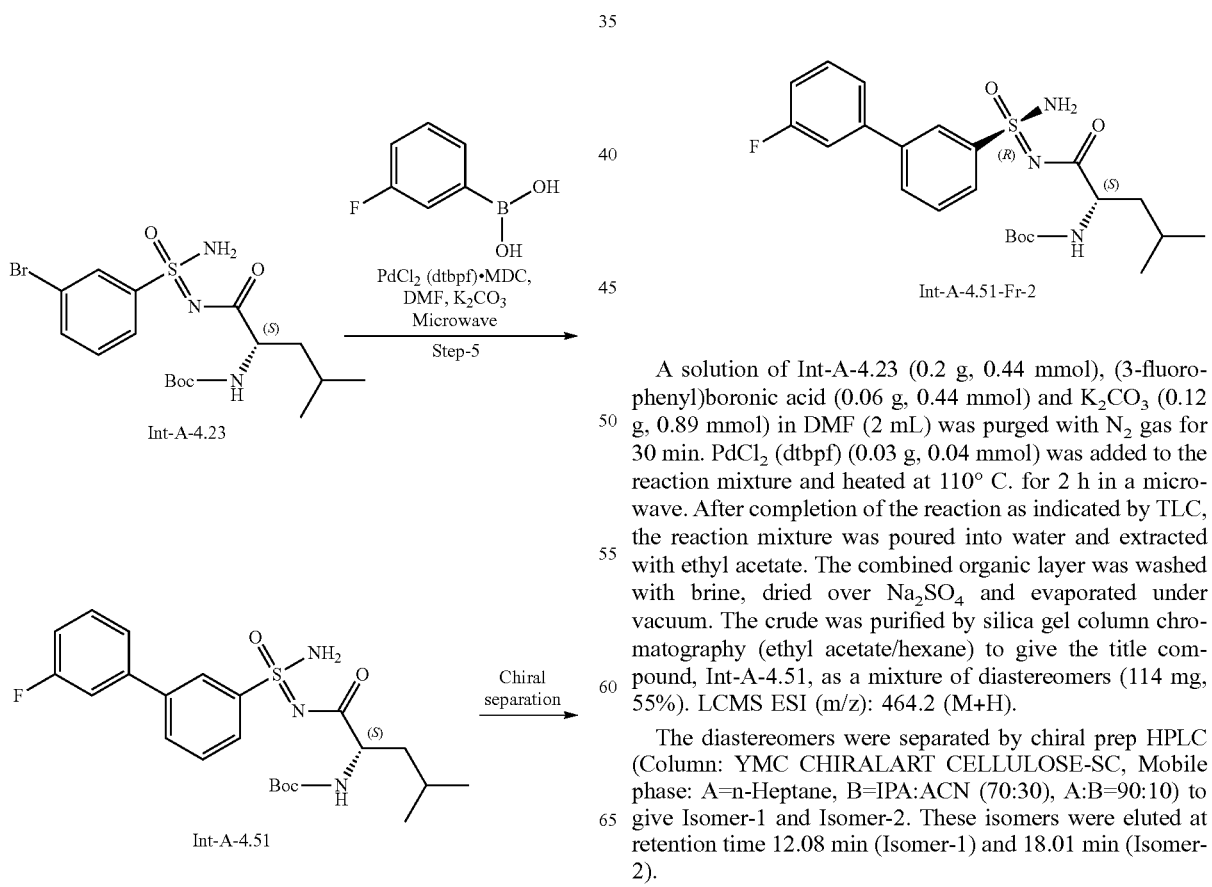

A solution of Int-A-4.23 (0.2 g, 0.44 mmol), (3-fluorophenyl)boronic acid (0.06 g, 0.44 mmol) and K$_2$CO$_3$ (0.12 g, 0.89 mmol) in DMF (2 mL) was purged with N$_2$ gas for 30 min. PdCl$_2$ (dtbpf) (0.03 g, 0.04 mmol) was added to the reaction mixture and heated at 110° C. for 2 h in a microwave. After completion of the reaction as indicated by TLC, the reaction mixture was poured into water and extracted with ethyl acetate. The combined organic layer was washed with brine, dried over Na$_2$SO$_4$ and evaporated under vacuum. The crude was purified by silica gel column chromatography (ethyl acetate/hexane) to give the title compound, Int-A-4.51, as a mixture of diastereomers (114 mg, 55%). LCMS ESI (m/z): 464.2 (M+H).

The diastereomers were separated by chiral prep HPLC (Column: YMC CHIRALART CELLULOSE-SC, Mobile phase: A=n-Heptane, B=IPA:ACN (70:30), A:B=90:10) to give Isomer-1 and Isomer-2. These isomers were eluted at retention time 12.08 min (Isomer-1) and 18.01 min (Isomer-2).

Step-2: Synthesis of ANASIA-051-1 and ANASIA-051-2

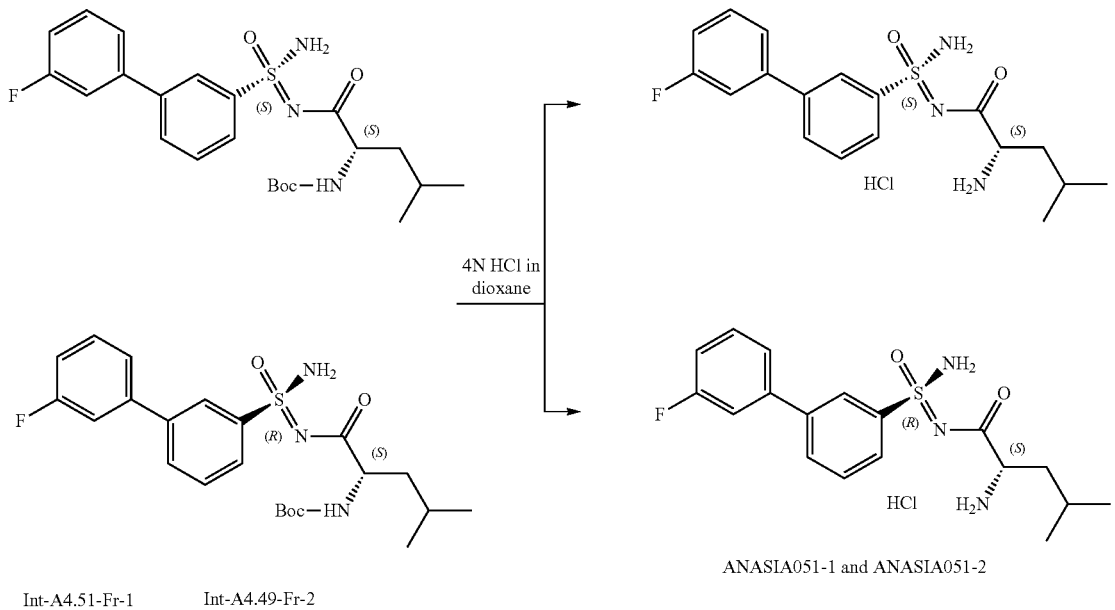

Int-A4.51-Fr-1    Int-A4.49-Fr-2

ANASIA051-1 and ANASIA051-2

To a solution of Int-A-4.51-Fr-1 (Isomer-1) (29 mg, 0.06 mmol) was added 4 M HCl in 1,4-dioxane (1 mL) at 0° C. The reaction mixture was allowed to stir at room temperature for 1 h. After completion of the reaction as indicated by TLC, the reaction mixture was concentrated under vacuum followed by trituration with n-pentane:diethyl ether to give the title compound, ANASIA-051-1, as a hydrochloride salt (16 mg, 70%). $^1$H NMR (400 MHz, DMSO-$d_6$) δ 8.19 (s, 1H), 8.12-7.89 (m, 7H), 7.73 (t, J=7.9 Hz, 1H), 7.68-7.51 (m, 3H), 7.34-7.26 (m, 1H), 3.73 (brs, 1H), 1.80-1.34 (m, 3H), 0.85 (d, J=6.1 Hz, 6H); LCMS ESI (m/z): 364.2 (M+1); Purity at 220 nm: 96.14%.

To a solution of Int-A-4.51-Fr-2 (Isomer-2) (23 mg, 0.04 mmol) was added 4 M HCl in 1,4-dioxane (1 mL) at 0° C. The reaction mixture was allowed to stir at room temperature for 1 h. After completion of the reaction as indicated by TLC, the reaction mixture was concentrated under reduced pressure. The product was triturated with n-pentane:diethyl ether to give the title compound, ANASIA-051-2, as a hydrochloride salt (17 mg, 88%). $^1$H NMR (400 MHz, DMSO-$d_6$) δ 8.20 (s, 1H), 8.04-8.00 (m, 3H), 7.95-7.90 (m, 4H), 7.73 (t, J=7.9 Hz, 1H), 7.65-7.55 (m, 3H), 7.35-7.25 (m, 1H), 3.73 (brs, 1H), 1.78-1.54 (m, 3H), 0.91-0.85 (m, 6H); LCMS ESI (m/z): 364.2 (M+1); Purity at 220 nm: 91.50%.

Synthesis of (2S)—N-((3-allylphenyl)(amino)(oxo)-λ6-sulfanylidene)-2-amino-4-methylpentanamide hydrochloride (ANASIA-085

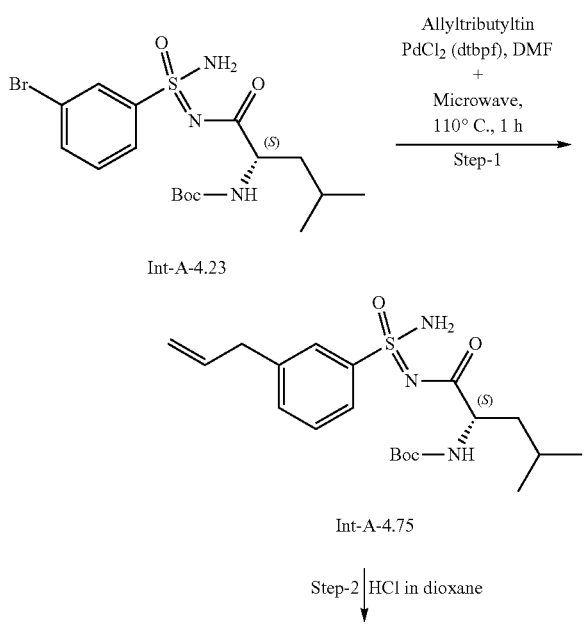

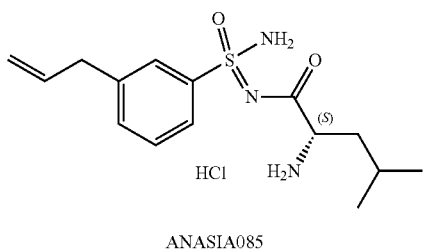

ANASIA085

Step-1: A solution of tert-butyl ((2S)-1-((amino(3-bromophenyl)(oxo)-λ6-sulfanylidene) amino)-4-methyl-1-oxopentan-2-yl)carbamate (0.3 g, 0.66 mmol), allyltributyltin (0.24 g, 0.74 mmol) in DMF (2 mL) was purged with $N_2$ gas for 30 min. $PdCl_2$ (dtbpf).DCM complex (0.04 g, 0.06 mmol) was added to the reaction mixture and heated at 120° C. for 2 h under microwave. After completion of the reaction as indicated by TLC, the reaction mixture was poured into water and extracted with ethyl acetate. The combined organic layer was washed with brine, dried over $Na_2SO_4$ and evaporated under vacuum. The crude was purified by silica gel column chromatography (ethyl acetate/hexane 28:72) to give Int-A-4.75 as a mixture of diastereomers (75 mg, 27.37%). LCMS ESI (m/z): 310.2 (M+H).

Step-2: The Boc de-protection of Int-A-4.75 was carried out as shown for the ANASIA-051 using 4 M HCl in dioxane to give ANASIA-085.

$^1$H NMR (400 MHz, MeOD) δ 7.85-7.80 (m, 2H), 7.55-7.49 (m, 2H), 6.03-5.96 (m, 1H), 5.16-5.10 (m, 2H), 3.79-3.74 (m, 1H), 3.50 (d, 2H), 1.85-1.54 (m, 3H), 1.00-0.86 (m, 6H). LCMS ESI (m/z): 310.2 (M+H). Purity at 230 nm: 100%.

Synthesis of (S)-2-amino-4-methyl-N—((S)-(methylamino)(oxo)(phenyl)-λ6-sulfanylidene)pentanamide and (S)-2-amino-4-methyl-N—((R)-(methylamino)(oxo)(phenyl)-λ6-sulfanylidene)pentanamide (ANASIA-010-1/2

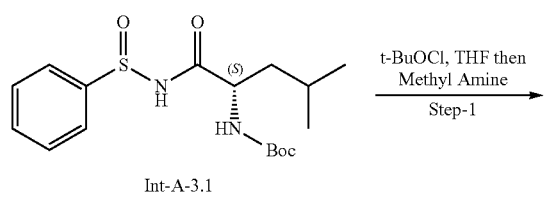

Int-A-3.1

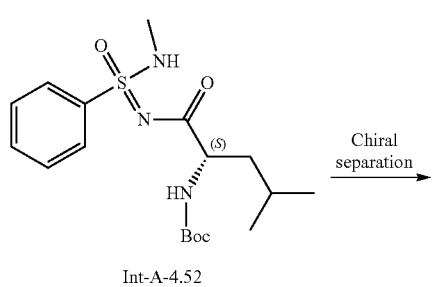

Int-A-4.52

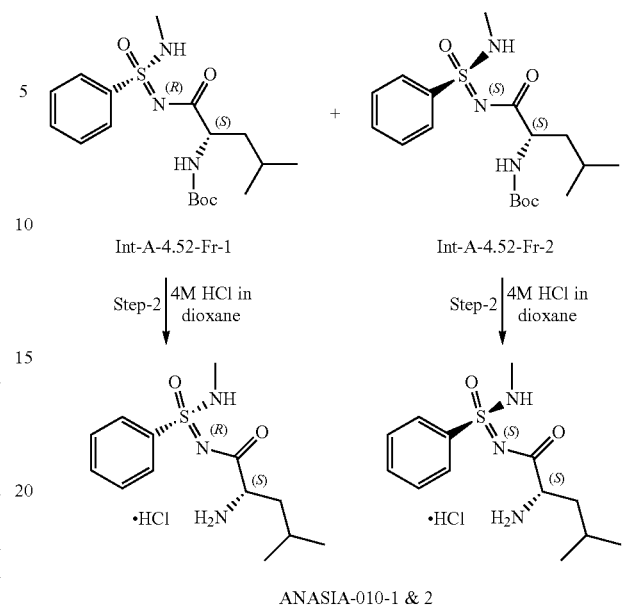

ANASIA-010-1 & 2

Step-1: To a stirred solution of Int-A-3.1 (1 g, 2.8 mmol) in THF (10 mL) was added tert-butyl hypochlorite (0.40 mL, 3.6 mmol) at 0° C. and stirred for another 1 h. Methylamine solution (5 mL) was added to the reaction mixture and allowed to stir at room temperature for 1 h. After completion of the reaction as indicated by TLC, the reaction mixture was poured into water and extracted with ethyl acetate. The combined organic layer was washed with brine, dried over $Na_2SO_4$ and evaporated under vacuum to give the crude product. The crude was purified by silica gel column chromatography (ethyl acetate/hexane) to give Int-A-4.54 as a mixture of diastereomers (0.292 g, 27%). The diastereomers were separated by chiral prep HPLC (Column: DIACEL Chiral PAK_IG, Mobile phase: A=Heptane, B=IPA:MeOH (70:30), A:B=70:30) to give Isomer-1 and Isomer-2. These isomers were eluted at retention time 15.66 min (Isomer-1) and 21.41 min (Isomer-2).

Step-2: The Boc de-protection of Int-A-4.52-Fr-1 and Int-A-4.52-Fr-2 was carried out as shown for the ANASIA-003 using 4 M HCl in dioxane.

Isomer-1: $^1$H NMR (400 MHz, DMSO-$d_6$) δ 8.08 (brs, 5H), 7.90-7.84 (m, 2H), 7.75-7.61 (m, 3H), 3.75-3.65 (m, 1H), 2.42 (s, 3H), 1.84-1.40 (m, 3H), 0.88 (d, J=6.4 Hz, 6H). LCMS ESI (m/z): 284.0 (M+H), Purity at 210 nm: 100%.

Isomer-2: $^1$H NMR (400 MHz, DMSO-$d_6$) δ 8.15-7.99 (m, 5H), 7.75-7.61 (m, 2H), 7.88-7.74 (m, 3H), 3.72 (brs, 1H), 2.42 (d, 3H), 1.84-1.40 (m, 3H), 0.88 (two d, 6H). LCMS ESI (m/z): 284.1 (M+H), Purity at 210 nm: 96.13%.

Synthesis of pyridine-4-sulfonyl chloride (Int-B-2.1

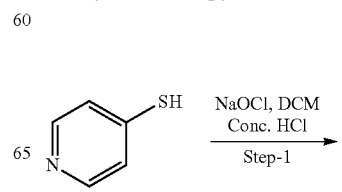

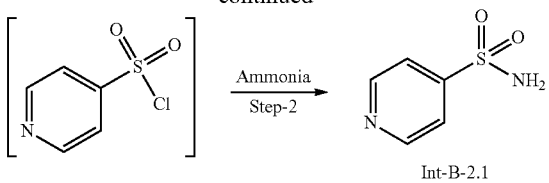

Step-1: A mixture of 4-mercapto pyridine (1.5 g, 13.51 mmol), conc. HCl (18 mL) and dichloromethane (18 mL) were stirred at −5° C. and 5% solution of NaOCl (3.33 g, 44.93 mmol) was added drop wise to the reaction mixture. After completion of the addition, the reaction mixture was slowly stirred for 1 h at −5° C. After completion of the reaction, the reaction mixture was diluted with water and extracted with dichloromethane (3×25 mL). The combined organic layer was used for next step without evaporation.

Step-2: Ammonia gas was purged in THF (30 mL) at −78° C. and to it was added a freshly prepared solution of pyridine-4-sulfonyl chloride (100 mL) in dichloromethane at −78° C., the reaction mixture was stirred for additional 1 h. After completion of the reaction as indicated by TLC, the reaction mixture was evaporated under vacuum to give the title compound, Int-B-2.1, as a light yellow solid (0.7 g, 33% over 2 steps). LCMS ESI (m/z): 159.06 (M+1).

Synthesis of 4-methylthiazole-2-sulfonamide (Int-B-2.2

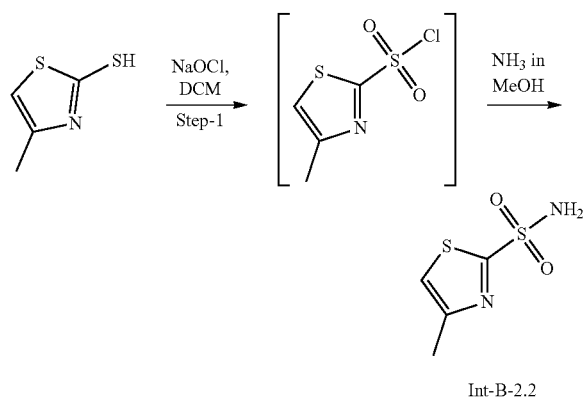

To a stirred solution of 4-methylthiazole-2-thiol (3 g, 22.8 mmol) in $H_2SO_4$ (75 mL) was added drop-wise 5% NaOCl (150 mL, 75.4 mmol) at 0° C. and stirred at room temperature for 30 min. After completion of the reaction as indicated by TLC, the reaction mixture was poured into water and extracted with DCM. The combined organic layer was immediately added drop-wise to a pre-cooled, stirred mixture of a saturated $NH_3$ solution in MeOH (60 mL) and DCM (135 mL) at 0° C. and stirred at room temperature for 3 h. After completion of the reaction as indicated by TLC, the reaction mixture was poured into water and extracted with DCM. The combined organic layer was washed with brine, dried over $Na_2SO_4$ and evaporated under vacuum to give the crude product. The crude was purified by silica gel column chromatography (ethyl acetate/hexane: 4:6) to give the title compound, Int-B-2.2, as a white solid (300 mg, 7.5%).

Synthesis of Quinoline-7-sulfonamide (Int-B-2.3

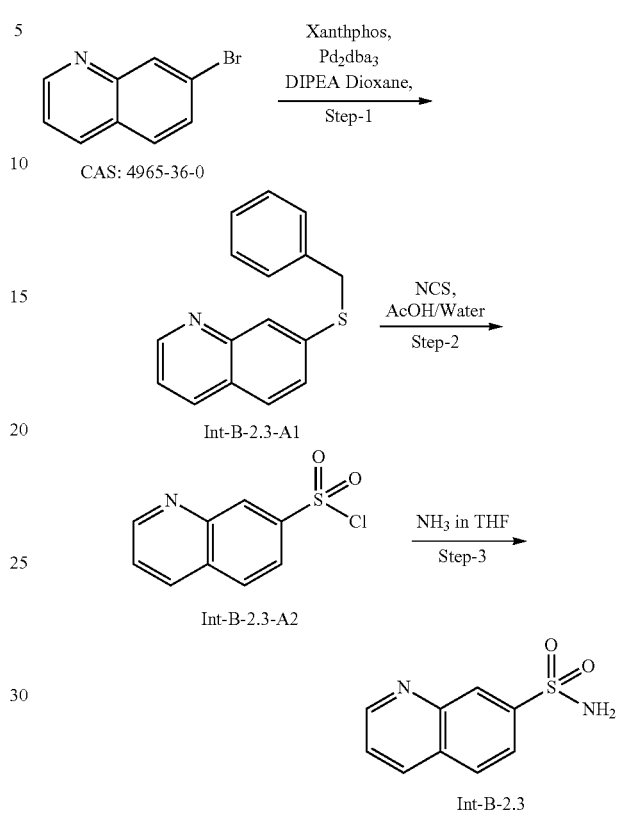

Step-1: To a stirred solution of 7-bromoquinoline (5 g, 24 mmol) in dioxane (50 mL) was added DIPEA (8.21 mL, 48 mmol) and purged with $N_2$ gas for 30 min followed by the addition of Xantphos (1.38 g, 2.4 mmol), $Pd_2dba_3$ (1.09 g, 1.2 mmol) and benzyl mercaptan (2.98 mL, 24 mmol). The reaction mixture was heated at 100° C. for 4 h. After completion of the reaction as indicated by TLC, the reaction mixture was filtered through celite. The filtrate was poured into water and extracted with ethyl acetate (3×25 mL). The combined organic layer was washed with brine, dried over $Na_2SO_4$ and evaporated under vacuum. The crude was purified by silica gel column chromatography (ethyl acetate/hexane) to give Int-B-2.3-A1 (4 g, 66%). LCMS ESI (m/z): 252.0 [M+H]+.

Step-2: To a stirred solution of Int-B-2.3-A1 (4 g, 15.9 mmol) in acetic acid (60 mL)/water (8 mL) was added N-chloro succinimide (8.4 g, 63.6 mmol) and stirred for 6 h at room temperature. After completion of the reaction as indicated by TLC, the reaction mixture was poured into water and extracted with ethyl acetate. The combined organic layer was washed with brine, dried over $Na_2SO_4$ and evaporated under vacuum. The crude was purified by silica gel column chromatography (ethyl acetate/hexane) to give Int-B-2.3-A2 (3 g, 82%).

Step-3: A THF (20 mL) solution of Int-B-2.3-A2 (3 g, 13 mmol) was added to a stirred saturated ammonia solution in THF (100 mL) at 0° C. The solid was precipitate out. It was evaporated to dryness and triturated with diethyl ether to obtain the title compound, Int-B-2.3 (2 g, 73%). LCMS ESI (m/z): 209.0 (M+H).

Synthesis of 4-chlorothiazole-2-sulfonamide (Int-B-2.4

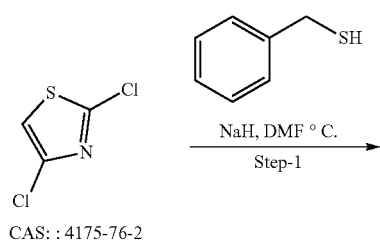

CAS: : 4175-76-2

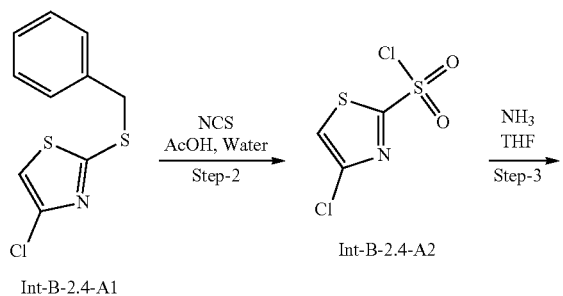

Synthesis of 5-methylthiazole-2-sulfonamide (Int-B-2.5

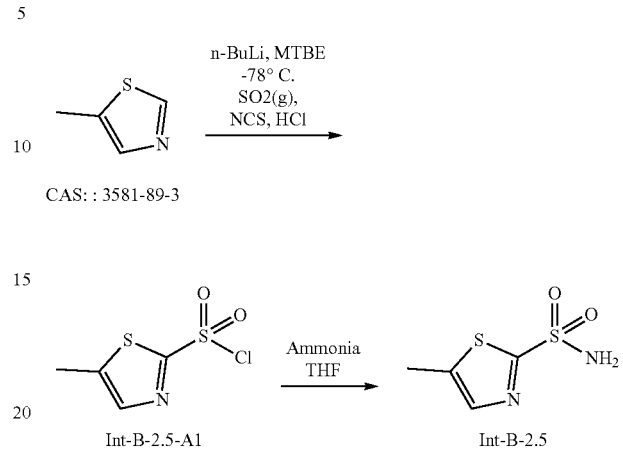

Step-1: To a stirred solution of 5-methyl thiazole (2 g, 20 mmol) in MTBE (20 mL) was added n-BuLi (13 mL, 20 mmol, 1.6 M) at −78° C. and stirred for another 1 h at the same temperature. Gaseous $SO_2$ was passed into the reaction mixture for 1 h, at the same temperature. NCS (4 g, 30 mmol) was added to the reaction mixture and allowed to stir at room temperature for 2 h. After completion of the reaction as indicated by TLC, the reaction mixture was poured into water and extracted with ethyl acetate. The combined organic layer was washed with brine, dried over $Na_2SO_4$ and evaporated under vacuum to give crude product. The crude product was purified by silica gel column chromatography (ethyl acetate/hexane: 1:1) to give Int-B-2.5-A1 (1.5 g, 38%). $^1$H-NMR (400 MHz, DMSO-$d_6$) δ: 7.76 (s, 1H), 2.66 (s, 3H).

Step-2: Int-B-2.5 was prepared by following similar procedure as described for Int-B-2.3 (Step-3). LCMS ESI (m/z): 178.9 (M+H).

Procedure: To a stirred solution of 2,4-dichlorothiazole (5 g, 32 mmol) in DMF (50 mL), 60% NaH (2.3 g, 96 mmol) was added at 0° C. and stirred for 1 h. Benzyl mercaptan (10 mL, 32 mmol) was added to the reaction mixture and the reaction mixture was heated at 60° C. for 4 h. After completion of the reaction as indicated by TLC, the reaction mixture was poured into water and extracted with ethyl acetate. The combined organic layer was washed with brine, dried over $Na_2SO_4$ and evaporated under vacuum. The crude was purified by silica gel column chromatography (ethyl acetate/hexane) to give Int-B-2.4-A1 (1.5 g, 19%). LCMS ESI (m/z): 242.2 & 244.2 (M+H).

Step-2: To a stirred solution of Int-B-2.4-A1 (1.5 g, 6.2 mmol) in acetic acid (36 mL)/water (4 mL) was added N-chlorosuccinimide (3.3 g, 24.8 mmol) and stirred for 6 h at room temperature. After completion of the reaction as indicated by TLC, the reaction mixture was poured into water and extracted with ethyl acetate. The combined organic layer was washed with brine, dried over $Na_2SO_4$ and evaporated under vacuum. The crude was purified by silica gel column chromatography (ethyl acetate/hexane) to give Int-B-2.4-A2 (1 g, 73%). Which was used immediately after isolation.

Step-3: Int-B-2.4 was prepared by following similar procedure as described for Int-B-2.3 (Step-3). LCMS ESI (m/z): 197.0 (M−H).

Synthesis of 2,6-difluorobenzenesulfonamide (Int-B-2.6

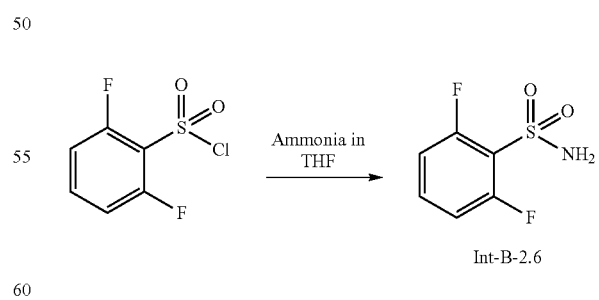

Ammonia gas was passed into the solution of 2,6-difluorobenzenesulfonyl chloride (2 g, 9.4 mmol) in THF (100 mL) at 0° C. and the mixture was allowed to stir at room temperature overnight. The reaction mixture was concentrated in vacuo to give the title compound, Int-B-2.6 (1.8 g, 99%). LCMS ESI (m/z): 211.4 (M+18).

Synthesis of 2,4-dichlorothiazole-5-sulfonamide (Int-B-2.7

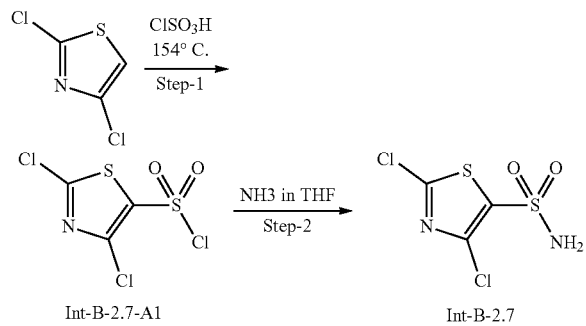

Step-1: 2,4-dichlorothiazole (0.5 g, 3.2 mmol) was added to a chlorosulfonic acid (3 mL) at 0° C. under stirring and the resulting reaction mixture stirred at 154° C. for 8 h. After completion of the reaction as indicated by TLC, the reaction mixture was poured into cold water (50 mL) and extracted with ether (3×20 mL). The combined organic layer was washed with brine, dried over Na$_2$SO$_4$ and evaporated under vacuum to give 2,4-dichlorothiazole-5-sulfonyl chloride (0.550 g, 68.51%). The crude material was used in next step without purification.

Step-2: To a freshly prepared saturated solution of ammonia in THF (10 mL) was added 2,4-dichlorothiazole-5-sulfonyl chloride in THF (10 mL) at -78° C. The reaction mixture was stirred for 1 h at -78° C. After completion of the reaction as indicated by TLC, the reaction mixture was allowed to come to room temperature and evaporated under vacuum to afford the crude, which was purified by silica gel column chromatography (ethyl acetate/hexane) to give 2,4-dichlorothiazole-5-sulfonamide (0.275 g, 56.18%). LCMS ESI (-ve) (m/z): 232.1 & 234.1 (M & M-2).

Synthesis of 3,4-dichlorothiophene-2-sulfonamide (Int-B-2.8

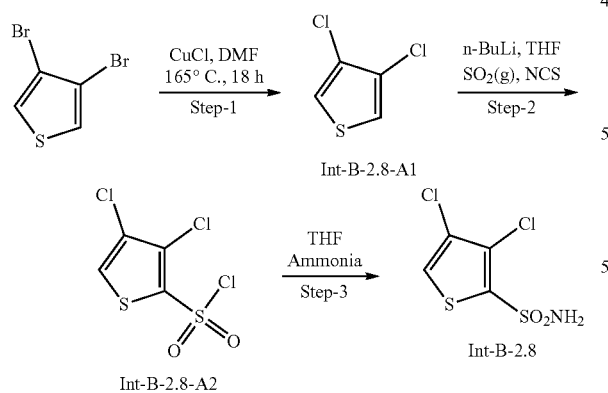

Step-1: To a stirred solution of 3,4-dibromothiophene (3 g, 12.4 mmol) in DMF (20 mL) was added CuCl$_2$ (5.0 g, 37.2 mmol) and the reaction mixture stirred at 180° C. for 8 h. After completion of the reaction as indicated by TLC, the reaction mixture was poured into water (150 mL) and extracted with ether (3×150 mL). The combined organic layer was washed with brine, dried over Na$_2$SO$_4$ and evaporated under vacuum to give 3,4-dichlorothiophene (1.6 g, 84.92%). $^1$H NMR (400 MHz, DMSO) δ 7.27 (s, 1H), 7.22 (s, 1H).

Step-2: To a stirred solution of 3,4-dichlorothiophene (1.6 g, 10 mmol) in THF (20 mL) was added n-BuLi (8 mL, 12.6 mmol, 2M in THF) at -78° C. and stirred for 1 h. SO$_2$ gas was then purged through the reaction mixture at -78° C. for 1 h. NCS (1.3 g, 10 mmol) was added to the reaction mixture and stirred at room temperature for 2 h. After completion of the reaction as indicated by TLC, the reaction mixture was poured into water (200 mL) and extracted with ethyl acetate (3×150 mL). The combined organic layer was washed with brine, dried over Na$_2$SO$_4$ and evaporated under vacuum to give 3,4-dichlorothiophene-2-sulfonyl chloride. (1.5 g, 60%). The crude material was directly used in next step, without any purification.

Step-3: To a freshly prepared solution of sat. ammonia in THF (20 mL) was added freshly prepared 3,4-dichlorothiophene-2-sulfonyl chloride in THF at -78° C. and the reaction mixture was stirred for 1 h. After completion of the reaction as indicated by TLC, the reaction mixture was evaporated under vacuum. The crude was purified by silica gel column chromatography (ethyl acetate/hexane) to give 3,4-dichlorothiophene-2-sulfonamide as a light yellow solid (0.159 g, 8.36% over 2 steps). LCMS ESI (-ve)(m/z): 230.1 & 232.1 (M & M-2).

Synthesis of 2-methylthiophene-3-sulfonamide (Int-B-2.9

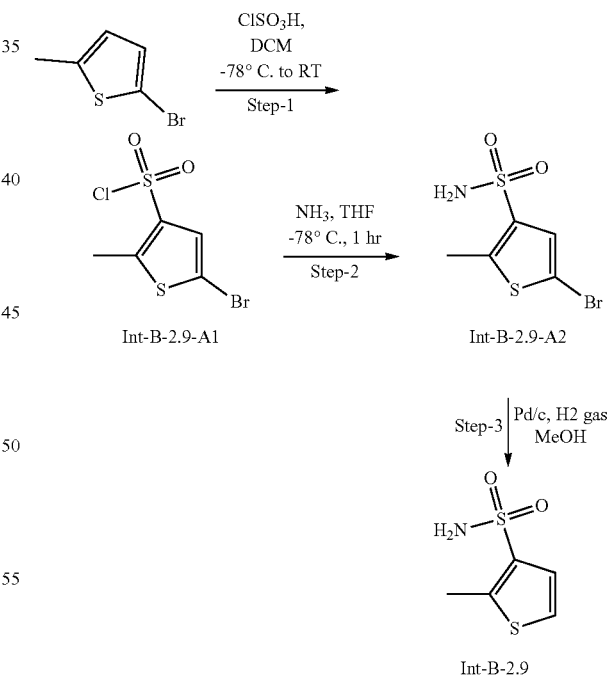

Step-1: To a solution of chlorosulphonic acid (12.1 mL, 181.8 mmol) in DCM was added 2-bromo-5-methylthiophene (5 g, 28.4 mmol) at -78° C. The reaction mixture was stirred at -78° C. for 15 min and then allowed to stir at room temperature for 1 h. After completion of the reaction as indicated by TLC, the reaction mixture was poured into water (200 mL) and extracted with DCM (3×100 mL). The combined organic layer was dried over Na₂SO₄ and evaporated under vacuum. The crude was used for next step directly.

Step-2: Ammonia gas was purged in THF (40 mL) at −78° C. A solution of 5-bromo-2-methylthiophene-3-sulfonyl chloride (7.7 g, 28.2 mmol) in THF (10 mL) was added to a freshly prepared ammonia in THF at −78° C. The reaction mixture was stirred for an additional 30 min. After completion of the reaction as indicated by TLC, the reaction mixture was evaporated under vacuum to give 5-bromo-2-methylthiophene-3-sulfonamide (5 g, 70%). LCMS ESI (m/z): 254.12 & 256.13 (M & M+2).

Step-3: To a suspension of 10% Pd/C (2 g) in methanol (20 mL) was added a solution of Int-B-2.9-A2 (2 g, 7.81 mmol, 1 eq) in Methanol (10 mL) at room temperature. The H₂ gas was purged through the reaction mixture for 2 h. After completion of the reaction, monitored by TLC (mobile phase: 30% ethyl acetate in Hexane). The reaction mixture was filtered with using celite and the filtrate concentrated under reduced pressure. The crude was purified using a silica column (60×120 mesh silica-elution with 15% ethyl acetate in Hexane) to obtain Int-B-2.9 (1.2 g, 92%) as a yellow solid. LCMS ESI (−ve) (m/z): 176.01 (M−H).

Synthesis of 2-chlorothiophene-3-sulfonamide
(Int-B-2.10

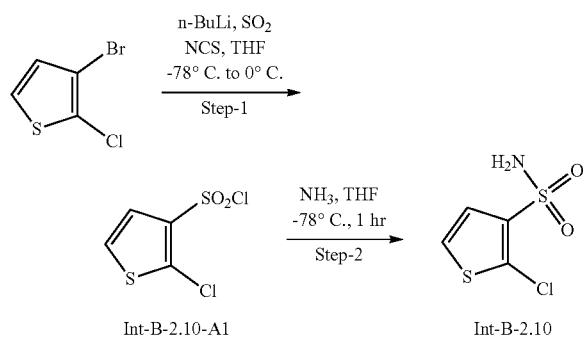

Step-1: To a stirred solution of 3-bromo-2-chlorothiophene (1 g, 5 mmol) in THF (10 mL) was added n-BuLi (4.1 mL, 6.5 mmol, 1.6 M) at −78° C. and stirred for 45 min at the same temperature. The SO₂ gas was passed through the reaction mixture for 1 h, at the same temperature. NCS (0.67 g, 5 mmol) was the added to the reaction mixture and allowed to stir at 0° C. for 2 h. After completion of the reaction as indicated by TLC, the reaction mixture was poured into water and extracted with ethyl acetate. The combined organic layer was washed with brine, dried over Na₂SO₄ and evaporated under vacuum to give crude product (1.31 g, 100%). It was used immediately for the next step without analysis.

Step-2: To a solution of 2-chlorothiophene-3-sulfonyl chloride (1.31 g, 6 mmol) in THF (10 mL) was added a freshly prepared saturated ammonia solution in THF (13 mL) at −78° C. The solid precipitated out and was evaporated to dryness and the crude purified by reverse phase column chromatography (ACN/Water) to obtain the title compound, Int-B-2.10 (0.302 g, 25.32%). ¹H-NMR (400 MHz, DMSO-d₆) δ: 7.83 (bs, 2H), 7.43 (d, J=4.0, 1H), 7.22 (d, J=4.0, 1H).

Synthesis of 4-cyanothiophene-3-sulfonamide
(Int-B-2.11

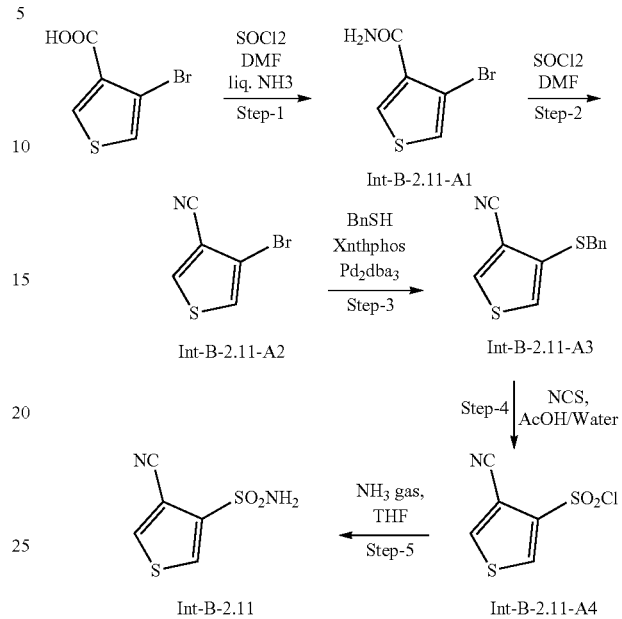

Step-1: To a solution of 4-bromothiophene-3-carboxylic acid (5 g, 24.1 mmol) in THF (50 mL) was added SOCl₂ (3.5 mL, 48.2 mmol) and a catalytic amount of DMF at 0° C. and the reaction stirred for 1 h. The reaction mixture was then poured into liq. ammonia solution (50 mL) at 10° C. The reaction mixture was allowed to stir room temperature for 1 h. After completion of the reaction as indicated by TLC, the reaction mixture was poured into water (200 mL) and extracted with ethyl acetate (3×100 mL). The combined organic layer was dried over Na₂SO₄ and evaporated under vacuum to give 4-bromothiophene-3-carboxamide (2.6 g, 53%). LCMS ESI (m/z): 206.1 & 208.0 (M & M+2).

Step-2: To a solution of 4-bromothiophene-3-carboxamide (0.4 g, 1.94 mmol) in DMF (5 mL) was added SOCl₂ (0.28 mL, 3.88 mmol) at 0° C. and allowed to stir at the same temperature for 4 h. After completion of the reaction as indicated by TLC, the reaction mixture was poured into water (30 mL) and extracted with ethyl acetate (3×30 mL). The combined organic layer was dried over Na₂SO₄ and evaporated under vacuum to give 4-bromothiophene-3-carbonitrile (0.25 g, 68%). ¹H NMR (400 MHz, DMSO) δ 8.72 (d, J=3.2 Hz, 1H), 8.00 (d, J=3.2 Hz, 1H).

Step-3: To a degassed solution of 4-bromothiophene-3-carbonitrile (0.25 g, 1.32 mmol) in dioxane (25 mL) was added benzyl mercaptan (0.19 mL, 1.59 mmol) and DIPEA (0.46 mL, 2.65 mmol), Xantphos (0.077 g, 0.13 mmol) and Pd₂(dba)₃ (0.12 g, 0.13 mmol). The reaction mixture was heated at 100° C. for 16 h. After completion of the reaction as indicated by TLC, the reaction mixture was poured into water and extracted with ethyl acetate (3×30 mL). The combined organic layer was dried over Na₂SO₄ and evaporated under vacuum. The crude was purified by silica gel column chromatography (ethyl acetate/hexane) to 4-(benzylthio)thiophene-3-carbonitrile (0.15 g, 48.8%). LCMS ESI (m/z): 249.2 (M+18).

Step-4: To a stirred solution of 4-(benzylthio)thiophene-3-carbonitrile (0.1 g, 0.43 mmol) in acetic acid (0.9 mL) and water (0.1 mL) was added N-chlorosuccinimide (0.23 g, 1.72 mmol) and stirred for 1 h at room temperature. After completion of the reaction as indicated by TLC, the reaction mixture was poured into water and extracted with ethyl acetate. The combined organic layer was dried over Na$_2$SO$_4$ and evaporated under vacuum. The crude was directly used for next step.

Step-5: To a freshly prepared sat. ammonia solution in THF (30 mL) was added a solution of 4-cyanothiophene-3-sulfonyl chloride (1.2 g, 5.78 mmol) in THF (20 mL) at −78° C. The reaction mixture was stirred for an additional 30 min. After completion of the reaction as indicated by TLC, the reaction mixture was evaporated under vacuum. The crude was purified by silica gel column chromatography (ethyl acetate/hexane) to give the 5-cyanothiophene-3-sulfonamide (0.54 g, 54%).

Synthesis of 5-chlorothiophene-3-sulfonamide (Int-B-2.12

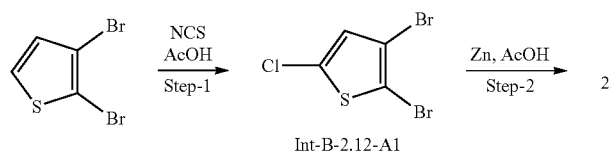

succinimide (5.84 g, 43.81 mmol) portion wise and the reaction mixture refluxed for 3 h. After completion of the reaction as indicated by TLC, the reaction mixture was poured into water (500 mL) and extracted with ethyl acetate (500 mL). The organic layer was washed with dilute NaOH solution (3×500 mL), brine (500 mL) and dried over Na$_2$SO$_4$ and evaporated under vacuum to give Int-B-2.12-A1 (10.1 g, 88%). $^1$H NMR (400 MHz, CDCl3) δ 6.80 (s, 1H).

Step-2: To the suspension of 2,3-dibromo-5-chlorothiophene (7.2 g, 26.05 mmol) in acetic acid (80 mL) was added Zn dust (17 g, 260.51 mmol) and the reaction mixture was heated at 100° C. for 16 h. After 16 h the reaction mixture was filtered through celite and the filtrate partitioned between water (300 mL) and ethyl acetate (300 mL). The organic layer was washed with saturated solution of sodium bicarbonate (5×300 mL), dried over Na$_2$SO$_4$ and evaporated under vacuum to give Int-B-2.12-A2 (4.5 g, 82%). $^1$H NMR (400 MHz, CDCl3) δ 7.05 (d, J=1.6 Hz, 1H) 6.88 (d, J=1.6 Hz, 1H).

Step-3: Reaction performed using a similar reaction procedure described for Int-B-2.4 to give 5-chlorothiophene-3-sulfonamide, Int-B-2.12. LCMS ESI (m/z): 198.1 (M+H).

Synthesis of 3,4-difluorothiophene-2-sulfonamide (Int-B-2.13

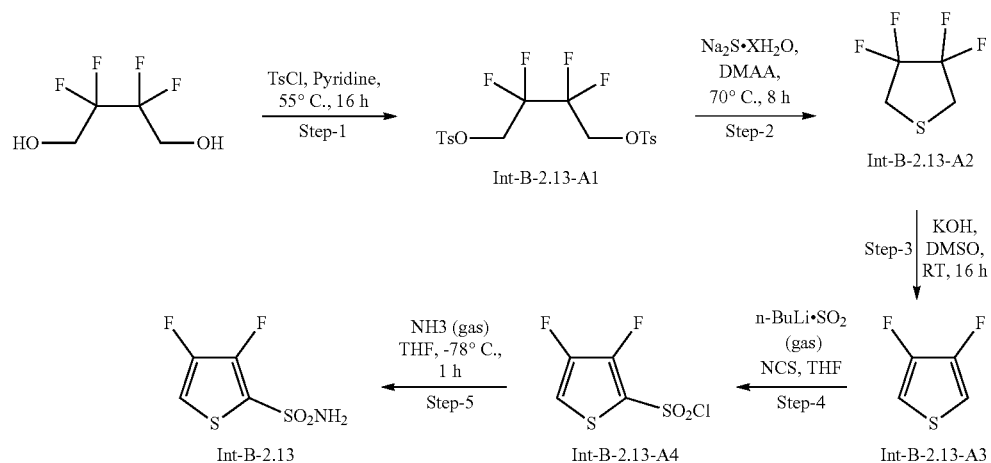

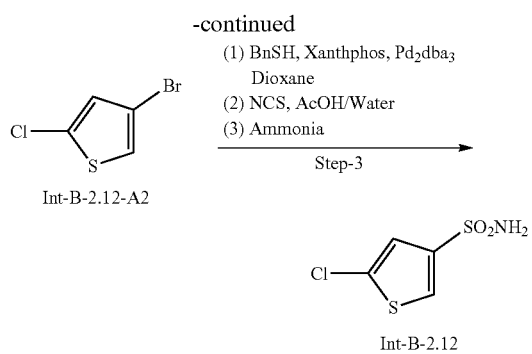

Step-1: To a solution of 2,2,3,3-tetrafluorobutane-1,4-diol (20 g, 123 mmol) in pyridine (120 mL), tosyl chloride (70.5 g, 370 mmol) was added at 0° C. The reaction mixture was heated at 55° C. for 16 h. After completion of the reaction as indicated by TLC, the reaction mixture was poured into cold water (1000 mL) and the solid fell out. It was dissolved in DCM (1000 mL) and washed with of 5% H2SO4 solution (2×200 mL). The organic layer was dried over Na$_2$SO$_4$ and evaporated under vacuum to give 2,2,3,3-tetrafluorobutane-1,4-diyl bis(4-methylbenzenesulfonate) (56 g, 96%). LCMS ESI (m/z): 471.5 (M+H).

Step-2: To a solution of 2,2,3,3-tetrafluorobutane-1,4-diyl bis(4-methylbenzenesulfonate) (56 g, 119 mmol) in N,N-Dimethylacetamide (260 mL), Na$_2$S·H$_2$O (56 g, 718 mmol) was added and the reaction mixture was heated at 70° C. for 8 h. After completion of the reaction, the reaction mixture was distilled at 70° C. at 20-25 mbar and the product collected at −78° C. (6 g, 31.4%). The isolated material was directly used in next step.

Step-3: To a solution of 3,3,4,4-tetrafluorotetrahydrothiophene (6 g, 38 mmol) in DMSO (60 mL) was added KOH (10.5 g, 187 mmol) at room temperature. The reaction mixture was stirred at room temperature for 16 h. After 16 h, the reaction mixture was subjected to downward distillation (Bath temperature: 70° C., vacuum: 24 mbar) and the product collected in a receiver at −78° C. vacuum to give 3,4-difluorothiophene (3.5 g, 78.7%). The isolated material was directly used in next step.

Step-4: To a stirred solution of 3,4-difluorothiophene (3.5 g, 29.1 mmol) in THF (35 mL) was added n-BuLi (36 mL, 58 mmol, 1.6 M in THF) at −78° C. and stirred for 1 h. $SO_2$ gas was purged through the reaction mixture at −78° C. for 1 h. NCS (5.8 g, 43 mmol) was then added to the reaction mixture and allowed to stir at room temperature for 2 h. After completion of the reaction as indicated by TLC, the reaction mixture was poured into water (200 mL) and extracted with ethyl acetate (3×150 mL). The combined organic layer was washed with brine, dried over $Na_2SO_4$ and evaporated under vacuum to give 3,4-difluorothiophene-2-sulfonyl chloride (6.8 g, Quantitative). The crude material was directly used in next step, without any purification.

Step-5: To a freshly prepared sat. ammonia solution of in THF (20 mL) was added solution of 3,4-difluorothiophene-2-sulfonyl chloride (6.8 g) in THF (20 mL) at −78° C. and reaction mixture was stirred for 1 h. After completion of the reaction as indicated by TLC, the reaction mixture was evaporated under vacuum. The crude was purified by silica gel column chromatography (22%, ethyl acetate/hexane) to give 3,4-difluorothiophene-2-sulfonamide as a white solid (1.6 g, 27.5% over 2 steps). LCMS ESI (−ve) (m/z): 198.3 (M−1).

Synthesis of 3,4-dimethylthiophene-2-sulfonamide
(Int-B-2.14

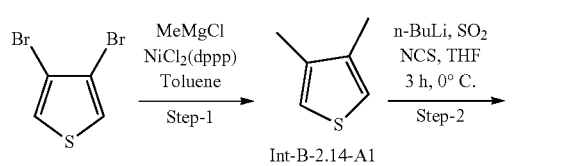

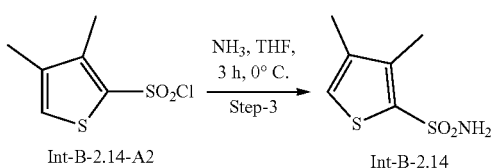

Step-1: To a stirred solution of 3,4-dibromothiophene (5 g, 20.66 mmol) in THF (10 mL) was added $NiCl_2$(dppf) (0.112 g, 20.66 mmol) at room temperature. MeMgBr (20 mL, 61.98 mmol) was added to the reaction mixture and stirred at 50° C. for 12 h. After completion of the reaction as indicated by TLC, the reaction mixture was poured into water (200 mL) and extracted with diethyl ether (3×100 mL). The combined organic layer was dried over $Na_2SO_4$ and evaporated under vacuum to give the crude of 3,4-dimethyl thiophene as brown liquid (2.1 g, 90.75%). The isolated material was used in next step without purification.

Step-2: To a stirred solution of 3,4-dimethyl thiophene (1.8 g, 16.07 mmol) in THF (10 mL), was added 1.6M n-BuLi (21 mL, 32.14 mmol) at −78° C. and stirred for 1 h. NCS (3.5 g, 24.10 mmol) was added to the reaction mixture and stirred for 30 min. After completion of the reaction as indicated by TLC, the reaction mixture was poured into water (200 mL) and extracted with ethyl acetate (3×100 mL). The combined organic layer was dried over $Na_2SO_4$ and evaporated under vacuum to give 3,4-dimethylthiophene-2-sulfonyl chloride as a yellow liquid (1.9 g, 56.03%). The isolated material was used in next step without purification.

Step-3: To a freshly prepared sat. ammonia solution in THF (20 mL) was added a solution of 3,4-dimethylthiophene-2-sulfonyl chloride (1.9 g, 16.07 mmol) in THF (10 mL) at −78° C. The reaction mixture was stirred for 1 h. After completion of the reaction as indicated by TLC, the reaction mixture was poured into water (100 mL) and extracted with ethyl acetate (3×50 mL). The combined organic layer was dried over $Na_2SO_4$ and evaporated under vacuum. The crude was purified by column chromatography (22% EtOAc:Hexane) to give 3,4-dimethylthiophene-2-sulfonamide as a white solid (0.2 g, 11.57%). LCMS ESI (m/z): 192.21 (M+1).

Synthesis of 5-bromothiophene-2-sulfonamide
(Int-B-2.15

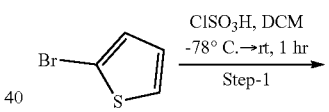

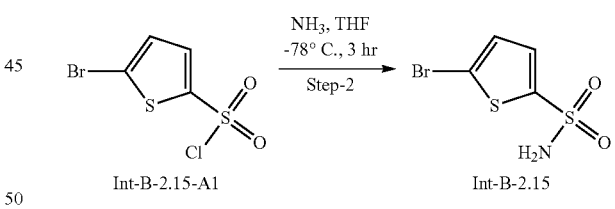

Step-1: To a solution of 2-bromothiophene (5.0 g, 30.566 mmol) in DCM (50 mL) was added chlorosulfuric acid (17.86 g, 153.34 mmol) at −78° C. and allowed to stir at room temperature for 1 h. After completion of the reaction as indicated by TLC, the reaction mixture was poured into water (200 mL) and extracted with DCM (2×200 mL). The combined organic layer was dried over $Na_2SO_4$ and evaporated under vacuum to give Int-B-2.15-A1 (6.2 g, 77.30%). It was used immediately for the next step without analysis.

Step-2: To solution of 3,5-dichlorothiophene-2-sulfonyl chloride (6.2 g, 23.70 mmol) in THF (10 mL), saturated ammonia solution in THF (60 mL) was added at −78° C. The solid precipitated out and evaporated to dryness and the crude triturated with pentane to obtain the title compound, Int-B-2.15 (4.4 g, 76.66%). LCMS ESI (−ve) (m/z): 240.0 (M−2).

Synthesis of 3-isopropylthiophene-2-sulfonamide (Int-B-2.16

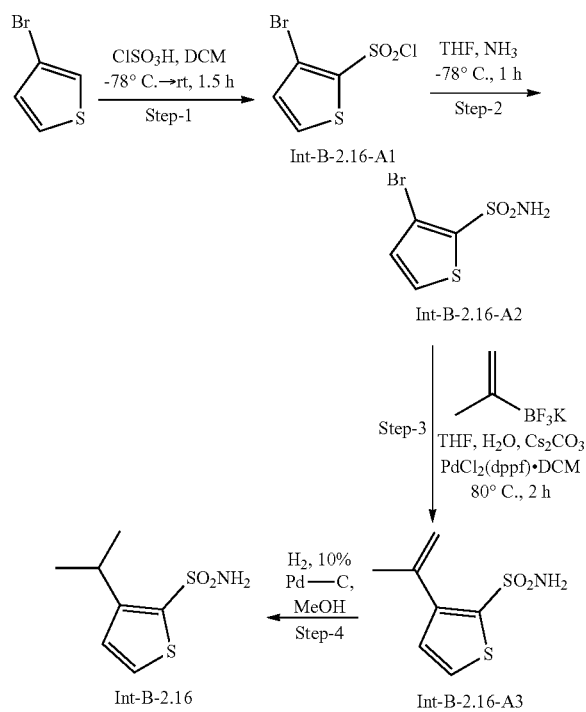

Step-1: To a stirred solution of ClSO$_3$H (10.7 g, 92.00 mmol) in DCM (20 mL) was added solution of 3-bromothiophene (3 g, 18.40 mmol) in DCM (10 mL) at −78° C. and stirred for 15 min at −78° C. and then allowed to stir at room temperature for 1 h. After completion of the reaction as indicated by TLC, the reaction mixture was poured into cold water and extracted with dichloromethane. The combined organic layer was washed with brine, dried over Na$_2$SO$_4$ and evaporated under vacuum to give crude product. The crude product was directly used in next step.

Step-2: To a freshly prepared saturated ammonia in THF (30 mL), 3-bromothiophene 2-sulfonyl chloride (10 mL) in THF (10 mL) was added at −78° C. The reaction mixture was stirred at the same temperature for additional 1 h. After completion of the reaction as indicated by TLC, the reaction mixture was evaporated under vacuum to give crude product. The crude product was purified by silica gel column chromatography (ethyl acetate/hexane: 5:5) to give 3-bromothiophene-2-sulfonamide as a white solid (1.5 g, 54.01%). (1.5 g, 33.66% over 2 steps). $^1$H NMR (400 MHz, DMSO) δ 7.90 (s, 2H), 7.86 (d, J=5.2 Hz, 1H), 7.24 (d, J=5.2 Hz, 1H).

Step-3: To a degassed solution of 3-bromothiophene-2-sulfonamide (2.0 g, 8.26 mmol), Potassium trifluoro(prop-1-en-2-yl)borate (1.83 g, 12.39 mmol), Cs$_2$CO$_3$ (8.07 g, 24.79 mmol) and Pd$_2$(dppf)Cl$_2$.DCM complex (1.01 g, 1.23 mmol) were added in THF:H$_2$O (56 mL: 10.4 mL) and stirred at 80° C. for 2 h. After completion of the reaction as indicated by TLC, the reaction mixture was poured into cold water and extracted with ethyl acetate. The combined organic layer was washed with brine, dried over Na$_2$SO$_4$ and evaporated under vacuum to give crude product. The crude product was purified by silica gel column chromatography (25% ethyl acetate/hexane) to give 3-(prop-1-en-2-yl) thiophene-2-sulfonamide as a white solid (1.4 g, 83.40%). LCMS ESI (m/z): 204.24 (M+H). $^1$H NMR (400 MHz, DMSO d6) δ: 7.71 (d, J=5.2 Hz, 1H), 7.61 (s, 2H), 7.08 (d, J=5.2 Hz, 1H), 5.24 (d, J=20 Hz, 2H), 2.05 (s, 3H).

Step-4: To a stirred solution of 3-(prop-1-en-2-yl) thiophene-2-sulfonamide (1.2 g, 5.90 mmol) in MeOH (30 mL), 10% Pd—C(2.4 gm) was added and purged with H$_2$ gas for 2 h. The reaction mixture was filtered through a celite bed and the filtrate evaporated under vacuum to give the crude. The crude was purified by silica gel column chromatography (ethyl acetate/hexane: 1.8:8.2) to give 3-isopropylthiophene-2-sulfonamide as a white solid (0.5 g, 41.26%). LCMS ESI (−ve) (m/z): 204.1 (M−1).

Synthesis of 2-((2,4-dimethoxybenzyl)oxy)benzenesulfonamide (Int-B-2.17

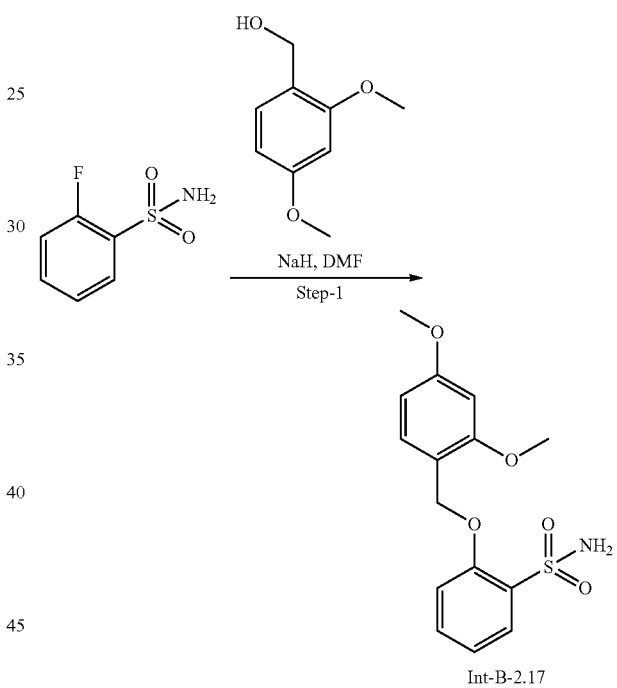

To a suspension of NaH (0.456 g, 1.14 mmol) in DMF (5 mL) was added 2-fluorobenzenesulfonamide (0.5 g, 2.85 mmol) and (2,4-dimethoxyphenyl)methanol (0.480 g, 2.85 mmol) and the reaction mixture was heated at 120° C. for 16 h. After completion of the reaction as indicated by TLC, the reaction mixture was poured into water (50 mL) and extracted with ethyl acetate (3×50 mL). The combined organic layer was washed with brine, dried over Na$_2$SO$_4$ and evaporated under vacuum. The crude product subjected to silica gel column chromatography to give the title compound, Int-B-2.17 (0.4 g, 43.34%).

$^1$H NMR (400 MHz, DMSO) δ 7.74 (d, J=7.6 Hz, 1H), 7.57-7.52 (m, 1H), 7.41 (d, J=8.4 Hz, 1H), 7.27 (d, J=8.4 Hz, 1H), 7.08-7.04 (m, 1H), 6.84 (s, 2H), 6.64 (s, 1H), 6.55-6.53 (dd, J=8.2 Hz, J=1.8 Hz, 1H), 5.21 (s, 2H), 3.82 (s, 3H), 3.77 (s, 3H).

Synthesis of 3-ethylthiophene-2-sulfonamide (Int-B-2.21

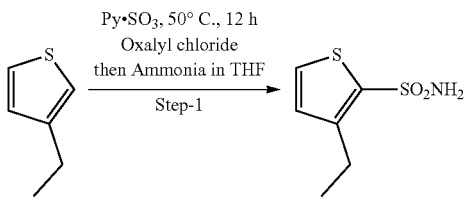

To a stirred solution of 3-ethylthiophene (3 g, 26.7 mmol) in acetonitrile (4 mL) was added sulfur trioxide pyridine complex (5.5 g, 34.7 mmol) at room temperature. The reaction mixture was stirred for at 50° C. for 12 h. The reaction mixture was cooled to 0° C. and ethyl acetate added to the reaction mixture and stirred for 2 h. The solid was filtered.

The solid was suspended in DME (20 mL) and DMF (2.1 mL) followed by the addition of (COCl)$_2$ (4.93 g, 38.8 mmol) at 0° C. The reaction mixture was stirred at 0° C. for 1.5 h. Ammonia solution (15 mL) was added to the reaction mixture and allowed to stir at 0° C. for 20 min. After completion of the reaction as indicated by TLC, the reaction mixture was poured into water (200 mL) and extracted with ethyl acetate (3×100 mL). The combined organic layer was washed with brine, dried over Na$_2$SO$_4$ and evaporated under vacuum.

The crude was purified by silica gel column chromatography (20% ethyl acetate/hexane) to give 3-ethylthiophene-2-sulfonamide as a solid (1.4 g, 28.27%). LCMS ESI (−ve) (m/z): 190.0 (M−H).

Synthesis of 3,5-dichlorothiophene-2-sulfonamide (Int-B-2.22

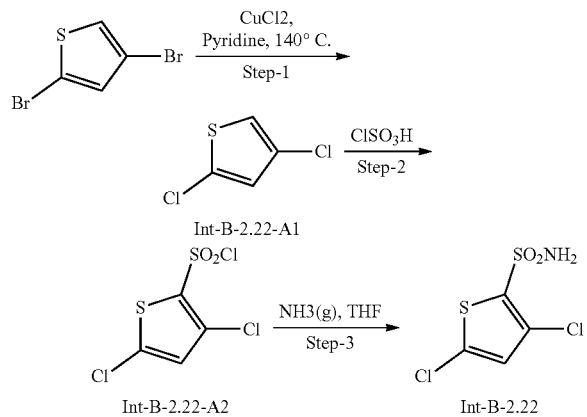

Step-1: The reaction was carried out in three divided batches of 3 g each. To a solution of 2,4-dibromothiophene (9.0 g, 37.2 mmol) in pyridine (30 mL) was added copper(I) chloride (11.1 g, 41.22 mmol) and the mixture allowed to stir at 140° C. overnight. After completion of the reaction as indicated by TLC, the reaction mixture was poured with water (250 mL) and extracted with diethyl ether (2×300 mL). The combined organic layer was dried over Na$_2$SO$_4$ and concentrated under vacuum (5.9 g, Quantitative).

Step-2: Chlorosulfuric acid (22.46 g, 192.78 mmol) was added drop-wise to a stirring solution of 2,4-dichlorothiophene (5.9 g, 38.56 mmol) in DCM (100 mL) at −78° C. and allowed to stir at room temperature for 1 h. After completion of the reaction as indicated by TLC, the reaction mixture was poured into water (200 mL) and extracted with DCM (2×200 mL). The combined organic layer was dried over Na$_2$SO$_4$ and evaporated under vacuum. It was forwarded for net step immediately.

Step-3: A solution of 3,5-dichlorothiophene-2-sulfonyl chloride (9.7 g, 38.56 mmol) in THF was added to a stirred saturated ammonia solution (50 mL) at −78° C. The solid precipitated out and evaporated to dryness and the crude purified by silica gel column chromatography to obtain the title compound, Int-B-2.22 (0.8 g, 08.93%, over three steps)

Synthesis of 4-methylthiophene-2-sulfonamide (Int-B-2.23

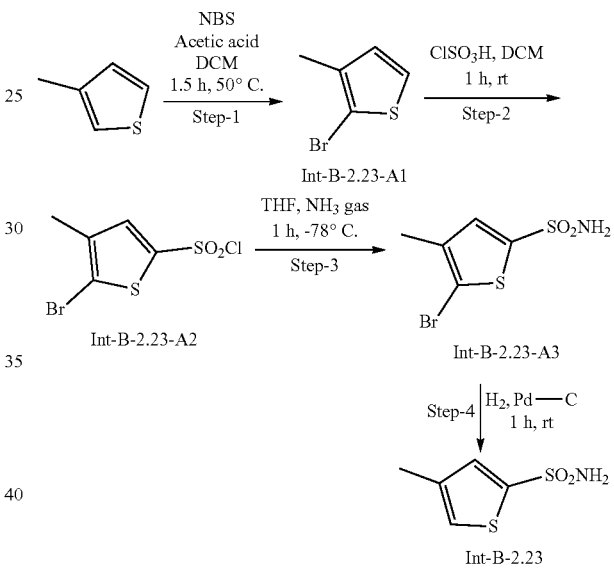

Step-1: To a stirred solution of 3-methylthiophene (1.0 g, 10.18 mmol) in acetic acid (10 mL) and DCM (10 mL) was added NBS (1.9 g, 10.69 mmol) at room temperature and allowed to stir at 50° C. for 1.5 h. After completion of the reaction as indicated by TLC, the reaction mixture was poured into cold water (100 mL) and extracted with ethyl acetate (3×50 mL). The combined organic layer was washed with brine and 1M NaOH solution, dried over Na$_2$SO$_4$ and evaporated under vacuum to give crude product. The crude product was directly used in next step.

Step-2-3: Reaction performed using a similar reaction procedure described for Int-B-2.15 to give 5-bromo-4-methylthiophene-2-sulfonamide. LCMS ESI (m/z): LCMS ESI (−ve) (m/z): 254.0 (M−H)

Step-4: To a suspension of 10% Pd/C (1 g, W/W) in methanol (10 mL) was added 5-bromo-4-methylthiophene-2-sulfonamide (0.9 g, 3.5 mmol) at room temperature. The H$_2$ gas was purged through the reaction mixture for 2 h. After completion of the reaction as indicated by TLC, the reaction mixture was filtered through celite bed. The filtrate was concentrated under vacuum to get 4-methylthiophene-2-sulfonamide as a solid. LCMS ESI (−ve) (m/z): 176.0 (M−H).

Synthesis of 4-chlorothiophene-2-sulfonamide (Int-B-2.24

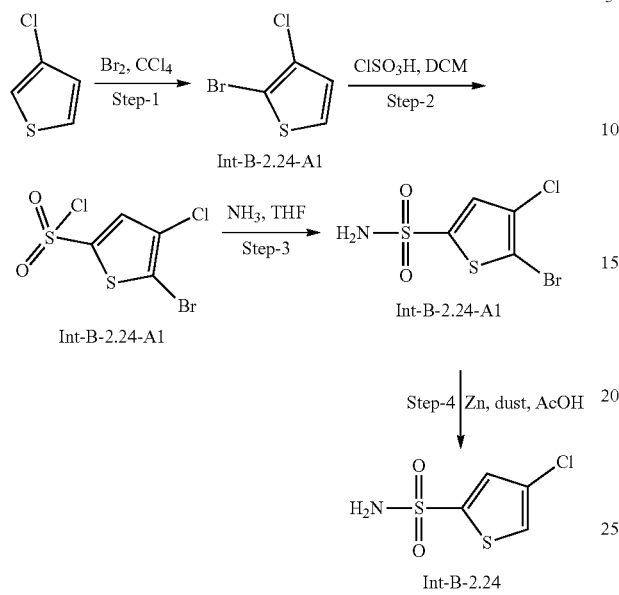

Step-1: To a solution of 3-chlorothiophene (10 g, 84.7 mmol) in CCl₄ was added a bromine solution (4.3 mL, 84.7 mmol) at 0° C. The reaction was allowed to stir at room temperature for 12 h. After completion of the reaction, the reaction mixture was poured into water and extracted with DCM. The combined organic layer was dried over Na$_2$SO$_4$ and evaporated under vacuum. The crude was used for next step directly.

Step-2: To a solution of chlorosulphonic acid (34 mL, 508.4 mmol) in DCM was added a solution of 2-bromo-3-chlorothiophene (16.7 g, 84.7 mmol) in DCM (20 mL) at −78° C. The reaction was allowed to stir at −78° C. for 15 min and then at room temperature for 1 h. After completion of the reaction, the reaction mixture was poured into water and extracted with DCM. The combined organic layer was dried over Na$_2$SO$_4$ and evaporated under vacuum. The crude was used for next step without further purification.

Step-3: A solution of 5-bromo-2-methylthiophene-3-sulfonyl chloride (25 g, 84.7 mmol) in THF (30 mL) was added to a saturated ammonia solution in (100 L) at −78° C. The reaction mixture was stirred for additional 30 min. After completion of the reaction as indicated by TLC, the reaction mixture was evaporated under vacuum to give mixture of 5-bromo-4-chlorothiophene-2-sulfonamide and 5-bromo-3-chlorothiophene-2-sulfonamide. After completion of the reaction, the reaction mixture was evaporated under vacuum and crude was used for next step directly. LCMS ES (−ve) (m/z): 274.03 & 276.1 (M & M−2).

Step-4: To a solution of mixture 5-bromo-4-chlorothiophene-2-sulfonamide and 5-bromo-3-chlorothiophene-2-sulfonamide (17.5 g, 63.2 mmol) in acetic acid was added Zinc dust (20.6 g, 316.0 mmol) and stirred at 100° C. for 12 h. After completion of the reaction, the reaction mixture was poured into water and extracted with ethyl acetate. The combined organic layer was dried over Na$_2$SO$_4$ and evaporated under vacuum to give the crude material that contains mixture of isomers 4-chlorothiophene-2-sulfonamide and 3-chlorothiophene-2-sulfonamide which was purified by normal phase flash chromatography using Hexane:Ethyl acetate (8:2) to generate the 4-chlorothiophene-2-sulfonamide as pale yellow solid. (1.5 g, 9.37%). $^1$H NMR (400 MHz, DMSO) δ 7.89-7.89 (d, J=1.6 Hz, 1H), 7.83 (s, 2H), 7.53-7.53 (d, J=1.2 Hz, 1H).

Synthesis of 4-(difluoromethyl)thiazole-2-sulfonamide (Int-B-2.25

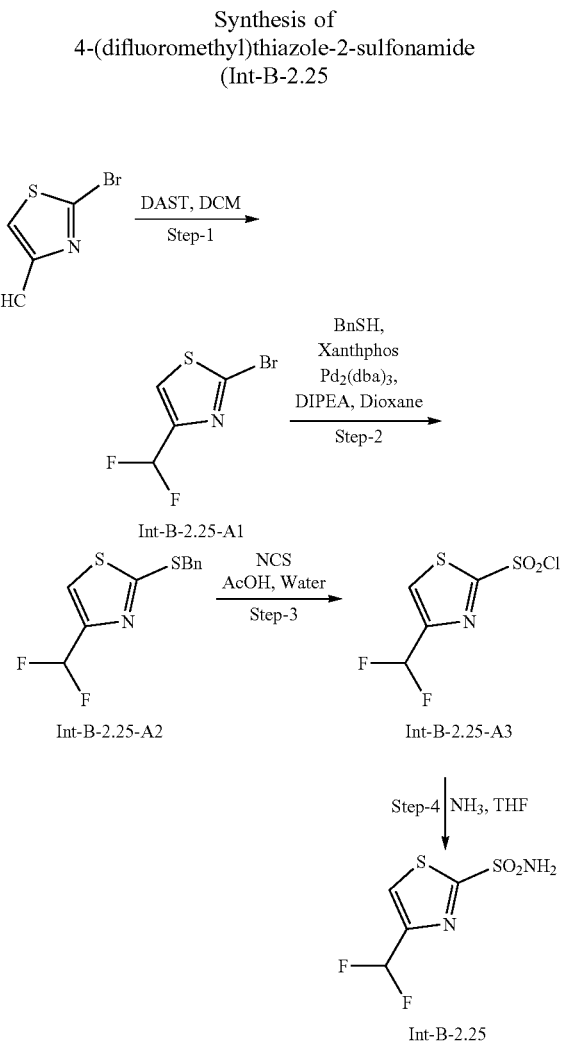

Step-1: To a cooled solution of 2-bromothiazole-4-carbaldehyde (5 g, 26.03 mmol) in DCM (50 mL), DAST (6.29 g, 39.05 mmol) was added and allowed to stir at room temperature for 1 h. The reaction mixture was quenched with ice water and extracted with DCM (2×150 mL). The combined organic layer was dried over Na$_2$SO$_4$ and concentrated under vacuum. The crude was purified by silica gel column chromatography to obtain Int-B-2.25-A1 (2.6 g, 46.65%). $^1$H NMR (400 MHz, DMSO-d$_6$) δ 8.19 (s, 1H), 7.08 (t, J=54 Hz, 1H)

Step-2: To a degassed solution of 2-bromo-4-(difluoromethyl)thiazole (2.6 g, 12.14 mmol) and DIPEA (3.14 g, 24.29 mmol) in dioxane (26 mL), Xantphos (0.702 g, 1.21 mmol), Pd$_2$dba$_3$ (0.556 g, 0.6 mmol) and benzyl mercaptan (1.5 g, 12.14 mmol) were added and the reaction mixture heated at 100° C. for 2 h. After completion of the reaction as indicated by TLC, the reaction mixture was filtered through celite and the filtrate poured into water and extracted with ethyl acetate (2×80 mL). The combined organic layer was washed with brine (2×150 mL), dried over Na$_2$SO$_4$ and evaporated under vacuum. The crude product was subjected to silica gel column chromatography to give Int-B-2.25-A2 (2.35 g, 75.18%). LCMS ESI (m/z): 258.38 (M+H).

Step-3: To a stirred solution of 2-(benzylthio)-4-(difluoromethyl)thiazole (2.35 g, 9.13 mmol) in acetic acid (47 mL) and water (4.7 mL), N-chlorosuccinimide (6.09 g, 45.66 mmol) was added in portions at room temperature and stirred for 2 h. After completion of the reaction as indicated by TLC, the reaction mixture was evaporated under vacuum to remove acetic acid then partitioned between water (100 mL) and ethyl acetate (100 mL). The organic layer was washed with water (100 mL), dried over $Na_2SO_4$ and evaporated under vacuum. The crude mixture was directly used for next step (3 g, quantitative)

Step-4: A THF (15 mL) solution of 4-(difluoromethyl)thiazole-2-sulfonyl chloride (3 g, 12.84 mmol) was added to a saturated ammonia solution in THF (20 mL) at −78° C. The solid precipitated out and evaporated to dryness and the crude purified by silica gel column chromatography to obtain the title compound, Int-B-2.25 (1.4 g, 50.90%) LCMS ESI (−ve) (m/z): 213.3 (M−H).

Synthesis of 4,5-dimethylthiazole-2-sulfonamide
(Int-B-2.26

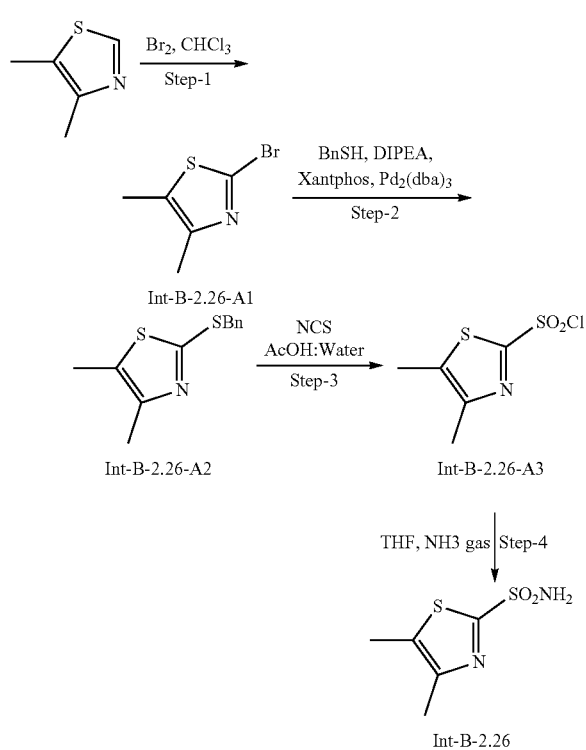

Step-1: To a solution of 4,5-dimethylthiazole (5.0 g, 44.17 mmol) in $CHCl_3$ (50 mL) was added bromine (21.17 g, 132.52 mmol) at 0° C. and allowed to stir at room temperature for 5 h. After completion of the reaction as indicated by TLC, the reaction mixture was poured into ice cold water (150 mL) and extracted with DCM (2×150 mL). The combined organic layer was washed with sat. sodiumthiosulfate solution (2×150 mL), dried over $Na_2SO_4$ and concentrated under vacuum. The crude was purified by silica gel column chromatography to obtain Int-B-2.26-A1 (5.0 g, 58.96%). LCMS ESI (m/z): 192.2 & 194.2 (M & M+2).

Step-2-4: Reaction performed using a similar reaction procedure as described for Int-B-2.25 to give 5-bromo-4-methylthiophene-2-sulfonamide. LCMS ESI (m/z): 193.3 (M+H)

Synthesis of 2-methylthiazole-4-sulfonamide
(Int-B-2.27

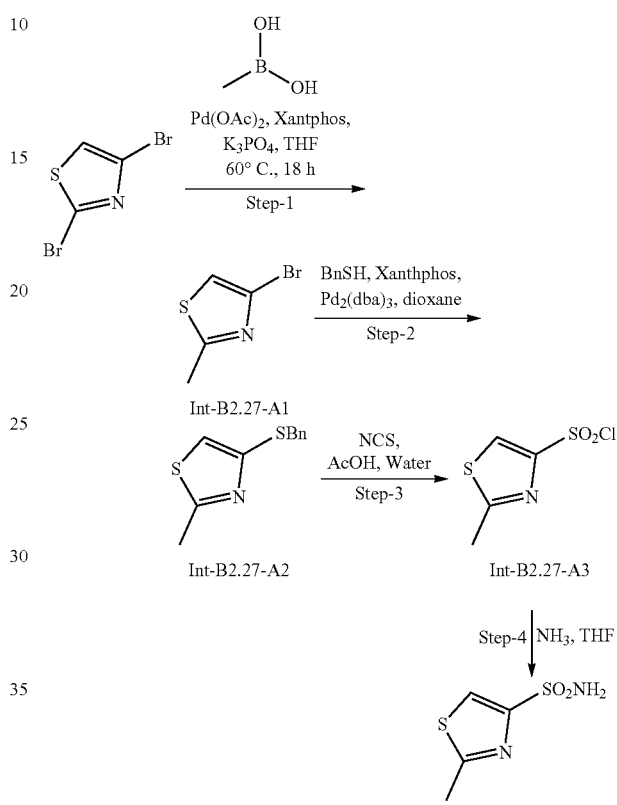

Step-1: To a solution of 2,4-dibromothiazole (8 g, 32.92 mmol) in THF (80 mL) was added potassium phosphate (20.98 g, 98.78 mmol) and methyl boronic acid (2.08 g, 34.90 mmol) and the mixture degassed for 30 min. After that $Pd(OAc)_3$ (0.02 g, 0.82 mmol) and Xanthphos (0.46 g, 0.82 mmol) was added to the reaction mixture and allowed to stir at 60° C. for 18 h. After completion of the reaction as indicated by TLC, the reaction mixture was filtered through celite and washed with DCM then evaporated under vacuum. (3.8 g, 64.80%). LCMS ESI (m/z): 178.2 & 180.2 (M & M+2)

Step-2-4: Reaction performed using a similar reaction procedure as described for Int-B-2.25 to give 2-methylthiazole-4-sulfonamide. LCMS ESI (m/z): 179.2 (M+H)

Synthesis of 4-phenylthiophene-3-sulfonamide
(Int-B-2.28

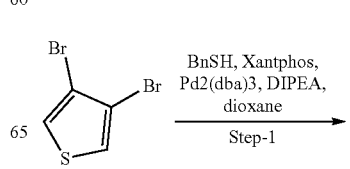

253

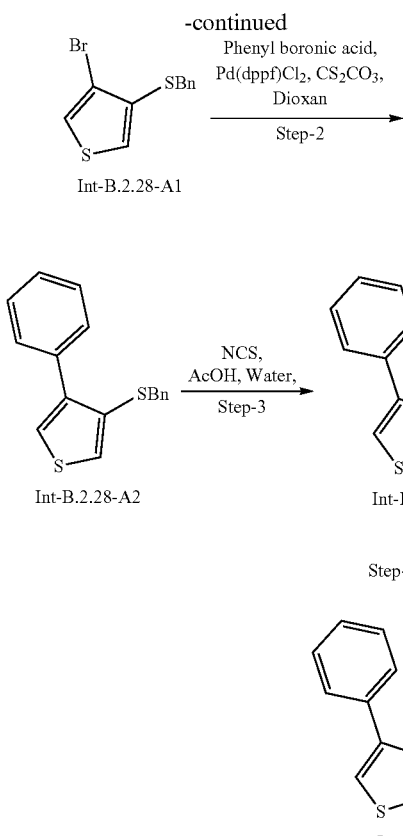

Int-B.2.28-A1

Int-B.2.28-A2

Int-B.2.28-A3

Int-B.2.28

Step-1: To a degassed solution of 3,4-dibromothiophene (5 g, 20.66 mmol) and DIPEA (7.1 mL, 41.33 mmol) in dioxane (50 mL) was added benzyl mercapton (2.5 g, 20.66 mmol), Xantphos (1.2 g, 2.06 mmol) and Pd$_2$(dba)$_3$ (0.94 g, 1.03 mmol) and the reaction mixture heated at 100° C. for 16 h. After completion of the reaction as indicated by TLC, the reaction mixture was poured into water (200 mL) and extracted with ethyl acetate (4×100 mL). The combined organic layer was washed with brine, dried over Na$_2$SO$_4$ and evaporated under vacuum. The crude mixture was purified by silica gel column chromatography to give Int-B-2.28-A1 (3 g, 84.88%). DMSO-d$_6$) δ: 7.80 (d, J=3.2 Hz, 1H), 7.44 (d, J=3.2 Hz, 1H), 7.32-7.23 (m, 5H), 4.17 (s, 2H).

Step-2: To a degassed solution of 3-(benzylthio)-4-bromothiophene (1 g, 35.08 mmol), phenyl boronic acid (0.64 g, 52.63 mmol) and Cs$_2$CO$_3$ (3.4 g, 10.52 mmol in dioxane (10 mL) was added Pd(dppf)Cl$_2$.DCM complex (0.28 g, 35.08 mmol)) and the reaction mixture heated at 100° C. for 2 h. After completion of the reaction as indicated by TLC, the reaction mixture was poured into water (100 mL) and extracted with ethyl acetate (2×100 mL). The combined organic layer was washed with brine, dried over Na$_2$SO$_4$ and evaporated under vacuum. The crude mixture was purified by silica gel column chromatography to give Int-B-2.28-A2 (0.9 g, 90.83%). $^1$H-NMR (400 MHz, DMSO-d$_6$) δ: 7.63 (d, J=4 Hz, 1H), 7.50-7.35 (m, 6H), 7.30-7.20 (m, 5H), 4.04 (s, 2H).

Step-3-4: Reaction performed using a similar reaction procedure as described for Int-B-2.25 to give 4-phenylthiophene-3-sulfonamide, Int-B.2.28. LCMS ESI (m/z): 179.2 (M+H)

254

Synthesis of thieno[3,2-b]pyridine-3-sulfonamide (Int-B-2.29

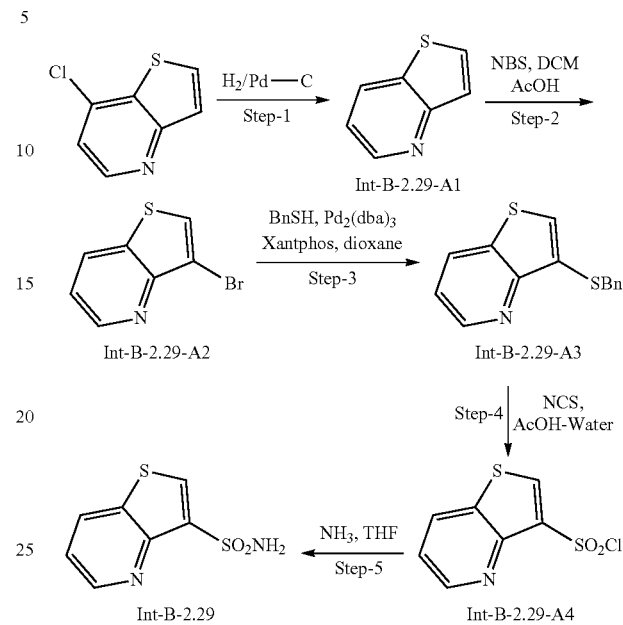

Int-B-2.29-A1

Int-B-2.29-A2

Int-B-2.29-A3

Int-B-2.29

Int-B-2.29-A4

Step-1: To a suspension of 10% Pd/C (5 g) in methanol (100 mL) was added 7-chlorothieno[3,2-b]pyridine (5 g, 29.47 mmol) at room temperature. H$_2$ gas was purged through the reaction mixture for 0.5 h. After completion of the reaction as indicated by TLC, the reaction mixture was filtered through celite bed. The filtrate was concentrated under vacuum to get thieno[3,2-b]pyridine as a solid. LCMS (m/z): 136.01 (M+H).

Step-2: To a stirred solution of thieno[3,2-b]pyridine (4.6 g, 34.04 mmol) in acetic acid (24 mL) and DCM (46 mL) was added NBS (9.09 g, 35.75 mmol) at room temperature and allowed to stir at 50° C. for 1.5 h. After completion of the reaction as indicated by TLC, the reaction mixture was poured into cold water and extracted with ethyl acetate. The combined organic layer was washed with brine and NaOH solution, dried over Na$_2$SO$_4$ and evaporated under vacuum to give crude product. The crude product was directly used in next step. $^1$H-NMR (400 MHz, DMSO-d$_6$) δ: 7.48-7.51 (m, 1H), 8.38 (s, 1H), 8.57-8.59 (d, J=8.4 Hz, 1H), 8.77-8.78 (d, J=4.4 Hz, 1H).

Step-3-4: Reaction were performed using similar reaction procedure described for Int-B-2.25 to give thieno[3,2-b]pyridine-3-sulfonamide. LCMS ESI (m/z): 215.3 (M+H)

Synthesis of 4-bromothiophene-2-sulfonamide (Int-B-2.30

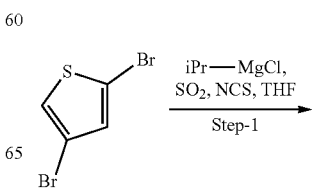

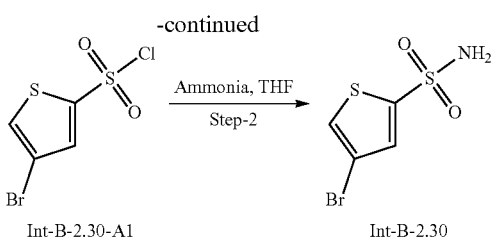

Step-1: To a stirred solution of 2,4-dibromothiophene (10 g, 41.322 mmol) in THF (100 mL), 2M iPrMgCl (23 mL, 45.454 mmol) was added at 0° C. and allowed to stir at room temperature for 1 h. The reaction mixture was cooled to −40° C. and purged with SO$_2$ gas at −40° C. for 30 min. The reaction mixture was cooled 0° C. and N-chlorosuccinimide (8.24 g, 61.983 mmol) added and stirred at room temperature for 1 h. After completion of the reaction as monitored by TLC (mobile phase: 100% ethyl acetate), the reaction mixture was quenched in 10% HCl (100 mL) and extracted by diethyl ether (2×100 mL) and the organic layer was dried over Na$_2$SO$_4$ and concentrated under reduced pressure to get Int-B-2.30-A1 (10 g, 92.50%) as a yellow liquid. The crude was used for next step without any further purification and without any analytical confirmation.

Step-2: Reaction performed using a similar reaction procedure as described for Int-B-2.6 to give 4-bromothiophene-2-sulfonamide, Int-B-2.30. LCMS ESI (−ve) (m/z): 242.2 & 240.2 (M & M−2).

Synthesis of 5-cyanothiophene-3-sulfonamide (Int-B-2.31

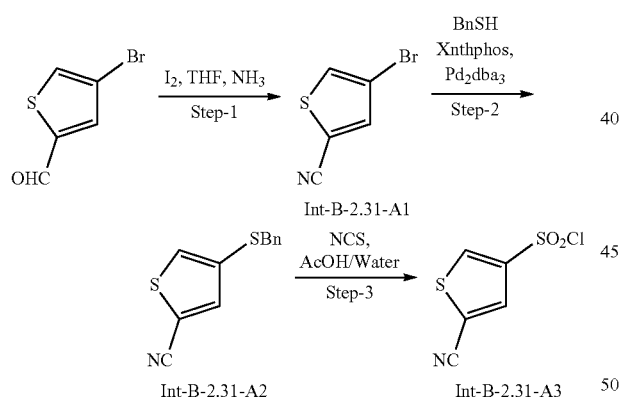

Step-1: To a solution of 4-bromothiophene-2-carbaldehyde (1 g, 26.1 mmol) in THF (10 mL) was added aqueous ammonia (100 mL) at 0° C. and stirred for 10 min. After that 12 (iodine) (9.9 g, 39.6 mmol) was added and the reaction mixture allowed to stir at room temperature for 12 h. The reaction mixture was poured into sat. solution of sodium thiosulphate and extracted with ethyl acetate (3×100 mL). The combined organic layer was dried over Na$_2$SO$_4$ and evaporated under vacuum. The crude was purified by column chromatography to give the 4-bromothiophene-2-carbonitrile. (0.65 g, 66.3%). $^1$H NMR (400 MHz, DMSO) δ 8.19 (s, 1H), 8.10 (s, 1H).

Step-2-4: Reaction performed using a similar reaction procedure as described for Int-B-2.25 to give 5-cyanothiophene-3-sulfonamide. LCMS ESI (−ve) (m/z): 187.0 (M−H).

Synthesis of 4-cyanothiophene-2-sulfonamide (Int-B-2.32

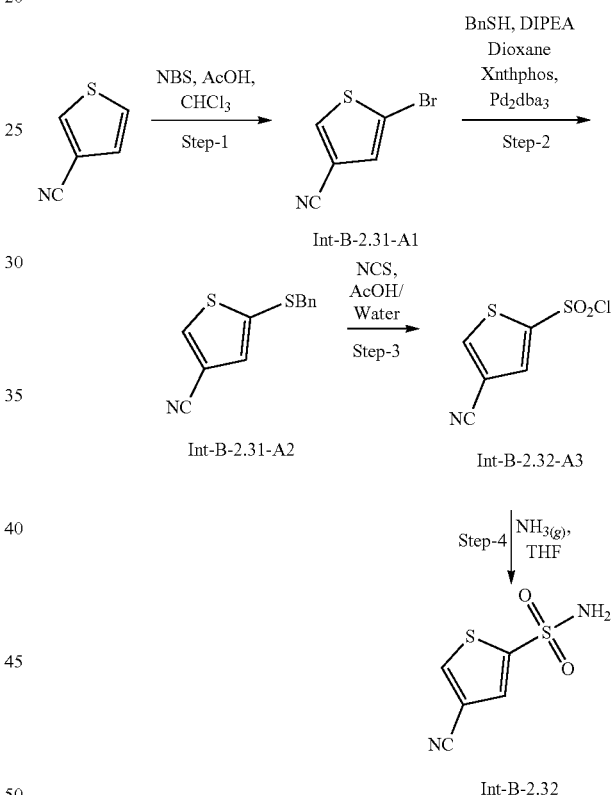

Step-1: To a solution of thiophene-3-carbonitrile (1 g, 9.16 mmol) in CHCl$_3$ (10 mL) and acetic acid (5 mL), N-bromosuccinimide (2.52 g, 13.74 mmol) was added portion-wise and the mixture allowed to stir at 70° C. overnight. The reaction mixture was quenched with water and extracted with DCM (2×50 mL). The combined organic layer was washed with dil. NaOH solution (3×100 mL), dried over Na$_2$SO$_4$ and concentrated under vacuum. The crude was purified by silica gel column chromatography to obtain Int-B-2.32-A1 (0.540 g, 31.34%). $^1$H NMR (400 MHz, DMSO-d$_6$) δ 8.58 (s, 1H), 7.72 (s, 1H).

Step-2-4: Reaction performed using a similar reaction procedure as described for Int-B-2.25 to give 4-cyanothiophene-2-sulfonamide, Int-B-2.32. LCMS ESI (−ve) (m/z): 186.9 (M−H)

Synthesis of 4-methylthiophene-3-sulfonamide (Int-B-2.33)

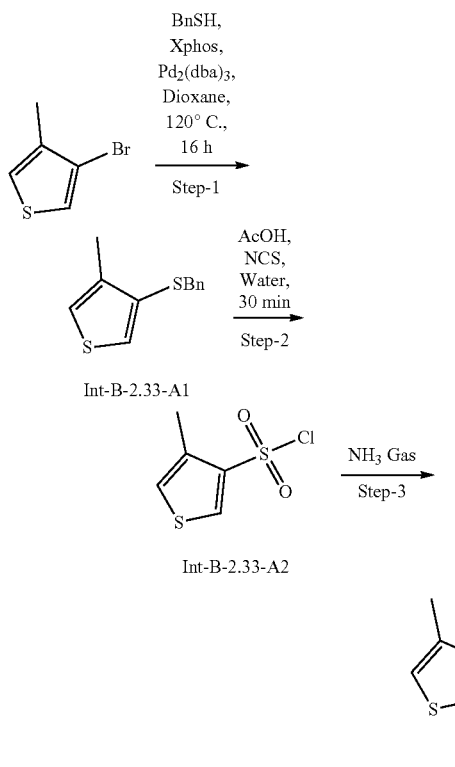

Int-B-2.33

Step-1: To a degassed solution of 3-bromo-4-methylthiophene (1 g, 5.6 mmol) and DIPEA (1.46 g, 11.2 mmol) in dioxane (5 mL) was added Xantphos (0.40 g, 0.7 mmol), Pd$_2$dba$_3$ (0.32 g, 0.35 mmol) and benzyl mercaptan (0.510 g, 0.5 mmol) and the reaction mixture heated at 120° C. for 16 h. After completion of the reaction as indicated by TLC, the reaction mixture was filtered through celite and the filtrate poured into water (100 mL) and extracted with ethyl acetate (3×100 mL). The combined organic layer was washed with brine, dried over Na$_2$SO$_4$ and evaporated under vacuum to afford crude. The crude was subjected to silica gel column chromatography to give Int-B-2.33-A1 (1 g, 80.44%). $^1$H NMR (400 MHz, DMSO) δ 7.33-7.23 (m, 7H), 4.07 (s, 2H), 2.08 (s, 3H).

Step-2: To a stirred solution of 3-(benzylthio)-4-methylthiophene (2 g, 9.085 mmol) in acetic acid (18 mL) and water (2 mL) was added N-chlorosuccinimide (4.8 g, 36.3 mmol) in portions at room temperature and stirred for 30 min. After completion of the reaction as indicated by TLC, the reaction mixture was poured into water (100 mL) and extracted with ethyl acetate (3×150 mL). The combined organic layer was washed with brine, dried over Na$_2$SO$_4$ and evaporated under vacuum to give Int-B-2.332-A2 (2 g, crude) it was used immediately for the next step without analysis. $^1$H NMR (400 MHz, DMSO) δ 8.01 (d, J=3.2 Hz, 1H), 7.35 (bs, 2H), 7.33 (d, J=1.6 Hz, 1H), 2.36 (s, 3H).

Step-3: To a THF (10 mL) solution of 4-(difluoromethyl)thiazole-2-sulfonyl chloride (2 g, 10.20 mmol) ammonia gas was purged at −78° C. for 2 h and then allowed to stir at room temperature. The reaction mixture was quenched with water (100 mL) and extracted with ethyl acetate (2×100 mL). The combined organic layer was dried over anhydrous Na$_2$SO$_4$ and concentrated under vacuum to obtain the crude title compound, Int-B-2.33 (2 g, quantitative). 1H NMR (400 MHz, DMSO) δ 8.01 (d, J=3.2 Hz, 1H), 7.35 (bs, 2H), 7.33 (d, J=1.6 Hz, 1H), 2.36 (s, 3H).

Synthesis of 5-chloro-4-methylthiophene-3-sulfonamide (Int-B-2.34)

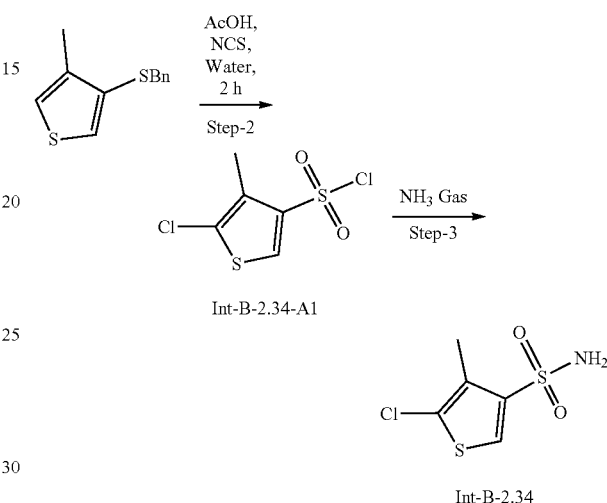

Int-B-2.34

Step-2: To a stirred solution of 3-(benzylthio)-4-methylthiophene (1.2 g, 5.44 mmol) in acetic acid (7 mL) and water (1 mL) was added N-chlorosuccinimide (2.9 g, 21.78 mmol) in portions at room temperature and stirred for 2 h. After completion of the reaction as indicated by TLC, the reaction mixture was poured into water (100 mL) and extracted with ethyl acetate (3×150 mL). The combined organic layer was washed with brine, dried over Na$_2$SO$_4$ and evaporated under vacuum to give the title compound (1 g, 80%) it was used immediately for the next step without purification and analysis.

Step-3: Reaction performed using a similar reaction procedure as described for Int-B-2.33 to give 4-methyl-5-chlorothiophene-3-sulfonamide, Int-B-2.34. LCMS ESI (−ve) (m/z): 210.01 (M−1).

Synthesis of benzo[d]isothiazole-3-sulfonamide (Int-B-2.51)

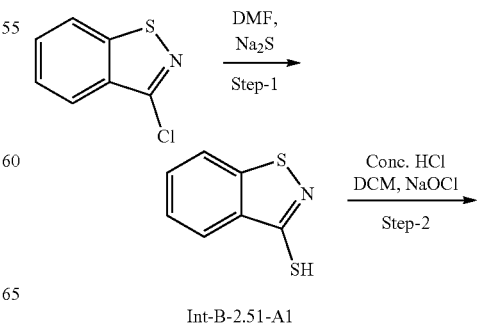

Int-B-2.51-A1

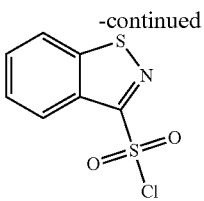

Int-B-2.51-A2

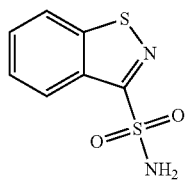

Int-B-2.51

Step-1: To a stirred solution of 3-chlorobenzo[d]isothiazole (5.0 g, 29.5 mmol) in DMF (30 mL) was added Na$_2$S and the reaction mixture heated at 80° C. for 1 h. After completion of the reaction as indicated by TLC, the reaction mixture was poured into cold water (100 mL) and acidified with 2N HCl (pH ~2) extracted with ethyl acetate (3×100 mL). The combined organic layer was washed with brine, dried over Na$_2$SO$_4$ and evaporated under vacuum to give Int-B-2.51-A1 as crude (5.0 g, quantitative) LCMS ESI (m/z): 168.2 (M+H).

Step-2: To a solution of benzo[d]isothiazole-3-thiol (5 g, 29.5 mmol) in dichloromethane (40 mL) was added con. HCl (40 mL) at −5° C. and a 5% solution of NaOCl (11.1 g, 215.74 mmol) and then stirred at −5° C. for 1 h. After completion of the reaction as indicated by TLC, the reaction mixture was diluted with water (100 mL) and extracted with dichloromethane (3×25 mL). The combined organic layer was dried over Na$_2$SO$_4$ and directly used in next step without evaporation.

Step-3: To a freshly prepared sat. ammonia solution in THF (30 mL), benzo[d]isothiazole-3-sulfonyl chloride in DCM (75 mL) at −78° C. was added and stirred for 1 h. After completion of the reaction as indicated by TLC, the reaction mixture was evaporated under vacuum. The crude was purified by silica gel column chromatography (50% ethyl acetate/hexane) to give benzo[d]isothiazole-3-sulfonamide, Int-B-2.51 (1.4 g, 21.85% over 3 steps). $^1$H NMR (400 MHz, DMSO) δ 8.44 (d, J=8.4 Hz, 1H), 8.36 (d, J=8.4 Hz, 1H), 8.10 (s, 2H), 7.73 (t, J=7.6 Hz, 1H), 7.65 (t, J=7.6 Hz, 1H) The following intermediates were made following a similar procedure to the above shown methods.

Synthesis Table 10

| Structure | Compound ID | Precursor | Procedure similar to Int. | Analytical data |
|---|---|---|---|---|
| (pyridine-2-sulfonamide) | Int-B-2.35 | (pyridine-2-thiol) | Int-B-2.1 | LCMS ESI (m/z): 159.16 (M + H) |
| (methyl 3-sulfamoylthiophene-2-carboxylate) | Int-B-2.37 | (methyl 3-(chlorosulfonyl)thiophene-2-carboxylate) | Int-B-2.6 | LCMS ESI (m/z): 222.1 (M + H) |
| (methyl 4-sulfamoylthiophene-3-carboxylate) | Int-B-2.38 | (methyl 4-bromothiophene-3-carboxylate) | Int-B-2.3 | LCMS ESI (m/z): 222.2 (M + H) |
| (5-methylthiophene-3-sulfonamide) | Int-B-2.39 | (4-bromo-2-methylthiophene) | Int-B-2.3 | $^1$H NMR (400 MHz, DMSO-d$_6$) δ 7.79 (s, 1H), 7.31 (s, 2H), 7.05 (s, 1H), 2.45 (s, 3H) |
| (thieno[3,2-b]thiophene-3-sulfonamide) | Int-B-2.40 | (thieno[3,2-b]thiophene-3-sulfonyl chloride) (Int-Y4) | Int-B-2.6 | LCMS ESI (−ve) (m/z): 218.2 (M − H) |

-continued

Synthesis Table 10

| Structure | Compound ID | Precursor | Procedure similar to Int. | Analytical data |
|---|---|---|---|---|
| 3-bromothiophene-2-sulfonamide | Int-B-2.41 | 3-bromothiophene | Int-B-2.15 | LCMS ESI (−ve) (m/z): 239.9 & 241.9 (M & M − 2) |
| 3,4-dibromothiophene-2-sulfonamide | Int-B-2.42 | 3,4-dibromothiophene | Int-B-2.15 | LCMS ESI (−ve) (m/z): 318.1 (M − H) |
| 3-methoxythiophene-2-sulfonamide | Int-B-2.43 | 3-methoxythiophene | Int-B-2.15 | LCMS ESI (m/z): 194.2 (M + H) |
| 5-methoxythiophene-2-sulfonamide | Int-B-2.44 | 2-methoxythiophene | Int-B-2.5 | LCMS ESI (m/z): 194.1 (M + H) |
| 5-isopropylthiophene-2-sulfonamide | Int-B-2.45 | 2-bromothiophene | Int-B-2.16 | 1H-NMR (400 MHz, DMSO-$d_6$) δ: 7.57 (s, 2H), 7.37 (d, J = 4 Hz, 1H), 6.91 (d, J = 4 Hz, 1H), 3.21-3.18 (m, 1H), 1.28 (d, J = 7.2 Hz, 6H). |
| 5-acetyl-3-sulfamoylthiophene | Int-B-2.46 | 3-bromo-2-acetylthiophene | Int-B-2.3 | LCMS ESI (m/z): 206.2 (M + H) |
| 4,5-dichlorothiophene-2-sulfonamide | Int-B-2.48 | 2,3-dichlorothiophene | Int-B-2.15 | LCMS ESI(−ve) (m/z): 229.9, 232.0 (M & M − 2) |
| 2-(difluoromethyl)-3-sulfamoylthiophene | Int-B-2.49 | 3-bromothiophene-2-carbaldehyde | Int-B-2.25 | LCMS ESI(−ve) (m/z): 212.0 (M − H) |
| 2-methylthiazole-5-sulfonamide | Int-B-2.50 | 2-methylthiazole | Int-B-2.50 | LCMS ESI (m/z): 179.2 (M + H) |

Synthesis of 4,5-difluorothiophene-2-sulfonyl chloride (Int-C-4.0)

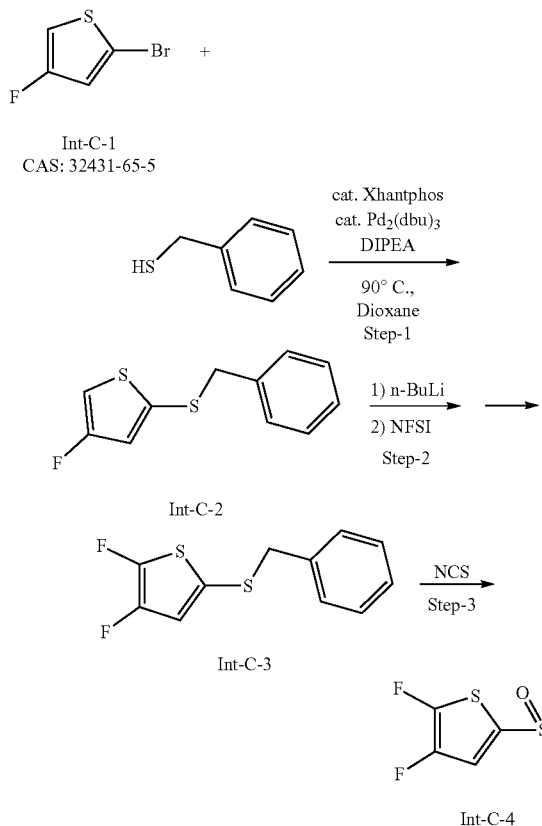

Step-1: Starting material Int-C-1 (450 mg, 2.5 mmol) was dissolved in dioxane (5 mL). To the solution added was Xanthphos (143.83 mg), Pd$_2$(dba)$_3$ (113.82 mg), DIPEA (860 uL, 643 mg, 5 mmol) and benzylmercaptan (309 mg, 2.5 mmol). The mixture was heated at 90° C. in a pressure vessel under Ar atmosphere for 4 h. After cooling to room temperature, the mixture was applied to silica gel column and the product Int-C-2 (480 mg, 86%) was isolated by eluting with a mixture of hexane and ethyl acetate (20:1-10:1). $^1$H NMR (400 MHz, CDCl$_3$) δ 7.32-7.21 (m, 3H), 7.20-7.15 (m, 2H), 6.73-6.58 (m, 2H), 3.97 (s, 2H).

Step-2: nBuLi (2.5 M in hexane, 0.72 mL, 1.79 mmol) was added dropwise at a temperature below −78° C. to a solution of Int-C-2 (365 mg, 1.62 mmol) in THF (15 mL) under Ar. After stirring the mixture for 1 h, N-fluorobenzenesulfonimide (923.6 mg, 2.9 mmol) in THF (5 mL) was added dropwise. The reaction mixture was allowed to warm to room temperature. Aqueous NH$_4$Cl was added to the reaction mixture and it was then extracted with Et$_2$O (80 mL), washed with water, dried with MgSO$_4$, and concentrated. Column chromatography (silica, hexane) gave Int-C-3 (119 mg, 30%). The product was subjected to the next step without characterization.

Step-3: To the mixture of aq 2M HCl (1 mL) and CH$_3$CN (3 mL) was added NCS (304.2 mg, 2.29 mmol) and the solution was cooled to 10° C. and the solution of Int-C-3 (138 mg, 0.57 mmol) in CH$_3$CN (5 mL) was slowly added. The mixture was stirred at low temp for 30 min (UPLC) control. The reaction mixture was diluted with Et$_2$O and washed with water. The organic phase was dried over MgSO$_4$ and evaporated. The residue was purified by column chromatography on silica gel eluting with the mixture of hexane and ethyl acetate (15:1) to give product Int-C-4 (102 mg, 82%) $^1$H NMR (400 MHz, Chloroform-d) δ 7.59 (d, J=3.8 Hz, 1H).

Synthesis of 5-cyano-2-fluorobenzenesulfonamide (Int-D-2.0)

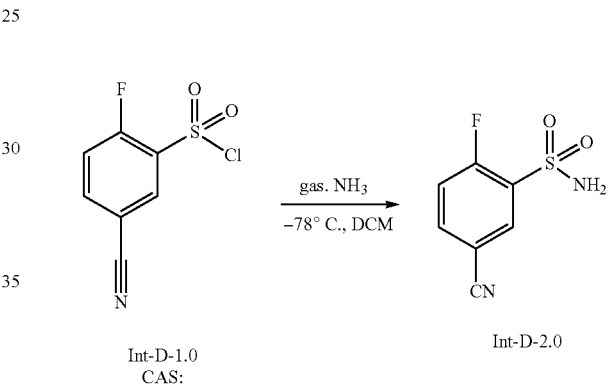

Int-D-1.0 (1.0 g, 4.55 mmol) was dissolved in DCM and the solution was cooled to −78° C. Ammonia gas was passed through the solution to achieve saturation. The mixture was warmed to room temperature and the solvent evaporated. The residue was purified by flash chromatography on silica gel eluting with the mixture of light petroleum ether and ethyl acetate to give Int-D-2.0 (720 mg, 79%). $^1$H NMR (300 MHz, DMSO-d$_6$) δ 8.25-8.14 (m, 2H), 7.94 (s, 2H), 7.71 (dd, J=9.9, 9.2 Hz, 1H).

The following intermediates were made according to the procedure described for Int-D-2.0.

Synthesis Table 11

| Structure | Compound ID | Precursor | Analytical data |
| --- | --- | --- | --- |
| ![structure] | Int-D-2.1 | ![structure] 128852-20-0 | $^1$H NMR (300 MHz, DMSO-d$_6$) δ 7.89 (s, 2H), 7.81 (dd, J = 5.6, 4.2 Hz, 1H), 7.10 (dd, J = 5.6, 0.6 Hz, 1H). |

Synthesis Table 11

| Structure | Compound ID | Precursor | Analytical data |
|---|---|---|---|
| 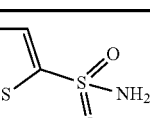 | Int-D-2.2 | 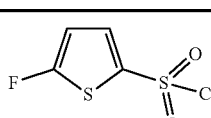<br>1132652-99-3 | $^1$H NMR (300 MHz, CDCl$_3$) δ 7.37 (t, J = 4.0 Hz, 1H), 6.52 (dd, J = 4.3, 1.2 Hz, 1H), 5.02 (s, 2H). |
| 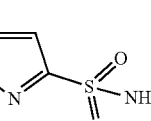 | Int-D-2.3 | 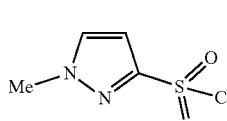<br>CAS: 89501-90-6 | $^1$H NMR (300 MHz, DMSO-d$_6$) δ 7.78 (d, J = 2.3 Hz, 1H), 7.37 (s, 2H), 6.55 (d, J = 2.3 Hz, 1H), 3.88 (s, 3H). |
| 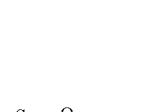 | Int-D-2.4 | Int-C-4 | $^1$H NMR (300 MHz, CDCl$_3$) δ 7.33 (d, J = 3.8 Hz, 1H), 5.09 (s, 3H). |

Synthesis of 2-bromo-3-phenylthiophene (Int-E-3

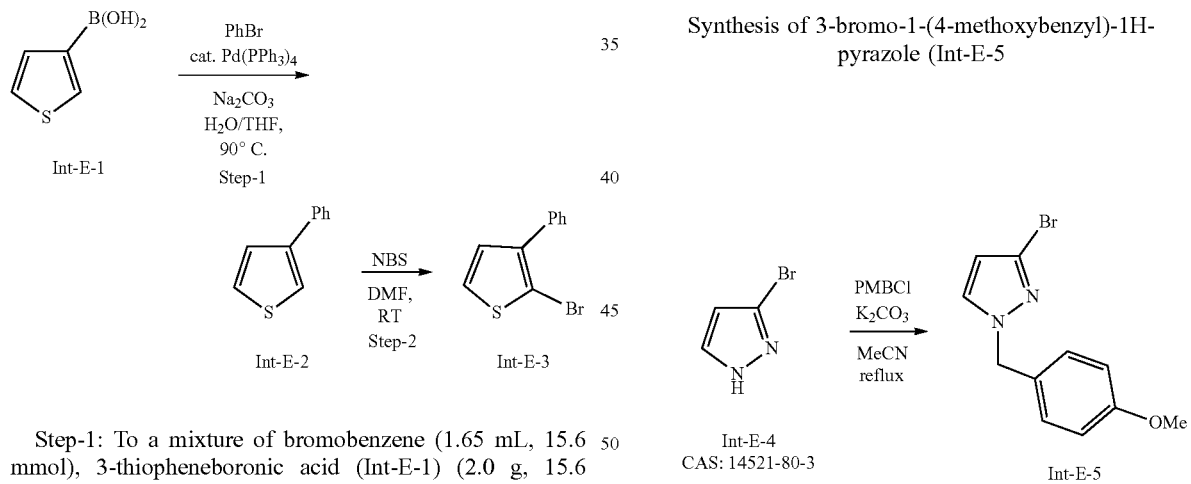

Step-1: To a mixture of bromobenzene (1.65 mL, 15.6 mmol), 3-thiopheneboronic acid (Int-E-1) (2.0 g, 15.6 mmol) and 1,2-dimethoxyethane (32 mL) were added a 2 M aqueous solution of sodium carbonate (12 mL) and tetrakis(triphenylphosphine)palladium(0) (903 mg) at ambient temperature. The mixture was heated for 3 h at 90° C. After cooling, the reaction mixture was diluted with ethyl acetate (200 mL) and washed with water (50 mL×3) and brine (50 mL). The organic layer was dried over magnesium sulfate and filtered. After evaporation, the residue was purified by chromatography on a silica gel eluting with a mixture of ethyl acetate and n-hexane (1:2) to give Int-E-2 (2.0 g, 79%)

Step-2: To a solution of Int-E-2 (1.1 g, 6.9 mmol) in DMF (30 mL) was added NBS (1.34 g, 7.55 mmol) in one portion. The reaction mixture was stirred overnight then diluted with water and the product was extracted with EtOAc. The organic phase was separated and dried over Na$_2$SO$_4$, filtered and evaporated to provide the yellow oily product (1.6 g 97%). which was used further without additional purification.

Synthesis of 3-bromo-1-(4-methoxybenzyl)-1H-pyrazole (Int-E-5

Int-E-4 (2.0 g, 13.6 mmol) was dissolved in MeCN (20 mL) and K$_2$CO$_3$ (2.85 g, 20.6 mmol) was added to the solution followed by paramethoxybenzylchloride (2.3 mL, 16.6 mmol). The reaction mixture was refluxed for 18 h, cooled to room temperature and diluted with water (30 mL). The resulting mixture was extracted with EtOAc, the organic phase was separated and washed with aqueous saturated NaCl. The organic extract was dried over Na$_2$SO$_4$, the solvent evaporated and the residue was purified by flash chromatography on silica gel eluting with the mixture of light petroleum ether and ethyl acetate (5:1) to give Int-E-5 (3.17 g, 87%). $^1$H NMR (300 MHz, CDCl$_3$) δ 7.41-7.20 (m, 3H), 6.98-6.88 (m, 2H), 6.33 (d, J=2.3 Hz, 1H), 5.27 (s, 2H), 3.88 (s, 3H).

Synthesis of N-((4-bromothiophen-2-yl)methyl)-N-(4-methoxybenzyl)acetamide (Int-E-7

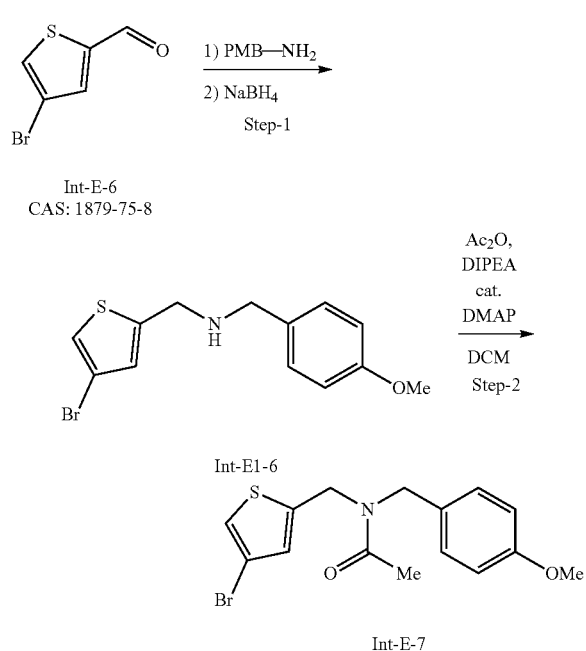

Synthesis of 2-fluoro-3-bromothiophene (Int-E-9

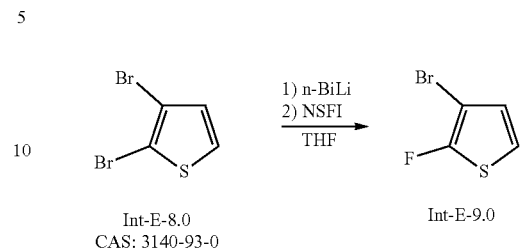

n-BuLi (2.5 M in hexanes, 8.0 mL, 19.9 mmol) was added dropwise at temperature below −60° C. to a solution of Int-E-8.0 (2 mL, 18.1 mmol) in dry diethyl ether (70 mL) under Ar. After stirring the mixture for 1 h, N-fluorobenzenesulfonimide (11.4 g, 36.2 mmol) in THF (70 mL) was added dropwise. The reaction mixture was allowed to warm to room temperature. Aqueous NH$_4$Cl was added to the reaction mixture and then extracted with Et$_2$O, washed with water, dried with MgSO$_4$, and concentrated. Product was purified by column chromatography on silica gel eluting with pentane to give Int-E-9.0 (2.1 g, 64%) $^1$H NMR (300 MHz, Chloroform-d) δ 6.74-6.65 (m, 2H). GC/MS m/z 181 (M).

The following intermediate was made according to the procedure described for Int-F-3.0.

Synthesis Table 12

| Structure | Compound ID | Precursor | Analytical data |
|---|---|---|---|
| 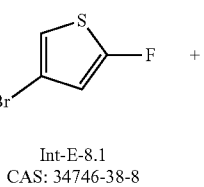<br>Int-E-8.1<br>CAS: 3140-92-9 | Int-E-9.1 | Br, F-thiophene | $^1$H NMR (300 MHz, Chloroform-d) δ 6.49 (ddd, J = 3.2, 2.0, 1.0 Hz, 1H), 6.32 (dt, J = 2.0, 1.1 Hz, 1H). GC/MS m/z 181 (M) |

Step-1: 4-Bromo-2-thiophenecarboxaldehyde (Int-E-6) (2.77 g, 14.5 mmol) was dissolved in MeOH (27 mL) and the mixture stirred at room temperature overnight. Then NaBH$_4$ (880 mg, 23.3 mmol) was added portionwise. After 2 h stirring at room temperature, water and ethyl acetate was added, the organic layer separated, washed with brine and dried over anhydrous Na$_2$SO$_4$. Solvent was removed under reduced pressure and the residue was purified by column chromatography on silica gel (Hex:EtOAc=5:1 to 3:1) to afford Int-E1-6 (3.14 g, 69%) as an off-white amorphous solid. $^1$H NMR (300 MHz, Chloroform-d) δ 7.32-7.23 (m, 2H), 7.15 (d, J=1.5 Hz, 1H), 6.94-6.89 (m, 2H), 6.88-6.86 (m, 1H), 3.96 (d, J=1.0 Hz, 2H), 3.84 (s, 3H), 3.79 (s, 2H).

Step-2: To a solution of Int-E1-6 (1.27 g, 4.06 mmol) in DCM (30 mL) was added DIPEA (1.4 mL, 8.1 mmol), acetic anhydride (0.58 mL, 6.1 mmol), and DMAP (149 mg, 1.2 mmol). The mixture was stirred at room temperature overnight. Extractive work-up provided practically pure Int-E-7 (1.4 g, 97%). $^1$H NMR (400 MHz, CDCl$_3$) δ 7.22-7.05 (m, 3H), 6.98-6.62 (m, 3H), 4.64-4.36 (m, 4H), 3.81 (d, J=7.5 Hz, 3H), 2.40-1.99 (m, 3H).

Synthesis of 5-fluorothiophene-3-sulfonamide (Int-G-3.0

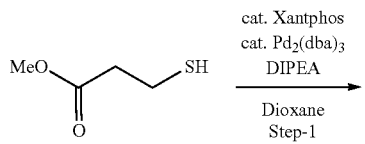

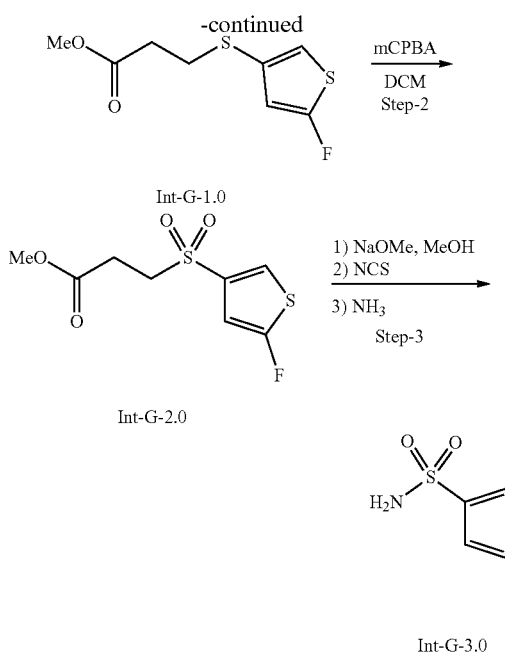

Step-1: A mixture of Int-E-8.1 (1.159 g, 6.6 mmol), methyl 3-mercaptopropionate (1.42 mL, 13.2 mmol), Pd$_2$(dba)$_3$ (181 mg, 0.2 mmol), xanthphos (229 mg, 0.4 mmol), and DIPEA (2.85 mL, 16.5 mmol) were heated in Dioxane (20 mL) at 90° C. for 2 h. The mixture was cooled to room temperature and filtered through a short celite column. The solvent was evaporated and the residue purified by column chromatography on silica gel column eluting by a mixture of light petroleum ether and EtOAc (10:1) to give Int-G-1.0 which was subjected to step-2.

Step-2: Starting material Int-E-3.0 (1.33 g, 6.02 mmol) was dissolved in dry DCM (16 mL) under Ar atmosphere. The solution was cooled to 0° C. and m-CPBA (2.6 g, 15.04 mmol) were added in portions. The mixture was left to stir at the same temperature for 1 h then the mixture was allowed to warm to room temperature. After 2 h, additional m-CPBA was added (1 equiv). The mixture was left to stir until completion of starting material. The reaction mixture was diluted with aq NaHCO$_3$. The organic phase was separated, and the aqueous phase was extracted with DCM (twice). The combined organic phase was dried over Na$_2$SO$_4$, filtered, and evaporated. Product was purified via column chromatography on silica gel eluting with a mixture light petroleum ether and EtOAc (10:1 to 3:1). Fractions containing product and defluorinated impurity were purified a second time (same eluent system). The desired product Int-G-2.0 was obtained as a colourless oil which was subjected to step-3.

Step-3: Int-G-2.0 (1.05 g, 4.16 mmol, 1 equiv) was dissolved in dry MeOH (9 mL). To the solution was added NaOMe (0.81 mL, 4.37 mmol, 1.05 equiv). The solution was stirred at room temperature until completion of a starting material (TLC control). The solvent was evaporated under reduced pressure (with toluene). The crude residue was suspended in dry DCM (9 mL) at 0° C. and NCS (583.55 mg, 4.37 mmol) was added. The mixture was stirred at the same temperature until completion (TLC control). Water was then added. The phases were separated and the aqueous layer extracted with DCM (twice). The combined organic phase was dried over anh. Na$_2$SO$_4$, filtered, and the solvent was partly evaporated under reduced pressure (until ~20-30 mL). The solution was cooled to 0° C. and ammonia (gas) was passed through. The reaction mixture was evaporated on silica and the product purified via column chromatography on silica gel eluting with a mixture of light petroleum ether and EtOAc (10:1 to 1:1). $^1$H NMR (400 MHz, DMSO-d$_6$) δ 7.55 (dd, J=3.9, 2.1 Hz, 1H), 7.45 (s, 2H), 6.98 (dd, J=2.1, 1.2 Hz, 1H).

The following intermediates were made according to the procedure described for Int-G-3.0.

Synthesis Table 13

| Structure | Compound ID | Precursor | Analytical data |
|---|---|---|---|
| (H$_2$N-SO$_2$-pyrazole-CH$_2$-phenyl-OMe) | Int-G-3.1 | Int-E-5 | $^1$H NMR (300 MHz, CDCl$_3$) δ 7.53 (d, J = 2.0 Hz, 1H), 7.25-7.20 (m, 2H), 6.92-6.84 (m, 2H), 6.81 (d, J = 2.0 Hz, 1H), 5.60 (s, 2H), 4.21 (s, 2H), 3.79 (s, 3H). |
| (thiophene-CH$_2$-N(Ac)-CH$_2$-phenyl-OMe, SO$_2$NH$_2$) | Int-G-3.2 | Int-E-7 | $^1$H NMR (300 MHz, CDCl$_3$) δ 7.90-7.78 (m, 1H), 7.18-7.03 (m, 3H), 6.94-6.64 (m, 2H), 5.38-5.27 (m, 2H), 4.57-4.38 (m, 4H), 3.87-3.64 (m, 3H), 2.31-2.10 (m, 3H). UPLCMS ESI (m/z): 355 (M + H)$^+$ |
| (H$_2$N-SO$_2$-thiophene-F) | Int-G-3.3 | Int-E-9 | $^1$H NMR (300 MHz, DMSO-d$_6$) δ 7.67 (s, 2H), 7.10 (dd, J = 6.3, 4.1 Hz, 1H), 6.98 (dd, J = 6.3, 3.3 Hz, 1H). |

Synthesis of 4-fluorothiophene-2-sulfonamide (Int-G-3.4

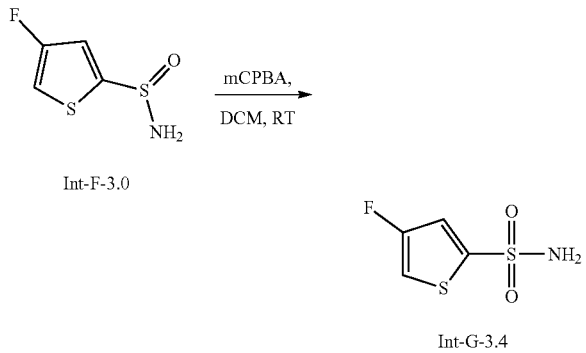

Starting material Int-F-3.0 (267 g, 1.6 mmol) was dissolved in a mixture of dry DCM (16 mL) and DME (4 mL) under Ar atmosphere. The solution was cooled to 0° C. and m-CPBA (517 mg, 2.1 mmol) was added. The mixture was allowed to warm to room temperature and left to stir at room temperature overnight. The reaction mixture was diluted with aq. NaHCO$_3$. The organic phase was separated, and the aqueous phase was extracted with DCM (twice). The combined organic phase was dried over Na$_2$SO$_4$, filtered, and evaporated. Product Int-G-3.4 (290 mg, 99%) was purified via column chromatography on silica gel eluting with a mixture light petroleum ether and EtOAc (2:1). $^1$H NMR (300 MHz, CDCl$_3$) δ 7.43 (dd, J=1.8, 1.1 Hz, 1H), 7.01 (dd, J=1.8, 0.7 Hz, 1H), 4.98 (s, 2H).

Synthesis of 4-methoxythiophene-2-sulfonamide (Int-G-3.8

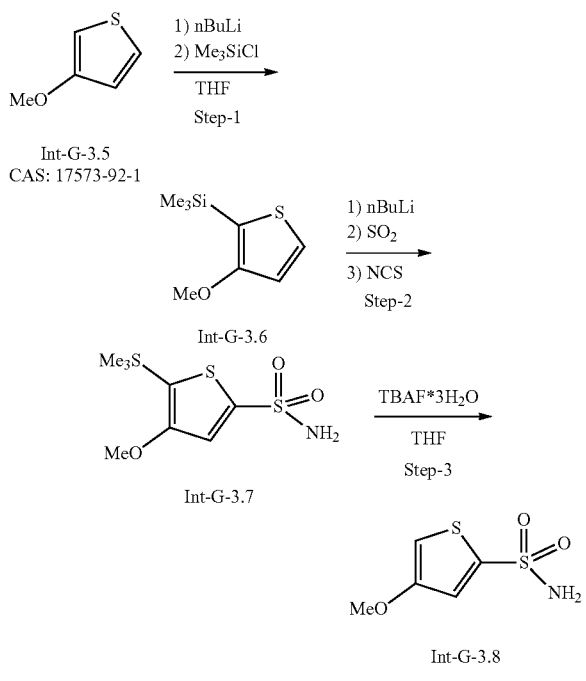

Step-1: A solution of n-BuLi (14.4 mL of 2.5 M in hexanes, 36.0 mmol) was added dropwise to a solution of 3-methoxythiophene (Int-G-3.5) (3.0 mL, 30.0 mmol) in anhydrous Et$_2$O (20 mL) under nitrogen at −70° C. The mixture was stirred at −70° C. for 2 h. Chlorotrimethylsilane (5.0 mL, 39.0 mmol) was added slowly to the solution. The mixture was warmed to room temperature and stirred overnight. The reaction mixture was quenched with water (50 mL) and hexane (100 mL) was added. The organic phase was separated, and the aqueous layer was extracted with hexane (50 mL). The combined organic extracts were dried over Na$_2$SO$_4$, filtered, and concentrated. The crude product was purified by chromatography on silica gel, eluting with hexanes to afford Int-G-3.6 (2.05 g, 37%). $^1$H NMR (300 MHz, CDCl$_3$) δ 7.32 (d, J=4.9 Hz, 1H), 6.84 (d, J=4.9 Hz, 1H), 3.73 (s, 3H), 0.20 (s, 9H).

Step-2: A solution of n-BuLi (6.6 mL of 2.5 M in hexanes, 16.5 mmol) was added dropwise to a solution of Int-G-3.6 (2.05 g, 11.0 mmol) in anhydrous THF (40 mL) under nitrogen at −70° C. The mixture was stirred at −70° C. for 2 h then sulfur dioxide was passed through the solution for 5 min. The reaction mixture was evaporated and dissolved in DCM (40 mL). N-Chlorosuccinimide (1.47 g, 11.0 mmol) was added and the mixture was stirred for 1 h at room temperature. Water was added, and the organic phase was separated and washed with water. Organic phase was dried and evaporated. The residue was dissolved in THF (40 mL), the mixture cooled in a dry ice bath and NH$_3$ gas was passed through. The mixture was warmed to room temperature and left overnight, then evaporated. The product was purified by chromatography on silica gel eluting with a mixture of light petroleum ether and ethyl acetate (2:1, 1:1) to give Int-G-3.7 (1.7 g, 58%). $^1$H NMR (300 MHz, DMSO-d$_6$) δ 7.61 (s, 2H), 7.50 (s, 1H), 3.80 (s, 3H), 0.27 (s, 9H).

Step-3: To a solution of Int-G-3.7 (1.7 g, 6.4 mmol) in THF (30 mL) was added tetra-butylammonium fluoride (4.04 g, 12.8 mmol). The reaction mixture was stirred at room temperature for 2 h. The THF was removed under reduced pressure. The residue was dissolved in EtOAc (200 mL). The organic layer was washed with brine then dried (Na$_2$SO$_4$), filtered, and concentrated in vacuo. The crude product was chromatographed on silica gel, eluting with Hex:EtOAc (3:1) to afford Int-G-3.8 (Yield 1.2 g, 98%). $^1$H NMR (300 MHz, DMSO-d$_6$) δ 7.64 (s, 2H), 7.20 (d, J=2.0 Hz, 1H), 6.91 (d, J=2.0 Hz, 1H), 3.76 (s, 3H).

Synthesis of N-(tert-butyldimethylsilyl)pyridine-4-sulfonamide (Int-B-3.1

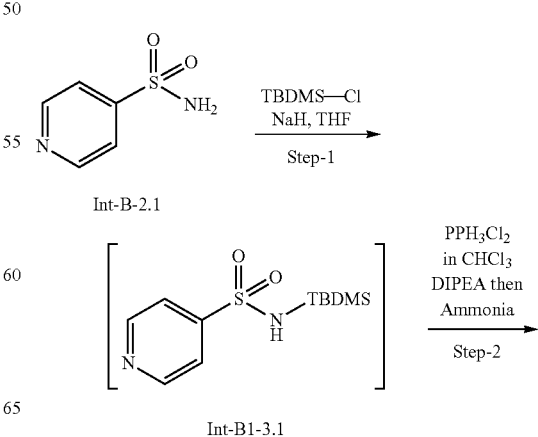

-continued

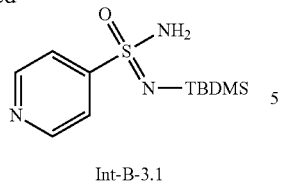

Int-B-3.1

-continued

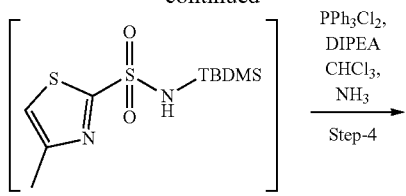

Step-1: To a stirred solution of pyridine-4-sulfonamide (0.65 g, 4.11 mmol) in THF (26 mL), sodium hydride (0.33 g, 8.23 mmol) was added at 0° C. and stirred for 20 minutes. TBDMS-Cl (0.65 g, 1.05 mmol) was added to the reaction mixture and stirred at room temperature for 1 h. After completion of the reaction as indicated by TLC, the reaction mixture was poured into water and extracted with ethyl acetate. The combined organic layer was washed with brine, dried over $Na_2SO_4$ and evaporated under vacuum to give the crude material which was triturated using n-pentane to afford Int-B-2.1 as a white solid (1 g, 49%). It was then used in the next step.

Step-2: To a stirred solution of triphenylphosphine (0.5 g, 1.91 mmol) in chloroform (5 mL) was added hexachloroethane (0.45 g, 1.91 mmol) and stirred for 16 h at 75° C. After completion of the reaction as indicated by TLC, the product 1,1-dichloro-2-4-diphosphane was directly used for the next step.

A solution of 1,1-dichloro-2-4-diphosphane (0.63 g, 1.90 mmol) in chloroform (5 mL) was added DIPEA (0.43 g, 3.31 mmol) at 0° C. and the reaction mixture stirred for 10 minutes. A solution of Int-B1-3.1 (0.45 g, 1.6544 mmol) in chloroform (4.5 mL) was added to the reaction mixture and stirred for additional 30 min. Ammonia gas was purged to the reaction mixture and stirred at room temperature for 1 h. After completion of the reaction as indicated by TLC, the reaction mixture was poured into 5% aq. citric acid solution and extracted with dichloromethane. The combined organic layer was washed with brine, dried over $Na_2SO_4$ and evaporated under vacuum to give the crude material which was triturated using n-pentane to afford the title compound, Int-B-3.1, as a yellow oil (0.93 g, Quantitative). LCMS ESI (m/z): 272.5 (M+1).

Step-1: Synthesis of Int-B-3.2

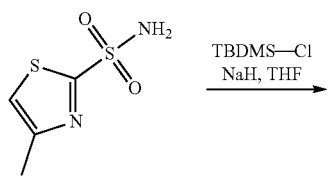

Int-B-2.2

Step-1: To a stirred solution of Int-B-2.2 (300 mg, 1.68 mmol) in THF (3 mL) was added 60% NaH (130 mg, 3.37 mmol) followed by TBDMS-Cl (300 mg, 2.02 mmol) at 0° C. under $N_2$ atmosphere and allowed to stir at room temperature for 4 h. After completion of the reaction as indicated by TLC, the reaction mixture was poured into water and extracted with ethyl acetate. The combined organic layer was washed with brine, dried over $Na_2SO_4$ and evaporated under vacuum to give Int-B-2.2 as an off-white solid (350 mg, 71.42%).

Step-2: A solution of triphenylphosphine (800 mg, 3.05 mmol) and hexachloroethane (720 mg, 3.05 mmol) in $CHCl_3$ (24 mL) was heated at 70° C. with stirring overnight. DIPEA (0.25 mL, 1.4 mmol) was added at room temperature and stirred for 30 min under $N_2$ atmosphere. This was followed by addition of N-(tert-butyl dimethylsilyl)-4-methylthiazole-2-sulfonamide (350 mg, 1.19 mmol) in $CHCl_3$ (5 mL) at 0° C. and stirred for 30 min at 0° C. $NH_3$ gas was passed into the reaction mixture for 1 h at 0° C. and the mixture was stirred for 30 min at room temperature. After completion of the reaction as indicated by TLC, the reaction mixture was poured into water and extracted with DCM. The combined organic layer was washed with brine, dried over $Na_2SO_4$, and evaporated under vacuum to give crude product. The crude product was purified by silica gel column chromatography (ethyl acetate/hexane: 4:6) to give the title compound, Int-B-3.2, as a white solid (130 mg, 38.23%). $^1$H-NMR (400 MHz, DMSO-$d_6$) δ: 7.48 (s, 1H), 7.17 (s, 2H), 2.37 (s, 3H), 0.86 (s, 9H), 0.01 (s, 3H), 0.015 (s, 3H).

The following intermediates were made according to the procedure described for Int-B-3.2.

Synthesis Table 14

| Structure | Compound ID | Precursor | Analytical data |
|---|---|---|---|
| quinoline sulfonimide TBDMS structure | Int-B-3.3 | Int-B-2.3 | $^1$H NMR (400 MHz, DMSO-$d_6$) δ 8.99 (m, 1H), 8.46-8.42 (m, 2H), 8.12 (d, J = 8.8 Hz, 1H), 8.02 (dd, J = 8.4 Hz, 1H), 7.65-7.60 (m, 1H), 6.87 (s, 2H), 0.84 (s, 9H), 0.01 (s, 6H) |

-continued

Synthesis Table 14

| Structure | Compound ID | Precursor | Analytical data |
|---|---|---|---|
| (4-chloro-thiazol-2-yl sulfonimidamide N-TBDMS) | Int-B-3.4 | Int-B-2.4 | ¹H NMR (400 MHz, DMSO-d$_6$) δ 7.91 (s, 1H), 7.42 (s, 2H), 0.84 (s, 9H), 0.03 (s, 6H) |
| (5-methyl-thiazol-2-yl sulfonimidamide N-TBDMS) | Int-B-3.5 | Int-B-2.5 | LCMS ESI (m/z): 292.9 [M + H]+ |
| (2,6-difluorophenyl sulfonimidamide N-TBDMS) | Int-B-3.6 | Int-B-2.6 | LCMS ESI (m/z): 307.0 [M + H]+ |
| (2,4-dichloro-thiazol-5-yl sulfonimidamide N-TBDMS) | Int-B-3.7 | Int-B-2.7 | LCMS ESI (m/z): 346.2 & 348.2 (M & M + 2) |
| (3,4-dichloro-thiophen-2-yl sulfonimidamide N-TBDMS) | Int-B-3.8 | Int-B-2.8 | LCMS ESI (m/z): 345.3 & 347.3 (M & M + 2) |
| (2-methyl-thiophen-3-yl sulfonimidamide N-TBDMS) | Int-B-3.9 | Int-B-2.9 | LCMS ESI (m/z): 291.42 (M + H) |
| (2-chloro-thiophen-3-yl sulfonimidamide N-TBDMS) | Int-B-3.10 | Int-B-2.10 | LCMS ESI (m/z): 311.6 & 313.6 (M & M + 2) |
| (4-cyano-thiophen-3-yl sulfonimidamide N-TBDMS) | Int-B-3.11 | Int-B-2.11 | LCMS ESI (m/z): 302.3 (M + H) |

-continued

Synthesis Table 14

| Structure | Compound ID | Precursor | Analytical data |
|---|---|---|---|
| (5-chlorothiophene-3-sulfonimidamide with NH-TBDMS) | Int-B-3.12 | Int-B-2.12 | NA |
| (3,4-difluorothiophene-2-sulfonimidamide with N-TBDMS) | Int-B-3.13 | Int-B-2.13 | LCMS ESI (m/z): 313.5 (M + H) |
| (3,4-dimethylthiophene-2-sulfonimidamide with NH-TBDMS) | Int-B-3.14 | Int-B-2.14 | LCMS ESI (m/z): 305.3 (M + H) |
| (5-bromothiophene-2-sulfonimidamide with N-TBDMS) | Int-B-3.15 | Int-B-2.15 | LCMS ESI (m/z): 355.3 & 357.3 (M & M + 2) |
| (3-isopropylthiophene-2-sulfonimidamide with N-TBDMS) | Int-B-3.16 | Int-B-2.16 | NA |
| (2,4-dimethoxybenzyloxy phenyl sulfonimidamide with TBDMS) | Int-B-3.17 | Int-B-2.17 | NA |
| (3-ethylthiophene-2-sulfonimidamide with NH-TBDMS) | Int-B-3.21 | Int-B-2.21 | LCMS ESI (m/z): 305.4 (M + H) |
| (3,5-dichlorothiophene-2-sulfonimidamide with NH-TBDMS) | Int-B-3.22 | Int-B-2.22 | LCMS ESI (m/z): 345.4 & 347.4 (M & M + 2) |

-continued

Synthesis Table 14

| Structure | Compound ID | Precursor | Analytical data |
|---|---|---|---|
| (4-methylthiophene-2-sulfonimidamide, N-TBDMS) | Int-B-3.23 | Int-B-2.23 | LCMS ESI (m/z): 177.0 (M − TBDMS) |
| (4-chlorothiophene-2-sulfonimidamide, N-TBDMS) | Int-B-3.24 | Int-B-2.24 | LCMS ESI (m/z): 311.3 & 313.4 (M & M + 2) |
| (4-(difluoromethyl)thiazole-2-sulfonimidamide, N-TBDMS) | Int-B-3.25 | Int-B-2.25 | LCMS ESI (m/z): 328.4 (M + H) |
| (4,5-dimethylthiazole-2-sulfonimidamide, N-TBDMS) | Int-B-3.26 | Int-B-2.26 | LCMS ESI (m/z): 306.5 (M + H) |
| (2-methylthiazole-4-sulfonimidamide, N-TBDMS) | Int-B-3.27 | Int-B-2.27 | LCMS ESI (m/z): 292.4 (M + H) |
| (4-phenylthiophene-3-sulfonimidamide, N-TBDMS) | Int-B-3.28 | Int-B-2.28 | LCMS ESI (m/z): 239.1 (M − TBDMS) |
| (thieno[3,2-b]pyridine-3-sulfonimidamide, N-TBDMS) | Int-B-3.29 | Int-B-2.29 | LCMS ESI (m/z): 328.5 (M + H) |

-continued

Synthesis Table 14

| Structure | Compound ID | Precursor | Analytical data |
|---|---|---|---|
| (4-bromothiophene-2-sulfonimidamide with TBDMS) | Int-B-3.30 | Int-B-2.30 | LCMS ESI (m/z): 355.5 & 357.5 (M & M + 2) |
| (5-cyanothiophene-3-sulfonimidamide with TBDMS) | Int-B-3.31 | Int-B-2.31 | LCMS ESI (m/z): 302.4 (M + H) |
| (4-cyanothiophene-2-sulfonimidamide with TBDMS) | Int-B-3.32 | Int-B-2.32 | LCMS ESI (m/z): 302.4 (M + H) |
| (4-methylthiophene-3-sulfonimidamide with TBDMS) | Int-B-3.33 | Int-B-2.33 | NA |
| (5-chloro-4-methylthiophene-3-sulfonimidamide with TBDMS) | Int-B-3.34 | Int-B-2.34 | NA |
| (pyridine-2-sulfonimidamide with TBDMS) | Int-B-3.35 | Int-B-2.35 | MS (m/z): 272.5 (M + H) |
| (methyl 3-sulfonimidamide-thiophene-2-carboxylate with TBDMS) | Int-B-3.37 | Int-B-2.37 | LCMS ESI (m/z): 221.1 (M − TBDMS) |
| (methyl 3-sulfonimidamide-thiophene-4-carboxylate with TBDMS) | Int-B-3.38 | Int-B-2.38 | $^1$H NMR (400 MHz, DMSO) δ 8.35 (d, J = 3.6 Hz, 1H), 8.07 (d, J = 3.2 Hz, 1H), 6.55 (s, 2H), 3.81 (s, 1H), 0.81 (s, 9H), −0.06 (d, J = 2 Hz, 6H). |
| (5-methylthiophene-3-sulfonimidamide with TBDMS) | Int-B-3.39 | Int-B-2.39 | MS ESI (m/z): 291.7 (M + H) |

Synthesis Table 14

| Structure | Compound ID | Precursor | Analytical data |
|---|---|---|---|
| (thieno-sulfoximine with TBDMS-NH, NH) | Int-B-3.40 | Int-B-2.40 | LCMS ESI (m/z): 333.5 (M + H) |
| (3-bromothiophene sulfonimidamide, NH$_2$, N-TBDMS) | Int-B-3.41 | Int-B-2.41 | LCMS ESI (m/z): 355.3 & 357.3 (M & M + 2) |
| (3,4-dibromothiophene sulfonimidamide, NH$_2$, N-TBDMS) | Int-B-3.42 | Int-B-2.42 | $^1$H NMR (400 MHz, DMSO) δ 8.00 (s, 1H), 7.18 (s, 2H), 0.87 (s, 9H), 0.01 (d, J = 3.2 Hz, 6H). |
| (3-methoxythiophene sulfoximine, NH, NH, TBDMS) | Int-B-3.43 | Int-B-2.43 | $^1$H NMR (400 MHz, DMSO-d$_6$) δ: 7.55 (d, J 5.6 Hz, 1H), 7.31 (d, J = 5.6 Hz, 1H), 6.56 (s, 2H), 3.87 (s, 3H), 0.86 (s, 9H), −0.023 (d, J = 3.2, 6H) |
| (5-methoxythiophene sulfonimidamide, H$_2$N, N-TBDMS) | Int-B-3.44 | Int-B-2.44 | LCMS ESI (m/z): 307.6 (M + H) |
| (5-isopropylthiophene sulfonimidate, N-TBDMS) | Int-B-3.45 | Int-B-2.45 | NA |
| (acetyl-thiophene sulfoximine, NH, HN-TBDMS) | Int-B-3.46 | Int-B-2.46 | NA |
| (4,5-dichlorothiophene sulfonimidamide, NH$_2$, N-TBDMS) | Int-B-3.48 | Int-B-2.48 | LCMS ESI (m/z): 345.3 & 347.3 (M & M + 2) |

Synthesis Table 14

| Structure | Compound ID | Precursor | Analytical data |
|---|---|---|---|
| (structure: 2-(difluoromethyl)thiophene-3-sulfonimidamide N-TBDMS) | Int-B-3.49 | Int-B-2.49 | NA |
| (structure: 2-methyl-thiazole-5-sulfonimidamide N-TBDMS) | Int-B-3.50 | Int-B-2.50 | LCMS ESI (m/z): 292.4 (M + H) |
| (structure: benzo[d]isothiazole-3-sulfonimidamide N-TBDMS) | Int-B-3.51 | Int-B-2.51 | LCMS ESI (m/z): 328.5 (M + H) |
| (structure: 3-methoxyphenyl sulfonimidamide NHTBDMS) | Int-B-3.52 | CAS: 58734-57-9 | $^1$H NMR (400 MHz, CDCl$_3$) δ 7.59-7.45 (m, 2H), 7.42-7.26 (m, 1H), 7.02 (ddd, J = 8.3, 2.6, 1.0 Hz, 1H), 4.51 (s, 2H), 3.85 (s, 3H), 0.93 (s, 9H), 0.13 (d, J = 1.6 Hz, 6H) |
| (structure: 5-fluorothiophene-3-sulfonimidamide NHTBDMS) | Int-B-3.53 | Int-G-3.0 | $^1$H NMR (400 MHz, CDCl$_3$) δ 7.26 (dd, J = 2.1 Hz, 1H), 6.78 (dd, J = 2.0, 0.8 Hz, 1H), 4.59 (s, 2H), 0.91 (s, 9H), 0.11 (d, J = 1.6 Hz, 6H). $^{19}$F NMR (376 MHz, CDCl$_3$) δ −125.03 (d, J = 4.0 Hz) |
| (structure: 4-methoxythiophene-2-sulfonimidamide NHTBDMS) | Int-B-3.54 | Int-G-3.8 | $^1$H NMR (300 MHz, CDCl$_3$) δ 7.18 (d, J = 2.0 Hz, 1H), 6.38 (d, J = 1.9 Hz, 1H), 4.72 (s, 2H), 3.79 (s, 3H), 0.92 (s, 9H), 0.13 (s, 6H). UPLCMS ESI (m/z): 307 [M + H]$^+$ |
| (structure: 4-fluorothiophene-2-sulfonimidamide NHTBDMS) | Int-B-3.55 | Int-G-3.4 | $^1$H NMR (300 MHz, CDCl$_3$) δ 7.32-7.25 (m, 1H), 6.91-6.75 (m, 1H), 4.72 (s, 2H), 0.91 (s, 9H), 0.14 (s, 3H), 0.10 (s, 3H). UPLCMS ESI (m/z): 295 [M + H]$^+$ |
| (structure: 4,5-difluorothiophene-2-sulfonimidamide NHTBDMS) | Int-B-3.56 | Int-D-2.4 | NA |

-continued

Synthesis Table 14

| Structure | Compound ID | Precursor | Analytical data |
|---|---|---|---|
| (structure with OMe, thiazole, N-acetyl, S(=O)=NH, TBSHN) | Int-B-3.57 | Int-G-3.2 | $^1$H NMR (300 MHz, CDCl$_3$) δ 7.78-7.71 (m, 1H), 7.22-7.04 (m, 3H), 6.92-6.82 (m, 2H), 4.67-4.35 (m, 6H), 3.84-3.73 (m, 3H), 2.25-2.16 (m, 3H), 0.91 (s, 9H), 0.10 (s, 6H). UPLCMS ESI (m/z): 354 [M − TBS + H]$^+$ |
| (structure with F, CN, S(=O)(=NH)NHTBS phenyl) | Int-B-3.58 | Int-D-2.0 | $^1$H NMR (300 MHz, CDCl$_3$) δ 8.24 (dd, J = 6.8, 2.2 Hz, 1H), 7.79 (ddd, J = 8.6, 4.5, 2.2 Hz, 1H), 7.30 (dd, J = 9.5, 8.5 Hz, 1H), 4.91 (s, 2H), 0.92 (s, 9H), 0.12 (d, J = 1.3 Hz, 6H). UPLCMS ESI (m/z): 314 [M + H]$^+$ |
| (structure with OEt phenyl sulfonimidamide NHTBS) | Int-B-3.59 | CAS: 1247894-17-2 | UPLCMS ESI (m/z): 201 [M − TBS + H]$^+$ |
| (3-fluorothiophene sulfonimidamide NHTBDMS) | Int-B-3.60 | Int-D-2.1 | $^1$H NMR (300 MHz, DMSO-d$_6$) δ 7.63 (dd, J = 5.6, 4.2 Hz, 1H), 7.10 (s, 2H), 7.00 (dd, J = 5.6, 0.7 Hz, 1H), 0.86 (s, 9H), 0.00 (d, J = 1.7 Hz, 6H). UPLCMS ESI (m/z): 295 [M + H]$^+$ |
| (5-fluorothiophene sulfonimidamide NHTBDMS) | Int-B-3.61 | Int-D-2.2 | $^1$H NMR (300 MHz, DMSO-d$_6$) δ 7.14 (t, J = 4.0 Hz, 1H), 6.99 (s, 2H), 6.74 (dd, J = 4.2, 1.8 Hz, 1H), 0.87 (s, 9H), 0.02 (d, J = 2.2 Hz, 6H). UPLCMS ESI (m/z): 295 [M + H]$^+$ |
| (pyrazole with 4-OMe-benzyl, sulfonimidamide NHTBDMS) | Int-B-3.62 | Int-G-3.1 | $^1$H NMR (300 MHz, CDCl$_3$) δ 7.25 (d, J = 2.3 Hz, 1H), 7.23-7.17 (m, 2H), 6.92-6.85 (m, 2H), 6.59 (d, J = 2.3 Hz, 1H), 5.24 (s, 2H), 4.78 (s, 2H), 3.80 (s, 3H), 0.90 (s, 9H), 0.10 (d, J = 4.8 Hz, 6H). |

Synthesis Table 14

| Structure | Compound ID | Precursor | Analytical data |
|---|---|---|---|
| (pyrazole-S(=O)(=NH)NHTBDMS, N-Me) | Int-B-3.63 | Int-D-2.3 | ¹H NMR (300 MHz, DMSO-d$_6$) δ 7.71 (d, J = 2.2 Hz, 1H), 6.57 (s, 2H), 6.44 (d, J = 2.2 Hz, 1H), 3.85 (s, 3H), 0.84 (s, 9H), −0.03 (d, J = 7.7 Hz, 6H). |
| (2-fluorothiophene-3-S(=O)(=NH)NHTBDMS) | Int-B-3.64 | Int-G-3.3 | ¹H NMR (300 MHz, Chloroform-d) δ 7.00 (dd, J = 6.2, 3.3 Hz, 1H), 6.62 (dd, J = 6.2, 4.0 Hz, 1H), 4.77 (s, 2H), 0.91 (s, 9H), 0.11 (d, J = 1.2 Hz, 6H) |

Synthesis of Pyridine-4-sulfonimidamide (Int-B-4.1

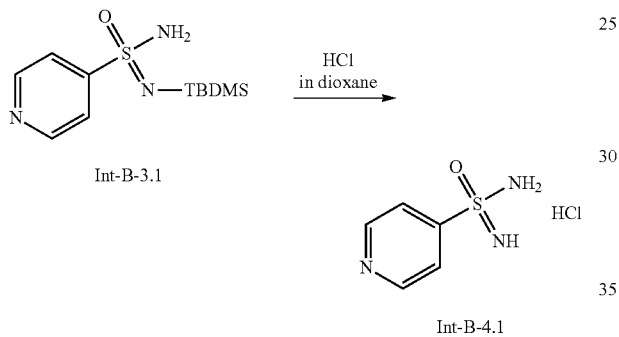

Int-B-3.1 → Int-B-4.1

To a stirred solution of (Int-B-3.1) (0.93 g, 3.43 mmol) in dichloromethane (20 mL) was added 4 M HCl in dioxane (0.25 g, 6.86 mmol) at 0° C. and then stirred for 1 h at room temperature. After completion of the reaction as indicated by TLC, the reaction mixture was concentrated in vacuo. The crude product was purified by trituration with ethyl acetate to give the title compound, Int-B-4.1 (0.2 g, 37%). LCMS ESI (m/z): 158.1 (M+1).

The following intermediates was made according to the procedure described for Int-B-4.1.

Synthesis Table 15

| Structure | Compound ID | Precursor | Analytical data |
|---|---|---|---|
| (2,6-difluorophenyl sulfonimidamide) | Int-B-4.7 | Int-B-3.6 | LCMS ESI (m/z): 192.9 (M + H) |
| (3,4-dichlorothiophene-2-sulfonimidamide·HCl) | Int-B-4.8 | Int-B-3.8 | NA |

-continued

| Synthesis Table 15 | | | |
|---|---|---|---|
| Structure | Compound ID | Precursor | Analytical data |
| (3-methylthiophene sulfonimidamide·HCl) | Int-B-4.9 | Int-B-3.9 | LCMS ESI (m/z): 177.09 (M + H) |
| (2-chlorothiophene-3-sulfonimidamide·HCl) | Int-B-4.10 | Int-B-3.10 | LCMS ESI (m/z): 197.1 & 199.1 (M & M + 2) |
| (4-cyanothiophene-3-sulfonimidamide·HCl) | Int-B-4.11 | Int-B-3.11 | LCMS ESI (m/z): 188.37 (M + H) |
| (3,4-difluorothiophene-2-sulfonimidamide·HCl) | Int-B-4.13 | Int-B-3.13 | LCMS ESI (m/z): 199.3 (M + H) |
| (3,4-dimethylthiophene-2-sulfonimidamide·HCl) | Int-B-4.14 | Int-B-3.14 | LCMS ESI (m/z): 191.2 (M + H) |
| (5-bromothiophene-2-sulfonimidamide·HCl) | Int-B-4.15 | Int-B-3.15 | LCMS ESI (m/z): 241.1 & 243.1 (M & M + 2) |
| (3-isopropylthiophene-2-sulfonimidamide·HCl) | Int-B-4.16 | Int-B-3.16 | LCMS ESI (m/z): 205.1 (M + H) |
| (3-ethylthiophene-2-sulfonimidamide·HCl) | Int-B-4.21 | Int-B-3.21 | LCMS ESI (m/z): 191.2 (M + H) |

-continued

Synthesis Table 15

| Structure | Compound ID | Precursor | Analytical data |
|---|---|---|---|
| (3,5-dichlorothiophene-2-sulfonimidamide, HCl) | Int-B-4.22 | Int-B-3.22 | LCMS ESI (m/z): 231.1 & 233.2 (M & M + 2) |
| (4-methylthiophene-2-sulfonimidamide, HCl) | Int-B-4.23 | Int-B-3.23 | LCMS ESI (m/z): 177.2 (M + H) |
| (4-chlorothiophene-2-sulfonimidamide, HCl) | Int-B-4.24 | Int-B-3.24 | LCMS ESI (m/z): 197.2 & 199.2 (M & M + 2) |
| (4-(difluoromethyl)thiazole-2-sulfonimidamide, HCl) | Int-B-4.25 | Int-B-3.25 | LCMS ESI (m/z): 214.3 (M + H) |
| (4,5-dimethylthiazole-2-sulfonimidamide, HCl) | Int-B-4.26 | Int-B-3.26 | LCMS ESI (m/z): 192.3 (M + H) |
| (2-methylthiazole-4-sulfonimidamide, HCl) | Int-B-4.27 | Int-B-3.27 | LCMS ESI (m/z): 178.2 (M + H) |
| (4-phenylthiophene-3-sulfonimidamide, HCl) | Int-B-4.28 | Int-B-3.28 | LCMS ESI (m/z): 239.1 (M + H) |
| (thieno[3,2-b]pyridine-3-sulfonimidamide, HCl) | Int-B-4.29 | Int-B-3.29 | LCMS ESI (m/z): 214.0 (M + H) |

-continued

Synthesis Table 15

| Structure | Compound ID | Precursor | Analytical data |
|---|---|---|---|
| 4-bromothiophene-2-sulfonimidamide·HCl | Int-B-4.30 | Int-B-3.30 | LCMS ESI (m/z): 241.2 & 243.2 (M & M + 2) |
| 5-cyanothiophene-3-sulfonimidamide·HCl | Int-B-4.31 | Int-B-3.31 | LCMS ESI (m/z): 188.0 (M + H) |
| 4-cyanothiophene-2-sulfonimidamide·HCl | Int-B-4.32 | Int-B-3.32 | LCMS ESI (m/z): 187.9 (M + H) |
| 4-methylthiophene-3-sulfonimidamide·HCl | Int-B-4.33 | Int-B-3.33 | LCMS ESI (m/z): 177.2 (M + H) |
| 5-chloro-4-methylthiophene-3-sulfonimidamide·HCl | Int-B-4.34 | Int-B-3.34 | $^1$H NMR (400 MHz, DMSO) δ 9.16 (bs, 4H), 8.44 (s, 1H), 2.36 (s, 3H). |
| pyridine-2-sulfonimidamide·HCl | Int-B-4.35 | Int-B-3.35 | LCMS ESI (m/z): 158.2 (M + H) |
| methyl 3-sulfamimidoylthiophene-2-carboxylate·HCl | Int-B-4.37 | Int-B-3.37 | LCMS ESI (m/z): 221.1 (M + H) |
| methyl 4-sulfamimidoylthiophene-3-carboxylate·HCl | Int-B-4.38 | Int-B-3.38 | LCMS ESI (m/z): 221.2 (M + H) |
| 5-methylthiophene-3-sulfonimidamide·HCl | Int-B-4.39 | Int-B-3.39 | LCMS ESI (m/z): 177.2 (M + H) |

-continued
Synthesis Table 15
| Structure | Compound ID | Precursor | Analytical data |
|---|---|---|---|
| 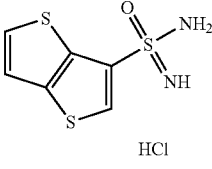 | Int-B-4.40 | Int-B-3.40 | LCMS ESI (m/z): 219.2 (M + H) |
| 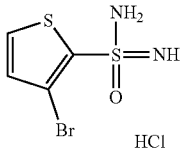 | Int-B-4.41 | Int-B-3.41 | LCMS ESI (m/z): 241.2 & 243.2 (M & M + 2) |
| 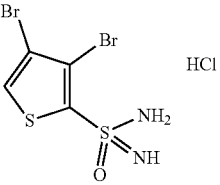 [SMILES: N=S(N)(=O)c1scc(Br)c1Br ; Cl] | Int-B-4.42 | Int-B-3.42 | NA |
| 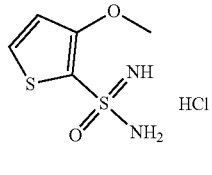 | Int-B-4.43 | Int-B-3.43 | $^1$H NMR (400 MHz, DMSO-$d_6$) δ: 9.22 (bs, 4H), 8.18 (d, J = 5.6 Hz, 1H), 7.29 (d, J = 5.6 Hz, 1H), 4.02 (s, 3H). |
| 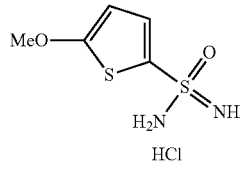 | Int-B-4.44 | Int-B-3.44 | LCMS ESI (m/z): 193.2 (M + H) |
| 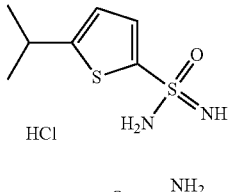 | Int-B-4.45 | Int-B-3.45 | LCMS ESI (m/z): 205.2 (M + H) |
| 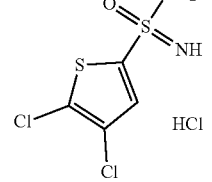 | Int-B-4.48 | Int-B-3.48 | LCMS ESI (m/z): 231.2 & 233.2 (M & M + 2) |
| 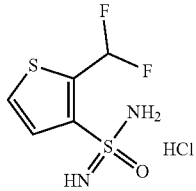 | Int-B-4.49 | Int-B-3.49 | LCMS ESI (m/z): 213.3 (M + H) |

Synthesis Table 15

| Structure | Compound ID | Precursor | Analytical data |
|---|---|---|---|
| (2-methylthiazol-5-yl sulfonimidamide) HCl | Int-B-4.50 | Int-B-3.50 | LCMS ESI (m/z): 178.0 (M + H) |
| (benzo[d]isothiazol-3-yl sulfonimidamide) HCl | Int-B-4.51 | Int-B-3.51 | LCMS ESI (m/z): 214.27 (M + H) |
| (4,5-difluorothiophen-2-yl sulfonimidamide) | Int-B-4.52 | Int-B-3.56 | UPLCMS ESI (m/z): 199 (M + H) |

Synthesis of tert-butyl ((2S)-1-((amino(oxo)(pyridin-4-yl)-λ6-sulfanylidene)amino)-4-methyl-1-oxopentan-2-yl)carbamate (Int-B-5.1. Int-B-5.1-Fr-1 and Int-B-5.1-Fr-2

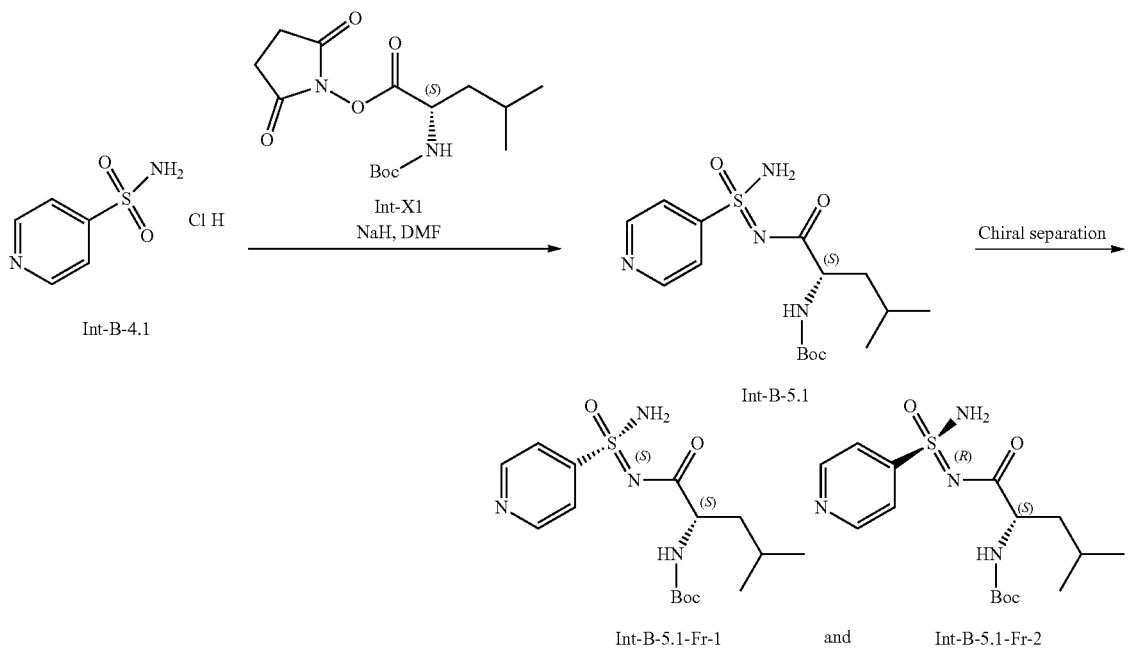

To a stirred solution of pyridine-4-sulfonimidamide (Int-B-4.1) (0.1 g, 0.64 mmol) in DMF (4 mL) was added sodium hydride (46 mg, 1.91 mmol) at 0° C. and the reaction mixture stirred for 20 minutes. Int-X1 (0.209 g, 0.63 mmol) was added to the reaction mixture and stirred for 6 h. After completion of the reaction as indicated by TLC, the reaction mixture was poured into water and extracted with ethyl acetate. The combined organic layer was washed with brine, dried over $Na_2SO_4$ and evaporated under vacuum to give the crude material which was purified by reverse phase flash chromatography using water:acetonitrile (3:1) to afford Int-B-5.1 as a mixture of diastereomers (90 mg, 38%). LCMS ESI (m/z): 371.3 (M+1).

The diastereomers were separated by Chiral prep HPLC (DIACEL Chiral PAK_IG, Mobile phase Mobile phase: A=Heptane, B=IPA:MeOH (70:30), A:B=70:30) to give Isomer-1 and Isomer-2. These isomers were eluted at retention time 9.62 min (Isomer-1) and 12.50 min (Isomer-2).

The following intermediates were made according to the procedure described for Int-B-5.1.

Synthesis Table 16

| Structure | Compound ID | Precursor | Analytical data |
|---|---|---|---|
| (2,6-difluorophenyl sulfonimidoyl) Boc-Leu structure | Int-B-5.7 | Int-B-4.7<br>Int-X1 | Chiral prep HPLC:<br>DIACEL Chiral PAK_IG<br>Mobile phase:<br>Heptane_IPA-ACN<br>(70-30)_75:25<br>Isomer-1 (Fr-1):<br>Retention time: 7.02 min<br>Isomer-2 (Fr-2):<br>Retention time: 11.20 min |
| (S)-isomer structure | | | |
| (R)-isomer structure | | | |
| 3,4-dichlorothiophene sulfonimidoyl Boc-Leu structure | Int-B-5.8<br>Int-B-5.8-Fr-1<br>Int-B-5.8-Fr-2 | Int-B-4.8<br>Int-X1 | LCMS ESI (m/z):<br>444.4 & 446.4<br>(M & M + 2)<br>Chiral prep HPLC:<br>CHIRALPAK IG SFC.<br>Mobile phase:<br>0.05% TFA in<br>MeOH_IPA:MEOH_95:5<br>Isomer-1 (Fr-1):<br>Retention time: 16.61 min<br>Isomer-2 (Fr-2):<br>Retention time: 35.39 min |
| (S)-isomer structure | | | |
| (R)-isomer structure | | | |
| 2-methylthiophene sulfonimidoyl Boc-Leu structure | Int-B-5.9<br>Int-B-5.9-Fr-1<br>Int-B-5.9-Fr-2 | Int-B-4.9<br>Int-X1 | LCMS ESI (m/z):<br>390.6 (M + H)<br>Chiral prep HPLC:<br>CHIRALART<br>CELLULOSE-SC<br>Mobile phase:<br>n-HEPTANE_IPA:ACN<br>(70:30)_92:8<br>Isomer-1 (Fr-1):<br>Retention time: 14.54 min<br>Isomer-2 (Fr-2):<br>Retention time: 32.25 min |
| (S)-isomer structure | | | |

-continued

Synthesis Table 16

| Structure | Compound ID | Precursor | Analytical data |
|---|---|---|---|
| [Structure: methyl-thiophene sulfoximine with (R) S, (S) leucine-Boc] | | | |
| [Structure: 2-chloro-thiophene sulfoximine with (S) leucine-Boc, three isomers] | Int-B-5.10<br>Int-B-5.10-Fr-1<br>Int-B-5.10-Fr-2 | Int-B-4.10<br>Int-X1 | LCMS ESI (m/z):<br>410.4 & 412.6<br>(M & M + 2)<br>Chiral prep HPLC:<br>YMC CHIRALART<br>CELLULOSE_SC<br>Mobile phase:<br>n-Heptane_IPA-MeOH<br>(70-30)_85:15<br>Isomer-1 (Fr-1):<br>Retention time: 10.32 min<br>Isomer-2 (Fr-2):<br>Retention time: 17.78 min |
| [Structure: 2-chloro-thiophene sulfoximine with (S,S) isoleucine-Boc, three isomers] | Int-B-5.11<br>Int-B-5.11-Fr-1<br>Int-B-5.11-Fr-2 | Int-B-4.10<br>Int-X2 | LCMS ESI (m/z):<br>410.4 (M + H)<br>Chiral prep HPLC:<br>CHIRALPAK IG SFC<br>Mobile phase:<br>n-Heptane_IPA-ACN<br>(70-30)_90:10<br>Isomer-1 (Fr-1):<br>Retention time: 31.65 min<br>Isomer-2 (Fr-2):<br>Retention time: 42.47 min |
| [Structure: 4-cyano-thiophene sulfoximine with leucine-Boc] | Int-B-5.12 | Int-B-4.11<br>Int-X1 | LCMS ESI (m/z):<br>401.5 (M + H) |

-continued

Synthesis Table 16

| Structure | Compound ID | Precursor | Analytical data |
|---|---|---|---|
| 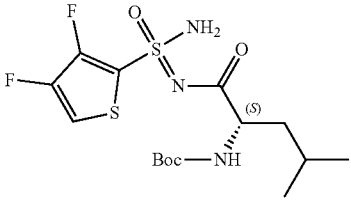 | Int-B-5.13<br>Int-B-5.13-Fr-1<br>Int-B-5.13-Fr-2 | Int-B-4.13<br>Int-X1 | LCMS ESI (m/z):<br>412.7 (M + H)<br>Chiral prep YMC<br>CELLULOSE SC<br>Mobile phase:<br>n-Hepatane_IPA (90:10)<br>Isomer-1 (Fr-1):<br>Retention time: 16.37 min<br>Isomer-2 (Fr-2):<br>Retention time: 34.74 min |
| 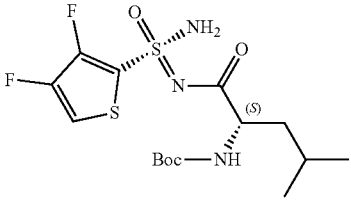 | | | |
| 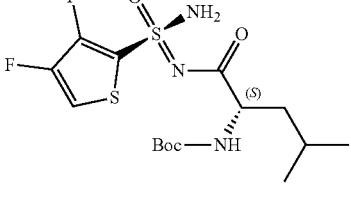 | | | |
| 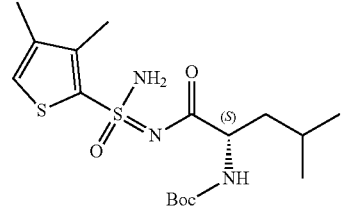 | Int-B-5.14<br>Int-B-5.14-Fr-1<br>Int-B-5.14-Fr-2 | Int-B-4.14<br>Int-X1 | LCMS ESI (m/z):<br>404.5 (M + H)<br>Chiral prep HPLC:<br>YMC CHIRALART<br>CELLULOSE_SC<br>Mobile phase:<br>Heptane_IPA-MeOH<br>(70-30)_88:12<br>Isomer-1 (Fr-1):<br>Retention time: 17.20 min<br>Isomer-2 (Fr-2):<br>Retention time: 34.39 min |
| 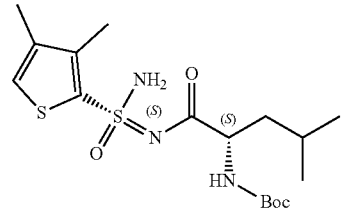 | | | |
| 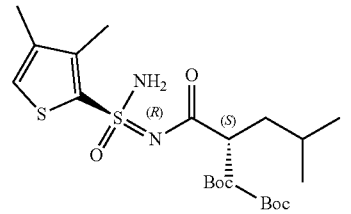 | | | |
| 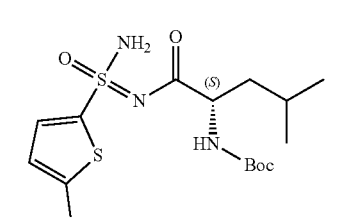 | Int-B-5.15 | Int-B-4.15<br>Int-X1 | LCMS ESI (m/z):<br>454.4 & 456.4<br>(M & M + 2) |

Synthesis Table 16

| Structure | Compound ID | Precursor | Analytical data |
|---|---|---|---|
| (three stereoisomer structures: isopropyl-thiophene sulfoximine-Leu-Boc) | Int-B-5.16 | Int-B-4.16<br>Int-X1 | LCMS ESI (m/z): 418.8 (M + H)<br>Chiral prep HPLC: YMC CHIRALART CELLULOSE_SC<br>Mobile phase: Heptane_IPA (80-20)<br>Isomer-1 (Fr-1): Retention time: 8.87 min<br>Isomer-2 (Fr-2): Retention time: 25.07 min |
| (three stereoisomer structures: ethyl-thiophene sulfoximine-Leu-Boc) | Int-B-5.20<br>Int-B-5.20-Fr-1<br>Int-B-5.20-Fr-2 | Int-B-4.21<br>Int-X1 | LCMS ESI (m/z): 404.5 (M + H)<br>Chiral prep HPLC: YMC CHIRALART CELLULOSE_SC<br>Mobile phase: Heptane_IPA-MeOH (70-30)_90:10<br>Isomer-1 (Fr-1): Retention time: 16.26 min<br>Isomer-2 (Fr-2): Retention time: 31.34 min |
| (two stereoisomer structures: dichloro-thiophene sulfoximine-Leu-Boc) | Int-B-5.21<br>Int-B-5.21-Fr-1<br>Int-B-5.21-Fr-1 | Int-B-4.22<br>Int-X1 | LCMS ESI (m/z): 444.6 & 446.6 (M & M + 2)<br>Chiral prep HPLC: CHIRALPAK IG SFC<br>Mobile phase: Heptane_IPA-ACN (70-30)_80:20<br>Isomer-1 (Fr-1): Retention time: 9.45 min<br>Isomer-2 (Fr-2): Retention time: 18.88 min |

Synthesis Table 16

| Structure | Compound ID | Precursor | Analytical data |
|---|---|---|---|
| | | | |
| | Int-B-5.22<br>Int-B-5.22-Fr-1<br>Int-B-5.22-Fr-2 | Int-B-4.23<br>Int-X1 | LCMS ESI (m/z):<br>390.5 (M + H)<br>Chiral prep HPLC:<br>YMC CHIRALART<br>CELLULOSE_SC<br>Mobile phase:<br>Heptane_IPA-ACN<br>(70-30)_95:5<br>Isomer-1 (Fr-1):<br>Retention time: 22.97 min<br>Isomer-2 (Fr-2):<br>Retention time: 35.68 min |
| | Int-B-5.23<br>Int-B-5.23-Fr-1<br>Int-B-5.23-Fr-2 | Int-B-4.24<br>Int-X1 | LCMS ESI (m/z):<br>410.6 & 412.5<br>(M & M + 2)<br>Chiral prep HPLC:<br>CHIRALART<br>CELLULOSE-SC<br>Mobile phase:<br>n-HEPTANE_IPA (80:20)<br>Isomer-1 (Fr-1):<br>Retention time: 7.22 min<br>Isomer-2 (Fr-2):<br>Retention time: 10.82 min |

Synthesis Table 16

| Structure | Compound ID | Precursor | Analytical data |
|---|---|---|---|
| 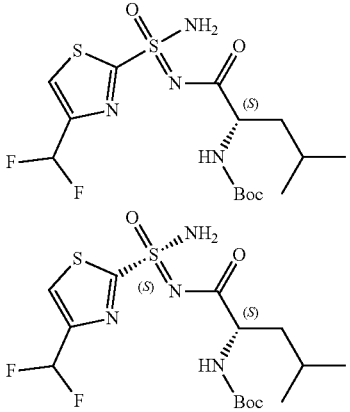 | Int-B-5.24<br>Int-B-5.24-Fr-1<br>Int-B-5.24-Fr-2 | Int-B-4.25<br>Int-X1 | LCMS ESI (m/z):<br>427.7 (M + H)<br>Chiral prep HPLC:<br>CHIRALPAK IG SFC<br>Mobile phase:<br>Heptane_IPA-ACN<br>(70-30)_82:18<br>Isomer-1 (Fr-1):<br>Retention time: 33.94 min<br>Isomer-2 (Fr-2):<br>Retention time: 44.31 min |
| 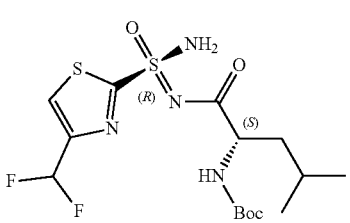 | | | |
| 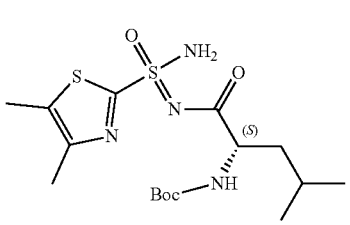 | | | |
| 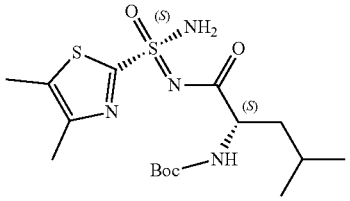 | Int-B-5.25<br>Int-B-5.25-Fr-1<br>Int-B-5.25-Fr-2 | Int-B-4.26<br>Int-X1 | LCMS ESI (m/z):<br>405.8 (M + H)<br>Chiral prep HPLC:<br>CHIRALPAK IG SFC<br>Mobile phase:<br>Heptane_IPA-ACN<br>(70-30)_80:20<br>Isomer-1 (Fr-1):<br>Retention time: 20.87 min<br>Isomer-2 (Fr-2):<br>Retention time: 32.98 min |
| 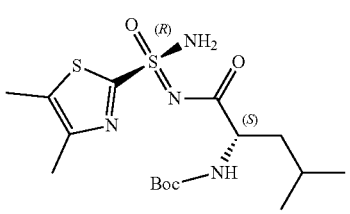 | | | |

Synthesis Table 16

| Structure | Compound ID | Precursor | Analytical data |
|---|---|---|---|
| [structures of thiazole sulfoximine leucine derivatives, three stereoisomers] | Int-B-5.26<br>Int-B-5.26-Fr-1<br>Int-B-5.26-Fr-2 | Int-B-4.27<br>Int-X1 | LCMS ESI (m/z):<br>391.7 (M + H)<br>Chiral prep HPLC:<br>YMC CHIRALART<br>CELLULOSE-SC<br>Mobile phase:<br>n-Heptane_IPA (84:16)<br>Isomer-1 (Fr-1):<br>Retention time: 21.65 min<br>Isomer-2 (Fr-2):<br>Retention time: 37.45 min |
| [structures of phenyl-thiophene sulfoximine leucine derivatives, three stereoisomers] | Int-B-5.27<br>Int-B-5.27-Fr-1<br>Int-B-5.27-Fr-2 | Int-B-4.28<br>Int-X1 | Chiral prep HPLC:<br>YMC CHIRALART<br>CELLULOSE_SC<br>Mobile phase:<br>Heptane-IPA:ACN<br>(70:30)_90:10<br>Isomer-1 (Fr-1):<br>Retention time: 14.31 min<br>Isomer-2 (Fr-2):<br>Retention time: 22.33 min |

Synthesis Table 16

| Structure | Compound ID | Precursor | Analytical data |
|---|---|---|---|
| | Int-B-5.28<br>Int-B-5.28-Fr-1<br>Int-B-5.28-Fr-2 | Int-B-4.29<br>Int-X1 | LCMS ESI (m/z):<br>427.1 (M + H)<br>Chiral prep HPLC:<br>YMC CHIRALART<br>CELLULOSE_SC<br>Mobile phase:<br>Heptane-IPA_60:40<br>Isomer-1 (Fr-1):<br>Retention time: 15.63 min<br>Isomer-2 (Fr-2):<br>Retention time: 40.25 min |
| 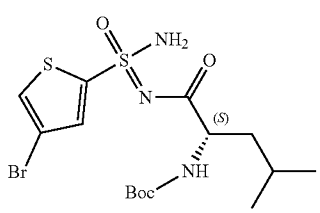 | Int-B-5.29 | Int-B-4.30<br>Int-X1 | LCMS ESI (m/z):<br>454.7 & 456.7<br>(M & M + 2) |
| | Int-B-5.30<br>Int-B-5.30-Fr-1<br>Int-B-5.30-Fr-2 | Int-B-4.31<br>Int-X1 | LCMS ESI (m/z):<br>401.2 (M + H)<br>Chiral prep HPLC:<br>YMC CELLULOSE-SC<br>Mobile phase:<br>Liq. $CO_2$_IPA_85:15<br>Isomer-1 (Fr-1):<br>Retention time: 4.5 min<br>Isomer-2 (Fr-2):<br>Retention time: 6.5 min |

Synthesis Table 16

| Structure | Compound ID | Precursor | Analytical data |
|---|---|---|---|
| 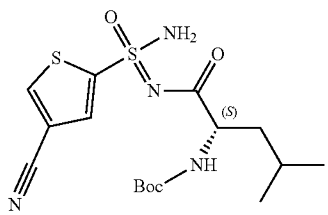 | Int-B-5.31<br>Int-B-5.31-Fr-1<br>Int-B-5.31-Fr-2 | Int-B-4.32<br>Int-X1 | LCMS ESI (m/z):<br>401.0 (M + H)<br>Chiral prep HPLC:<br>CHIRALPAK IG<br>Mobile phase:<br>Heptane_IPA-ACN<br>(70:3)_75:25<br>Isomer-1 (Fr-1):<br>Retention time: 7.01 min<br>Isomer-2 (Fr-2):<br>Retention time: 8.45 min |
| 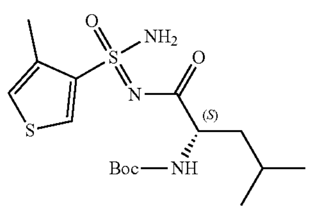 | Int-B-5.32<br>Int-B-5.32-Fr-1<br>Int-B-5.32-Fr-2 | Int-B-4.33<br>Int-X1 | LCMS ESI (m/z):<br>390.44 (M + H)<br>Chiral prep HPLC:<br>YMC CHIRALART<br>CELLULOSE-SC,<br>Mobile phase:<br>n-HEPTANE_IPA:MEOH<br>(70:30)_93:7<br>Isomer-1 (Fr-1):<br>Retention time: 17.88 min<br>Isomer-2 (Fr-2):<br>Retention time: 33.96 min |

-continued

Synthesis Table 16

| Structure | Compound ID | Precursor | Analytical data |
|---|---|---|---|
| (three structures: 4-methylthiophen-3-yl sulfonimidoyl variants with Boc-Ile, stereochemistry labels (S), (S)/(S), (R)/(S)) | Int-B-5.33<br>Int-B-5.33-Fr-1<br>Int-B-5.33-Fr-2 | Int-B-4.33<br>Int-X2 | LCMS ESI (m/z):<br>390.5 (M + H)<br>Chiral prep HPLC:<br>CHIRALPAK IG SFC<br>Mobile phase:<br>n-HEPTANE_IPA:ACN<br>(70:30)_87:13<br>Isomer-1 (Fr-1):<br>Retention time: 23.03 min<br>Isomer-2 (Fr-2):<br>Retention time: 29.31 min |
| (three structures: 5-chloro-4-methylthiophen-3-yl sulfonimidoyl with Boc-Leu) | Int-B-5.34<br>Int-B-5.34-Fr-1<br>Int-B-5.34-Fr-2 | Int-B-4.34<br>Int-X1 | LCMS ESI (m/z):<br>424.3 (M + H)<br>Chiral prep HPLC:<br>YMC CHIRALART<br>CELLULOSE-SC<br>Mobile phase:<br>n-HEPTANE_IPA (80:20)<br>Isomer-1 (Fr-1):<br>Retention time: 7.59 min<br>Isomer-2 (Fr-2):<br>Retention time: 17.44 min |
| (two structures: pyridin-2-yl sulfonimidoyl with Boc-Leu) | Int-B-5.35<br>Int-B-5.35-Fr-1<br>Int-B-5.35-Fr-2 | Int-B-4.35<br>Int-X1 | LCMS ESI (m/z):<br>371.3 (M + H)<br>Chiral prep HPLC:<br>CHIRALART<br>CELLULOSE-SC<br>Mobile phase:<br>n-HEPTANE_IPA:ACN<br>(70:30)_(92:8)<br>Isomer-1 (Fr-1):<br>Retention time: 18 min<br>Isomer-2 (Fr-2):<br>Retention time: 25 min |

-continued

Synthesis Table 16

| Structure | Compound ID | Precursor | Analytical data |
|---|---|---|---|
| 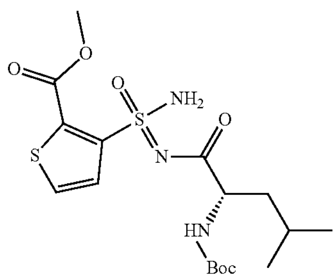 [SMILES: COC(=O)c1sccc1S(N)(=O)=NC(=O)[C@H](CC(C)C)NC(=O)OC(C)(C)C] | Int-B-5.37 | Int-B-4.37<br>Int-X1 | LCMS ESI (m/z):<br>434.4 (M + H) |
| 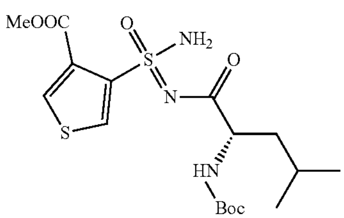 [SMILES: COC(=O)c1cscc1S(N)(=O)=NC(=O)[C@H](CC(C)C)NC(=O)OC(C)(C)C] | Int-B-5.38 | Int-B-4.38<br>Int-X1 | LCMS ESI (m/z):<br>434.5 (M + H) |
| | Int-B-5.39<br>Int-B-5.39-Fr-1<br>Int-B-5.39-Fr-2 | Int-B-4.39<br>Int-X1 | LCMS ESI (m/z):<br>390.5 (M + H)<br>Chiral prep HPLC:<br>YMC CHIRALART<br>CELLULOSE-SC<br>Mobile phase:<br>n-HEPTANE_IPA:MEOH<br>(70:30)_90:10<br>Isomer-1 (Fr-1):<br>Retention time: 18.25 min<br>Isomer-2 (Fr-2):<br>Retention time: 27.53 min |

Synthesis Table 16

| Structure | Compound ID | Precursor | Analytical data |
|---|---|---|---|
| | Int-B-5.40<br>Int-B-5.40-Fr-1<br>Int-B-5.40-Fr-2 | Int-B-4.40<br>Int-X1 | LCMS ESI (m/z):<br>432.8 (M + H)<br>Chiral prep HPLC:<br>YMC CHIRALART<br>CELLULOSE_SC<br>Mobile phase:<br>Heptane_IPA-ACN<br>(70-30)_90:10<br>Isomer-1 (Fr-1):<br>Retention time: 8.90 min<br>Isomer-2 (Fr-2):<br>Retention time: 23.76 min |
| 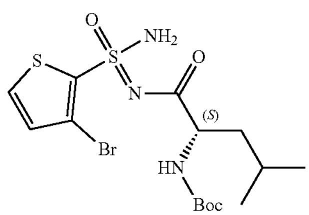 | Int-B-5.41 | Int-B-4.41<br>Int-X1 | LCMS ESI (m/z):<br>454.4 & 456.4<br>(M & M + 2) |
| | Int-B-5.42<br>Int-B-5.42-Fr-1<br>Int-B-5.42-Fr-2 | Int-B-4.42<br>Int-X1 | LCMS ESI (m/z):<br>534.4 (M + H)<br>Chiral prep HPLC:<br>CHIRALART<br>CELLULOSE-SC<br>Mobile phase:<br>n-Heptane_IPA:MeOH<br>(70:30)_92:8<br>Isomer-1 (Fr-1):<br>Retention time: 19.81 min<br>Isomer-2 (Fr-2):<br>Retention time: 36.97 min |

Synthesis Table 16

| Structure | Compound ID | Precursor | Analytical data |
|---|---|---|---|
| (3,4-dibromothiophene sulfoximine (R) coupled with (S)-Leu-Boc) | | | |
| (3,4-dibromothiophene sulfoximine coupled with (S)-Ile-Boc); three stereoisomers shown | Int-B-5.43<br>Int-B-5.43-Fr-1<br>Int-B-5.43-Fr-2 | Int-B-4.42<br>Int-X2 | LCMS ESI (m/z):<br>534.3 (M + H)<br>Chiral prep HPLC:<br>CHIRALPAK IG SFC<br>Mobile phase:<br>n-Heptane_IPA:ACN<br>(70:30)_86:14<br>Isomer-1 (Fr-1):<br>Retention time: 24.32 min<br>Isomer-2 (Fr-2):<br>Retention time: 41.43 min |
| (3-methoxythiophene sulfoximine coupled with (S)-Leu-Boc); three stereoisomers shown | Int-B-5.44<br>Int-B-5.44-Fr-1<br>Int-B-5.44-Fr-2 | Int-B-4.43<br>Int-X1 | LCMS ESI (m/z):<br>406.44 (M + H)<br>Chiral prep HPLC:<br>YMC CHIRALPAK<br>IG SFC<br>Mobile phase:<br>Heptane_IPA-MeOH<br>(70-30)_70:30<br>Isomer-1 (Fr-1):<br>Retention time: 20.89 min<br>Isomer-2 (Fr-2):<br>Retention time: 29.49 min |

Synthesis Table 16

| Structure | Compound ID | Precursor | Analytical data |
|---|---|---|---|
| 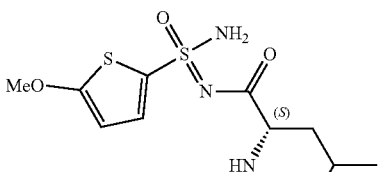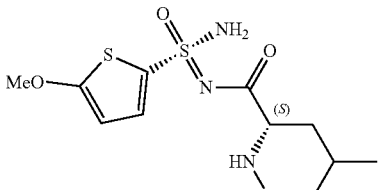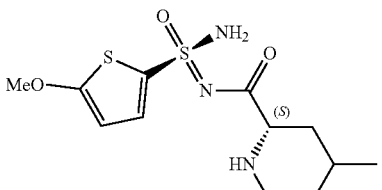 | Int-B-5.45<br>Int-B-5.45-Fr-1<br>Int-B-5.45-Fr-2 | Int-B-4.44<br>Int-X1 | LCMS ESI (m/z):<br>410.4 [M + H]<br>Chiral prep HPLC:<br>CHIRALPAK IG SFC<br>Mobile phase:<br>Heptane_IPA-ACN<br>(70-30)_82:18<br>Isomer-1 (Fr-1):<br>Retention time: 25.30 min<br>Isomer-2 (Fr-2):<br>Retention time: 34.09 min |
| 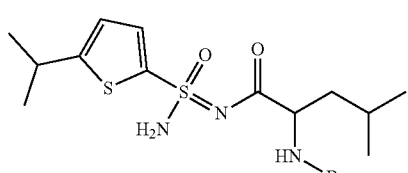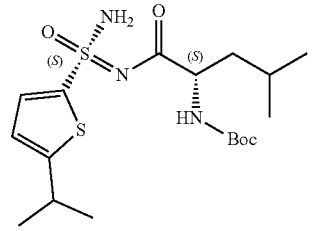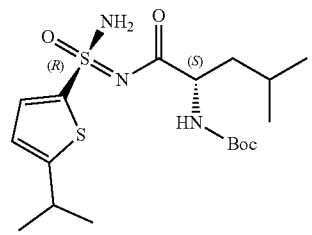 | Int-B-5.46<br>Int-B-5.46-Fr-1<br>Int-B-5.46-Fr-2 | Int-B-4.45<br>Int-X1 | LCMS ESI (m/z):<br>418.5 (M + H)<br>Chiral prep HPLC:<br>YMC CHIRALART<br>CELLULOSE_SCM<br>Mobile phase:<br>Heptane_IPA-Methanol<br>(70-30)_92:8<br>Isomer-1 (Fr-1):<br>Retention time: 19.77 min<br>Isomer-1 (Fr-2):<br>Retention time: 34.22 min |

Synthesis Table 16

| Structure | Compound ID | Precursor | Analytical data |
|---|---|---|---|
| 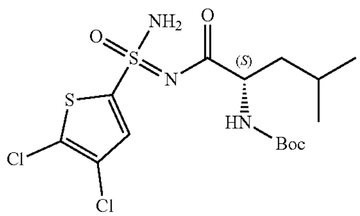 | Int-B-5.48<br>Int-B-5.48-Fr-1<br>Int-B-5.48-Fr-2 | Int-B-4.48<br>Int-X1 | LCMS ESI (m/z):<br>444.5 & 446.5<br>(M & M + 2)<br>Chiral prep HPLC:<br>CHIRALPAK IG SFC<br>Mobile phase:<br>n-Heptane_IPA-MeOH<br>(70-30)<br>Isomer-1 (Fr-1):<br>Retention time: 7.02 min<br>Isomer-2 (Fr-2):<br>Retention time: 16.71 min |
| 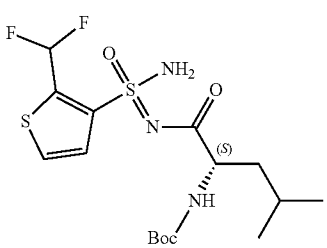 | Int-B-5.49<br>Int-B-5.49-Fr-1<br>Int-B-5.49-Fr-2 | Int-B-4.49<br>Int-X1 | LCMS ESI (m/z):<br>426.6 (M + H)<br>Chiral prep HPLC:<br>YMC CHIRALART<br>CELLULOSE_SC<br>Mobile phase:<br>Heptane_IPA-ACN<br>(70-30)_90:10<br>Isomer-1 (Fr-1):<br>Retention time: 21.97 min<br>Isomer-2 (Fr-2):<br>Retention time: 37.23 min |

-continued

Synthesis Table 16

| Structure | Compound ID | Precursor | Analytical data |
|---|---|---|---|
| 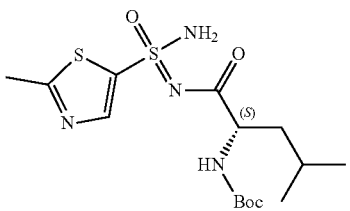 | Int-B-5.50<br>Int-B-5.50-Fr-1<br>Int-B-5.50-Fr-2 | Int-B-4.50<br>Int-X1 | LCMS ESI (m/z):<br>391.2 (M + H)<br>Chiral prep HPLC:<br>YMC IG SFC<br>Mobile phase:<br>Heptane_IPA-ACN<br>(70-30)<br>Isomer-1 (Fr-1):<br>Retention time: 10.09 min<br>Isomer-2 (Fr-2):<br>Retention time: 21.01 min |
| 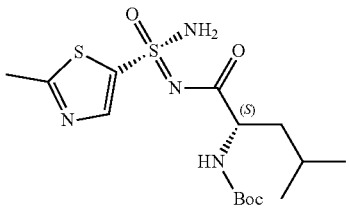 | | | |
| 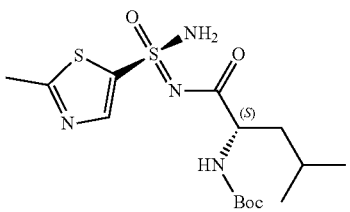 | | | |
| 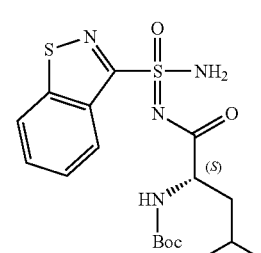 | Int-B-5.55<br>Int-B-5.55-Fr-1<br>Int-B-5.55-Fr-2 | Int-B-4.51<br>Int-X1 | LCMS ESI (m/z):<br>427.7 (M + H)<br>Chiral prep HPLC:<br>YMC CHIRALART<br>CELLULOSE-SC<br>Mobile phase:<br>Hepatane_IPA (79:21)<br>Isomer-1 (Fr-1):<br>Retention time: 16.18 min<br>Isomer-2 (Fr-2):<br>Retention time: 31.82 min |
| 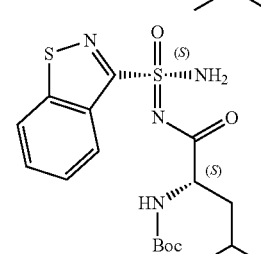 | | | |
| 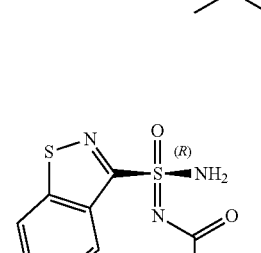 | | | |

Synthesis Table 16

| Structure | Compound ID | Precursor | Analytical data |
|---|---|---|---|
| 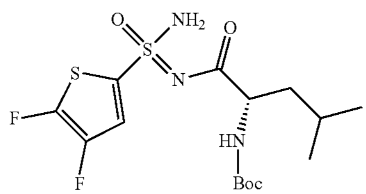 [SMILES: CC(C)C[C@H](NC(=O)OC(C)(C)C)C(=O)N=S(N)(=O)c1cc(F)c(F)s1] | Int-B-5.56 | Int-B-4.52<br>Int-X1 | UPLCMS ESI (m/z):<br>412 (M + H)⁺ |

Synthesis of tert-butyl ((2S)-1-((amino(4-methylthiazol-2-yl)(oxo)-λ6-sulfanylidene)amino)-4-methyl-1-oxopentan-2-yl)carbamate (Int-B-5.2

Route A

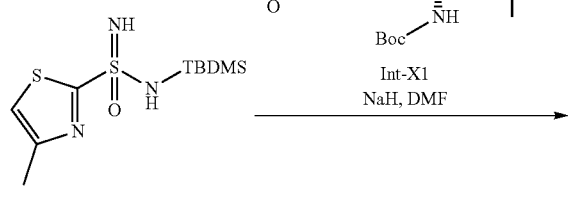

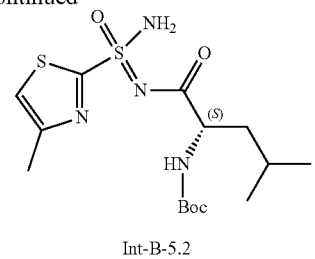

Int-B-5.2

To a stirred solution of Int-B-3.2 (70 mg, 0.24 mmol) in DMF (0.7 mL) was added 60% NaH (28 mg, 0.72 mmol) followed by Int-X1 (78 mg, 0.24 mmol) at room temperature and stirred for 3 h. After completion of the reaction as indicated by TLC, the reaction mixture was poured into water and extracted with ethyl acetate. The combined organic layer was washed with brine, dried over Na₂SO₄ and evaporated under vacuum to give the crude product. The crude was purified by silica gel column chromatography (ethyl acetate/hexane: 4:6) to give the title compound, Int-B-5.2, as a white solid (35 mg, 28.92%). It was observed that during the work up/purification that the TBDMS group was cleaved. LCMS ESI (m/z): 413.1 (M+Na).

Route B

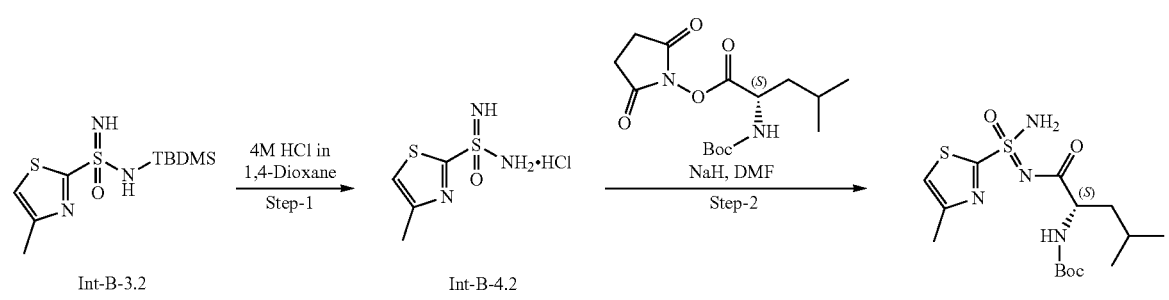

Chiral isomer separation

-continued

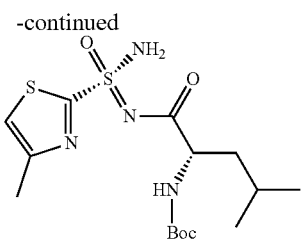
Int-B-5.2-Fr-1

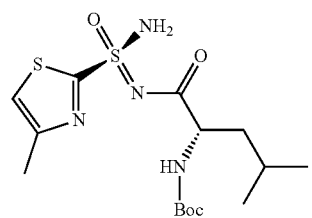
Int-B-5.2-Fr-2

Step-1: Int-B-4.2 was made according to the procedure described for Int-B-4.1. ¹H NMR (400 MHz, DMSO) δ 7.63 (s, 1H), 2.43 (s, 3H).

Step-2: Int-B-5.2 was made according to the procedure described for Int-B-5.1. Further the diastereomers were separated by Chiral prep HPLC (Chiral prep HPLC: YMC CHIRALART CELLULOSE_SC, Mobile phase: Heptane_IPA-ACN (70-30) 85:15 to give Isomer-1 and Isomer-2. These isomers were eluted at retention time 13.16 min (Isomer-1) and 18.41 min (Isomer-2).

The following intermediates were made according to the procedure described for Int-B-5.2.

Synthesis Table 17

| Structure | Compound ID | Precursor | Analytical data |
|---|---|---|---|
| (quinoline sulfonimidamide-Ile-Boc, stereochem unspecified) | Int-B-5.3 | Int-B-3.3 Int-X2 | LCMS ESI (m/z): 421.3 [M + H]+ Chiral prep HPLC: YMC CHIRALART CELLULOSE_SC Mobile phase: Heptane_IPA-ACN (70-30)_85:15 Isomer-1 (Fr-1): Retention time: 11.46 min Isomer-2 (Fr-2): Retention time: 13.18 min |
| (quinoline sulfonimidamide (S)-Ile-Boc) | | | |
| (quinoline sulfonimidamide (R)-Ile-Boc) | | | |
| (4-Cl-thiazole sulfonimidamide-Leu-Boc) | Int-B-5.4 Int-B-5.4-Fr-1 Int-B-5.4-Fr-2 | Int-B-3.4 Int-X1 | LCMS ESI (m/z): 411.2 & 413.2 [M + H]+ Chiral prep HPLC: CHIRALART CELLULOSE-SC Mobile phase: n-Heptane_IPA (82:18) Isomer-1 (Fr-1): Retention time: 12.66 min Isomer-2 (Fr-2): Retention time: 21.56 min |
| (4-Cl-thiazole (S)-sulfonimidamide-(S)-Leu-Boc) | | | |

Synthesis Table 17

| Structure | Compound ID | Precursor | Analytical data |
|---|---|---|---|
| (structure: 4-chlorothiazole sulfoximine with (R) at S, acyl-Leu-Boc with (S)) | | | |
| (structure: 4-chlorothiazole sulfoximine, acyl-Ile-Boc with (S),(S)) | Int-B-5.5 | Int-B-3.4<br>Int-X2 | LCMS ESI (m/z):<br>311.1 & 313.0<br>[M + H − Boc]+ |
| (structure: 5-methylthiazole sulfoximine, acyl-Leu-Boc with (S)) | Int-B-5.6 | Int-B-3.5<br>Int-X1 | LCMS ESI (m/z):<br>291.0<br>[M + H − Boc]+ |
| (structure: 2,4-dichlorothiazole sulfoximine, acyl-Leu-Boc with (S)) | Int-B-5.51 | Int-B-3.7<br>Int-X1 | LCMS ESI (m/z):<br>444.3 (M + H) |
| (structure: 5-chlorothiophene sulfoximine, acyl-Leu-Boc with (S); and (S) and (R) isomers shown) | Int-B-5.52<br>Int-B-5.52-Fr-1<br>Int-B-5.52-Fr-2 | Int-B-3.12<br>Int-X1 | LCMS ESI (m/z):<br>410.4 & 414.4<br>(M & M + 2)<br>Chiral prep HPLC:<br>YMC CHIRALART<br>CELLULOSE_SC<br>Mobile phase:<br>Heptane_IPA-85:15<br>Isomer-1 (Fr-1):<br>Retention time: 16.70 min<br>Isomer-2 (Fr-2):<br>Retention time: 30.73 min |

Synthesis Table 17

| Structure | Compound ID | Precursor | Analytical data |
|---|---|---|---|
| 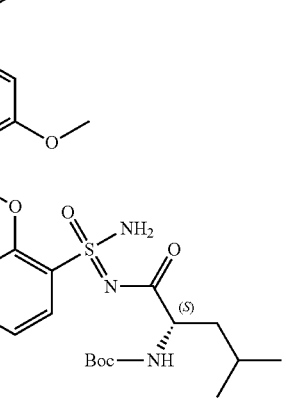 | Int-B-5.53 | Int-B-3.17<br>Int-X1 | LCMS ESI (m/z): 536.68 (M + H) |
| 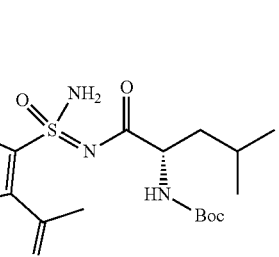 | Int-B-5.54<br>Int-B-5.54-Fr-1<br>Int-B-5.54-Fr-2 | Int-B-3.46<br>Int-X1 | LCMS ESI (m/z): 418.5 (M + H)<br>Chiral prep HPLC:<br>YMC CHIRALART<br>CELLULOSE_SC<br>Mobile phase:<br>Heptane_IPA-MeOH<br>(70-30)_87:13<br>Isomer-1 (Fr-1):<br>Retention time: 27.71 min<br>Isomer-2 (Fr-2):<br>Retention time: 35.40 min |
| 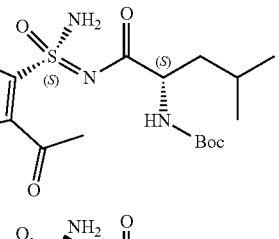 | Int-B-5.57 | Int-B-3.58<br>Int-X1 | $^1$H NMR (400 MHz, CDCl$_3$) δ 8.44-8.28 (m, 1H), 7.90 (ddd, J = 8.6, 4.5, 2.2 Hz, 1H), 7.37 (ddd, J = 10.1, 8.6, 1.5 Hz, 1H), 6.67 (s, 2H), 4.90 (d, J = 8.1 Hz, 1H), 4.25-4.11 (m, 1H), 1.81-1.56 (m, 2H), 1.53-1.44 (m, 1H), 1.40 (d, J = 10.0 Hz, 9H), 0.94 (d, J = 6.1 Hz, 6H).<br>LCMS ESI (m/z): 413 [M + H]$^+$ |

Synthesis Table 17

| Structure | Compound ID | Precursor | Analytical data |
|---|---|---|---|
| (structure: 4-fluorothiophene sulfoximine with Boc-leucine amide, two diastereomers shown) | Int-B-5.58 | Int-B-3.55<br>Int-X1 | UPLCMS ESI (m/z): 394 (M + H)+<br>Chiral prep HPLC: CHIRALPAK IC<br>Mobile phase: Heptane-IPA-DCM (66-19-15)<br>Isomer-1 (Fr-1): Retention time: 5.89 min<br>Isomer-2 (Fr-2): Retention time: 12.92 min<br>Isomer-1:<br>$^1$H NMR (300 MHz, CDCl$_3$) δ 7.57 (t, J = 1.5 Hz, 1H), 7.06 (d, J = 1.9 Hz, 1H), 6.42 (s, 2H), 4.96 (d, J = 8.6 Hz, 1H), 4.28-4.12 (m, 1H), 1.82-1.56 (m, 3H), 1.42 (s, 10H), 0.93 (d, J = 6.1 Hz, 6H).<br>Isomer-2:<br>$^1$H NMR (300 MHz, CDCl$_3$): δ 7.62-7.41 (m, 1H), 7.04 (d, J = 1.9 Hz, 1H), 6.55 (s, 2H), 4.95 (d, J = 8.5 Hz, 1H), 4.27-4.09 (m, 1H), 1.78-1.54 (m, 3H), 1.40 (s, 10H), 0.92 (dd, J = 6.3, 2.2 Hz, 6H) |
| (structure: 1-methylpyrazole sulfoximine with Boc-protected amino acid) | Int-B-5.59 | Int-B-3.63<br>Int-X1 | $^1$H NMR (300 MHz, CDCl$_3$) δ 7.42 (d, J = 2.3 Hz, 1H), 6.78 (d, J = 2.4 Hz, 1H), 6.29 (s, 2H), 5.00 (t, J = 10.4 Hz, 1H), 4.28-4.10 (m, 1H), 3.97 (d, J = 1.5 Hz, 3H), 1.79-1.56 (m, 3H), 1.53-1.32 (m, 10H), 1.01-0.71 (m, 6H) |

Synthesis of (2S)-2-amino-N-(amino(oxo)(pyridin-4-yl)-λ$^6$-sulfanylidene)-4-methylpentanamide (2S)-2-amino-N-(amino(oxo)(pyridin-4-yl)-λ$^6$-sulfanylidene)-4-methylpentanamide

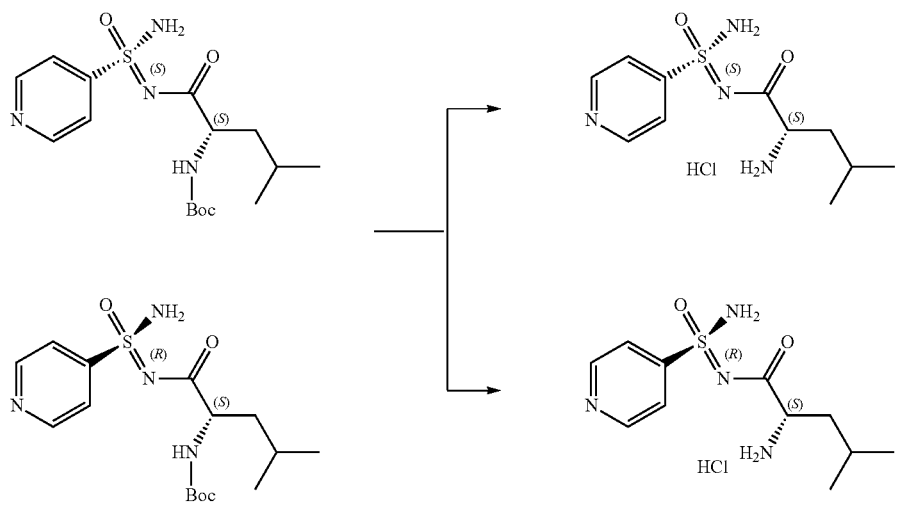

Int-B-5.1-Fr-1 and Int-B-5.1-Fr-2

To a solution of Int-B-5.1-Fr-1 (Isomer-1) (16 mg, 0.04 mmol) in dichloromethane (1 mL) was added 4 M HCl in 1,4-dioxane (0.1 mL) at 0° C. The reaction mixture was allowed to stir at room temperature for 1 h. After completion of the reaction as indicated by TLC, the reaction mixture was concentrated under reduced pressure followed by trituration with n-pentane and diethyl ether to give the title compound, ANASIA-059-1, as a hydrochloride salt (11 mg, 94%). $^1$H-NMR (400 MHz, DMSO-d$_6$) δ: 8.90 (d, J=5.6 Hz, 2H), 8.33 (brs, 2H), 8.10 (brs, 3H), 7.89 (d, J=6 Hz, 2H); 3.80-3.70 (m, 1H); 1.79-1.57 (m, 3H), 0.91-0.87 (two d, 6H). LCMS ESI (m/z): 271.44 (M+1). Purity at 210 nm: 95.04%.

To a solution of Int-B-5.1-Fr-2 (Isomer-2) (30 mg, 0.08 mmol) in dichloromethane (1 mL) was added 4 M HCl in 1,4-dioxane (0.1 mL) at 0° C. The reaction mixture was allowed to stir at room temperature for 1 h. After completion of the reaction as indicated by TLC, the reaction mixture was concentrated under reduced pressure followed by trituration with n-pentane and diethyl ether to give the title compound, ANASIA-059-2, as a hydrochloride salt (13 mg, 59.38%). $^1$H-NMR (400 MHz, DMSO-d$_6$) δ: 8.97 (brs, 2H), 8.39 (brs, 2H), 8.14 (brs, 3H), 7.93 (brs, 2H); 3.66 (brs, 1H); 1.74-1.45 (m, 3H), 0.87-0.84 (two d, 6H). LCMS ESI (m/z): 271.40 (M+1). Purity at 210 nm: 97.87%.

Synthesis of (2S)-2-amino-N-(amino(4-methylthiazol-2-yl)(oxo)-λ6-sulfanylidene)-4-methyl pentanamide hydrochloride (ANASIA-004

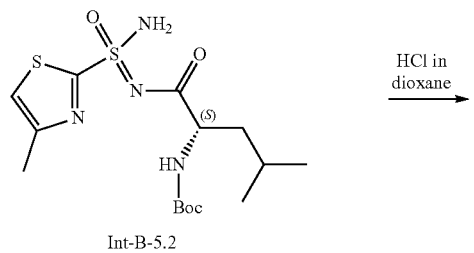

Int-B-5.2

HCl in dioxane →

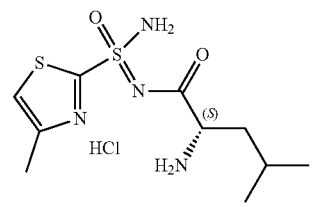

ANASIA004

A solution of Int-B-5.2 (33 mg, 0.06 mmol) in 4 M HCl in 1,4-dioxane (0.5 mL) was allowed to stir at room temperature for 2 h. After completion of the reaction as indicated by TLC, the reaction mixture was concentrated under reduced pressure followed by trituration with n-pentane and diethyl ether to give the title compound, ANASIA-004, as a hydrochloride salt (11 mg, 57.89%). $^1$H-NMR (400 MHz, DMSO-d$_6$) δ: 8.50-8.45 (m, 2H), 8.06 (m, 3H), 7.73 (s, 1H), 3.69-3.65 (m, 1H), 2.41-1.47 (m, 3H), 2.31 (s, 3H), 0.91-0.86 (m, 6H). LCMS ESI (m/z): 291.0 (M+H), Purity at 210 nm: 100%.

The following compounds were made according to the procedure described for compound ANASIA-004 using HCl or TFA.

Synthesis Table 18

| Structure | Precursor | Analytical data |
|---|---|---|
| ![ANASIA-004-1 structure with CF₃COOH] ANASIA-004-1 | Int-B-5.2-Fr-1<br>Int-B-5.2-Fr-2 | Isomer-1<br>$^1$H NMR (400 MHz, DMSO) δ 8.48 (s, 2H), 7.99 (s, 3H), 7.74 (s, 1H), 3.76 (bs, 1H), 2.41 (s, 3H), 1.82-1.77 (m, 1H), 1.71-1.64 (m, 1H), 1.49-1.42 (m, 1H), 0.89 (d, 6H).<br>LCMS ESI (m/z): 291.3 (M + H)<br>Purity at 210 nm: 97.51%<br>Isomer-2<br>$^1$H NMR (400 MHz, DMSO) δ 8.54 (s, 2H), 7.99 (bs, 3H), 7.74 (s, 1H), 3.71 (bs, 1H), 2.42 (s, 3H), 1.80-1.68 (m, 2H), 1.60-1.55 (m, 1H), 0.92-0.84 (m, 6H).<br>LCMS ESI (m/z): 291.3 (M + H)<br>Purity at 210 nm: 99.02% |
| ![ANASIA-004-2 structure with CF₃COOH] ANASIA-004-2 | | |

Synthesis Table 18

| Structure | Precursor | Analytical data |
|---|---|---|
| 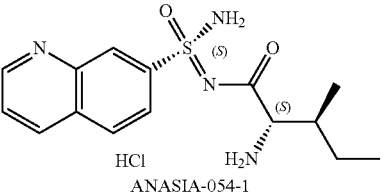<br>ANASIA-054-1<br><br>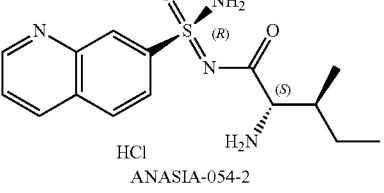<br>ANASIA-054-2 | Int-B-5.3-Fr-1<br>Int-B-5.3-Fr-2 | Isomer-1<br>$^1$H NMR (400 MHz, DMSO-d$_6$) δ 9.08 (s, 1H), 8.65-8.49 (m, 2H), 8.32-8.17 (m, 3H), 8.04 (d, J = 8.6 Hz, 1H), 7.92 (brs, 3H), 7.74 (dd, J = 8.3, 1H), 3.65 (brs, 1H), 1.93 (brs, 1H), 1.52-1.21 (m, 2H), 0.95-0.73 (m, 6H).<br>LCMS ESI (m/z): 321.4 (M + 1)<br>Purity at 210 nm: 99.57%<br>Isomer-2<br>$^1$H NMR (400 MHz, DMSO-d$_6$) δ 9.07 (s, 1H), 8.64-8.46 (m, 2H), 8.34-8.14 (m, 3H), 8.00 (d, J = 9.2 Hz, 1H), 7.85 (brs, 3H), 7.79-7.68 (m, 1H), 3.69 (brs, 1H), 1.91 (brs, 1H), 1.19-0.99 (m, 2H), 0.89-0.60 (m, 6H).<br>LCMS ESI (m/z): 321.4 (M + 1)<br>Purity at 210 nm: 92.21% |
| 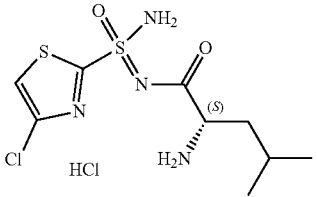<br>ANASIA-045<br><br>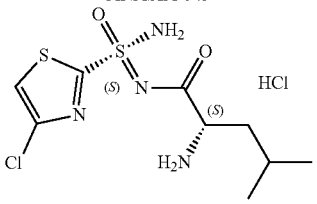<br>ANASIA-045-1<br><br>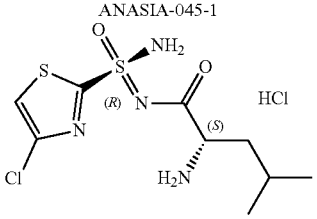<br>ANASIA-045-2 | Int-B-5.4<br>Int-B-5.4-Fr-1<br>Int-B-5.4-Fr-2 | Racemic<br>$^1$H NMR (400 MHz, DMSO-d$_6$) δ 8.76 (brs, 2H), 8.20 (s, 1H), 8.05 (brs, 3H), 3.78 (brs, 1H), 1.86-1.44 (m, 3H), 0.98-0.78 (m, 6H).<br>LCMS ESI (m/z): 311.2 & 313.2 (M + 1)<br>Purity at 210 nm: 100%<br>Isomer-1<br>1H NMR (400 MHz, DMSO) δ 8.59 (bs, 3H), 8.18 (s, 1H), 8.05 (bs, 2H), 3.77 (m, 1H), 1.84-1.79 (m, 1H), 1.71-1.64 (m, 1H), 1.54-1.45 (m, 1H), 0.91-0.88 (m, 6H).<br>LCMS ESI (m/z): 311.0 & 313.0 (M & M + 2)<br>Purity at 210 nm: 100.00%<br>Isomer-2<br>$^1$H NMR (400 MHz, DMSO) δ 8.76 (bs, 2H), 8.20 (s, 1H), 8.05 (bs, 3H), 3.75 (m, 1H), 1.82-1.73 (m, 1H), 1.71-1.68 (m, 1H), 1.62-1.55 (m, 1H), 0.91 (two d, J = 6.4 Hz, 6H).<br>LCMS ESI (m/z): 311.0 & 313.1 (M & M + 2)<br>Purity at 210 nm: 100.00% |
| 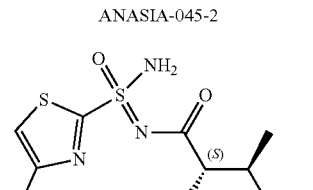<br>ANASIA-058 | Int-B-5.5 | $^1$H NMR (400 MHz, DMSO-d$_6$) δ 8.88-8.61 (m, 2H), 8.19 (s, 1H), 7.99 (brs, 3H), 3.83-3.68 (m, 1H), 1.95 (brs, 1H), 1.52-1.18 (m, 2H), 0.99-0.79 (m, 6H)<br>LCMS ESI (m/z): 311.1 & 313.1 (M + 1)<br>Purity at 210 nm: 100% |
| 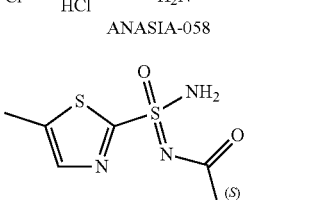<br>ANASIA-039 | Int-B-5.6 | $^1$H NMR (400 MHz, DMSO-d$_6$, D$_2$O exchange) δ 7.41 (s, 1H), 3.34 (brs, 1H), 2.39 (s, 3H), 1.77-1.30 (m, J = 94.9, 51.1 Hz, 3H), 0.81 (d, J = 6.2 Hz, 6H).<br>LCMS ESI (m/z): 291.0 (M + 1)<br>Purity at 210 nm: 97.83% |

Synthesis Table 18

| Structure | Precursor | Analytical data |
|---|---|---|
| ANASIA-026-1<br>ANASIA-026-2 | Int-B-5.7 | Isomer-1<br>$^1$H NMR (400 MHz, DMSO-d$_6$) δ 8.51 (brs, 2H), 8.02 (brs, 3H), 7.78-7.66 (m, 1H), 7.29 (t, 2H), 3.65 (brs, 1H), 1.82-1.53 (m, 3H), 0.99-0.76 (m, 6H).<br>LCMS ESI (m/z): 306.3 (M + 1)<br>Purity at 210 nm: 95.12%<br>Isomer-2<br>$^1$H NMR (400 MHz, DMSO-d$_6$) δ 8.51 (brs, 2H), 8.02 (brs, 3H), 7.77-7.67 (m, 1H), 7.34-7.25 (m, 2H), 3.71-3.62 (m, 1H), 1.80-1.53 (m, 3H), 0.96-0.76 (m, 6H).<br>LCMS ESI (m/z): 306.3 (M + 1)<br>Purity at 210 nm: 95.02% |
| ANASIA-081-1<br>ANASIA-081-2 | Int-B-5.8-Fr-1<br>Int-B-5.8-Fr-2 | Isomer-1<br>$^1$H NMR (400 MHz, DMSO)<br>δ 8.66 (s, 2H), 8.25 (s, 1H), 7.97 (bs, 2H), 3.78 (s, 1H), 1.81-1.71 (m, 2H), 1.50-1.45 (m, 1H), 0.91-0.89 (m, 6H).<br>LCMS ESI (m/z): 344.3, 346.2 (M & M + 2)<br>Purity at 250 nm: 96.64%<br>Isomer-2<br>$^1$H NMR (400 MHz, DMSO)<br>δ 8.66 (s, 2H), 8.25 (s, 1H), 8.00 (s, 2H), 3.76-3.74 (m, 1H), 1.79-1.70 (m, 2H), 1.61-1.58 (m, 1H), 0.93-0.88 (m, 6H).<br>LCMS ESI (m/z): 344.3, 346.3 (M+ & M + 2)<br>Purity at 250 nm: 97.19% |
| ANASIA-091-1<br>ANASIA-091-2 | Int-B-5.9-Fr-1<br>Int-B-5.9-Fr-2 | Isomer-1<br>$^1$H NMR (400 MHz, DMSO) δ 8.02-7.99 (m, 5H), 7.44 (d, J = 5.6 Hz, 1H), 7.27 (d, J = 5.6 Hz, 1H), 3.68 (bs, 1H), 2.67 (s, 3H), 1.80-1.50 (m, 2H), 1.50-1.44 (m, 1H), 0.88-0.85 (m, 6H).<br>LCMS ESI (m/z): 290.5 (M + H)<br>Purity at 210 nm: 96.47%<br>Isomer-2<br>$^1$H NMR (400 MHz, DMSO) δ 8.02 (bs, 4H), 7.43 (d, J = 5.6 Hz, 1H), 7.29 (d, J = 5.6 Hz, 1H), 3.65 (s, 1H), 2.70 (s, 3H), 1.80-1.56 (m, 3H), 0.92-0.88 (m, 6H).<br>LCMS ESI (m/z): 290.4 (M + H)<br>Purity at 254 nm: 99.56% |

Synthesis Table 18

| Structure | Precursor | Analytical data |
|---|---|---|
| ANASIA-092-1 (HCl)<br>ANASIA-092-2 (CF₃COOH) | Int-B-5.10-Fr-1<br>Int-B-5.10-Fr-2 | Isomer-1<br>$^1$H NMR (400 MHz, DMSO-$d_6$) δ 8.41 (bs, 2H), 7.99 (bs, 3H), 7.59 (d, J = 4.4 Hz, 1H), 7.29 (d, J = 4.4 Hz, 1H), 3.74-3.71 (m, 1H), 1.76-1.72 (m, 1H), 1.65-1.59 (m, 1H), 1.50-1.47 (s, 1H), 0.89-0.87 (m, 6H).<br>LCMS ESI (m/z): 310.3 & 312.3 (M & M + 2)<br>Purity at 210 nm: 100.0%<br>Isomer-2<br>$^1$H NMR (400 MHz, DMSO-$d_6$) δ 8.45 (s, 2H), 7.97 (s, 3H), 7.61 (d, J = 4.4 Hz, 1H), 7.29 (d, J = 4.4 Hz, 1H), 3.71 (s, 1H), 1.78 (s, 1H), 1.80-1.67-1.56 (m, 3H), 0.93-0.89 (m, 6H).<br>LCMS ESI (m/z): 310.3 & 312.3 (M & M + 2)<br>Purity at 210 nm: 100.0% |
| ANASIA-078-1 (HCl)<br>ANASIA-078-2 (HCl) | Int-B-5.11-Fr-1<br>Int-B-5.11-Fr-2 | Isomer-1<br>$^1$H NMR (400 MHz, DMSO-$d_6$) δ 8.42 (bs, 2H), 8.01 (bs, 3H), 7.62 (d, J = 4.4 Hz, 1H), 7.29 (d, J = 4.4 Hz, 1H), 3.67 (bs, 1H), 1.91 (bs, 1H), 1.52-1.46 (m, 1H), 1.33-1.23 (m, 1H), 0.93-0.87 (m, 6H).<br>LCMS ESI (m/z): 310.3 & 312.3 (M & M + 2)<br>Purity at 210 nm: 98.57%<br>Isomer-2<br>$^1$H NMR (400 MHz, DMSO-$d_6$) δ 8.45 (s, 2H), 7.97 (bs, 3H), 7.61 (d, J = 4.4 Hz, 1H), 7.31 (d, J = 4.4 Hz, 1H), 3.70 (bs, 1H), 1.91-1.90 (m, 1H), 1.30-1.19 (m, 2H), 0.87-0.83 (m 6H).<br>LCMS ESI (m/z): 310.3 & 312.3 (M & M + 2)<br>Purity at 210 nm: 97.05% |
| ANASIA-096 | Int-B-5.12 | $^1$H NMR (400 MHz, DMSO) δ 8.76 (s, 1H), 8.51 (bs, 1H), 8.03 (m, 5H), 3.72 (bs, 1H), 1.92-1.40 (m, 3H), 0.88-0.86 (m, 6H).<br>LCMS ESI (m/z): 301.3 (M + H)<br>Purity at 210 nm: 96.39% |
| ANASIA-103-1 (HCl)<br>ANASIA-103-2 | Int-B-5.13-Fr-1<br>Int-B-5.13-Fr-1 | Isomer-1<br>$^1$H NMR (400 MHz, DMSO)<br>δ 8.67 (bs, 2H), 8.12 (bs, 3H), 7.89 (d, J = 3.4 Hz, 1H), 3.76 (bs, 1H), 1.80-1.76 (m, 1H), 1.69-1.62 (m, 1H), 1.53-1.46 (m, 1H), 0.90-0.88 (m, 6H).<br>LCMS ESI (m/z): 312.5 (M + H)<br>Purity at 210 nm: 99.51%<br>Isomer-2<br>$^1$H NMR (400 MHz, DMSO)<br>δ 8.74 (bs, 2H), 8.12-8.09 (bs, 3H), 7.90 (d, J = 3.6 Hz, 1H), 3.71 (bs, 1H), 1.82-1.76 (m, 1H), 1.73-1.66 (m, 1H), 1.62-1.57 (m, 1H), 0.91 (m, 6H).<br>LCMS ESI (m/z): 312.3 (M + H)<br>Purity at 210 nm: 97.39% |

-continued

Synthesis Table 18

| Structure | Precursor | Analytical data |
|---|---|---|
| 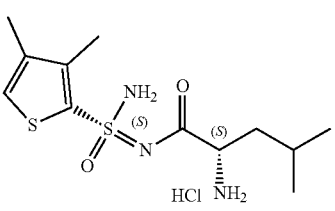<br>ANASIA-104-1<br><br>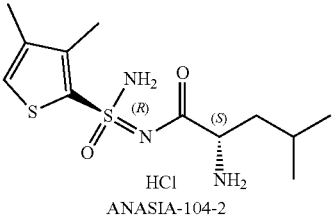<br>ANASIA-104-2 | Int-B-5.14-Fr-1<br>Int-B-5.14-Fr-1 | Isomer-1<br>$^1$H NMR (400 MHz, DMSO-d$_6$) δ 8.19 (bs, 1H), 7.94 (bs, 3H), 7.54 (s, 1H), 3.70 (bs, 1H), 2.30 (s, 3H), 2.12 (s, 3H), 1.78-1.76 (m, 1H), 1.68-1.62 (m, 1H), 1.49-1.44 (m, 1H), 0.89 (d, J = 6.4 Hz, 6H).<br>LCMS ESI (m/z): 304.3 (M + H)<br>Purity at 210 nm: 95.53%<br>Isomer-2<br>$^1$H NMR (400 MHz, DMSO-d$_6$) δ 7.99 (bs, 5H), 7.53 (s, 1H), 3.68-3.64 (m, 1H), 2.32 (s, 3H), 2.12 (s, 3H), 1.80-1.67 (m, 2H), 1.58-1.53 (m, 1H), 0.93-0.89 (m, 6H).<br>LCMS ESI (m/z): 304.4 (M + H)<br>Purity at 210 nm: 97.06% |
| 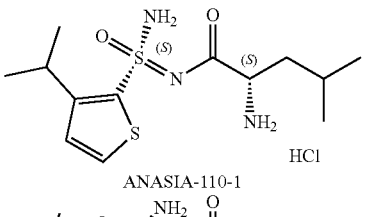<br>ANASIA-110-1<br><br>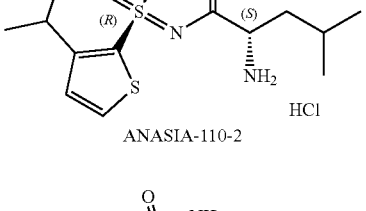<br>ANASIA-110-2 | Int-B-5.16-Fr-1<br>Int-B-5.16-Fr-2 | Isomer-1<br>$^1$H NMR (400 MHz, DMSO) δ 8.30 (bs, 2H), 8.00 (bs, 3H), 7.87 (d, J = 5.2 Hz, 1H), 7.23 (d, J = 5.2 Hz, 1H), 3.70-3.60 (m, 2H), 1.80 (m, 1H), 1.68-1.62 (m, 1H), 1.51-1.47 (m,1H), 1.20-1.15 (m, 6H), 0.90-0.86 (m, 6H).<br>LCMS ESI (m/z): 318.3 (M + 1)<br>Purity at 254 nm: 97.20%<br>Isomer-2<br>$^1$H NMR (400 MHz, DMSO) δ 8.29 (s, 2H), 8.03 (bs, 3H), 7.86 (d, J = 5.2 Hz, 1H), 7.24 (d, J = 5.2 Hz, 1H), 3.36-3.57 (m, 2H), 1.84-1.79 (m, 1H), 1.76-1.69 (m, 1H), 1.62-1.55 (m, 1H), 1.31-1.15 (m, 6H), 0.91-0.84 (m, 6H).<br>LCMS ESI (m/z): 318.2 (M + 1)<br>Purity at 254 nm: 97.11% |
| 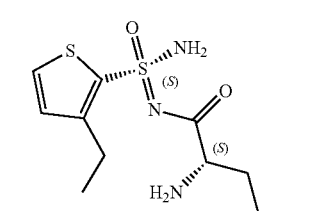<br>ANASIA-119-1<br><br>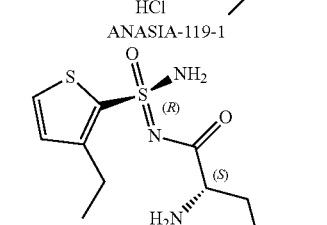<br>ANASIA-119-2 | Int-B-5.20-Fr-1<br>Int-B-5.20-Fr-2 | Isomer-1<br>$^1$H NMR (400 MHz, DMSO-d$_6$) δ $^1$H NMR (400 MHz, DMSO) δ 8.27 (s, 2H), 8.06 (bs, 3H), 7.87 (d, J = 4.8 Hz, 1H), 7.13 (d, J = 4.8 Hz, 1H), 3.64 (bs, 1H), 2.91-2.83 (q, 2H), 1.84-1.79 (m, 1H), 1.74-1.67 (m, 1H), 1.61-1.56 (m, 1H), 1.19 (t, J = 7.6 Hz, 3H), 0.93 (d, J = 6.4 Hz, 6H).<br>LCMS ESI (m/z): 304.4 (M + 1)<br>Purity at 210 nm: 97.25%<br>Isomer-2<br>$^1$H NMR (400 MHz, DMSO-d$_6$) δ $^1$H NMR (400 MHz, DMSO) δ 8.27 (s, 2H), 8.04 (brs, 3H), 7.86 (d, J = 5.2 Hz, 1H), 7.13 (d, J = 5.2 Hz, 1H), 3.64 (bs, 1H), 2.91-2.83 (q, 2H), 1.83-1.78 (m, 1H), 1.74-1.67 (m, 1H), 1.61-1.56 (m, 1H), 1.19 (t, J = 7.6 Hz, 3H), 0.93-0.84 (m, 6H).<br>LCMS ESI (m/z): 304.4 (M + 1)<br>Purity at 210 nm: 99.43% |

Synthesis Table 18

| Structure | Precursor | Analytical data |
|---|---|---|
| 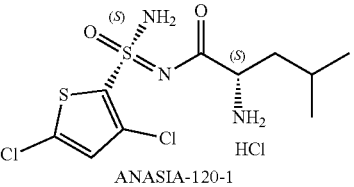<br>ANASIA-120-1<br>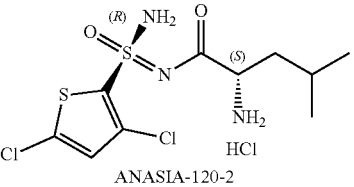<br>ANASIA-120-2 | Int-B-5.21-Fr-1<br>Int-B-5.21-Fr-1 | Isomer-1<br>$^1$H-NMR (400 MHz, DMSO-d$_6$): δ 8.64 (bs, 2H), 8.06 (bs, 3H), 7.51 (s, 1H), 3.76-3.72 (m, 1H), 1.82-1.66 (m, 2H), 1.52-1.46 (m, 1H), 0.89 (d, J = 6.4 Hz, 6H)<br>LCMS ESI (m/z): 344.4 & 346.4 (M & M + 2)<br>Purity at 210 nm: 100%<br>Isomer-2<br>$^1$H-NMR (400 MHz, DMSO-d$_6$) δ: 8.68 (bs, 2H), 8.07 (bs, 3H), 7.51 (s, 1H), 3.70 (bs, 1H); 1.81-1.77 (m, 1H); 1.74-1.68 (m, 1H), 1.62-1.55 (m, 1H), 0.91 (t, J = 6.8 Hz, 6H)<br>LCMS ESI (m/z): 344.4 & 346.4 (M & M + 2)<br>Purity at 210 nm: 95.10% |
| 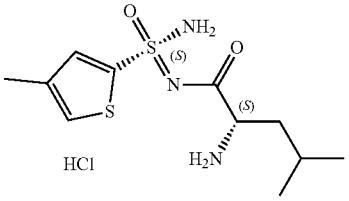<br>ANASIA-095-1<br>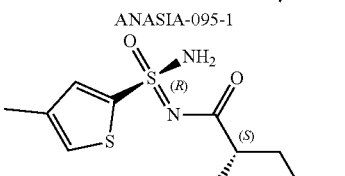<br>ANASIA-095-2 | Int-B-5.22-Fr-1<br>Int-B-5.22-Fr-2 | Isomer-1<br>$^1$H NMR (400 MHz, DMSO) δ 8.21 (bs, 2H), 8.03 (bs, 3H), 7.59 (s, 1H), 7.55 (s, 1H), 3.68-3.67 (m, 1H), 2.23 (s, 3H), 1.80-1.73 (m, 1H), 1.66-1.59 (m, 1H), 1.51-1.42 (m, 1H), 0.88 (d, J = 6.4 Hz, 6H).<br>LCMS ESI (m/z): 290.4 (M + H)<br>Purity at 210 nm: 100%<br>Isomer-2<br>$^1$H NMR (400 MHz, DMSO) δ 8.23 (bs, 2H), 8.03 (bs, 3H), 7.58 (s, 2H), 3.65 (bs, 1H), 2.23 (s, 3H), 1.81-1.76 (m, 1H), 1.72-1.65 (m, 1H), 1.60-1.53 (m, 1H), 0.90 (t, J = 7.6 Hz, 6H).<br>LCMS ESI (m/z): 290.4 (M + H)<br>Purity at 254 nm: 100% |
| 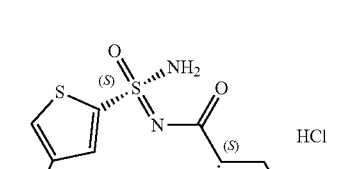<br>ANASIA-124-1<br>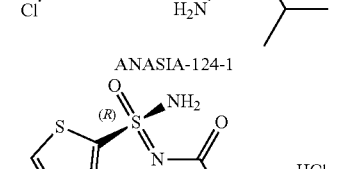<br>ANASIA-124-2 | Int-B-5.23-Fr-1<br>Int-B-5.23-Fr-2 | Isomer-1<br>$^1$H NMR (400 MHz, DMSO) δ 8.41 (bs, 2H), 8.03 (s, 1H), 7.95 (bs, 3H), 7.69 (s, 1H), 3.75-3.72 (m, 1H), 1.76-1.71 (m, 1H), 1.67-1.65 (m, 1H), 1.49-1.44 (m, 1H), 0.89-0.87 (m, 6H)<br>LCMS ESI (m/z): 310.4 & 312.5 (M & M + 2)<br>Purity at 210 nm: 100%<br>Isomer-2<br>$^1$H NMR (400 MHz, DMSO) δ 8.13 (bs, 5H), 8.02 (s, 1H), 7.70 (s, 1H), 3.74-3.71 (m, 1H), 1.77-1.65 (m, 2H), 1.59-1.52 (m, 1H), 0.90 (two d, 6H).<br>LCMS ESI (m/z): 310.5 & 312.5 (M & M + 2)<br>Purity at 210 nm: 100% |

-continued

Synthesis Table 18

| Structure | Precursor | Analytical data |
|---|---|---|
| ANASIA-127-1 (CF₃COOH) <br> ANASIA-127-2 (CF₃COOH) | Int-B-5.24-Fr-1 <br> Int-B-5.24-Fr-2 | Isomer-1 <br> $^1$H NMR (400 MHz, DMSO-$d_6$) δ 8.53 (s, 1H), 8.04 (bs, 4H), 7.18 (t, J = 54 Hz, 1H), 3.73 (bs, 1H), 1.78-1.70 (m, 2H), 1.58-1.56 (m, 1H), 0.92-0.89 (m, 6H) <br> LCMS ESI (m/z): 327.5 (M + H) <br> Purity at 210 nm: 95.47% <br> Isomer-2 <br> $^1$H NMR (400 MHz, DMSO-$d_6$) δ 8.74 (s, 2H), 8.55 (s, 1H), 8.06 (s, 3H), 7.18 (t, J = 53.6 Hz, 1H), 3.80 (bs, 1H), 1.80-1.75 (m, 1H), 1.70-1.63 (m, 1H), 1.48-1.42 (m, 1H), 0.89-0.87 (m, 6H). <br> LCMS ESI (m/z): 327.1 (M + H) <br> Purity at 210 nm: 100.0% |
| ANASIA-128-1 (HCl) <br> ANASIA-128-2 (HCl) | Int-B-5.25-Fr-1 <br> Int-B-5.25-Fr-2 | Isomer-1 <br> $^1$H-NMR (400 MHz, DMSO-$d_6$) δ: 8.00 (bs, 3H), 7.24 (bs, 2H), 3.72-3.69 (m, 1H), 2.43 (s, 3H), 2.30 (s, 2H) 1.83-1.79 (m, 1H); 1.69-1.63 (m, 1H), 1.49-1.41 (m, 1H), 0.90-0.84 (m, 6H). <br> LCMS ESI (m/z): 305.1 (M + H) <br> Purity at 210 nm: 100.00% <br> Isomer-2 <br> $^1$H-NMR (400 MHz, DMSO-$d_6$) δ: 8.11 (bs, 3H), 7.26 (bs, 2H), 3.67 (bs, 1H), 2.43 (s, 3H), 2.31 (s, 3H) 1.80-1.71 (m, 2H), 1.58-1.55 (m, 1H), 0.91-0.89 (m, 6H). <br> LCMS ESI (m/z): 305.61 (M + H) <br> Purity at 210 nm: 98.60% |
| ANASIA-129-1 (HCl) <br> ANASIA-129-2 (HCl) | Int-B-5.26-Fr-1 <br> Int-B-5.26-Fr-2 | Isomer-1 <br> $^1$H NMR (400 MHz, DMSO-$d_6$) δ 8.34 (s, 1H), 8.02 (bs, 5H), 3.66 (bs, 1H), 2.68 (s, 3H), 1.85-1.78 (m, 1H), 1.70-1.63 (m, 1H), 1.50-1.43 (m, 1H), 0.89-0.88 (d, J = 6.4 Hz, 6H). <br> LCMS ESI (m/z): 291.5 (M + H) <br> Purity at 210 nm: 100.0% <br> Isomer-2 <br> $^1$H NMR (400 MHz, DMSO-$d_6$) δ 8.36 (s, 1H), 8.20-8.00 (m, 5H), 3.66 (bs, 1H), 2.68 (s, 3H), 1.85-1.78 (m, 1H), 1.70-1.63 (m, 1H), 1.50-1.43 (m, 1H), 0.89-0.88 (d, J = 6.4 Hz, 6H). <br> LCMS ESI (m/z): 291.1 (M + H) <br> Purity at 210 nm: 100.0% |

Synthesis Table 18

| Structure | Precursor | Analytical data |
|---|---|---|
| 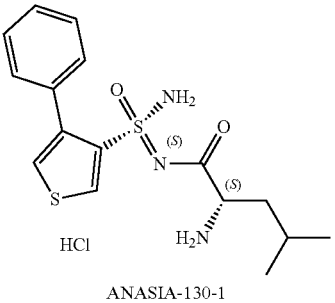<br>ANASIA-130-1<br><br>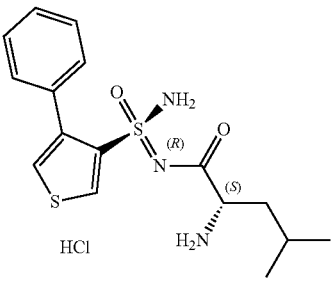<br>ANASIA-130-2 | Int-B-5.27-Fr-1<br>Int-B-5.27-Fr-2 | Isomer-1<br>$^1$H-NMR (400 MHz, DMSO-d$_6$) δ 8.49 (d, J = 3.6 Hz, 1H), 7.95 (bs, 5H), 7.65 (d, J = 3.2 Hz, 1H), 7.55 (d, J = 3.6 Hz, 2H), 7.38 (m, 3H), 3.30 (bs, 1H), 1.60 (s, 1H), 1.11-1.04 (m, 2H), 0.79-0.73 (m, 6H).<br>LCMS ESI (m/z): 352.2 (M + 1)<br>Purity at 254 nm: 95.97%<br>Isomer-2<br>$^1$H-NMR (400 MHz, DMSO-d$_6$) δ 8.49 (d, J = 3.2 Hz, 1H), 7.93 (bs, 5H), 7.65 (d, J = 3.2 Hz, 1H), 7.51-7.50 (m, 2H), 7.38-7.37 (m, 3H), 3.14 (t, J = 7 Hz, 1H), 1.65-1.61 (m, 1H), 1.35-1.31 (m, 2H), 0.80-0.74 (m, 6H).<br>LCMS ESI (m/z): 352.1 (M + 1)<br>Purity at 254 nm: 100% |
| 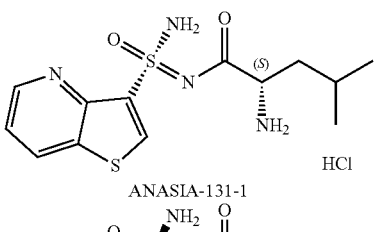<br>ANASIA-131-1<br><br>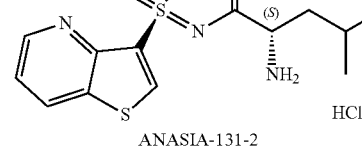<br>ANASIA-131-2 | Int-B-5.28-Fr-1<br>Int-B-5.28-Fr-2 | Isomer-1<br>$^1$H NMR (400 MHz, DMSO) δ 8.96 (s, 1H), 8.76 (d, J = 4.4 Hz, 1H), 8.63 (d, J = 8.2 Hz, 1H), 7.93 (bs, 5H), 7.56-7.52 (m, 1H), 3.63 (bs, 1H), 1.74-1.64 (m, 2H), 1.25-1.19 (m, 1H), 0.88-0.78 (m, 6H).<br>LCMS ESI (m/z): 327.0 (M + 1)<br>Purity at 254 nm: 100.0%<br>Isomer-2<br>$^1$H NMR (400 MHz, DMSO) δ 8.97 (s, 1H), 8.76 (d, J = 4.4 Hz, 1H), 8.63 (d, J = 8.2 Hz, 1H), 7.93 (bs, 5H), 7.56-7.52 (m, 1H), 3.63 (bs, 1H), 1.74-1.64 (m, 2H), 1.60-1.50 (m, 1H), 0.88-0.78 (m, 6H).<br>LCMS ESI (m/z): 327.0 (M + 1)<br>Purity at 254 nm: 100.0% |
| 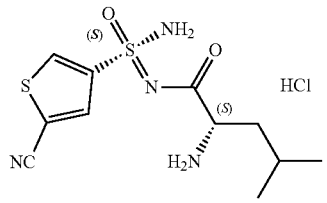<br>ANASIA-135-1<br><br>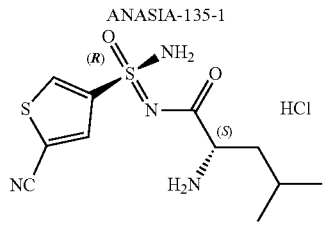<br>ANASIA-135-2 | Int-B-5.30-Fr-1<br>Int-B-5.30-Fr-2 | Isomer-1<br>$^1$H NMR (400 MHz, DMSO) δ 8.67 (d, J = 1.6 Hz, 1H), 8.28 (s, 2H), 8.24 (d, J = 1.2 Hz, 1H), 8.05 (bs, 3H), 3.69-3.67 (m, 1H), 1.75-1.68 (m, 1H), 1.65-1.58 (m, 1H), 1.51-1.44 (m, 1H), 0.86 (two d, J = 6.6 Hz, 6H).<br>LCMS ESI (m/z): 301.0 (M + H)<br>Purity at 254 nm: 95.10%<br>Isomer-2<br>$^1$H NMR (400 MHz, DMSO) δ 8.68 (d, J = 1.2 Hz, 1H), 8.27 (bs, 2H), 8.24 (d, J = 1.6 Hz, 1H), 8.01 (bs, 3H), 3.69-3.68 (m, 1H), 1.78-1.69 (m, 1H), 1.67-1.64 (m, 1H), 1.59-1.54 (m, 1H), 0.91-0.87 (m, 6H).<br>LCMS ESI (m/z): 301.0 (M + H)<br>Purity at 210 nm: 98.83% |

-continued

Synthesis Table 18

| Structure | Precursor | Analytical data |
|---|---|---|
| 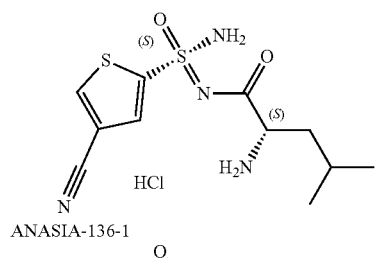<br>ANASIA-136-1<br>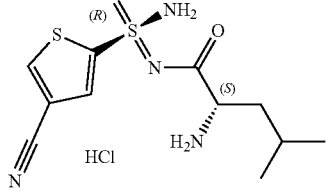<br>ANASIA-136-2 | Int-B-5.31-Fr-1<br>Int-B-5.31-Fr-2 | Isomer-1<br>$^1$H NMR (400 MHz, DMSO-d$_6$) δ 8.89 (d, J = 1.4 Hz, 1H), 8.50 (bs, 2H), 8.12 (d, J = 1.4 Hz, 1H), 8.07 (s, 3H), 3.71 (bs, 1H), 1.78-1.71 (m, 1H), 1.66-1.59 (m, 1H), 1.52-1.45 (m, 1H), 0.89-0.85 (m, 6H)<br>LCMS ESI (m/z): 301.0 (M + H)<br>Purity at 254 nm: 95.04%<br>Isomer-1<br>$^1$H NMR (400 MHz, DMSO-d$_6$) δ 8.89 (d, J = 1.4 Hz, 1H), 8.50 (bs, 2H), 8.13 (d, J = 1.4 Hz, 1H), 8.10 (s, 3H), 3.70 (bs, 1H), 1.78-1.50 (m, 3H), 0.89-0.85 (m, 6H)<br>LCMS ESI (m/z): 301.0 (M + H)<br>Purity at 254 nm: 95.02% |
| 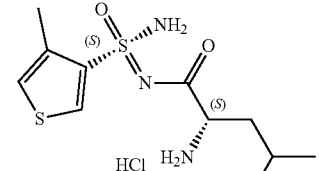<br>ANASIA-094-1<br>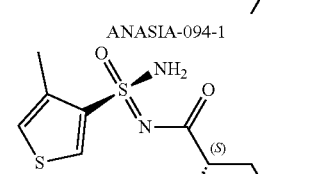<br>ANASIA-094-2 | Int-B-5.32-Fr-1<br>Int-B-5.32-Fr-2 | Isomer-1<br>$^1$H NMR (400 MHz, DMSO) δ 8.31 (s, 1H), 8.15-7.95 (m, 5H), 7.39 (s, 1H), 3.65 (bs, 1H), 2.35 (s, 3H), 1.85-1.70 (m, 1H), 1.68-1.61 (m, 1H), 1.52-1.50 (m, 1H), 0.88-0.87 (d, J = 6.4 Hz 6H).<br>LCMS ESI (m/z): 290.3 (M + 1)<br>Purity at 210 nm: 100%<br>Isomer-2<br>$^1$H NMR (400 MHz, DMSO) δ 8.32 (s, 1H), 8.15-7.95 (m, 5H), 7.39 (s, 1H), 3.65 (bs, 1H), 2.35 (s, 3H), 1.85-1.70 (m, 1H), 1.68-1.61 (m, 1H), 1.52-1.50 (m, 1H), 0.88-0.87 (two d, J = 6.4 Hz 6H).<br>LCMS ESI (m/z): 290.3 (M + 1)<br>Purity at 210 nm: 100% |
| 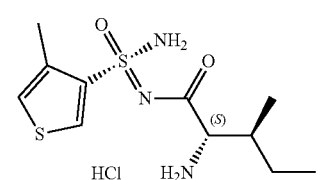<br>ANASIA-079-1<br>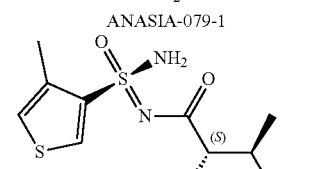<br>ANASIA-079-2 | Int-B-5.33-Fr-1<br>Int-B-5.33-Fr-2 | Isomer-1<br>$^1$H NMR (400 MHz, DMSO) δ 8.22 (bs, 2H), 8.01 (bs, 3H), 7.62-7.55 (m, 2H), 3.64-3.62 (m, 1H), 2.23 (s, 3H), 1.94-1.93 (m, 1H), 1.52-1.46 (m, 1H), 1.33-1.28 (m, 1H), 0.93-0.87 (m, 6H).<br>LCMS ESI (m/z): 290.3 (M + 1)<br>Purity at 238 nm: 97.87%<br>Isomer-2<br>$^1$H NMR (400 MHz, DMSO) δ 8.22 (bs, 2H), 7.98 (bs, 3H), 7.59 (s, 1H), 7.56 (s, 1H), 3.72-3.68 (m, 1H), 2.23 (s, 3H), 1.98-1.90 (m, 1H), 1.31-1.28 (m, 1H), 1.24-1.18 (m, 1H), 0.91-0.83 (m, 6H).<br>LCMS ESI (m/z): 290.3 (M + 1)<br>Purity at 254 nm: 96.06% |

Synthesis Table 18

| Structure | Precursor | Analytical data |
|---|---|---|
| ANASIA-122-1 (HCl) <br> ANASIA-122-2 (HCl) | Int-B-5.34-Fr-1 <br> Int-B-5.34-Fr-2 | Isomer-1 <br> $^1$H NMR (400 MHz, DMSO) δ 8.26 (s, 1H), 8.21 (s, 2H), 8.02 (bs, 3H), 3.70 (bs, 1H), 2.28 (s, 3H), 1.76-1.75 (m, 1H), 1.67-1.62 (m, 1H), 1.52-1.49 (m, 1H), 0.88 (d, J = 6 Hz, 6H). <br> LCMS ESI (m/z): 324.1 & 326.1 (M & M + 2) <br> Purity at 210 nm: 95.86% <br> Isomer-2 <br> $^1$H NMR (400 MHz, DMSO) δ 8.26 (s, 1H), 8.02 (bs, 5H), 3.68-3.64 (m, 1H), 2.30 (s, 3H), 1.81-1.72 (m, 1H), 1.70-1.65 (m, 1H), 1.60-1.55 (m, 1H), 0.92-0.89 (two d, 6H). <br> LCMS ESI (m/z): 324.1 & 326.1 (M & M + 1) <br> Purity at 210 nm: 100% |
| ANASIA-075-1 (HCl) <br> ANASIA-075-2 (HCl) | Int-B-5.35-Fr-1 <br> Int-B-5.35-Fr-2 | Isomer-1 <br> $^1$H NMR (400 MHz, DMSO) δ 8.71 (d, J = 4.4 Hz, 1H), 8.14-8.07 (m, 2H), 7.98-7.95 (m, 5H), 7.67 (dd, J = 5.4 Hz, 1H), 3.67 (bs, 1H), 1.85-1.55 (m, 3H), 0.88-0.85 (m, 6H). <br> LCMS ESI (m/z): 271.3 (M + H) <br> Purity at 220 nm: 92.76% <br> Isomer-2 <br> $^1$H NMR (400 MHz, DMSO) δ 8.72 (d, J = 4.4 Hz, 1H), 8.15-8.11 (m, 2H), 8.03-8.00 (m, 5H), 7.69-7.66 (m, 1H), 3.70 (bs, 1H), 1.80-55 (m, 3H), 0.91-0.84 (m, 6H). <br> LCMS ESI (m/z): 271.2 (M + H) <br> Purity at 220 nm: 99.41% |
| ANASIA-098-1 (HCl) <br> ANASIA-098-2 (HCl) | Int-B-5.39-Fr-1 <br> Int-B-5.39-Fr-2 | Isomer-1 <br> $^1$H NMR (400 MHz, DMSO-d$_6$) δ 8.06 (d, J = 1.2 Hz, 1H), 8.01 (bs, 3H), 7.93 (bs, 2H), 7.09 (s, 1H), 3.66-3.64 (m, 1H), 2.46 (s, 3H), 1.77-1.73 (m, 1H), 1.66-1.59 (m, 1H), 1.51-1.45 (m, 1H), 0.88 (d, J = 6.4 Hz, 6H). <br> LCMS ESI (m/z): 290.4 (M + H) <br> Purity at 210 nm: 98.15% <br> Isomer-2 <br> $^1$H NMR (400 MHz, DMSO-d$_6$) δ 8.20-8.00 (m, 4H), 7.95 (bs, 2H), 7.14 (s, 1H), 3.64-3.62 (m, 1H), 2.47 (s, 3H), 1.80-1.75 (m, 1H), 1.75-1.65 (m, 1H), 1.60-1.54 (m, 1H), 0.92-0.88 (m, 6H). <br> LCMS ESI (m/z): 290.3 (M + H) <br> Purity at 210 nm: 100.00% |

-continued

Synthesis Table 18

| Structure | Precursor | Analytical data |
| --- | --- | --- |
| ANASIA-100-1<br>ANASIA-100-2 | Int-B-5.40-Fr-1<br>Int-B-5.40-Fr-2 | Isomer-1<br>$^1$H NMR (400 MHz, DMSO-d$_6$) δ 8.43 (s, 1H), 8.09 (bs, 5H), 7.83 (d, J = 5.1 Hz, 1H), 7.52 (d, J = 5.2 Hz, 1H), 3.71-3.68 (m, 1H), 1.76-1.66 (m, 2H), 1.47-1.41 (m, 1H), 0.87 (two d, J = 7 Hz, 6H).<br>LCMS ESI (m/z): 332.5 (M + 1)<br>Purity at 254 nm: 99.76%<br>Isomer-2<br>$^1$H NMR (400 MHz, DMSO-d$_6$) δ 8.45 (s, 1H), 8.29 (bs, 2H), 8.06 (bs, 3H), 7.82 (d, J = 5.2 Hz, 1H), 7.52 (d, J = 5.2 Hz, 1H), 3.67 (s, 1H), 1.80-1.74 (m, 2H), 1.61-1.60 (m, 1H), 0.91 (two d, J = 6.4 Hz, 6H).<br>LCMS ESI (m/z): 332.5 (M + 1) |
| ANASIA-107-1<br>ANASIA-107-2 | Int-B-5.42-Fr-1<br>Int-B-5.42-Fr-2 | Isomer-1<br>$^1$H NMR (400 MHz, DMSO)<br>δ 8.62 (s, 2H), 8.31 (s, 1H), 8.01 (s, 3H), 3.74 (bs, 1H), 1.82-1.73 (m, 2H), 1.52-1.45 (m, 1H), 0.90 (d, J = 6.4 Hz 6H).<br>LCMS ESI (m/z): 434.2 (M + H)<br>Purity at 210 nm: 100%<br>Isomer-2<br>$^1$H NMR (400 MHz, DMSO)<br>δ 8.61 (s, 2H), 8.30 (s, 1H), 8.10 (s, 3H), 3.72-3.67 (m, 1H), 1.84-1.70 (m, 2H), 1.64-1.57 (m, 1H), 0.92 (two d, J = 6.4 Hz, 6H).<br>LCMS ESI (m/z): 434.24 (M + H)<br>Purity at 210 nm: 100% |
| ANASIA-116-1<br>ANASIA-116-2 | Int-B-5.43-Fr-1<br>Int-B-5.43-Fr-2 | Isomer-1<br>$^1$H NMR (400 MHz, DMSO)<br>δ 8.59 (s, 2H), 8.30 (s, 1H), 7.98 (bs, 3H), 3.70 (bs, 1H), 1.99 (bs, 1H), 1.49-1.47 (m, 1H), 1.33-1.31 (m, 1H), 0.96-0.89 (m, 6H).<br>LCMS ESI (m/z): 434.3 (M + H)<br>Purity at 210 nm: 100%<br>Isomer-2<br>$^1$H NMR (400 MHz, DMSO)<br>δ 8.66 (s, 2H), 8.32 (s, 1H), 7.96 (bs, 3H), 3.73 (bs, 1H), 2.02 (bs, 1H), 1.32-1.23 (m, 1H), 1.21-1.17 (m, 1H), 0.92-0.84 (m, 6H).<br>LCMS ESI (m/z): 434.2 (M + H)<br>Purity at 210 nm: 100% |

-continued

Synthesis Table 18

| Structure | Precursor | Analytical data |
|---|---|---|
| ANASIA-108-1 / ANASIA-108-2 | Int-B-5.44-Fr-1<br>Int-B-5.44-Fr-2 | Isomer-1<br>$^1$H NMR (400 MHz, DMSO-$d_6$)<br>δ: 8.01 (bs, 3H), 7.90-7.88 (m, 3H), 7.13 (d, J = 5.6 Hz, 1H), 3.91 (s, 3H), 3.63 (bs, 1H), 1.80-1.79 (m, 1H), 1.71-1.65 (m, 1H), 1.49-1.46 (m, 1H), 0.91-0.89 (m, 6H).<br>LCMS ESI (m/z): 306.3 (M + H)<br>Purity at 210 nm: 100%<br>Isomer-2<br>$^1$H NMR (400 MHz, DMSO-$d_6$) δ 8.03 (bs, 3H), 7.96 (bs, 2H), 7.90 (d, J = 5.6 Hz, 1H), 7.13 (d, J = 5.6 Hz, 1H), 3.91 (s, 3H), 3.61-3.59 (m, 1H), 1.81-1.73 (m, 1H), 1.72-1.66 (m, 1H), 1.60-1.56 (m, 1H), 0.93-0.89 (two d, 6H)<br>LCMS ESI (m/z): 306.3 (M + H)<br>Purity at 210 nm: 99.72% |
| ANASIA-109-1 / ANASIA-109-2 | Int-B-5.45-Fr-1<br>Int-B-5.45-Fr-2 | Isomer-1<br>$^1$H NMR (400 MHz, DMSO-$d_6$) δ 8.14 (bs, 2H), 7.99 (bs, 3H), 7.45 (d, J = 4 Hz, 1H), 6.44 (d, J = 4.4 Hz, 1H), 3.93 (s, 3H), 3.66 (bs, 1H), 1.75-1.73 (m, 1H), 1.65-1.60 (m, 1H), 1.48-1.45 (s, 1H), 0.87 (d, J = 6.5 Hz, 6H).<br>LCMS ESI (m/z): 306.3 (M + 1)<br>Purity at 232 nm: 92.47%<br>Isomer-1<br>$^1$H NMR (400 MHz, DMSO-$d_6$) δ 8.16 (bs, 2H), 7.99 (bs, 3H), 7.46 (d, J = 4.4 Hz, 1H), 6.44 (d, J = 4.4 Hz, 1H), 3.92 (s, 3H), 3.66 (bs, 1H), 1.75-1.73 (m, 1H), 1.65-1.60 (m, 1H), 1.48-1.45 (s, 1H), 0.87 (d, J = 6.5 Hz, 6H).<br>LCMS ESI (m/z): 306.3 (M + 1)<br>Purity at 232 nm: 97.72% |
| ANASIA-111-1 / ANASIA-111-2 | Int-B-5.46-Fr-1<br>Int-B-5.46-Fr-2 | Isomer-1<br>$^1$H NMR (400 MHz, DMSO-$d_6$) δ:<br>8.19 (bs, 2H), 8.07 (bs, 3H), 7.56 (d, J = 3.6 Hz, 1H), 6.98 (d, J = 3.6 Hz, 1H), 3.65 (bs, 1H), 3.24-3.20 (m, 1H), 1.79-1.75 (m, 1H), 1.66-1.59 (m, 1H), 1.52-1.45 (m, 1H), 1.28 (d, J = 6.8 Hz, 6H), 0.87 (d, J = 6.4 Hz, 6H).<br>LCMS ESI (m/z): 318.4 (M + 1)<br>Purity at 210 nm: 98.37%<br>Isomer-2<br>$^1$H NMR (400 MHz, DMSO-$d_6$) δ:<br>8.08 (bs, 5H),<br>7.58 (d, J = 3.6 Hz, 1H), 6.98 (d, J = 3.6 Hz, 1H), 3.66 (bs, 1H), 3.26-3.20 (m,1H), 1.79-1.56 (m, 3H), 1.28 (d, J = 6.4 Hz, 6H), 0.87 (two d, 6H).<br>LCMS ESI (m/z): 318.0 (M + 1)<br>Purity at 210 nm: 92.00% |

-continued

Synthesis Table 18

| Structure | Precursor | Analytical data |
| --- | --- | --- |
| ANASIA-121-1<br>ANASIA-121-2 | Int-B-5.48-Fr-1<br>Int-B-5.48-Fr-2 | Isomer-1<br>$^1$H NMR (400 MHz, DMSO-d$_6$) δ 8.61 (s, 2H), 8.07 (s, 3H), 7.81 (s, 1H), 3.74 (s, 1H), 1.77-1.72 (m, 1H), 1.67-1.60 (m, 1H), 1.54-1.47 (m, 1H), 0.89-0.87 (m, 6H).<br>LCMS ESI (m/z): 344.4 & 346.4 (M & M + 2)<br>Purity at 210 nm: 100.0%<br>Isomer-2<br>$^1$H NMR (400 MHz, DMSO-d$_6$) δ 8.59 (bs, 2H), 8.02 (s, 3H), 7.80 (s, 1H), 3.77-3.71 (m, 1H), 1.81-1.65 (m, 2H), 1.60-1.53 (m, 1H), 0.92-0.89 (m, 6H).<br>LCMS ESI (m/z): 344.4 & 346.3 (M & M + 2)<br>Purity at 210 nm: 100.0% |
| ANASIA-126-1<br>ANASIA-126-2 | Int-B-5.49-Fr-1<br>Int-B-5.49-Fr-2 | Isomer-1<br>$^1$H NMR (400 MHz, DMSO-d$_6$) δ 8.51 (bs, 2H), 8.02-8.00 (m, 4H), 7.82-7.55 (t, J = 54.6 Hz, 1H), 7.44 (d, J = 4.4 Hz, 1H), 3.74 (bs, 1H), 1.69-1.65 (m, 1H), 1.59-1.54 (m, 1H), 1.44-1.36 (m, 1H), 0.86-0.82 (m, 6H).<br>LCMS ESI (m/z): 326.5 (M + H)<br>Purity at 210 nm: 97.81%<br>Isomer-2<br>$^1$H NMR (400 MHz, DMSO-d$_6$) δ 8.52 (s, 2H), 8.00-7.99 (m, 4H), 7.82-7.55 (t, J = 54.4, 1H), 7.45 (d, J = 4.8 Hz, 1H), 3.68 (bs, 1H), 1.78-1.68 (m, 2H), 1.62-1.58 (m, 1H), 0.92-0.88 (m, 6H).<br>LCMS ESI (m/z): 326.5 (M + H)<br>Purity at 244 nm: 99.30% |
| ANASIA-137-1<br>ANASIA-137-2 | Int-B-5.50-Fr-1<br>Int-B-5.50-Fr-2 | Isomer-1<br>$^1$H NMR (400 MHz, DMSO) δ 8.49 (bs, 2H), 8.16 (s, 1H), 8.08 (bs, 3H), 3.69 (bs, 1H), 2.73 (s, 3H), 1.76-1.74 (m, 1H), 1.62-1.60 (m, 1H), 1.53-1.49 (m, 1H), 0.89-0.87 (m, 6H).<br>LCMS ESI (m/z): 291.2 (M + 1)<br>Purity at 210 nm: 100%<br>Isomer-2<br>$^1$H NMR (400 MHz, DMSO) δ 8.52 (bs, 2H), 8.18 (s, 1H), 8.11 (sb, 3H), 3.65 (bs, 1H), 2.74 (s, 3H), 1.82-1.77 (m, 1H), 1.77-1.54 (m, 2H), 0.92-0.88 (m, 6H).<br>LCMS ESI (m/z): 291.1 (M + 1)<br>Purity at 210 nm: 100% |

-continued

Synthesis Table 18

| Structure | Precursor | Analytical data |
|---|---|---|
| 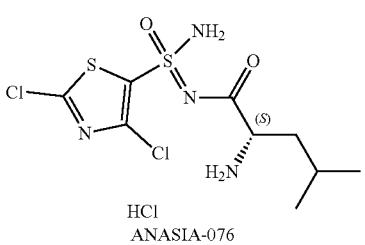<br>HCl<br>ANASIA-076 | Int-B-5.51 | ¹H NMR (400 MHz, DMSO) δ 8.98 (s, 2H), 8.12 (bs, 3H), 3.77-3.71 (m, 1H), 1.82- 1.77 (m, 1H), 1.70-1.59 (m, 2H), 1.54-1.50 (m, 1H), 0.91-0.87 (m, 6H). LCMS ESI (m/z): 345.2 (M + H) |
| 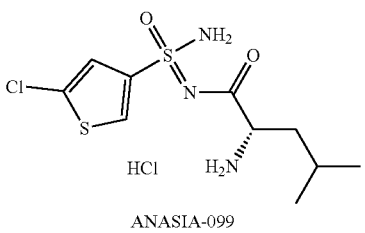<br>HCl<br>ANASIA-099<br>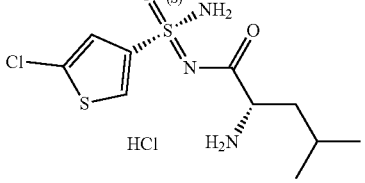<br>HCl<br>ANASIA-099-1<br>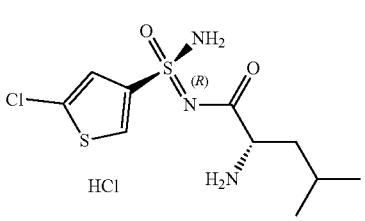<br>HCl<br>ANASIA-099-2 | Int-B-5.52-Fr-1<br>Int-B-5.52-Fr-2 | Isomer-1<br>¹H-NMR (400 MHz, DMSO-d₆) δ 8.19 (s, 1H), 8.00 (bs, 5H), 7.39 (s, 1H), 3.69 (s, 1H), 1.73-1.63 (m, 2H), 1.49-1.47 (m, 1H), 0.88 (bs, 6H).<br>LCMS ESI (m/z): 310.3, 312.3 (M, M + 2)<br>Purity at 210 nm: 100.00%<br>Isomer-2<br>¹H-NMR (400 MHz, DMSO-d₆) δ 8.21 (s, 1H), 8.19 (bs, 2H), 8.02 (bs, 3H), 7.44 (s, 1H), 3.69-3.68 (m, 1H), 1.77-1.67 (m, 2H), 1.59-1.56 (m, 1H), 0.92-0.88 (m, 6H).<br>LCMS ESI (m/z): 310.3, 312.3 (M, M + 2)<br>Purity at 254 nm: 97.88% |
| 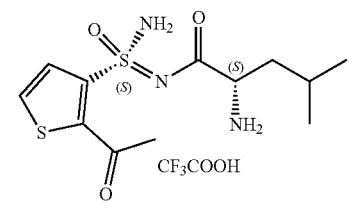<br>ANASIA-112-1 | Int-B-5.54-Fr-1 | Isomer-1<br>¹H NMR (400 MHz, DMSO-d₆) δ 8.03-8.00 (m, 5H), 7.54 (d, J = 5.2 Hz, 1H), 3.68 (bs, 1H), 2.68 (s, 3H), 1.78-1.71 (m, 1H), 1.63-1.56 (m, 1H), 1.46-1.39 (m, 1H), 0.89-0.87 (m, 6H).<br>LCMS ESI (m/z): 318.3 (M + H)<br>Purity at 210 nm: 100.0% |

-continued

Synthesis Table 18

| Structure | Precursor | Analytical data |
|---|---|---|
| 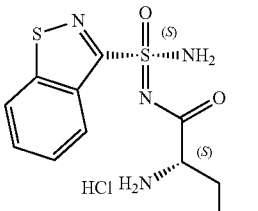<br>ANASIA-132-1<br>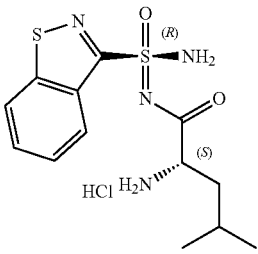<br>ANASIA-132-2 | Int-B-5.55-Fr-1<br>Int-B-5.55-Fr-2 | Isomer-1<br>$^1$H NMR (400 MHz, DMSO) δ 8.56 (bs, 2H), 8.50 (d, J = 8.3 Hz, 1H), 8.38 (d, J = 8.2 Hz, 1H), 7.96 (bs, 3H), 7.74 (t, J = 7.5 Hz, 1H), 7.66 (t, J = 7.6 Hz, 1H), 3.78 (bs, 1H), 1.76-1.75 (m, 1H), 1.69-1.62 (m, 1H), 1.42-1.38 (m, 1H), 0.87 (tow d, J = 7.0 Hz, 6H).<br>LCMS ESI (m/z): 327.1 (M + 1)<br>Purity at 254 nm: 99.18%<br>Isomer-2<br>$^1$H NMR (400 MHz, DMSO) δ 8.56 (d, J = 8 Hz, 1H), 8.27 (d, J = 8.4 Hz, 1H), 7.65 (t, J = 7.2 Hz, 1H), 7.57 (t, J = 8 Hz, 1H), 7.40 (bs, 4H), 3.50 (bs, 1H), 1.68-1.55 (m, 2H), 1.69-1.62 (m, 1H), 1.50-1.35 (m, 1H), 0.87 (d, J = 7.0 Hz, 6H).<br>LCMS ESI (m/z): 327.1 (M + 1)<br>Purity at 210 nm: 100% |
| 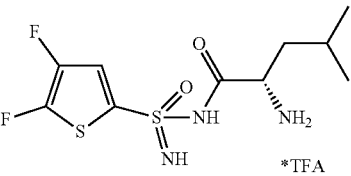 [SMILES: CC(C)C[C@H](N)C(=O)NS(=N)(=O)c1cc(F)c(F)s1]<br>ANASIA-063 | Int-B-5.56 | $^1$H NMR (400 MHz, MeOD): 7.69-7.48 (m, 1H), 3.86-3.73 (m, 1H), 1.90-1.72 (m, 2H), 1.69-1.52 (m, 1H), 1.15-0.79 (m, 6H).<br>$^{13}$C NMR (101 MHz, MeOD): 177.04, 162.32 (q, J = 36.1 Hz, TFA), 152.50 (d, J = 295.7 Hz), 152.36 (d, J = 296.7 Hz), 141.14 (dd, J = 260.3, 4.0 Hz), 141.07 (dd, J = 260.3, 4.0 Hz), 127.72 (d, J = 5.3 Hz), 127.66 (d, J = 4.8 Hz), 122.43 (d, J = 22.3 Hz), 117.92 (q, J = 296.1 Hz, TFA), 55.55, 55.48, 41.45, 41.32, 25.64, 22.94, 22.15, 22.09.<br>19F NMR (376 MHz, MeOD): −77.09 (TFA), −145.88 (t, J = 3.5 Hz), −145.97- −146.00 (m), −146.44−−146.49 (m).<br>Purity at 210 nm: 98.38%; at 254 nm: 97.29% |
| 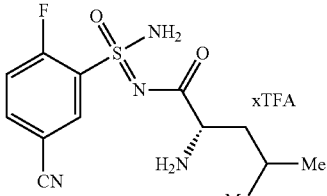<br>ANASIA-065 | Int-B-5.57 | $^1$H NMR (400 MHz, MeOD) d 8.25 (dd, J = 6.6, 2.2 Hz, 1H), 7.99 (ddd, J = 8.6, 4.4, 2.1 Hz, 1H), 7.45 (ddd, J = 10.0, 8.6, 3.3 Hz, 1H), 3.70 (ddd, J = 17.0, 8.3, 5.6 Hz, 1H), 1.81-1.63 (m, 2H), 1.60-1.39 (m, 1H), 0.95-0.83 (m, 6H).<br>$^{13}$C NMR (101 MHz, MeOD) d 176.02, 175.89, 161.90, 161.80, 159.27, 159.18, 139.35, 139.33, 139.25, 139.22, 135.18, 135.09, 131.32, 131.18, 118.71, 118.66, 118.47, 118.43, 116.28, 116.26, 109.03, 109.00, 108.96, 54.13, 54.04, 40.09, 39.93, 24.23, 24.19, 21.61, 21.50, 20.78, 20.59. (list of all peaks).<br>$^{19}$F NMR (376 MHz, MeOD) d −76.90, −101.93, −102.45 (m).<br>UPLCMS ESI (m/z): 313 (M + H)$^+$<br>Purity at 210 nm: 98.49%; at 254 nm: 90.82% |

Synthesis Table 18

| Structure | Precursor | Analytical data |
|---|---|---|
| 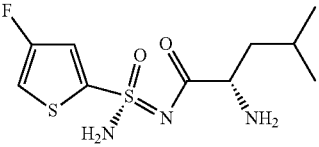 ANASIA-062-1 <br> 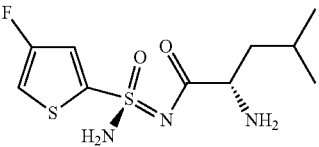 ANASIA-062-2 | Int-B-5.58 | Isomer-1 <br> $^1$H NMR (400 MHz, MeOD): 7.62 (dd, J = 1.9, 1.0 Hz, 1H), 7.42 (dd, J = 2.0, 1.0 Hz, 1H), 3.80 (dd, J = 8.3, 5.6 Hz, 1H), 1.86-1.73 (m, 2H), 1.63-1.55 (m, 1H), 0.98 (t, J = 6.0 Hz, 6H). <br> $^{13}$C NMR (101 MHz, MeOD): 176.97, 157.42 (d, J = 261.4 Hz), 142.33 (d, J = 6.9 Hz), 123.28 (d, J = 27.0 Hz), 113.11 (d, J = 21.7 Hz), 55.57, 41.37, 25.62, 22.94, 22.13. <br> $^{19}$F NMR (376 MHz, MeOD): −76.89 (TFA), −127.11. <br> Purity at 210 nm: 98.49%; at 254 nm: 99.77% <br> Isomer-2 <br> $^1$H NMR (400 MHz, MeOD): 7.62 (dd, J = 2.0, 0.9 Hz, 1H), 7.42 (dd, J = 2.0, 1.0 Hz, 1H), 3.79 (dd, J = 8.2, 5.6 Hz, 1H), 1.90-1.73 (m, 2H), 1.68-1.59 (m, 1H), 1.01 (d, J = 6.4 Hz, 3H), 0.98 (d, J = 6.3 Hz, 3H). <br> $^{13}$C NMR (101 MHz, MeOD): 176.95, 157.47 (d, J = 261.5 Hz), 142.32 (d, J = 6.9 Hz), 123.27 (d, J = 27.0 Hz), 113.11 (d, J = 21.6 Hz), 55.53, 41.50, 25.64, 22.93, 22.17. <br> $^{19}$F NMR (376 MHz, MeOD): −76.92 (TFA), −127.10. <br> Purity at 210 nm: 98.46%; at 254 nm: 99.42% |
| 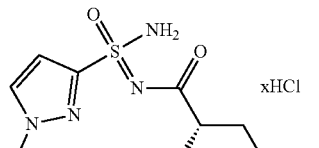 ANASIA-073 | Int-B-5.59 | $^1$H NMR (400 MHz, MeOD) 7.76 (d, J = 3.2 Hz, 1H), 6.82 (dd, J = 3.7, 2.4 Hz, 1H), 3.97 (s, 3H), 3.78 (ddd, J = 8.3, 5.8, 2.6 Hz, 1H), 1.91-1.77 (m, 2H), 1.68-1.55 (m, 1H), 1.05-0.94 (m, 6H). <br> $^{13}$C NMR (101 MHz, MeOD) 177.13, 177.05, 151.81, 134.06, 134.04, 108.73, 108.68, 55.63, 55.60, 41.49, 41.41, 39.98, 25.59, 25.54, 22.95, 22.93, 22.22. <br> UPLCMS ESI (m/z): 274.4 (M + H)$^+$ <br> Purity at 210 nm: 98.3%; at 254 nm: 96.9% |

Synthesis of 3-(N'-(L-leucyl)sulfamidimidoyl)thiophene-2-carboxamide hydrochloride (ANASIA-093

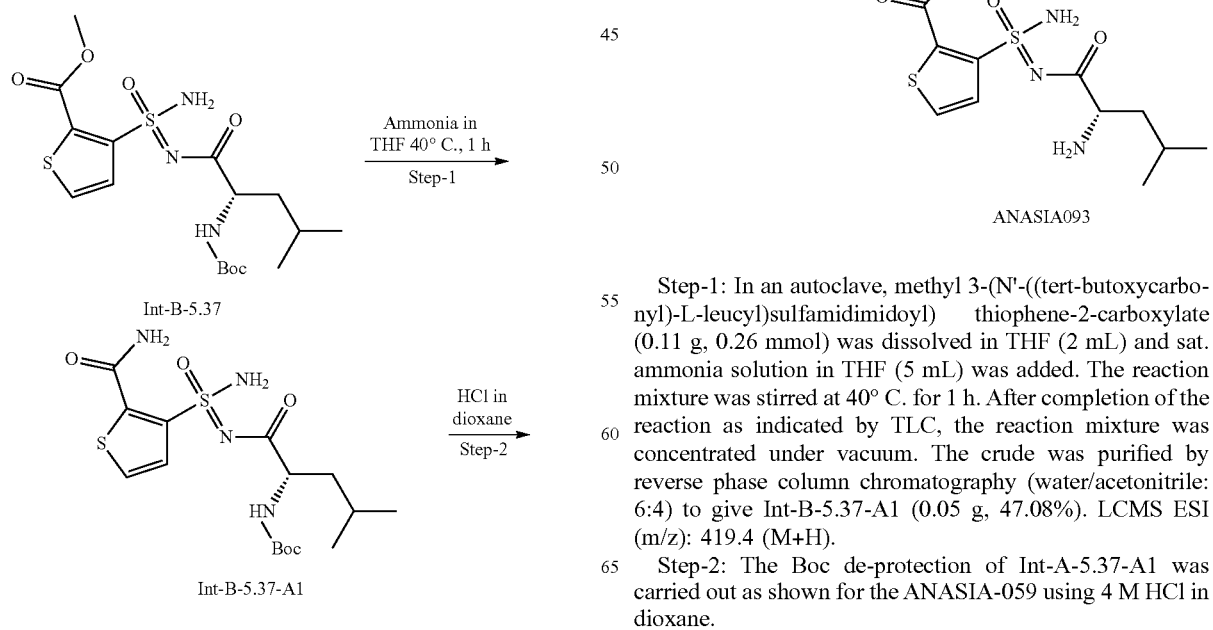

Step-1: In an autoclave, methyl 3-(N'-((tert-butoxycarbonyl)-L-leucyl)sulfamidimidoyl) thiophene-2-carboxylate (0.11 g, 0.26 mmol) was dissolved in THF (2 mL) and sat. ammonia solution in THF (5 mL) was added. The reaction mixture was stirred at 40° C. for 1 h. After completion of the reaction as indicated by TLC, the reaction mixture was concentrated under vacuum. The crude was purified by reverse phase column chromatography (water/acetonitrile: 6:4) to give Int-B-5.37-A1 (0.05 g, 47.08%). LCMS ESI (m/z): 419.4 (M+H).

Step-2: The Boc de-protection of Int-A-5.37-A1 was carried out as shown for the ANASIA-059 using 4 M HCl in dioxane.

¹H NMR (400 MHz, DMSO) δ 8.29 (bs, 2H), 8.22-8.17 (m, 2H), 8.08 (bs, 2H), 7.85 (t, J=5.6 Hz, 1H), 7.44 (t, J=5.8 Hz, 1H), 3.75 (bs, 1H), 1.75-1.57 (m, 2H), 1.45-1.44 (m, 1H), 0.92-0.85 (m, 6H). LCMS ESI (m/z): 319.3 (M+H). Purity at 210 nm: 100%

Synthesis of 4-(N'-(L-leucyl)sulfamidimidoyl)thiophene-3-carboxamide 2,2,2-trifluoroacetate (ANASIA-097

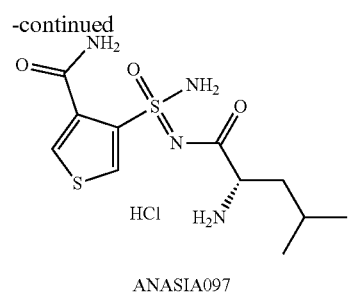

ANASIA097

Step-1: To a stirred solution of methyl 4-(N'-((tert-butoxycarbonyl)-L-leucyl)sulfamidimidoyl)thiophene-3-carboxylate (0.24 g, 0.55 mmol) in THF (20 mL) was purged ammonia gas for 20 min and then stirred at 60° C. for 3 h. After completion of the reaction as indicated by TLC, the reaction mixture was evaporated under vacuum. The crude was purified by silica gel column chromatography (ethyl acetate/hexane) to give tert-butyl ((2S)-1-((amino(4-carbamoylthiophen-3-yl)(oxo)-λ6-sulfanylidene)amino)-4-methyl-1-oxopentan-2-yl)carbamate (1.5 g, 40%). LCMS ESI (m/z): 419.5 (M+1)

Step-2: The Boc de-protection of Int-B-5.38-A1 was carried out as shown for the ANASIA-059 using 4 M HCl in dioxane. ¹H NMR (400 MHz, DMSO) δ 8.35 (d, J=3.2 Hz, 1H), 8.30-8.20 (m, 2H), 7.91-7.81 (m, 6H), 3.66-3.65 (m, 1H), 1.71-1.58 (m, 2H), 1.43-1.23 (m. 1H), 0.88 (d, J=6 Hz, 6H). LCMS ESI (m/z): 319.2 (M+H). Purity at 210 nm: 100%

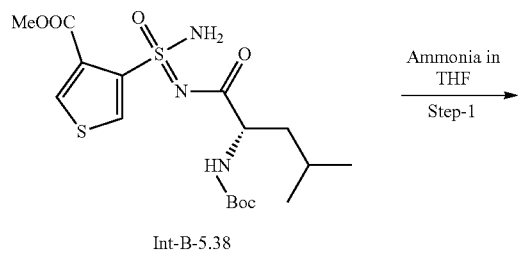

Int-B-5.38

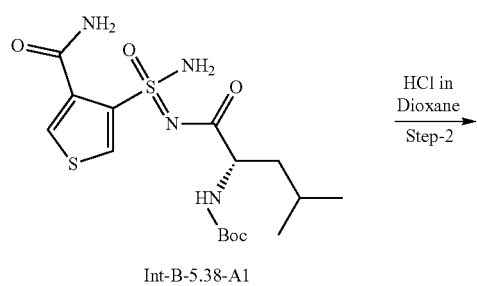

Int-B-5.38-A1

Synthesis of (S)-2-amino-N—((S)-amino(4-ethylthiophen-2-yl)(oxo)-λ6-sulfanylidene)-4-methylpentanamide and (S)-2-amino-N—((R)-amino(4-ethylthiophen-2-yl)(oxo)-λ6-sulfanylidene)-4-methylpentanamide (ANASIA-133-1 & ANASIA-133-2

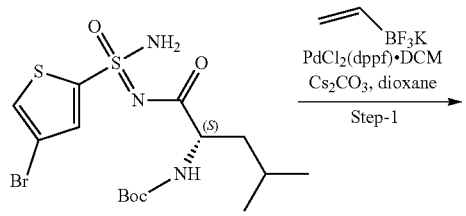

Int-B-5.29

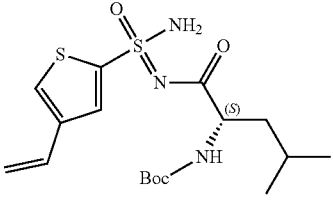

Int-B-5.29-A1

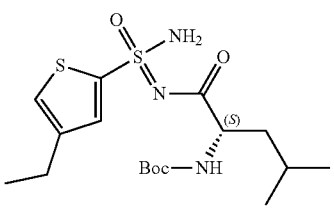

Int-B-5.29

Chiral isomer separation

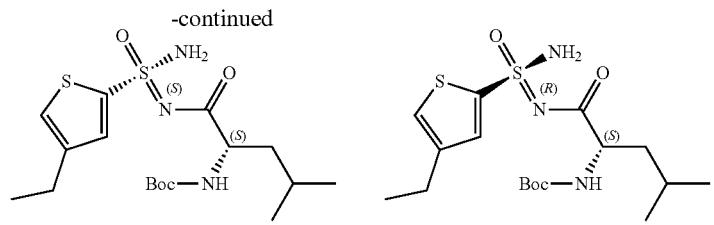

Int-B-5.29-Fr1          Int-B-5.29-Fr2

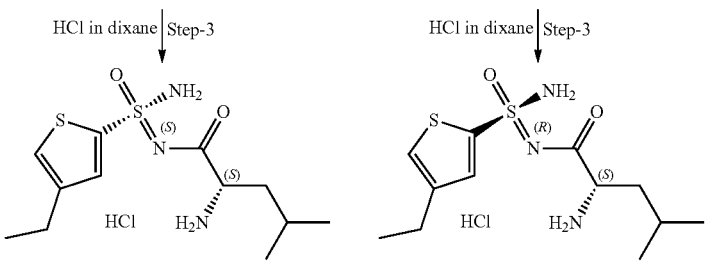

ANASIA133-1          ANASIA133-2

Step-1: To a degassed solution of tert-butyl ((2S)-1-((amino(4-bromothiophen-2-yl)(oxo)-λ6-sulfanylidene)amino)-4-methyl-1-oxopentan-2-yl)carbamate (0.25 g, 0.55 mmol) in 1,4-dioxane (2.5 mL), $Cs_2CO_3$ (0.536 g, 1.65 mmol) and trifluoro(vinyl)-14-borane potassium salt (0.09 g, 0.66 mmol) and $PdCl_2$(dppf).DCM (0.045 g, 0.055 mmol) was added and stirred at 100° C. for 16 h. After completion of the reaction as monitored by TLC (50% ethyl acetate in Hexane), the reaction mixture was poured into water (30 mL) and extracted with ethyl acetate (2×20 mL). The combined organic layer was dried over $Na_2SO_4$ and concentrated under reduced pressure. The crude was purified by column chromatography (35% ethyl acetate in hexane) to obtain Int-B-5.29-A1 as a yellow oil (0.20 g, 77.60%).

Step-2: To a suspension of 10% Pd/C (0.050 g) in methanol (2 mL) was added a solution of tert-butyl ((2S)-1-((amino(oxo)(4-vinylthiophen-2-yl)-λ6-sulfanylidene)amino)-4-methyl-1-oxopentan-2-yl)carbamate (0.20 g, 0.498 mmol, 1 eq) in Methanol (4 mL) at room temperature. The $H_2$ gas was purged through the reaction mixture for 2 h. After completion of the reaction as monitored by TLC, the reaction mixture was filtered using celite and the filtrate was concentrated under reduced pressure. The crude was purified by column chromatography (27% ethyl acetate in hexane) to obtain the title compound, Int-B-5.29, as a yellow sticky solid (0.120 g, 49.75%). LCMS ESI (m/z): 404.7 (M+1)

The diastereomers were separated by Chiral prep HPLC (YMC CHIRALART CELLULOSE-SC, Mobile phase n-Heptane:IPA (82:18) to give Isomer-1 (Fr-1): Retention time: 14.70 min & Isomer-2 (Fr-2): Retention time: 32.61 min Step-3: The Boc de-protection of Int-A-5.29-Fr-1 and Int-A-5.29-Fr-2 was carried out as shown for the ANASIA-059 using 4 M HCl in dioxane to give ANASIA-133-1 and ANASIA-133-2.

Isomer-1: $^1$H NMR (400 MHz, DMSO-$d_6$) δ 8.09 (s, 5H), 7.61 (m, 2H), 3.66 (bs, 1H), 2.63-2.57 (q, 2H), 1.77-1.61 (m, 2H), 1.50-1.48 (m, 1H), 1.17 (t, J=7.4 Hz, 3H), 0.88-0.87 (d, J=6 Hz, 6H). LCMS ESI (m/z): 304.1 (M+H). Purity at 210 nm: 99.01%

Isomer-2: $^1$H NMR (400 MHz, DMSO-$d_6$) δ 8.22 (bs, 2H), 8.02 (bs, 3H), 7.62 (m, 2H), 3.66 (bs, 1H), 2.61-2.57 (q, 2H), 1.80-1.77 (m, 1H), 1.72-1.66 (m, 1H), 1.59-1.54 (m, 1H), 1.81 (t, J=7.6 Hz, 3H), 0.90 (two d, J=7 Hz, 6H). LCMS ESI (m/z): 304.1 (M+H). Purity at 210 nm: 100%

Synthesis of (S)-2-amino-N—((S)-amino(oxo)(5-vinylthiophen-2-yl)-λ6-sulfanylidene)-4-methylpentanamide and (S)-2-amino-N—((R)-amino(oxo)(5-vinylthiophen-2-yl)-λ6-sulfanylidene)-4-methylpentanamide (ANASIA-105-1

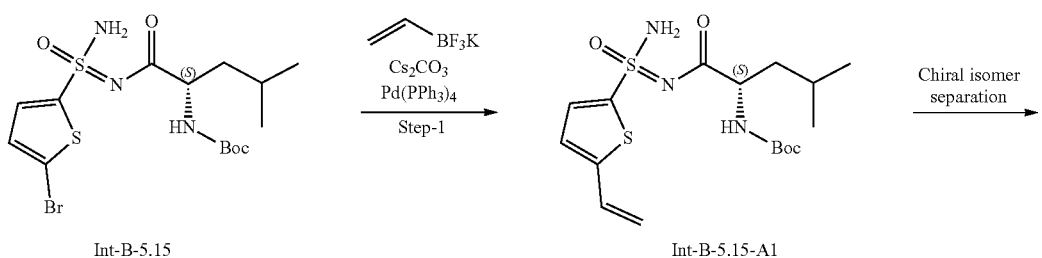

Int-B-5.15          Int-B-5.15-A1

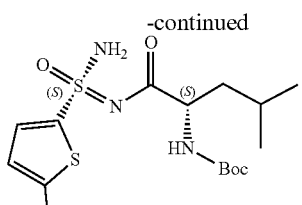

Int-B-5.15-A1-Fr-1

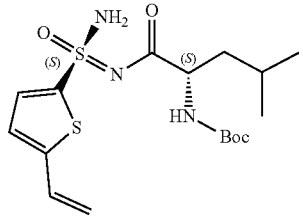

Int-B-5.15-A1-Fr-2

Step-2 | HCl in dioxane

Step-2 | HCl in dioxane

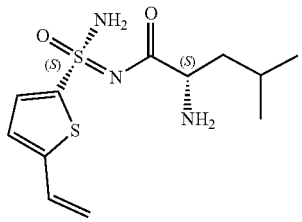

ANASIA105-1

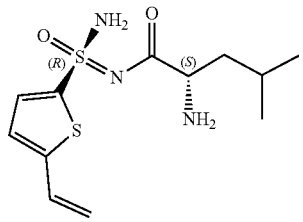

ANASIA105-2

Step-1: To a degassed solution of tert-butyl ((2S)-1-((amino(5-bromothiophen-2-yl)(oxo)-λ6-sulfanylidene)amino)-4-methyl-1-oxopentan-2-yl)carbamate (0.2 g, 0.44 mmol), Potassium vinyl trifluoroborate (0.795 g, 5.94 mmol) and $Cs_2CO_3$ (1.16 g, 3.56 mmol) in $THF:H_2O$ (5:0.5 mL) was added $Pd(PPh_3)_4$ (0.13 g, 0.11 mmol) and heated at 100° C. for 48 h. After completion of the reaction as indicated by TLC, the reaction mixture was poured into water and extracted with ethyl acetate. The combined organic layer was washed with brine, dried over $Na_2SO_4$, and evaporated under vacuum. The crude was purified by silica gel column chromatography (ethyl acetate/hexane) to give the title compound, Int-B-5.15-A1, as a mixture of diastereomers (207 mg, 43.38%). LCMS ESI (m/z): 402.5 (M+H).

The diastereomers were separated by Chiral prep HPLC (YMC CHIRALART Cellulose_SC, Mobile phase: n-Heptane_IPA-ACN (70-30)+2% MTBE_94:6 to give Isomer-1 (Fr-1): Retention time: 26.71 min & Isomer-2 (Fr-2): Retention time: 44.50 min Step-3: The Boc de-protection of Int-A-5.15-Fr-1 and Int-A-5.15-Fr-2 was carried out as shown for the ANASIA-059 using 4 M HCl in dioxane to give ANASIA-105-1 and ANASIA-105-2.

Isomer-1: $^1$H NMR (400 MHz, DMSO d6) δ 8.31 (bs, 2H), 8.04 (s, 3H), 7.61 (d, J=3.8 Hz, 1H), 7.20 (d, J=3.4 Hz, 1H), 6.96-6.89 (m, 1H), 5.75 (d, J=17.4 Hz, 1H), 5.38 (d, J=10.9 Hz, 1H), 3.68 (bs, 1H), 1.76-1.48 (m, 3H), 0.88 (d, 6H). LCMS ESI (m/z): 302.3 (M+H). Purity at 210 nm: 94.53%

Isomer-2: LCMS ESI (m/z): 302.4 (M+H). Purity at 210 nm: 84.46%

Synthesis of (2S)-2-amino-N-(amino(oxo)(3-vinyl-thiophen-2-yl)-λ6-sulfanylidene)-4-methylpentanamide hydrochloride (ANASIA-106

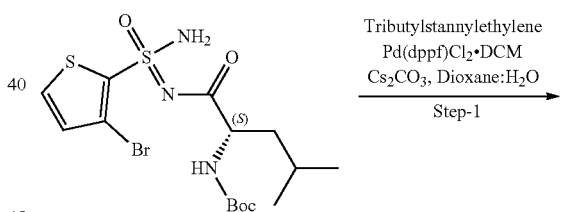

Int-B-5.41

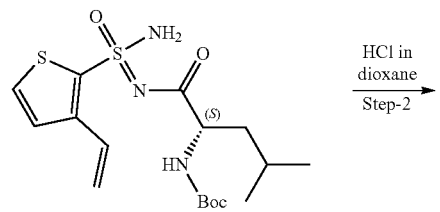

Int-B-5.41-A1

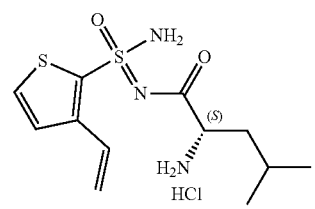

ANASIA-106

Step-1: To a degassed solution of tert-butyl ((2S)-1-((amino(3-bromothiophen-2-yl)(oxo)-λ6-sulfanylidene)amino)-4-methyl-1-oxopentan-2-yl)carbamate (0.440 g, 0.96 mmol) and Cs$_2$CO$_3$ (0.945 g, 2.90 mmol) in dioxane:water (9:1) (4.4 mL), Tributylstannylethylene (1.53 g, 4.84 mmol) and PdCl$_2$(dppf) DCM complex (0.095 g, 0.11 mmol) was added and the reaction mixture was heated at 100° C. for 2 h under microwave. After completion of the reaction as indicated by TLC, the reaction mixture was poured into water (30 mL) and extracted with ethyl acetate (2×25 mL). The combined organic layer was dried over Na$_2$SO$_4$ and concentrated under vacuum. The crude product was subjected to silica gel column chromatography to give Int-B-5.41-A1 (0.090 g, 23%). LCMS ESI (m/z): 402.5 (M+H).

Step-2: The Boc de-protection of Int-B-5.41-A1 was carried out as shown for the ANASIA-059 using 4 M HCl in dioxane.

$^1$H NMR (400 MHz, DMSO d6) δ 8.3-8-8 (bs, 2H), 7.97 (bs, 3H), 7.89 (d, J=5.2 Hz, 1H), 7.55 (d, J=5.2 Hz, 1H), 7.24-7.15 (m, 1H), 5.93 (d, J=17.6 Hz, 1H), 5.49 (t, J=11.2 Hz, 1H), 3.70-3.66 (m, 1H), 1.78-1.57 (m, 2H), 1.43-1.38 (m, 1H), 0.92-0.87 (m, 6H). LCMS ESI (m/z): 302.1 (M+H). Purity at 210 nm: 95.32%.

Synthesis of (2S)-2-amino-N-(amino(2-hydroxyphenyl)(oxo)-λ6-sulfanylidene)-4-methylpentanamide (ANASIA-113

Step-1: The Boc de-protection of Int-B-5.53 was carried out as shown for the ANASIA-059 using 4 M HCl in dioxane to give ANASIA-113.

$^1$H NMR (400 MHz, DMSO) δ 10.94 (bs, 1H), 7.91 (bs, 3H), 7.76 (d, J=6.4 Hz, 1H), 7.45-7.44 (m, 3H), 7.03-6.94 (m, 2H), 3.63-3.58 (m, 1H), 1.74-1.70 (m, 1H), 1.55-1.44 (m, 2H), 0.91-0.88 (m, 6H). LCMS ESI (m/z): 286.2 (M+1). Purity at 210 nm: 100%

Synthesis of tert-butyl ((2S)-1-((((tert-butyldimethylsilyl)amino)(3-methoxyphenyl)(oxo)-λ6-sulfaneylidene)amino)-4-methyl-1-oxopentan-2-yl)carbamate (Int-I-1.0

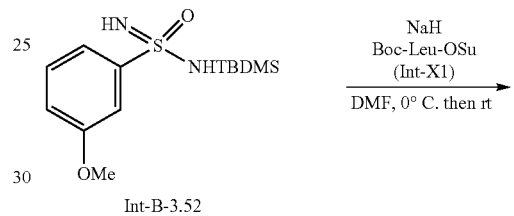

Int-B-3.52

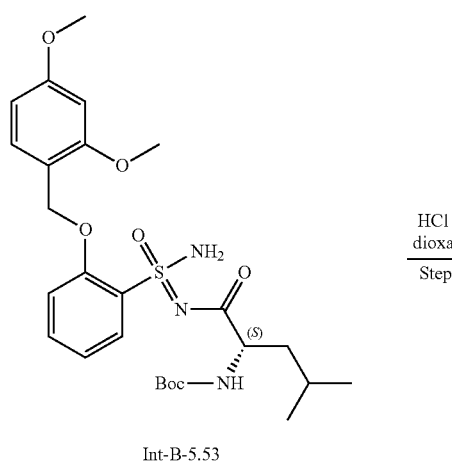

Int-B-5.53

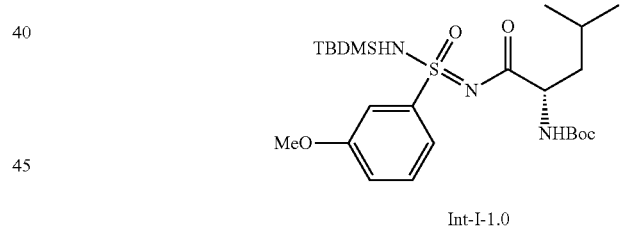

Int-I-1.0

Int-B-3.52 (400 mg, 1.33 mmol, 1 equiv) was dissolved in dry DMF (7 mL). The solution was cooled to 0° C. and NaH (60% in oil, 138 mg, 3.46 mmol, 2.6 equiv) was added (the solution turned yellow). The mixture was stirred at the same temperature for 10 min. Then Boc-Leu-OSu Int-X1 (437 mg, 1.33 mmol, 1 equiv) was added. The mixture was allowed to warm to room temperature and left to stir until completion as indicated by TLC then it was poured into water and extracted with ethyl acetate. The combined organic layer was washed with brine, dried over Na$_2$SO$_4$, and evaporated under vacuum to give the crude material which was purified chromatography to afford the title compound, Int-3-1.3 (as a mixture of diastereomers (120 mg, 18%). UPLCMS ESI (m/z): 514.78 (M+H)$^+$ The following intermediates were made according to the procedure described for Int-I-1.0.

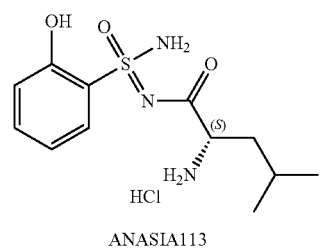

ANASIA113

Synthesis Table 19

| Structure | Compound ID | Precursor | Analytical data |
|---|---|---|---|
| (structure) | Int-I-1.1 | Int-B-3.59 | UPLCMS ESI (m/z): 528.84 (M + H)+ |
| (structure) | Int-I-1.3 | Int-B-3.53 | UPLCMS ESI (m/z): 294 (M + H)+ |
| (structure) | Int-I-1.4 | Int-B-3.54 | UPLCMS ESI (m/z): 520.77 (M + H)+ |
| (structure) | Int-I-1.5 | Int-B-3.60 | UPLCMS ESI (m/z): 508.6 (M + H)+ |
| (structure) | Int-I-1.6 | Int-B-3.61 | UPLCMS ESI (m/z): 508.7 (M + H)+ |
| (structure) | Int-I-1.7 | Int-B-3.62 | $^1$H NMR (300 MHz, CDCl$_3$) δ 7.28 (d, J = 2.4 Hz, 1H), 7.23-7.15 (m, 2H), 6.87 (d, J = 8.5 Hz, 2H), 6.69 (s, 1H), 5.24 (d, J = 1.5 Hz, 2H), 4.95 (s, 1H), 4.22-4.10 (m, 1H), 3.80 (s, 3H), 1.74-1.55 (m, 3H), 1.50-1.35 (m, 10H), 0.98-0.82 (m, 15H), 0.32-0.08 (m, 6H). |

Synthesis Table 19

| Structure | Compound ID | Precursor | Analytical data |
|---|---|---|---|
| (structure shown) | Int-I-1.8 | Int-B-3.64 | $^1$H NMR (300 MHz, CDCl$_3$) δ 7.06-6.99 (m, 1H), 6.65 (t, J = 5.2 Hz, 1H), 4.82 (s, 1H), 4.24-3.99 (m, 1H), 1.76-1.31 (m, 12H), 1.07-0.83 (m, 15H), 0.44--0.08 (m, 6H). |

Synthesis of (2S)-2-amino-N-(amino(3-methoxyphenyl)(oxo)-16-sulfaneylidene)-4-methylpentanamide

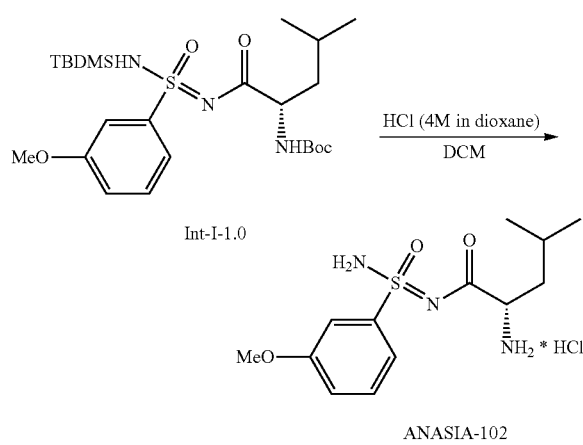

Int-I-1.0 (120 mg, 0.23 mmol, 1 equiv) was dissolved in DCM (0.5 mL). To the solution was added HCl (4 M, in Diox, 4 equiv) and the solution was stirred until complete Boc-group deprotection. The solvent was evaporated under reduced pressure and the crude product was purified via reverse phase chromatography. (H$_2$O/MeCN) (100:0 to 80:20) to give ANASIA-102 (26 mg, 37%) $^1$H NMR (400 MHz, ACN) δ 7.67-7.34 (m, 3H), 7.34-7.11 (m, 1H), 3.89-3.80 (m, 3H), 3.80-3.71 (m, 1H), 1.77-1.52 (m, 3H), 0.97-0.81 (in, 6H). $^{13}$C NMR (101 MHz, ACN) δ 176.66, 176.53, 160.81, 142.66, 142.62, 131.51, 120.49, 120.46, 120.05, 120.01, 112.79, 112.76, 56.64, 55.27, 55.24, 40.61, 25.18, 22.69, 22.60, 22.14, 22.10. Purity at 210 nm: 93.14%; at 254 nm: 89.21% UPLCMS ESI (m/z): 300.49 (M+H)+.

The following compounds were made according to the procedure described for compound ANASIA-102 using HCl or TFA.

Synthesis Table 20

| Structure | Precursor | Analytical data |
|---|---|---|
| ANASIA-060 (structure shown) | Int-I-1.3 | $^1$H NMR (400 MHz, CD$_3$CN): 7.70-7.66 (m, 1H), 7.39 (s, 2H), 7.01-6.98 (m, 1H), 4.17 (s, 1H), 3.87-3.76 (m, 1H), 1.84-1.73 (m, 2H), 1.70-1.63 (m, 1H), 0.96 (t, J = 6 Hz, 3H), 0.95 (t, J = 5.81 Hz, 3H). $^{19}$F NMR (376 MHz, CD$_3$CN) -76.26, -126.92 (dd, J = 18.7, 3.9 Hz). $^{13}$C NMR (101 MHz, CD$_3$CN): 176.0, 175.8, 166.3 (d, J = 293.2 Hz), 137.0 (d, J = 5.2 Hz), 121.6 (d, J = 3.7 Hz), 107.1 (d, J = 14.1 Hz), 55.8, 55.8, 40.5, 25.2, 25.2, 22.6, 22.6, 22.0, 22.0. Purity at 210 nm: 99.3%; at 254 nm: 96.09% |

-continued

Synthesis Table 20

| Structure | Precursor | Analytical data |
|---|---|---|
| ANASIA-061 | Int-I-1.4 | $^1$H NMR (400 MHz, Methanol-d4): 7.42 (dd, J = 4.0, 2.0 Hz, 1H), 6.92 (d, J = 2.0 Hz, 1H), 3.82 (d, J = 0.5 Hz, 3H), 3.81-3.74 (m, 1H), 1.89-1.76 (m, 2H), 1.67-1.54 (m, 1H), 1.02-0.94 (m, 6H). $^{13}$C NMR (101 MHz, MeOD): 176.9, 176.85, 158.9, 158.8, 141.5, 141.46, 125.50, 125.48, 106.53, 106.48, 58.3, 55.6 55.5, 41.5, 41.4, 25.6, 22.94, 22.92, 22.19, 22.15. Purity at 210 nm: 96.03%; at 254 nm: 94.64% |
| ANASIA-066 | Int-I-1.1 | $^1$H NMR (400 MHz, MeOD): 7.59-7.44 (m, 3H), 7.21-7.17 (m, 1H), 4.20-4.06 (m, 2H), 3.84-3.72 (m, 1H), 1.91-1.70 (m, 2H), 1.69-1.51 (m, 1H), 1.42 (t, J = 7.0 Hz, 3H), 1.04-0.93 (m, 6H). $^{13}$C NMR (101 MHz, MeOD) 177.01, 176.98, 160.6, 143.6, 143.6, 131.2, 120.6, 120.2, 120.1, 114.1, 114.0, 65.2, 55.5, 41.6, 41.5, 25.6, 23.0, 22.9, 22.24, 22.18, 15.0. UPLCMS ESI (m/z): 314 (M + H)$^+$ Purity at 210 nm: 97.6%; at 254 nm: 99.08% |
| ANASIA-070 | Int-I-1.5 | $^1$H NMR (400 MHz, CD$_3$CN) 8.06 (s, 2H), 7.76 (dd, J = 5.6, 3.9 Hz, 1H), 7.26 (s, 1H), 6.96 (d, J = 5.5 Hz, 1H), 3.82 (s, 1H), 1.91-1.70 (m, 3H), 0.99-0.88 (m, 6H). $^{13}$C NMR (101 MHz, CD$_3$CN) 176.20, 175.90, 157.93 (d, J = 273.2 Hz), 157.89 (d, J = 273.1 Hz), 133.08 (d, J = 3.0 Hz), 132.99 (d, J = 3.0 Hz), 121.26 (d, J = 3.3 Hz), 121.14 (d, J = 3.4 Hz), 119.44, 119.20, 55.85, 55.81, 40.65, 40.61, 25.27, 25.24, 22.83, 22.76, 22.39, 22.36 (mixture of two diastereomers). $^{19}$F NMR (376 MHz, CD$_3$CN) −114.51 (dd, J = 7.7, 3.9 Hz) (mixture of two diastereomers). UPLCMS ESI (m/z): 294 (M + H)$^+$ Purity at 210 nm: 95.29%; at 254 nm: 97% |
| ANASIA-071 | Int-I-1.6 | $^1$H NMR (400 MHz, DMSO-d$_6$) 8.41 (s, 1H), 8.13 (s, 2H), 7.52 (dt, J = 6.1, 4.1 Hz, 1H), 6.93 (d, J = 4.4 Hz, 1H), 3.64 (s, 2H), 1.85-1.45 (m, 3H), 0.93-0.83 (m, 6H). $^{13}$C NMR (101 MHz, DMSO-d$_6$) 175.49, 175.36, 168.19 (d, J = 297.8 Hz), 168.25 (d, J = 297.7 Hz), 131.02 (d, J = 3.4 Hz), 130.88 (d, J = 3.4 Hz), 130.56 (t, J = 5.0 Hz), 109.81, 109.69, 53.55, 53.49, 23.76, 23.71, 22.64, 22.61, 21.90, 21.88 (mixture of two diastereomers). $^{19}$F NMR (376 MHz, DMSO-d$_6$) −121.08 (d, J = 4.1 Hz), −121.21 (d, J = 4.1 Hz) (mixture of two diastereomers). Purity at 210 nm: 96.39%; at 254 nm: 97.46% |

Synthesis Table 20 -continued

| Structure | Precursor | Analytical data |
|---|---|---|
| ANASIA-074 | Int-I-1.8 | $^1$H NMR (400 MHz, MeOD): 7.12-7.06 (m, 1H), 7.03-6.97 (m, 1H), 3.83-3.72 (m, 1H), 1.90-1.72 (m, 2H), 1.67-1.53 (m, 1H), 1.03-0.88 (m, 6H). $^{19}$F NMR (376 MHz, MeOD): −76.93 (TFA), −120.43 (t, J = 4.0 Hz), −120.56 (t, J = 4.0 Hz). $^{13}$C NMR (101 MHz, MeOD): 177.25, 177.17, 166.83 (d, J = 300.5 Hz), 166.76 (d, J = 300.4 Hz), 162.89 (q, J = 34.6 Hz, TFA), 125.13 (d, J = 4.9 Hz), 123.00 (d, J = 3.8 Hz), 122.94 (d, J = 3.7 Hz), 118.34 (q, J = 301.6 Hz, TFA), 114.84 (d, J = 3.3 Hz), 114.83 (d, J = 3.4 Hz), 55.55, 55.49, 41.55, 41.41, 25.62, 25.61, 22.98, 22.93, 22.16, 22.07. Purity at 210 nm: 99.08%; at 254 nm: 99.03% |

Synthesis of (2S)-2-amino-N-(amino(oxo)(1H-pyrazol-5-yl)-16-sulfaneylidene)-4-methylpentanamide (ANASIA-064

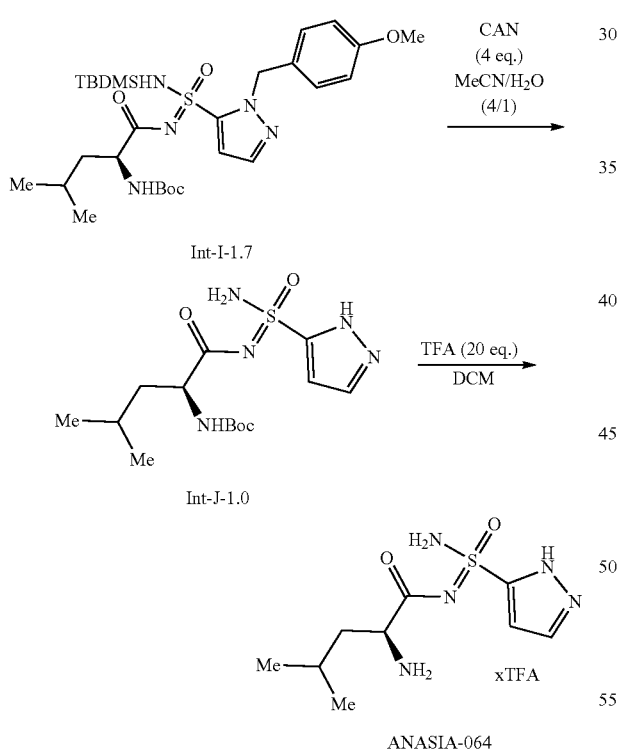

Step-1: The flask was charged with Int-1-1.7 (320 mg, 0.54 mmol), CH$_3$CN (12 mL), H$_2$O (4 mL), and ammonium cerium nitrate (1.18 mg, 2.15 mmol). After stirring at room temperature for 3 h, H$_2$O (50 mL) was added to the reaction mixture. The product was extracted with ethyl acetate (70 mL×3), and the organic layers were combined, washed with saturated sodium hydrogen carbonate and brine, dried over anhydrous MgSO$_4$. The mixture was subjected to purification by column chromatography to give product Int-J-1.0 (148 mg, 76%): UPLCMS ESI (m/z): 360 (M+H)+

Step-2: Int-J-1.0 (148 mg, 0.41 mmol) was dissolved in DCM (1 mL) and TFA (0.5 mL) was added. The mixture was evaporated, and the residue was subjected to the reverse phase chromatography to give ANASIA-064 (175 mg, 87%). $^{13}$C NMR (101 MHz, MeOD): 177.13, 177.07, 152.59, 131.72, 131.68, 107.75, 107.69, 55.65, 55.60, 49.80, 48.26, 48.25, 48.23, 48.22, 48.20, 48.19, 48.17, 48.16, 48.14, 48.13, 48.11, 48.08, 41.50, 41.43, 25.61, 25.56, 22.95, 22.93, 22.17, 22.14. $^1$H NMR (400 MHz, MeOD): 7.81 (dd, J=2.5, 1.2 Hz, 1H), 6.87 (dd, J=3.8, 2.4 Hz, 1H), 3.77 (dd, J=8.3, 5.6 Hz, 1H), 1.93-1.72 (m, 2H), 1.67-1.51 (m, 1H), 1.03-0.94 (m, 6H). $^{19}$F NMR (376 MHz, MeOD): −77.22 (TFA) Purity at 210 nm: 98.09%.

Biological Methods

Study 1—Enzyme Inhibition

The aminoacylation reaction catalyzed by aminoacyl-tRNA synthetases (aaRS) takes place in two steps. In the first step, aaRS activates its cognate amino acid with ATP; and in the second step the activated amino acid is loaded to its corresponding tRNA. This reaction can be summarized as follows:

aaRS+aa+ATP=aaRS-aa-AMP+PPi aaRS-aa-AMP+tRNA=aa-tRNA+AMP+aaRS wherein: aaRS, aminoacyl-tRNA synthetase; aa, amino acid; aaRS-aa-AMP, enzyme-bound to aminoacyl-adenylate; AMP, adenosine monophosphate; aa-tRNA, aminoacyl-tRNA, PPi, inorganic pyrophosphate.

Leucyl-tRNA Synthetase a. Single Point Percentage Inhibition

The activity of the pathogenic aaRSs was monitored by measuring AMP production using the commercial kit AMP-Glo (Promega, Madison, USA).

Ligand stock solutions were prepared in 100% DMSO at 10 mM concentration. An assay buffer consisting of 100 mM Tris HCl pH 7.6, 40 mM MgCl, 20 mM KCl and 150 mM NaCl was prepared in dH$_2$O. An enzyme solution containing 72.95 µM LeuRS was prepared in assay buffer to provide 20 nM final assay concentration and 50 nM reservoir concentration for a 1:2.5 dilution in the assay. A substrate solution was also prepared in assay buffer with 50 mM L-leucine, 10 mM ATP and 100 mg/mL tRNA. A final assay concentration of 500 µM L-leucine, 16.7 µM ATP and 0.5 mg/mL tRNA and reservoir concentration of 833.33 µM L-leucine, 27.83 µM ATP and 0.83 mg/mL tRNA was used for a 1:1.66 dilution in assay.

Enzyme percentage inhibition values were recorded in triplicate at a single point concentration of 100 µM. If the tested compound inhibited the aminoacylation reaction above 25% in at least two replicates, an $IC_{50}$ was performed with the same enzymatic assay.

b. Determination of $IC_{50}$

Using the same enzymatic assay in a 384-well plate format, ten point concentration response curves were generated for each compound using a top concentration of 10 µM. The known inhibitor LeuAMS was used as a positive control for the LeuRS assay. 100% DMSO was used as a negative control. The $IC_{50}$ was calculated based on non-linear regression analysis.

Isoleucyl-tRNA Synthetase a. Single Point Percentage Inhibition

The activity of the pathogenic aaRSs was monitored by measuring AMP production using the commercial kit AMP-Glo (Promega, Madison, USA).

Ligand stock solutions were prepared in 100% DMSO at 10 mM concentration. An assay buffer consisting of 100 mM Tris HCl pH 7.6, 40 mM MgCl, 20 mM KCl and 150 mM NaCl was prepared in $dH_2O$. An enzyme solution containing 51.77 µM IleRS was prepared in assay buffer to provide 30 nM final assay concentration and 75 nM reservoir concentration for a 1:2.5 dilution in the assay. A substrate solution was also prepared in assay buffer with 50 mM L-isoleucine, 10 mM ATP and 100 mg/mL tRNA. A final assay concentration of 500 µM L-isoleucine, 5 µM ATP and 1 mg/mL tRNA and reservoir concentration of 833.33 µM L-isoleucine, 8.33 µM ATP and 1.67 mg/mL tRNA was used for a 1:1.66 dilution in assay.

Enzyme percentage inhibition values were recorded in triplicate at a single point concentration of 100 µM. If the tested compound inhibited the aminoacylation reaction above 25% in at least two replicates, an $IC_{50}$ was performed with the same enzymatic assay.

b. Determination of $IC_{50}$

Using the same enzymatic assay in a 384-well plate format, ten point concentration response curves were generated for each compound using a top concentration of 100 µM. The known inhibitor, IleAMS was used as a positive control for the IleRS assay. 100% DMSO was used as a negative control. The $IC_{50}$ was calculated based on non-linear regression analysis.

Valyl-tRNA Synthetase a. Single Point Percentage Inhibition

The activity of the pathogenic aaRSs was monitored by measuring AMP production using the commercial kit AMP-Glo (Promega, Madison, USA).

Ligand stock solutions were prepared in 100% DMSO at 10 mM concentration. An assay buffer consisting of 100 mM Tris HCl pH 7.6, 40 mM MgCl, 20 mM KCl and 150 mM NaCl was prepared in $dH_2O$. An enzyme solution containing 42.33 µM ValRS was prepared in assay buffer to provide 30 nM final assay concentration and 75 nM reservoir concentration for a 1:2.5 dilution in the assay. A substrate solution was also prepared in assay buffer with 50 mM L-valine, 10 mM ATP and 100 mg/mL tRNA. A final assay concentration of 500 µM L-valine, 2.5 µM ATP and 0.5 mg/mL tRNA and reservoir concentration of 833.33 µM L-valine, 9.3 µM ATP and 0.83 mg/mL tRNA was used for a 1:1.66 dilution in assay.

Enzyme percentage inhibition values were recorded in triplicate at a single point concentration of 100 µM. If the tested compound inhibited the aminoacylation reaction above 25% in at least two replicates, an $IC_{50}$ was performed with the same enzymatic assay.

b. Determination of $IC_{50}$

Using the same enzymatic assay in a 384-well plate format, ten point concentration response curves were generated for each compound using a top concentration of 100 µM. The known inhibitor, ValAMS was used as a positive control for the ValRS assay. 100% DMSO was used as a negative control. The $IC_{50}$ was calculated based on non-linear regression analysis.

The data are summarised in the following table.

Biological Data Table 1
Enzyme Inhibition - $IC_{50}$ (nM)

| Compound | E. coli LeuRS | E. coli IleRS | E. coli ValRS |
| --- | --- | --- | --- |
| ANASIA-001 | 429 | | |
| ANASIA-001-1 | 535 | | |
| ANASIA-001-2 | 3530 | | |
| ANASIA-002 | 110 | | |
| ANASIA-002-1 | 27.5 | | |
| ANASIA-002-2 | 1050 | | |
| ANASIA-003 | 92.9 | | |
| ANASIA-003-1 | 61.5 | | |
| ANASIA-003-2 | 2260 | | |
| ANASIA-004 | 91.6 | | |
| ANASIA-005 | 381 | | |
| ANASIA-005-1 | 3030 | | |
| ANASIA-005-2 | 151 | | |
| ANASIA-006 | 708 | | |
| ANASIA-007-1 | 63.3 | | |
| ANASIA-007-2 | 4900 | | |
| ANASIA-008 | 144 | | |
| ANASIA-008-1 | 30.6 | | |
| ANASIA-008-2 | 2000 | | |
| ANASIA-009-1 | 1830 | | |
| ANASIA-009-2 | 149 | | |
| ANASIA-010-1 | 9150 | | |
| ANASIA-011 | 71.9 | | |
| ANASIA-011-1 | 26.2 | | |
| ANASIA-011-2 | 729 | | |
| ANASIA-012 | 155 | | |
| ANASIA-012-1 | 87.4 | | |
| ANASIA-012-2 | 3230 | | |
| ANASIA-013 | 3570 | | |
| ANASIA-014-1 | 81.1 | | |
| ANASIA-014-2 | 3980 | | |
| ANASIA-015-1 | 56.5 | | |
| ANASIA-015-2 | 1860 | | |
| ANASIA-016 | 3040 | | |
| ANASIA-016-1 | 2200 | | |
| ANASIA-016-2 | 5560 | | |
| ANASIA-017 | 145 | | |
| ANASIA-018-1 | 223 | | |
| ANASIA-018-2 | 2970 | | |
| ANASIA-019 | 2260 | | |
| ANASIA-020-1 | 2050 | | |
| ANASIA-020-2 | 4090 | | |
| ANASIA-021-1 | 2060 | | |
| ANASIA-022-1 | 6570 | | |
| ANASIA-023 | 1290 | | |
| ANASIA-024-1 | 141 | | |
| ANASIA-024-2 | 6280 | | |
| ANASIA-025 | | >100000 | 21900 |
| ANASIA-026-1 | 564 | | |
| ANASIA-026-2 | 4420 | | |
| ANASIA-027-1 | 4530 | | |
| ANASIA-028-1 | | 46500 | |
| ANASIA-029-1 | | 67400 | |
| ANASIA-029-2 | | 4590 | |
| ANASIA-030 | | 9590 | |
| ANASIA-031 | | 6700 | |
| ANASIA-031-2 | | 2650 | |

Biological Data Table 1
Enzyme Inhibition - IC$_{50}$ (nM)

| Compound | E. coli LeuRS | E. coli IleRS | E. coli ValRS |
|---|---|---|---|
| ANASIA-032-1 | | 50800 | |
| ANASIA-033-1 | | 67600 | |
| ANASIA-034-1 | | 14700 | |
| ANASIA-035-1 | | 18300 | |
| ANASIA-035-2 | | 4650 | |
| ANASIA-036-1 | | 7860 | |
| ANASIA-036-2 | | 30600 | |
| ANASIA-037 | | 2740 | |
| ANASIA-038 | | 15800 | |
| ANASIA-039 | 8830 | | |
| ANASIA-040-1 | 2540 | | |
| ANASIA-041-1 | 17.7 | | |
| ANASIA-041-2 | 832 | | |
| ANASIA-042-1 | 1110 | | |
| ANASIA-042-2 | 7920 | | |
| ANASIA-043-1 | 112 | | |
| ANASIA-043-2 | 735 | | |
| ANASIA-044-1 | 71 | | |
| ANASIA-044-2 | 2160 | | |
| ANASIA-045 | 5520 | | |
| ANASIA-046-1 | 960 | | |
| ANASIA-046-2 | 2570 | | |
| ANASIA-047-1 | 76.4 | | |
| ANASIA-047-2 | 1290 | | |
| ANASIA-048 | 6530 | | |
| ANASIA-049-1 | 296 | | |
| ANASIA-049-2 | 2630 | | |
| ANASIA-050-1 | 4330 | | |
| ANASIA-051-1 | 601 | | |
| ANASIA-052-1 | | 37700 | |
| ANASIA-052-2 | | 40100 | |
| ANASIA-053-1 | | 20200 | |
| ANASIA-054-1 | | 83700 | |
| ANASIA-054-2 | | 19900 | |
| ANASIA-055-1 | | 35100 | |
| ANASIA-056-1 | | 84000 | |
| ANASIA-057-1 | | 27500 | |
| ANASIA-058 | | 58600 | |
| ANASIA-059-1 | 46% at 10 µM | | |
| ANASIA-060 | 227 | | |
| ANASIA-061 | 465 | | |
| ANASIA-062-1 | 47.5 | | |
| ANASIA-062-2 | 715 | | |
| ANASIA-063 | 223 | | |
| ANASIA-064 | 2170 | | |
| ANASIA-065 | 670 | | |
| ANASIA-066 | 553 | | |
| ANASIA-067-1 | 1920 | | |
| ANASIA-068 | 141 | | |
| ANASIA-069-2 | | 13700 | |
| ANASIA-070 | 143 | | |
| ANASIA-071 | 173 | | |
| ANASIA-072-1 | | 53100 | |
| ANASIA-073 | 238 | | |
| ANASIA-074 | 99.2 | | |
| ANASIA-075-1 | 420 | | |
| ANASIA-075-2 | 2540 | | |
| ANASIA-076 | 2260 | | |
| ANASIA-077-1 | | 40800 | |
| ANASIA-078-1 | | 16400 | |
| ANASIA-078-2 | | 599 | |
| ANASIA-079-1 | | 19800 | |
| ANASIA-079-2 | | 372 | |
| ANASIA-080-1 | | 1140 | |
| ANASIA-080-2 | | 41300 | |
| ANASIA-081-1 | 33.9 | | |
| ANASIA-081-2 | 488 | | |
| ANASIA-082 | 449 | | |
| ANASIA-083-1 | 157 | | |
| ANASIA-083-2 | 2300 | | |
| ANASIA-084 | | 2820 | |
| ANASIA-085 | 594 | | |
| ANASIA-086-1 | 3330 | | |
| ANASIA-087-1 | 289 | | |
| ANASIA-087-2 | 4920 | | |
| ANASIA-088-1 | 75.3 | | |
| ANASIA-088-2 | 1560 | | |
| ANASIA-089-1 | 195 | | |
| ANASIA-089-2 | 2390 | | |
| ANASIA-090 | 199 | | |
| ANASIA-091-1 | 847 | | |
| ANASIA-091-2 | 8150 | | |
| ANASIA-092-1 | 48.4 | | |
| ANASIA-092-2 | 1970 | | |
| ANASIA-093 | 1330 | | |
| ANASIA-094-1 | 476 | | |
| ANASIA-095-1 | 29 | | |
| ANASIA-095-2 | 1890 | | |
| ANASIA-096 | 700 | | |
| ANASIA-097 | 2160 | | |
| ANASIA-098-1 | 148 | | |
| ANASIA-098-2 | 5140 | | |
| ANASIA-099 | 72.2 | | |
| ANASIA-099-1 | 124 | | |
| ANASIA-099-2 | 511 | | |
| ANASIA-100 | 32.8 | | |
| ANASIA-100-1 | 27.8 | | |
| ANASIA-100-2 | 945 | | |
| ANASIA-101-1 | 1670 | | |
| ANASIA-102 | 385 | | |
| ANASIA-103-1 | 19.5 | | |
| ANASIA-103-2 | 210 | | |
| ANASIA-104-1 | 241 | | |
| ANASIA-104-2 | 3250 | | |
| ANASIA-105-1 | 489 | | |
| ANASIA-106 | 897 | | |
| ANASIA-107-1 | 106 | | |
| ANASIA-107-2 | 1290 | | |
| ANASIA-108-1 | 127 | | |
| ANASIA-108-2 | 4310 | | |
| ANASIA-109-1 | 2560 | | |
| ANASIA-110-1 | 425 | | |
| ANASIA-110-2 | 6240 | | |
| ANASIA-111-1 | 779 | | |
| ANASIA-112-1 | 294 | | |
| ANASIA-113 | 3230 | | |
| ANASIA-114-1 | 61.8 | | |
| ANASIA-114-2 | 982 | | |
| ANASIA-115-1 | | 4700 | |
| ANASIA-116-1 | | 3830 | |
| ANASIA-116-2 | | 950 | |
| ANASIA-117-1 | | | 47900 |
| ANASIA-118 | | 52900 | 38600 |
| ANASIA-119-1 | 99.7 | | |
| ANASIA-119-2 | 4650 | | |
| ANASIA-120-1 | 293 | | |
| ANASIA-120-2 | 7600 | | |
| ANASIA-121-1 | 41.7 | | |
| ANASIA-121-2 | 1100 | | |
| ANASIA-122-1 | 167 | | |
| ANASIA-122-2 | 1930 | | |
| ANASIA-123 | 4870 | >100E+03 | |
| ANASIA-124-1 | 21.3 | | |
| ANASIA-124-2 | 4800 | | |
| ANASIA-125-1 | 304 | | |
| ANASIA-125-2 | 1930 | | |
| ANASIA-126-1 | 208 | | |
| ANASIA-126-2 | 1720 | | |
| ANASIA-127-1 | 6890 | | |
| ANASIA-127-2 | 192 | | |
| ANASIA-128-1 | 2610 | | |
| ANASIA-128-2 | 3440 | | |
| ANASIA-129-1 | 319 | | |
| ANASIA-130-1 | 324 | | |
| ANASIA-130-2 | 3700 | | |
| ANASIA-131-1 | 530 | | |
| ANASIA-132-1 | 4140 | | |
| ANASIA-133-1 | 97.3 | | |

Biological Data Table 1
Enzyme Inhibition - IC$_{50}$ (nM)

| Compound | E. coli LeuRS | E. coli IleRS | E. coli ValRS |
|---|---|---|---|
| ANASIA-133-2 | 6370 | | |
| ANASIA-134-1 | 5150 | | |
| ANASIA-135-1 | 5070 | | |
| ANASIA-135-2 | 262 | | |
| ANASIA-136-1 | 71.8 | | |
| ANASIA-136-2 | 1410 | | |
| ANASIA-137-1 | 2670 | | |
| ANASIA-137-2 | 8890 | | |
| ANASIA-138 | | 383 | |

Study 2—Antibacterial Activity

Minimum Inhibitory Concentrations (MICs) were determined by the broth micro-dilution method performed according to Clinical Laboratory Standards Institute guidelines. For testing, 5 mg/mL DMSO solutions were prepared by dissolving solids in DMSO. Standard antibiotics were prepared according to CLSI guidelines as 5 mg/mL stock solutions. Upon DMSO stock solutions preparation, the working solutions in MH media were prepared by adding 38.4 µL of stock solution to 1461.6 µL of MH media. Out of these working solutions 100 µL were transferred to wells in the third column of 96-well assay plates. Assay plates were previously filled with 50 µL of MH media in all wells except for the wells in the third column. Upon compounds and antibiotics addition, 50 µL was transferred from the third to the fourth column, then from the fourth to the fifth and so on. In this manner, the compounds and antibiotics were plated in 96-well assay plates in serial two fold dilutions starting from a top concentration of 256 µg/mL or 64 µg/mL.

MIC value was determined by visual inspection of bacterial growth within 96-well plates. The first column in which there was no visible growth of bacteria was determined as MIC value for compound or antibiotic tested in that particular row. ATCC strains were used as reference strains for which there is a determined value of MIC values for standard antibiotics. The assay is considered valid when MIC values for standard antibiotics are within ALSI designated range for ATCC strain tested.

The data are summarised in the following table.

Biological Data Table 2
Antibacterial Activity (MIC, mg/L)

| Cpd Code | A | B | C | D | E | F | G |
|---|---|---|---|---|---|---|---|
| ANASIA-001 | 32 | >64.0 | >64.0 | >64.0 | >64.0 | >64.0 | |
| ANASIA-001-1 | 16 | >64.0 | >64.0 | >64.0 | >64.0 | 32 | |
| ANASIA-002 | 2.83 | >45.3 | >22.6 | >64.0 | >45.3 | 5.66 | |
| ANASIA-002-1 | 1 | 8 | 32 | >64.0 | 32 | 2 | 4 |
| ANASIA-002-2 | 64 | >64.0 | >64.0 | >64.0 | >64.0 | >64.0 | |
| ANASIA-003 | 2.83 | 16 | 8 | 50.8 | 32 | 16 | |
| ANASIA-003-1 | 4 | 16 | 16 | 64 | 64 | 8 | |
| ANASIA-004 | 16 | >64.0 | >64.0 | 64 | 64 | 8 | |
| ANASIA-004-1 | 4 | >64.0 | >64.0 | 64 | 32 | | 64 |
| ANASIA-005 | 8 | 32 | 32 | >64.0 | 64 | 32 | |
| ANASIA-005-2 | 8 | 64 | >64.0 | >64.0 | >64.0 | 16 | 32 |
| ANASIA-006 | 64 | >64.0 | >64.0 | >64.0 | >64.0 | >64.0 | |
| ANASIA-007-1 | 1 | 8 | 8 | 16 | 8 | 2 | 5.04 |
| ANASIA-008 | 2 | 16 | 8 | 32 | 32 | 16 | |
| ANASIA-008-1 | 2 | 8 | 8 | 32 | 32 | 4 | |
| ANASIA-009-2 | 4 | 32 | 32 | >64.0 | 64 | 8 | |
| ANASIA-011 | 1 | 8 | 8 | 32 | 16 | 4 | |
| ANASIA-011-1 | 0.707 | 4 | 8 | 64 | 16 | 2 | 2.52 |
| ANASIA-011-2 | 64 | >64.0 | >64.0 | >64.0 | >64.0 | >64.0 | |
| ANASIA-012 | 8 | 64 | >64.0 | >64.0 | >64.0 | 16 | 32 |
| ANASIA-012-1 | 4 | 32 | 64 | >64.0 | 64 | 8 | 16 |
| ANASIA-014-1 | 4 | 16 | 64 | >64.0 | 64 | 4 | |
| ANASIA-015-1 | 2 | 16 | 16 | 64 | 64 | 8 | 5.66 |
| ANASIA-017 | 16 | >64.0 | >64.0 | >64.0 | >64.0 | 8 | |
| ANASIA-017-1 | 4 | >256 | >64.0 | >64.0 | >64.0 | 4 | 22.6 |
| ANASIA-024-1 | 16 | >64.0 | >64.0 | >64.0 | >64.0 | 16 | |
| ANASIA-029-2 | 64 | >64.0 | >64.0 | >64.0 | >64.0 | 16 | |
| ANASIA-031 | >64.0 | >64.0 | >64.0 | >64.0 | >64.0 | 64 | |
| ANASIA-031-2 | 64 | 64 | >64.0 | >64.0 | >64.0 | 16 | |
| ANASIA-034-1 | >64.0 | >64.0 | >64.0 | >64.0 | >64.0 | 64 | |
| ANASIA-035-2 | >64.0 | >64.0 | >64.0 | >64.0 | >64.0 | 64 | |
| ANASIA-037 | >64.0 | >64.0 | >64.0 | >64.0 | >64.0 | 32 | |
| ANASIA-038 | >64.0 | >64.0 | >64.0 | >64.0 | >64.0 | 64 | |
| ANASIA-041-1 | 5.66 | >64.0 | >64.0 | >64.0 | >64.0 | 2.83 | 64 |
| ANASIA-043-1 | >64.0 | >64.0 | >64.0 | >64.0 | >64.0 | 45.3 | |
| ANASIA-044-1 | 2 | 16 | 64 | >64.0 | 64 | 2 | |
| ANASIA-045-1 | 4 | >64.0 | >64.0 | >64.0 | 64 | | 45.3 |
| ANASIA-046-1 | >64.0 | >64.0 | >64.0 | >64.0 | >64.0 | 64 | |
| ANASIA-047-1 | >64.0 | >64.0 | >64.0 | >64.0 | >64.0 | 64 | |
| ANASIA-060 | | | 32 | | | | 16 |
| ANASIA-061 | 16 | | 256 | | | | 64 |
| ANASIA-062-1 | | | 32 | | | | 8 |
| ANASIA-063 | | | >256 | | | | 64 |
| ANASIA-066 | 64 | | | | | | >64.0 |
| ANASIA-068 | 32 | | | | | | >64.0 |

Biological Data Table 2
Antibacterial Activity (MIC, mg/L)

| Cpd Code | A | B | C | D | E | F | G |
|---|---|---|---|---|---|---|---|
| ANASIA-070 | | | 64 | | | | 32 |
| ANASIA-071 | | | 32 | | | | 8 |
| ANASIA-074 | | | 32 | | | | 16 |
| ANASIA-075-1 | 32 | | | | | >64.0 | |
| ANASIA-079-2 | 64 | | | | | | |
| ANASIA-081-1 | 2 | | 256 | >64.0 | 32 | 1 | 8 |
| ANASIA-083-1 | 32 | | | | | 32 | |
| ANASIA-087-1 | 11.3 | 64 | >64.0 | >64.0 | >64.0 | 32 | |
| ANASIA-088-1 | 4 | 64 | >256 | >64.0 | >64.0 | 4 | 32 |
| ANASIA-089-1 | 64 | | | | | 64 | |
| ANASIA-091-1 | 64 | | | | | | >64.0 |
| ANASIA-092-1 | 2 | | 64 | >64.0 | 64 | 2 | 11.3 |
| ANASIA-094-1 | 8 | | 128 | | | | 64 |
| ANASIA-095-1 | 0.794 | 8 | 10.1 | 32 | 8 | | 2 |
| ANASIA-098-1 | 3.17 | 16 | 32 | 64 | 64 | | 4 |
| ANASIA-099 | 1 | | 16 | >64.0 | 32 | 2 | 2.83 |
| ANASIA-099-1 | 0.5 | 4 | 8 | 64 | 16 | | 4 |
| ANASIA-100 | 0.5 | | 64 | >64.0 | 32 | 0.5 | 4 |
| ANASIA-100-1 | 1 | 16 | 45.3 | 64 | 16 | | 5.66 |
| ANASIA-101-1 | 64 | | | | | | |
| ANASIA-102 | 16 | | | | | | >64.0 |
| ANASIA-103-1 | 1 | | 64 | 64 | 16 | 1 | 10.1 |
| ANASIA-103-2 | 16 | | | | | | |
| ANASIA-104-1 | 8 | | 128 | | | | 16 |
| ANASIA-105-1 | 32 | | | | | | |
| ANASIA-107-1 | 32 | | | | | | |
| ANASIA-108-1 | 8 | | 64 | 64 | >64.0 | 32 | 16 |
| ANASIA-109-1 | 32 | | | | | | 32 |
| ANASIA-112-1 | 32 | | | | | | 64 |
| ANASIA-113 | 64 | | | | | | |
| ANASIA-119-1 | 4 | 32 | 64 | >64.0 | 32 | | 8 |
| ANASIA-120-1 | 32 | | | | | | |
| ANASIA-121-1 | 8 | | >256 | | | | 16 |
| ANASIA-122-1 | 32 | | | | | | |
| ANASIA-124-1 | 0.25 | 8 | 16 | 32 | 8 | | 1.59 |
| ANASIA-125-1 | | | >256 | | | | 64 |
| ANASIA-126-1 | 5.66 | >64.0 | 256 | >64.0 | >64.0 | | 32 |
| ANASIA-129-1 | | | 128 | | | | 64 |
| ANASIA-131-1 | 32 | | 256 | | | | >64.0 |
| ANASIA-133-1 | | | 128 | | | | 8 |
| ANASIA-135-2 | 8 | | >256 | | | | 64 |
| ANASIA-136-1 | 8 | | >256 | | | | >64.0 |
| ANASIA-138 | >64.0 | >64.0 | >64.0 | >64.0 | >64.0 | 16 | |
| Azithromycin | 4 | 16 | 32 | 32 | 16 | 2 | |
| Ceftazidime | 0.25 | 0.5 | >64 | >64 | 2 | 16 | >64.0 |
| Ciprofloxacin | <0.125 | <0.125 | 1 | 64 | <0.125 | <0.125 | >64.0 |
| Meropenem | 0.5 | 0.5 | 0.5 | >64 | 8 | 4 | >62.0 |

Key:
A = *E. coli* ATCC 25922
B = *Enterobacter cloacae* B1966
C = *K. pneumoniae* ATCC 700603
D = *P. aeruginosa* ATCC 27853
E = *A. baumannii* B1931
F = *H. influenzae* ATCC 49247
G = *E. coli* BAA-2469

Study 3—Human Cell Viability

Compounds were assessed for potential non-specific cytotoxic effects against a human hepatic cell line (HepG2 ATCC HB-8065). 96-well plates were seeded with HepG2 cells in concentration of 15,000 cells per well in 100 μL of MEM growth media completed with 1% NEAA and 1% sodium pyruvate. Border wells were filled with 100 μL of sterile PBS. Two days upon cells incubation, the compounds were added. Compound dilutions were prepared in 96-well V-bottom plate in pure DMSO. Growth media from 5 plates were aspirated and replaced with 98.7 μL of fresh growth media. 1.28 μL of compounds prepared in V-bottom plates were transferred with multichannel pipette into test plates (78.1× dilution). Final DMSO concentration was 1.28% per well. In control wells, 1.28 μL of DMSO was added in 98.7 μL of media. Compounds were tested in duplicates. Cells were incubated with compounds for 24 hours when cell viability was assessed by measuring ATP levels. ATP levels were measured by adding 50 μL of CellTiter-Glo reagent to each well and after 5 minutes of incubation luminescence was measured with SpectraMax i3. The potential effect of tested compounds on cell viability was determined by comparing the signal obtained in presence of different concentrations of the compounds with those obtained in the presence of DMSO only. The potential effects were then calculated and presented as $IC_{50}$ values (μg/mL).

The data are summarised in the following table.

Biological Data Table 3
Cytotoxicity in HepG2 ATCC HB-8065 Cell Line

| Compound No. | IC$_{50}$ (μg/mL) |
|---|---|
| ANASIA-001 | >64.0 |
| ANASIA-001-1 | >64.0 |
| ANASIA-001-2 | >64.0 |
| ANASIA-002 | >64.0 |
| ANASIA-002-1 | >64.0 |
| ANASIA-002-2 | >64.0 |
| ANASIA-003 | >64.0 |
| ANASIA-003-1 | >64.0 |
| ANASIA-003-2 | >64.0 |
| ANASIA-004 | >64.0 |
| ANASIA-005 | >64.0 |
| ANASIA-005-1 | >64.0 |
| ANASIA-005-2 | >64.0 |
| ANASIA-006 | >64.0 |
| ANASIA-007-1 | >64.0 |
| ANASIA-007-2 | >64.0 |
| ANASIA-008 | >64.0 |
| ANASIA-008-1 | >64.0 |
| ANASIA-008-2 | >64.0 |
| ANASIA-009-1 | >64.0 |
| ANASIA-009-2 | >64.0 |
| ANASIA-011 | >64.0 |
| ANASIA-011-1 | >64.0 |
| ANASIA-011-2 | >64.0 |
| ANASIA-012 | >64.0 |
| ANASIA-012-1 | >64.0 |
| ANASIA-012-2 | >64.0 |
| ANASIA-013 | >64.0 |
| ANASIA-014-1 | >64.0 |
| ANASIA-014-2 | >64.0 |
| ANASIA-015-1 | >64.0 |
| ANASIA-015-2 | >64.0 |
| ANASIA-016 | >64.0 |
| ANASIA-016-1 | >64.0 |
| ANASIA-016-2 | >64.0 |
| ANASIA-017 | >64.0 |
| ANASIA-017-1 | >64.0 |
| ANASIA-018-1 | >64.0 |
| ANASIA-018-2 | >64.0 |
| ANASIA-019 | >64.0 |
| ANASIA-020-1 | >64.0 |
| ANASIA-020-2 | >64.0 |
| ANASIA-021-1 | >64.0 |
| ANASIA-022-1 | >64.0 |
| ANASIA-023 | >64.0 |
| ANASIA-024-1 | >64.0 |
| ANASIA-024-2 | >64.0 |
| ANASIA-025 | >64.0 |
| ANASIA-026-1 | >64.0 |
| ANASIA-026-2 | >64.0 |
| ANASIA-027-1 | >64.0 |
| ANASIA-029-2 | >64.0 |
| ANASIA-030 | >64.0 |
| ANASIA-031 | >64.0 |
| ANASIA-031-2 | >64.0 |
| ANASIA-034-1 | >64.0 |
| ANASIA-035-1 | >64.0 |
| ANASIA-035-2 | >64.0 |
| ANASIA-036-1 | >64.0 |
| ANASIA-037 | >64.0 |
| ANASIA-038 | >64.0 |
| ANASIA-039 | >64.0 |
| ANASIA-040-1 | >64.0 |
| ANASIA-041-1 | >64.0 |
| ANASIA-041-2 | >64.0 |
| ANASIA-042-1 | >64.0 |
| ANASIA-042-2 | >64.0 |
| ANASIA-043-1 | >64.0 |
| ANASIA-043-2 | >64.0 |
| ANASIA-044-1 | >64.0 |
| ANASIA-046-1 | >64.0 |
| ANASIA-046-2 | >64.0 |
| ANASIA-047-1 | 46.5 |
| ANASIA-047-2 | 45.3 |
| ANASIA-049-1 | >64.0 |
| ANASIA-051-1 | >64.0 |
| ANASIA-052-1 | >64.0 |
| ANASIA-081-1 | >64.0 |
| ANASIA-087-1 | >64.0 |
| ANASIA-088-1 | >64.0 |
| ANASIA-092-1 | >64.0 |
| ANASIA-099 | >64.0 |
| ANASIA-100 | >64.0 |
| ANASIA-103-1 | >64.0 |
| ANASIA-108-1 | >64.0 |
| ANASIA-138 | >64.0 |

Study 4—Efficacy in a Murine Model of Urinary Tract Infection (*E. coli* UT189)

Methods

Animals

All animal studies were performed under UK Home Office License PA67E0BAA (protocol E9 for UTI model) with local ethical committee clearance. All studies were performed by technicians who have completed parts A, B and C of the UK Home Office Personal License course and hold current personal licenses. All experiments were performed in dedicated Biohazard 2 facilities (the site holds a Certificate of Designation).

Female mice used in these studies were supplied by Janvier laboratories and were specific pathogen free. The strain of mouse used was C3H/HeNRj, which is a well characterized inbred strain. Mice were 16-20 g on receipt and were allowed to acclimatize for at least 7 days prior to any intervention. Five days prior to infection mice were transferred onto drinking water containing 5% glucose.

Test Articles

Ciprofloxacin was provided as 2 mg/mL stock (POM, Claris) and was administered intravenously at 5 mL/kg to achieve a 10 mg/kg dose. It was stored at 4° C. between doses. Test articles were prepared by solubilising in water for injection, taking the salt correction factor into account. The vehicle for studies was water for injection (Braun) and was clear and colourless.

Procedure

Previously prepared frozen stocks of *E. coli* UT189 were diluted to $2.3 \times 10^9$ cfu/mL immediately prior to infection. Mice (n=6 per group) were infected by directly administering 0.05 mL of inoculum via the urethra into the bladder under parenteral anaesthesia. Drinking water was withheld two hours pre-infection and bladders were emptied prior to infection. Once infected, infection catheters were left in the urinary tract for 10 minutes to reduce the risk of the organism flowing back out.

The mice were monitored at a frequency appropriate for their clinical condition. Mouse weights were recorded at least once daily both to ensure animals remained within ethical limits and to monitor efficacy of treatment.

Twenty-four hours post infection, urine was collected from pre-treatment animals and used to assess the infection level. Urine samples were quantitatively cultured onto MacConkey's agar plates and incubated at 37° C. for 24 hours before colonies were counted. In addition, five mice were euthanised by pentobarbitone overdose to provide a 24 hour pre-treatment control group.

Forty-eight hours post-infection, urine was collected from all mice. Seventy-two hours post infection, the clinical condition and body weight of all remaining animals was assessed and urine samples were collected. Animals were then euthanised by pentobarbitone overdose and kidneys and bladders were removed and weighed. Tissue samples were homogenized using a Precellys 24 dual bead beater in 2 mL ice cold sterile phosphate buffered saline. Homogenates and urine samples were quantitatively cultured onto MacConkey's agar plates and incubated at 37° C. for 24 hours before colonies were counted.

Data Analysis

The data from the culture burdens were analysed using appropriate non-parametric statistical models (Kruskal-Wallis using Conover-Inman to make all pairwise comparisons between groups) with StatsDirect software, and compared to pretreatment and vehicle controls.

Experiment 1

The compound ANASIA-103-1 was administered subcutaneously via cannula (pinports) in water for injection 24 hr post-infection and then every 4 hours at 5, 15 and 45 mg/kg/dose. Efficacy was compared against ciprofloxacin (10 mg/kg/dose) administered intravenously at 24, 36, 48 and 60 hr post-infection. Mice were inoculated with $7.5 \times 10^7$ cfu of *E. coli* UT189. The geometric mean microbial burden in the urine was 7.42 $\log_{10}$ cfu/mL at pre-treatment and stayed relatively constant through the experiment: 7.31 $\log_{10}$ cfu/mL at 48 hr and 7.33 $\log_{10}$ cfu/mL at harvest (72 hr) in the vehicle-treated group. Microbial burden in the bladder also remained fairly constant at 8.16 $\log_{10}$ cfu/g pre-treatment and 7.99 $\log_{10}$ cfu/g at harvest. Microbial burden in the kidney increased from 5.31 $\log_{10}$ cfu/g in the pre-treatment group to 6.20 $\log_{10}$ cfu/g at harvest. The reductions in microbial burden for the test article treated groups relative to the vehicle control group are shown in the following table.

Biological Data Table 4

| Compound | Dose mg/kg/dose | Reduction in burden from vehicle control ($\log_{10}$ cfu/g or mL) | | | |
|---|---|---|---|---|---|
| | | Urine 48 hr | Urine 72 hr | Bladder 72 hr | Kidney 72 hr |
| ANASIA-103-1 | 5 sc | 1.36 (P = 0.02) | 0.11 (NS) | 1.28 (P = 0.02) | 0.93 (NS) |
| | 15 sc | 2.14 (P = 0.0006) | 2.71 (P < 0.0001) | 2.08 (P = 0.0004) | 2.28 (P = 0.0001) |
| | 45 sc | 1.74 (P = 0.009) | 2.64 (P < 0.0001) | 1.49 (P = 0.02) | 1.25 (NS) |
| Ciprofloxacin | 10 iv | 6.26 (P < 0.0001) | 4.82 (P < 0.0001) | 2.99 (P < 0.0001) | 4.19 (P < 0.0001) |

NS, not significant

Experiment 2

The compound ANASIA-124-1 was administered subcutaneously in water for injection 24 hr post-infection and then every 4 hours at 15 and 45 mg/kg/dose. Efficacy was compared against ciprofloxacin (10 mg/kg/dose) administered intravenously at 24, 36, 48 and 60 hr post-infection. Mice were inoculated with $1.3 \times 10^7$ cfu of *E. coli* UT189. The geometric mean microbial burden in the urine was 7.05 $\log_{10}$ cfu/mL at pre-treatment and increased to 7.01 $\log_{10}$ cfu/mL at 48 hr and 7.12 $\log_{10}$ cfu/mL at harvest (72 hr) in the vehicle-treated group. Microbial burden in the bladder remained fairly constant at 8.20 $\log_{10}$ cfu/g pre-treatment and 7.98 $\log_{10}$ cfu/g at harvest. Microbial burden in the kidney increased from 5.54 $\log_{10}$ cfu/g in the pre-treatment group to 6.37 $\log_{10}$ cfu/g at harvest. The reductions in microbial burden for the test article treated groups relative to the vehicle control group are shown in the following table.

Biological Data Table 5

| Compound | Dose mg/kg/dose | Reduction in burden from vehicle control ($\log_{10}$ cfu/g or mL) | | | |
|---|---|---|---|---|---|
| | | Urine 48 hr | Urine 72 hr | Bladder 72 hr | Kidney 72 hr |
| ANASIA-124-1 | 15 sc | 0.71 (P = 0.007) | 0.66 (P = 0.04) | 1.24 (NS) | 1.60 (NS) |
| | 45 sc | 1.85 (P < 0.0001) | 1.21 (P = 0.01) | 1.38 (NS) | 2.40 (P = 0.001) |
| Cinprofloxacin | 10 iv | 5.32 (P < 0.0001) | 4.76 (P < 0.0001) | 2.74 (P < 0.0001) | 4.12 (P < 0.0001) |

NS, not significant

Study 5—Efficacy in a Murine Model of Disseminated infection (*E. coli* ATCC 25922)

Methods

Animals

Animal experiments were performed under UK Home Office Licence PA67E0BAA (protocol E1 for sepsis efficacy), with local ethical committee clearance. All experiments were performed by technicians that have completed parts A-C of the Home Office Personal License course and hold current personal licenses.

Mice used in these studies were supplied by Charles River (Margate UK) and were specific pathogen free. The strain of mice used was ICR (also known as CD1 Mice) which is a well characterized outbred murine strain. Mice (male) were 15-18 g on receipt at the facility and were allowed to acclimatise for at least 7 days.

Mice were housed in sterilised individual ventilated cages exposing the mice at all times to HEPA filtered sterile air. Mice had free access to food and water and had aspen chip bedding (changed at least once weekly). The room temperature was 22° C.+/−1° C., with a relative humidity of 60% and maximum background noise of 56 dB. Mice were exposed to 12 hour light/dark cycles.

Test Articles

Test articles were prepared by solubilising in water for injection, taking the salt correction factor into account. The vehicle for studies was water for injection (Braun) and was clear and colourless.

Procedure

Mice (n=5 per group) were not immunosuppressed. The bacterial strain used was *E. coli* ATCC 25922. An aliquot of a previously prepared frozen stock of the strain was thawed and diluted in sterile PBS and hog mucin to the desired inoculum containing 5% hog mucin, just prior to infection. Mice were infected with 0.2 mL of the bacterial strain suspensions by intravenous injection.

Test articles were administered subcutaneously 1 and 3 hours post-infection. Additional control groups comprising an infected pre-treatment group, which was euthanised 1 hour after infection, a vehicle treated group dosed at 1 and 3 hours post-infection, and a group that received comparator test article tigecycline once (1 hr post-infection) at 30 mg/kg SC were included.

At 5 hours post-infection, the clinical condition of all animals was assessed prior to a terminal cardiac bleed under terminal anaesthesia. The spleen and kidneys were dissected out and homogenized in 2 mL ice cold sterile PBS; the homogenates and blood were quantitatively cultured onto CLED agar and incubated at 37° C. for 18-24 hours before colonies were counted.

Data Analysis

The data from the culture burdens were analysed using appropriate non-parametric statistical models (Kruskal-Wallis using Conover-Inman to make all pairwise comparisons between groups) with StatsDirect software, and compared to vehicle control.

Experiment 1

The compound ANASIA-103-1 was administered subcutaneously in water for injection 1 and 3 hr post-infection at 1.875, 7.5 and 30 mg/kg/dose. Separate groups of animals were dosed by oral gavage at the same time points at 7.5 and 30 mg/kg. Efficacy was compared against tigecycline (30 mg/kg) administered subcutaneously at 1 hr post-infection. Mice were inoculated with $4.8 \times 10^7$ cfu of *E. coli* ATCC 25922. The geometric mean microbial burden in the blood was 5.46 $\log_{10}$ cfu/mL at pre-treatment rising to 6.08 $\log_{10}$ cfu/mL at the 5 hr harvest point in the vehicle-treated group. Microbial burden in the kidney was 6.19 $\log_{10}$ cfu/mL at pre-treatment rising to 8.09 $\log_{10}$ cfu/mL at harvest. Microbial burden in the spleen was 6.75 $\log_{10}$ cfu/mL at pre-treatment rising to 8.68 $\log_{10}$ cfu/mL at harvest. The reductions in microbial burden for the test article treated groups relative to the vehicle control group are shown in the following table.

Biological Data Table 6

| Compound | Dose mg/kg/dose | Reduction in burden from vehicle control ($\log_{10}$ cfu/g or mL) | | |
|---|---|---|---|---|
| | | Blood | Kidney | Spleen |
| ANASIA-103-1 | 1.875 sc | 0.32 (NS) | 1.26 (NS) | 0.60 (NS) |
| | 7.5 sc | 1.26 (P = 0.01) | 1.66 (P = 0.0008) | 1.64 (P = 0.001) |
| | 30 sc | 2.18 (P < 0.0001) | 3.06 (P < 0.0001) | 2.24 (P < 0.0001) |
| | 7.5 po | 0.43 (NS) | 1.28 (NS) | 1.46 (P = 0.01) |
| | 30 po | 0.81 (NS) | 1.59 (P = 0.003) | 1.61 (P = 0.003) |
| Tigecycline | 30 sc | 5.13 (P < 0.0001) | 5.62 (P < 0.0001) | 5.15 (P < 0.0001) |

NS, not significant

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below.

Each of these references is incorporated herein by reference in its entirety into the present disclosure, to the same extent as if each individual reference was specifically and individually indicated to be incorporated by reference.

Finn et al., 2018, "2-Amino-N-(arylsulfinyl)-acetamide compounds as inhibitors of bacterial aminoacyl-tRNA synthetase", international (PCT) patent publication number WO 2018/065611 A1 published 12 Apr. 2018.

Gadahk et al., 2012, "Aminoacyl-tRNA synthetase inhibitors as antimicrobial agents: a patent review from 2006 till present", *Expert Opin. Ther. Patents*, Vol. 22, No. 12, pp. 1453-1465.

Hurdle et al., 2005, "Prospects for aminoacyl-tRNA synthetase inhibitors as new antimicrobial agents", *Antimicrobial Agents and Chemotherapy*, Vol. 49, pp. 4821-4833.

Jirgensons et al., 2016, "Novel N-acyl-sulfonamide derivatives as aminoacyl-tRNA synthetase inhibitors", international (PCT) patent publication number WO 2016/129983 A1 published 18 Aug. 2016.

Laupland et al., 2003, "Treatment of *Staphylococcus aureus* colonization and prophylaxis for infection with topical intranasal mupirocin: An evidence-based review", *Clinical Infectious Diseases*, Vol. 37, pp. 933-938.

Ochsner et al., 2007, "Aminoacyl-tRNA synthetases: essential and still promising targets for new anti-infective agents", *Expert Opinion on Investigational Drugs*, Vol. 16, pp. 573-593.

Pham et al., 2014, "Aminoacyl-tRNA synthetases as drug targets in eukaryotic parasites", *Int. J. Parasitol. Drugs Drug Resist.*, Vol. 4, Issue 1, pp. 1-13.

Vondenhoff et al., 2011, "Aminoacyl-tRNA synthetase inhibitors as potential antibiotics", *Eur. J. Med. Chem.*, Vol. 46, pp. 5227-5236.

The invention claimed is:

1. A compound selected from compounds of the following formula, and pharmaceutically acceptable salts thereof:

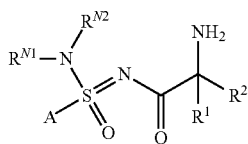

wherein:
-A is independently -$A^C$ or -$A^H$;
-$A^C$ is independently phenyl or naphthyl, and is optionally substituted with one or more substituents —$R^X$;
-$A^H$ is independently $C_{5-12}$heteroaryl, and is optionally substituted with one or more substituents —$R^X$;
and wherein:
each —$R^X$ is independently selected from:
—$R^{XX}$, —$R^{XXU}$, —$R^{XXV}$,
—F, —Cl, —Br, —I,
—OH, —$OR^{XX}$,
-$L^{XX}$-OH, -$L^{XX}$-$OR^{XX}$,
—$CF_3$, —$CHF_2$, —$OCF_3$, —$OCHF_2$,
—$NH_2$, —$NHR^{XX}$, —$NR^{XX}_2$, —$R^{XM}$,
-$L^{XX}$-$NH_2$, -$L^{XX}$-$NHR^{XX}$, -$L^{XX}$-$NR^{XX}_2$, -$L^{XX}$-$R^{XM}$,
—C(=O)OH, —C(=O)$OR^{XX}$, —OC(=O)$R^{XX}$,
—C(=O)$NH_2$, —C(=O)$NHR^{XX}$, —C(=O)$NR^{XX}_2$,
—C(=O)$R^{XM}$,
—NHC(=O)$R^{XX}$, —$NR^{XN}$C(=O)$R^{XX}$,
—NHC(=O)$NH_2$, —NHC(=O)$NHR^{XX}$, —NHC(=O)$NR^{XX}_2$, —NHC(=O)$R^{XM}$,
—$NR^{XN}$C(=O)$NH_2$, —$NR^{XN}$C(=O)$NHR^{XX}$,
—$NR^{XN}$C(=O)$NR^{XX}_2$, —$NR^{XN}$C(=O)$R^{XM}$,
—NHC(=O)$OR^{XX}$, —$NR^{XN}$C(=O)$OR^{XX}$,
—OC(=O)$NH_2$, —OC(=O)$NHR^{XX}$, —OC(=O)$NR^{XX}_2$, —OC(=O)$R^{XM}$,
—NHC(=NH)$NH_2$,
—C(=O)$R^{XX}$,
—S(=O)$NH_2$, —S(=O)$NHR^{XX}$, —S(=O)$NR^{XX}_2$,
—S(=O)$R^{XM}$,
—S(=O)$_2NH_2$, —S(=O)$_2NHR^{XX}$, —S(=O)$_2NR^{XX}_2$,
—S(=O)$_2R^{XM}$,
—NHS(=O)$R^{XX}$, —$NR^{XN}$S(=O)$R^{XX}$,
—NHS(=O)$_2R^{XX}$, —$NR^{XN}$S(=O)$_2R^{XX}$,
—S(=O)$R^{XX}$, —S(=O)$_2R^{XX}$,
—SH, —$SR^{XX}$, —CN, and —$NO_2$;
and additionally, two adjacent groups —$R^X$, if present, may together form:
—O—$CH_2$—O—, —O—$CH_2CH_2$—O—, —$CH_2$—$CH_2$—O—, —$CH_2$—$CH_2CH_2$—O—,
—$CH_2$—O—$CH_2$—, or —$CH_2$—$CH_2$—O—$CH_2$—;
wherein:
each -$L^{XX}$- is linear or branched saturated $C_{1-4}$alkylene;
each —$R^{XX}$ is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$;
each —$R^{XXU}$ is independently linear or branched $C_{2-4}$alkenyl;
each —$R^{XXV}$ is independently linear or branched $C_{2-4}$alkynyl;
each —$R^{XN}$ is linear or branched saturated $C_{1-4}$alkyl;
each —$R^{XM}$ is independently azetidino, pyrrolidino, piperidino, piperazino, morpholino, azepano, or diazepano, and is:
optionally substituted with one or more groups selected from:
—$R^{XMM}$, —C(=O)$R^{XMM}$, —C(=O)$OR^{XMM}$, and —S(=O)$_2R^{XMM}$;
wherein each —$R^{XMM}$ is independently linear or branched saturated $C_{1-4}$alkyl, phenyl, or —$CH_2$-phenyl, wherein each phenyl is optionally substituted with one or more groups selected from —F, —Cl, —Br, -Me, —OH, —OMe, —$CF_3$, and —$OCF_3$;
—$R^1$ is independently —H or —$R^{11}$;
—$R^{11}$ is independently —$R^{11A}$ or —$R^{11B}$;
—$R^{11A}$ is independently:
—$R^{A1}$, —$R^{A2}$, —$R^{A3}$, —$R^{A4}$, —$R^{A5}$, -$L^A$-$R^{A2}$, -$L^A$-$R^{A3}$, -$L^A$-$R^{A4}$, or -$L^A$-$R^{A5}$;
each —$R^{A1}$ is linear or branched saturated $C_{1-6}$alkyl, and is optionally substituted with one or more groups —$R^{AA2}$;
each —$R^{A2}$ is saturated $C_{3-6}$cycloalkyl, and is optionally substituted with one or more groups —$R^{AA1}$ and one or more groups —$R^{AA2}$;
each —$R^{A3}$ is non-aromatic $C_{3-7}$heterocyclyl, and is optionally substituted with one or more groups —$R^{AA1}$ and one or more groups —$R^{AA2}$;
each —$R^{A4}$ is independently phenyl or naphthyl, and is optionally substituted with one or more groups —$R^{AA1}$ and one or more groups —$R^{AA2}$;
each —$R^{A5}$ is $C_{5-10}$heteroaryl, and is optionally substituted with one or more groups —$R^{AA1}$ and one or more groups —$R^{AA2}$;
each -$L^A$- is linear or branched saturated $C_{1-4}$alkylene;
each —$R^{AA1}$ is independently selected from:
—$R^{AA}$,
-$L^{AA}$-OH, -$L^{AA}$-$OR^{AA}$,
-$L^{AA}$-$NH_2$, -$L^{AA}$-$NHR^{AA}$, -$L^{AA}$-$N(R^{AA})_2$, and -$L^{AA}$-$R^{AM}$;
each —$R^{AA2}$ is independently selected from:
—F, —Cl, —Br, —I,
—OH, —$OR^{AA}$,
—$CF_3$, —$CHF_2$, —$OCF_3$, —$OCHF_2$,
—$NH_2$, —$NHR^{AA}$, —$N(R^{AA})_2$, —$R^{AM}$,
—C(=O)OH, —C(=O)$OR^{AA}$, —OC(=O)$R^{AA}$,
—C(=O)$NH_2$, —C(=O)$NHR^{AA}$, —C(=O)$N(R^{AA})_2$,
—C(=O)$R^{AM}$,
—NHC(=O)$R^{AA}$, —$NR^{AN}$C(=O)$R^{AA}$,
—NHC(=O)$NH_2$, —NHC(=O)$NHR^{AA}$, —NHC(=O)$N(R^{AA})_2$, —NHC(=O)$R^{AM}$,
—$NR^{AN}$C(=O)$NH_2$, —$NR^{AN}$C(=O)$NHR^{AA}$,
—$NR^{AN}$C(=O)$N(R^{AA})_2$, —$NR^{AN}$C(=O)$R^{AM}$,
—NHC(=O)$OR^{AA}$, —$NR^{AN}$C(=O)$OR^{AA}$,
—OC(=O)$NH_2$, —OC(=O)$NHR^{AA}$, —OC(=O)$N(R^{AA})_2$, —OC(=O)$R^{AM}$,
—NHC(=NH)$NH_2$,
—C(=O)$R^{AA}$,
—S(=O)$NH_2$, —S(=O)$NHR^{AA}$, —S(=O)$N(R^{AA})_2$,
—S(=O)$R^{AM}$, —S(=O)$_2$NH$_2$, —S(=O)$_2$NHR$^{AA}$, —S(=O)$_2$N(R$^{AA}$)$_2$, —S(=O)$_2$R$^{AM}$,
—NHS(=O)R$^{AA}$, —NR$^{AN}$S(=O)R$^{AA}$,
—NHS(=O)$_2$R$^{AA}$, —NR$^{AN}$S(=O)$_2$R$^{AA}$,
—S(=O)R$^{AA}$, —S(=O)$_2$R$^{AA}$,
—SH, —SR$^{AA}$, —CN, and —NO$_2$;
wherein:
  each -L$^{AA}$- is linear or branched saturated C$_{1-4}$alkylene;
  each —R$^{AA}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
  each —R$^{AN}$ is linear or branched saturated C$_{1-4}$alkyl;
  each —R$^{AM}$ is independently azetidino, pyrrolidino, piperidino, piperazino, morpholino, azepano, or diazepano, and is:
  optionally substituted with one or more groups selected from:
  —R$^{AMM}$, —C(=O)R$^{AMM}$, —C(=O)OR$^{AMM}$, and —S(=O)$_2$R$^{AMM}$;
  wherein each —R$^{AMM}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
  —R$^{11B}$ is independently selected from:
  —F, —Cl, —Br, —I,
  —OH, —OR$^{BB}$,
  —CF$_3$, —CHF$_2$, —OCF$_3$, —OCHF$_2$,
  —NH$_2$, —NHR$^{BB}$, —NR$^{BB}$$_2$, —R$^{BM}$,
  —C(=O)OH, —C(=O)OR$^{BB}$, —OC(=O)R$^{BB}$,
  —C(=O)NH$_2$, —C(=O)NHR$^{BB}$, —C(=O)NR$^{BB}$$_2$, —C(=O)R$^{BM}$,
  —NHC(=O)R$^{BB}$, —NR$^{BN}$C(=O)R$^{BB}$,
  —NHC(=O)NH$_2$, —NHC(=O)NHR$^{BB}$, —NHC(=O)NR$^{BB}$$_2$, —NHC(=O)R$^{BM}$,
  —NR$^{BN}$C(=O)NH$_2$, —NR$^{BN}$C(=O)NHR$^{BB}$, —NR$^{BN}$C(=O)NR$^{BB}$$_2$, —NR$^{BN}$C(=O)R$^{BM}$,
  —NHC(=O)OR$^{BB}$, —NR$^{BN}$C(=O)OR$^{BB}$,
  —OC(=O)NH$_2$, —OC(=O)NHR$^{BB}$, —OC(=O)NR$^{BB}$$_2$, —OC(=O)R$^{BM}$,
  —NHC(=NH)NH$_2$,
  —C(=O)R$^{BB}$,
  —S(=O)NH$_2$, —S(=O)NHR$^{BB}$, —S(=O)NR$^{BB}$$_2$, —S(=O)R$^{BM}$,
  —S(=O)$_2$NH$_2$, —S(=O)$_2$NHR$^{BB}$, —S(=O)$_2$NR$^{BB}$$_2$, —S(=O)$_2$R$^{BM}$,
  —NHS(=O)R$^{BB}$, —NR$^{BN}$S(=O)R$^{BB}$,
  —NHS(=O)$_2$R$^{BB}$, —NR$^{BN}$S(=O)$_2$R$^{BB}$,
  —S(=O)R$^{BB}$, —S(=O)$_2$R$^{BB}$,
  —SH, —SR$^{BB}$, —CN, and —NO$_2$;
wherein:
  each —R$^{BB}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
  each —R$^{BN}$ is linear or branched saturated C$_{1-4}$alkyl;
  each —R$^{BM}$ is independently azetidino, pyrrolidino, piperidino, piperazino, morpholino, azepano, or diazepano, and is:
  optionally substituted with one or more groups selected from:
  —R$^{BMM}$, —C(=O)R$^{BMM}$, —C(=O)OR$^{BMM}$, and —S(=O)$_2$R$^{BMM}$;
  wherein each —R$^{BMM}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
  —R$^2$ is independently —H or —R$^{22}$;
  —R$^{22}$ is independently —R$^{22C}$ or —R$^{22D}$;
  —R$^{22C}$ is independently:
  —R$^{C1}$, —R$^{C2}$, —R$^{C3}$, —R$^{C4}$, —R$^{C5}$, -L$^C$-R$^{C2}$, -L$^C$-R$^{C3}$, -L$^C$-R$^{C4}$, or -L$^C$-R$^{C5}$;
  each —R$^{C1}$ is linear or branched saturated C$_{1-6}$alkyl, and is optionally substituted with one or more groups —R$^{CC2}$;
  each —R$^{C2}$ is saturated C$_{3-6}$cycloalkyl, and is optionally substituted with one or more groups —R$^{CC1}$ and one or more groups —R$^{CC2}$;
  each —R$^{C3}$ is non-aromatic C$_{3-6}$heterocyclyl, and is optionally substituted with one or more groups —R$^{CC1}$ and one or more groups —R$^{CC2}$;
  each —R$^{C4}$ is independently phenyl or naphthyl, and is optionally substituted with one or more groups —R$^{CC1}$ and one or more groups —R$^{CC2}$;
  each —R$^{C5}$ is C$_{5-10}$heteroaryl, and is optionally substituted with one or more groups —R$^{CC1}$ and one or more groups —R$^{CC2}$;
  each -L$^C$- is linear or branched saturated C$_{1-4}$alkylene;
  each —R$^{CC1}$ is independently selected from:
  —R$^{CC}$,
  -L$^{CC}$-OH, -L$^{CC}$-OR$^{CC}$,
  -L$^{CC}$-NH$_2$, -L$^{CC}$-NHR$^{CC}$, -L$^{CC}$-N(R$^{CC}$)$_2$, and -L$^{CC}$-R$^{CM}$;
  each —R$^{CC2}$ is independently selected from:
  —F, —Cl, —Br, —I,
  —OH, —OR$^{CC}$,
  —CF$_3$, —CHF$_2$, —OCF$_3$, —OCHF$_2$,
  —NH$_2$, —NHR$^{CC}$, —N(R$^{CC}$)$_2$, —R$^{CM}$,
  —C(=O)OH, —C(=O)OR$^{CC}$, —OC(=O)R$^{CC}$,
  —C(=O)NH$_2$, —C(=O)NHR$^{CC}$, —C(=O)N(R$^{CC}$)$_2$, —C(=O)R$^{CM}$,
  —NHC(=O)R$^{CC}$, —NR$^{CN}$C(=O)R$^{CC}$,
  —NHC(=O)NH$_2$, —NHC(=O)NHR$^{CC}$, —NHC(=O)N(R$^{CC}$)$_2$, —NHC(=O)R$^{CM}$,
  —NR$^{CN}$C(=O)NH$_2$, —NR$^{CN}$C(=O)NHR$^{CC}$, —NR$^{CN}$C(=O)N(R$^{CC}$)$_2$, —NR$^{CN}$C(=O)R$^{CM}$,
  —NHC(=O)OR$^{CC}$, —NR$^{CN}$C(=O)OR$^{CC}$,
  —OC(=O)NH$_2$, —OC(=O)NHR$^{CC}$, —OC(=O)N(R$^{CC}$)$_2$, —OC(=O)R$^{CM}$,
  —NHC(=NH)NH$_2$,
  —C(=O) R$^{CC}$,
  —S(=O)NH$_2$, —S(=O)NHR$^{CC}$, —S(=O)N(R$^{CC}$)$_2$, —S(=O)R$^{CM}$,
  —S(=O)$_2$NH$_2$, —S(=O)$_2$NHR$^{CC}$, —S(=O)$_2$N(R$^{CC}$)$_2$, —S(=O)$_2$R$^{CM}$,
  —NHS(=O)R$^{CC}$, —NR$^{CN}$S(=O)R$^{CC}$,
  —NHS(=O)$_2$R$^{CC}$, —NR$^{CN}$S(=O)$_2$R$^{CC}$,
  —S(=O)R$^{CC}$, —S(=O)$_2$R$^{CC}$,
  —SH, —SR$^{CC}$, —CN, and —NO$_2$;
wherein:
  each -L$^{CC}$- is linear or branched saturated C$_{1-4}$alkylene;
  each —R$^{CC}$ is independently linear or branched saturated C$_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
  each —R$^{CN}$ is linear or branched saturated C$_{1-4}$alkyl;

each —$R^{CM}$ is independently azetidino, pyrrolidino, piperidino, piperazino, morpholino, azepano, or diazepano, and is:
optionally substituted with one or more groups selected from:
—$R^{CMM}$, —C(=O)$R^{CMM}$, —C(=O)O$R^{CMM}$, and —S(=O)$_2R^{CMM}$;
wherein each —$R^{CMM}$ is independently linear or branched saturated $C_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
—$R^{22D}$ is independently selected from:
—F, —Cl, —Br, —I,
—OH, —OR$^{DD}$,
—CF$_3$, —CHF$_2$, —OCF$_3$, —OCHF$_2$,
—NH$_2$, —NHR$^{DD}$, —NR$^{DD}_2$, —R$^{DM}$,
—C(=O)OH, —C(=O)OR$^{DD}$, —OC(=O)R$^{DD}$,
—C(=O)NH$_2$, —C(=O)NHR$^{DD}$, —C(=O)NR$^{DD}_2$, —C(=O)R$^{DM}$,
—NHC(=O)R$^{DD}$, —NR$^{DN}$C(=O)R$^{DD}$,
—NHC(=O)NH$_2$, —NHC(=O)NHR$^{DD}$, —NHC(=O)NR$^{DD}_2$, —NHC(=O)R$^{DM}$,
—NR$^{DN}$C(=O)NH$_2$, —NR$^{DN}$C(=O)NHR$^{DD}$, —NR$^{DN}$C(=O)NR$^{DD}_2$, —NR$^{DN}$C(=O)R$^{DM}$,
—NHC(=O)OR$^{DD}$, —NR$^{DN}$C(=O)OR$^{DD}$,
—OC(=O)NH$_2$, —OC(=O)NHR$^{DD}$, —OC(=O)NR$^{DD}_2$, —OC(=O)R$^{DM}$,
—NHC(=NH)NH$_2$,
—C(=O)R$^{DD}$,
—S(=O)NH$_2$, —S(=O)NHR$^{DD}$, —S(=O)NR$^{DD}_2$, —S(=O)R$^{DM}$,
—S(=O)$_2$NH$_2$, —S(=O)$_2$NHR$^{DD}$, —S(=O)$_2$NR$^{DD}_2$, —S(=O)$_2$R$^{DM}$,
—NHS(=O)R$^{DD}$, —NR$^{DN}$S(=O)R$^{DD}$,
—NHS(=O)$_2$R$^{DD}$, —NR$^{DN}$S(=O)$_2$R$^{DD}$,
—S(=O)R$^{DD}$, —S(=O)$_2$R$^{DD}$,
—SH, —SR$^{DD}$, —CN, and —NO$_2$;
wherein:
each —$R^{DD}$ is independently linear or branched saturated $C_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
each —$R^{DN}$ is linear or branched saturated $C_{1-4}$alkyl;
each —$R^{DM}$ is independently azetidino, pyrrolidino, piperidino, piperazino, morpholino, azepano, or diazepano, and is:
optionally substituted with one or more groups selected from:
—$R^{DMM}$, —C(=O)$R^{DMM}$, —C(=O)O$R^{DMM}$, and —S(=O)$_2R^{DMM}$;
wherein each —$R^{DMM}$ is independently linear or branched saturated $C_{1-4}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$;
or —$R^1$ and —$R^2$, together with the carbon atom to which they are attached, form a saturated $C_{3-6}$cycloalkyl or a non-aromatic $C_{3-7}$heterocyclyl, and is optionally substituted with one or more groups —$R^{CC2}$;
and wherein:
—$R^{N1}$ is independently —H or —$R^N$;
—$R^{N2}$ is independently —H or —$R^N$;
each —$R^N$ is independently linear or branched saturated $C_{1-6}$alkyl, phenyl, or —CH$_2$-phenyl, wherein each phenyl is optionally substituted with one or more groups selected from —F, —Cl, —Br, -Me, —OH, —OMe, —CF$_3$, and —OCF$_3$; or
—$R^{N1}$ and $R^{N2}$, taken together, form $C_{2-6}$alkylene.

2. A compound according to claim 1, wherein:
—$R^{N1}$ is —H; and
—$R^{N2}$ is —H.

3. A compound according to claim 2, wherein:
—$R^1$ is —$R^{11}$;
—$R^{11}$ is —$R^{11A}$;
—$R^{11A}$ is —$R^{41}$; and
—$R^2$ is —H.

4. A compound according to claim 3, wherein:
$R^2$ is —H; and
the compound is a compound selected from compounds of the following formula, and pharmaceutically acceptable salts thereof:

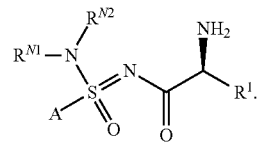

5. A compound according to claim 4, wherein:
—$R^1$ is independently —CH(CH$_3$)CH$_2$CH$_3$, —CH$_2$CH(CH$_3$)$_2$, or —CH(CH$_3$)$_2$; and
—$R^2$ is —H.

6. A compound according to claim 4, wherein:
—$R^1$ is —CH$_2$CH(CH$_3$)$_2$; and
—$R^2$ is —H.

7. A compound according to claim 3, wherein:
-$A^C$, if present, is phenyl or naphthyl, and is optionally substituted with 1, 2, or 3 substituents —$R^X$; and
-$A^H$, if present, is furanyl, thienyl, pyrrolyl, pyrazolyl, imidazolyl, oxazolyl, isoxazolyl, thiazolyl, isothiazolyl, pyridyl, pyridazinyl, pyrimidinyl, pyrazinyl, and is optionally substituted with one or more substituents —$R^X$.

8. A compound according to claim 3, wherein:
-A is -$A^C$; and
-$A^C$ is phenyl, and is optionally substituted with 1, 2, or 3 substituents —$R^X$.

9. A compound according to claim 3, wherein:
-A is -$A^H$; and
-$A^H$ is thien-2-yl, and is optionally substituted with one or more substituents —$R^X$.

10. A compound according to claim 6, wherein:
-A is -$A^H$; and
-$A^H$ is thien-2-yl, and is optionally substituted with one or more substituents —$R^X$.

11. A compound according to claim 3, wherein:
-A is -$A^H$; and
-$A^H$ is independently selected from:

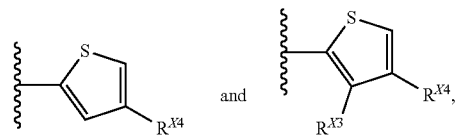

wherein each —$R^{X3}$ and —$R^{X4}$ is independently as defined for —$R^X$.

12. A compound according to claim 6, wherein:
-A is -A$^H$; and
-A$^H$ is independently selected from:

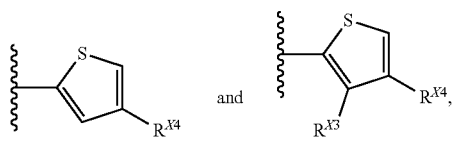

wherein each —R$^{X3}$ and —R$^{X4}$ is independently as defined for —R$^X$.

13. A compound according to claim 7, wherein:
each —R$^X$, if present, is independently selected from:
—R$^{XX}$,
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}{}_2$, —R$^{XM}$,
—C(=O)OH, —C(=O)OR$^{XX}$, —OC(=O)R$^{XX}$,
—C(=O)NH$_2$, —C(=O)NHR$^{XX}$, —C(=O)NR$^{XX}{}_2$, —C(=O)R$^{XM}$,
—NHC(=O)R$^{XX}$, —NR$^{XN}$C(=O)R$^{XX}$,
—C(=O)R$^{XX}$,
—S(=O)NH$_2$, —S(=O)NHR$^{XX}$, —S(=O)NR$^{XX}{}_2$, —S(=O)R$^{XM}$,
—S(=O)$_2$NH$_2$, —S(=O)$_2$NHR$^{XX}$, —S(=O)$_2$NR$^{XX}{}_2$, —S(=O)$_2$R$^{XM}$,
—NHS(=O)R$^{XX}$, —NR$^{XN}$S(=O)R$^{XX}$,
—NHS(=O)$_2$R$^{XX}$, —NR$^{XN}$S(=O)$_2$R$^{XX}$,
—S(=O)R$^{XX}$, —S(=O)$_2$R$^{XX}$,
—SR$^{XX}$, —CN, and —NO$_2$.

14. A compound according to claim 10, wherein:
each —R$^X$, if present, is independently selected from:
—R$^{XX}$,
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}{}_2$, —R$^{XM}$, and
—CN;
each —R$^{XX}$, if present, is linear or branched saturated C$_{1-4}$alkyl;
each —R$^{XM}$, if present, is independently pyrrolidino, piperidino, piperazino, or morpholino, and is: optionally substituted with one or more groups selected from: —R$^{XMM}$, —C(=O)R$^{XMM}$, —C(=O)OR$^{XMM}$, and —S(=O)$_2$R$^{XMM}$; and
each —R$^{XMM}$, if present, is linear or branched saturated C$_{1-4}$alkyl.

15. A compound according to claim 11, wherein:
each —R$^X$, if present, is independently selected from:
—R$^{XX}$,
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}{}_2$, —R$^{XM}$, and
—CN;
each —R$^{XX}$, if present, is linear or branched saturated C$_{1-4}$alkyl;
each —R$^{XM}$, if present, is independently pyrrolidino, piperidino, piperazino, or morpholino, and is: optionally substituted with one or more groups selected from: —R$^{XMM}$, —C(=O)R$^{XMM}$, —C(=O)OR$^{XMM}$, and —S(=O)$_2$R$^{XMM}$; and
each —R$^{XMM}$, if present, is linear or branched saturated C$_{1-4}$alkyl.

16. A compound according to claim 12, wherein:
each —R$^X$, if present, is independently selected from:
—R$^{XX}$,
—F, —Cl, —Br, —I,
—OH, —OR$^{XX}$,
—CF$_3$, —CHF$_2$, —OCF$_3$, —OCHF$_2$,
—NH$_2$, —NHR$^{XX}$, —NR$^{XX}{}_2$, —R$^{XM}$, and
—CN;
each —R$^{XX}$, if present, is linear or branched saturated C$_{1-4}$alkyl;
each —R$^{XM}$, if present, is independently pyrrolidino, piperidino, piperazino, or morpholino, and is: optionally substituted with one or more groups selected from: —R$^{XMM}$, —C(=O)R$^{XMM}$, —C(=O)OR$^{XMM}$ and —S(=O)$_2$R$^{XMM}$; and
each —R$^{XMM}$, if present, is linear or branched saturated C$_{1-4}$alkyl.

17. A compound according to claim 1, which is selected from compounds of the following formulae, and pharmaceutically acceptable salts thereof:

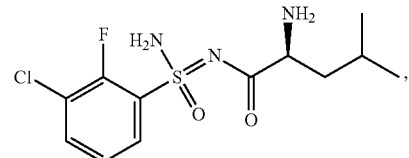

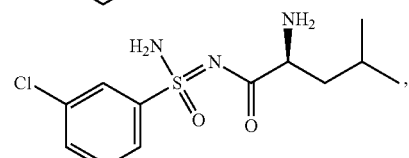

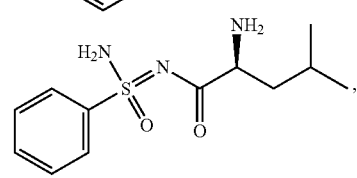

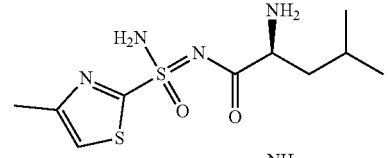

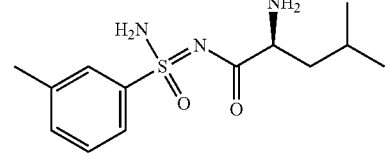

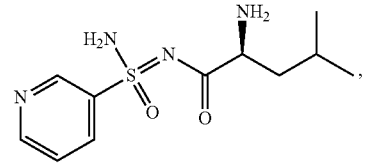

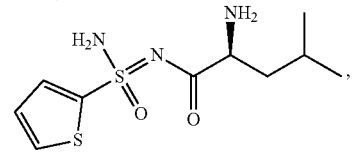

413
-continued
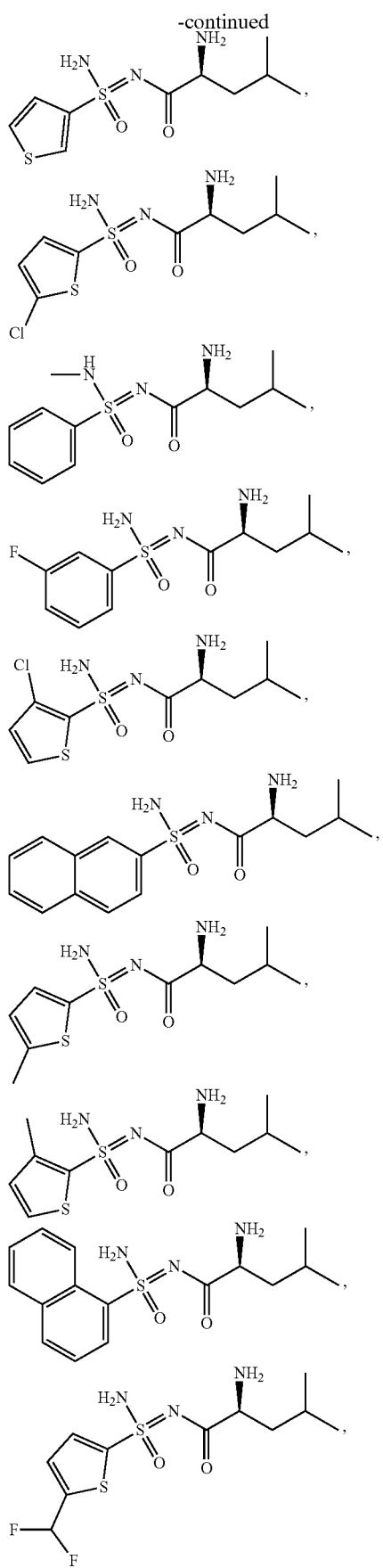
414
-continued
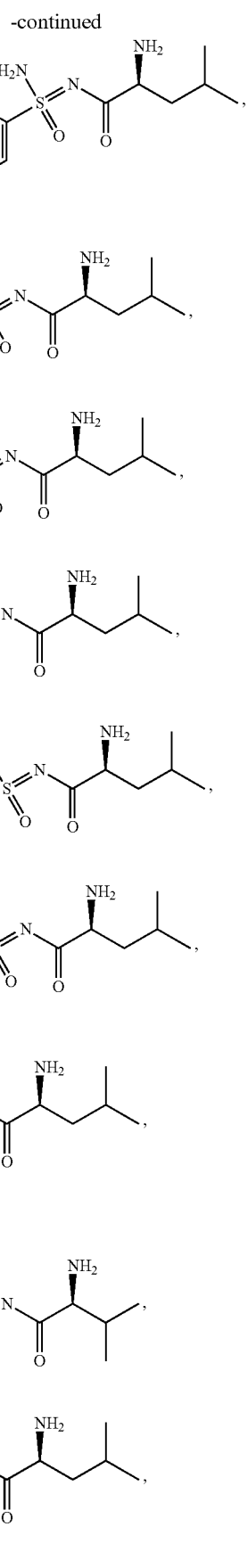

-continued
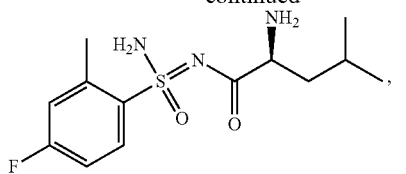
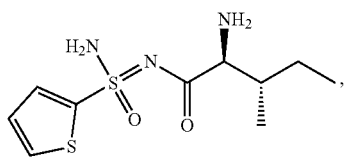
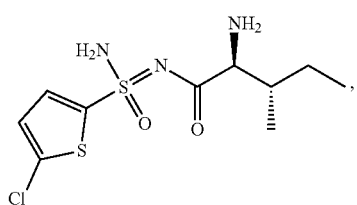
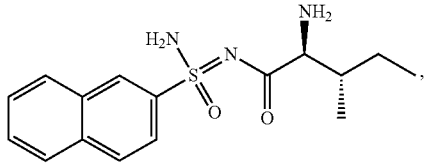
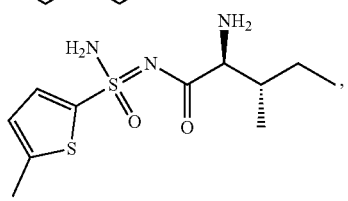
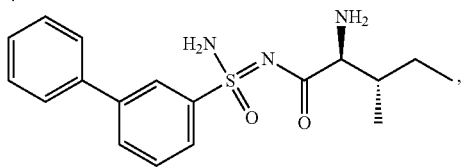
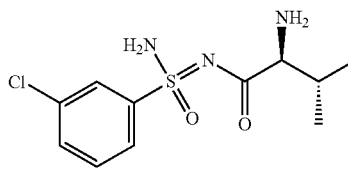
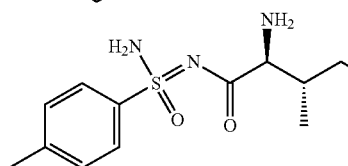
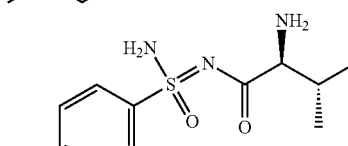
-continued
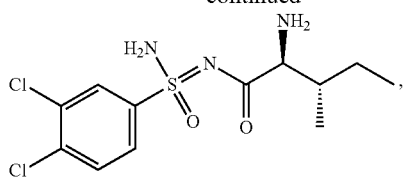
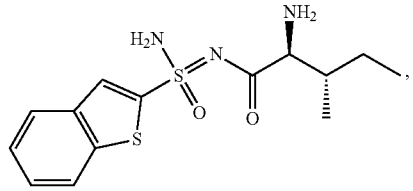
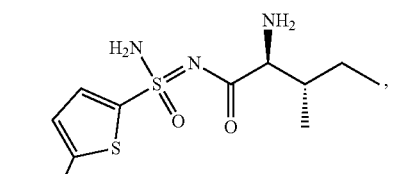
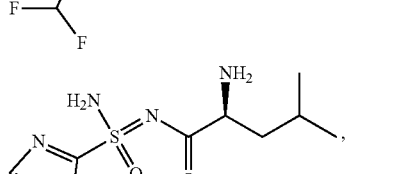
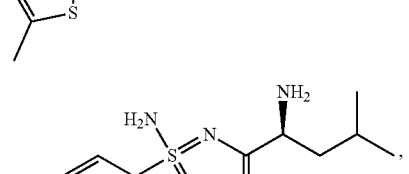
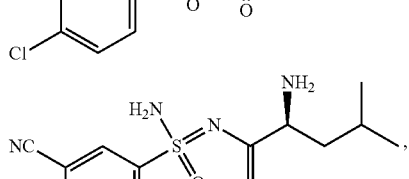
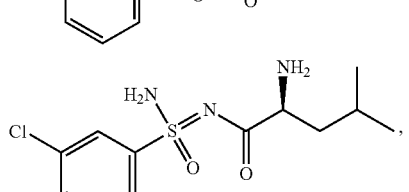
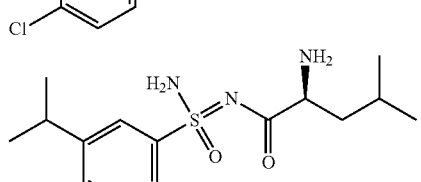
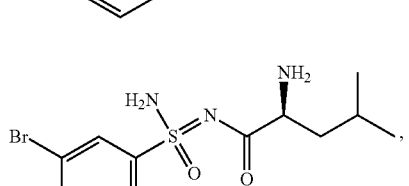

417
-continued
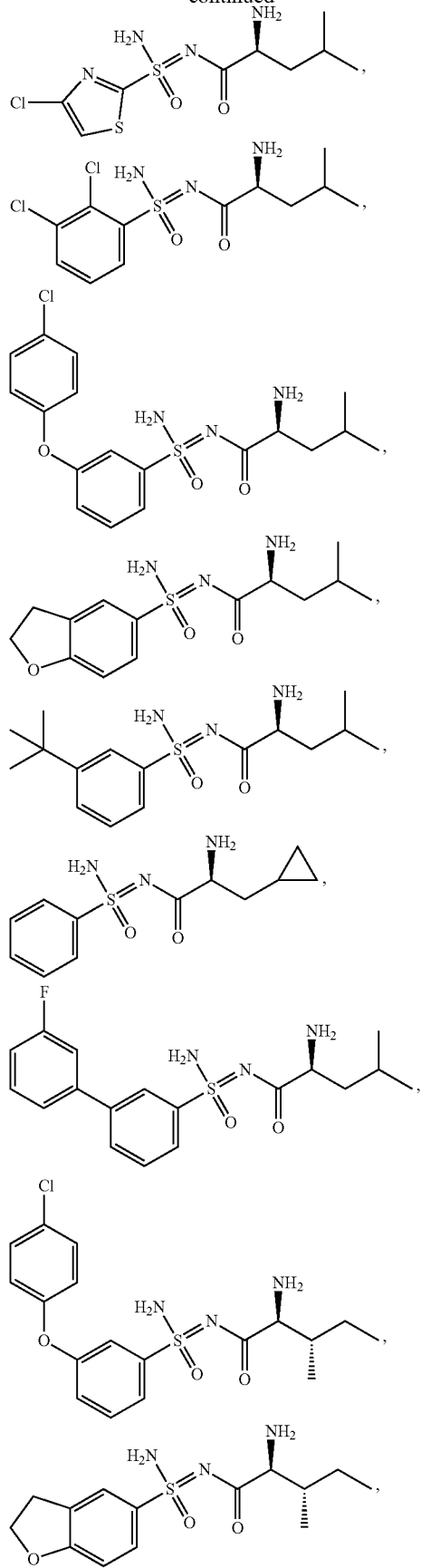
418
-continued
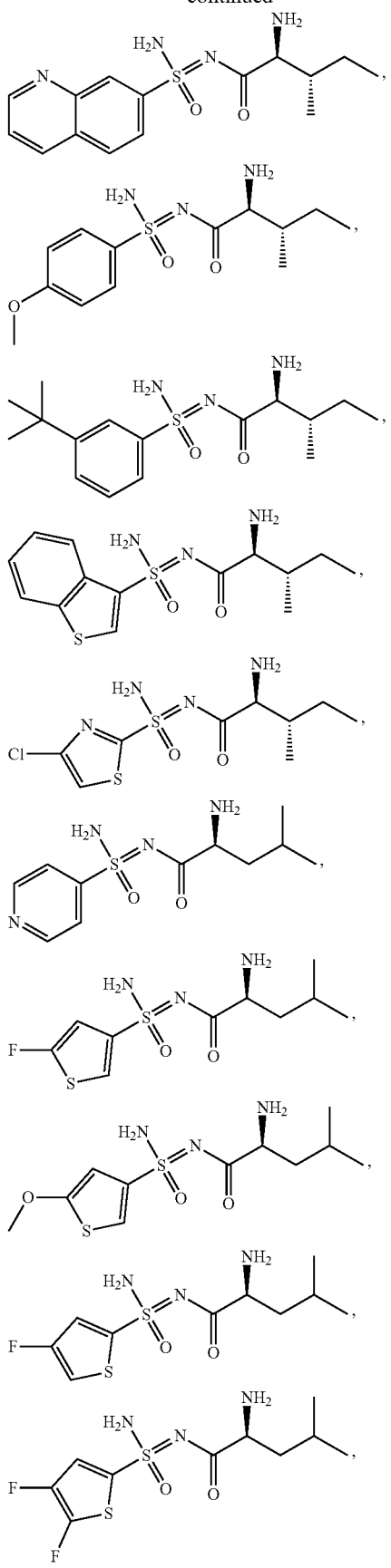

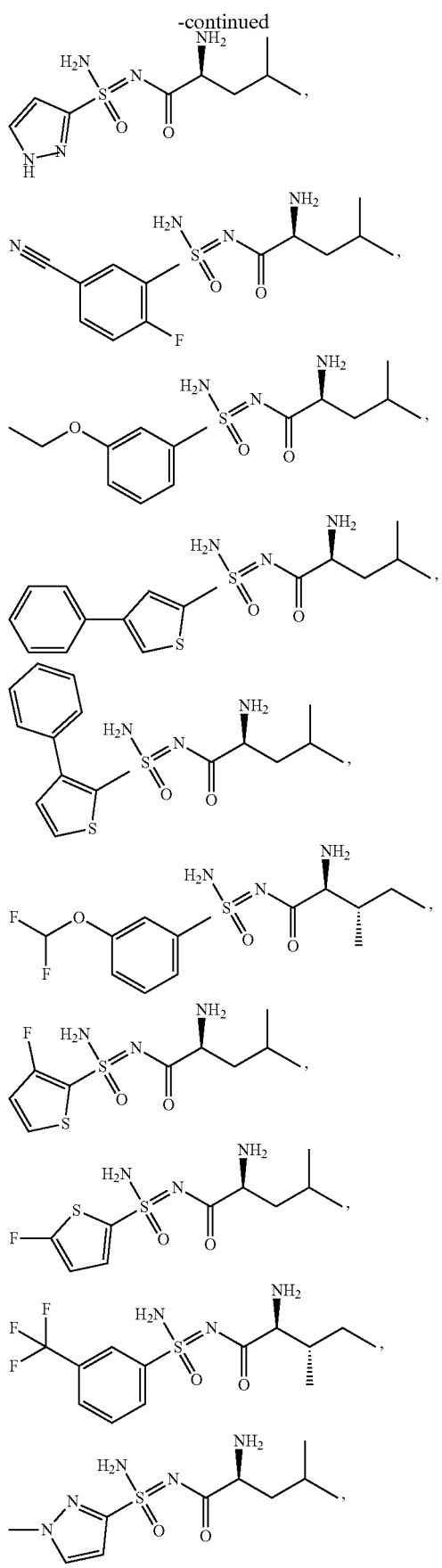

-continued
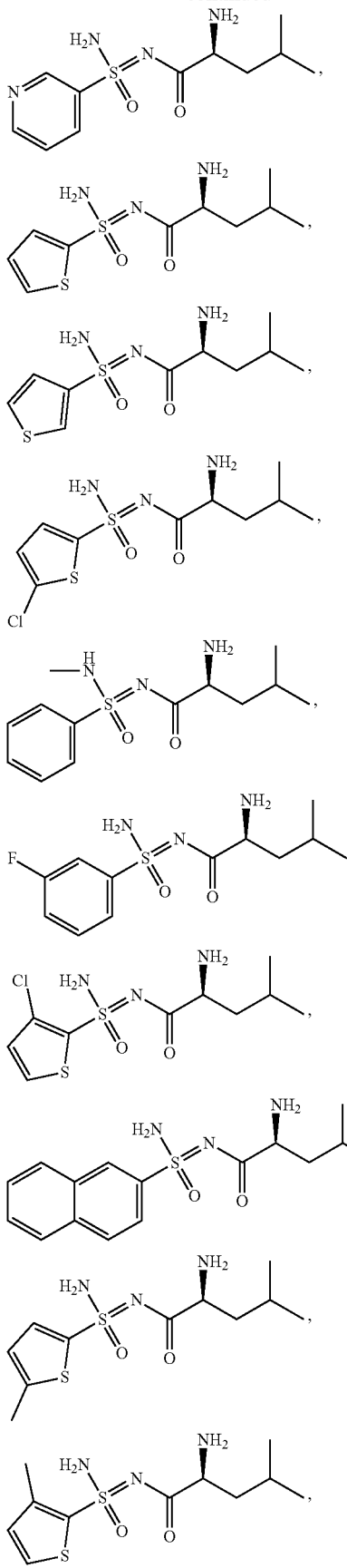
-continued
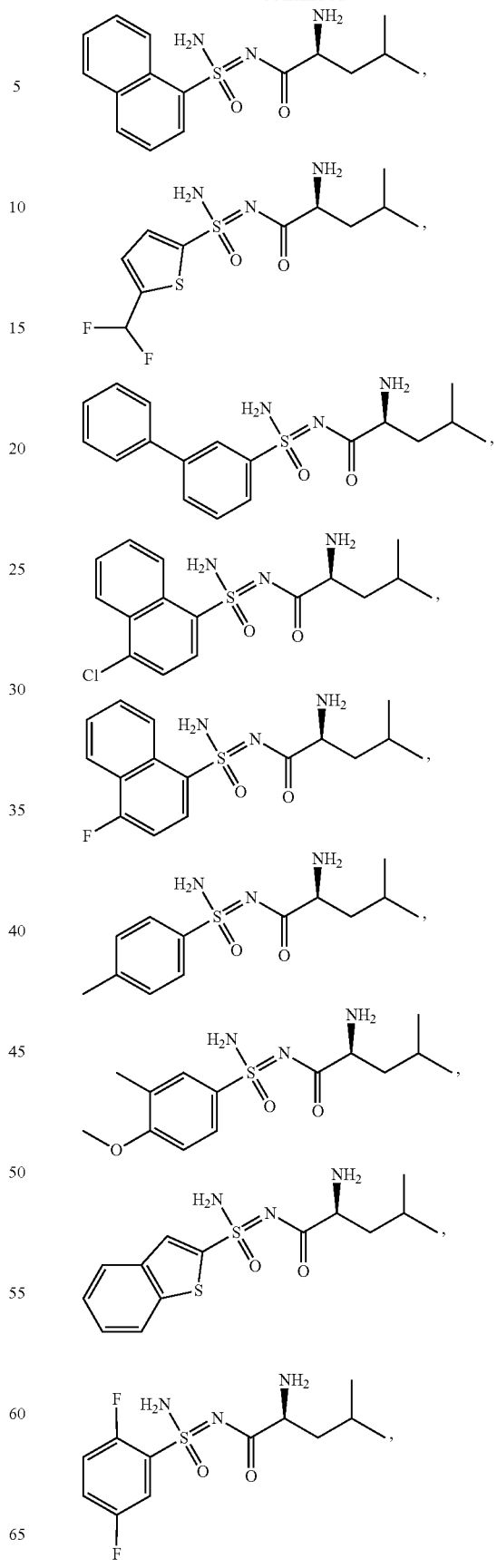

423
-continued
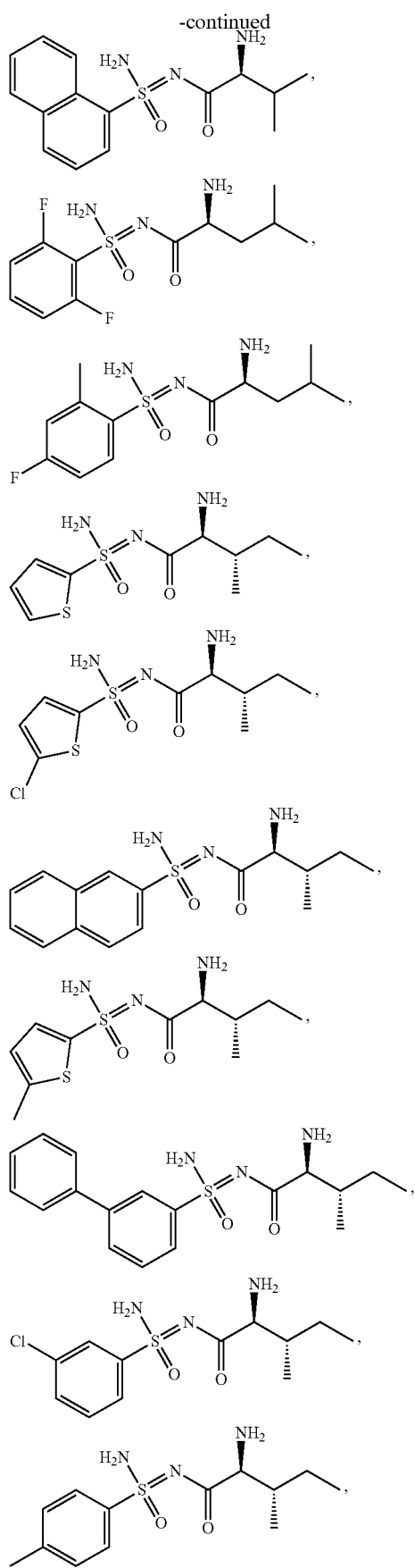
424
-continued
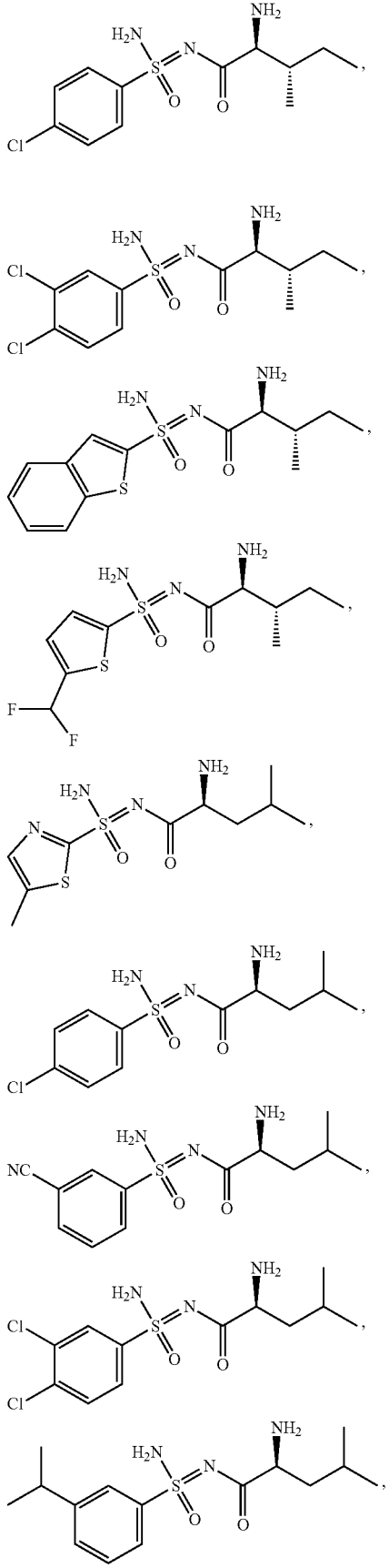

425
-continued
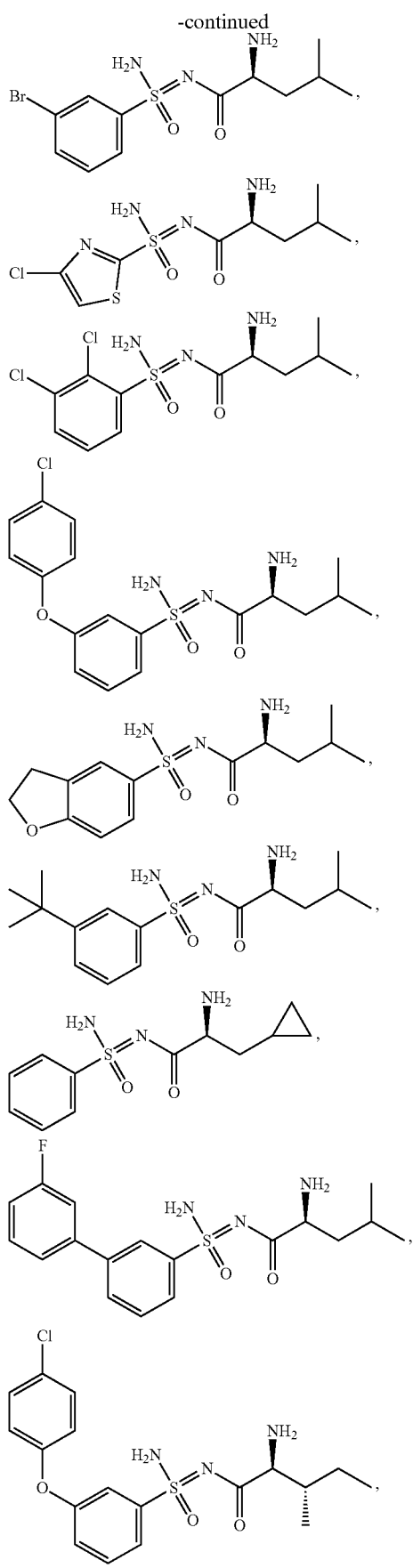
426
-continued
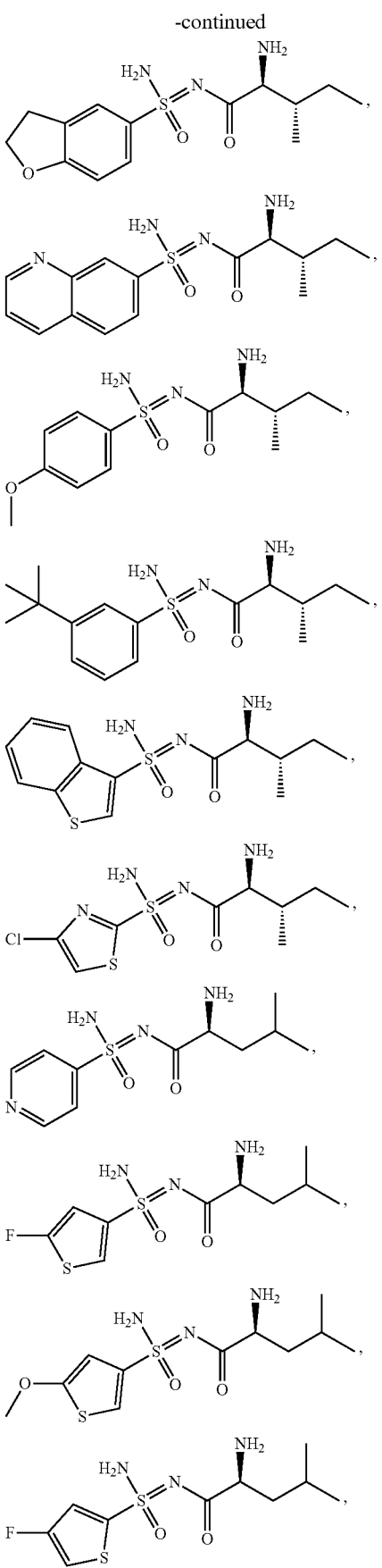

427
-continued
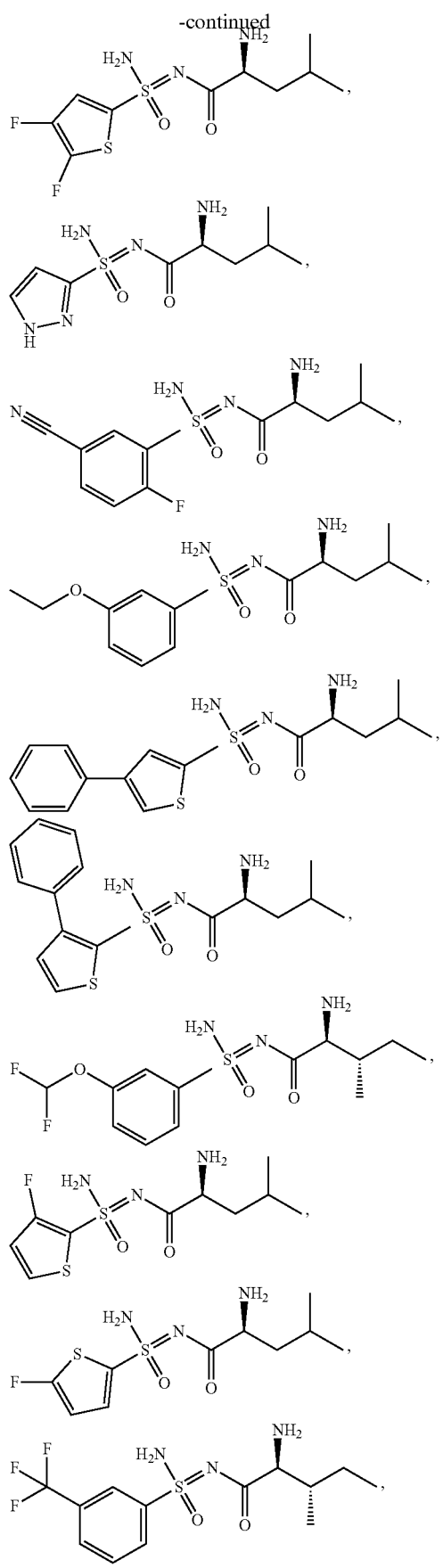
428
-continued
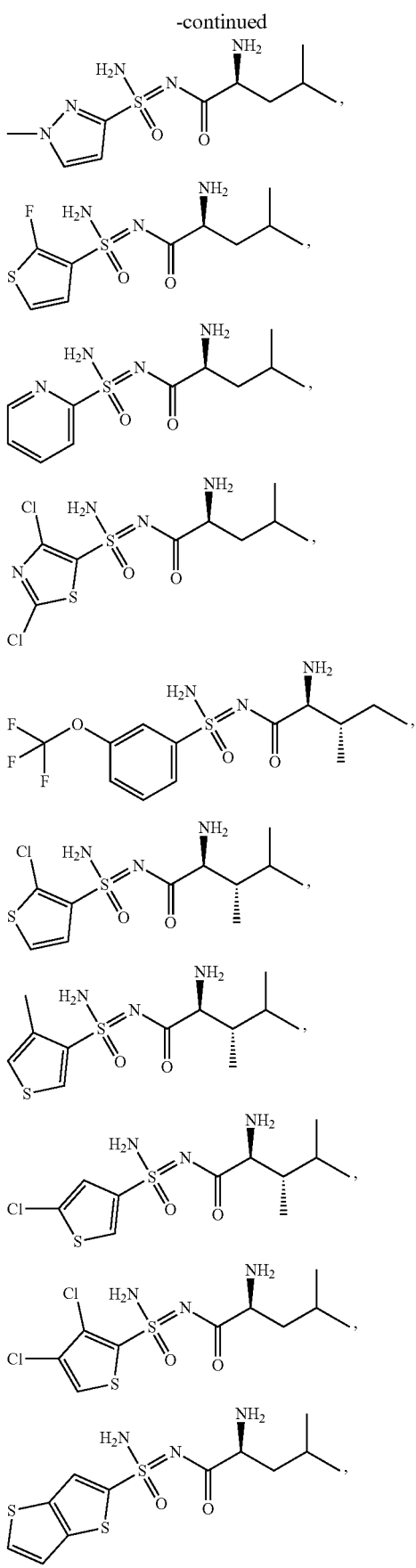

-continued
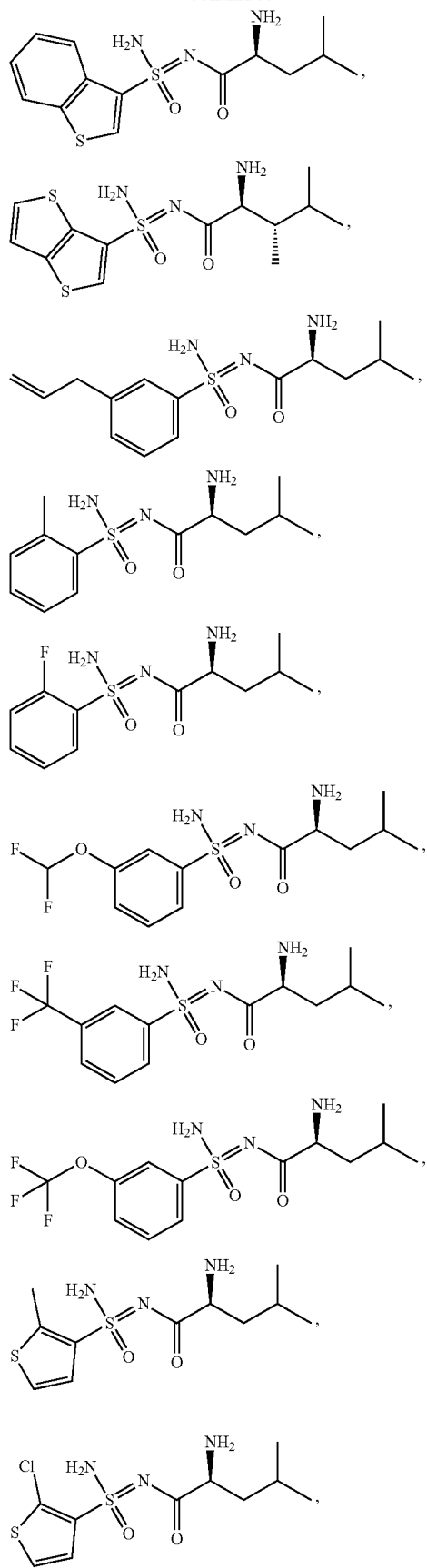
-continued
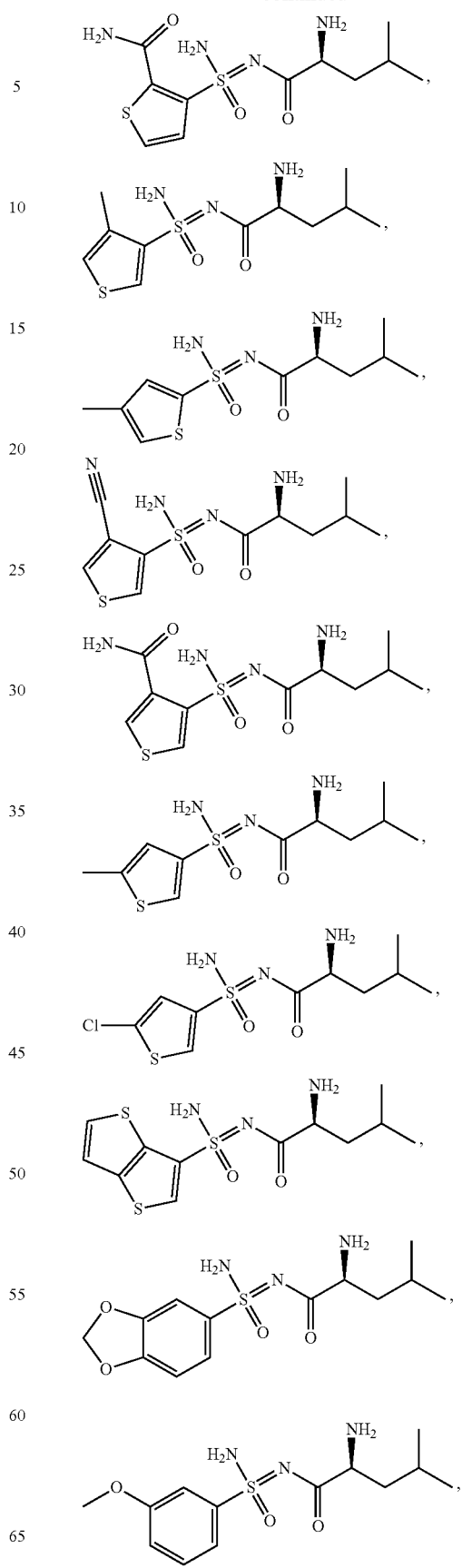

431
-continued
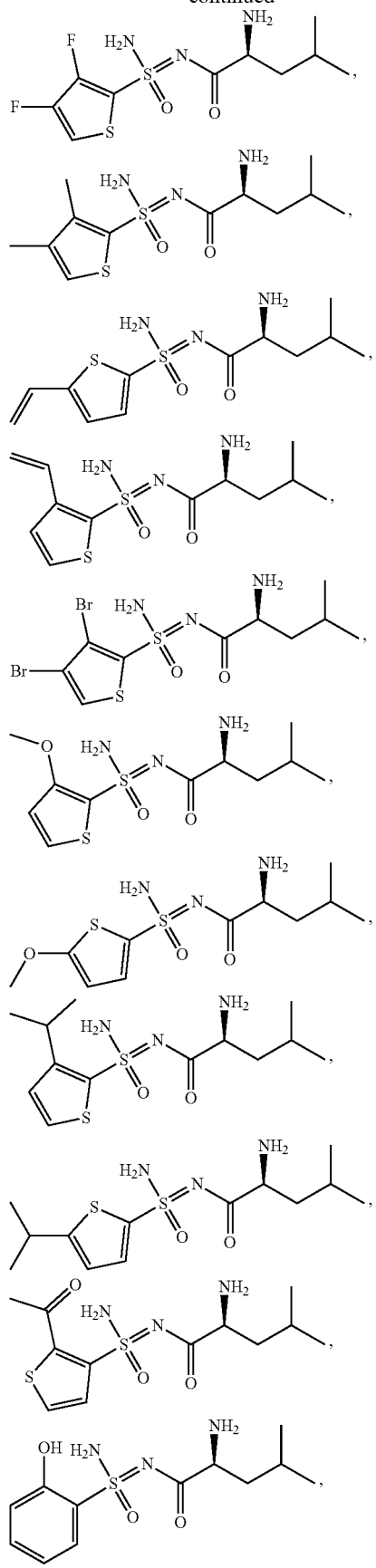
432
-continued
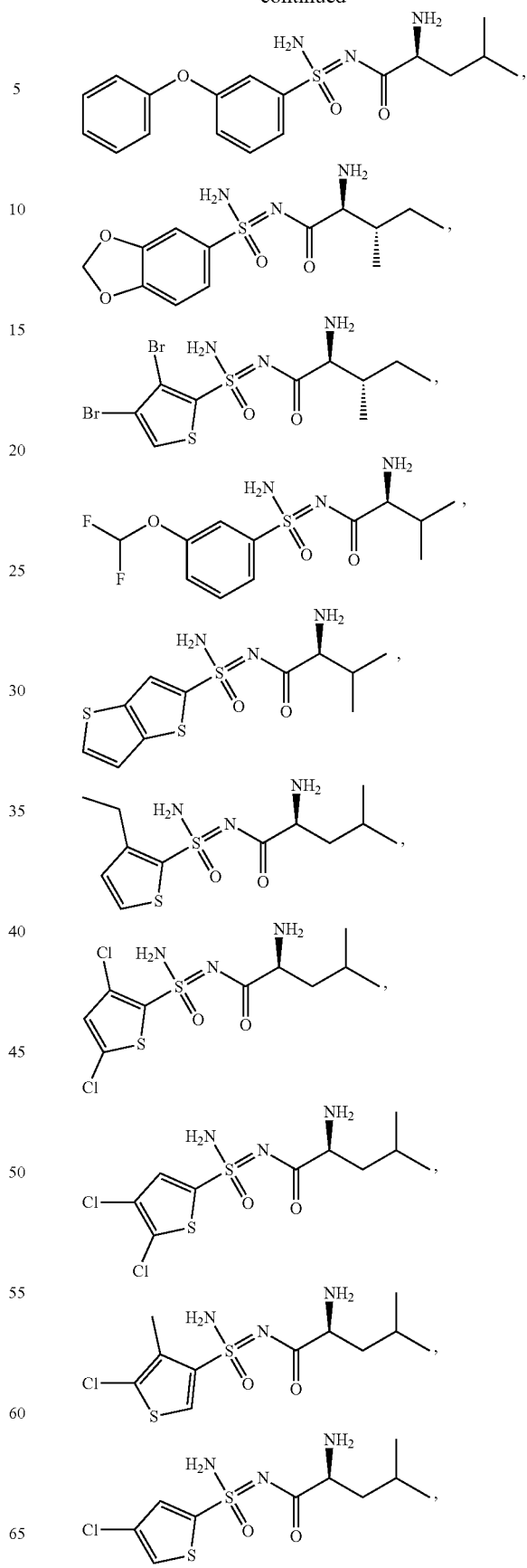

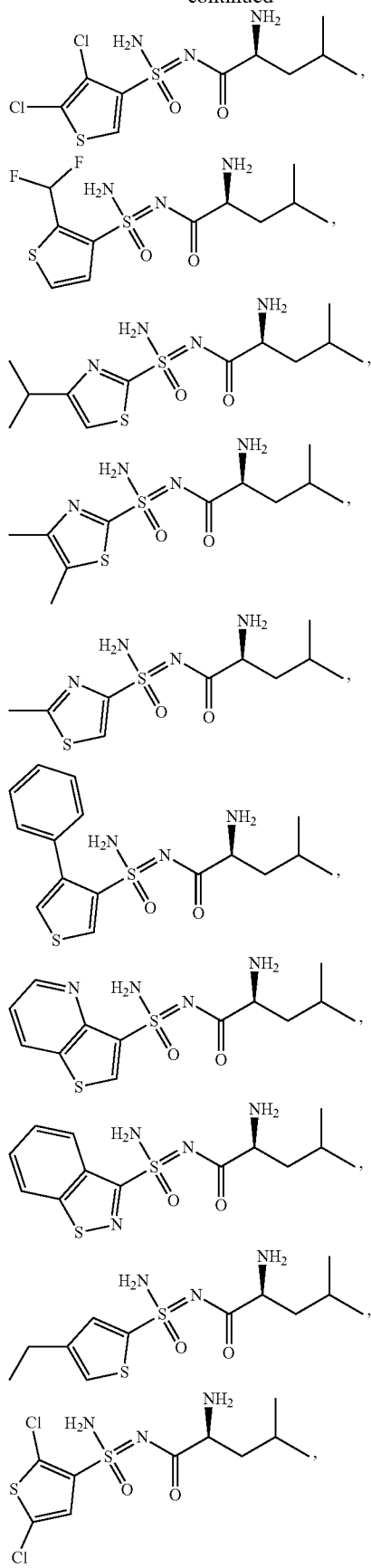

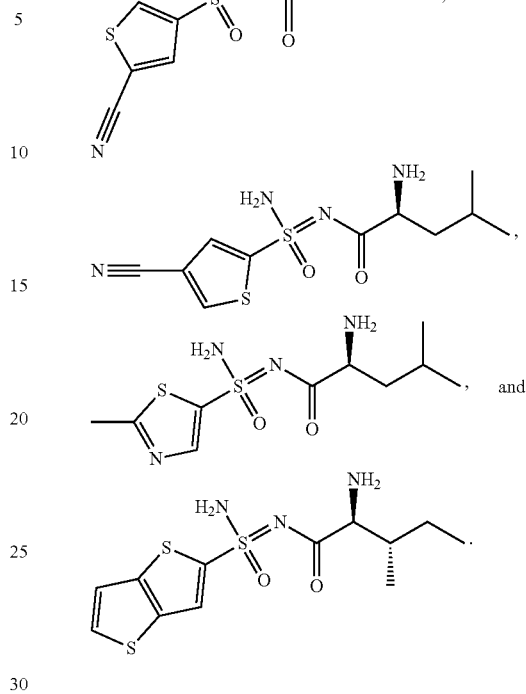

18. A pharmaceutical composition comprising a compound according to claim 1, and a pharmaceutically acceptable carrier or diluent.

19. A method of preparing a pharmaceutical composition comprising the step of mixing a compound according to claim 1, and a pharmaceutically acceptable carrier or diluent.

20. A method of inhibiting bacterial aminoacyl-tRNA synthetase, in vitro or in vivo, comprising contacting the synthetase with an effective amount of a compound according to claim 1.

21. A method of inhibiting bacterial aminoacyl-tRNA synthetase function in a cell, in vitro or in vivo, comprising contacting the cell with an effective amount of a compound according to claim 1.

22. A method of treatment of a disorder of the human or animal body, comprising administering to a subject in need of treatment a therapeutically-effective amount of a compound according to claim 1, wherein the disorder is a bacterial infection.

23. A method according to claim 22, wherein the bacteria are:
Staphylococci, for example *S. aureus;*
Enterococci, for example *E. faecalis;*
Streptococci, for example *S. pneumoniae;*
Haemophilus, for example *H. influenza;*
Moraxella, for example *M. catarrhalis;*
Klebsiella, for example *K. pneumoniae;*
Acinetobacter, for example *A. baumanii;*
Pseudomonas, for example *P. aeruginosa;*
Proteus, for example *P. mirabilis;*
Neisseria, for example *Neisseria gonorrhoeae;*
Clostridioides, for example Clostridioides *difficile;*
Campylobacter, for example *C. jejuni;*
Salmonella, for example *S. typhi;*
Shigella, for example *S. flexneri;*

*Enterobacter*, for example *E. cloacae;*
*Citrobacter*, for example *C. freundii;*
*Serratia*, for example *Serratia marcescens;* or
*Escherichia*, for example *E. coli.*

24. A method according to claim 22, wherein the infection is:
- a central nervous system infection;
- an external ear infection;
- an infection of the middle ear, including acute otitis media;
- an infection of the cranial sinuses;
- an eye infection;
- an infection of the oral cavity, including an infection of the teeth, gums, or mucosa;
- an upper respiratory tract infection;
- a lower respiratory tract infection;
- a genitourinary infection;
- a urinary tract infection;
- an intra-abdominal infection;
- a gastrointestinal infection;
- a gynecological infection;
- septicemia,
- a bone or joint infection;
- a skin or skin structure infection;
- bacterial endocarditis; or
- a burn infection.

\* \* \* \* \*